US008163509B2

(12) United States Patent
Eckhardt et al.

(10) Patent No.: US 8,163,509 B2
(45) Date of Patent: Apr. 24, 2012

(54) BIOLOGICAL MARKERS PREDICTIVE OF ANTI-CANCER RESPONSE TO INSULIN-LIKE GROWTH FACTOR-1 RECEPTOR KINASE INHIBITORS

(75) Inventors: Sue Gail Eckhardt, Evergreen, CO (US); Todd Michael Pitts, Thornton, CO (US); Aik Choon Tan, Englewood, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 9 days.

(21) Appl. No.: 12/582,013

(22) Filed: Oct. 20, 2009

(65) Prior Publication Data

US 2010/0240665 A1 Sep. 23, 2010

Related U.S. Application Data

(60) Provisional application No. 61/251,112, filed on Oct. 13, 2009, provisional application No. 61/196,885, filed on Oct. 20, 2008.

(51) Int. Cl.

| | |
|---|---|
| ***G01N 33/574*** | (2006.01) |
| ***G01N 33/53*** | (2006.01) |
| ***C12Q 1/68*** | (2006.01) |

(52) U.S. Cl. ............................ 435/7.23; 435/6; 435/7.1

(58) Field of Classification Search ........................ None
See application file for complete search history.

(56) References Cited

U.S. PATENT DOCUMENTS

| | | | | |
|---|---|---|---|---|
| 2006/0235031 | A1 | 10/2006 | Arnold et al. | |
| 2010/0184125 | A1 * | 7/2010 | Huang et al. | 435/40.5 |

OTHER PUBLICATIONS

Wang Y. et al., "Profiling MicroRNA Expression in Hepatocellular Carcinoma Reveals MicroRNA-224 Up-Regulation and Apoptosis Inhibitor-5 as a MicroRNA-224-Specific Target", *The Journal of Biological Chemistry 283*(19):13205-13215 (2008).

Marcucci G. et al., "MicroRNA Expression in Cytogenetically Normal Acute Myeloid Leukemia", *The New England Journal of Medicine* 358(18):1919-1928 (2008).

Rowe D.L. et al., "Nordihydroguaiaretic Acid, a Cytotoxic Insulin-Like Growth Factor-I Receptor/HER2 Inhibitor in Trastuzumab-Resistant Breast Cancer", *Mol. Cancer Ther.* 7(7): 1900- 1908 (2008).

International Search Report and Written Opinion dated Jul. 9, 2010 received from the Korean Intellectual Property Office.

* cited by examiner

*Primary Examiner* — Laura B Goddard

(74) *Attorney, Agent, or Firm* — Scully, Scott, Murphy & Presser, P.C.

(57) ABSTRACT

The present invention provides diagnostic methods for predicting the effectiveness of treatment of a cancer patient with an IGF-1R kinase inhibitor. Methods are provided for predicting the sensitivity of tumor cell growth to inhibition by an IGF-1R kinase inhibitor, comprising assessing whether the tumor cell expresses certain sensitivity or resistance biomarkers, or genomic classifiers. Improved methods for treating cancer patients with IGF-1R kinase inhibitors that incorporate this methodology are also provided.

21 Claims, 34 Drawing Sheets

Figure 1

| | Patient Characteristics | | Genetic Status | | | | | | | | Protein |
|---|---|---|---|---|---|---|---|---|---|---|---|
| Cell Line | Stage | Gender | ras | raf | p53 status | PTEN | PI3K | Src | APC | EGFR | IGF1R |
| HCT116 | Unk | M | mut | wt | wt | wt | mut | (wt) | wt | wt | pos |
| HT29 | Unk | F | wt | mut | mut (overexp.) | wt | mut | mut | mut | wt | pos |
| HCT15 | Dukes' Type C | M | mut | wt | mut | wt | mut | Unk | mut | wt | Unk |
| SW480 | Dukes' Type B | M | mut | Unk | mut | wt | wt | Unk | mut | wt | pos |
| SW620 | Dukes' Type C | M | mut | wt | mut | wt | wt | Unk | mut | wt | pos |
| Colo320 | Dukes' Type C | F | Unk | Unk | Unk | Unk | Unk | Unk | | Unk | Unk |
| Colo205 | Dukes' Type D | M | wt | mut | mut | wt | wt | (wt) | mut | wt | Unk |
| RKO | Unk | Unk | wt | mut | wt | wt | mut | Unk | wt | wt | Unk |
| RKO E6 | Unk | Unk | wt | Unk | wt | wt | Unk | Unk | | Unk | Unk |
| RKO AS45.1 | Unk | Unk | wt | Unk | wt (underexp.) | wt | Unk | Unk | | Unk | Unk |
| LS1034 | Dukes' Type C | M | mut | wt | mut | wt | wt | Unk | mut | wt | pos |
| LS513 | Dukes' Type C | M | mut | wt | wt | wt | wt | Unk | wt | wt | pos |
| CaCo2 | Unk | M | Unk | Unk | Unk | Unk | Unk | Unk | | Unk | pos |
| HCT8 | Unk | M | mut | Unk | Unk | wt | mut | Unk | | Unk | Unk |
| LoVo | Dukes' Type C | M | mut | wt | wt | wt | mut | Unk | mut | wt | pos |
| LS123 | Dukes' Type B | F | mut | wt | wt | wt | wt | Unk | mut | wt | Unk |
| T84 | Unk | M | mut | wt | wt | wt | mut | Unk | wt | wt | Unk |
| LS174T | Dukes' Type B | F | mut | wt | wt | wt | mut | Unk | wt | wt | pos |
| LS180 | Dukes' Type B | F | Unk | Unk | null | Unk | Unk | Unk | mut | Unk | Unk |
| SW1417 | Dukes' Type C | F | wt | mut | wt | wt | wt | Unk | mut | wt | Unk |
| Colo201 | Dukes' Type B | M | Unk | Unk | Unk | Unk | Unk | Unk | Unk | Unk | Unk |
| SW1116 | Dukes' Type A-grade II | M | mut | Unk | Unk | Unk | Unk | Unk | Unk | Unk | Unk |
| SW48 | Dukes's Type C-grade IV | F | wt | wt | wt | wt | wt | wt | Unk | wt | Unk |
| HS675.T | Unk | M | Unk | Unk | Unk | Unk | Unk | Unk | Unk | Unk | Unk |
| SK-CO-1 | Unk | M | mut | wt | wt | wt | wt | wt | Unk | mut | Unk |
| SW948 | Dukes' Type C-grade III | F | mut | wt | wt | wt | mut | Unk | mut | wt | Unk |
| SW837 | Grade IV | M | mut | wt | mut | wt | wt | Unk | mut | wt | Unk |
| SW1463 | Dukes' Type C | F | mut | wt | mut | wt | wt | Unk | mut | wt | Unk |
| SW403 | Dukes' Type C-grade III | F | Unk | Unk | Unk | Unk | Unk | Unk | Unk | Unk | Unk |

Data was obtained from ATCC, PubMed Literature & www.sange.ac.uk

Figure 4A. RT-PCR expression of caldesmon as function of sensitivity to PQIP.
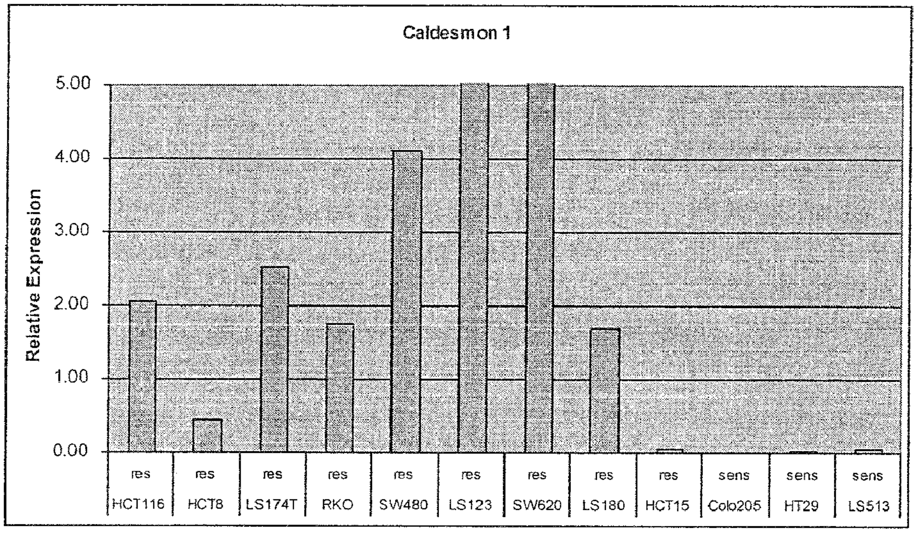
Figure 4B. RT-PCR expression of metallothionein 1E as function of sensitivity to PQIP.
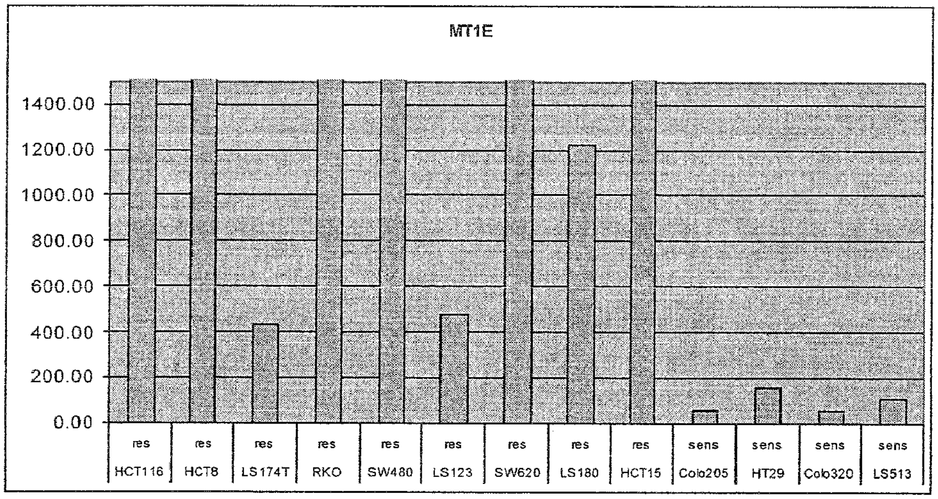

Figure 4C. RT-PCR of ALDH1A1 as a function of sensitivity to PQIP.
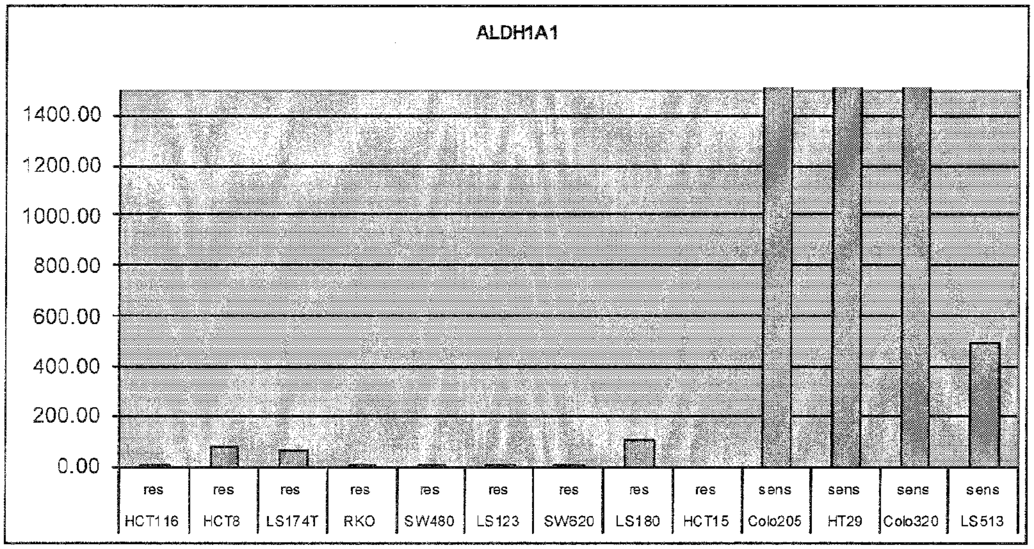

Figure 6: Effect of PQIP on IGF1R and downstream intracellular pathways by immunoblotting.
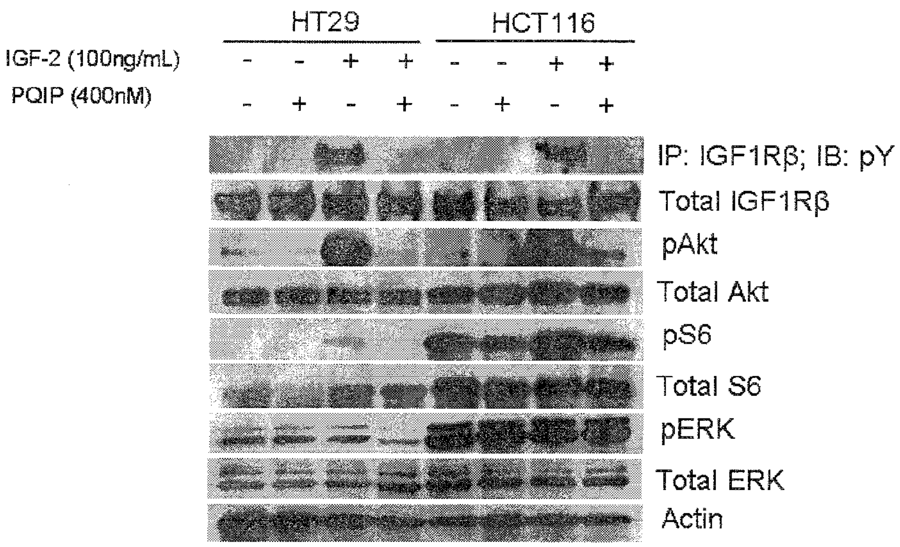

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Combination effects of PQIP and chemotherapy on PQIP resistant CRC cell lines

Figure 9: Phosphorylation levels of IGF1R in CRC cell lines following exposure to PQIP alone and in combination with SN38 (A) or oxaliplatin (B).
A.
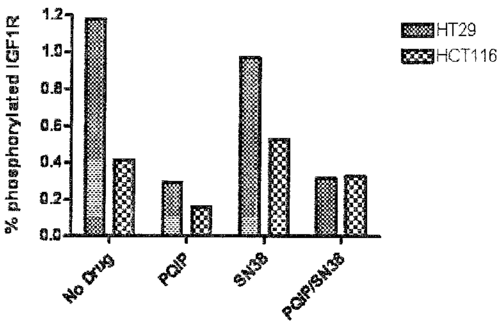
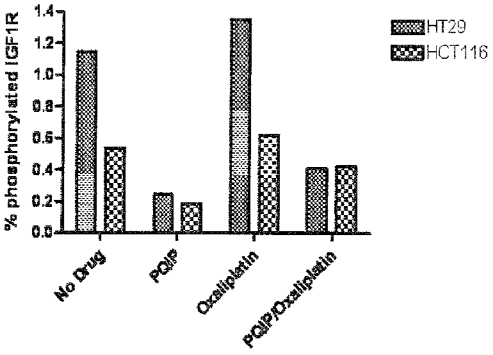
B.

Figure 10 A. Summary of comparison between IGF1R genomic status and sensitivity to PQIP

| Cell Line | IGF1R/Ploidy | S/I/R to PQIP |
|---|---|---|
| CaCo2 | Gain - Low | S |
| CoLo201 | Balanced | I |
| CoLo205 | Gain - High | S |
| HCT15 | Balanced | R |
| HCT116 | Balanced | R |
| HCT8 | Balanced | R |
| HT29 | Gain - Low | S |
| LoVo | Gain - High | R |
| LS123 | Gain - Low | R |
| LS174T | Balanced | R |
| LS180 | Balanced | R |
| LS513 | Gain - Low | S |
| NCI-H508 | Balanced | R |
| RKO | Balanced | R |
| SK-CO-1 | Gain - High | I |
| SW1116 | Balanced | R |
| SW1417 | Balanced | R |
| SW1463 | Loss | R |
| SW403 | Balanced | R |
| SW48 | Balanced | R |
| SW480 | Balanced | R |
| SW620 | Balanced | I |
| SW837 | Balanced | R |

| Cell Line | IGF1R/Ploidy | S/I/R to PQIP |
|---|---|---|
| HCT116 | Balanced | R |
| HCT15 | Balanced | R |
| HCT8 | Balanced | R |
| LS174T | Balanced | R |
| LS180 | Balanced | R |
| NCI-H508 | Balanced | R |
| RKO | Balanced | R |
| SW1116 | Balanced | R |
| SW1417 | Balanced | R |
| SW403 | Balanced | R |
| SW48 | Balanced | R |
| SW480 | Balanced | R |
| SW837 | Balanced | R |
| LoVo | Gain - High | R |
| LS123 | Gain - Low | R |
| SW1463 | Loss | R |
| CoLo201 | Balanced | I |
| SW620 | Balanced | I |
| SK-CO-1 | Gain - High | I |
| CoLo205 | Gain - High | S |
| CaCo2 | Gain - Low | S |
| HT29 | Gain - Low | S |
| LS513 | Gain - Low | S |

Figure 10B. Distribution of lines according to IGF1R genomic status and sensitivity to PQIP

| Sensitivity to PQIP | Genomic IGF1R status: Balanced | Loss | Gain |
|---|---|---|---|
| Resistant | 13 | 1 | 2 |
| Intermediate | 2 | 0 | 1 |
| Sensitive | 0 | 0 | 4 |

| | B+L | Gain |
|---|---|---|
| Resistant | 14 | 2 |
| I+S | 2 | 5 |

Chi-square 5.45

The two-tailed P value equals 0.0196.

By conventional criteria, this difference is considered to be statistically significant.

Note that for df=1 the chi-square value reported is the Yates chi-square, corrected for continuity. The Pearson chi-square, uncorrected for continuity, is 7.99.

Figure 11

| CRC cell line | Ploidy | Chromosomes harboring regions homologous to the IGF1R/CEP15 probe set tested | Comparison with published cytogenetic data |
|---|---|---|---|
| COLO 205 | near 3n | 4 apparently normal copies of chromosome 15 | |
| COLO 201 | near 3n | 3 apparently normal copies of chromosome 15 | confirmed with Tsushimi et al |
| HCT116 | near 2n | 2 apparently normal copies of chromosome 15 | confirmed with Rahman et al |
| HCT8 | near 2n | 2 apparently normal copies of chromosome 15 | |
| RKO | near 2n | 2-4 apparently normal copies of chromosome 15 | confirmed with Kleivi et al |
| HT29 | near 2n-near 3n | 2-5 apparently normal copies of chromosome 15 | confirmed with Abdel-Rahman et al |
| SW480 | near 3n | 2 cell clones, both had 1 copy of an acrocentric and 2-4 copies of a small metacentric der(15) without IGF1R. Clone A had 2 copies of normal 15, clone B had 1 copy of normal 15, 1 copy each of a submetacentric and of an acrocentric with only IGF1R sequences | 2 clones also detected by Abdel-Rahman et al; der(15) abnormalities not reported |
| LS174T | near 2n | 2 apparently normal copies of chromosome 15 | does not match Abdel-Rahman et al, 3 normal copies of chr 15 reported |
| LS513 | near 2n | 1 apparently normal copy of chromosome 15, and 1 copy of an acrocentric der(15) chromosome with duplicated IGF1R sequences | |

RKO Cell Line, Resistant, $IC_{50}$> 5uM.

COLO205 Cell Line, Sensitive, $IC_{50}$ 0.46 uM.

Figure 14

| sens/res | pvalue | Probe set | Representati\ | symbol | name |
|---|---|---|---|---|---|
| 81.048 | 0.0027262 | 212224_at | NM_000689 | ALDH1A1 | aldehyde dehydrogenase 1 family, member A1 |
| 43.672 | 0.0024001 | 219263_at | NM_024539 | RNF128 | ring finger protein 128 |
| 10.817 | 0.0013845 | 205698_s_at | NM_002758 | MAP2K6 | mitogen-activated protein kinase kinase 6 |
| 10.207 | 0.0044443 | 204044_at | NM_014298 | QPRT | quinolinate phosphoribosyltransferase (nicotinate-nucleotide pyrophosphorylase (carboxylating)) |
| 9.309 | 0.0010931 | 205992_s_at | NM_000585 | IL15 | interleukin 15 |
| 6.387 | 0.0033081 | 226636_at | AI378587 | PLD1 | phospholipase D1, phosphatidylcholine-specific |
| 5.438 | 0.00033 | 232040_at | AK025743 | LOC157860 | hypothetical protein LOC157860 |
| 3.901 | 0.0029232 | 232138_at | AW276914 | MBNL2 | Muscleblind-like 2 (Drosophila) |
| 3.833 | 0.0006881 | 238067_at | AW172431 | TBC1D8B | TBC1 domain family, member 8B (with GRAM domain) |
| 3.487 | 0.003875 | 230918_at | BE856598 | GALK2 | Galactokinase 2 |
| 3.255 | 0.002166 | 231832_at | AI890347 | GALNT4 | UDP-N-acetyl-alpha-D-galactosamine:polypeptide N-acetylgalactosaminyltransferase 4 (GalNAc-T4) |
| 3.131 | 0.0037244 | 239597_at | AA993566 | PAN3 | PAN3 polyA specific ribonuclease subunit homolog (S. cerevisiae) |
| 3.096 | 0.0007604 | 202971_s_at | NM_006482 | DYRK2 | dual-specificity tyrosine-(Y)-phosphorylation regulated kinase 2 |
| 3.003 | 0.0043306 | 219132_at | NM_021255 | PELI2 | pellino homolog 2 (Drosophila) |
| 2.809 | 0.0023251 | 212239_at | AI680192 | PIK3R1 | phosphoinositide-3-kinase, regulatory subunit 1 (p85 alpha) |
| 2.615 | 0.0045788 | 229553_at | AA736452 | PGM2L1 | phosphoglucomutase 2-like 1 |
| 2.541 | 0.0038363 | 202739_s_at | NM_000293 | PHKB | phosphorylase kinase, beta |
| 2.484 | 0.0024928 | 242490_at | AA564255 | LOC644010 | Hypothetical protein LOC644009 |
| 2.442 | 0.0044632 | 208022_s_at | NM_003671 | CDC14B | CDC14 cell division cycle 14 homolog B (S. cerevisiae)//CDC14 cell division cycle 14 homolog B (S. cerevisiae) |
| 2.335 | 0.0042281 | 1553974_at | BC030758 | LOC128977 | hypothetical protein LOC128977 |
| 2.329 | 0.0007545 | 227620_at | AV721564 | SLC44A1 | solute carrier family 44, member 1 |
| 2.327 | 0.0048819 | 228051_at | AI979261 | LOC202451 | hypothetical protein LOC202451 |
| 2.258 | 0.0013447 | 223201_s_at | AW205122 | TMEM164 /// | transmembrane protein 164 /// similar to hypothetical protein FLJ22679 |
| 2.229 | 0.0013851 | 217104_at | AL109714 | LOC400410 | similar to cervical cancer suppressor-1 |
| 2.227 | 0.0020227 | 228594_at | H94910 | FLJ30596 | hypothetical protein FLJ30596 |
| 2.215 | 0.0019437 | 226671_at | AI150000 | LAMP2 | lysosomal-associated membrane protein 2 |
| 2.205 | 0.0047641 | 209296_at | AF136972 | PPM1B | protein phosphatase 1B (formerly 2C), magnesium-dependent, beta isoform |
| 2.177 | 0.0038001 | 238032_at | T68858 | DHRS3 | Dehydrogenase/reductase (SDR family) member 3 |
| 2.112 | 0.0006824 | 226532_at | AL563613 | LZIC | Leucine zipper and CTNNBIP1 domain containing |
| 2.003 | 0.0035691 | 204190_at | NM_005800 | USPL1 | ubiquitin specific peptidase like 1 |
| 1.913 | 0.0035714 | 201057_s_at | NM_004487 | GOLGB1 | golgi autoantigen, golgin subfamily b, macrogolgin (with transmembrane signal), 1 |
| 1.895 | 0.000601 | 239660_at | BF110518 | C20orf74 | chromosome 20 open reading frame 74 |
| 1.881 | 0.0048096 | 239091_at | AA497043 | CCDC52 | Coiled-coil domain containing 52 |
| 1.818 | 0.0026373 | 217597_x_at | AI344141 | RAB40B | RAB40B, member RAS oncogene family |
| 1.702 | 0.0047187 | 209864_at | AB045118 | FRAT2 | frequently rearranged in advanced T-cell lymphomas 2 |

| res/sens | pvalue | Probe set | Reprentative | symbol | name |
|---|---|---|---|---|---|
| 61.557 | 0.0002089 | 212077 at | AL583520 | CALD1 | caldesmon 1 |
| 38.446 | 0.0015777 | 226001 at | AK002174 | KLHL5 | kelch-like 5 (Drosophila) |
| 36.446 | 9.20E-06 | 212859 x at | BF217861 | MT1E | metallothionein 1E (functional) |
| 29.815 | 0.0001728 | 223374 s at | AF154848 | B3GALNT1 | beta-1, 3-N-acetvlgalactosaminyltransferase 1 (globoside blood group) |
| 23.316 | 0.0036975 | 210764 s at | AF003114 | CYR61 | cysteine-rich, angiogenic inducer, 61 |
| 17.802 | 0.0001326 | 208581 x at | NM 005952 | MT1X | metallothionein 1X |
| 15.799 | 0.0005803 | 213201 s at | AJ011712 | TNNT1 | troponin T type 1 (skeletal, slow) |
| 15.487 | 6.40E-05 | 211456 x at | AF333388 | LOC645745 | metallothionein 1H-like protein /// hypothetical protein LOC650610 |
| 15.399 | 7.65E-05 | 206461 x at | NM 005951 | MT1H | metallothionein 1H |
| 15.113 | 1.34E-05 | 217165 x at | M10943 | MT1F | metallothionein 1F (functional) |
| 14.986 | 3.12E-05 | 212185 x at | NM 005953 | MT2A | metallothionein 2A |
| 13.072 | 0.0002844 | 216336 x at | AL031602 | MT1M | metallothionein 1M |
| 12.172 | 0.0036978 | 206247 at | NM 005931 | MICB | MCH class I polypeptide-related sequence B |
| 10.746 | 0.0016578 | 213428 s at | AA292373 | COL6A1 | collagen, type VI, alpha 1 |
| 9.713 | 3.00E-07 | 201058 s at | NM 006097 | MYL9 | myosin, light polypeptide 9, regulatory |
| 9.113 | 0.0016865 | 204745 x at | NM 005950 | MT1G | metallothionein 1G |
| 8.947 | 0.0042275 | 210139 s at | L03203 | PMP22 | peripheral myelin protein 22 |
| 8.768 | 0.0022793 | 218546 at | NM 024709 | C1orf115 | chromosome 1 open reading frame 115 |

| | | | | | |
|---|---|---|---|---|---|
| 7.932 | 0.0022187 | 204099 at | NM 003078 | SMARCD3 | SWI/SNF related, matrix associated, actin dependent regulator of chromatin, subfamily d, member 3 |
| 7.917 | 0.0030738 | 208792 s at | M25915 | CLU | clusterin |
| 7.246 | 0.0005024 | 204967 at | NM 001649 | SHROOM2 | shroom family member 2 |
| 6.513 | 0.0009856 | 210448 s at | U49396 | P2RX5 | purinergic receptor P2X, ligand-gated ion channel, 5 |
| 6.494 | 0.004649 | 218802 at | NM 017918 | CCDC109B | coiled-coil domain containing 109B |
| 5.971 | 0.0029005 | 230467 at | BE552414 | TMEM52 | transmembrane protein 52 |
| 5.229 | 0.0004507 | 211814 s at | AF112857 | CCNE2 | cyclin E2 |
| 5.030 | 0.0011383 | 203085 s at | BC000125 | TGFB1 | transforming growth factor, beta 1 (Camurati-Engelmann disease) |
| 4.657 | 0.0029224 | 227697 at | AI244908 | SOCS3 | suppressor of cytokine signaling 3 |
| 4.620 | 0.0006381 | 1552531 a | NM 145007 | NALP11 | NACHT, leucine rich repeat and PYD containing 11 |
| 4.466 | 0.0046798 | 202756 s at | NM 002081 | GPC1 | glypican 1 |
| 4.328 | 0.0006321 | 239853 at | AI279514 | KLC3 | kinesin light chain 3 |
| 4.303 | 0.0012305 | 220588 at | NM 017843 | BCAS4 | breast carcinoma amplified sequence 4 |
| 4.086 | 0.0023224 | 235588 at | AA740849 | ESCO2 | establishment of cohesion 1 homolog 2 (S. cerevisiae) |
| 4.080 | 0.0004973 | 227816 at | BF591483 | NTN1 | Netrin 1 |
| 4.068 | 0.0001861 | 223234 at | AF080398 | MAD2L2 | MAD2 mitotic arrest deficient-like 2 (yeast) |

| | | | | | |
|---|---|---|---|---|---|
| 3.941 | 0.0039405 | 219882 at | NM 024686 | TTLL7 | tubulin tyrosine ligase-like family, member 7 |
| 3.935 | 0.0012019 | 223842 s at | AB007830 | SCARA3 | scavenger receptor class A, member 3 |
| 3.896 | 0.0027327 | 209305 s at | AF078077 | GADD45B | growth arrest and DNA-damage-inducible, beta |
| 3.894 | 0.0008743 | 215259 s at | AC005525 | IGSF4C | immunoglobulin superfamily, member 4C |
| 3.764 | 0.0017922 | 225970 at | AA029818 | DDHD1 | DDHD domain containing 1 |
| 3.574 | 0.0032678 | 205548 s at | NM 006806 | BTG3 | BTG family, member 3 |
| 3.480 | 0.00256 | 234307 s at | AK026406 | KIF26A | kinesin family member 26A |
| 3.476 | 0.0024062 | 220673 s at | NM 020958 | KIAA1622 | KIAA1622 |
| 3.450 | 0.0020887 | 204187 at | NM 006877 | GMPR | guanosine monophosphate reductase /// guanosine monophosphate reductase |
| 3.378 | 0.0010381 | 1553202 at | NM 152709 | STOX1 | storkhead box 1 |
| 3.324 | 0.0019953 | 205414 s at | NM 014859 | KIAA0672 | KIAA0672 gene product |
| 3.295 | 0.001471 | 220651 s at | NM 018518 | MCM10 | MCM10 minichromosome maintenance deficient 10 (S. cerevisiae) |
| 3.102 | 0.0029669 | 225971 at | AI741411 | DDHD1 | DDHD domain containing 1 |
| 3.052 | 0.0006241 | 203865 s at | NM 015833 | ADARB1 | adenosine deaminase, RNA-specific, B1 (RED1 homolog rat) |
| 2.930 | 0.0046297 | 226017 at | AI708432 | CMTM7 | CKLF-like MARVEL transmembrane domain containing 7 |
| 2.823 | 0.0004903 | 205935 at | NM 001451 | FOXF1 | forkhead box F1 |

| | | | | |
|---|---|---|---|---|
| 2.803 | 0.0020059 | 222424 s at | BC000805 | NUCKS1 | nuclear casein kinase and cyclin-dependent kinase substrate 1 |
| 2.680 | 0.00051 | 220141 at | NM 024806 | C11orf63 | chromosome 11 open reading frame 63 |
| 2.622 | 0.0025739 | 215728 s at | AL031848 | ACOT7 | acyl-CoA thoiesterase 7 |
| 2.524 | 0.0011576 | 1557684 at | BM968434 | ZNF286 | zinc finger protein 286 |
| 2.492 | 0.0005103 | 209462 at | U48437 | APLP1 | amyloid beta (A4) precurosr-like protein 1 |
| 2.450 | 0.0026111 | 201599 at | NM 000274 | OAT | ornithine aminotransferase (gyrate atrophy) |
| 2.421 | 0.0023787 | 209996 x at | AA931266 | PCM1 | pericentriolar material 1 |
| 2.380 | 0.0042549 | 230640 at | AW027431 | PRPF40B | PRP40 pre-mRNA processing factor 40 homolog B (S. cerevisiae) |
| 2.329 | 0.0035589 | 209401 s at | AI817690 | SLC12A4 | solute carrier family 12 (potassium/chloride transporters), member 4 |
| 2.293 | 0.0014059 | 238974 at | N47077 | FLJ38973 | hypothetical protein FLJ38973 |
| 2.290 | 0.0013675 | 205008 s at | NM 006383 | CIB2 | calcium and integrin binding family member 2 |
| 2.231 | 0.0001961 | 216331 at | AK022548 | ITGA7 | integrin, alpha 7 |
| 2.218 | 0.0036012 | 201457 x at | AF081496 | BUB3 | BUB3 budding uninhibited by benzimidazoles 3 homolog (yeast) |
| 2.199 | 0.0037235 | 222946 s at | BC000209 | C1orf135 | chromosome 1 open reading frame 135 |
| 2.147 | 0.002677 | 217879 at | AL566824 | CDC27 | cell division cycle 27 |

| | | | | | |
|---|---|---|---|---|---|
| 2.104 | 0.0010709 | 211121 s at | AF180527 | DOK1 | docking protein 1, 62kDa (downstream of tyrosine kinase 1) |
| 2.078 | 0.0021952 | 204119 s at | Y90339 | ADK | adenosine kinase |
| 2.065 | 0.0001373 | 228327 x at | AL359938 | MEIS3 | Meis1, myeloid ecotropic viral integration site 1 homolog 3 (mouse) |
| 2.008 | 0.0004266 | 219692 at | NM 024507 | KREMEN2 | kringle containing transmembrane protein 2 |
| 2.003 | 0.0002426 | 220941 s at | NM017447 | C21orf91 | chromosome 21 open reading frame 91 |
| 2.000 | 0.0043122 | 205918 at | NM 005070 | SLC4A3 | solute carrier family 4, anion exchanger, member 3 |
| 1.988 | 0.0007806 | 227810 at | AW119060 | ZNF558 | zinc finger protein 558 |
| 1.963 | 0.0028687 | 233850 s at | AL035460 | RP5-860F19 | KIAA1442 protein |
| 1.919 | 0.0036444 | 222037 at | AI859865 | MCM4 | MCM4 minichromosome maintenance deficient 4 (S. cerevisiae) |
| 1.888 | 0.0042031 | 1552264 at | NM 138957 | MAPK1 | mitogen-activated protein kinase 1 |

Fig. 15E

Figure 16. Results of analyses performed in at least 100 interphase nuclei of each colorectal cell line hybridized with the IGF1R/CEP15 probe set. Ploidy was estimated on at least 20 metaphase spreads.

| Cell Line | CytoCore Login | FISH assay | Ploidy | IGF1R | | % of cells with IGF1R copies | | | | IGF1R / CEP15 | CEP15 | | IGF1R/Ploidy | S/I/R to PQIP | PQIP (IC50) |
|---|---|---|---|---|---|---|---|---|---|---|---|---|---|---|---|
| | | | | Mean | SD | ≤2 | 3 | ≥4 | ≥15 | | Mean | SD | | | |
| CaCo2 | 08CY203 | 08265.2 | near 4n | 4.60 | 1.42 | 0.00% | 10.00% | 90.00% | 0.00% | 0.68 | 6.77 | 2.23 | Gain - Low | S | 1.5 uM |
| CoLo201 | 07CY270 | 07330.1 | near 3n | 2.97 | 0.22 | 3.92% | 95.10% | 0.98% | 0.00% | 1.00 | 2.97 | 0.17 | Balanced | I | 3 uM |
| CoLo205 | 07CY269 | 08003.1 | near 3n | 4.20 | 1.36 | 0.00% | 2.80% | 97.20% | 0.93% | 1.11 | 3.79 | 0.41 | Gain - High | S | 0.6 uM |
| CoLo205 | 08CY168 | 08246.2 | near 3n | 4.17 | 1.25 | 0.00% | 1.00% | 99.00% | 1.00% | 1.06 | 3.93 | 0.71 | | | |
| HCT15 | 08CY213 | 08269.6 | 2n | 2.16 | 0.55 | 86.00% | 9.00% | 5.00% | 0.00% | 1.06 | 2.04 | 0.42 | Balanced | R | >5 uM |
| HCT116 | 07CY271 | 07330.3 | near 2n | 2.01 | 0.10 | 99.01% | 0.99% | 0.00% | 0.00% | 1.00 | 2.00 | 0.00 | Balanced | R | >5 uM |
| HCT8 | 07CY272 | 07330.4 | near 2n | 2.06 | 0.39 | 95.24% | 1.90% | 2.86% | 0.00% | 1.02 | 2.02 | 0.34 | Balanced | R | 5 uM |
| HT29 | 07CY274 | 07330.6 | near 2n/near 3n | 3.79 | 0.65 | 0.93% | 25.23% | 73.83% | 0.00% | 1.03 | 3.67 | 0.70 | Gain - Low | S | 0.3 uM |
| LoVo | 08CY170 | 08246.5 | near 2n | 3.24 | 1.02 | 2.00% | 89.00% | 9.00% | 0.00% | 3.03 | 1.07 | 0.33 | Gain - High | R | > 5 uM |
| LS123 | 08CY204 | 08261.3 | hyper2n/hypo3n | 3.67 | 1.65 | 4.00% | 65.00% | 31.00% | 0.00% | 0.62 | 5.93 | 2.38 | Gain - Low | R | > 5 uM |
| LS174T | 08CY167 | 08246.1 | near 2n | 1.97 | 0.41 | 98.00% | 1.00% | 1.00% | 0.00% | 1.03 | 1.91 | 0.38 | Balanced | R | > 5 uM |
| LS174T | 07CY277 | 07336.2 | near 2n | 2.12 | 0.40 | 87.04% | 12.04% | 0.93% | 0.00% | 1.01 | 2.10 | 0.43 | | | |
| LS180 | 08CY228 | 08277.1 | 2n | 2.25 | 0.59 | 82.00% | 12.00% | 6.00% | 0.00% | 0.88 | 2.57 | 0.76 | Balanced | R | > 5 uM |
| LS513 | 07CY278 | 07336.3 | near 2n | 2.81 | 0.52 | 23.36% | 72.90% | 3.74% | 0.00% | 1.43 | 1.96 | 0.19 | Gain - Low | S | 0.3 uM |
| NCI-H508 | 08CY235 | 08277.6 | hyper 4n | 4.48 | 1.33 | 0.00% | 3.00% | 97.00% | 0.00% | 1.16 | 3.87 | 0.94 | Balanced | R | > 5 uM |
| RKO | 07CY273 | 07330.5 | near 2n | 2.14 | 0.58 | 88.07% | 5.50% | 6.42% | 0.00% | 1.00 | 2.14 | 0.60 | Balanced | R | > 5 uM |
| SK-CO-1 | 08CY230 | 08277.3 | near 3n | 4.49 | 2.98 | 0.0% | 7.0% | 93.0% | 1.0% | 1.62 | 2.78 | 0.60 | Gain - High | I | 3 uM |
| SW1116 | 08CY231 | 08277.4 | hyper2n/hypo3n | 3.36 | 1.06 | 4.00% | 73.00% | 23.00% | 0.00% | 1.10 | 3.06 | 1.82 | Balanced | R | > 5 uM |
| SW1417 | 08CY169 | 08246.4 | near 3n | 3.22 | 1.23 | 5.00% | 87.00% | 8.00% | 0.00% | 1.41 | 2.28 | 0.77 | Balanced | R | > 5 uM |
| SW1463 | 08CY229 | 08277.2 | near 3n | 2.17 | 0.62 | 81.00% | 14.00% | 5.00% | 0.00% | 1.08 | 2.01 | 0.58 | Loss | R | > 5 uM |
| SW403 | 08CY232 | 08277.5 | near 3n | 2.95 | 0.58 | 13.00% | 76.00% | 11.00% | 0.00% | 1.54 | 1.92 | 0.34 | Balanced | R | > 5 uM |
| SW48 | 08CY205 | 08261.4 | 2n | 2.12 | 0.41 | 62.00% | 16.00% | 17.00% | 0.00% | 0.70 | 3.04 | 0.65 | Balanced | R | > 5 uM |
| SW480 | 07CY276 | 07336.1 | near 3n | 2.87 | 1.12 | 40.95% | 48.57% | 10.48% | 0.00% | 0.59 | 4.84 | 1.16 | Balanced | R | 5 uM |
| SW620 | 08CY212 | 08269.5 | hyper 2n | 2.41 | 0.95 | 78.00% | 10.00% | 12.00% | 0.00% | 0.92 | 2.63 | 1.05 | Balanced | I | 4 uM |
| SW837 | 08CY171 | 08246.3 | hypo 2n | 2.15 | 0.58 | 89.00% | 4.00% | 7.00% | 0.00% | 1.03 | 2.08 | 0.54 | Balanced | R | > 5 uM |

CUCRC001

CUCRC006

BIOLOGICAL MARKERS PREDICTIVE OF ANTI-CANCER RESPONSE TO INSULIN-LIKE GROWTH FACTOR-1 RECEPTOR KINASE INHIBITORS

CROSS-REFERENCE TO RELATED APPLICATIONS

This application claims the benefit of U.S. Provisional Application No. 61/196,885, filed on Oct. 20, 2008 and U.S. Provisional Application No. 61/251,112 filed on Oct. 13, 2009.

BACKGROUND OF THE INVENTION

Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body. The present invention is directed to methods for diagnosing and treating cancer patients. In particular, the present invention is directed to methods for determining which patients will most benefit from treatment with an insulin-like growth factor-1 receptor (IGF-1R) kinase inhibitor.

IGF-1R belongs to the insulin receptor family that includes the Insulin Receptor (IR), IGF-1R (homodimer), IGF-1R/IR (hybrid receptor), and IGF-2R (mannose 6-phosphate receptor). IGF-1R/IR hybrids act as homodimers, preferentially binding and signaling with IGFs. IR exists in two isoforms: IR-B (traditional insulin receptor) and IR-A (a fetal form which is re-expressed in selected tumors and preferentially binds IGF-II). IGF-2R is a non-signaling receptor that acts as a "sink" for IGF-II (Pollak M. N., et al. Nat Rev Cancer 2004 4:505-18). Six well-characterized insulin-like growth factor binding proteins (IGFBP-1 through -6) associate with IGF ligands to stabilize the IGFs and modulate their ability to bind the IGF-IR.

IGF-1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation, phosphorylation of cellular substrates, including IRS1 and Shc, leading to activation of the PI3K/Akt and mitogen-activated protein kinase (MAPK) pathways (Adams T. E., et al. Cell Mol Life Sci 2000 57:1050-93; Pollak M. N., et al. Nat Rev Cancer 2004 4:505-18; Baserga R., Exp Cell Res 1999 253:1-6). The ligand-activated IGF-1R induces mitogenic activity in normal cells and plays an important role in abnormal growth. A major physiological role of the IGF-1 system is the promotion of normal growth and regeneration. Overexpressed IGF-1R (type 1 insulin-like growth factor receptor) can initiate mitogenesis and promote ligand-dependent neoplastic transformation. Furthermore, IGF-1R plays an important role in the establishment and maintenance of the malignant phenotype. Unlike the epidermal growth factor (EGF) receptor, no mutant oncogenic forms of the IGF-1R have been identified. However, several oncogenes have been demonstrated to affect IGF-1 and IGF-1R expression. A correlation between a reduction of IGF-1R expression and resistance to transformation has been seen. Exposure of cells to mRNA antisense to IGF-1R RNA prevents soft agar growth of several human tumor cell lines. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

The IGF-1 pathway has an important role in human tumor development. IGF-1R overexpression is frequently found in various tumors (breast, colon, lung, sarcoma) and is often associated with an aggressive phenotype. High circulating IGF1 concentrations are strongly correlated with prostate, lung and breast cancer risk. Furthermore, IGF-1R is required for establishment and maintenance of the transformed phenotype in vitro and in vivo (Baserga R. *Exp. Cell. Res.,* 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models. The IGF-1R signaling pathway also appears to be a robust target in colorectal cancer (CRC), based upon data demonstrating overexpression of the receptor and ligands in CRC, association with a more malignant phenotype, chemotherapy resistance, and correlation with a poor prognosis (Saltz, L. B., et al. J Clin Oncol 2007; 25(30): 4793-4799; Tripkovic I., et al. Med Res. 2007 July; 38(5):519-25. Epub 2007 Apr. 26; Miyamoto S., et al. Clin Cancer Res. 2005 May 1; 11(9):3494-502; Nakamura M., et al. Clin Cancer Res. 2004 Dec. 15; 10(24):8434-41; Grothey A, et al. J Cancer Res Clin Oncol. 1999; 125(3-4): 166-73).

It has been recognized that inhibitors of protein-tyrosine kinases are useful as selective inhibitors of the growth of mammalian cancer cells. For example, Gleevec™ (also known as imatinib mesylate), a 2-phenylpyrimidine tyrosine kinase inhibitor that inhibits the kinase activity of the BCR-ABL fusion gene product, has been approved by the U.S. Food and Drug Administration for the treatment of CML. The 4-anilinoquinazoline compound Tarceva™ (erlotinib HCl) has also been approved by the FDA, and selectively inhibits EGF receptor kinase with high potency. The development for use as anti-tumor agents of compounds that directly inhibit the kinase activity of IGF-1R, as well as antibodies that reduce IGF-1R kinase activity by blocking IGF-1R activation or antisense oligonucleotides that block IGF-1R expression, are areas of intense research effort (e.g. see Larsson, O. et al (2005) Brit. J. Cancer 92:2097-2101; Ibrahim, Y. H. and Yee, D. (2005) Clin. Cancer Res. 11:944s-950s; Mitsiades, C. S. et al. (2004) Cancer Cell 5:221-230; Camirand, A. et al. (2005) Breast Cancer Research 7:R570-R579 (DOI 10.1186/bcr1028); Camirand, A. and Pollak, M. (2004) Brit. J. Cancer 90:1825-1829; Garcia-Echeverria, C. et al. (2004) Cancer Cell 5:231-239; Sachdev D, and Yee D., Mol Cancer Ther. 2007 January; 6(1):1-12; Hofmann F., and Garcia-Echeverria C., Drug Discov Today 2005 10:1041-7). Agents inhibiting the IGF-1R pathway have demonstrated anti-tumor efficacy in multiple human cancer models both in vitro and in vivo, particularly in pediatric models of Ewing's sarcoma and rhabdomyosarcoma (Manara M C, et al. Int J Oncol 2005 27:1605-16). Despite early hints of efficacy in patients with sarcoma, results to date of IGF-1R inhibitors in early clinical trials have not been impressive, indicating that patient selection strategies and rational combinations may be needed to move forward with this approach (Tolcher A. W., et al. Journal of Clinical Oncology, 2007 ASCO Annual Meeting Proceedings Part I. Vol 25, No. 18S (June 20 Supplement), 2007: 3002). Data acquired this far, has not indicated that activation, overexpression, or amplification of members of the IGF-1R pathway will predict responsiveness.

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well. Additionally, for any given cancer type one frequently cannot predict which patient is likely to respond to a particular treatment, even with newer gene-targeted therapies, such as protein-tyrosine kinase inhibitors, thus necessitating considerable trial and error, often at considerable risk and discomfort to the patient, in order to find the most effective therapy.

Thus, there is a need for more efficacious treatment for neoplasia and other proliferative disorders, and for more effective means for determining which tumors will respond to which treatment. Strategies for enhancing the therapeutic efficacy of existing drugs have involved changes in the schedule for their administration, and also their use in combination with other anticancer or biochemical modulating agents. Combination therapy is well known as a method that can result in greater efficacy and diminished side effects relative to the use of the therapeutically relevant dose of each agent alone. In some cases, the efficacy of the drug combination is additive (the efficacy of the combination is approximately equal to the sum of the effects of each drug alone), but in other cases the effect is synergistic (the efficacy of the combination is greater than the sum of the effects of each drug given alone). Target-specific therapeutic approaches are generally associated with reduced toxicity compared with conventional cytotoxic agents, and therefore lend themselves to use in combination regimens.

Several groups have investigated potential biomarkers to predict a patient's response to protein-tyrosine kinase inhibitors (see for example, PCT publications: WO 2004/063709, WO 2005/017493, WO 2004/111273, and WO 2004/071572; and US published patent applications: US 2005/0019785, US 2007/0065858, and US 2004/0132097). However, no diagnostic or prognostic tests have yet emerged that can effectively guide practicing physicians in the treatment of their patients with such inhibitors, or can indicate to the physician which tumors will respond most favorable to a combination of such an inhibitor with a standard chemotherapy agent.

Thus, there remains a critical need for improved methods for determining the best mode of treatment for any given cancer patient. The present invention provides methods for determining which tumors will respond most effectively to treatment with IGF-1R kinase inhibitors based on whether the tumor cells express novel "sensitivity" or "resistance" biomarkers, and for the incorporation of such determinations into more effective treatment regimens for cancer patients, whether such inhibitors are used as single agents or combined with other anti-cancer agents.

SUMMARY OF THE INVENTION

The present invention provides diagnostic methods for predicting the effectiveness of treatment of a cancer patient with an IGF-1R kinase inhibitor. These methods are based on the surprising discovery that the sensitivity of tumor cell growth to inhibition by IGF-1R kinase inhibitors is predicted by whether such tumor cells express certain "sensitivity" or "resistance" biomarkers, or genomic classifiers.

Improved methods for treating cancer patients with IGF-1R kinase inhibitors that incorporate the above methodology are also provided. Thus, the present invention further provides a method for treating tumors or tumor metastases in a patient, comprising the steps of diagnosing a patient's likely responsiveness to an IGF-1R kinase inhibitor by assessing whether the tumor cells express high levels of sensitivity and/or resistance biomarkers, or certain genomic classifiers, and administering to said patient a therapeutically effective amount of an IGF-1R kinase inhibitor (e.g. OSI-906) where sensitivity to the inhibitor is predicted.

BRIEF DESCRIPTION OF THE FIGURES

FIG. 1: Characteristics of CRC tumor cell lines

FIG. 4: RT-PCR determination of the expression of caldesmon (A), metallothionein 1E (B), and ALDH1A1 (C) as function of sensitivity to PQIP.

FIG. 6: Effect of PQIP on IGF-1R and downstream intracellular pathways in HT29 and HCT116 CRC tumor cells by immunoblotting analysis.

FIG. 9: Phosphorylation levels of IGF1R in CRC cell lines following exposure to PQIP alone and in combination with SN38 (A) or oxaliplatin (B).

FIG. 10: (A) Summary of comparison between IGF1R genomic status (IGF-1R/ploidy) and sensitivity to PQIP (S/I/R (sensitive, intermediate, resistant) to PQIP), and (B) Distribution of lines according to IGF1R genomic status and sensitivity to PQIP.

FIG. 11: Cell line ploidy and identification of chromosomes recognizing homology with the IGF1R/CEP15 probe mix.

FIG. 14: Table listing sensitivity markers deduced from array data (the 35 markers more abundant in sensitive tumor cell lines). Column A lists the mean fold difference between the two groups of lines (sensitive and resistant), and they are sorted by this value. Column B lists the p-value for the comparison of these two groups. Markers were only included when this value is less than 0.005. Column C lists the Affymetrix probe set ID, which is the direct link to the sequence used for the measurement (the probe set). Column D lists a Representative Public ID, a nucleotide sequence accession number. Column E lists a Gene Symbol. Column F lists a NCBI-supplied common name for the marker.

FIG. 15: Table listing resistance markers deduced from array data (the 75 markers more abundant in resistant tumor cell lines). Column A lists the mean fold difference between the two groups of lines (sensitive and resistant), and are sorted by this value. Column B lists the p-value for the comparison of these two groups. Markers were only included when this value is less than 0.005. Column C lists the Affymetrix probe set ID, which is the direct link to the sequence used for the measurement (the probe set). Column D lists a Representative Public ID, a nucleotide sequence accession number. Column E lists a Gene Symbol. Column F lists a NCBI-supplied common name for the marker.

FIG. 16: Results of analyses performed in at least 100 interphase nuclei of each colorectal cell line hybridized with the IGF1R/CEP15 probe set. Ploidy was estimated on at least 20 metaphase spreads.

DETAILED DESCRIPTION OF THE INVENTION

Figure 2:
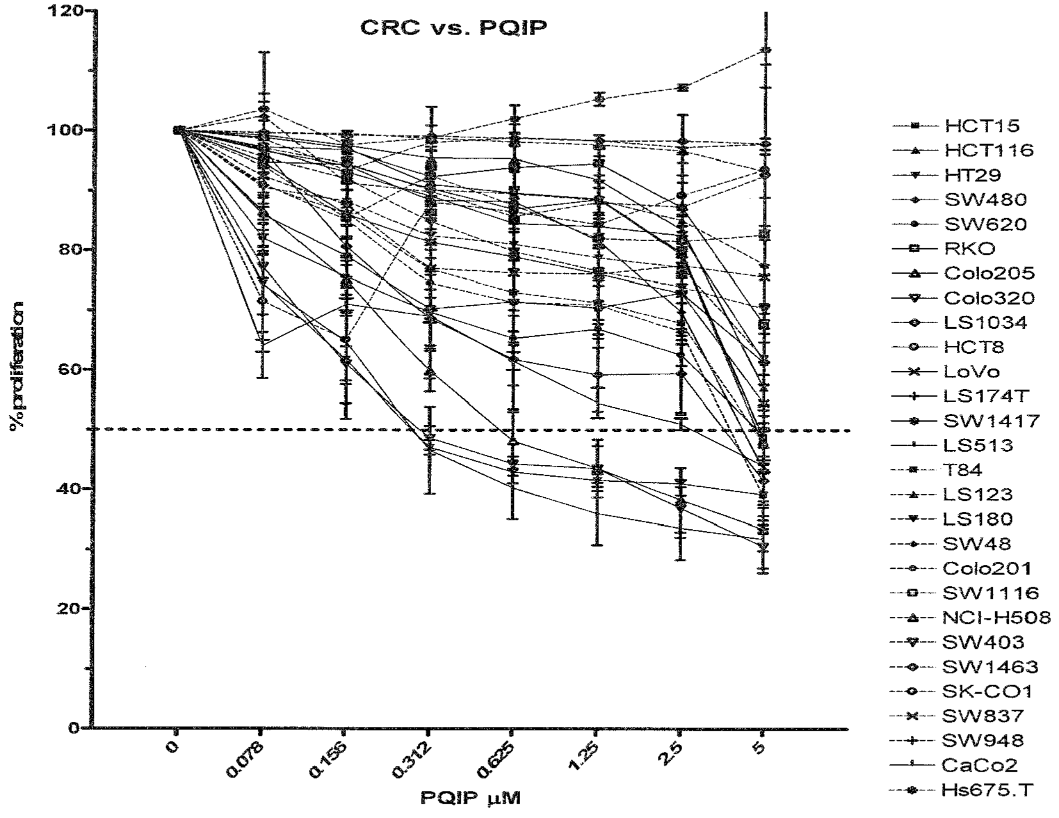
FIG. 2: Proliferation curves of 28 CRC cell lines exposed to varying concentrations of PQIP. Each experiment was performed in triplicate.
Figure 3:
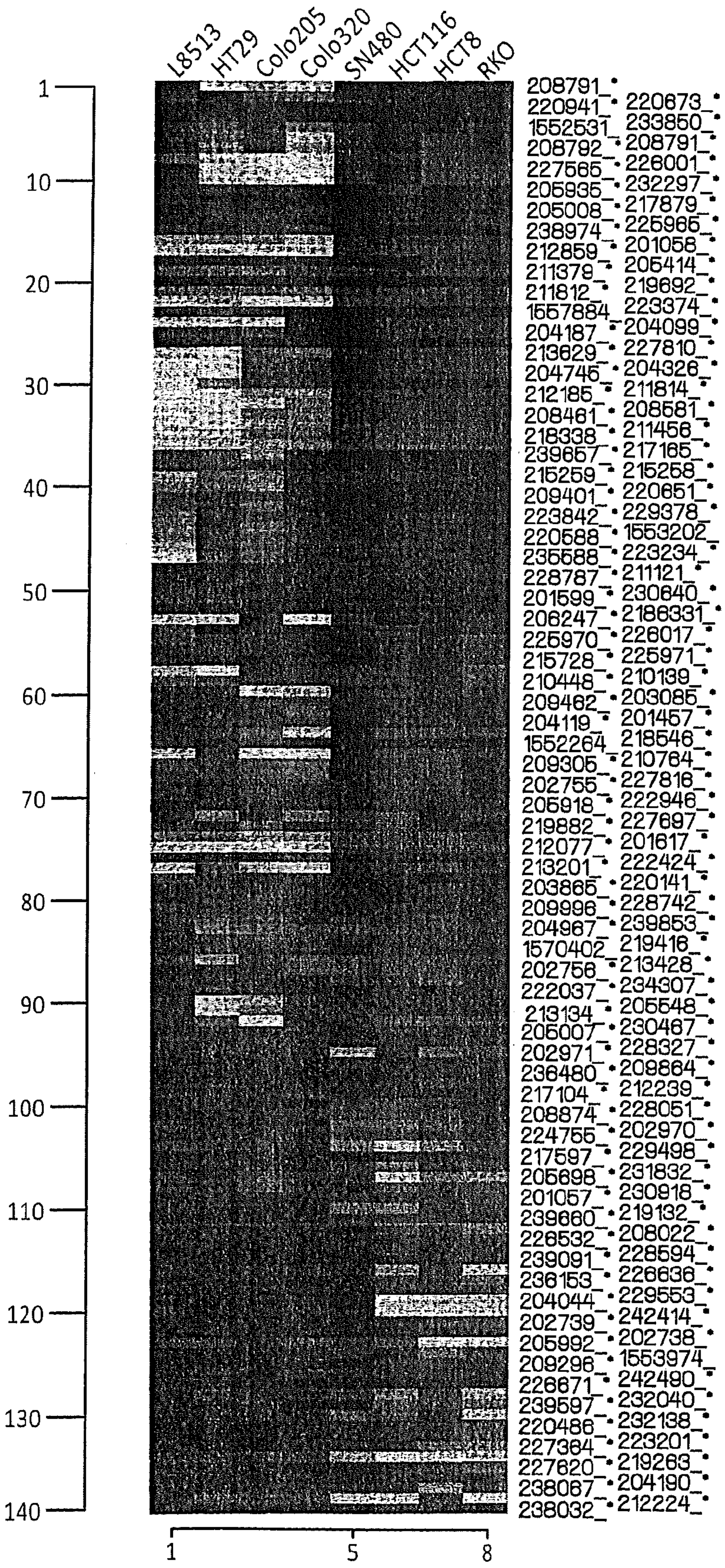
FIG. 3: Differential Expression Between PQIP-S and R CRC Cell Lines: Heat map depicting the relative expression levels of genes differentially expressed between PQIP-sensitive and resistant CRC cell lines. The leftmost four columns are each of the first sensitive (S) cell lines (LS513, HT29, Colo205, Colo320), and the rightmost four columns are each of the first resistant (R) cell lines (SW480, HCT116, HCT8, RKO). Red, relatively high expression; green, relatively low expression. The numbers on the right are Affymetrix probe set numbers used to quantify biomarker levels (see FIGS. 14 and 15 for identification of biomarkers associated with probe sets).
Figure 5A:
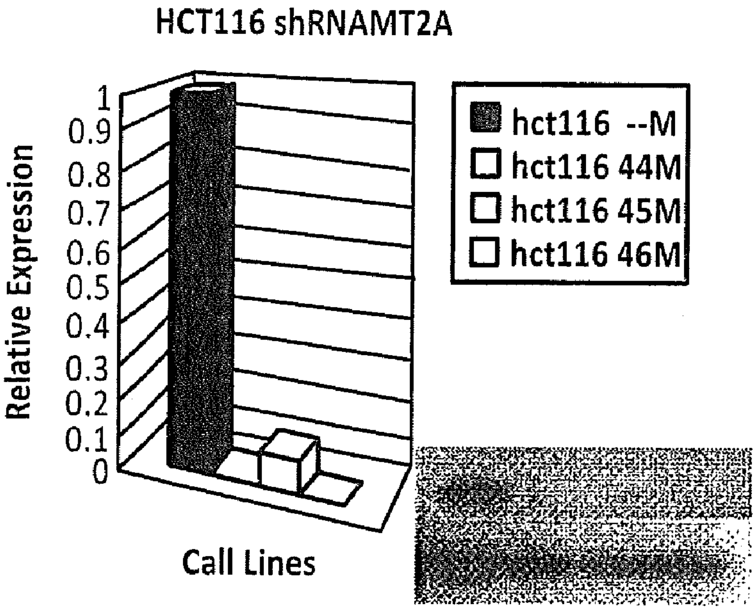
FIG. 5: Gene expression of MT2A following shRNA knockdown in HCT116 and SW480 CRC cell lines (A and B). Proliferation curves following PQIP exposure of HCT116 and SW480 CRC cell lines knocked down in MT2A (C and D).
Figure 5B:
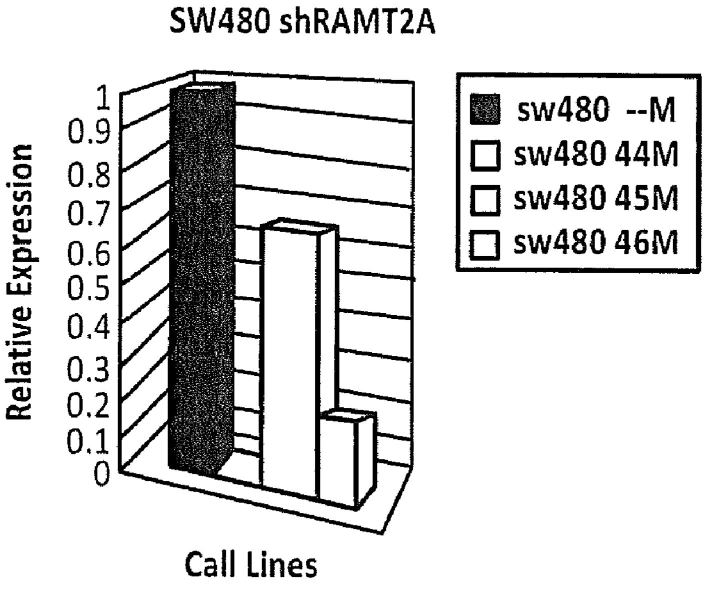
Figure 5C:
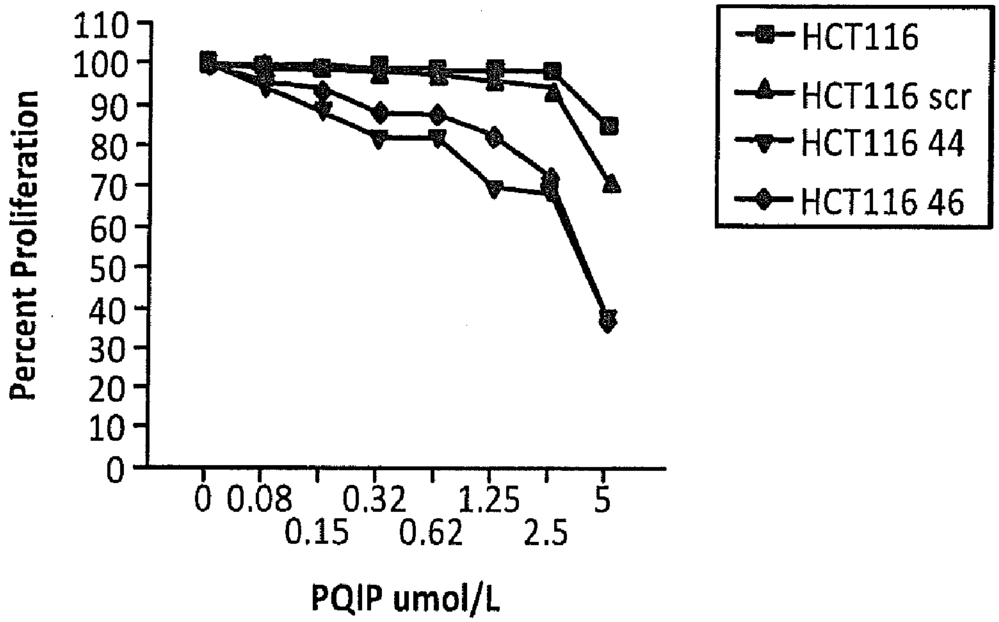
Figure 5D:
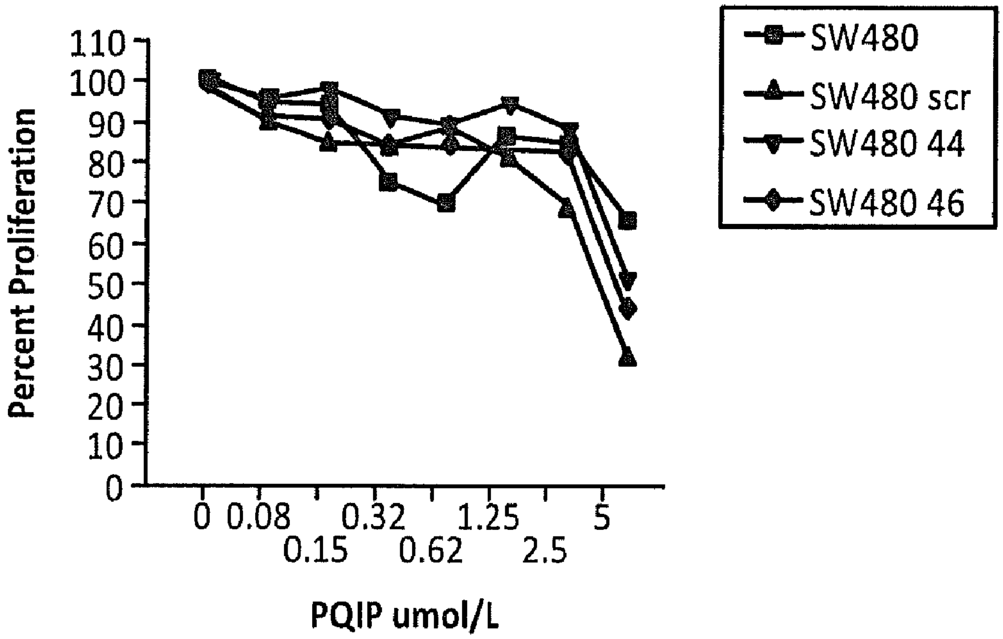
Figure 7B:
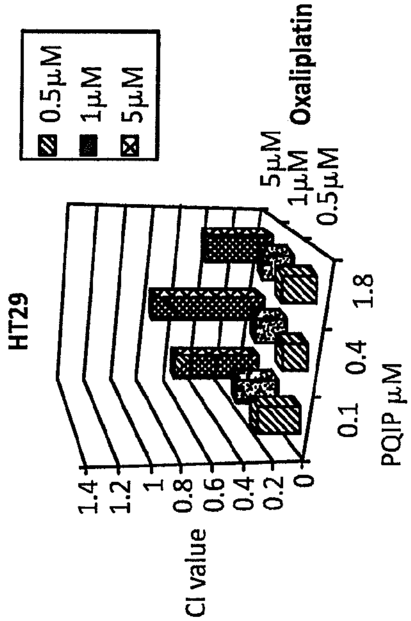
FIG. 7: Combination effects of PQIP and chemotherapy on PQIP sensitive CRC cell lines. (A) HT29 cells, PQIP and SN-38. (B) HT29 cells, PQIP and oxaliplatin. (C) HT29 cells, PQIP and 5-FU. (D) LS513 cells, PQIP and SN-38. (E) LS513 cells, PQIP and oxaliplatin. (F) LS513 cells, PQIP and 5-FU.
Figure 7A:
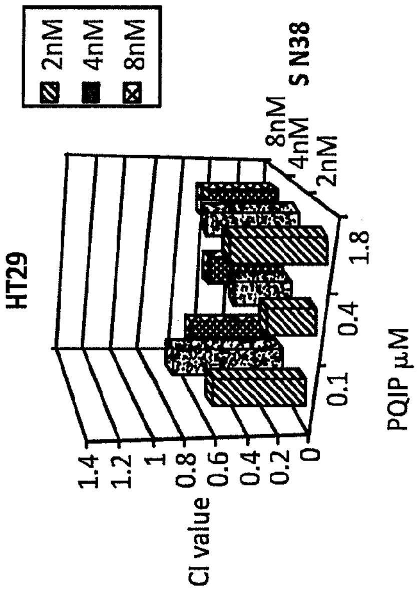
Figure 7C:
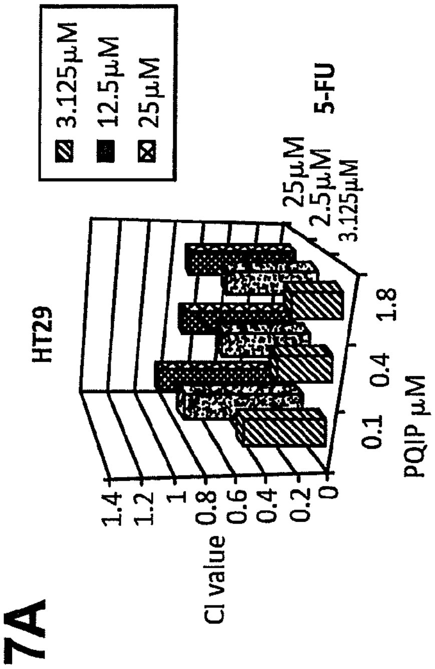
Figure 7D:
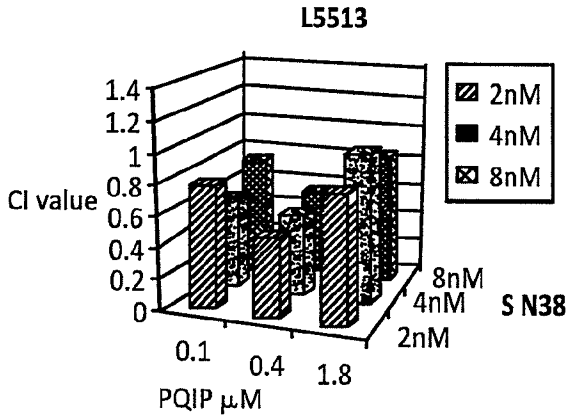
Figure 7E:
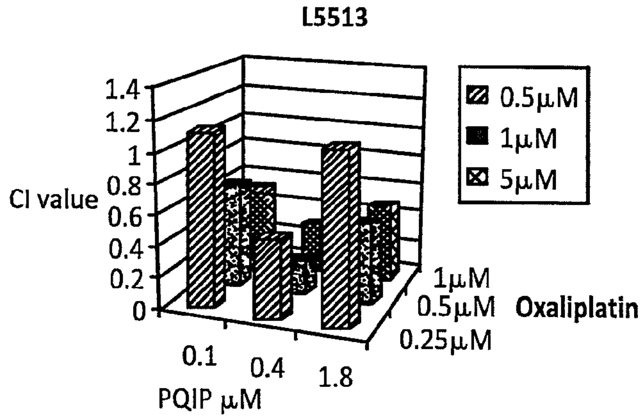
Figure 7F:
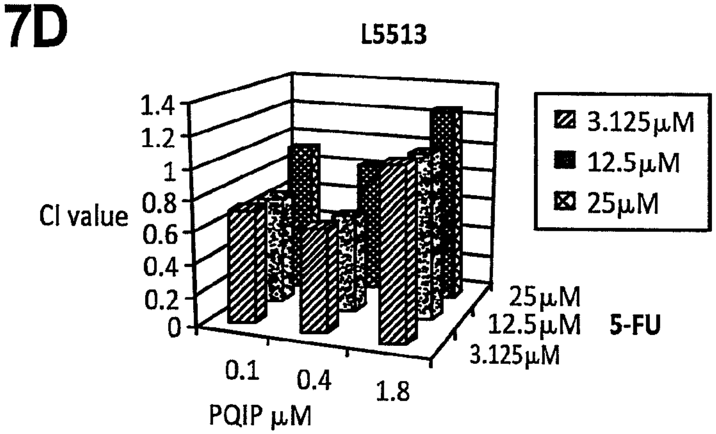
Figure 8A:
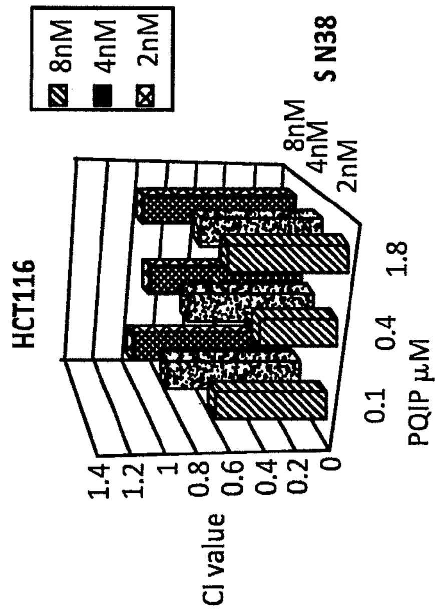
FIG. 8: Combination effects of PQIP and chemotherapy on PQIP resistant CRC cell lines. (A) HCT116 cells, PQIP and SN-38. (B) HCT116 cells, PQIP and oxaliplatin. (C) HCT116 cells, PQIP and 5-FU. (D) RKO cells, PQIP and SN-38. (E) RKO cells, PQIP and oxaliplatin. (F) RKO cells, PQIP and 5-FU.
Figure 8B:
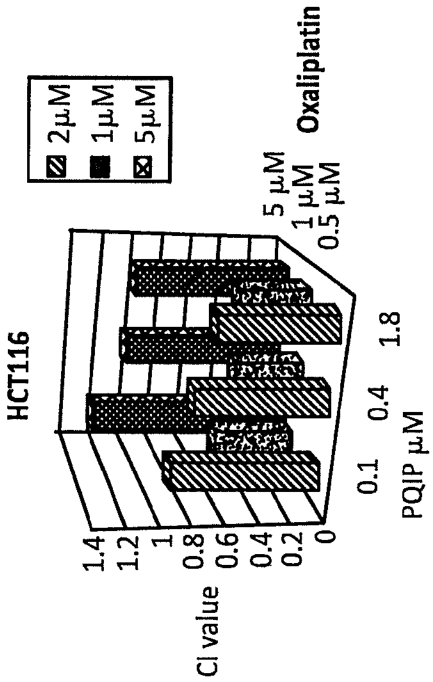
Figure 8C:
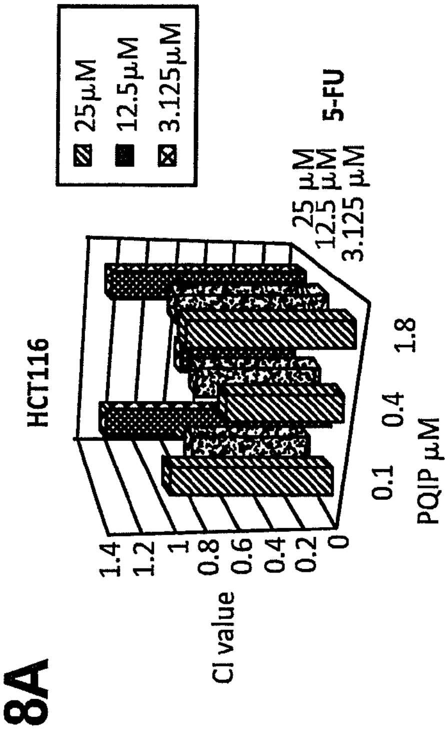
Figure 8E:
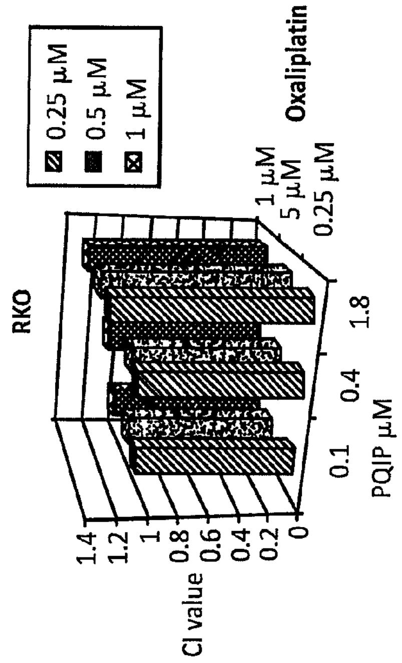
Figure 8D:
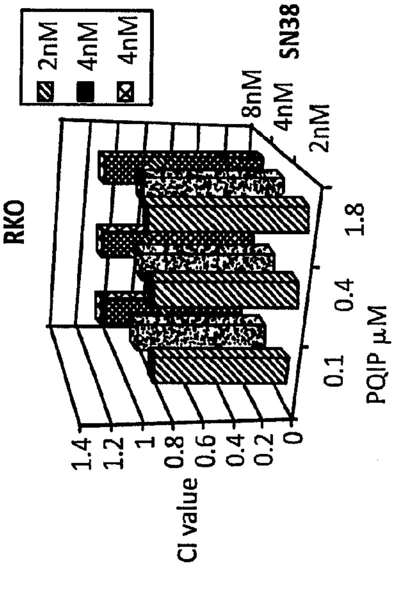
Figure 8F:
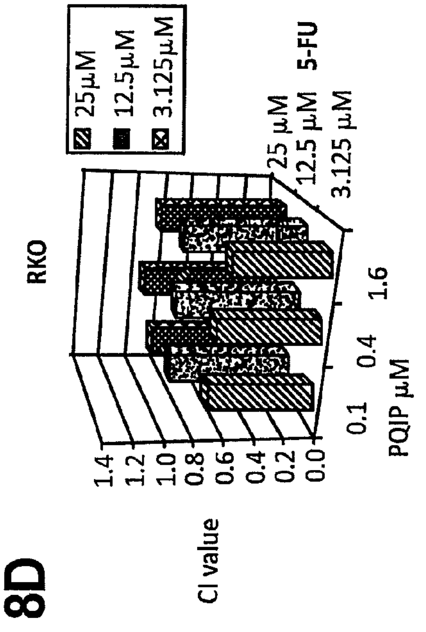

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient with cancer. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The data presented in the Experimental Details section herein below demonstrate that tumor cells, such as CRC (colorectal cancer) cells, show a range of sensitivities to growth inhibition by an IGF-1R kinase inhibitor (e.g. PQIP, OSI-906). It is demonstrated that the degree of sensitivity of tumor cells to an IGF-1R kinase inhibitor can be assessed by determining the level of biomarkers expressed by a tumor cell, that are characteristic for cells that are either relatively sensitive (i.e. "sensitivity" biomarker) or relatively resistant ("resistance" biomarker) to inhibition by an IGF-1R kinase inhibitor. For example, high levels of tumor cell expression of "sensitivity" biomarkers such as Mitogen Activated Protein Kinase Kinase 6 (MAP2K6) and Aldehyde Dehydrogenase 1-A1 (ALDH1A1), correlate with high sensitivity to IGF-1R kinase inhibitors. Conversely, high levels of tumor cell expression of "resistance" biomarkers such as Metallothionein 1E (MT-1E) and Caldesmon (CALD1) correlate with low sensitivity to IGF-1R kinase inhibitors. Additional sensitivity or resistance biomarkers that can be used to predict the level of sensitivity of tumor cells to an IGF-1R kinase inhibitor are listed herein below, and in FIGS. 14 and 15. Thus, these observations can form the basis of valuable new diagnostic methods for predicting the effects of IGF-1R kinase inhibitors on tumor growth, and give oncologists additional tools to assist them in choosing the most appropriate treatment for their patients. The data also indicates that tumor cells which are predicted to be sensitive to an IGF-1R kinase inhibitor by determining sensitivity or resistance biomarker expression are also likely to respond in a synergistic manner to treatment with a combination of an IGF-1R kinase inhibitor and an anti-cancer agent, wherein the anticancer agent is SN38, oxaliplatin, or 5-Fluorouracil. Furthermore, the data suggests that resistance biomarkers may also be useful for predicting which tumors develop resistance to IGF-1R kinase inhibitors.

Sensitivity biomarkers useful in any of the methods of this invention include expression products of the following genes: aldehyde dehydrogenase 1 family, member A1 (ALDH1A1, GeneID: 216); ring finger protein 128 (RNF128, GeneID: 79589); mitogen-activated protein kinase kinase 6 (MAP2K6, GeneID: 5608); quinolinate phosphoribosyltransferase (nicotinate-nucleotide pyrophosphorylase (carboxylating)) (QPRT, GeneID: 23475); interleukin 15 (IL15, GeneID: 3600); phospholipase D1, phosphatidylcholine-specific (PLD1, GeneID: 5337); hypothetical protein LOC157860 (LOC157860, GeneID: 157860); Muscleblind-like 2 (*Drosophila*) (MBNL2, GeneID: 10150); TBC1 domain family, member 8B (with GRAM domain) (TBC1D8B, GeneID: 54885); Galactokinase 2 (GALK2, GeneID: 2585); UDP-N-acetyl-alpha-D-galactosamine: polypeptide N-acetylgalactosaminyltransferase 4 (GalNAc-T4) (GALNT4, GeneID: 8693); PAN3 polyA specific ribonuclease subunit homolog (*S. cerevisiae*) (PAN3, GeneID: 255967); dual-specificity tyrosine-(Y)-phosphorylation regulated kinase 2 (DYRK2, GeneID: 8445); pellino homolog 2 (*Drosophila*) (PELI2, GeneID: 57161); phosphoinositide-3-kinase, regulatory subunit 1 (p85 alpha) (PIK3R1, GeneID: 5295); phosphoglucomutase 2-like 1 (PGM2L1, GeneID: 283209); phosphorylase kinase, beta (PHKB, GeneID: 5257); Hypothetical protein LOC644009 (LOC644010, GeneID: 644010); CDC14 cell division cycle 14 homolog B (*S. cerevisiae*)///CDC14 cell division cycle 14 homolog B (*S. cerevisiae*) (CDC14B, GeneID: 8555); hypothetical protein LOC128977 (C22orf39, GeneID: 128977); solute carrier family 44, member 1 (SLC44A1, GeneID: 23446); hypothetical protein LOC202451 (LOC202451, GeneID: 202451); transmembrane protein 164///similar to hypothetical protein FLJ22679 (TMEM164, GeneID: 84187); similar to cervical cancer suppressor-1 (ST20, GeneID: 400410 (also known as LOC400410)); hypothetical protein FLJ30596 (C5orf33, GeneID: 133686); lysosomal-associated membrane protein 2 (LAMP2, GeneID: 3920); protein phosphatase 1B (formerly 2C), magnesium-dependent, beta isoform (PPM1B, GeneID: 5495); Dehydrogenase/reductase (SDR family) member 3 (DHRS3, GeneID: 9249); Leucine zipper and CTNNBIP1 domain containing (LZIC, GeneID: 84328); ubiquitin specific peptidase like 1 (USPL1, GeneID: 10208); golgi autoantigen, golgin subfamily b, macrogolgin (with transmembrane signal), 1 (GOLGB1, GeneID: 2804); chromosome 20 open reading frame 74 (C20orf74, GeneID: 57186); Coiled-coil domain containing 52 (CCDC52, GeneID: 152185); RAB40B, member RAS oncogene family (RAB40B, GeneID: 10966); frequently rearranged in advanced T-cell lymphomas 2 (FRAT2, GeneID: 23401); hsa-miR-224 (GeneID: 407009); hsa-miR-181a (GeneID: 406995); hsa-miR-194 (GeneID: 406969, 406970); hsa-miR-192 (GeneID: 406967); hsa-miR-215 (GeneID: 406997); hsa-miR-200b (GeneID:); hsa-miR-429 (GeneID: 554210); hsa-miR-200a (GeneID: 406983); hsa-miR-192* (GeneID: 406967); hsa-miR-200b* (GeneID: 406984); and hsa-miR-584 (GeneID: 693169).

Resistance biomarkers useful in any of the methods of this invention include expression products of the following genes: caldesmon 1 (CALD1, GeneID: 800); kelch-like 5 (*Drosophila*) (KLHL5, GeneID: 51088); metallothionein 1E (functional) (MT1E, GeneID: 4493); beta-1,3-N-acetylgalactosaminyltransferase 1 (globoside blood group) (B3GALNT1, GeneID: 8706); cysteine-rich, angiogenic inducer, 61 (CYR61, GeneID: 3491); metallothionein 1X (MT1X, GeneID: 4501); troponin T type 1 (skeletal, slow) (TNNT1, GeneID: 7138); metallothionein 1H-like protein///hypothetical protein LOC650610 (MT1P2, GeneID: 645745 (also known as LOC645745)); metallothionein 1H (MT1H, GeneID: 4496); metallothionein 1F (functional) (MT1F, GeneID: 4494); metallothionein 2A (MT2A, GeneID: 4502); metallothionein 1M (MT1M, GeneID: 4499); MHC class I polypeptide-related sequence B (MICB, GeneID: 4277); collagen, type VI, alpha 1 (COL6A1, GeneID: 1291); myosin, light polypeptide 9, regulatory (MYL9, GeneID: 10398); metallothionein 1G (MT1G, GeneID: 4495); peripheral myelin protein 22 (PMP22, GeneID: 5376); chromosome 1 open reading frame 115 (C1orf115, GeneID: 79762); SWI/SNF related, matrix associated, actin dependent regulator of chromatin, subfamily d, member 3 (SMARCD3, GeneID: 6604); clusterin (CLU, GeneID: 1191); shroom family member 2 (SHROOM2, GeneID: 357); purinergic receptor P2X, ligand-gated ion channel, 5 (P2RX5, GeneID: 5026); coiled-coil domain containing 109B (CCDC109B, GeneID: 55013); transmembrane protein 52 (TMEM52, GeneID: 339456); cyclin E2 (CCNE2, GeneID: 9134); transforming growth factor, beta 1 (Camurati-Engelmann disease) (TGFB1, GeneID: 7040); suppressor of cytokine signaling 3 (SOCS3, GeneID: 9021); NACHT, leucine rich repeat and PYD containing 11 (NLRP11, GeneID: 204801); glypican 1 (GPC1, GeneID: 2817); kinesin light chain 3 (KLC3, GeneID: 147700); breast carcinoma amplified sequence 4 (BCAS4, GeneID: 55653); establishment of cohesion 1 homolog 2 (*S. cerevisiae*) (ESCO2, GeneID: 157570); Netrin 1 (NTN1, GeneID: 9423); MAD2 mitotic arrest deficient-like 2 (yeast) (MAD2L2, GeneID: 1045); tubulin tyrosine ligase-like family (TTLL7, GeneID: 79739), member 7; scavenger receptor class A, member 3 (SCARA3, GeneID: 51435); growth arrest and DNA-damage-inducible, beta (GADD45B, GeneID:

4616); immunoglobulin superfamily, member 4C (CADM4, GeneID: 199731 (also known as IGSF4C)); DDHD domain containing 1 (DDHD1, GeneID: 80821); BTG family, member 3 (BTG3, GeneID: 10950); kinesin family member 26A (KIF26A, GeneID: 26153); KIAA1622 (PPP4R4, GeneID: 57718); guanosine monophosphate reductase///guanosine monophosphate reductase (GMPR, GeneID: 2766); storkhead box 1 (STOX1, GeneID: 219736); KIAA0672 gene product (RICH2, GeneID: 9912); MCM10 minichromosome maintenance deficient 10 (*S. cerevisiae*) (MCM10, GeneID: 55388); DDHD domain containing 1 (DDHD1, GeneID: 80821); adenosine deaminase, RNA-specific, B1 (RED1 homolog rat) (ADARB1, GeneID: 104); CKLF-like MARVEL transmembrane domain containing 7 (CMTM7, GeneID: 112616); forkhead box F1 (FOXF1, GeneID: 2294); nuclear casein kinase and cyclin-dependent kinase substrate 1 (NUCKS1, GeneID: 64710); chromosome 11 open reading frame 63 (C11orf63, GeneID: 79864); acyl-CoA thioesterase 7 (ACOT7, GeneID: 11332); zinc finger protein 286 (ZNF286A, GeneID: 57335); amyloid beta (A4) precursor-like protein 1 (APLP1, GeneID: 333); ornithine aminotransferase (gyrate atrophy) (OAT, GeneID: 4942); pericentriolar material 1 (MBD1, GeneID: 4152 (also known as PCM1)); PRP40 pre-mRNA processing factor 40 homolog B (*S. cerevisiae*) (PRPF40B, GeneID: 25766); solute carrier family 12 (potassium/chloride transporters), member 4 (SLC12A4, GeneID: 6560); hypothetical protein FLJ38973 (C2orf69, GeneID: 205327); calcium and integrin binding family member 2 (CIB2, GeneID: 10518); integrin, alpha 7 (ITGA7, GeneID: 3679); BUB3 budding uninhibited by benzimidazoles 3 homolog (yeast) (BUB3, GeneID: 9184); chromosome 1 open reading frame 135 (C1orf135, GeneID: 79000); cell division cycle 27 (CDC27, GeneID: 996); docking protein 1, 62 kDa (downstream of tyrosine kinase 1) (DOK1, GeneID: 1796); adenosine kinase (ADK, GeneID: 132); Meis1, myeloid ecotropic viral integration site 1 homolog 3 (mouse) (MEIS3, GeneID: 56917); kringle containing transmembrane protein 2 (KREMEN2, GeneID: 79412); chromosome 21 open reading frame 91 (C21orf91, GeneID: 54149); solute carrier family 4, anion exchanger, member 3 (SLC4A3, GeneID: 6508); zinc finger protein 558 (ZNF558, GeneID: 148156); KIAA1442 protein (EBF4, GeneID: 57593 (also known as RP5-860F19.3)); MCM4 minichromosome maintenance deficient 4 (*S. cerevisiae*) (MCM4, GeneID: 4173); mitogen-activated protein kinase 1 (MAPK1, GeneID: 5594); hsa-miR-886-3p (GeneID: 100126299); hsa-miR-521 (GeneID: 574494, 574481); and hsa-miR-432 (GeneID: 574451).

The NCBI GeneID numbers listed herein are unique identifiers of the biomarker gene from the NCBI Entrez Gene database record (National Center for Biotechnology Information (NCBI), U.S. National Library of Medicine, 8600 Rockville Pike, Building 38A, Bethesda, Md. 20894. The sequences of representative mRNAs expressed from the biomarker gene are also listed herein below. Proteins expressed from these mRNAs represent biomarker proteins that may be used in any of the methods of this invention.

Accordingly, the present invention provides a method of predicting the sensitivity of tumor cell growth to inhibition by an IGF-1R kinase inhibitor, comprising: assessing the level of a sensitivity biomarker expressed by a tumor cell; and predicting the sensitivity of tumor cell growth to inhibition by an IGF-1R kinase inhibitor, wherein high expression levels of tumor cell sensitivity biomarkers correlate with high sensitivity to inhibition by IGF-1R kinase inhibitors. Preferred examples of sensitivity biomarkers include Mitogen Activated Protein Kinase Kinase 6 (MAP2K6) and Aldehyde Dehydrogenase 1-A1 (ALDH1A1). Additional examples of sensitivity biomarkers that can be utilized in the methods of this invention include those listed herein, above, and in FIG. 14.

The present invention also provides a method of predicting the sensitivity of tumor cell growth to inhibition by an IGF-1R kinase inhibitor, comprising: assessing the level of a resistance biomarker expressed by a tumor cell; and predicting the sensitivity of tumor cell growth to inhibition by an IGF-1R kinase inhibitor, wherein high expression levels of tumor cell resistance biomarkers correlate with low sensitivity to inhibition by IGF-1R kinase inhibitors. Preferred examples of resistance biomarkers include Metallothionein 1E (MT-1E) and Caldesmon (CALD1). Additional examples of resistance biomarkers that can be utilized in the methods of this invention include those listed herein, above, and in FIG. 15.

Assessment of the level of a sensitivity or resistance biomarker expressed by a tumor cell in any of the methods of this invention will typically be determined relative to the expression level of said sensitivity or resistance biomarker in a control cell sample where sensitivity to inhibition by an IGF-1R kinase inhibitor is known, or can readily be determined (e.g. a tumor cell line such as those listed in FIG. 1). Alternatively, a panel of tumor cell lines, each with a different level of expression of a sensitivity or resistance biomarker, and thus different sensitivity to inhibition by an IGF-1R kinase inhibitor, can be used construct a standard curve from which relative sensitivity to inhibition by an IGF-1R kinase inhibitor can be predicted. Expression levels of a sensitivity or resistance biomarker in a test tumor cell sample, or a control cell sample, may be determined relative to cell number, total protein or total RNA level, or the expression level of a housekeeping gene whose expression varies little or not at all from one cell to another, to give a "relative expression level.". Comparison of biomarker expression levels in a test tumor cell sample versus a control cell sample may be performed by comparing such relative expression levels.

In the context of this invention, whether expression of biomarkers is defined as high or low may be determined relative to a control tumor cell(s) with a known biomarker expression level and sensitivity to IGF-1R inhibitor. For example, the CRC tumor cell lines listed in FIG. 1 herein may be used as control tumor cells. For example, of these cell lines, some are sensitive to the IGF-1R kinase inhibitors PQIP and OSI-906 (e.g. Colo205, HT29, and LS513), and express high levels of sensitivity biomarkers and low levels of resistance biomarkers. Other cell lines in FIG. 1 are relatively resistant to the IGF-1R kinase inhibitors PQIP and OSI-906, and express high levels of resistance biomarkers and low levels of sensitivity biomarkers (e.g. SW948, SW48, NCI-H508, HCT116, HCT15, SW480, RKO, HCT8, LoVo, LS123, T84, LS174T, LS180, SW1417, SW1116, SW837, SW1463, and SW403). Sensitivity of tumor cell growth to PQIP is defined as high if the tumor cell is inhibited with an IC50 of less than 0.5 μM, and low (i.e. relatively resistant) if the tumor cell is inhibited with an IC50 of greater than 5.0 μM. With other IGF-1R kinase inhibitors, particularly compounds of Formula I as described herein below, such as OSI-906, a qualitatively similar result is expected since they inhibit tumor cell growth by inhibiting the same signal transduction pathway as PQIP, although quantitatively the IC50 values may differ depending on the relative potency of the other inhibitor versus PQIP. OSI-906 and PQIP have almost identical IC50 values when tested on the same tumor cell type. Thus, sensitivity of tumor cell growth to OSI-906 is defined as high if the tumor cell is inhibited with an IC50 of less than or equal to 1.5 μM, and low (i.e. relatively resistant)

if the tumor cell is inhibited with an IC50 of greater than 5.0 μM. The sensitivity range for other IGF-1R inhibitors may be different if the potency of the compound is different. However, the same two groups of sensitive and resistant tumor cells as described above, with their corresponding levels of sensitivity and resistance biomarker levels, can be used to predict whether new test tumors are sensitive to such other IGF-1R inhibitors by determining whether the sensitivity and/or resistance biomarker levels of such test tumor cells are more similar to cell types in the sensitive or the resistant tumor cell groups. For example, sensitivity of tumor cell growth to antibody IGF-1R kinase inhibitors can thus readily be determined. One of skill in the art would also readily be able to identify additional tumor cell types with high or low biomarker expression levels that might also be used as control tumor cells.

It will be appreciated by those of skill in the art that a control cell sample need not be established for each assay as the assay is performed but rather, a baseline or control can be established by referring to a form of stored information regarding a previously determined control level for sensitive and resistant patients (responders and non-responders), such as a control level established by any of the methods described herein. Such a form of stored information can include, for example, but is not limited to, a reference chart, listing or electronic file of population or individual data regarding sensitive and resistant tumors/patients, or any other source of data regarding control levels of expression of sensitivity or resistance biomarkers that is useful for the patient to be evaluated.

The present invention thus provides a method of predicting the sensitivity of tumor cell growth to inhibition by an IGF-1R kinase inhibitor, comprising: assessing the level of a sensitivity biomarker expressed by a test tumor cell; comparing said level with the level of a sensitivity biomarker expressed by a control tumor cell of known sensitivity to an IGF-1R kinase inhibitor, and predicting the sensitivity of tumor cell growth to inhibition by the IGF-1R kinase inhibitor, wherein high expression levels of tumor cell sensitivity biomarkers correlate with high sensitivity to inhibition by IGF-1R kinase inhibitors.

The present invention also provides a method of predicting the sensitivity of tumor cell growth to inhibition by an IGF-1R kinase inhibitor, comprising: assessing the level of a resistance biomarker expressed by a test tumor cell; comparing said level with the level of a resistance biomarker expressed by a control tumor cell of known sensitivity to an IGF-1R kinase inhibitor, and predicting the sensitivity of tumor cell growth to inhibition by the IGF-1R kinase inhibitor, wherein high expression levels of tumor cell resistance biomarkers correlate with low sensitivity to inhibition by IGF-1R kinase inhibitors.

Although many of the examples provided herein are directed to the IGF-1R kinase inhibitors PQIP or OSI-906, the methods of the present invention are not limited to the prediction of patients or tumors that will respond or not respond to this particular IGF-1R kinase inhibitor, but rather, can be used to predict patient's outcome to any IGF-1R kinase inhibitor, including inhibitors that are small molecules, peptides, antibodies, nucleic acids, or other types of inhibitors. In one embodiment, the small molecule IGF-1R kinase inhibitor may be one of a new class of relatively specific, orally-available, small-molecule compounds, as described by Formula I herein (see also US Published Patent Application US 2006/0235031; e.g. OSI-906).

In any of the methods, compositions or kits of the invention described herein, the term "small molecule IGF-1R kinase inhibitor" refers to a low molecular weight (i.e. less than 5000 Daltons; preferably less than 1000, and more preferably between 300 and 700 Daltons) organic compound that inhibits IGF-1R kinase by binding to the kinase domain of the enzyme. Examples of such compounds include IGF-1R kinase inhibitors of Formula (I) as described herein. The IGF-1R kinase inhibitor of Formula (I) can be any IGF-1R kinase inhibitor compound encompassed by Formula (I) that inhibits IGF-1R kinase upon administration to a patient. Examples of such inhibitors have been published in US Published Patent Application US 2006/0235031, which is incorporated herein in its entirety, and include OSI-906 (cis-3-[8-amino-1-(2-phenyl-quinolin-7-yl)-imidazo[1,5-a]pyrazin-3-yl]-1-methyl-cyclobutanol), as used in the experiments described herein.

For any given sensitivity or resistance biomarker, the range of expression level between tumor cells that are relatively insensitive to IGF-1R kinase inhibitors and those that are sensitive, can readily be assessed by one of skill in the art, for example by testing on a panel of tumor cells as described herein (e.g. FIG. 1), or by testing in tumor biopsies from patients whose tumor cells display a range of sensitivities to an IGF-1R kinase inhibitor (e.g. PQIP, OSI-906).

In addition, one of skill in the medical arts, particularly pertaining to the application of diagnostic tests and treatment with therapeutics, will recognize that biological systems are somewhat variable and not always entirely predictable, and thus many good diagnostic tests or therapeutics are occasionally ineffective. Thus, it is ultimately up to the judgement of the attending physician to determine the most appropriate course of treatment for an individual patient, based upon test results, patient condition and history, and his own experience. There may even be occasions, for example, when a physician will choose to treat a patient with an IGF-1R kinase inhibitor even when a tumor is not predicted to be particularly sensitive to IGF-1R kinase inhibitors, based on data from diagnostic tests or from other criteria, particularly if all or most of the other obvious treatment options have failed, or if some synergy is anticipated when given with another treatment. The fact that the IGF-1R kinase inhibitors as a class of compounds are relatively well tolerated compared to many other anti-cancer compounds, such as more traditional chemotherapy or cytotoxic agents used in the treatment of cancer, makes this a more viable option. Also, it should be noted that while the biomarkers disclosed herein predict which patients with tumors are likely to receive the most benefit from IGF-1R kinase inhibitors, it does not necessarily mean that patients with tumors which do not possess the optimal biomarker signature will receive no benefit, just that a more modest effect is to be anticipated.

Since diagnostic assays in biological systems are rarely infallible, this invention also provides additional embodiments wherein simultaneous assessment of the expression level in tumor cells of more than one biomarker level is utilized. In such embodiments (described below) there is likely to be a lower chance of a false prediction, compared to methods employing just a single biomarker expression level determination.

Accordingly, the present invention provides a method of predicting the sensitivity of tumor cell growth to inhibition by an IGF-1R kinase inhibitor, comprising: assessing the level of two or more (or a panel of) sensitivity biomarkers expressed by a tumor cell; and predicting the sensitivity of tumor cell growth to inhibition by an IGF-1R kinase inhibitor, wherein simultaneous high expression levels of all of the assessed tumor cell sensitivity biomarkers correlates with high sensitivity to inhibition by IGF-1R kinase inhibitors. In one preferred embodiment of this method the sensitivity biomarkers comprise Mitogen Activated Protein Kinase Kinase 6 (MAP2K6) and Aldehyde Dehydrogenase 1-A1 (ALDH1A1), wherein simultaneous high expression level of the two tumor cell sensitivity biomarkers correlates with high sensitivity to inhibition by IGF-1R kinase inhibitor. Note that in the latter embodiment a high expression level of both biomarkers is required to indicate high sensitivity.

The present invention also provides a method of predicting the sensitivity of tumor cell growth to inhibition by an IGF-1R kinase inhibitor, comprising: assessing the level of two or more (or a panel of) resistance biomarkers expressed by a tumor cell; and predicting the sensitivity of tumor cell growth to inhibition by an IGF-1R kinase inhibitor, wherein simultaneous low or undetectable expression levels of all of the assessed tumor cell resistance biomarkers correlates with high sensitivity to inhibition by IGF-1R kinase inhibitors. In one preferred embodiment of this method the resistance biomarkers comprise Metallothionein-1E (MT-1E) and Caldesmon (CALD1), wherein simultaneous low or undetectable expression level of the two tumor cell resistance biomarkers correlates with high sensitivity to inhibition by IGF-1R kinase inhibitor. Note that in the latter embodiment a low or undetectable expression of both biomarkers is required to indicate high sensitivity.

The present invention also provides a method of predicting the sensitivity of tumor cell growth to inhibition by an IGF-1R kinase inhibitor, comprising: assessing the level of a sensitivity biomarker expressed by a tumor cell; assessing the level of a resistance biomarker expressed by, a tumor cell; and predicting the sensitivity of tumor cell growth to inhibition by an IGF-1R kinase inhibitor, wherein a high ratio of sensitivity to resistance biomarker expression levels correlates with high sensitivity to inhibition by IGF-1R kinase inhibitors. In one preferred embodiment of this method the sensitivity biomarker comprises Mitogen Activated Protein Kinase Kinase 6 (MAP2K6) or Aldehyde Dehydrogenase 1-A1 (ALDH1A1) and the resistance biomarker comprises Metallothionein-1E (MT-1E) or Caldesmon (CALD1).

The present invention also provides a method of predicting the sensitivity of tumor growth to inhibition by an IGF-1R kinase inhibitor, comprising: assessing the level of two or more (or a panel of) sensitivity biomarkers expressed by cells of the tumor; and predicting the sensitivity of tumor growth to inhibition by an IGF-1R kinase inhibitor, wherein simultaneous high expression levels of all of the assessed tumor cell sensitivity biomarkers correlates with high sensitivity to inhibition by IGF-1R kinase inhibitors. In one preferred embodiment of this method the sensitivity biomarkers comprise Mitogen Activated Protein Kinase Kinase 6 (MAP2K6) and Aldehyde Dehydrogenase 1-A1 (ALDH1A1), wherein simultaneous high expression level of the two tumor cell sensitivity biomarkers correlates with high sensitivity to inhibition by IGF-1R kinase inhibitor. Note that in the latter embodiment a high expression level of both biomarkers is required to indicate high sensitivity.

The present invention also provides a method of predicting the sensitivity of tumor growth to inhibition by an IGF-1R kinase inhibitor, comprising: assessing the level of two or more (or a panel of) resistance biomarkers expressed by cells of the tumor; and predicting the sensitivity of tumor growth to inhibition by an IGF-1R kinase inhibitor, wherein simultaneous low or undetectable expression levels of all of the assessed tumor cell resistance biomarkers correlates with high sensitivity to inhibition by IGF-1R kinase inhibitors. In one preferred embodiment of this method the resistance biomarkers comprise Metallothionein 1E (MT-1E) and Caldesmon (CALD1), wherein simultaneous low or undetectable expression level of the two tumor cell resistance biomarkers correlates with high sensitivity to inhibition by IGF-1R kinase inhibitor. Note that in the latter embodiment a low or undetectable expression of both biomarkers is required to indicate high sensitivity.

The present invention also provides a method of predicting the sensitivity of tumor growth to inhibition by an IGF-1R kinase inhibitor, comprising: assessing the level of an sensitivity biomarker expressed by cells of the tumor; assessing the level of a resistance biomarker expressed by cells of the tumor; and predicting the sensitivity of tumor growth to inhibition by an IGF-1R kinase inhibitor, wherein a high ratio of sensitivity to resistance biomarker expression levels correlates with high sensitivity to inhibition by IGF-1R kinase inhibitors. In one preferred embodiment of this method the sensitivity biomarker comprises Mitogen Activated Protein Kinase Kinase 6 (MAP2K6) or Aldehyde Dehydrogenase 1-A1 (ALDH1A1) and the resistance biomarker comprises Metallothionein-1E (MT-1E) or Caldesmon (CALD1).

The present invention also provides a method of predicting whether a cancer patient is afflicted with a tumor that will respond effectively to treatment with an IGF-1R kinase inhibitor, comprising: assessing the level of two or more (or a panel of) sensitivity biomarkers expressed by cells of the tumor; and predicting if the tumor will respond effectively to treatment with an IGF-1R kinase inhibitor, wherein simultaneous high expression levels of all of the tumor cell sensitivity biomarkers correlates with a tumor that will respond effectively to treatment with an IGF-1R kinase inhibitor. In one preferred embodiment of this method the sensitivity biomarkers comprise Mitogen Activated Protein Kinase Kinase 6 (MAP2K6) and Aldehyde Dehydrogenase 1-A1 (ALDH1A1), wherein simultaneous high expression level of the two tumor cell sensitivity biomarkers correlates with a tumor that will respond effectively to treatment with an IGF-1R kinase inhibitor. Note that in the latter embodiment a high expression level of both biomarkers is required to indicate a tumor that will respond effectively to treatment with an IGF-1R kinase inhibitor.

The present invention also provides a method of predicting whether a cancer patient is afflicted with a tumor that will respond effectively to treatment with an IGF-1R kinase inhibitor, comprising: assessing the level of two or more (or a panel of) resistance biomarkers expressed by cells of the tumor; and predicting if the tumor will respond effectively to treatment with an IGF-1R kinase inhibitor, wherein simultaneous low or undetectable expression levels of all of the tumor cell resistance biomarkers correlates with a tumor that will respond effectively to treatment with an IGF-1R kinase inhibitor. In one preferred embodiment of this method the resistance biomarkers comprise Metallothionein (MT) and Caldesmon (CALD1), wherein simultaneous low or undetectable expression level of the two tumor cell resistance biomarkers correlates with a tumor that will respond effectively to treatment with an IGF-1R kinase inhibitor. Note that in the latter embodiment a low or undetectable expression of both biomarkers is required to indicate a tumor that will respond effectively to treatment with an IGF-1R kinase inhibitor.

The present invention also provides a method of predicting whether a cancer patient is afflicted with a tumor that will respond effectively to treatment with an IGF-1R kinase inhibitor, comprising: assessing the level of an sensitivity biomarker expressed by cells of the tumor; assessing the level of a resistance biomarker expressed by cells of the tumor; and predicting if the tumor will respond effectively to treatment with an IGF-1R kinase inhibitor, wherein a high ratio of sensitivity to resistance biomarker expression levels correlates with a tumor that will respond effectively to treatment with an IGF-1R kinase inhibitor. In one preferred embodiment of this method the sensitivity biomarker comprises Mitogen Activated Protein Kinase Kinase 6 (MAP2K6) or Aldehyde Dehydrogenase 1-A1 (ALDH1A1) and the resistance biomarker comprises Metallothionein 1E (MT-1E) or Caldesmon (CALD1).

The present invention also provides a method of predicting whether a cancer patient is afflicted with a tumor that will respond effectively to treatment with an IGF-1R kinase inhibitor, comprising: obtaining a sample of the patient's tumor; assessing the level of a sensitivity biomarker expressed by cells of the tumor; determining whether said level is statistically more similar to the level of the same sensitivity biomarker of tumor cells that are known to be sensitive to the IGF-1R kinase inhibitor or to the level of the same sensitivity biomarker of tumor cells that are known to be resistant to the IGF-1R kinase inhibitor; and predicting that the tumor will respond effectively to treatment with an IGF-1R kinase inhibitor if the level of the sensitivity biomarker is statistically more similar to the level of the sensitivity biomarker of tumor cells that are known to be sensitive to the IGF-1R kinase inhibitor, wherein the sensitivity biomarker is selected from any of those listed herein.

The present invention also provides a method of predicting whether a cancer patient is afflicted with a tumor that will respond effectively to treatment with an IGF-1R kinase inhibitor, comprising: obtaining a sample of the patient's tumor; assessing the level of a resistance biomarker expressed by cells of the tumor; determining whether said level is statistically more similar to the level of the same resistance biomarker of tumor cells that are known to be sensitive to the IGF-1R kinase inhibitor or to the level of the same resistance biomarker of tumor cells that are known to be resistant to the IGF-1R kinase inhibitor; and predicting that the tumor will respond effectively to treatment with an IGF-1R kinase inhibitor if the level of the resistance biomarker is statistically more similar to the level of the resistance biomarker of tumor cells that are known to be sensitive to the IGF-1R kinase inhibitor, wherein the resistance biomarker is selected from any of those listed herein.

The present invention also provides a method of treating a cancer patient with an IGF-1R kinase inhibitor, comprising: predicting whether the patient is afflicted with a tumor that will respond effectively to treatment with an IGF-1R kinase inhibitor, by: obtaining a sample of the patients tumor; assessing the level of a sensitivity biomarker expressed by cells of the tumor; determining whether said level is statistically more similar to the level of the same sensitivity biomarker of tumor cells that are known to be sensitive to the IGF-1R kinase inhibitor or to the level of the same sensitivity biomarker of tumor cells that are known to be resistant to the IGF-1R kinase inhibitor; and predicting that the tumor will respond effectively to treatment with an IGF-1R kinase inhibitor if the level of the sensitivity biomarker is statistically more similar to the level of the sensitivity biomarker of tumor cells that are known to be sensitive to the IGF-1R kinase inhibitor; and treating the patient with a therapeutically effective amount of an IGF-1R kinase inhibitor if the patient is afflicted with a tumor that is predicted to respond effectively to treatment with an IGF-1R kinase inhibitor; wherein the sensitivity biomarker is selected from any of those listed herein.

The present invention also provides a method of treating a cancer patient with an IGF-1R kinase inhibitor, comprising: predicting whether the patient is afflicted with a tumor that will respond effectively to treatment with an IGF-1R kinase inhibitor, by: obtaining a sample of the patients tumor; assessing the level of a resistance biomarker expressed by cells of the tumor; determining whether said level is statistically more similar to the level of the same resistance biomarker of tumor cells that are known to be sensitive to the IGF-1R kinase inhibitor or to the level of the same resistance biomarker of tumor cells that are known to be resistant to the IGF-1R kinase inhibitor; and predicting that the tumor will respond effectively to treatment with an IGF-1R kinase inhibitor if the level of the resistance biomarker is statistically more similar to the level of the resistance biomarker of tumor cells that are known to be sensitive to the IGF-1R kinase inhibitor; and treating the patient with a therapeutically effective amount of an IGF-1R kinase inhibitor if the patient is afflicted with a tumor that is predicted to respond effectively to treatment with an IGF-1R kinase inhibitor; wherein the resistance biomarker is selected from any of those listed herein.

In any of the methods described herein, the "tumor cells that are known to be sensitive to the IGF-1R kinase inhibitor" or "the tumor cells that are known to be resistant to the IGF-1R kinase inhibitor", which are used as a reference or control for comparison with the tumor cells of a patient's tumor, may be of the same tumor type (e.g. CRC, NSCLC, breast cancer etc) as the cells of the tumor from the patient being examined, or they may be from a tumor type that has similar characteristics with respect to sensitivity or resistance biomarker expression levels and their correlation with sensitivity of the tumor cells to growth inhibition by an IGF-1R kinase inhibitor.

In any of the methods described herein, in "determining whether said level is statistically more similar to the level of the same sensitivity biomarker of tumor cells that are known to be sensitive to the IGF-1R kinase inhibitor or to the level of the same sensitivity biomarker of tumor cells that are known to be resistant to the IGF-1R kinase inhibitor", the biomarker expression level of the tumor cells "known to be sensitive" or "known to be resistant" may be a level corresponding to that from one sensitive or one resistant tumor cell type respectively (e.g. one of the CRC tumor cell lines used in the experimental section herein), or the level may be an average value deduced from panels of sensitive or resistant tumor cell types.

The present invention also provides a method for treating tumors or tumor metastases in a patient, comprising administering to said patient simultaneously or sequentially a therapeutically effective amount of a combination of a synthetic, cell permeable miRNA mimic of hsa-miR-224 or hsa-miR-181, and an IGF-1R kinase inhibitor. In this method the IGF-1R kinase inhibitor may be a small molecule IGF-1R kinase inhibitor, such as for example an IGF-1R kinase inhibitor of Formula (I), such as PQIP or OSI-909, or may be an anti-IGF-1R antibody, such as those described herein. In one embodiment, the patient is a human in need of treatment for cancer.

The present invention also provides a pharmaceutical composition comprising a synthetic, cell permeable miRNA mimic of hsa-miR-224 or hsa-miR-181, and an IGF-1R kinase inhibitor, in a pharmaceutically acceptable carrier. In this composition, the IGF-1R kinase inhibitor may be a small molecule IGF-1R kinase inhibitor, such as for example an IGF-1R kinase inhibitor of Formula (I), such as PQIP or OSI-909, or may be an anti-IGF-1R antibody, such as those described herein.

The present invention also provides a kit comprising one or more containers, comprising a synthetic, cell permeable miRNA mimic of hsa-miR-224 or hsa-miR-181, and an IGF-1R kinase inhibitor. In this kit, the IGF-1R kinase inhibitor may be a small molecule IGF-1R kinase inhibitor, such as for example an IGF-1R kinase inhibitor of Formula (I), such as PQIP or OSI-909, or may be an anti-IGF-1R antibody, such as those described herein.

In the context of this invention, a "synthetic, cell permeable miRNA mimic" is an agent that is capable of entering the tumor cells of a patient, and producing a similar sensitizing effect with respect to inhibitors of IGF-1R kinase as observed herein for the miRNA mimic of hsa-miR-224 (see Experimental section). In one embodiment this agent may comprise a vector capable of expressing hsa-miR-224 or hsa-miR-181 in the tumor cells of the patient (e.g. an adeno-associated viral (AAV) vector; e.g. see Wang, Z., et al (2005) Nat. Biotechnol. 23, 321-328.). In another embodiment, the agent may comprise an oligonucleotide modified to be resistant to cell and/or blood degradative enzymes (e.g. a phosphorothioate or 2'-0-methoxyethyl modified oligonucleotide, with for example 2-O-methyl RNA bases at both 5' and 3' ends), that may be delivered to tumor cells via for example a complex with liposomes and/or a cell permeable peptide (e.g. see Torchilin V P. (2006) Adv Drug Deliv Rev. 2006 Dec. 1; 58 (14):1532-55). Such agents are readily prepared by methods known in the art. For example, fully phosphorothioated oligonucleotides may be synthesized using β-cyanoethylphosphoramidite chemistry on a DNA synthesizer (e.g. see Agrawal S, et al. Proc Natl Acad Sci USA 1997; 94:2620-2625). After the synthesis, oligonucleotides can be deprotected using standard protocols, and purified by high-performance liquid chromatography.

The genes coding for examples of sensitivity or resistance molecular biomarkers that can be used in the practice of the methods of the invention are described herein, above, and in FIGS. 14 and 15. The sensitivity or resistance molecular biomarkers can include any product expressed by these genes, e.g. expressed mRNA or protein, splice variants, polymorphic variants etc. Thus, the biomarkers include mRNAs expressed by these biomarker genes as listed in the sequence list herein, below, or mRNAs that hybridize under stringent conditions to the complement of these nucleic acids, wherein the stringent conditions comprise, for example, incubating at 42° C. in a solution comprising 50% formamide, 5×SSC, and 1% SDS and washing at 65° C. in a solution comprising 0.2×SSC and 0.1% SDS, or polypeptides encoded by any of these mRNAs. In an additional embodiment where the tumor is present in a non-human patient the biomarker is an animal homologue of the human gene product (e.g. from dog, mouse, rat, rabbit, cat, monkey, ape, etc.).

As described herein, this invention provides methods using different biomarkers to predict tumor sensitivity to inhibition by IGF-1R kinase inhibitors. Each of these methods have potential advantages and disadvantages, and while the preferred method will ultimately depend on individual patient circumstances, the use of multiple diagnostic methods will likely improve one's ability to predict the likely outcome of a therapeutic regimen comprising use of an IGF-1R kinase inhibitor. Therefore, this invention provides the method for treating tumors or tumor metastases in a patient comprising the initial use, either simultaneously or sequentially, of two or more of any of the diagnostic methods as described hereinfor for predicting sensitivity to inhibition by IGF-1R kinase inhibitors, followed by administering to said patient a therapeutically effective amount of an IGF-1R kinase inhibitor if one or more of the diagnostic methods indicate that the patient is potentially responsive to an IGF-1R kinase inhibitor.

Factors to be considered in determining the preferred diagnostic method for predicting tumor sensitivity to inhibition by IGF-1R kinase inhibitors include both inherent characteristics of each of the methods and technical considerations affecting the use of the methods. For example, as described above, certain sensitivity or resistance biomarkers are preferred over others in diagnostic methods using a single biomarker. An improved ability to correctly predict sensitivity to IGF-1R kinase inhibitors may be achieved by employing two or more biomarker determinations in the diagnostic method.

Determination of sensitivity or resistance biomarker level can be assessed by a number of different approaches, including direct analysis of proteins that segregate as sensitivity or resistance biomarkers. An advantage of this approach is that markers are read directly. However, this approach also requires sufficient quantities of tissue in order to perform an analysis (e.g. immunohistochemistry). Sufficient quantities of tissue may be difficult to obtain from certain procedures such as FNA (fine needle aspiration). Core biopsies provide larger amounts of tissue, but are sometimes not routinely performed during diagnoses. Alternatively, these biomarkers could be evaluated based upon the expression level of their encoding RNA transcripts using a quantitative PCR based approach. An advantage of this approach is that very few tumor cells are required for this measurement, and it is very likely that sufficient material may be obtained via an FNA. However, here the transcript levels for a given biomarker may be derived from both tumor cells as well as infiltrating stromal cells from the tumor. Given that stromal cells might also express sensitivity or resistance biomarkers, this may obscure detection of the IGF-1R kinase inhibitor sensitivity status for the tumor cells. Use of in situ hybridization (e.g. FISH) or tissue microdisection may be useful here to overcome this potential limitation.

In the methods described herein the tumor cell will typically be from a patient diagnosed with cancer, a precancerous condition, or another form of abnormal cell growth, and in need of treatment. The cancer may be lung cancer (e.g. non-small cell lung cancer (NSCLC)), pancreatic cancer, head and neck cancer, gastric cancer, breast cancer, colon cancer, ovarian cancer, or any of a variety of other cancers described herein below. The cancer is preferably one known to be potentially treatable with an IGF-1R kinase inhibitor.

In the methods of this invention, sensitivity or resistance biomarker expression level can be assessed relative to a control molecule whose expression level remains relatively constant in different tumor cells (e.g. a "housekeeping" gene, such as GAPDH, β-actin, tubulin, or the like). Biomarker expression level can also be assessed relative to another type of tumor cell biomarker (i.e. sensitivity compared to resistance), or to the biomarker level in non-tumor cells of the same tissue, or another cell or tissue source used as an assay reference.

In the methods of this invention, the level of an sensitivity or resistance biomarker expressed by a tumor cell can be assessed by using any of the standard bioassay procedures known in the art for determination of the level of expression of a gene, including for example ELISA, RIA, immunoprecipitation, immunoblotting, immunofluorescence microscopy, RT-PCR, in situ hybridization, cDNA microarray, or the like, as described in more detail below.

In the methods of this invention, the expression level of a tumor cell sensitivity or resistance biomarker is preferably assessed by assaying a tumor biopsy. However, in an alternative embodiment, expression level of the tumor cell biomarker can be assessed in bodily fluids or excretions containing detectable levels of biomarkers originating from the tumor or tumor cells. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor sensitivity or resistance biomarkers in such bodily fluids or excretions can sometimes be preferred in circumstances where an invasive sampling method is inappropriate or inconvenient.

In the methods of this invention, the tumor cell can be a lung cancer tumor cell (e.g. non-small cell lung cancer (NSCLC)), a pancreatic cancer tumor cell, a breast cancer tumor cell, a head and neck cancer tumor cell, a gastric cancer tumor cell, a colon cancer tumor cell, an ovarian cancer tumor cell, or a tumor cell from any of a variety of other cancers as described herein below. The tumor cell is preferably of a type known to or expected to express IGF-1R kinase, as do all tumor cells from solid tumors. The IGF-1R kinase can be wild type or a mutant form.

In the methods of this invention, the IGF-1R kinase inhibitor can be any IGF-1R kinase inhibitor as described herein below, including pharmacologically acceptable salts or polymorphs thereof.

The following methods represent additional specific embodiments of the methods of the invention.

The present invention provides a method of predicting the sensitivity of tumor growth to inhibition by an IGF-1R kinase inhibitor, comprising: assessing the level of an sensitivity biomarker expressed by cells of the tumor; and predicting the sensitivity of tumor growth to inhibition by an IGF-1R kinase inhibitor, wherein high expression levels of tumor cell sensitivity biomarkers correlate with high sensitivity of tumor growth to inhibition by IGF-1R kinase inhibitors.

The present invention provides a method of predicting the sensitivity of tumor growth to inhibition by an IGF-1R kinase inhibitor, comprising: assessing the level of a resistance biomarker expressed by cells of the tumor; and predicting the sensitivity of tumor growth to inhibition by an IGF-1R kinase inhibitor, wherein high expression levels of tumor cell resistance biomarkers correlate with low sensitivity of tumor growth to inhibition by IGF-1R kinase inhibitors.

The present invention provides a method of predicting whether a cancer patient is afflicted with a tumor that will respond effectively to treatment with an IGF-1R kinase inhibitor, comprising: assessing the level of an sensitivity biomarker expressed by cells of the tumor; and predicting if the tumor will respond effectively to treatment with an IGF-1R kinase inhibitor, wherein high expression levels of tumor cell sensitivity biomarkers correlate with a tumor that will respond effectively to treatment with an IGF-1R kinase inhibitor.

In the methods of this invention, the tumor can be a lung cancer tumor (e.g. non-small cell lung cancer (NSCLC)), a pancreatic cancer tumor, a breast cancer tumor, a head and neck cancer tumor, a gastric cancer tumor, a colon cancer tumor, an ovarian cancer tumor, or a tumor from any of a variety of other cancers as described herein below. The tumor is preferably of a type whose cells are known to or expected to express IGF-1R kinase, as do all solid tumors. The IGF-1R kinase can be wild type or a mutant form.

The present invention provides a method of predicting whether a cancer patient is afflicted with a tumor that will respond effectively to treatment with an IGF-1R kinase inhibitor, comprising: assessing the level of a resistance biomarker expressed by cells of the tumor; and predicting if the tumor will respond effectively to treatment with an IGF-1R kinase inhibitor, wherein high expression levels of tumor cell resistance biomarkers correlate with a tumor that will respond less effectively to treatment with an IGF-1R kinase inhibitor.

The present invention provides a method of predicting the sensitivity of tumor cell growth to inhibition by an IGF-1R kinase inhibitor comprising: determining the tumor cell level of a sensitivity biomarker polypeptide; determining the tumor cell level of a control polypeptide; comparing the tumor cell level of the sensitivity biomarker polypeptide to the tumor cell level of the control polypeptide; wherein a high ratio of tumor cell biomarker polypeptide to tumor cell control polypeptide indicates a high predicted sensitivity of tumor cell growth to inhibition by an IGF-1R kinase inhibitor. For this method, examples of useful sensitivity biomarker polypeptides include Mitogen Activated Protein Kinase Kinase 6 (MAP2K6) and Aldehyde Dehydrogenase 1-A1 (ALDH1A1).

The present invention provides a method of predicting the sensitivity of tumor cell growth to inhibition by an IGF-1R kinase inhibitor comprising: determining the tumor cell level of a sensitivity biomarker polynucleotide that encodes a polypeptide; determining the tumor cell level of a control polynucleotide; comparing the tumor cell level of the sensitivity biomarker polynucleotide that encodes a polypeptide to the tumor cell level of the control polynucleotide; wherein a high ratio of tumor cell biomarker polynucleotide to tumor cell control polynucleotide indicates a high predicted sensitivity of, tumor cell growth to inhibition by an IGF-1R kinase inhibitor. For this method examples of polypeptides encoded by the sensitivity biomarker polynucleotide include Mitogen Activated Protein Kinase Kinase 6 (MAP2K6) and Aldehyde Dehydrogenase 1-A1 (ALDH1A1).

The present invention provides a method of predicting the sensitivity of tumor cell growth to inhibition by an IGF-1R kinase inhibitor comprising: determining the tumor cell level of a resistance biomarker polypeptide; determining the tumor cell level of a control polypeptide; comparing the tumor cell level of the resistance biomarker polypeptide to the tumor cell level of the control polypeptide; wherein a low ratio of tumor cell biomarker polypeptide to tumor cell control polypeptide indicates a high predicted sensitivity of tumor cell growth to inhibition by an IGF-1R kinase inhibitor. For this method, examples of useful resistance biomarker polypeptides include Metallothionein 1E (MT-1E) and Caldesmon (CALD1).

The present invention provides a method of predicting the sensitivity of tumor cell growth to inhibition by an IGF-1R kinase inhibitor comprising: determining the tumor cell level of a resistance biomarker polynucleotide that encodes an polypeptide; determining the tumor cell level of a control polynucleotide; comparing the tumor cell level of the resistance biomarker polynucleotide that encodes an polypeptide to the tumor cell level of the control polynucleotide; wherein a low ratio of tumor cell biomarker polynucleotide to tumor cell control polynucleotide indicates a high predicted sensitivity of tumor cell growth to inhibition by an IGF-1R kinase inhibitor. For this method, examples of useful polypeptides encoded by the biomarker polynucleotide include Metallothionein 1E (MT-1E) and Caldesmon (CALD1).

The present invention provides a method of predicting the sensitivity of tumor cell growth to inhibition by an IGF-1R kinase inhibitor comprising: determining the tumor cell level of a sensitivity biomarker polypeptide; determining a non-tumor cell level of a sensitivity biomarker polypeptide; comparing the tumor cell level of the sensitivity biomarker polypeptide to the non-tumor cell level of the sensitivity biomarker polypeptide; wherein a high ratio of tumor cell biomarker polypeptide to non-tumor cell biomarker polypeptide indicates a high predicted sensitivity of tumor cell growth to inhibition by an IGF-1R kinase inhibitor. For this method, examples of useful sensitivity biomarker polypeptide include Mitogen Activated Protein Kinase Kinase 6 (MAP2K6) and Aldehyde Dehydrogenase 1-A1 (ALDH1A1).

The present invention provides a method of predicting the sensitivity of tumor cell growth to inhibition by an IGF-1R kinase inhibitor comprising: determining the tumor cell level of a sensitivity biomarker polynucleotide that encodes an polypeptide; determining a non-tumor cell level of a sensitivity biomarker polynucleotide that encodes an polypeptide; comparing the tumor cell level of the sensitivity biomarker polynucleotide that encodes an polypeptide to the non-tumor cell level of the sensitivity biomarker polynucleotide that encodes an polypeptide; wherein a high ratio of tumor cell biomarker polynucleotide to non-tumor cell biomarker polynucleotide indicates a high predicted sensitivity of tumor cell growth to inhibition by an IGF-1R kinase inhibitor. For this method, examples of useful polypeptides encoded by the sensitivity biomarker polynucleotide include Mitogen Activated Protein Kinase Kinase 6 (MAP2K6) and Aldehyde Dehydrogenase 1-A1 (ALDH1A1).

The present invention provides a method of predicting the sensitivity of tumor cell growth to inhibition by an IGF-1R kinase inhibitor comprising: determining the tumor cell level of a resistance biomarker polypeptide; determining a non-tumor cell level of a resistance biomarker polypeptide; comparing the tumor cell level of the resistance biomarker polypeptide to the non-tumor cell level of the resistance biomarker polypeptide; wherein a low ratio of tumor cell biomarker polypeptide to non-tumor cell biomarker polypeptide indicates a high predicted sensitivity of tumor cell growth to inhibition by an IGF-1R kinase inhibitor. For this method, examples of useful resistance biomarker polypeptides include Metallothionein 1E (MT-1E) and Caldesmon (CALD1).

The present invention provides a method of predicting the sensitivity of tumor cell growth to inhibition by an IGF-1R kinase inhibitor comprising: determining the tumor cell level of a resistance biomarker polynucleotide that encodes an polypeptide; determining a non-tumor cell level of a resistance biomarker polynucleotide that encodes an polypeptide; comparing the tumor cell level of the resistance biomarker polynucleotide that encodes an polypeptide to the non-tumor cell level of the resistance biomarker polynucleotide that encodes an polypeptide; wherein a low ratio of tumor cell biomarker polynucleotide to non-tumor cell biomarker polynucleotide indicates a high predicted sensitivity of tumor cell growth to inhibition by an IGF-1R kinase inhibitor. For this method, examples of useful polypeptides encoded by the biomarker polynucleotide include Metallothionein 1E (MT-1E) and Caldesmon (CALD1).

The present invention provides a method of predicting the sensitivity of tumor cell growth to inhibition by an IGF-1R kinase inhibitor comprising: determining the tumor cell level of a sensitivity biomarker polypeptide; determining the tumor cell level of a resistance biomarker polypeptide; comparing the level of the sensitivity biomarker polypeptide to the level of the resistance biomarker polypeptide; wherein a high ratio of sensitivity biomarker polypeptide to resistance biomarker polypeptide indicates a high predicted sensitivity of tumor cell growth to inhibition by an IGF-1R kinase inhibitor. For this method, examples of useful sensitivity biomarker polypeptides include Mitogen Activated Protein Kinase Kinase 6 (MAP2K6) and Aldehyde Dehydrogenase 1-A1 (ALDH1A1). For this method, examples of useful resistance biomarker polypeptides include Metallothionein 1E (MT-1E) and Caldesmon (CALD1).

The present invention provides a method of predicting the sensitivity of tumor cell growth to inhibition by an IGF-1R kinase inhibitor comprising: determining the tumor cell level of a sensitivity biomarker polynucleotide that encodes a polypeptide; determining the tumor cell level of a resistance biomarker polynucleotide that encodes a polypeptide; (c) comparing the level of the sensitivity biomarker polynucleotide to the level of the resistance biomarker polynucleotide; wherein a high ratio of sensitivity biomarker polynucleotide to resistance biomarker polynucleotide indicates a predicted high sensitivity of tumor cell growth to inhibition by an IGF-1R kinase inhibitor. For this method, examples of useful polypeptides encoded by the sensitivity biomarker polynucleotide include Mitogen Activated Protein Kinase Kinase 6 (MAP2K6) and Aldehyde Dehydrogenase 1-A1 (ALDH1A1). For this method, examples of useful polypeptides encoded by the resistance biomarker polynucleotide include Metallothionein 1E (MT-1E) and Caldesmon (CALD1).

The present invention provides a method of assessing whether a cancer patient is afflicted with a cancer that will respond effectively to treatment with an IGF-1R kinase inhibitor, the method comprising comparing: the level of expression of a resistance biomarker in a patient sample; and the normal level of expression of the biomarker in a control non-cancer sample, wherein a significant increase in the level of expression of the resistance biomarker in the patient sample over the normal level is an indication that the patient is afflicted with a cancer which is less likely to respond effectively to treatment with an IGF-1R kinase inhibitor. For this method, examples of useful resistance biomarkers include Metallothionein 1E (MT-1E) and Caldesmon (CALD1), and nucleic acids encoding for these proteins.

The present invention provides a method of assessing whether a cancer patient is afflicted with a cancer that will respond effectively to treatment with an IGF-1R kinase inhibitor; the method comprising comparing: the level of expression of an sensitivity biomarker in a patient sample; and the normal level of expression of the biomarker in a control non-cancer sample, wherein a significant decrease in the level of expression of the sensitivity biomarker in the patient sample over the normal level is an indication that the patient is afflicted with a cancer which is less likely to respond effectively to treatment with an IGF-1R kinase inhibitor. For this method, examples of useful sensitivity biomarkers include Mitogen Activated Protein Kinase Kinase 6 (MAP2K6) and Aldehyde Dehydrogenase 1-A1 (ALDH1A1), and nucleic acids encoding for these proteins.

The present invention provides a method of assessing whether a cancer patient is afflicted with a cancer that will respond effectively to treatment with an IGF-1R kinase inhibitor, the method comprising comparing: the level of expression of an sensitivity biomarker in a patient sample; and the level of expression of a resistance biomarker in a patient sample, wherein a high ratio of the level of expression of the sensitivity biomarker to the level of expression of the resistance biomarker is an indication that the patient is afflicted with a cancer which is likely to respond effectively to treatment with an IGF-1R kinase inhibitor. For this method, examples of useful sensitivity biomarkers include Mitogen Activated Protein Kinase Kinase 6 (MAP2K6) and Aldehyde Dehydrogenase 1-A1 (ALDH1A1), and nucleic acids encoding for these proteins. For this method, examples of useful resistance biomarkers include Metallothionein 1E (MT-1E) and Caldesmon (CALD1), and nucleic acids encoding for these proteins.

In any of the above methods referring to a patient sample, an example of such a sample can be a tumor biopsy.

The present invention provides a method of determining whether in a human subject a tumor will be responsive to treatment with an IGF-1R kinase inhibitor, comprising: (a) collecting a sample of a bodily substance containing human nucleic acid or protein, said nucleic acid or protein having originated from cells of the human subject, (b) determining quantitatively or semi-quantitatively in the sample a level of expression for a sensitivity biomarker protein or a sensitivity biomarker mRNA; and (c) comparing the expression level in (b) to the level of biomarker expression in a normal control, or to the level of a control polypeptide or nucleic acid in the sample, wherein reduced expression of the sensitivity biomarker protein or the sensitivity biomarker mRNA, with respect to the control level, indicates the presence in the human subject of a tumor which is less likely to respond effectively to treatment with an IGF-1R kinase inhibitor.

The present invention provides a method of determining whether in a human subject a tumor will be responsive to treatment with an IGF-1R kinase inhibitor, comprising: (a) collecting a sample of a bodily substance containing human nucleic acid or protein, said nucleic acid or protein having originated from cells of the human subject, (b) determining quantitatively or semi-quantitatively in the sample a level of expression for a resistance biomarker protein or a resistance biomarker mRNA; and (c) comparing the expression level in (b) to the level of biomarker expression in a normal control, or to the level of a control polypeptide or nucleic acid in the sample, wherein increased expression of the resistance biomarker protein or the resistance biomarker mRNA, with respect to the control level, indicates the presence in the human subject of a tumor which is less likely to respond effectively to treatment with an IGF-1R kinase inhibitor.

The present invention provides a method of determining the likelihood that a patient with a tumor will show relatively long survival benefit from therapy with an IGF-1R kinase inhibitor, comprising determining the level of a sensitivity biomarker in the cells of the tumor, comparing said level with the level of sensitivity biomarker expression in a non-tumor control, or to the level of a control polypeptide or nucleic acid in the tumor sample, and determining whether the cells of the tumor contain a relatively high level of the sensitivity biomarker, a high level being indicative that a patient with a tumor will show relatively long survival benefit from therapy with an IGF-1R kinase inhibitor.

The present invention provides a method of determining the likelihood that a patient with a tumor will show relatively long survival benefit from therapy with an IGF-1R kinase inhibitor, comprising determining the level of a resistance biomarkers in the cells of the tumor, comparing said level with the level of resistance biomarker expression in a non-tumor control, or to the level of a control polypeptide or nucleic acid in the tumor sample, and determining whether the cells of the tumor contain a relatively low level of the resistance biomarker, a low level being indicative that a patient with a tumor will show relatively long survival benefit from therapy with an IGF-1R kinase inhibitor.

The present invention provides a method for determining for a patient with a tumor the likelihood that said patient will show relatively long survival benefit from therapy with an IGF-1R kinase inhibitor, comprising: determining the level of a sensitivity biomarker in the cells of the tumor, comparing said level with the level of sensitivity biomarker expression in a non-tumor control, or to the level of a control polypeptide or nucleic acid in the tumor sample, and determining whether the cells of the tumor contain a relatively high level of the sensitivity biomarkers; determining the level of a resistance biomarker in the cells of the tumor, comparing said level with the level of resistance biomarker expression in a non-tumor control, or to the level of a control polypeptide or nucleic acid in the tumor sample, and determining whether the cells of the tumor contain a relatively low level of the resistance biomarker, wherein a high level of the sensitivity biomarker and a low level of the resistance biomarker is indicative that a patient with a tumor will show relatively long survival benefit from therapy with an IGF-1R kinase inhibitor.

The present invention provides a method of determining a prognosis for survival for a patient with a neoplastic condition in response to therapy with an IGF-1R kinase inhibitor, comprising: measuring the level of an sensitivity biomarker associated with neoplastic cells, and comparing said level of sensitivity biomarker to a non-neoplastic sensitivity biomarker reference level, or to the level of a control polypeptide or nucleic acid associated with the neoplastic cells, wherein a decreased level of sensitivity biomarker associated with the neoplastic cells correlates with decreased survival of said patient.

The present invention provides a method of determining a prognosis for survival for a patient with a neoplastic condition in response to therapy with an IGF-1R kinase inhibitor, comprising: measuring the level of an resistance biomarker associated with neoplastic cells, and comparing said level of resistance biomarker to a non-neoplastic resistance biomarker reference level, or to the level of a control polypeptide or nucleic acid associated with the neoplastic cells, wherein an increased level of resistance biomarker associated with the neoplastic cells correlates with decreased survival of said patient.

The present invention also provides methods of predicting which tumor cells will be inhibited in a synergistic manner by treatment with a combination of an IGF-1R inhibitor and an anti-cancer agent, wherein the anticancer agent is SN38, oxaliplatin, or 5-Fluorouracil, by determining tumor cell sensitivity or resistance biomarker expression. Tumor cells predicted to be sensitive to an IGF-1R kinase inhibitor will also be inhibited in a synergistic manner by treatment with a combination of an IGF-1R inhibitor and an anti-cancer agent. Thus any of the methods described herein for predicting the sensitivity of tumor cells to an IGF-1R kinase inhibitor will also predict which tumor cells will be inhibited in a synergistic manner by treatment with a combination of an IGF-1R inhibitor and an anti-cancer agent, wherein the anticancer agent is SN38, oxaliplatin, or 5-Fluorouracil.

The present invention thus provides a method of predicting whether tumor cells of a patient will be inhibited in a synergistic manner by treatment with a combination of an IGF-1R inhibitor and an anti-cancer agent, wherein the anticancer agent is SN38, oxaliplatin, or 5-Fluorouracil, comprising: assessing the level of a resistance biomarker expressed by the tumor cell; and predicting the likelihood that tumor cell growth inhibition by the IGF-1R kinase inhibitor anti-cancer agent combination will be synergistic, wherein low levels of resistance biomarker expression by tumor cells correlates with a high probability that inhibition by the IGF-1R kinase inhibitor anti-cancer agent combination will be synergistic.

The present invention also provides a method of predicting whether tumor cells of a patient will be inhibited in a synergistic manner by treatment with a combination of an IGF-1R inhibitor and an anti-cancer agent, wherein the anticancer agent is SN38, oxaliplatin, or 5-Fluorouracil, comprising:

assessing the level of a sensitivity biomarker expressed by the tumor cell; and predicting the likelihood that tumor cell growth inhibition by the IGF-1R kinase inhibitor anti-cancer agent combination will be synergistic, wherein high levels of resistance biomarker expression by tumor cells correlates with a high probability that inhibition by the IGF-1R kinase inhibitor anti-cancer agent combination will be synergistic.

The present invention also provides a method for treating tumors or tumor metastases in a patient with an IGF-1R kinase inhibitor chemotherapy combination, comprising the steps of: predicting whether the tumor cells of the patient will be inhibited in a synergistic manner by treatment with a combination of an IGF-1R kinase inhibitor and an anti-cancer agent, wherein the anticancer agent is SN38, oxaliplatin, or 5-Fluorouracil, by assessing the level of a resistance biomarker expressed by the tumor cells, wherein low levels of resistance biomarker expression by tumor cells correlates with a high probability that inhibition by the IGF-1R kinase inhibitor chemotherapy combination will be synergistic, and administering to said patient a therapeutically effective amount of a combination of an IGF-1R kinase inhibitor and one of SN38, oxaliplatin, or 5-Fluorouracil if the patient is diagnosed to be potentially responsive to the IGF-1R kinase inhibitor chemotherapy combination in a synergistic manner. In one embodiment of this method the IGF-1R kinase inhibitor administered to said patient is OSI-906. In another embodiment the tumor cells are NSCL, colon, breast, ovarian, head and neck, or pancreatic tumor cells.

The present invention also provides a method for treating tumors or tumor metastases in a patient with an IGF-1R kinase inhibitor chemotherapy combination, comprising the steps of: predicting whether the tumor cells of the patient will be inhibited in a synergistic manner by treatment with a combination of an IGF-1R kinase inhibitor and an anti-cancer agent, wherein the anticancer agent is SN38, oxaliplatin, or 5-Fluorouracil, by assessing the level of a sensitivity biomarker expressed by the tumor cells, wherein high levels of sensitivity biomarker expression by tumor cells correlates with a high probability that inhibition by the IGF-1R kinase inhibitor chemotherapy combination will be synergistic, and administering to said patient a therapeutically effective amount of a combination of an IGF-1R kinase inhibitor and one of SN38, oxaliplatin, or 5-Fluorouracil if the patient is diagnosed to be potentially responsive to the IGF-1R kinase inhibitor chemotherapy combination in a synergistic manner. In one embodiment the IGF-1R kinase inhibitor administered to said patient is OSI-906. In another embodiment the tumor cells are NSCL, colon, breast, ovarian, head and neck, or pancreatic tumor cells.

The present invention also provides a method of predicting whether tumor cells have developed resistance to inhibition by an IGF-1R kinase inhibitor, comprising: assessing the level of a resistance biomarker expressed by a tumor cell; and predicting the sensitivity of tumor cell growth to inhibition by an IGF-1R kinase inhibitor, wherein high levels of the resistance biomarker expression by tumor cells correlates with low sensitivity to inhibition by IGF-1R kinase inhibitors, and thus resistance to inhibition by an IGF-1R kinase inhibitor. In one embodiment of this method the resistance biomarker is selected from caldesmon 1 (CALD1, GeneID: 800); kelch-like 5 (*Drosophila*) (KLHL5, GeneID: 51088); metallothionein 1E (functional) (MT1E, GeneID: 4493); beta-1,3-N-acetylgalactosaminyltransferase 1 (globoside blood group) (B3GALNT1, GeneID: 8706); cysteine-rich, angiogenic inducer, 61 (CYR61, GeneID: 3491); metallothionein 1X (MT1X, GeneID: 4501); troponin T type 1 (skeletal, slow) (TNNT1, GeneID: 7138); metallothionein 1H-like protein/// hypothetical protein LOC650610 (MT1P2, GeneID: 645745); metallothionein 1H (MT1H, GeneID: 4496); metallothionein 1F (functional) (MT1F, GeneID: 4494); metallothionein 2A (MT2A, GeneID: 4502); metallothionein 1M (MT1M, GeneID: 4499); MHC class I polypeptide-related sequence B (MICB, GeneID: 4277); collagen, type VI, alpha 1 (COL6A1, GeneID: 1291); myosin, light polypeptide 9, regulatory (MYL9, GeneID: 10398); and metallothionein 1G (MT1G, GeneID: 4495). The method can also be incorporated into a treatment regimen such that the method is used to predict if resistance to an IGF-1R kinase inhibitor has developed prior to administration of further doses of the IGF-1R kinase inhibitor being administered. If resistance has not developed then further doses of the IGF-1R kinase inhibitor are indicated, assuming that goals for efficacy and lack of toxicity are being met. If resistance has developed then further doses of the IGF-1R kinase inhibitor may be contra-indicated, and the physician may choose to treat with another anti-cancer agent or treatment.

The data presented in the Experimental Details section herein below, using the K-TSP algorithm as a discriminative classifier, identified three human gene pairs, (PROM1 (GeneID: 8842), MT1E (GeneID: 4493)), (LY75 (GeneID: 4065), OXCT1 (GeneID: 5019)) and (HSD17B2 (GeneID: 3294), CALD1 (GeneID: 800)), that can be utilized in predicting the sensitivity of tumor cell growth (e.g. colorectal tumor cells) to IGF-1R kinase inhibitors (e.g. PQIP, OSI-906). Thus, if the expression of the first member of each of these gene pairs is greater than the expression of the second member, tumor cell growth is likely to be sensitive to an IGF-1R kinase inhibitor.

The present invention thus provides a method of predicting the sensitivity of tumor cell growth to an IGF-1R kinase inhibitor, comprising: assessing the level of the gene MT1E expressed by the tumor cells; assessing the level of the gene PROM1 expressed by the tumor cells; determining whether the tumor cells express a higher level of PROM1 than MT1E; and predicting that tumor cell growth is likely to be sensitive to an IGF-1R kinase inhibitor if the tumor cells express a higher level of PROM1 than MT1E. This method may be utilized to select a cancer patient who is predicted to benefit from therapeutic administration of an IGF-1R kinase inhibitor, by applying it to a sample of the cells of a tumor of the patient (e.g. a tumor biopsy, or circulating tumor cells isolated from a blood sample), either alone, or in addition to other diagnostic tests to predict response to administration of an IGF-1R kinase inhibitor. The present invention thus provides a method of identifying patients with cancer who are most likely to benefit from treatment with an IGF-1R kinase inhibitor, comprising: obtaining a sample of the patient's tumor; assessing the level of the gene MT1E expressed by the tumor cells; assessing the level of the gene PROM1 expressed by the tumor cells; determining whether the tumor cells express a higher level of PROM1 than MT1E; and identifying the patient as one most likely to benefit from treatment with an IGF-1R kinase inhibitor if the tumor cells express a higher level of PROM1 than MT1E.

The present invention thus provides a method of predicting the sensitivity of tumor cell growth to an IGF-1R kinase inhibitor, comprising: assessing the level of the gene OXCT1 expressed by the tumor cells; assessing the level of the gene LY75 expressed by the tumor cells; determining whether the tumor cells express a higher level of LY75 than OXCT1; and predicting that tumor cell growth is likely to be sensitive to an IGF-1R kinase inhibitor if the tumor cells express a higher level of LY57 than OXCT1. This method may be utilized to select a cancer patient who is predicted to benefit from therapeutic administration of an IGF-1R kinase inhibitor, by applying it to a sample of the cells of a tumor of the patient (e.g. a tumor biopsy, or circulating tumor cells isolated from a blood sample), either alone, or in addition to other diagnostic tests to predict response to administration of an IGF-1R kinase inhibitor. The present invention thus provides a method of identifying patients with cancer who are most likely to benefit from treatment with an IGF-1R kinase inhibitor, comprising: obtaining a sample of the patient's tumor; assessing the level of the gene OXCT1 expressed by the tumor cells; assessing the level of the gene LY75 expressed by the tumor cells; determining whether the tumor cells express a higher level of LY75 than OXCT1; and identifying the patient as one most likely to benefit from treatment with an IGF-1R kinase inhibitor if the tumor cells express a higher level of LY75 than OXCT1.

The present invention thus provides a method of predicting the sensitivity of tumor cell growth to an IGF-1R kinase inhibitor, comprising: assessing the level of the gene CALD1 expressed by the tumor cells; assessing the level of the gene HSD17B2 expressed by the tumor cells; determining whether the tumor cells express a higher level of HSD17B2 than CALD1; and predicting that tumor cell growth is likely to be sensitive to an IGF-1R kinase inhibitor if the tumor cells express a higher level of HSD17B2 than CALD1. This method may be utilized to select a cancer patient who is predicted to benefit from therapeutic administration of an IGF-1R kinase inhibitor, by applying it to a sample of the cells of a tumor of the patient (e.g. a tumor biopsy, or circulating tumor cells isolated from a blood sample), either alone, or in addition to other diagnostic tests to predict response to administration of an IGF-1R kinase inhibitor. The present invention thus provides a method of identifying patients with cancer who are most likely to benefit from treatment with an IGF-1R kinase inhibitor, comprising: obtaining a sample of the patient's tumor; assessing the level of the gene CALD1 expressed by the tumor cells; assessing the level of the gene HSD17B2 expressed by the tumor cells; determining whether the tumor cells express a higher level of HSD17B2 than CALD1; and identifying the patient as one most likely to benefit from treatment with an IGF-1R kinase inhibitor if the tumor cells express a higher level of HSD17B2 than CALD1.

Determination of the gene expression level for each of the genes of the three gene pairs, (PROM1, MT1E), (LY75, OXCT1) and (HSD17B2, CALD1), can be accomplished by any of the methods known in the art for assessing the expression level of genes, as for example described herein for biomarkers. In a preferred embodiment, the level of mRNA expressed by the gene is determined. In an alternative embodiment, the level of protein expressed by the gene is determined.

The data presented in the Experimental Details section herein below demonstrates that tumor cells, such as CRC (colorectal cancer) cells, show a range of sensitivities to growth inhibition by an IGF-1R kinase inhibitor (e.g. PQIP, OSI-906) and that the degree of sensitivity of tumor cells to an IGF-1R kinase inhibitor can be assessed by determining the presence of mutant K-RAS in the tumor cells, such that the presence of mutant K-RAS is indicative that the cells are likely to have low sensitivity, or be relatively resistant, to growth inhibition by an IGF-1R kinase inhibitor, or conversely, the absence of mutant K-RAS (i.e. wild type K-RAS) is indicative that the cells are likely to have high sensitivity to growth inhibition by an IGF-1R kinase inhibitor.

The present invention thus provides a method of predicting the sensitivity of tumor cell growth to an IGF-1R kinase inhibitor, comprising: determining whether the tumor cells possess a mutant K-RAS gene; and predicting that tumor cell growth is likely to be sensitive to an IGF-1R kinase inhibitor if the tumor cells do not possess a mutant K-RAS gene. This method may be utilized to select a cancer patient who is predicted to benefit from therapeutic administration of an IGF-1R kinase inhibitor, by applying it to a sample of the cells of a tumor of the patient (e.g. a tumor biopsy, or circulating tumor cells isolated from a blood sample), either alone, or in addition to other diagnostic tests to predict response to administration of an IGF-1R kinase inhibitor. The present invention thus provides a method of identifying patients with cancer who are most likely to benefit from treatment with an IGF-1R kinase inhibitor, comprising: obtaining a sample of the patient's tumor; determining whether the tumor cells possess a mutant K-RAS gene; and identifying the patient as one most likely to benefit from treatment with an IGF-1R kinase inhibitor if the tumor cells do not possess a mutant K-RAS gene. The mutant K-RAS gene may be a K-RAS gene (GeneID: 3845) with an activating mutation at any one of seven known KRAS point mutations in codons 12 and 13 as follows: Gly12Asp (GGT>GAT), Gly12Ala (GGT>GCT), Gly12Val (GGT>GTT), Gly12Ser (GGT>AGT), Gly12Arg (GGT>CGT), Gly12Cys (GGT>TGT), and Gly13Asp (GGC>GAC)). Inherent in this method is the recognition that expression of a mutant KRAS gene in tumor cells correlates with lower sensitivity of the tumor cells to growth inhibition by an IGF-1R kinase inhibitor than tumor cells that have wild type KRAS.

In any of the methods described herein the IGF-1R kinase inhibitor may be a small molecule kinase inhibitor, such as a compound of Formula I as disclosed herein, such as for example OSI-906, or an anti-IGF-1R antibody. The tumor cells of the patient may be NSCL, colon, CRC, breast, ovarian, head and neck, or pancreatic tumor cells. In one embodiment, one or more additional anti-cancer agents may be co-administered simultaneously or sequentially with the IGF-1R kinase inhibitor. Such additional anti-cancer agents may for example comprise an EGFR kinase inhibitor (e.g. erlotinib, an anti-EGFR antibody), or any of the other anti-cancer agents described herein.

The data presented in the Experimental Details section herein below also demonstrates that tumor cells, such as CRC (colorectal cancer) cells, displaying an increase in IGF-1R gene copy number (or genomic gain, i.e. unbalanced genomic gain) are predicted to be especially responsive to treatment with IGF-1R kinase inhibitors (e.g. PQIP, OSI-906), and therefore patients having tumors with such cells are the best candidates for the use of this line of therapy. In contrast, patients having tumors with little or no gain in copy number of the IGF-1R gene are predicted to have a poorer outcome to treatment with IGF-1R kinase inhibitors, as their tumor cells are more resistant to inhibition. IGF-1R gene copy number thus represents an additional "sensitivity" biomarker that can be used to predict the sensitivity of tumor cell growth to inhibition by an IGF-1R kinase inhibitor. Assessment or quantitation of the expression level or amount of this biomarker (i.e. IGF-1R gene copy number) in tumor cells can thus be used to assist with patient selection for potential treatment with an IGF-1R kinase inhibitor.

The present invention thus provides a method of predicting the sensitivity of tumor cell growth to an IGF-1R kinase inhibitor, comprising: assessing IGF-1R gene copy number in the tumor cells; determining if there is an increased IGF-1R gene copy number (i.e. unbalanced gain when normalized to ploidy); and predicting that tumor cell growth is likely to be sensitive to an IGF-1R kinase inhibitor if the tumor cells have increased IGF-1R gene copy number. The present invention also provides a method of identifying patients with cancer who are most likely to benefit from treatment with an IGF-1R kinase inhibitor, comprising: obtaining a sample of the patient's tumor; assessing IGF-1R gene copy number in the tumor cells; determining if there is an increased IGF-1R gene copy number relative to ploidy; and identifying the patient as one most likely to benefit from treatment with an IGF-1R kinase inhibitor if the tumor cells have increased IGF-1R gene copy number.

In the studies presented herein, IGF-1R gene copy number was studied by FISH because this method presents several advantages, although the practice of the present invention is not limited to this technique. FISH is DNA-based and can be successfully performed in fresh or preserved paraffin-embedded tumor samples. The technology is well established, has short turn-around in clinical cytogenetics and molecular pathology laboratories, and an IGF-1R FISH probe is available, and could readily be made commercially available. These results thus support the routine use of IGF-1R-FISH analysis and related techniques (e.g. CISH, SISH) for selecting patients for IGF-1R kinase inhibitor (e.g. OSI-906) therapy.

The methods and test kits provided by the present invention are extremely useful for patients with any cancer that can be treated with IGF-1R kinase inhibitors, such as NSCLC, CRC, breast cancer, ovarian cancer, head and neck cancer, pancreatic cancer etc. Such patients might, as a result of the methods provided herein, be spared from side effects and financial costs of an ineffective therapy in the event that they do not have genomic gain affecting the IGF-1R locus.

The copy number of genes in tumor cells according to the invention can be measured, for example in FISH assays, e.g. in nuclei. Such tests, as well as other detection methods, can be performed in primary tumors, metastatic tumors, locally recurring tumors, sputum, bronchial lavage, ascites, spinal fluid, or other tumoral settings. The markers can be measured in tumor specimens that are fresh, frozen, fixed or otherwise preserved. Quantitation of the gene copy number according to the present invention can also be accomplished using a variety of other types of hybridization assays well known in the art, and described herein, e.g. CISH (Chromogenic In Situ Hybridization), SISH (Silver In Situ Hybridization), PCR based techniques, genomic arrays including SNPs.

The nucleotide sequence of the human IGF-1R gene (GeneID: 3480) is known in the art and can be found under GenBank Accession No. NC_000015 (incorporated herein by reference), for example. Nucleotide probes are also known in the art and available for use as probes to detect IGF-1R genes. For example, probes for detecting both IGF-1R and chromosome 15 centromere sequences are available, as described herein.

In the methods of this invention, the level or amount of IGF-1R gene copy number in the tumor cell sample may be compared to a control level of IGF-1R gene copy number selected from: (i) a control level that has been correlated with sensitivity to an IGF-1R kinase inhibitor (e.g. PQIP, OSI-906); and (ii) a control level that has been correlated with resistance to the IGF-1R kinase inhibitor. A patient is selected as being predicted to benefit from therapeutic administration of an IGF-1R kinase inhibitor, if the level of IGF-1R gene copy number in the patient's tumor cells is statistically similar to or greater than the control level of IGF-1R gene copy number that has been correlated with sensitivity to the IGF-1R kinase inhibitor, or if the level of IGF-1R gene copy number in the patient's tumor cells is statistically greater than the level of IGF-1R gene copy number that has been correlated with resistance to the IGF-1R kinase inhibitor. A patient is selected as being predicted to not benefit from therapeutic administration of an IGF-1R kinase inhibitor, if the level of IGF-1R gene copy number in the patient's tumor cells is statistically less than the control level of IGF-1R gene copy number that has been correlated with sensitivity to the IGF-1R kinase inhibitor, or if the level of IGF-1R gene copy number in the patient's tumor cells is statistically similar to or less than the level of IGF-1R gene copy number that has been correlated with resistance to the IGF-1R kinase inhibitor. The IGF-1R kinase inhibitor sensitive or resistant tumor cells listed in FIGS. 1 and 2 are examples of cells that may be used for control levels of IGF-1R gene copy number. Preferred resistant tumor cells for determining control levels of IGF-1R gene copy number include for example HCT116, HCT15, HCT8, LS174T, and RKO. Preferred sensitive tumor cells for determining control levels of IGF-1R gene copy number include for example Colo205, HT29, CaCo2, and LS513.

More specifically, according to the present invention, a "control level" is a control level of IGF-1R gene copy number, which can include a level that is correlated with sensitivity to the IGF-1R kinase inhibitor or a level that is correlated with resistance to the IGF-1R kinase inhibitor. Therefore, it can be determined, as compared to the control or baseline level of IGF-1R gene copy number, whether a patient sample is more likely to be sensitive to or resistant to the IGF-1R kinase inhibitor therapy (e.g., a good responder or responder (one who will benefit from the therapy), or a poor responder or non-responder (one who will not benefit or will have little benefit from the therapy)).

The method for establishing a control level of IGF-1R gene copy number is selected based on the sample type, the tissue or organ from which the sample is obtained, and the status of the patient to be evaluated. Preferably, the method is the same method that will be used to evaluate the sample in the patient. In a preferred embodiment, the control level is established using the same cell type as the cell to be evaluated. In a preferred embodiment, the control level is established from control samples that are from patients or cell lines known to be resistant or sensitive to an IGF-1R kinase inhibitor. In one aspect, the control samples are obtained from a population of matched individuals. According to the present invention, the phrase "matched individuals" refers to a matching of the control individuals on the basis of one or more characteristics which are suitable for the type of cell or tumor growth to be evaluated. For example, control individuals can be matched with the patient to be evaluated on the basis of gender, age, race, or any relevant biological or sociological factor that may affect the baseline of the control individuals and the patient (e.g., preexisting conditions, consumption of particular substances, levels of other biological or physiological factors). To establish a control level, samples from a number of matched individuals are obtained and evaluated in the same manner as for the test samples. The number of matched individuals from whom control samples must be obtained to establish a suitable control level (e.g., a population) can be determined by those of skill in the art, but should be statistically appropriate to establish a suitable baseline for comparison with the patient to be evaluated (i.e., the test patient). The values obtained from the control samples are statistically processed using any suitable method of statistical analysis to establish a suitable baseline level using methods standard in the art for establishing such values.

It will be appreciated by those of skill in the art that a control level need not be established for each assay as the assay is performed but rather, a baseline or control can be established by referring to a form of stored information regarding a previously determined control level for sensitive and resistant patients (responders and non-responders), such as a control level established by any of the above-described methods. Such a form of stored information can include, for example, but is not limited to, a reference chart, listing or electronic file of population or individual data regarding sensitive and resistant tumors/patients, or any other source of data regarding control level IGF-1R gene copy number that is useful for the patient to be evaluated. For example, one can use the guidelines established above and further described in the Experimental section for establishing increased IGF-1R gene copy number, which have already been correlated with responsiveness to an IGF-1R kinase inhibitor, to rate a given patient sample.

The invention thus provides a method to select a cancer patient who is predicted to benefit or not benefit from therapeutic administration of an IGF-1R kinase inhibitor, comprising: a) detecting in a sample of tumor cells from a patient a level of a biomarker selected from the group consisting of: i) an expression level or amount of IGF-1R gene copy number; ii) an expression level of a sensitivity biomarker; and iii) an expression level of a resistance biomarker; b) comparing the level of the biomarker in the tumor cell sample to a control level of the biomarker selected from the group consisting of: i) a control level of the biomarker that has been correlated with sensitivity to the IGF-1R kinase inhibitor; and ii) a control level of the biomarker that has been correlated with resistance to the IGF-1R kinase inhibitor; and c) selecting the patient as being predicted to benefit from therapeutic administration of the IGF-1R kinase inhibitor, if the level of the biomarker in the patient's tumor cells is statistically similar to or greater than the control level of the biomarker that has been correlated with sensitivity to the IGF-1R kinase inhibitor, or if the level of the biomarker in the patient's tumor cells is statistically greater than the level of the biomarker that has been correlated with resistance to the IGF-1R kinase inhibitor; or d) selecting the patient as being predicted to not benefit from therapeutic administration of the IGF-1R kinase inhibitor, if the level of the biomarker in the patient's tumor cells is statistically less than the control level of the biomarker that has been correlated with sensitivity to the IGF-1R kinase inhibitor, or if the level of the biomarker in the patient's tumor cells is statistically similar to or less than the level of the biomarker that has been correlated with resistance to the IGF-1R kinase inhibitor. In one embodiment the step of detecting in (a)(i) or (a)(ii) is performed using a nucleotide probe that hybridizes to the IGF-1R gene. In this embodiment, the step of detecting further comprises using a nucleotide probe that hybridizes to chromosome 15 centromere sequences. Alternatively, a chimeric nucleotide probe that hybridizes to the IGF-1R gene and to chromosome 15 centromere sequences may be used.

The invention further provides a method of treating tumors or tumor metastases in a patient, comprising (a) performing the steps of a method to select a cancer patient who is predicted to benefit or not benefit from therapeutic administration of an IGF-1R kinase inhibitor, and (b) administering to said patient a therapeutically effective amount of an IGF-1R kinase inhibitor (e.g. OSI-906) if the patient is predicted to benefit from an IGF-1R kinase inhibitor, or administering to said patient an alternative therapy or no therapy if the patient is not predicted to benefit from administration of an IGF-1R kinase inhibitor.

The invention further provides a method of predicting the sensitivity of tumor cell growth to inhibition by an IGF-1R kinase inhibitor, comprising: assessing the level of IGF-1R gene copy number in a tumor cell; and predicting the sensitivity of tumor cell growth to inhibition by an IGF-1R kinase inhibitor, wherein increased levels of tumor cell IGF-1R gene copy number correlate with high sensitivity to inhibition by IGF-1R kinase inhibitors.

The invention further provides a method for treating tumors or tumor metastases in a patient, comprising the steps of: diagnosing a patient's likely responsiveness to an IGF-1R kinase inhibitor by assessing the IGF-1R gene copy number of the tumor cells of the patient, wherein increased levels of IGF-1R gene copy number in the tumor cells correlates with high sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor. In one embodiment the IGF-1R kinase inhibitor administered to said patient is OSI-906. In another embodiment of the method the tumor cells are NSCL, colon, breast, ovarian, head and neck, or pancreatic tumor cells.

Another embodiment of the invention includes an assay kit for performing any of the methods of the present invention. The assay kit can include a means for detecting in a sample of tumor cells a level of IGF-1R gene copy number, or other biomarker. The assay kit preferably also includes one or more controls. The controls could include: (i) a control sample for detecting sensitivity to the IGF-1R kinase inhibitor being evaluated for use in a patient; (ii) a control sample for detecting resistance to the IGF-1R kinase inhibitor; (iii) information containing a predetermined control level of particular biomarker to be measured with regard to IGF-1R kinase inhibitor sensitivity or resistance (e.g., a predetermined control level of IGF-1R gene copy number, or other biomarker, that has been correlated with sensitivity to the IGF-1R kinase inhibitor or resistance to IGF-1R kinase inhibitor).

The data presented in the Experimental Details section herein below demonstrates that several of the classifiers of sensitivity of tumor cell growth to IGF-1R kinase inhibitors can be integrated together to develop a signature of sensitivity to such inhibitors. These classifiers, or characteristics, of tumor cells that have high sensitivity include the following five classifiers: higher expression level of the PROM1 gene than the MT1E gene; higher expression level of the LY75 gene than the OXCT1 gene; higher expression level of the HSD17B2 gene than the CALD1 gene; IGF-1R gene copy number (i.e. unbalanced gain when normalized to ploidy); and the absence of a mutant K-RAS gene. For an integrated genomic classifier, in order for a tumor cell to predict as sensitive to an IGF-1R kinase inhibitor, at least four of these classifiers must be present in the tumor cells. This integrated genomic classifier was able to correctly predict the IGF-1R kinase inhibitor sensitivity of test tumor cell lines with 89% success rate, and of test human tumor explants with 100% success rate, a superior result to that achieved with any of the individual predictors.

Accordingly, the invention further provides a method of identifying patients with cancer who are most likely to benefit from treatment with an IGF-1R kinase inhibitor, comprising: (1) obtaining a sample of the patient's tumor, (2) determining if tumor cells of the sample exhibit the following classifiers of tumor cells that are more likely to be sensitive to growth inhibition by an IGF-1R kinase inhibitor: (a) higher expression level of the PROM1 gene than the MT1E gene; (b) higher expression level of the LY75 gene than the OXCT1 gene; (c) higher expression level of the HSD17B2 gene than the CALD1 gene; (d) increased IGF-1R gene copy number (i.e. unbalanced gain when normalized to ploidy); (e) the absence of a mutant K-RAS gene; and (3) identifying the patient as one most likely to benefit from treatment with an IGF-1R kinase inhibitor if at least four of the five assessed characteristics are present in the tumor cells. In step 1, obtaining a sample of the patient's tumor may be accomplished, for example, by performing a tumor biopsy, or isolating circulating tumor cells from a blood sample.

The invention further provides the use of the preceding method as part of a treatment regimen in order to determine which patients would most benefit from administration of an IGF-1R kinase inhibitor. Accordingly, the invention further provides a method for treating cancer in a patient, comprising the steps of: (A) diagnosing a patient's likely responsiveness to an IGF-1R kinase inhibitor by determining if the patient has a tumor that is likely to respond to treatment with an IGF-1R kinase inhibitor, by (1) obtaining a sample of the patient's tumor, (2) determining if tumor cells of the sample exhibit the following classifiers of tumor cells that are more likely to be sensitive to growth inhibition by an IGF-1R kinase inhibitor: (a) higher expression level of the PROM1 gene than the MT1E gene; (b) higher expression level of the LY75 gene than the OXCT1 gene; (c) higher expression level of the HSD17B2 gene than the CALD1 gene; (d) increased IGF-1R gene copy number (i.e. unbalanced gain when normalized to ploidy); (e) the absence of a mutant K-RAS gene; and (3) identifying the patient as having a tumor that is likely to likely to respond to treatment with an IGF-1R kinase inhibitor if at least four of the five assessed characteristics are present; and (B) administering to said patient a therapeutically effective amount of an IGF-1R kinase inhibitor if the patient is diagnosed to be potentially responsive to an IGF-1R kinase inhibitor.

The invention further provides a method for treating cancer in a patient, comprising the steps of: (A) diagnosing a patient's likely responsiveness to an IGF-1R kinase inhibitor by determining if the patient has a tumor that is likely to respond to treatment with an IGF-1R kinase inhibitor, by: obtaining a sample of the patient's tumor, determining if tumor cells of the sample exhibit the following classifiers of tumor cells that are more likely to be sensitive to growth inhibition by an IGF-1R kinase inhibitor: (a) higher expression level of the PROM1 gene than the MT1E gene; (b) higher expression level of the LY75 gene than the OXCT1 gene; (c) higher expression level of the HSD17B2 gene than the CALD1 gene; (d) increased levels of IGF-1R gene copy number relative to ploidy; (e) the absence of a mutant K-RAS gene; and identifying the patient as having a tumor that is likely to respond to treatment with an IGF-1R kinase inhibitor if at least four of the five assessed classifiers are present in the tumor cells; and (B) administering to said patient a therapeutically effective amount of an IGF-1R kinase inhibitor if the patient is diagnosed to be potentially responsive to an IGF-1R kinase inhibitor.

The invention further provides an alternative integrated genomic classifier, wherein in order for a tumor cell to predict as sensitive to an IGF-1R kinase inhibitor, at least three of the five classifiers must be present. The invention further provides an integrated genomic classifier, wherein in order for a tumor cell to predict as sensitive to an IGF-1R kinase inhibitor, at least two of the five classifiers must be present. The invention thus provides the corresponding methods using these alternative integrated genomic classifiers, for identifying patients with cancer who are most likely to benefit from treatment with an IGF-1R kinase inhibitor, and methods for treating cancer in a patient, as described above for the integrated genomic classifier.

The invention further provides a method for treating cancer in a patient, comprising the steps of: (A) diagnosing a patient's likely responsiveness to an IGF-1R kinase inhibitor by determining if the patient has a tumor that is likely to respond to treatment with an IGF-1R kinase inhibitor by: obtaining a sample of the patient's tumor; assessing the level of the gene MT1E expressed by the tumor cells; assessing the level of the gene PROM1 expressed by the tumor cells; determining whether the tumor cells express a higher level of PROM1 than MT1E; and identifying the patient as likely to benefit from treatment with an IGF-1R kinase inhibitor if the tumor cells express a higher level of PROM1 than MT1E, and (B) administering to said patient a therapeutically effective amount of an IGF-1R kinase inhibitor if the patient is diagnosed to be potentially responsive to an IGF-1R kinase inhibitor.

The invention further provides a method for treating cancer in a patient, comprising the steps of: (A) diagnosing a patient's likely responsiveness to an IGF-1R kinase inhibitor by determining if the patient has a tumor that is likely to respond to treatment with an IGF-1R kinase inhibitor by: obtaining a sample of the patient's tumor; assessing the level of the gene OXCT1 expressed by the tumor cells; assessing the level of the gene LY75 expressed by the tumor cells; determining whether the tumor cells express a higher level of LY75 than OXCT1; and identifying the patient as likely to benefit from treatment with an IGF-1R kinase inhibitor if the tumor cells express a higher level of LY75 than OXCT1, and (B) administering to said patient a therapeutically effective amount of an IGF-1R kinase inhibitor if the patient is diagnosed to be potentially responsive to an IGF-1R kinase inhibitor.

The invention further provides a method for treating cancer in a patient, comprising the steps of: (A) diagnosing a patient's likely responsiveness to an IGF-1R kinase inhibitor by determining if the patient has a tumor that is likely to respond to treatment with an IGF-1R kinase inhibitor by: obtaining a sample of the patient's tumor; assessing the level of the gene CALD1 expressed by the tumor cells; assessing the level of the gene HSD17B2 expressed by the tumor cells; determining whether the tumor cells express a higher level of HSD17B2 than CALD1; and identifying the patient as likely to benefit from treatment with an IGF-1R kinase inhibitor if the tumor cells express a higher level of HSD17B2 than CALD1, and (B) administering to said patient a therapeutically effective amount of an IGF-1R kinase inhibitor if the patient is diagnosed to be potentially responsive to an IGF-1R kinase inhibitor.

The invention further provides a method for treating cancer in a patient, comprising the steps of: (A) diagnosing a patient's likely responsiveness to an IGF-1R kinase inhibitor by determining if the patient has a tumor that is likely to respond to treatment with an IGF-1R kinase inhibitor by: obtaining a sample of the patient's tumor; assessing IGF-1R gene copy number in the tumor cells; determining if there is an increased IGF-1R gene copy number relative to ploidy; and identifying the patient as likely to benefit from treatment with an IGF-1R kinase inhibitor if the tumor cells have increased IGF-1R gene copy number, and (B) administering to said patient a therapeutically effective amount of an IGF-1R kinase inhibitor if the patient is diagnosed to be potentially responsive to an IGF-1R kinase inhibitor.

The invention further provides a method for treating cancer in a patient, comprising the steps of: (A) diagnosing a patient's likely responsiveness to an IGF-1R kinase inhibitor by determining if the patient has a tumor that is likely to respond to treatment with an IGF-1R kinase inhibitor by: obtaining a sample of the patient's tumor; determining whether the tumor cells possess a mutant K-RAS gene; and identifying the patient as likely to benefit from treatment with an IGF-1R kinase inhibitor if the tumor cells do not possess a mutant K-RAS gene, and (B) administering to said patient a therapeutically effective amount of an IGF-1R kinase inhibitor if the patient is diagnosed to be potentially responsive to an IGF-1R kinase inhibitor.

For assessment of tumor cell sensitivity or resistance biomarker expression, patient samples containing tumor cells, or proteins or nucleic acids produced by these tumor cells, may be used in the methods of the present invention. In these embodiments, the level of expression of the biomarker can be assessed by assessing the amount (e.g. absolute amount or concentration) of the marker in a tumor cell sample, e.g., a tumor biopsy obtained from a patient, or other patient sample containing material derived from the tumor (e.g. blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies may also be subjected to post-collection preparative and storage techniques, e.g., fixation.

In the methods of the invention, one can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the tumor cell (e.g. using a labeled antibody which binds specifically with a cell-surface domain of the protein).

Expression of a biomarkers described in this invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a biomarker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

In another embodiment, expression of a biomarker is assessed by preparing mRNA/cDNA (i.e. a transcribed polynucleotide) from cells in a patient sample, and by hybridizing the mRNA/cDNA with a reference polynucleotide which is a complement of a biomarker nucleic acid, or a fragment thereof. cDNA can, optionally, be amplified using any of a variety of polymerase chain reaction methods prior to hybridization with the reference polynucleotide. Expression of biomarkers can likewise be detected using quantitative PCR to assess the level of expression of the biomarker(s). Alternatively, any of the many known methods of detecting mutations or variants (e.g. single nucleotide polymorphisms, deletions, etc.) of a biomarker of the invention may be used to detect occurrence of a biomarker in a patient.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biomarker nucleic acid. If polynucleotides complementary to or homologous with are differentially detectable on the substrate (e.g. detectable using different chromophores or fluorophores, or fixed to different selected positions), then the levels of expression of a plurality of biomarkers can be assessed simultaneously using a single substrate (e.g. a "gene chip" microarray of polynucleotides fixed at selected positions). When a method of assessing biomarker expression is used which involves hybridization of one nucleic acid with another, it is preferred that the hybridization be performed under stringent hybridization conditions.

When a plurality of biomarkers of the invention are used in the methods of the invention, the level of expression of each biomarker in a patient sample can be compared with the normal level of expression of each of the plurality of biomarkers in non-cancerous samples of the same type (or with biomarker levels in a control cell), either in a single reaction mixture (i.e. using reagents, such as different fluorescent probes, for each biomarker) or in individual reaction mixtures corresponding to each of the biomarkers.

The level of expression of a biomarker in normal (i.e. non-cancerous) human tissue can be assessed in a variety of ways. In one embodiment, this normal level of expression is assessed by assessing the level of expression of the biomarker in a portion of cells which appears to be non-cancerous, and then comparing this normal level of expression with the level of expression in a portion of the tumor cells. Alternately, and particularly as further information becomes available as a result of routine performance of the methods described herein, population-average values for normal expression of the biomarkers of the invention may be used. In other embodiments, the 'normal' level of expression of a biomarker may be determined by assessing expression of the biomarker in a patient sample obtained from a non-cancer-afflicted patient, from a patient sample obtained from a patient before the suspected onset of cancer in the patient, from archived patient samples, and the like.

An exemplary method for detecting the presence or absence of a biomarker protein or nucleic acid in a biological sample involves obtaining a biological sample (e.g. a tumor-associated body fluid) from a test subject and contacting the biological sample with a compound or an agent capable of detecting the polypeptide or nucleic acid (e.g., mRNA, cDNA). The detection methods of the invention can thus be used to detect mRNA, protein, or cDNA, for example, in a biological sample in vitro as well as in vivo. For example, in vitro techniques for detection of mRNA include Northern hybridizations and in situ hybridizations. In vitro techniques for detection of a biomarker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay would involve anchoring the biomarker or probe onto a solid phase support, also referred to as a substrate, and detecting target biomarker/probe complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid phase. The detection of biomarker/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to'directly detect biomarker/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S. and Urbaniczky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the biomarker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N. H., 1998, J. Mol. Recognit. Winter 11(1-6):141-8; Hage, D. S., and Tweed, S. A. J. Chromatogr B Biomed Sci Appl 1997 Oct. 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of biomarker mRNA can be determined both by in situ and by in vitro formats in a biological sample using methods known in the art. The term “biological sample” is intended to include tissues, cells, biological fluids and isolates thereof, isolated from a subject, as Well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 1988, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations may be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or a tumor cell-specific gene that is expressed at a constant level in the tumor cell type of interest. This normalization allows the comparison of the expression level in one sample, e.g., a patient sample, to another sample, e.g., a non-tumor sample, a control sample, or between samples from different sources.

Alternatively, the expression level can be provided as a relative expression level. To determine a relative expression level of a biomarker (e.g. a resistance biomarker), the level of expression of the biomarker is determined for 10 or more samples of normal versus cancer cell isolates (or resistant cell versus sensitive cell isolates), preferably 50 or more samples, prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. A preferred agent for detecting biomarker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term “labeled”, with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbent assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are $^{125}I$ and $^{3}H$. Standard radioactive isotopic labeling procedures include the chloramine T, lactoperoxidase and Bolton-Hunter methods for $^{125}I$ and reductive methylation for $^{3}H$. The term "detectably-labeled" refers to a molecule labeled in such a way that it can be readily detected by the intrinsic enzymic activity of the label or by the binding to the label of another component, which can itself be readily detected.

Enzymes suitable for use in this invention include, but are not limited to, horseradish peroxidase, alkaline phosphatase, (3-galactosidase, glucose oxidase, luciferases, including firefly and renilla, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

The invention also encompasses kits for detecting the presence of a biomarker protein or nucleic acid in a biological sample. Such kits can be used to determine if a subject is suffering from or is at increased risk of developing a tumor that is less susceptible to inhibition by IGF-1R kinase inhibitors. For example, the kit can comprise a labeled compound or agent capable of detecting a biomarker protein or nucleic acid in a biological sample and means for determining the amount of the protein or mRNA in the sample (e.g., an antibody which binds the protein or a fragment thereof, or an oligonucleotide probe which binds to DNA or mRNA encoding the protein). Kits can also include instructions for interpreting the results obtained using the kit.

For antibody-based kits, the kit can comprise, for example: (1) a first antibody (e.g., attached to a solid support) which binds to a biomarker protein; and, optionally, (2) a second, different antibody which binds to either the protein or the first antibody and is conjugated to a detectable label.

For oligonucleotide-based kits, the kit can comprise, for example: (1) an oligonucleotide, e.g., a detectably labeled oligonucleotide, which hybridizes to a nucleic acid sequence encoding a biomarker protein or (2) a pair of primers useful for amplifying a biomarker nucleic acid molecule. The kit can also comprise, e.g., a buffering agent, a preservative, or a protein stabilizing agent. The kit can further comprise components necessary for detecting the detectable label (e.g., an enzyme or a substrate). The kit can also contain a control sample or a series of control samples which can be assayed and compared to the test sample. Each component of the kit can be enclosed within an individual container and all of the various containers can be within a single package, along with instructions for interpreting the results of the assays performed using the kit.

The present invention further provides a method for treating tumors or tumor metastases in a patient, comprising the steps of diagnosing a patient's likely responsiveness to an IGF-1R kinase inhibitor using any of the methods described herein for determining the expression level of tumor cell sensitivity and/or resistance biomarkers, and administering to said patient a therapeutically effective amount of an IGF-1R kinase inhibitor. For this method, an example of a preferred IGF-1R kinase inhibitor would be one with similar characteristics (e.g. selectivity, potency) to PQIP, (e.g. OSI-906, including pharmacologically acceptable salts or polymorphs thereof). In this method one or more additional anti-cancer agents or treatments can be co-administered simultaneously or sequentially with the IGF-1R kinase inhibitor, as judged to be appropriate by the administering physician given the prediction of the likely responsiveness of the patient to an IGF-1R kinase inhibitor, in combination with any additional circumstances pertaining to the individual patient.

It will be appreciated by one of skill in the medical arts that the exact manner of administering to said patient of a therapeutically effective amount of an IGF-1R kinase inhibitor following a diagnosis of a patient's likely responsiveness to an IGF-1R kinase inhibitor will be at the discretion of the attending physician. The mode of administration, including dosage, combination with other anti-cancer agents, timing and frequency of administration, and the like, may be affected by the diagnosis of a patient's likely responsiveness to an IGF-1R kinase inhibitor, as well as the patient's condition and history. Thus, even patients diagnosed with tumors predicted to be relatively insensitive to IGF-1R kinase inhibitors may still benefit from treatment with such inhibitors, particularly in combination with other anti-cancer agents, or agents that may alter a tumor's sensitivity to IGF-1R kinase inhibitors.

The present invention further provides a method for treating tumors or tumor metastases in a patient, comprising the steps of diagnosing a patient's likely responsiveness to an IGF-1R kinase inhibitor by assessing whether the tumor cells are sensitive to inhibition by an IGF-1R kinase inhibitor, by for example any of the methods described herein for determining the expression level of tumor cell sensitivity and/or resistance biomarkers, identifying the patient as one who is likely to demonstrate an effective response to treatment with an IGF-1R kinase inhibitor, and administering to said patient a therapeutically effective amount of an IGF-1R kinase inhibitor. In one embodiment the IGF-1R kinase inhibitor used for treatment comprises OSI-906.

The present invention also provides a method for inhibiting tumor cell growth in a patient, comprising the steps of diagnosing a patient's likely responsiveness to an IGF-1R kinase inhibitor by using any of the methods described herein to predict the sensitivity of tumor cell growth to inhibition by an IGF-1R kinase inhibitor, identifying the patient as one who is likely to demonstrate an effective response to treatment with an IGF-1R kinase inhibitor, and administering to said patient a therapeutically effective amount of an IGF-1R kinase inhibitor. In one embodiment the IGF-1R kinase inhibitor used for treatment comprises OSI-906.

The present invention also provides a method for treating tumors or tumor metastases in a patient, comprising the steps of: diagnosing a patient's likely responsiveness to an IGF-1R kinase inhibitor by assessing the level of a resistance biomarker expressed by the tumor cells of the patient, wherein the resistance biomarker is selected from any of those listed herein (e.g. see FIG. 15), and wherein high levels of expression of the biomarker by tumor cells correlates with low sensitivity to inhibition by IGF-1R kinase inhibitors, and administering to said patient a therapeutically effective amount of an IGF-1R kinase inhibitor if the level of the resistance biomarker expressed by the tumor cells of the patient is low, implying that the patient is potentially responsive to an IGF-1R kinase inhibitor. In one embodiment the IGF-1R kinase inhibitor used for treatment comprises OSI-906.

The present invention also provides a method for treating tumors or tumor metastases in a patient, comprising the steps of: diagnosing a patient's likely responsiveness to an IGF-1R kinase inhibitor by assessing the level of a sensitivity biomarker expressed by the tumor cells of the patient, wherein the sensitivity biomarker is selected from any of those listed herein (e.g. see FIG. 14), and wherein high levels of expression of the biomarker by tumor cells correlates with high sensitivity to inhibition by IGF-1R kinase inhibitors, and administering to said patient a therapeutically effective amount of an IGF-1R kinase inhibitor if the level of the sensitivity biomarker expressed by the tumor cells of the patient is high, implying that the patient is potentially responsive to an IGF-1R kinase inhibitor. In one embodiment the IGF-1R kinase inhibitor used for treatment comprises OSI-906.

The present invention also provides a method for treating tumors or tumor metastases in a patient, comprising the steps of: diagnosing a patient's likely responsiveness to an IGF-1R kinase inhibitor by assessing the level of any of the resistance biomarkers listed herein (e.g. see FIG. 15) expressed by the tumor cells of the patient, wherein high levels of resistance biomarker expression by tumor cells correlates with low sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor (i.e. if low levels of resistance biomarkers predict high sensitivity to inhibition by IGF-1R kinase inhibitors). In one embodiment the IGF-1R kinase inhibitor used for treatment comprises OSI-906. In another embodiment the resistance biomarker is selected from caldesmon 1 (CALD1, GeneID: 800); kelch-like 5 (*Drosophila*) (KLHL5, GeneID: 51088); metallothionein 1E (functional) (MT1E, GeneID: 4493); beta-1,3-N-acetylgalactosaminyltransferase 1 (globoside blood group) (B3GALNT1, GeneID: 8706); cysteine-rich, angiogenic inducer, 61 (CYR61, GeneID: 3491); metallothionein 1X (MT1X, GeneID: 4501); troponin T type 1 (skeletal, slow) (TNNT1, GeneID: 7138); metallothionein 1H-like protein/// hypothetical protein LOC650610 (MT1P2, GeneID: 645745); metallothionein 1H (MT1H, GeneID: 4496); metallothionein IF (functional) (MT1F, GeneID: 4494); metallothionein 2A (MT2A, GeneID: 4502); metallothionein 1M (MT1M, GeneID: 4499); MHC class I polypeptide-related sequence B (MICB, GeneID: 4277); and collagen, type VI, alpha 1 (COL6A1, GeneID: 1291). In the above methods, mRNA or protein expressed by the biomarker gene may be determined.

The present invention also provides a method for treating tumors or tumor metastases in a patient, comprising the steps of: diagnosing a patient's likely responsiveness to an IGF-1R kinase inhibitor by assessing the level of any of the sensitivity biomarkers listed herein (e.g. see FIG. 14) expressed by the tumor cells of the patient, wherein high levels of sensitivity biomarker expression by tumor cells correlates with high sensitivity to inhibition by IGF-1R kinase inhibitors, and administering to said patient a therapeutically effective amount of an IGF-1R kinase inhibitor if the patient is diagnosed to be potentially responsive to an IGF-1R kinase inhibitor (i.e. if high levels of sensitivity biomarkers predict high sensitivity to inhibition by IGF-1R kinase inhibitors). In one embodiment the IGF-1R kinase inhibitor used for treatment comprises OSI-906. In another embodiment the sensitivity biomarker is selected from aldehyde dehydrogenase 1 family, member A1 (ALDH1A1, GeneID: 216); ring finger protein 128 (RNF128, GeneID: 79589); mitogen-activated protein kinase kinase 6 (MAP2K6, GeneID: 5608); and quinolinate phosphoribosyltransferase (nicotinate-nucleotide pyrophosphorylase (carboxylating)) (QPRT, GeneID: 23475). In the above methods, mRNA or protein expressed by the biomarker gene may be determined.

The present invention further provides a method for treating tumors or tumor metastases in a patient, comprising the steps of diagnosing a patient's likely responsiveness to an IGF-1R kinase inhibitor by any of the methods described herein for determining the expression level of tumor cell sensitivity and/or resistance biomarkers, identifying the patient as one who is less likely or not likely to demonstrate an effective response to treatment with an IGF-1R kinase inhibitor, and treating said patient with an anti-cancer therapy other than an IGF-1R kinase inhibitor.

The present invention also provides for any of the methods of treatment with an IGF-1R kinase inhibitor described herein, the method as described but including prior to the step of administering to the patient an IGF-1R kinase inhibitor, an additional step of assessment of the level of IGF-1 and/or IGF-2 (i.e. insulin-like growth factors 1 and/or 2) in the tumor of the patient. Since IGF-1R has been reported to be activated only upon ligand (i.e. IGF-1 and/or IGF-2) binding, if there is no IGF-1R ligand present in a tumor, then even if one or more of the methods of the instant invention predict that it should be sensitive to inhibition by IGF-1R kinase inhibitors, the tumor cells cannot under such circumstances be relying on the IGF-1R signaling pathway for growth and survival, and thus an IGF-1R kinase inhibitor would probably not be an effective treatment. Many tumors have been found to express elevated levels of IGF-1 and/or IGF-2 (Pollack, M. N. et al. (2004) Nature Reviews Cancer 4:505-518), which could originate from the tumor cells themselves, from stromal cells present in the tumor, or via the vascular system from non-tumor cells (e.g. liver cells). Assessment of the level of IGF-1 and/or IGF-2 can be performed by any method known in the art, such as for example any of the methods described herein for assessment of biomarkers levels, e.g. immunoassay determination of IGF-1 and/or IGF-2 protein levels; determination of IGF-1 and/or IGF-2 mRNA transcript levels. In an alternative embodiment, the of step of assessment of the level of IGF-1 and/or IGF-2 (i.e. insulin-like growth factors 1 and/or 2) in the tumor of the patient can be replaced with a step of assessment of the level of IGF-1 and/or IGF-2 (i.e. insulin-like growth factors 1 and/or 2) in the blood or serum of the patient. This alternative, though not a direct measure of the level of IGF-1 and/or IGF-2 in the tumor, can give an indication of the potential availability of ligand to the IGF-1R in the tumor, and is a simpler and less expensive test. The potential disadvantage of this indirect assessment of IGF-1 and/or IGF-2 is that it may not give a true indication of the levels of ligand in the tumor if IGF-1 and/or IGF-2 is produced locally in the tumor, either by the tumor cells themselves, or by stromal cells within the tumor.

Accordingly, the invention provides a method for treating tumors or tumor metastases in a patient, comprising the steps of: diagnosing a patient's likely responsiveness to an IGF-1R kinase inhibitor, by assessing the level of a sensitivity and/or resistance biomarker expressed by a tumor cell, wherein high expression levels of a sensitivity biomarker correlates with high sensitivity to inhibition by IGF-1R kinase inhibitors, and wherein a high expression levels of an resistance biomarker correlates with low sensitivity to inhibition by IGF-1R kinase inhibitors; assessing the level of IGF-1 and/or IGF-2 in the tumor (or blood or serum) of the patient; and administering to said patient a therapeutically effective amount of an IGF-1R kinase inhibitor if the patient is diagnosed to be potentially responsive to an IGF-1R kinase inhibitor, and the tumor is determined to have IGF-1 and/or IGF-2 (or blood or serum levels indicate the potential availability of IGF-1 and/or IGF-2 to the tumor cells). In the context of this method, where more than one biomarker is assessed for predicting sensitivity to IGF-1R kinase inhibitors, the patient is diagnosed to be potentially responsive to an IGF-1R kinase inhibitor if at least one of the biomarkers indicates potential sensitivity.

The present invention also provides a method for treating tumors or tumor metastases in a patient, comprising the steps of: diagnosing a patient's likely responsiveness to an IGF-1R kinase inhibitor, by assessing the level of a resistance and/or sensitivity biomarker indicative of whether the tumor cells are sensitive to inhibition by an IGF-1R kinase inhibitor; assessing the level of IGF-1 and/or IGF-2 in the tumor of the patient; and administering to said patient a therapeutically effective amount of an IGF-1R kinase inhibitor if the patient is diagnosed to be potentially responsive to an IGF-1R kinase inhibitor, and the tumor is determined to have IGF-1 and/or IGF-2.

The present invention further provides a method of identifying a sensitivity biomarker whose expression level is predictive of the sensitivity of tumor cell growth to inhibition by an IGF-1R kinase inhibitor, comprising: (a) measuring the expression level of a candidate sensitivity biomarker in a panel of tumor cells that displays a range of sensitivities to an IGF-1R kinase inhibitor, and (b) identifying a correlation between the expression level of said candidate sensitivity biomarker in the tumor cells and the sensitivity of tumor cell growth to inhibition by the IGF-1R kinase inhibitor, wherein a correlation of high levels of the sensitivity biomarker with high sensitivity of tumor cell growth to inhibition by the IGF-1R kinase inhibitor indicates that the expression level of said sensitivity biomarker is predictive of the sensitivity of tumor cell growth to inhibition by an IGF-1R kinase inhibitor. In one embodiment of this method the panel of tumor cells is a panel of tumor cell lines. In an alternative embodiment the panel of tumor cells is a panel of primary tumor cells, prepared from tumor samples derived from patients or experimental animal models. In an additional embodiment the panel of tumor cells is a panel of tumor cell lines in mouse xenografts, wherein tumor cell growth can for example be determined by monitoring a molecular marker of growth or a gross measurement of tumor growth, e.g. tumor dimensions or weight.

The present invention further provides a method of identifying a resistance biomarker whose expression level is predictive of the sensitivity of tumor cell growth to inhibition by an IGF-1R kinase inhibitor, comprising: (a) measuring the expression level of a candidate resistance biomarker in a panel of tumor cells that displays a range of sensitivities to an IGF-1R kinase inhibitor, and (b) identifying a correlation between the expression level of said candidate resistance biomarker in the tumor cells and the sensitivity of tumor cell growth to inhibition by the IGF-1R kinase inhibitor, wherein a correlation of high levels of the resistance biomarker with low sensitivity of tumor cell growth to inhibition by the IGF-1R kinase inhibitor indicates that the expression level of said resistance biomarker is predictive of the lack of sensitivity of tumor cell growth to inhibition by an IGF-1R kinase inhibitor. In one embodiment of this method the panel of tumor cells is a panel of tumor cell lines. In an alternative embodiment the panel of tumor cells is a panel of primary tumor cells, prepared from tumor samples derived from patients or experimental animal models. In an additional embodiment the panel of tumor cells is a panel of tumor cell lines in mouse xenografts, wherein tumor cell growth can for example be determined by monitoring a molecular marker of growth or a gross measurement of tumor growth, e.g. tumor dimensions or weight.

The present invention further provides a method of identifying an sensitivity biomarker that is diagnostic for more effective treatment of a neoplastic condition with an IGF-1R kinase inhibitor, comprising: (a) measuring the level of a candidate sensitivity biomarker in neoplastic cell-containing samples from patients with a neoplastic condition, and (b) identifying a correlation between the level of said candidate sensitivity biomarker in the sample from the patient with the effectiveness of treatment of the neoplastic condition with an IGF-1R kinase inhibitor, wherein a correlation of high levels of the sensitivity biomarker with more effective treatment of the neoplastic condition with an IGF-1R kinase inhibitor indicates that said sensitivity biomarker is diagnostic for more effective treatment of the neoplastic condition with an IGF-1R kinase inhibitor.

The present invention further provides a method of identifying a resistance biomarker that is diagnostic for less effective treatment of a neoplastic condition with an IGF-1R kinase inhibitor, comprising: (a) measuring the level of a candidate resistance biomarker in neoplastic cell-containing samples from patients with a neoplastic condition, and (b) identifying a correlation between the level of said candidate resistance biomarker in the sample from the patient with the effectiveness of treatment of the neoplastic condition with an IGF-1R kinase inhibitor, wherein a correlation of high levels of the resistance biomarker with less effective treatment of the neoplastic condition with an IGF-1R kinase inhibitor indicates that said resistance biomarker is diagnostic for less effective treatment of the neoplastic condition with an IGF-1R kinase inhibitor.

The effectiveness of treatment in the preceding methods can for example be determined by measuring the decrease in size of tumors present in the patients with the neoplastic condition, or by assaying a molecular determinant of the degree of proliferation of the tumor cells.

The present invention provides a method of identifying an sensitivity biomarker that is diagnostic for increased survival of a patient with a neoplastic condition when treated with an IGF-1R kinase inhibitor, comprising: (a) measuring the level of the candidate sensitivity biomarker in neoplastic cell-containing samples from patients with a neoplastic condition, and (b) identifying a correlation between the level of said candidate sensitivity biomarker in the sample from the patient with the survival of that patient when treated with an IGF-1R kinase inhibitor, wherein the correlation of an sensitivity biomarker with survival in said patients indicates said sensitivity biomarker is diagnostic for increased survival of a patient with said neoplastic condition when treated with an IGF-1R kinase inhibitor.

The present invention provides a method of identifying a resistance biomarker that is diagnostic for decreased survival of a patient with a neoplastic condition when treated with an IGF-1R kinase inhibitor, comprising: (a) measuring the level of the candidate resistance biomarker in neoplastic cell-containing samples from patients with a neoplastic condition, and (b) identifying an inverse correlation between the level of said candidate resistance biomarker in the sample from the patient with the survival of that patient when treated with an IGF-1R kinase inhibitor, wherein the inverse correlation of a resistance biomarker with survival in said patients indicates said resistance biomarker is diagnostic for decreased survival of a patient with said neoplastic condition when treated with an IGF-1R kinase inhibitor.

The present invention further provides any of the methods described herein for treating tumors or tumor metastases in a patient comprising administering to the patient a therapeutically effective amount of an IGF-1R kinase inhibitor, and in addition, simultaneously or sequentially, one or more other cytotoxic, chemotherapeutic or anti-cancer agents, or compounds that enhance the effects of such agents.

In the context of this invention, additional other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6MP), 6-thiocguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

The present invention further provides any of the methods described herein for treating tumors or tumor metastases in a patient comprising administering to the patient a therapeutically effective amount of an IGF-1R kinase inhibitor, and in addition, simultaneously or sequentially, one or more anti-hormonal agents. As used herein, the term "anti-hormonal agent" includes natural or synthetic organic or peptidic compounds that act to regulate or inhibit hormone action on tumors.

Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g ANTIDEi®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide (2-methyl-N-[4,20-nitro-3-(trifluoromethyl)phenylpropanamide), commercially available as EULEXIN® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

The present invention further provides any of the methods described herein for treating tumors or tumor metastases in a patient comprising administering to the patient a therapeutically effective amount of an IGF-1R kinase inhibitor, and in addition, simultaneously or sequentially, one or more angiogenesis inhibitors.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 41,530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix-metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606,046, and 931,788; Great Britain Patent Publication No.

9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

The present invention further provides any of the methods described herein for treating tumors or tumor metastases in a patient comprising administering to the patient a therapeutically effective amount of an IGF-1R kinase inhibitor, and in addition, simultaneously or sequentially, one or more tumor cell pro-apoptotic or apoptosis-stimulating agents.

The present invention further provides any of the methods described herein for treating tumors or tumor metastases in a patient comprising administering to the patient a therapeutically effective amount of an IGF-1R kinase inhibitor, and in addition, simultaneously or sequentially, one or more signal transduction inhibitors.

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); EGFR kinase inhibitors (see herein below); ras inhibitors; raf inhibitors; MEK inhibitors; mTOR inhibitors, including mTOR inhibitors that bind to and directly inhibits both mTORC1 and mTORC2 kinases; mTOR inhibitors that are dual PI3K/mTOR kinase inhibitors, such as for example the compound PI-103 as described in Fan, Q-W et al (2006) Cancer Cell 9:341-349 and Knight, Z. A. et al. (2006) Cell 125:733-747; mTOR inhibitors that are dual inhibitors of mTOR kinase and one or more other PIKK (or PIK-related) kinase family members. Such members include MEC1, TEL1, RAD3, MEI-41, DNA-PK, ATM, ATR, TRRAP, PI3K, and PI4K kinases; cyclin dependent kinase inhibitors; protein kinase C inhibitors; PI-3 kinase inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

EGFR inhibitors include, for example: [6,7-bis(2-methoxyethoxy)-4-quinazolin-4-yl]-(3-ethynylphenyl)amine (also known as OSI-774, erlotinib, or TARCEVA™ (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); gefitinib (also known as ZD1839 or IRESSA™; Astrazeneca) (Woodburn et al., 1997, Proc. Am. Assoc. Cancer Res. 38:633); and antibody-based EGFR kinase inhibitors. A particularly preferred low molecular weight EGFR kinase inhibitor that can be used according to the present invention is [6,7-bis(2-methoxyethoxy)-4-quinazolin-4-yl]-(3-ethynylphenyl)amine (i.e. erlotinib), its hydrochloride salt (i.e. erlotinib HCl, TARCEVA™), or other salt forms (e.g. erlotinib mesylate). Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

EGFR kinase inhibitors also include, for example multi-kinase inhibitors that have activity on EGFR kinase, i.e. inhibitors that inhibit EGFR kinase and one or more additional kinases. Examples of such compounds include the EGFR and HER2 inhibitor CI-1033 (formerly known as PD183805; Pfizer); the EGFR and HER2 inhibitor GW-2016 (also known as GW-572016 or lapatinib ditosylate; GSK); the EGFR and JAK 2/3 inhibitor AG490 (a tyrphostin); the EGFR and HER2 inhibitor ARRY-334543 (Array BioPharma); BIBW-2992, an irreversible dual EGFR/HER2 kinase inhibitor (Boehringer Ingelheim Corp.); the EGFR and HER2 inhibitor EKB-569 (Wyeth); the VEGF-R2 and EGFR inhibitor ZD6474 (also known as ZACTIMA™; AstraZeneca Pharmaceuticals), and the EGFR and HER2 inhibitor BMS-599626 (Bristol-Myers Squibb).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

The present invention further provides any of the methods described herein for treating tumors or tumor metastases in a patient comprising administering to the patient a therapeutically effective amount of an IGF-1R kinase inhibitor, and in addition, simultaneously or sequentially, an anti-HER2 antibody or an immunotherapeutically active fragment thereof.

The present invention further provides any of the methods described herein for treating tumors or tumor metastases in a patient comprising administering to the patient a therapeutically effective amount of an IGF-1R kinase inhibitor, and in addition, simultaneously or sequentially, one or more additional anti-proliferative agents.

Additional antiproliferative agents include, for example: Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513, and International Patent Publication WO 01/40217, and FGFR kinase inhibitors.

Examples of PDGFR kinase inhibitors that can be used according to the present invention include Imatinib (GLEEVEC®; Novartis); SU-12248 (sunitib malate, SUTENT®; Pfizer); Dasatinib (SPRYCEL®; BMS; also known as BMS-354825); Sorafenib (NEXAVAR®; Bayer; also known as Bay-43-9006); AG-13736 (Axitinib; Pfizer); RPR127963 (Sanofi-Aventis); CP-868596 (Pfizer/OSI Pharmaceuticals); MLN-518 (tandutinib; Millennium Pharmaceuticals); AMG-706 (Motesanib; Amgen); ARAVA® (leflunomide; Sanofi-Aventis; also known as SU101), and OSI-930 (OSI Pharmaceuticals); Additional preferred examples of low molecular weight PDGFR kinase inhibitors that are also FGFR kinase inhibitors that can be used according to the present invention include XL-999 (Exelixis); SU6668 (Pfizer); CHIR-258/TKI-258 (Chiron); RO4383596 (Hoffmann-La Roche) and BIBF-1120 (Boehringer Ingelheim).

Examples of FGFR kinase inhibitors that can be used according to the present invention include RO-4396686 (Hoffmann-La Roche); CHIR-258 (Chiron; also known as TKI-258); PD 173074 (Pfizer); PD 166866 (Pfizer); ENK-834 and ENK-835 (both Enkam Pharmaceuticals A/S); and SU5402 (Pfizer). Additional preferred examples of low molecular weight FGFR kinase inhibitors that are also PDGFR kinase inhibitors that can be used according to the present invention include XL-999 (Exelixis); SU6668 (Pfizer); CHIR-258/TKI-258 (Chiron); RO4383596 (Hoffmann-La Roche), and BIBF-1120 (Boehringer Ingelheim).

The present invention further provides any of the methods described herein for treating tumors or tumor metastases in a patient comprising administering to the patient a therapeutically effective amount of an IGF-1R kinase inhibitor, and in addition, simultaneously or sequentially, a COX II (cyclooxygenase II) inhibitor. Examples of useful COX-II inhibitors include alecoxib (e.g. CELEBREX™), valdecoxib, and rofecoxib.

The present invention further provides any of the methods described herein for treating tumors or tumor metastases in a patient comprising administering to the patient a therapeutically effective amount of an IGF-1R kinase inhibitor, and in addition, simultaneously or sequentially, treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the IGF-1R kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides any of the methods described herein for treating tumors or tumor metastases in a patient comprising administering to the patient a therapeutically effective amount of an IGF-1R kinase inhibitor, and in addition, simultaneously or sequentially, treatment with one or more agents capable of enhancing antitumor immune responses.

Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

In the context of this invention, an “effective amount” of an agent or therapy is as defined above. A “sub-therapeutic amount” of an agent or therapy is an amount less than the effective amount for that agent or therapy, but when combined with an effective or sub-therapeutic amount of another agent or therapy can produce a result desired by the physician, due to, for example, synergy in the resulting efficacious effects, or reduced side effects.

As used herein, the term “patient” preferably refers to a human in need of treatment with an IGF-1R kinase inhibitor for any purpose, and more preferably a human in need of such a treatment to treat cancer, or a precancerous condition or lesion. However, the term “patient” can also refer to non-human animals, preferably mammals such as dogs, cats, horses, cows, pigs, sheep and non-human primates, among others, that are in need of treatment with an IGF-1R kinase inhibitor.

In a preferred embodiment, the patient is a human in need of treatment for cancer, a precancerous condition or lesion, or other forms of abnormal cell growth. The cancer is preferably any cancer or tumor treatable, either partially or completely, by administration of an IGF-1R kinase inhibitor. The cancer or tumor may be, for example, lung cancer, non small cell lung (NSCL) cancer, bronchioloalveolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, colorectal cancer (CRC), breast cancer, uterine cancer, carcinoma of the fallopian tubes, carcinoma of the endometrium, carcinoma of the cervix, carcinoma of the vagina, carcinoma of the vulva, Hodgkin’s Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The precancerous condition or lesion includes, for example, the group consisting of oral leukoplakia, actinic keratosis (solar keratosis), precancerous polyps of the colon or rectum, gastric sensitivity dysplasia, adenomatous dysplasia, hereditary nonpolyposis colon cancer syndrome (HNPCC), Barrett's esophagus, bladder dysplasia, and precancerous cervical conditions.

The term "refractory" as used herein is used to define a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

For purposes of the present invention, "co-administration of" and "co-administering" an IGF-1R kinase inhibitor with an additional anti-cancer agent (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The additional agent can be administered prior to, at the same time as, or subsequent to administration of the IGF-1R kinase inhibitor, or in some combination thereof. Where the IGF-1R kinase inhibitor is administered to the patient at repeated intervals, e.g., during a standard course of treatment, the additional agent can be administered prior to, at the same time as, or subsequent to, each administration of the IGF-1R kinase inhibitor, or some combination thereof, or at different intervals in relation to the IGF-1R kinase inhibitor treatment, or in a single dose prior to, at any time during, or subsequent to the course of treatment with the IGF-1R kinase inhibitor.

The IGF-1R kinase inhibitor will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the IGF-1R kinase inhibitor can be administered in any effective manner known in the art, such as by oral, topical, intravenous, intra-peritoneal, intramuscular, intra-articular, subcutaneous, intranasal, intra-ocular, vaginal, rectal, or intradermal routes, depending upon the type of cancer being treated, the type of IGF-1R kinase inhibitor being used (for example, small molecule, antibody, RNAi, ribozyme or antisense construct), and the medical judgement of the prescribing physician as based, e.g., on the results of published clinical studies.

The amount of IGF-1R kinase inhibitor administered and the timing of IGF-1R kinase inhibitor administration will depend on the type (species, gender, age, weight, etc.) and condition of the patient being treated, the severity of the disease or condition being treated, and on the route of administration. For example, small molecule IGF-1R kinase inhibitors can be administered to a patient in doses ranging from 0.001 to 100 mg/kg of body weight per day or per week in single or divided doses, or by continuous infusion (see for example, International Patent Publication No. WO 01/34574). In particular, compounds such as Compound 66, or similar compounds, can be administered to a patient in doses ranging from 5-200 mg per day, or 100-1600 mg per week, in single or divided doses, or by continuous infusion. A preferred dose is 150 mg/day. Antibody-based IGF-1R kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The IGF-1R kinase inhibitors and other additional agents can be administered either separately or together by the same or different routes, and in a wide variety of different dosage forms. For example, the IGF-1R kinase inhibitor is preferably administered orally or parenterally. Where the IGF-1R kinase inhibitor is Compound 66, or a similar such compound, oral administration is preferable. Both the IGF-1R kinase inhibitor and other additional agents can be administered in single or multiple doses.

The IGF-1R kinase inhibitor can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The IGF-1R kinase inhibitor can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous IGF-1R kinase inhibitors should be selected so as to avoid denaturation and/or degradation and loss of biological activity of the inhibitor.

Methods of preparing pharmaceutical compositions comprising an IGF-1R kinase inhibitor are known in the art, and are described, e.g. in International Patent Publication No. WO 01/34574. In view of the teaching of the present invention, methods of preparing pharmaceutical compositions comprising an IGF-1R kinase inhibitor will be apparent from the above-cited publications and from other known references, such as Remington's Pharmaceutical Sciences, Mack Publishing Company, Easton, Pa., $18^{th}$ edition (1990).

For oral administration of IGF-1R kinase inhibitors, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the IGF-1R kinase inhibitor may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous IGF-1R kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an IGF-1R kinase inhibitor in about 0.1% (w/v) to about 5% (w/v) concentration can be prepared.

For veterinary purposes, the active agents can be administered separately or together to animals using any of the forms and by any of the routes described above. In a preferred embodiment, the IGF-1R kinase inhibitor is administered in the form of a capsule, bolus, tablet, liquid drench, by injection or as an implant. As an alternative, the IGF-1R kinase inhibitor can be administered with the animal feedstuff, and for this purpose a concentrated feed additive or premix may be prepared for a normal animal feed. Such formulations are prepared in a conventional manner in accordance with standard veterinary practice.

As used herein, the term "IGF-1R kinase inhibitor" refers to any IGF-1R kinase inhibitor that is currently known in the art or that will be identified in the future, and includes any chemical entity that, upon administration to a patient, results in inhibition of a biological activity specifically associated with activation of the IGF-1 receptor in the patient, and resulting from the binding to IGF-1R of its natural ligand(s). Such IGF-1R kinase inhibitors include any agent that can block IGF-1R activation and the downstream biological effects of IGF-1R activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the IGF-1 receptor, thereby making the receptor inaccessible to its natural ligand so that its normal biological activity is prevented or reduced. Alternatively, such an inhibitor can act by modulating the dimerization of IGF-1R polypeptides, or interaction of IGF-1R polypeptide with other proteins, or enhance ubiquitination and endocytotic degradation of IGF-1R. An IGF-1R kinase inhibitor can also act by reducing the amount of IGF-1 available to activate IGF-1R, by for example antagonizing the binding of IGF-1 to its receptor, by reducing the level of IGF-1, or by promoting the association of IGF-1 with proteins other than IGF-1R such as IGF binding proteins (e.g. IGFBP3). IGF-1R kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the IGF-1R kinase inhibitor is a small organic molecule or an antibody that binds specifically to the human IGF-1R.

IGF-1R kinase inhibitors include, for example imidazopyrazine IGF-1R kinase inhibitors, quinazoline IGF-1R kinase inhibitors, pyrido-pyrimidine IGF-1R kinase inhibitors, pyrimido-pyrimidine IGF-1R kinase inhibitors, pyrrolo-pyrimidine IGF-1R kinase inhibitors, pyrazolo-pyrimidine IGF-1R kinase inhibitors, phenylamino-pyrimidine IGF-1R kinase inhibitors, oxindole IGF-1R kinase inhibitors, indolocarbazole IGF-1R kinase inhibitors, phthalazine IGF-1R kinase inhibitors, isoflavone IGF-1R kinase inhibitors, quinalone IGF-1R kinase inhibitors, and tyrphostin IGF-1R kinase inhibitors, and all pharmaceutically acceptable salts and solvates of such IGF-1R kinase inhibitors.

Additional examples of IGF-1R kinase inhibitors include those in International Patent Publication No. WO 05/097800, that describes 6,6-bicyclic ring substituted heterobicyclic protein kinase inhibitors, International Patent Publication No. WO 05/037836, that describes imidazopyrazine IGF-1R kinase inhibitors, International Patent Publication Nos. WO 03/018021 and WO 03/018022, that describe pyrimidines for treating IGF-1R related disorders, International Patent Publication Nos. WO 02/102804 and WO 02/102805, that describe cyclolignans and cyclolignans as IGF-1R inhibitors, International Patent Publication No. WO 02/092599, that describes pyrrolopyrimidines for the treatment of a disease which responds to an inhibition of the IGF-1R tyrosine kinase, International Patent Publication No. WO 01/72751, that describes pyrrolopyrimidines as tyrosine kinase inhibitors, and in International Patent Publication No. WO 00/71129, that describes pyrrolotriazine inhibitors of kinases, and in International Patent Publication No. WO 97/28161, that describes pyrrolo[2,3-d]pyrimidines and their use as tyrosine kinase inhibitors, Parrizas, et al., which describes tyrphostins with in vitro and in vivo IGF-1R inhibitory activity (Endocrinology, 138:1427-1433 (1997)), International Patent Publication No. WO 00/35455, that describes heteroaryl-aryl ureas as IGF-1R inhibitors, International Patent Publication No. WO 03/048133, that describes pyrimidine derivatives as modulators of IGF-1R, International Patent Publication No. WO 03/024967, WO 03/035614, WO 03/035615, WO 03/035616, and WO 03/035619, that describe chemical compounds with inhibitory effects towards kinase proteins, International Patent Publication No. WO 03/068265, that describes methods and compositions for treating hyperproliferative conditions, International Patent Publication No. WO 00/17203, that describes pyrrolopyrimidines as protein kinase inhibitors, Japanese Patent Publication No. JP 07/133280, that describes a cephem compound, its production and antimicrobial composition, Albert, A. et al., *Journal of the Chemical Society,* 11: 1540-1547 (1970), which describes pteridine studies and pteridines unsubstituted in the 4-position, and A. Albert et al., *Chem. Biol. Pteridines Proc. Int. Symp., 4th,* 4: 1-5 (1969) which describes a synthesis of pteridines (unsubstituted in the 4-position) from pyrazines, via 3-4-dihydropteridines.

IGF-1R kinase inhibitors particularly useful in this invention include compounds represented by Formula (I) (see below), as described in US Published Patent Application US 2006/0235031, where their preparation is described in detail. PQIP (cis-3-[3-(4-Methyl-piperazin-1-yl)-cyclobutyl]1-(2-phenyl-quinolin-7-yl)-imidazo[1,5-a]pyrazin-8-ylamine) and OSI-906 (cis-3-[8-amino-1-(2-phenyl-quinolin-7-yl)-imidazo[1,5-a]pyrazin-3-yl]-1-methyl-cyclobutanol) represents IGF-1R kinase inhibitors according to Formula (I).

OSI-906 has the structure as follows:

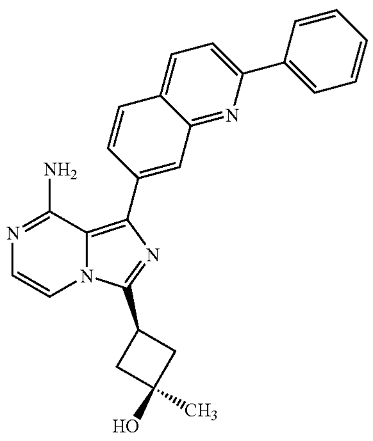

PQIP has the structure as follows:

PQIP

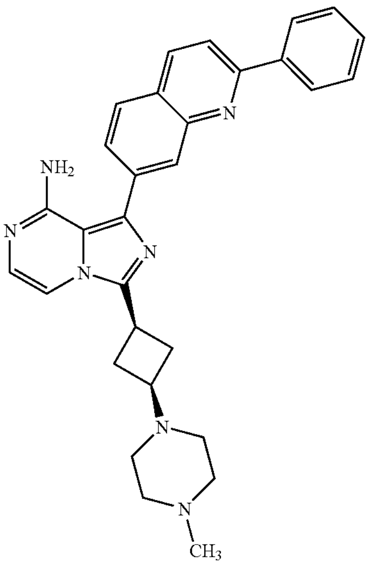

An IGF-1R kinase inhibitor of Formula (I), as described in US Published Patent Application US 2006/0235031, is represented by the formula:

I

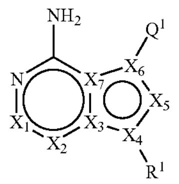

or a pharmaceutically acceptable salt thereof, wherein:

$X_1$, and $X_2$ are each independently N or C-$(E^1)_{aa}$;

$X_5$ is N, C-$(E^1)_{aa}$, or N-$(E^1)_{aa}$;

$X_3$, $X_4$, $X_6$, and $X_7$ are each independently N or C;

wherein at least one of $X_3$, $X_4$, $X_5$, $X_6$, and $X_7$ is independently N or N-$(E^1)_{aa}$;

$Q^1$ is

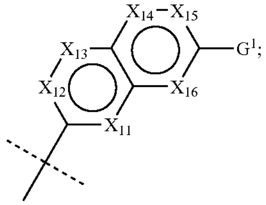

$X_{11}$, $X_{12}$, $X_{13}$, $X_{14}$, $X_{15}$, and $X_{16}$ are each independently N, C-$(E^{11})_{bb}$, or $N^+$—$O^-$;

wherein at least one of $X_{11}$, $X_{12}$, $X_{13}$, $X_{14}$, $X_{15}$, and $X_{16}$ is N or $N^+$—$O^-$;

$R^1$ is absent, $C_{0-10}$alkyl, cyclo$C_{3-10}$alkyl, bicyclo$C_{5-10}$alkyl, aryl, heteroaryl, aralkyl, heteroaralkyl, heterocyclyl, heterobicyclo$C_{5-10}$alkyl, spiroalkyl, or heterospiroalkyl, any of which is optionally substituted by one or more independent $G^{11}$ substituents;

$E^1$, $E^{11}$, $G^1$, and $G^{41}$ are each independently halo, —$CF_3$, —$OCF_3$, —$OR^2$, —$NR^2R^3(R^{2a})_{j1}$, —C(═O)$R^2$, —$CO_2R^2$, —$CONR^2R^3$, —$NO_2$, —CN, —$S(O)_{j1}R^2$, —$SO_2NR^2R^3$, —$NR^2C$(═O)$R^3$, —$NR^2C$(═O)$OR^3$, —$NR^2C$(═O)$NR^3R^{2a}$, —$NR^2S(O)_{j1}R^3$, —C(═S)$OR^2$, —C(═O)$SR^2$, —$NR^2C$(═$NR^3$)$NR^{2a}R^{3a}$, —$NR^2C$(═$NR^3$)$OR^{2a}$, —$NR^2C$(═$NR^3$)$SR^{2a}$, —OC(═O)$OR^2$, —OC(═O)$NR^2R^3$, —OC(═O)$SR^2$, —SC(═O)$OR^2$, —SC(═O)$NR^2R^3$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, oxo, —$CF_3$, —$OR^{222}$, —$NR^{222}R^{333}(R^{222a})_{j1a}$, —C(═O)$R^{222}$, —$CO_2R^{222}$, —C(═O)$NR^{222}R^{333}$, —$NO_2$, —CN, —S(═O)$_{j1a}R^{222}$, —$SO_2NR^{222}R^{333}$, —$NR^{222}C$(═O)$R^{333}$, —$NR^{222}C$(═O)$OR^{333}$, —$NR^{222}C$(═O)$NR^{333}R^{222a}$, —$NR^{222}S(O)_{j1a}R^{333}$, C(═S)$OR^{222}$, —C(═O)$SR^{222}$, —$NR^{222}C$(═$NR^{333}$)$NR^{222a}R^{333a}$, —$NR^{222}C$(═$NR^{333}$)$OR^{222a}$, —$NR^{222}C$(═$NR^{333}$)$SR^{222a}$, —OC(═O)$OR^{222}$, —OC(═O)$NR^{222}R^{333}$, —OC(═O)$SR^{222}$, —SC(═O)$OR^{222}$, or —SC(═O)$NR^{222}R^{333}$ substituents;

or $E^1$, $E^{11}$, or $G^1$ optionally is —$(W^1)_n$—$(Y^1)_m$—$R^4$;

or $E^1$, $E^{11}$, $G^1$, or $G^{41}$ optionally independently is aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, or hetaryl-$C_{2-10}$alkynyl, any of which is optionally substituted with one or more independent halo, —$CF_3$, —$OCF_3$, —$OR^{222}$, —$NR^{222}R^{333}(R^{222a})_{j2a}$, —C(O)$R^{222}$, —$CO_2R^{222}$, —C(═O)$NR^{222}R^{333}$, —$NO_2$, —CN, —$S(O)_{j2a}R^{222}$, —$SO_2NR^{222}R^{333}$, —$NR^{222}C$(═O)$R^{333}$, —$NR^{222}C$(═O)$OR^{333}$, —$NR^{222}C$(═O)$NR^{333}R^{222a}$, —$NR^{222}S(O)_{j2a}R^{333}$, —C(═S)$OR^{222}$, —C(═O)$SR^{222}$, —$NR^{222}C$(═$NR^{333}$)$NR^{222a}R^{333a}$, —$NR^{222}C$(═$NR^{333}$)$OR^{222a}$, —$NR^{222}C$(═$NR^{333}$)$SR^{222a}$, —OC(═O)$OR^{222}$, —OC(═O)$NR^{222}R^{333}$, —OC(═O)$SR^{222}$, —SC(═O)$OR^{222}$, or —SC(═O)$NR^{222}R^{333}$ substituents;

$G^{11}$ is halo, oxo, —$CF_3$, —$OCF_3$, —$OR^{21}$, —$NR^{21}R^{31}(R^{2a1})_{j4}$, —C(O)$R^{21}$, —$CO_2R^{21}$, —C(═O)$NR^{21}R^{31}$, —$NO_2$, —CN, —$S(O)_{j4}R^{21}$, —$SO_2NR^{21}R^{31}$, $NR^{21}$(C═O)$R^{31}$, $NR^{21}C$(═O)$OR^{31}$, $NR^{21}C$(═O)$NR^{31}R^{2a1}$, $NR^{21}$ S(O)$_{j4}$R$^{31}$, —C(═S)OR$^{21}$, —C(═O)SR$^{21}$, —NR$^{21}$C(═NR$^{31}$)NR$^{2a1}$R$^{3a1}$, —NR$^{21}$C(═NR$^{31}$)OR$^{2a1}$, —NR$^{21}$C(═NR$^{31}$)SR$^{2a1}$, —OC(═O)OR$^{21}$, —OC(═)NR$^{21}$R$^{31}$, —OC(═)SR$^{21}$, —SC(═O)OR$^{21}$, —SC(═O)NR$^{21}$R$^{31}$, —P(O)OR$^{21}$OR$^{31}$, C$_{1-10}$alkylidene, C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, or heterocyclyl-C$_{2-10}$alkynyl, any of which is optionally substituted with one or more independent halo, oxo, —CF$_3$, —OCF$_3$, —OR$^{2221}$, —NR$^{2221}$R$^{3331}$(R$^{222a1}$)$_{j4a}$, —C(O)R$^{2221}$, —CO$_2$R$^{2221}$, —C(═O)NR$^{2221}$R$^{3331}$, —NO$_2$, —CN, —S(O)$_{j4a}$R$^{2221}$, —SO$_2$NR$^{2221}$R$^{3331}$, —NR$^{2221}$C(═O)R$^{3331}$, —NR$^{2221}$C(═O)OR$^{3331}$, —NR$^{2221}$C(═O)NR$^{3331}$R$^{222a1}$, —NR$^{2221}$S(O)$_{j4a}$R$^{3331}$, —C(═S)OR$^{2221}$, —C(═O)SR$^{2221}$, —NR$^{2221}$C(═NR$^{3331}$)NR$^{222a1}$R$^{333a1}$, —NR$^{2221}$C(═NR$^{3331}$)OR$^{222a1}$, —NR$^{2221}$C(═NR$^{3331}$)SR$^{222a1}$, —OC(═O)OR$^{2221}$, —OC(═O)NR$^{2221}$R$^{3331}$, —OC(═O)SR$^{2221}$, —SC(═O)OR$^{2221}$, —P(O)OR$^{2221}$OR$^{3331}$, or —SC(═O)NR$^{2221}$R$^{3331}$ substituents;

or G$^{11}$ is aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{2221}$, —NR$^{2221}$R$^{3331}$(R$^{222a1}$)$_{j5a}$, —C(O)R$^{2221}$, —CO$_2$R$^{2221}$, —(═O)NR$^{2221}$R$^{3331}$, —NO$_2$, —CN, —S(O)$_{j5a}$R$^{2221}$, —SO$_2$NR$^{2221}$R$^{3331}$, —NR$^{2221}$C(═O)R$^{3331}$, —NR$^{2221}$C(═O)OR$^{3331}$, —NR$^{2221}$C(═O)NR$^{3331}$R$^{222a1}$, —NR$^{2221}$S(O)$_{j5a}$R$^{3331}$, —C(═S)OR$^{2221}$, —C(═O)SR$^{2221}$, —NR$^{2221}$C(═NR$^{3331}$)NR$^{222a1}$R$^{333a1}$, —NR$^{2221}$C(═NR$^{3331}$)OR$^{222a1}$, —NR$^{2221}$C(═NR$^{3331}$)SR$^{222a1}$, —OC(═O)OR$^{2221}$, —OC(═O)NR$^{2221}$R$^{3331}$, —OC(═O)SR$^{2221}$, —SC(═O)OR$^{2221}$, —P(O)OR$^{2221}$OR$^{3331}$, or —SC(═O)NR$^{2221}$R$^{3331}$ substituents;

or G$^{11}$ is C, taken together with the carbon to which it is attached forms a C═C double bond which is substituted with R$^5$ and G$^{111}$;

R$^2$, R$^{2a}$, R$^3$, R$^{3a}$, R$^{222}$, R$^{222a}$, R$^{333}$, R$^{333a}$, R$^{21}$, R$^{2a1}$, R$^{31}$, R$^{3a1}$, R$^{2221}$, R$^{222a1}$, R$^{3331}$, and R$^{333a1}$ are each independently C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, aryl-C$_{0-10}$alkyl, aryl-C$_{2-10}$alkenyl, or aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted by one or more independent G$^{111}$ substituents;

or in the case of —NR$^2$R$^3$(R$^{2a}$)$_{j1}$ or —NR$^{222}$R$^{333}$(R$^{2226}$)$_{j1a}$ or —NR$^{222}$R$^{333}$(R$^{222a}$)$_{j2a}$ or —NR$^{21}$R$^{31}$(R$^{2a1}$)$_{j4}$ or —NR$^{2221}$R$^{3331}$(R$^{222a1}$)$_{j4a}$ or —NR$^{2221}$R$^{3331}$(R$^{222a1}$)$_{j5a}$, then R$^2$ and R$^3$, or R$^{222}$ and R$^{333}$, or R$^{2221}$ and R$^{3331}$, respectfully, are optionally taken together with the nitrogen atom to which they are attached to form a 3-10 membered saturated or unsaturated ring, wherein said ring is optionally substituted by one or more independent G$^{1111}$ substituents and wherein said ring optionally includes one or more heteroatoms other than the nitrogen to which R$^2$ and R$^3$, or R$^{222}$ and R$^{333}$, or R$^{2221}$ and R$^{3331}$ are attached;

W$^1$ and Y$^1$ are each independently —O—, —NR$^7$—, —S(O)$_{j7}$—, —CR$^5$R$^6$—, —N(C(O)OR$^7$)—, —N(C(O)R$^7$)—, —N(SO$_2$R$^7$)—, —CH$_2$O—, —CH$_2$S—, —CH$_2$N(R$^7$)—, —CH(NR$^7$)—, —CH$_2$N(C(O)R$^7$)—, —CH$_2$N(C(O)OR$^7$)—, —CH$_2$N(SO$_2$R$^7$)—, —CH(NHR$^7$)—, —CH(NHC(O)R$^7$)—, —CH(NHSO$_2$R$^7$)—, —CH(NHC(O)OR$^7$)—, —CH(OC(O)R$^7$)—, —CH(OC(O)NHR$^7$)—, —CH═CH—, —C≡CH—, —C(═NOR$^7$)—, —C(O)—, —CH(OR$^7$)—, —C(O)N(R$^7$)—, —N(R$^7$)C(O)—, —N(R$^7$)S(O)—, —N(R$^7$)S(O)$_2$— —OC(O)N(R$^7$)—, —N(R$^7$)C(O)N(R$^8$)—, —NR$^7$C(O)O—, —S(O)N(R$^7$)—, —S(O)$_2$N(R$^7$)—, —N(C(O)R$^7$)S(O)—, —N(C(O)R$^7$)S(O)$_2$—, —N(R$^7$)S(O)N(R$^8$)—, —N(R$^7$)S(O)$_2$N(R$^8$)—, —C(O)N(R$^7$)C(O)—, —S(O)N(R$^7$)C(O)—, —S(O)$_2$N(R$^7$)C(O)—, —OS(O)N(R$^7$)—, —OS(O)$_2$N(R$^7$)—, —N(R$^7$)S(O)O—, —N(R$^7$)S(O)$_2$O—, —N(R$^7$)S(O)C(O)—, —N(R$^7$)S(O)$_2$C(O)—, —SON(C(O)R$^7$)—, —SO$_2$N(C(O)R$^7$)—, —N(R$^7$)SON(R$^8$)—, —N(R$^7$)SO$_2$N(R$^8$)—, —C(O)O—, —N(R$^7$)P(OR$^8$)O—, —N(R$^7$)P(OR$^8$)—, —N(R$^7$)P(O)(OR$^8$)O—, —N(R$^7$)P(O)(OR$^8$)—, —N(C(O)R$^7$)P(OR$^8$)O—, —N(C(O)R$^7$)P(OR$^8$)—, —N(C(O)R$^7$)P(O)(OR$^8$)O—, —N(C(O)R$^7$)P(OR$^8$)—, —CH(R$^7$)S(O)—, —CH(R$^7$)S(O)$_2$—, —CH(R$^7$)N(C(O)OR$^8$)—, —CH(R$^7$)N(C(O)R$^8$)—, —CH(R$^7$)N(SO$_2$R$^8$)—, —CH(R$^7$)O—, —CH(R$^7$)S—, —CH(R$^7$)N(R$^8$)—, —CH(R$^7$)N(C(O)R$^8$)—, —CH(R$^7$)N(C(O)OR$^8$)—, —CH(R$^7$)N(SO$_2$R$^8$)—, —CH(R$^7$)C(═NOR$^8$)—, —CH(R$^7$)C(O)—, —CH(R$^7$)CH(OR$^8$)—, —CH(R$^7$)C(O)N(R$^8$)—, —CH(R$^7$)N(R$^8$)C(O)—, —CH(R$^7$)N(R$^8$)S(O)—, —CH(R$^7$)N(R$^8$)S(O)$_2$—, —CH(R$^7$)OC(O)N(R$^8$)—, —CH(R$^7$)N(R$^8$)C(O)N(R$^{7a}$)—, —CH(R$^7$)NR$^8$C(O)O—, —CH(R$^7$)S(O)N(R$^8$)—, —CH(R$^7$)S(O)$_2$N(R$^8$)—, —CH(R$^7$)N(C(O)R$^8$)S(O)—, —CH(R$^7$)N(C(O)R$^8$)S(O)—, —CH(ON(R$^8$)S(O)N(R$^{7a}$)—, —CH(R$^7$)N(R$^8$)S(O)$_2$N(R$^{7a}$)—, —CH(R$^7$)C(O)N(R$^8$)C(O)—, —CH(R$^7$)S(O)N(R$^8$)C(O)—, —CH(R$^7$)S(O)$_2$N(R$^8$)C(O)—, —CH(R$^7$)OS(O)N(R$^8$)—, —CH(R$^7$)OS(O)$_2$N(R$^8$)—, —CH(R$^7$)N(R$^8$)S(O)O—, —CH(R$^7$)N(R$^8$)S(O)$_2$O—, —CH(R$^7$)N(R$^8$)S(O)C(O)—, —CH(R$^7$)N(R$^8$)S(O)$_2$C(O)—, —CH(R$^7$)SON(C(O)R$^8$)—, —CH(R$^7$)SO$_2$N(C(O)R$^8$)—, —CH(R$^7$)N(R$^8$)SON(R$^{7a}$)—, —CH(R$^7$)N(R$^8$)SO$_2$N(R$^{7a}$)—, —CH(R$^7$)C(O)O—, —CH(R$^7$)N(R$^8$)P(OR$^{7a}$)O—, —CH(R$^7$)N(R$^8$)P(OR$^{7a}$)—, —CH(R$^7$)N(R$^8$)P(O)(OR$^{7a}$)O—, —CH(R$^7$)N(R$^8$)P(O)(OR$^{7a}$)—, —CH(R$^7$)N(C(O)R$^8$)P(OR$^{7a}$)O—, —CH(R$^7$)N(C(O)R$^8$)O(OR$^{7a}$)—, —CH(R$^7$)N(C(O)R$^8$)P(O)(OR$^{7a}$)O—, or —CH(R$^7$)N(C(O)R$^8$)P(OR$^{7a}$)—;

R$^5$, R$^6$, G$^{111}$, and G$^{1111}$ are each independently C$_{0-10}$alkyl, C$_{2-10}$alkenyl, C$_{2-10}$alkynyl, C$_{1-10}$alkoxyC$_{1-10}$alkyl, C$_{1-10}$alkoxyC$_{2-10}$alkenyl, C$_{1-10}$alkoxyC$_{2-10}$alkynyl, C$_{1-10}$alkylthioC$_{1-10}$alkyl, C$_{1-10}$alkylthioC$_{2-10}$alkenyl, C$_{1-10}$alkylthioC$_{2-10}$alkynyl, cycloC$_{3-8}$alkyl, cycloC$_{3-8}$alkenyl, cycloC$_{3-8}$alkylC$_{1-10}$alkyl, cycloC$_{3-8}$alkenylC$_{1-10}$alkyl, cycloC$_{3-8}$alkylC$_{2-10}$alkenyl, cycloC$_{3-8}$alkenylC$_{2-10}$alkenyl, cycloC$_{3-8}$alkylC$_{2-10}$alkynyl, cycloC$_{3-8}$alkenylC$_{2-10}$alkynyl, heterocyclyl-C$_{0-10}$alkyl, heterocyclyl-C$_{2-10}$alkenyl, heterocyclyl-C$_{2-10}$alkynyl, aryl-C$_{0-10}$alkyl, aryl-C$_{2-10}$alkenyl, aryl-C$_{2-10}$alkynyl, hetaryl-C$_{0-10}$alkyl, hetaryl-C$_{2-10}$alkenyl, or hetaryl-C$_{2-10}$alkynyl, any of which is optionally substituted with one or more independent halo, —CF$_3$, —OCF$_3$, —OR$^{77}$, —NR$^{77}$R$^{87}$, —C(O)R$^{77}$, —CO$_2$R$^{77}$, —CONR$^{77}$R$^{87}$, —NO$_2$, —CN, —S(O)$_{j5a}$R$^{77}$, —SO$_2$NR$^{77}$R$^{87}$, —NR$^{77}$C(═O)R$^{87}$, —NR$^{77}$C(═O)OR$^{87}$, —NR$^{77}$C(═O)NR$^{78}$R$^{87}$, —NR$^{77}$S(O)$_{j5a}$R$^{87}$, —C(═S)OR$^{77}$, —C(═O)SR$^{77}$, —NR$^{77}$C(═NR$^{87}$)NR$^{78}$R$^{88}$, —NR$^{77}$C(═NR$^{87}$)OR$^{78}$, —NR$^{77}$C(═NR$^{87}$)SR$^{78}$, —OC(═O)OR$^{77}$, —OC(═O)NR$^{77}$R$^{87}$, —OC(═O)SR$^{77}$, —SC(═O)OR$^{77}$, —P(O)OR$^{77}$OR$^{87}$, or —SC(═O)NR$^{77}$R$^{87}$ substituents;

or $R^5$ with $R^6$ are optionally taken together with the carbon atom to which they are attached to form a 3-10 membered saturated or unsaturated ring, wherein said ring is optionally substituted with one or more independent $R^{69}$ substituents and wherein said ring optionally includes one or more heteroatoms;

$R^7$, $R^{7a}$, and $R^8$ are each independently acyl, $C_{0-10}$alkyl, $C_{2-10}$alkenyl, aryl, heteroaryl, heterocyclyl or cyclo$C_{3-10}$ alkyl, any of which is optionally substituted by one or more independent $G^{111}$ substituents;

$R^4$ is $C_{0-10}$alkyl, $C_{2-10}$alkenyl, $C_{2-10}$alkynyl, aryl, heteroaryl, cyclo$C_{3-10}$alkyl, heteroclycl, cyclo$C_{3-8}$alkenyl, or heterocycloalkenyl, any of which is optionally substituted by one or more independent $G^{111}$ substituents;

$R^{69}$ is halo, —$OR^{78}$, —SH, —$NR^{78}R^{88}$, —$CO_2R^{78}$, —C(=O)$NR^{78}R^{88}$, —$NO_2$, —CN, —$S(O)_{j8}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{778}$, —$SO_2NR^{778}R^{888}$, or —$NR^{778}R^{888}$ substituents;

or $R^{69}$ is aryl-$C_{0-10}$alkyl, aryl-$C_{2-10}$alkenyl, aryl-$C_{2-10}$ alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —C(=O)$NR^{778}R^{888}$, —$SO_2NR^{778}R^{888}$, or —$NR^{778}R^{888}$ substituents;

or in the case of —$NR^{78}R^{88}$, $R^{78}$ and $R^{88}$ are optionally taken together with the nitrogen atom to which they are attached to form a 3-10 membered saturated or unsaturated ring, wherein said ring is optionally substituted with one or more independent halo, cyano, hydroxy, nitro, $C_{1-10}$alkoxy, —$SO_2NR^{778}R^{888}$, or —$NR^{778}R^{888}$ substituents, and wherein said ring optionally includes one or more heteroatoms other than the nitrogen to which $R^{78}$ and $R^{88}$ are attached;

$R^{77}$, $R^{78}$, $R^{87}$, $R^{88}$, $R^{778}$, and $R^{888}$ are each independently $C_{0-10}$alkyl, $C_{2-10}$alkenyl, $C_{2-10}$alkynyl, $C_{1-10}$alkoxy$C_{1-10}$ alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N$($C_{0-4}$alkyl)($C_{0-4}$alkyl), or —N($C_{0-4}$alkyl)($C_{0-4}$alkyl) substituents;

or $R^{77}$, $R^{78}$, $R^{87}$, $R^{88}$, $R^{778}$, and $R^{888}$ are each independently aryl-$C_{0-10}$alkyl, aryl-$C_{2-10}$alkenyl, aryl-$C_{2-10}$alkynyl, hetaryl-$C_{0-10}$alkyl, hetaryl-$C_{2-10}$alkenyl, hetaryl-$C_{2-10}$alkynyl, mono($C_{1-6}$alkyl)amino$C_{1-6}$alkyl, di($C_{1-6}$alkyl)amino$C_{1-6}$ alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$ alkynyl, —COOH, $C_{1-4}$alkoxycarbonyl, —CON($C_{0-4}$alkyl)($C_{0-10}$alkyl), —$SO_2N$($C_{0-4}$alkyl)($C_{0-4}$alkyl), or —N($C_{0-4}$ alkyl)($C_{0-4}$alkyl) substituents;

n, m, j1, j1a, j2a, j4, j4a, j5a, j7, and j8 are each independently 0, 1, or 2; and aa and bb are each independently 0 or 1.

Additional, specific examples of IGF-1R kinase inhibitors that can be used according to the present invention include h7C10 (Centre de Recherche Pierre Fabre), an IGF-1 antagonist; EM-164 (ImmunoGen Inc.), an IGF-1R modulator; CP-751871 (figitumumab; Pfizer Inc.), an IGF-1 antagonist; lanreotide (Ipsen), an IGF-1 antagonist; IGF-1R oligonucleotides (Lynx Therapeutics Inc.); IGF-1 oligonucleotides (National Cancer Institute); IGF-1R protein-tyrosine kinase inhibitors in development by Novartis (e.g. NVP-AEW541, Garcia-Echeverria, C. et al. (2004) Cancer Cell 5:231-239; or NVP-ADW742, Mitsiades, C. S. et al. (2004) Cancer Cell 5:221-230); IGF-1R protein-tyrosine kinase inhibitors (Ontogen Corp); OSI-906 (OSI Pharmaceuticals); AG-1024 (Camirand, A. et al. (2005) Breast Cancer Research 7:R570-R579 (DOI 10.1186/bcr1028); Camirand, A. and Pollak, M. (2004) Brit. J. Cancer 90:1825-1829; Pfizer Inc.), an IGF-1 antagonist; the tyrphostins AG-538 and 1-OMe-AG 538; BMS-536924, a small molecule inhibitor of IGF-1R; PNU-145156E (Pharmacia & Upjohn SpA), an IGF-1 antagonist; BMS 536924, a dual IGF-1R and 1R kinase inhibitor (Bristol-Myers Squibb); AEW541 (Novartis); GSK621659A (Glaxo Smith-Kline); INSM-18 (Insmed); and XL-228 (Exelixis).

Antibody-based IGF-1R kinase inhibitors include any anti-IGF-1R antibody or antibody fragment that can partially or completely block IGF-1R activation by its natural ligand. Antibody-based IGF-1R kinase inhibitors also include any anti-IGF-1 antibody or antibody fragment that can partially or completely block IGF-1R activation. Non-limiting examples of antibody-based IGF-1R kinase inhibitors include those described in Larsson, O. et al (2005) Brit. J. Cancer 92:2097-2101 and Ibrahim, Y. H. and Yee, D. (2005) Clin. Cancer Res. 11:944s-950s, or being developed by Imclone (e.g. A12) or Schering-Plough Research Institute (e.g. 19D12; or as described in US Patent Application Publication Nos. US 2005/0136063 A1 and US 2004/0018191 A1). The IGF-1R kinase inhibitor can be a monoclonal antibody, or an antibody or antibody fragment having the binding specificity thereof.

Additional antibody-based IGF-1R kinase inhibitors can be raised according to known methods by administering the appropriate antigen or epitope to a host animal selected, e.g., from pigs, cows, horses, rabbits, goats, sheep, and mice, among others. Various adjuvants known in the art can be used to enhance antibody production.

Although antibodies useful in practicing the invention can be polyclonal, monoclonal antibodies are preferred. Monoclonal antibodies against IGF-1R can be prepared and isolated using any technique that provides for the production of antibody molecules by continuous cell lines in culture. Techniques for production and isolation include but are not limited to the hybridoma technique originally described by Kohler and Milstein (Nature, 1975, 256: 495-497); the human B-cell hybridoma technique (Kosbor et al., 1983, Immunology Today 4:72; Cote et al., 1983, Proc. Nati. Acad. Sci. USA 80: 2026-2030); and the EBV-hybridoma technique (Cole et al, 1985, Monoclonal Antibodies and Cancer Therapy, Alan R. Liss, Inc., pp. 77-96).

Alternatively, techniques described for the production of single chain antibodies (see, e.g., U.S. Pat. No. 4,946,778) can be adapted to produce anti-IGF-1R single chain antibodies. Antibody-based IGF-1R kinase inhibitors useful in practicing the present invention also include anti-IGF-1R antibody fragments including but not limited to F(ab').sub.2 fragments, which can be generated by pepsin digestion of an intact antibody molecule, and Fab fragments, which can be generated by reducing the disulfide bridges of the F(ab').sub.2 fragments. Alternatively, Fab and/or scFv expression libraries can be constructed (see, e.g., Huse et al., 1989, Science 246: 1275-1281) to allow rapid identification of fragments having the desired specificity to IGF-1R.

Techniques for the production and isolation of monoclonal antibodies and antibody fragments are well-known in the art, and are described in Harlow and Lane, 1988, Antibodies: A Laboratory Manual, Cold Spring Harbor Laboratory, and in J. W. Goding, 1986, Monoclonal Antibodies: Principles and Practice, Academic Press, London. Humanized anti-IGF-1R antibodies and antibody fragments can also be prepared according to known techniques such as those described in Vaughn, T. J. et al., 1998, Nature Biotech. 16:535-539 and references cited therein, and such antibodies or fragments thereof are also useful in practicing the present invention.

IGF-1R kinase inhibitors for use in the present invention can alternatively be based on antisense oligonucleotide constructs. Anti-sense oligonucleotides, including anti-sense RNA molecules and anti-sense DNA molecules, would act to directly block the translation of IGF-1R mRNA by binding thereto and thus preventing protein translation or increasing mRNA degradation, thus decreasing the level of IGF-1R kinase protein, and thus activity, in a cell. For example, antisense oligonucleotides of at least about 15 bases and complementary to unique regions of the mRNA transcript sequence encoding IGF-1R can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as IGF-1R kinase inhibitors for use in the present invention. IGF-1R gene expression can be reduced by contacting the tumor, subject or cell with a small double stranded RNA (dsRNA), or a vector or construct causing the production of a small double stranded RNA, such that expression of IGF-1R is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24):3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as IGF-1R kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of IGF-1R mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as IGF-1R kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

In the context of the methods of treatment of this invention, IGF-1R kinase inhibitors are used as a composition comprised of a pharmaceutically acceptable carrier and a non-toxic therapeutically effective amount of an IGF-1R kinase inhibitor compound (including pharmaceutically acceptable salts thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When a compound used in the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

Pharmaceutical compositions used in the present invention comprising an IGF-1R kinase inhibitor compound (including pharmaceutically acceptable salts thereof) as active ingredient, can include a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the IGF-1R kinase inhibitor compounds (including pharmaceutically acceptable salts thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, an IGF-1R kinase inhibitor compound (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

An IGF-1R kinase inhibitor compound (including pharmaceutically acceptable salts thereof) used in this invention, can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, the pharmaceutical composition can comprise an IGF-1R kinase inhibitor compound in combination with an anticancer agent, wherein said anti-cancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition used for this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions used in the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions used in the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions for the present invention can be in a form suitable for topical sue such as, for example, an aerosol, cream, ointment, lotion, dusting powder, or the like. Further, the compositions can be in a form suitable for use in transdermal devices. These formulations may be prepared, utilizing an IGF-1R kinase inhibitor compound (including pharmaceutically acceptable salts thereof), via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions for this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing an IGF-1R kinase inhibitor compound (including pharmaceutically acceptable salts thereof) may also be prepared in powder or liquid concentrate form.

Dosage levels for the compounds used for practicing this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

Many alternative experimental methods known in the art may be successfully substituted for those specifically described herein in the practice of this invention, as for example described in many of the excellent manuals and textbooks available in the areas of technology relevant to this invention (e.g. Using Antibodies, A Laboratory Manual, edited by Harlow, E. and Lane, D., 1999, Cold Spring Harbor Laboratory Press, (e.g. ISBN 0-87969-544-7); Roe B. A. et. al. 1996, DNA Isolation and Sequencing (Essential Techniques Series), John Wiley & Sons (e.g. ISBN 0-471-97324-0); Methods in Enzymology: Chimeric Genes and Proteins", 2000, ed. J. Abelson, M. Simon, S. Emr, J. Thorner. Academic Press; Molecular Cloning: a Laboratory Manual, 2001, 3rd Edition, by Joseph Sambrook and Peter MacCallum, (the former Maniatis Cloning manual) (e.g. ISBN 0-87969-577-3); Current Protocols in Molecular Biology, Ed. Fred M. Ausubel, et. al. John Wiley & Sons (e.g. ISBN 0-471-50338-X); Current Protocols in Protein Science, Ed. John E. Coligan, John Wiley & Sons (e.g. ISBN 0-471-11184-8); and Methods in Enzymology: Guide to protein Purification, 1990, Vol. 182, Ed. Deutscher, M. P., Academic Press, Inc. (e.g. ISBN 0-12-213585-7)), or as described in the many university and commercial websites devoted to describing experimental methods in molecular biology.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

EXPERIMENTAL DETAILS

Introduction

Colorectal cancer (CRC) represents a major health burden, and is the second-leading cause of cancer deaths in the U.S. In the past decade, the median survival among patients with metastatic CRC (mCRC) has increased, primarily due to the introduction of irinotecan, oxaliplatin and signal transduction modulators targeting the vascular endothelial growth factor (VEGF) and epidermal growth factor receptor (EGFR) pathways (Goldberg R. M., The Oncologist 2006; 11(9):981-7; Cunningham D., et al. The New England Journal of Medicine 2004; 351(4):337-45; Hurwitz H., et al. The New England Journal of Medicine, 2004; 350(23):2335-42; Van Cutsem E., et al. J Clin Oncol 2007; 25(13):1658-64). Increasingly, patients are receiving all of the above agents first- or second-line, so that for patients receiving subsequent salvage therapy, the median progression-free survival (PFS) is 8-10 weeks (Saltz L B, et al. J Clin Oncol 2007; 25(30): 4793-4799). For this population of CRC patients, options are limited and thus new agents are needed that can either induce tumor regression or disease stabilization. The IGF-1R signaling pathway appears to be a robust target in colorectal cancer (CRC), based upon data demonstrating overexpression of the receptor and ligands in CRC, association with a more malignant phenotype, chemotherapy resistance, and correlation with a poor prognosis (Saltz, L. B., et al. J Clin Oncol 2007; 25(30): 4793-4799; Tripkovic I., et al. Med Res. 2007 July; 38(5): 519-25. Epub 2007 Apr. 26; Miyamoto S., et al. Clin Cancer Res. 2005 May 1; 11(9):3494-502; Nakamura M., et al. Clin Cancer Res. 2004 Dec. 15; 10(24):8434-41; Grothey A, et al. J Cancer Res Clin Oncol. 1999; 125(3-4):166-73).

Patient selection is also an emerging area in CRC, where the development of EGFR-targeted antibodies has been fraught with controversies surrounding the most appropriate markers for selecting patients and predicting efficacy. These agents were initially developed using EGFR immunohistochemistry (IHC) as a selection tool, whereas the results of large randomized studies indicate that we have only begun to understand the determinants of response to this class of drugs (Khambata-Ford S., et al. J Clin Oncol. 2007 Aug. 1; 25(22): 3230-7; Lièvre A, et al. Cancer Res. 2006 Apr. 15; 66(8): 3992-5; Italiano A., et al. Ann Surg Oncol. 2007 Nov. 7; [Epub ahead of print]; Chung K. Y., et al. J Clin Oncol. 2005 Mar. 20; 23(9):1803-10. Epub 2005 Jan. 27). The strategy taken herein to identify biomarkers that can be used to select patients for treatment with IGF-1R inhibitors is to identify potential predictive markers before, or in parallel with, early clinical development of IGF-1R inhibitors in CRC. Such an approach has also been utilized recently in the development of dasatanib and the proapoptotic ligand, Apo2L/TRAIL (Coldren C. D., et al. Mol Cancer Res 2006; 4(8):521-8; Witta S. E., et al. Cancer Res. 2006; 66(2):944-50; Frederick B. A., et al. Molecular cancer therapeutics 2007; 6(6):1683-91; Huang F., et al. Cancer Res. 2007 Mar. 1; 67(5):2226-38; Wagner K. W., et al. Nat Med. 2007 September; 13(9):1070-7. Epub 2007 Sep. 2), and has resulted in valuable biological insights, including the relationship of epithelial-to-mesenchymal transition (EMT), the breast cancer "triple-negative" phenotype, and death receptor O-glycosylation to responsiveness to EGFR or IGF-1R tyrosine kinase inhibitors, dasatinib, and Apo2L/TRAIL, respectively (Witta S. E., et al. Cancer Res. 2006; 66(2):944-50; Frederick B. A., et al. Molecular cancer therapeutics 2007; 6(6):1683-91; Huang F., et al. Cancer Res. 2007 Mar. 1; 67(5):2226-38; Wagner K. W., et al. Nat Med. 2007 September; 13(9):1070-7. Epub 2007 Sep. 2).

Here we demonstrate that sensitivity of CRC tumor cells to IGF-1 receptor inhibition is predicted by various "sensitivity" biomarkers. Conversely insensitivity to IGF-1 receptor inhibition is predicted by various "resistance" biomarkers. Since many newly developed targeted agents may be eventually incorporated clinically into traditional chemotherapy regimens, we also examined the effects of an IGF-1R inhibitor in combination with standard chemotherapy agents (5-flurouracil, SN38 and oxaliplatin) in colon cancer cell lines. It was found that the "sensitivity" or "resistance" biomarkers not only predict which tumor cells will be sensitive to the IGF-1R inhibitor, but also predict which will respond in a synergistic manner when treated with a combination of an IGF-1R inhibitor and a chemotherapeutic agent.

PQIP Studies

Materials and Methods

IGF-1R Inhibitor Compound: IGF-1R inhibitor compound PQIP was provided by OSI Pharmaceuticals, (Melville, N.Y.). PQIP (cis-3-[3-(4-Methyl-piperazin-1-yl)-cyclobutyl] 1-(2-phenyl-quinolin-7-yl)-imidazo[1,5-a]pyrazin-8-ylamine) is a 1,3-disubstituted-8-amino-imidazopyrazine derivative synthesized by the methods described in patent application number WO 2005/097800 A1. Compound identity and purity (>99%) were verified by $^{1}H$ and $^{13}C$ nuclear magnetic resonance, mass spectrometry (MS), and high-performance liquid chromatography using Bruker Advance 400, WatersMicromass ZQ, and Waters LC Module I Plus instruments, respectively, as well as by elemental analysis. PQIP was dissolved in DMSO as a 10 mmol/L stock solution for use in biochemical or cellular assays in vitro.

Cell Lines and Culture. Twenty-eight human colon cancer cell lines, were obtained from American Type Culture Collection (Manassas, Va.). Cells were grown in RPMI medium supplemented with 10% fetal bovine serum, 1% non-essential amino acids, 1% penicillin/streptomycin and were maintained at 37° C. in an incubator under an atmosphere containing 5% $CO_2$. The cells were routinely screened for the presence of mycoplasma (MycoAlert, Cambrex Bio Science, Baltimore, Md.) and were exposed to PQIP when they reached approximately 70% confluence.

Microarray Analysis: Cells were plated at 2×106 in 6-well plates 24 h prior to harvest. After 24 hours cells were rinsed twice with PBS, and RNA was prepared using a RNeasy Plus mini kit (Qiagen, Valencia, Calif.). RNA stabilization, isolation, and microarray sample labeling were carried out using standard methods for reverse transcription and one round of in vitro transcription. HG-U133 set microarrays were hybridized with 10 μg of cRNA and processed according to the protocols of the manufacturer (Affymetrix). Hybridization signals and detection calls were generated in BioConductor, using the germa and affy software packages. Microarray data was analyzed using BRB ArrayTools v3.2 developed by Dr. Richard Simon and Amy Peng Lam. Multidimensional scaling, using centered correlation was performed and 110 genes were found to be significant at $p<0.005$.

RT-PCR analyses: Expression levels of genes of interest from array analyses were assessed using RT-PCR. Total RNA was isolated from cells using the RNeasy mini kit (Qiagen, Valencia, Calif.), cDNA synthesized from one mg of total RNA using the Taqman reverse transcription kit (Applied Biosystems, Foster City, Calif.), and expression levels detected from 100 ng of cDNA using Power SYBR Green detection chemistry (Applied Biosystems, Foster City Calif.), all according to the manufacturer's directions. Samples were run on an Applied Biosystems Step One Plus (Applied Biosystems, Foster City Calif.).

shRNA Knockdown: The pRS-shE2F6 gene-specific shRNA expression cassettes, along with control shRNA plasmids including the original pRS vector (TR20003, were purchased from OriGene (Rockville Md.). The sequence of the metallothionein 2A-specific 29mer shRNA is GTAAAGAACGCGACTTCCACAAACCTGGA SEQ ID NO:114. Stable clones were generated by transfecting HCT116 cells in 6-well dishes with 1 μg of each of the shRNA plasmids using Fugene 6 (Roche, Basel Switzerland), according to manufacturer's recommendations. Seventy-two hours after transfection, the cells were placed under selection with 2.0 μg/mL of puromycin, splitting 1:5 when the cells reached confluency. Multiple clones from the same transfection were pooled and grown under puromycin selection. Successful knockdown of specific genes and gene products was confirmed by semi-quantitative RT-PCR and immunoblotting with specific antibodies.

Preparation of cytogenetic slides with metaphase and interphase cells: Cells in culture for nine colorectal cancer (CRC) cell lines were subjected to mitotic arrest and were harvested after hypotonization in 0.075 M KCl for 20 min at 37° C. followed by fixation using methanol/acetic acid (3:1). Following three changes of fixative, four slides were dropped for each cell line while checking for optimal cell density, chromosome spreading, encapsulation/residual cytoplasm, and chromosome morphology.

Preparation of BAC clone as FISH probe: A FISH probe encompassing the IGF-1R gene was derived from the clone RP11-262P8. The IFG1R DNA was labeled with SpectrumRed conjugated dUTPS using the Vysis Nick translation kit (Abbott Molecular), according to manufacturer's instructions. The labeled DNA was ethanol precipitated using herring sperm DNA (1:50 v/v) as carrier and human Cot-1 DNA (1:10 v/v) for blocking repetitive sequences. The DNA pellet was diluted in 10 μl of hybridization mix (50% formamide/10% dextran sulphate/2×SSC).

Fluorescent in situ Hybridization Assays: Dual-color FISH assays were performed on the prepared slides of colorectal cancer cell lines using 120 ng of SpectrumRed-labeled IGF1R and 0.3 μl of SpectrumGreen-labeled CEP15 (Abbott Molecular) per 113 $mm^2$ hybridization area according to standard protocol in the laboratory. The slides were first washed in 70% acetic acid for 20-30 sec, then incubated in 0.008% pepsin/0.01 M HCl at 37° C. for 3-5 min, in 1% formaldehyde for 10 min and dehydrated in a graded ethanol series. The probe mix was applied to the selected hybridization areas, which were covered with glass cover slips and sealed with rubber cement. DNA co-denaturation was performed for 9 min at 85° C. and hybridization was allowed to occur at 37° C. for 40-48 hours. Post-hybridization washes were performed with 2×SSC/0.3% NP-40 at 72° C. and 2×SSC for 2 min at room temperature and dehydrated in a graded ethanol series. Chromatin was counterstained with DAPI (0.3 μg/ml in Vectashield Mounting Medium, Vector Laboratories). Analysis was performed on epifluorescence microscope using single interference filter sets for green (FITC), red (Texas red), and blue (DAPI) as well as dual (red/green) and triple (blue, red, green) band pass filters. Approximately 20 metaphase spreads and 100 interphase nuclei were analyzed in each cell line and in this setting we roughly estimated the ploidy and identified the chromosomes harboring homologous sequences to the IGF1R/CEP15 probe set. For documentation, images were captured using a CCD camera and merged using dedicated software (CytoVision, AI).

Immunoprecipitation and Immunoblotting: HT29 and HCT116 CRC cell lines were seeded into 6-well plates, allowed to attach for 24 hours and serum starved overnight. Cells were then exposed to IGF-2 (100 ng/mL) for 10 minutes with or without a 3 hour PQIP (0.4 μmol/L) pretreatment. After treatment cells were rinsed with PBS and scraped into RIPA lysis buffer containing protease inhibitors, EDTA, NaF, and sodium orthovanadate. Total protein was quantified using the BioRad Dc Protein Assay (BioRad, Hercules, Calif.). Total protein (30 μg) was electrophoresed on a 4-20% gradient SDS-polyacrylimide gel then electrophoretically transferred to Immobilon-P (Millipore, Bedford, Mass.). Membranes were blocked for 1 hour in 5% non-fat dry milk (BioRad, Hercules, Calif.) in TBS-Tween (0.1%) prior to overnight incubation at 4° C. with the appropriate primary antibody. Blots were then washed 3×20 minutes in TBS-Tween (0.1%) and were incubated with the appropriate secondary anti-rabbit or anti-mouse IgG1 horseradish peroxidase-linked antibody at 1:20,000 (Jackson ImmunoResearch, West Grove, Pa.) for one hour at room temperature. After three additional washes, the blots were developed by Immobilon Western Chemiluminescent HRP substrate (Millipore, Billerica, Mass.). Anti-IGF1Rβ rabbit polyclonal (Cell Signaling Technology, Danvers, Mass.) was used for immunoprecipitation at a 1:50 dilution. The following primary antibodies were used for immunoblotting (all from Cell Signaling Technology, Danvers, Mass.). Anti-phosphorylated Akt (T308) rabbit polyclonal, anti-phosphorylated S6 ribosomal protein (S235/236) rabbit mAb, anti-phosphorylated p44/42 MAPK (Thr202/Tyr204) rabbit mAb, and anti-phosphorylated tyrosine mouse mAb at 1:1.000. Anti-Akt (pan) rabbit mAb, anti-S6 ribosomal protein rabbit mAb, anti-p44/42 MAP Kinase rabbit mAb, anti Pan-Actin rabbit polyclonal, anti-IGF1Rβ rabbit polyclonal, anti-PARP rabbit polyclonal, and anti-cyclin D1 rabbit polyclonal at 1:5000.

Cytotoxicity and Combination Effects: HT29, HCT116, RKO, and LS513 CRC cell lines were exposed to 0-10 nM SN-38 (7-Ethyl-10-hydroxy-camptothecin), 0-10 μM Oxaliplatin, or 0-50 μM 5-Fluorouracil (5-FU) for 72 hours. HT29, HCT116, RKO, and LS513 CRC cell lines were exposed to PQIP in combination with SN-38, Oxaliplatin or 5-FU. In all combinations, cells were seeded in 96-well flat bottomed plates and left overnight. PQIP and chemotherapy were both added for 72 hours. The results of the combinations were analyzed by the Chou and Talalay method with Calcusyn (Biosoft, Ferguson, Mo.).

Detection of IGF1R using Meso Scale Discovery assays (MSD): HT29 and HCT116 CRC cell lines were seeded into 6-well plates, allowed to attach for 24 hours and exposed to PQIP and chemotherapy (SN38, or Oxaliplatin) alone or in combination for 72 h. Following exposure, cells were rinsed with PBS and scraped into RIPA lysis buffer containing protease inhibitors, EDTA, NaF, and sodium orthovanadate. Total protein was quantified using the BioRad Dc Protein Assay (BioRad, Hercules, Calif.). Fifty micrograms of protein in 25 μL was added per well for MSD detection of phosphorylated IGF-1R according to manufacturer's instructions (Meso Scale Discovery, Gaithersburg, Md.).

Results

CRC cell lines exhibit a range of sensitivities to the IGF-1R kinase inhibitor PQIP: The sensitivity of 26 colorectal cancer (CRC) cell lines to growth inhibition by the IGF-1R kinase inhibitor PQIP was tested using a sulforhodamine B (SRB) assay (see FIG. 1 for characteristics of the cell lines tested.). The CRC cell lines were treated with a range of concentrations of PQIP (from 0.05-5 μM) for 72 hours. As shown in FIG. 2 the majority of the cell lines failed to reach an IC50 up to 5 μmol/L, but a clear distinction could be made between the cell lines that were sensitive (i.e. cell lines Colo205, HT29, Colo320, and LS513, with IC50<0.5 μmol/L) and the cell lines that were resistant (HCT116, HCT15, SW480, RKO, LS1034, CaCo2, HCT8, LoVo, LS123, T84, LS174T, LS180, SW1417, SW1116, SW48, NCI-H508, SW948, SW837, SW1463, SW403, with IC50>5 umol/L). Several cell lines were of intermediate sensitivity (e.g. SW620, Colo201, SK-CO-1).

Differential Gene Expression Between PQIP-Sensitive and PQIP-Resistant CRC Cell Lines: To determine the genes associated with sensitivity or resistance to PQIP treatment, the gene expression profiles of PQIP-untreated samples of the 4 most sensitive (S) and the 5 most resistant (R) CRC cell lines were examined. This gene profile was generated by analyzing the differential expression of PQIP-resistant and PQIP-sensitive CRC cell lines. RNA was prepared from the nine cell lines using Affymetrix Human Gene 1.0 ST arrays. Using previously published methods, we were able to identify 110 genes that were significant at the p<0.005 level of univariate significance, using a two-sample T-test (FIGS. 14 and 15). Top scoring genes (i.e. p<0.0015) included caldesmon (CALD1), several metallothioneins (e.g. MT-1E), aldehyde dehydrogenase (ALDH1A1), and mitogen activated protein kinase kinase 6 (MAP2K6).

Caldesmon was expressed at high levels in R tumor cells (61-fold increased in R cells, p=0.0002; FIGS. 4A and 15). Caldesmon is an actin-binding protein that has recently been shown to play a critical role in regulating the formation and dynamics of podosomes and invadopodia, cell adhesion structures that protrude from the plasma membrane and degrade the extracellular matrix (ECM), thus promoting cancer cell invasion (Linder, S. and Aepfelbacher, M. Trends Cell Biol 2003 13: 376-385; Yoshio, T., et al. FEBS lett. 2007 581: 3777-3782; Koji-Owada, M., et al. Proc Natl Acad Sci USA 1984 81: 3133-3137). Interestingly, caldesmon is a negative regulator of the formation podosomes and invadopodia by sequestering actin, thus indicating that CRC cell lines with an invasive/malignant phenotype are more responsive to IGF-1R inhibition.

Also overrepresented in R compared to S cell lines are the metallothioneins (e.g. MT-1E), a family of ubiquitous, low molecular weight intracellular proteins that bind and detoxify heavy metal ions (Kagi, J. H. R. Meth Enzymol 1991 205: 613-626; Bauman, J. W. et al. Toxicol Appl Pharmacol 1991 110: 347-354) (FIG. 15; MT-1E RT-PCR, FIG. 4B (RT-PCR)). This family are among the highest ranked (15-36-fold; $p=9.2\times10^{-6}$–0.0001) group of differentially expressed genes (FIG. 15; MT-1E RT-PCR, FIG. 4B). Metallothioneins can be induced by a variety of stimuli, are involved in other cellular functions such development, differentiation proliferation, and carcinogenesis, and have been associated with a poor prognosis and metastasis in cancer (Bauman, J. W. et al. Toxicol Appl Pharmacol 1991 110: 347-354; Bruewer, M, et al. World J Surg 2002 26: 726-731; Sens, M A, et al. Am J Pathol 2001 159: 21-26; Cherian, M. G., et al. Mut Res 2003 533: 201-209; Jin, R., et al. Br J Cancer 2000 83: 319-323; Shmid, K. W., et al. Arch A Pathol Anat Histopathol 1993 422: 153-159). They may also play a functional role in cancer drug resistance, though the mechanism for this remains poorly understood (Surowiak, P, et al. Histol Histopathol 2005 20: 1037-1044; Saga, Y, et al. Int J Urol 2004 11: 407-415).

An example of a gene highly expressed in S tumor cell lines, is the aldehyde dehydrogenase gene, ALDH1A1 (83-fold; p=0.002; FIGS. 14, 4C (RT-PCR)), an enzyme involved in the metabolism of alcohol and interestingly, the oxidation of all-trans retinal to all-trans retinoic acid (Molotkov A, and Duester G. J Biol Chem. 2003 Sep. 19; 278(38):36085-90. Epub 2003 Jul. 7; Luo P, Wang A, et al. Stem Cells. 2007 October; 25(10):2628-37. Epub 2007 Jul. 12; Rice K. L., et al. Leuk Res. 2007 Dec. 12; [Epub ahead of print]). ALDH1A1 has also been associated with drug resistance. When ALDH1A1 is knocked down in lung cancer cell lines they become sensitive to 4-hydroperoxycyclophosphamide (4-HC) (Moreb, J. S., et al. Cancer Chemother Pharmacol. 2007 January; 59(1):127-36. Epub 2006 Apr. 14). This is the opposite of what is seen here, in that ALDH1A1 is up regulated in the PQIP sensitive lines.

Another example of a gene highly expressed in S tumor cell lines, is mitogen-activated protein kinase kinase 6 (MAP2K6). MAP2K6 is part of the p38 MAPK pathway and acts to directly activate p38. MAP2K6 has been shown to be activated following treatment with cisplatin in numerous cancer cell lines. This activation then activates p38 MAPK, which in turn leads to increase in cell killing following cisplatin treatment. If you block p38 activation the cancer cells become resistant. This shows that MAP2K6 can play a role in sensitivity to anti-cancer agents. (Losa J. H., et al. Oncogene 2003 Jun. 26; 22(26):3998-4006).

shRNA Knockdown of Selected Genes: To characterize the potential significance of these genes, we selectively reduced their expression in S and R cell lines using stably transfected shRNAs and examined their effects on the S or R phenotype. To characterize the potential functionality that the selected genes may play in the sensitivity or resistance to PQIP, resistant and sensitive CRC cell lines were stably transfected with specific shRNA, treated with increasing concentrations of PQIP and proliferation assays performed to observe, if when manipulated, these genes alter responsiveness (i.e. the S or R phenotype). Two resistant cell lines HCT116 and SW480 were transfected with metallothionein 2A (MT-2A) shRNA and were exposed to increasing concentrations of PQIP. RT-PCR indicated that a greater than 80% reduction in gene expression was achieved in two separate clones and a nearly complete reduction in protein expression. Both of these transfected cell lines were assayed for proliferation as described above. As shown in FIG. 5 HCT116 cells transfected with two different shRNA constructs to reduce MT2A expression demonstrated a left shift in sensitivity when compared to the parental cell line or the non-targeted scramble shRNA control. However the transfected SW480 cell lines showed a very modest if any left shift in sensitivity when compared to parental or the non-targeted scramble shRNA control (FIG. 5). HCT116 and SW480 cell lines transfected with caldesmon shRNA, to reduce the expression of calsesmon, the other gene highly upregulated in the PQIP resistant CRC cell lines, showed no left shift in sensitivity when compared to parental or the non-targeted scramble shRNA control (data not shown). HT29 tumor cells were transfected with shRNA for ALDH1A1, which is up regulated in the PQIP sensitive cell lines. When ALDH1A1 is knocked down in HT29 and exposed to PQIP at increasing concentrations, no left shift in sensitivity is observed (data not shown).

It appears that MT2A and not caldesmon increases the sensitivity to PQIP in the PQIP-resistant CRC cell line HCT116. Thus MT2A, in addition to being be a predictive marker for PQIP resistance, when down-modulated can increase sensitivity to IGF-1R kinase inhibitors in resistant cell lines, indicative of a causative relationship with resistance. This may lead to the ability to target MTs in patients with resistant tumors to increase their sensitivity to PQIP. So far no genes associated with sensitivity, when modulated show any right shift toward resistance.

Gene Expression Analysis Post PQIP Exposure: In order to identify genes that are modulated following exposure to PQIP, 5 sensitive and 5 resistant CRC cell lines were treated with 400 nM PQIP for 72 hours, total RNA was purified, and gene array analysis was performed as described previously. The gene expression profiles following PQIP exposure were compared to the respective untreated profiles. To characterize changes in gene expression profile, one PQIP resistant (HCT116) and one PQIP sensitive (HT29) tumor cell type was examined, and caldesmon, metallothioneins, ALDH1A1, and MAP2K6 expression levels were analyzed.

TABLE 1

Fold change of post exposure PQIP to untreated.

| Gene | HCT116 | HT29 |
|---|---|---|
| MT1E | 1.2 | 12.5 |
| MT1X | 2.0 | 16.0 |
| MT1H | 1.8 | 11.0 |
| MT1F | 1.6 | 10.8 |
| MT2A | 1.0 | 8.1 |
| MT1M | 1.5 | 15.2 |
| MT1G | 1.1 | 4.5 |
| CALD1 | 1.9 | 1.5 |
| ALDH1A1 | 2.3 | 0.56 |
| MAP2K6 | 0.7 | 0.87 |

As seen in Table 1, in both HCT116 and HT29 overall the expression of MTs is higher post PQIP exposure, with a much higher expression in the HT29 CRC cell line. These increases may be due to that fact that the cells that remain following PQIP exposure are more resistant to PQIP and therefore have higher expression of MTs. Since some of the MTs are also modestly upregulated following PQIP treatment in the resistant cells, this may show that PQIP may actually be able to modulate MT expression and MTs could be used as a surrogate biomarker in patients following PQIP treatment Caldesmon was also slightly higher in both CRC cell lines. ALDH1A1, which had higher expression in the untreated PQIP sensitive CRC cell line HT29, decreased expression post PQIP exposure However in the HCT116 PQIP resistant CRC cell line the expression of ALDH1A1 increased following PQIP exposure. Expression of MAP2K6 did not change much following PQIP exposure.

Figure 12:
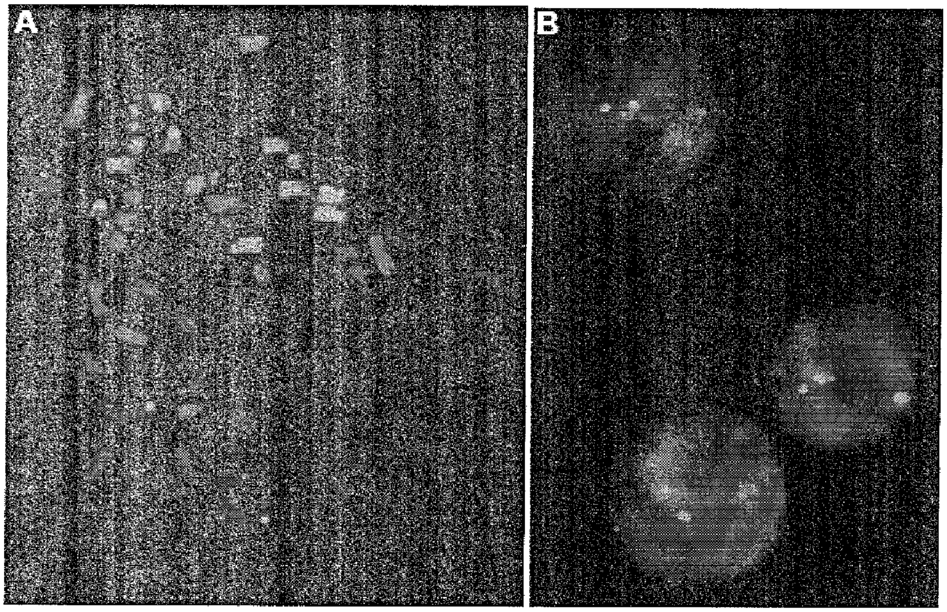
FIG. 12: Metaphase spread (A) and interphase nuclei (B) from the cell line RKO hybridized with the IGF1R (red)/CEP 15 (green) probe set.
Figure 13:
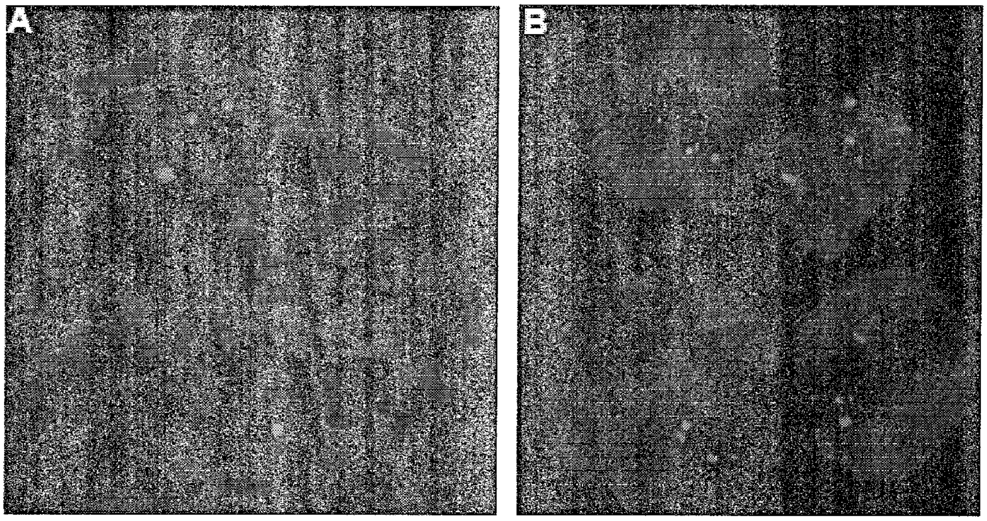
FIG. 13: Metaphase spread (A) and interphase nuclei (B) from the cell line COLO205 hybridized with the IGF1R (red)/CEP15 (green) probe set.

Fluorescent in situ hybridization of IGF1R in Colon Cancer Cell Lines: Recent studies have shown EGFR gene copy number detection by FISH can predict outcome of patients treated with cetuximab and chemotherapy (Hirsch F R, et. al. J Clin Oncol. 2008 Jul. 10; 26(20):3351-7). Gene copy number of IGF-1R in CRC cell lines was therefore examined to see if sensitivity to PQIP can be predicted in a similar fashion. Dual-color FISH assays were performed on the prepared slides of the colorectal cancer cell lines. Metaphase spread and interphase nuclei from the cell lines RK0 and Colo205 hybridized with the IGF1R (red)/CEP15 (green) probe set are exemplified in FIGS. 12 and 13. Detailed results of interphase and metaphase analyses are presented in FIGS. 10, 11, and 16, for 25 CRC cell lines. The ploidy for each cell line was roughly estimated based on chromosome count in the metaphases analyzed. None of these CRC cell lines showed IGF1R gene amplification or significant loss. However, interestingly, all four lines that are sensitive to PQIP showed slightly increased IGF-1R copy numbers (unbalanced gains when normalized to ploidy), i.e. COLO205, HT29, CaCo2, and LS513. By contrast, only 2 of 16 R cell lines exhibited unbalanced gains. Based on the results it does not appear that the any of the CRC cell lines have increased gene amplification or significant loss. However, IGF-1R gene copy number (unbalanced gains when normalized to ploidy) does appear to be a statistically significant predictor of sensitivity to PQIP.

Characterizing IGF1R Pathway of Colon Cancer Cell Lines by Immunohistochemistry: Previous studies have shown that combination of gene copy number and protein expression by IHC can predict the outcome of NSCLC patients to gefitinib treatment (44). There did not however appear to be any consistent correlation between EGFR expression and sensitivity to EGFR targeted agents (e.g. gefitinib, erlotinib). The IGF-1R pathway was thus evaluated by IHC to determine if over expression of any part of this pathway can be predictive of sensitivity. IGF1R and IGF2R protein expression was evaluated by IHC using established methods. Table 2 shows the scores (0-4) of IGF1R and IGF2R protein expression on a panel of CRC cell lines. There does not appear to be a correlation between IGF1R or IGF2R expression and sensitivity to PQIP, similar to results reported previously with the EGFR pathway.

TABLE 2

IHC scores for IGF1R and IGF2R on CRC cell lines.

| Cell Line | IGF2R | IGF1R |
|---|---|---|
| HCT15 | 3+ | 2+ |
| HCT116 | 2+ | 2+ |
| LS180 | 1+ | 2+ |
| SW620 | 2+ | 2+ |
| HCT8 | 2+ | 2+ |
| RKO | 2+ | 2+ |
| SW480 | 2+ | |
| HT29 | 2+ | 2+ |
| COLO201 | 2+ | 3+ |
| COLO205 | 2+ | 3+ |
| LS513 | 2+ | 2+ |

Effect of PQIP on receptor phosphorylation and pathway activation: Since PQIP is expected to inhibit autophosphorylation of IGF1R, we tested its ability to inhibit IGF-2 mediated activation of the receptor and pathway. One PQIP sensitive and one PQIP resistant CRC cell line were chosen for immunoprecipitation and immunoblotting analysis. Following 18 h serum starvation, HT29 and HCT116 CRC cell lines were stimulated or unstimulated for 10 minutes with 100 ng/mL of IGF-2 with or without a 3 h pre-exposure to PQIP (0.4 μmol/L). In both sensitive HT29 and resistant HCT116 CRC cell lines, PQIP almost fully inhibits IGF-2 induced tyrosine autophosphorylation of IGF1R (FIG. 6). In these CRC cell lines PQIP similarly inhibits phosphorylation of Akt, S6 ribosomal protein with or without IGF-2 stimulation. However, IGF-2 induced phosphorylation of p42/44 MAPK is only inhibited in the sensitive HT29 and not in resistant HCT116 CRC cell line (FIG. 6).

As expected, in both HT29 and HCT116 cell lines IGF1R, Akt, and S6 ribosomal protein are all successfully inhibited with addition of PQIP. Interestingly, PQIP inhibits ERK in the sensitive HT29 cells only, suggesting that resistance in HCT116 may be explained by dependence on growth factor receptors other than IGF1R. Similar results were previously reported in GEO CRC cells, showing inhibition of Akt, but not ERK (Ji Q. S., et. al. Mol Cancer Ther. 2007 August; 6(8):2158-67. Epub 2007 August 1).

Combination treatment of PQIP with Chemotherapy in Colon Cancer Cell Lines: IGF1R is overexpressed in CRC and has been associated with resistance to chemotherapy. Therefore, we investigated the effect of PQIP in combination with standard chemotherapy for CRC. Four CRC cell lines including, two PQIP sensitive and two PQIP resistant, were chosen for combinations. HT29 and LS513 CRC cell lines were classified as sensitive, with $IC_{50}$'s around 0.3 μmol/L. HCT116 and RKO CRC cell lines were classified as resistant, with $IC_{50}$>5 μmol/L. Concentrations were chosen based on single agent proliferation curves for each compound. Cells were exposed to PQIP and chemotherapy (SN38, oxaliplatin, or 5-Fluorouracil) concurrently for 72 h and combinations were assessed using the SRB assay. Sensitive HT29 and LS513 CRC cell line demonstrate synergy, with nearly all combination index (CI) values between 0.2-1.0 (FIG. 7). The resistant HCT116 and RKO CRC cell lines showed mostly additivity and some modest synergy (CI values 0.6-1.4) in nearly all combinations tested, displaying reduced sensitivity to the combination (FIG. 8). It thus appears that biomarkers which predict tumor cell sensitivity will also indicate which cells will respond in a synergistic manner to an IGF-1R kinase inhibitor (e.g. PQIP) and chemotherapy (i.e. SN38, oxaliplatin, or 5-Fluorouracil).

Additional combinatorial experiments involving analysis of IGF1R protein levels were carried out using PQIP sensitive HT29 and PQIP resistant HCT116 CRC cell lines. Cells were exposed to PQIP (0.4 μmol/L) and chemotherapy (SN38 0.004 μmol/L, or Oxaliplatin 1.0 μmol/L) alone or in combination for 72 h. Protein was extracted and analyzed for phospho/total IGF1R levels using a Meso Scale Discovery (MSD; Gaithersburg, Md. 20877) assay. As shown in FIG. 9, phosphorylated IGF1R was inhibited upon exposure to PQIP alone and in both combinations. SN38 or Oxaliplatin alone exhibited no significant effect on IGF1R phosphorylation (FIG. 9).

It has been shown that chemotherapy, specifically oxaliplatin, in HT29 and HCT116 induces an increase in expression levels of both total and phosphorylated Akt and ERK. Despite this, we were able to achieve a synergistic effect on proliferation indicating that inhibition of these prosurvival pathways is not an absolute requirement for the action of these compounds. Previous studies have shown that other compounds can increase phosphorylated ERK levels and this may be reflective of sustained versus transient ERK activation which has been associated with proapoptotic cell death (46).

Due to the synergistic effect with these compounds, further investigation was done on the chemotherapy combinations using MSD assays. Interestingly, the basal levels of phosphorylated IGF1R are higher in the sensitive HT29 cells than in the resistant HCT116 cells. In addition, all combinations display a similar decrease in phosphorylated IGF1R with PQIP alone. This suggests again that the synergy seen is independent of phosphorylated IGF1R and may be by other mechanisms, such as apoptosis.

OSIP-906 Studies

Materials and Methods

IGF-1R Inhibitor Compound: IGF-1R inhibitor compound OSI-906 was provided by OSI Pharmaceuticals, (Melville, N.Y.). OSIP-906 (cis-3-[8-amino-1-(2-phenyl-quinolin-7-yl)-imidazo[1,5-a]pyrazin-3-yl]-1-methyl-cyclobutanol) is synthesized by the methods described in patent application number WO 2005/097800.

Cell Lines and Culture: Twenty-seven human colon cancer cell lines, were obtained from American Type Culture Collection (Manassas, Va.). The GEO cells were a generous gift from Dr. Fortunato Ciardiello (Cattedra di Oncologia Medica, Dipartimento Medico-Chirurgico di Internistica Clinica e Sperimentale “F Magrassi e A Lanzara,” Seconda Università degli Studi di Napoli, Naples). All cells except GEO were grown in RPMI medium supplemented with 10% fetal bovine serum, 1% non-essential amino acids, 1% penicillin/streptomycin and were maintained at 37° C. in an incubator under an atmosphere containing 5% $CO_2$. GEO cells were grown in DMEM/F12 supplemented with 10% fetal bovine serum, 1% non-essential amino acids, 1% penicillin/streptomycin. The cells were routinely screened for the presence of mycoplasma (MycoAlert, Cambrex Bio Science, Baltimore, Md.) and were exposed to OSI-906 when they reached approximately 70% confluence. OSI-906 was provided by OSI Pharmaceuticals, (Boulder, Colo.) and prepared as a 10 mM stock solution in DMSO.

Fluorescent in situ Hybridization (FISH): Dual-color FISH assays were performed on the prepared slides of the CRC cell lines using 120 ng of Spectrum Red-labeled IGF-1R (University of Colorado Cancer Center Cytogenetics Lab) and 0.3 ul of Spectrum Green-labeled CEP15 (Abbott Molecular, Abbott Park, Ill.) per 113 $mm^2$ hybridization area according to standard protocol in the laboratory (1). The slides were first washed in 70% acetic acid for 20-30 sec, then incubated in 0.008% pepsin/0.01 M HCl at 37° C. for 3-5 min, in 1% formaldehyde for 10 min and dehydrated in a graded ethanol series. The probe mix was applied to the selected hybridization areas, which were covered with glass cover slips and sealed with rubber cement. DNA co-denaturation was performed for 9 min at 85° C. and hybridization was allowed to occur at 37° C. for 40-48 hours. Post-hybridization washes were performed with 2×SSC/0.3% NP-40 at 72° C. and 2×SSC for 2 min at room temperature (RT) and dehydrated in a graded ethanol series (Cappuzzo F, et al. Br J Cancer 2008; 99(1):83-9). Chromatin was counterstained with DAPI (0.3 μg/ml in Vectashield Mounting Medium, Vector Laboratories, Burlingame, Calif.). Analysis was performed on an epi-fluorescence microscope using single interference filter sets for green (FITC), red (Texas Red), and blue (DAPI) as well as dual (red/green) and triple (blue, red, green) band pass filters. Approximately 20 metaphase spreads and 100 interphase nuclei were analyzed in each cell line, ploidy was assessed along with identification of the chromosomes harboring homologous sequences to the IGF-1R/CEP15 probe set. For documentation, images were captured using a CCD camera and merged using dedicated software (CytoVision, AI, San Jose, Calif.).

Immunoblotting: Cells were seeded into 6-well plates 24 hr prior to treatment and new media was added with or without drug for an additional 72 hr. After treatment, cells were scraped into RIPA buffer containing protease inhibitors, EDTA, NaF, and sodium orthovanadate. The total protein in samples was determined using the BioRad $D_c$ Protein Assay (BioRad, Hercules, Calif.). Thirty micrograms of total protein was loaded onto a 10% gradient gel, electrophoresed, and then transferred to PVDF using the I-Blot (Invitrogen, Carlsbad, Calif.). The membranes were blocked for one hour at RT with 5% nonfat dry milk in TBS containing tween-20 (0.1%) prior to overnight incubation at 4° C. with the following primary antibodies: pIGF-1R, IGF-1R, pSHC, SHC, pIRS-1, IRS-1, pAKT, AKT, pERK, ERK, pS6RP, S6RP, pPI3K, and PI3K. (all from Cell Signaling, Beverly, Mass.). After the primary antibody, blots were washed 3×20 minutes in TBS-Tween (0.1%), incubated with the appropriate secondary anti-rabbit or anti-mouse IgG horseradish peroxidase-linked antibody at 1:20,000 (Jackson ImmunoResearch, West Grove, Pa.) for one hour at RT, washed three times and developed using the Immobilon Western Chemiluminescent HRP substrate (Millipore, Billerica, Mass.). Immunoblot experiments were performed in triplicate for each antibody.

Immunohistochemistry (IHC): IGF-1R and downstream effector protein expression was assessed by IHC using the following antibodies. IGF-1R (Ventana medical systems, Tucson, Ariz.), IGF-2R (Santa Cruz, Santa Cruz, Calif.), phospho-ERK (Cell Signaling, Beverly, Mass.), IGF2, (ABCAM, Cambridge, Mass.). The staining procedures were performed according to the antibody manufacturer's recommendations. For scoring of proteins, a staining index calculated as percent of stained tumor cells×average staining intensity graded from 0 to 4 was used, resulting in an index value between 0 and 400. Consistent with previous reports, samples with a staining index of 200 or higher were predefined as protein-positive (Jimeno A., et al. Cancer Res 2008; 68(8): 284:1-9) The scoring was performed by pathologists who were blinded to the exposure data.

KRAS/BRAF/PI3K mutation analyses. For both human primary tumor explants and CRC cell lines DNA was isolated using the Qiagen DNA extraction kit. KRAS mutations were analyzed by one of two methods. The human primary tumor explants were assayed by the University of Colorado Cancer Center Pathology Core with the DxS Scorpion method (DxS, Manchester, UK) using the manufacturer's instructions. Briefly, template DNA was analyzed for a set of seven known KRAS point mutations in codons 12 and 13 (i.e. Gly12Asp (GGT>GAT), Gly12Ala (GGT>GCT), Gly12Val (GGT>GTT), Gly12Ser (GGT>AGT), Gly12Arg (GGT>CGT), Gly12Cys (GGT>TGT), and Gly13Asp (GGC>GAC)) using the THERASCREEN® KRAS Mutation Detection kit (DxS Ltd., Manchester, UK). Reactions and analysis were performed on a Lightcycler 480 real-time PCR instrument (LC480) that was calibrated using a dye calibration kit provided by the kit manufacturer. Reactions were performed on a 96-well plate in 20 μl reactions using approximately 60 ng of each DNA template. Sample DNA was amplified with eight separate primer sets (one for the wild-type sequence and one for each of seven different point mutations) with an internal Scorpion reporter probe. Cycle cross point (CP) values were calculated using the LC480 Fit-point software suite, and the control Cp was subtracted from the Cp of each mutation specific primer set (FIG. 2). Because there may be spurious low level amplification in the absence of mutant template, amplification products are often visible at later cycle numbers for most of the primer sets. To avoid false-positive results due to, background amplification, the assay is considered valid only if the control Cp value is less than or equal to 35 cycles. Cp thresholds are calculated to compensate for this background amplification. Mutations are called when the Cp is less than the statistically-set 5% confidence-value threshold (Franklin W A H J, Sugita M, Bemis L, Jimeno A, Messersmith W A KRAS mutation: Comparison of testing methods and tissue sampling techniques in colon cancer. J Mol Diagn 2009).

The CRC cell lines were analyzed for KRAS mutations by the University of Colorado Cancer Center Pathology Core with a high resolution melting temperature method using custom primers and the Roche LC480 real time PCR machine (Mannheim, Germany). Briefly, template DNA was tested by High Resolution Melting (HRM) analysis using a Lightcycler 480 real-time PCR instrument (Roche Applied Science, Indianapolis, Ind.). Approximately 60 ng of tumor template DNA, wild type control DNA and mutant control DNA were amplified on the Lightcycler 480 instrument using HRM master mix (Roche cat #04909631001), with the RASO1 and RASA2 primers and 1.75 mM MgCl2 in a 10 μl on a 96 well plate, using a 2-step cycling program (95° melting, 72° annealing and extension) for 45 cycles. PCR products were analyzed by HRM with 25 data acquisitions per degree of temperature increase, from 40° to 90° C. Lightcycler 480 Gene Scanning software using the known wild-type control samples for baseline calculation was used for these analyses (3). BRAF and PI3K mutations were analyzed by PCR amplification and direct sequencing of the products as described previously (Jhawer M, et al. Cancer Res 2008; 68(6):1953-61). Primers used were F, AACACATTTCAAGCCCCAAA SEQ ID NO:115 and R, GAAACTGGTTTCAAAATATTCGTT SEQ ID NO:116 for amplification of exon 15 of BRAF; F, GCTTTTTCTGTAAATCATCTGTG SEQ ID NO:117 and R, CTGAG-ATCAGCCAAATTCAGT SEQ ID NO:118 for exon 9 of PIK3CA; and F, CATTTGCTC-CAAACTGACCA SEQ ID NO:119 and R, TACTC-CAAAGCCTCTTGCTC SEQ ID NO:120 (for codon 1023 mutation) and F, ACATTCGAAA-GACCCTAGCC SEQ ID NO:121 and R, CAATTCCTATGCAATCGGTCT SEQ ID NO:122 (for codon 1047 mutation) for exon 20 of PIK3CA.

Gene expression profiles: Cells were plated at $2\times10^6$ in 6-well plates 24 h prior to harvest. After 24-72 hours cells were rinsed twice with PBS, and RNA was prepared using a RNeasy Plus mini kit (Qiagen, Valencia, Calif.). RNA stabilization, isolation, and microarray sample labeling were carried out using standard methods for reverse transcription and one round of in vitro transcription. Total RNAs isolated from CRC cell lines and tumor xenografts were hybridized on Affymetrix U133 Plus 2.0 gene arrays at least in duplicates. This gene array has ~54,000 probes comprising ~20,000 genes. Sample preparation and processing procedure was performed as described in the Affymetrix GeneChip® Expression Analysis Manual (Affymetrix Inc., Santa Clara, Calif.). In addition, CRC cell line gene expression profiles were obtained from the GlaxoSmithKline (GSK) genomic profiling data via the NCI cancer Bioinformatics Grid (caBIG®). These data were also profiled using Affymetrix U133 Plus 2.0 gene arrays in triplicates. To integrate the data generated from our lab and GSK, absolute intensity signals from the microarray gene expression profiles were extracted and probe sets representing the same gene were collapsed based on maximum values. Next, the gene expression levels were converted to a rank-based matrix and standardized (mean=0, standard deviation=1) for each microarray. Using this pre-processing method, the same cell lines from different data sets were clustered based on their gene expression profiles. Data analyses were performed on this rank-based matrix.

shRNA knockdown: The pRS-shE2F6 gene-specific shRNA expression cassettes, along with control shRNA plasmids including the original pRS vector (TR20003, were purchased from OriGene (Rockville, Md.). The sequence of the metallothionein 2A-specific 29mer shRNA is GTAAA-GAACGCGACTTCCACA-AACCTGGA SEQ ID NO:123. Stable clones were generated by transfecting HCT116 cells in 6-well dishes with 1 μg of each of the shRNA plasmids using Eugene 6 (Roche, Basel Switzerland), according to manufacturer's recommendations. Seventy-two hours after transfection, the cells were placed under selection with 2.0 μg/mL of puromycin, splitting 1:5 when the cells reached confluency. Multiple clones from the same transfection were pooled and grown under puromycin selection. Successful knockdown of specific genes and gene products was confirmed by semi-quantitative RT-PCR and immunoblotting with specific antibodies.

Gene set enrichment analysis: Gene set analysis was performed using the GSEA software Version 2.0.1 obtained from the Broad Institute (Subramanian A. et al, Proc Natl Acad Sci USA. 2005 Oct. 25; 102(43):15545-50. Epub 2005 September 30; PMID: 16199517). Gene set permutations were performed 1000 times for each analysis. We used the nominal p-value and Normalized Enrichment Score (NES) to sort the pathways enriched in each phenotype. We used the 199 pathways defined by Kyoto Encyclopedia of Genes and Genomes (KEGG) database as the gene set in this study (PMID: 18077471; Kanehisa M., et al., Nucleic Acids Res. 2008 January; 36 (Database issue):D480-4. Epub 2007 December 12). Human pathway annotations were downloaded from KEGG (August 2007 release). The KEGG human pathways used in this study include metabolism, genetic information processing, environmental information processing, cellular processes and human diseases. One hundred and sixty-six gene sets passed the gene set size filter criteria (min=10, max=500).

K-TSP classifier: We used the K-TSP algorithm (PMID: 16105897; Kanehisa M. et al., Nucleic Acids Res. 2008 January; 36 (Database issue):D480-4. Epub 2007 Dec. 12.) to construct a discriminative classifier in predicting tumors sensitive to OSI-906. In brief, the algorithm exploits the information contained in the rank-based matrix by focusing on "marker gene pairs" (i, j) for which there is a significant difference in the probability of the event ($R_i<R_j$) across the N samples from class Y=1 (OSI-906 sensitive) to Y=−1 (OSI-906 resistant), where the event ($R_i<R_j$) is equivalent to the rank of gene i is less than the rank of gene j if and only if gene i is expressed less then gene j (relative expression). Here, the quantities of interest are $p_{ij}(m)=\mathrm{Prob}(R_i<R_j|Y=m)$, m=(1, −1), i.e., the probabilities of observing $R_i<R_j$ in each class. These probabilities are estimated by the relative frequencies of occurrences of $R_i<R_j$ within profiles and over samples. Let $\Delta_{ij}$ denote the "score" of gene pair (i, j), where $\Delta_{ij}=|p_{ij}(1)-p_{ij}(-1)|$. A score $\Delta_{ij}$ is computed for every pair of genes i, j$\in\{1, \ldots, P\}$, i≠j. Gene pairs with high scores are viewed as most informative for classification. Using an internal leave-one-out cross-validation, the final k-TSP classifier utilizes the k disjoint pairs of genes, which achieve the k best scores from the training set. In this study, maximum number of pairs (kmax) was fixed as 10.

In vivo Growth Studies: Five to six-week-old female athymic nude mice (Harlan Sprague Dawley) were used. The research protocol was approved by the University of Colorado Denver, Animal Care and Use Committee. Mice were caged in groups of five and kept on 12-h light/dark cycle and provided with sterilized food and water ad libitum. All of the studies were conducted in accordance with the NIH guidelines for the care and use of laboratory animals, and animals were housed in a facility accredited by the American Association for Accreditation of Laboratory Animal Care. Animals were allowed to acclimate for at least 7 days before any handling.

The primary CRC xenografts were generated according to published methodology (Rubio-Viqueira B, et al. Clin Cancer Res 2006; 12(15):4652-61.). Briefly, surgical specimens of patients operated at the University of Colorado Hospital were reimplanted s.c. to 5 mice for each patient. Tumors were let to grow to a size of 1000-1500 $mm^3$ at which point were harvested, divided, and transplanted to another 5 mice to maintain the tumor bank. After a subsequent growth passage, tumors were excised and propagated to cohorts of ≧25 mice, for treatment. Tumors from this cohort were allowed to grow until reaching ~150-300 $mm^3$, at which time they were evenly distributed by size in the two treatment groups. Tumors from this treatment stage were treated for 28 days with either vehicle control (25 mM tartaric acid), or OSI-906 (40 mg/kg). Mice were monitored daily for signs of toxicity and were weighed twice weekly. Tumor size was evaluated two times per week by caliper measurements using the following formula: tumor volume=$[\text{length}\times\text{width}^2]/0.52$. Relative tumor growth index was calculated by relative tumor growth of treated mice divided by relative tumor growth of control mice since the initiation of therapy (T/C).

For cell line xenografts mice were allowed to acclimate as above. All CRC cells were harvested in exponential phase growth and resuspended in a 1:1 mixture of serum-free RPMI 1640 and Matrigel (BD Biosciences). Five to 10 million cells per mouse were injected s.c. into the flank using a 23-gauge needle. Mice were monitored daily for signs of toxicity and were weighed twice weekly. Tumor size was evaluated two times per week by caliper measurements using the following formula: tumor volume=[length×width2]/0.52. When tumors reached 150-300 mm3 mice were randomized into two groups with at least 10 tumors per group. Mice were treated for 14 days with either vehicle or OSI-906 as above.

Statistical methods. Significance levels for comparison of groups were calculated using GraphPad Prism Software (La Jolla, Calif.). Differences were considered significant at $P<0.05$.

TABLE 2b miRNAs

| NCBI Official Symbol | NCBI Official Full Name | NCBI Gene ID #. | Sanger ID: Stem-loop sequence (SLS) | SLS, Sanger miRBase Accession # | Sanger: Mature sequence | Sanger: Minor sequence |
|---|---|---|---|---|---|---|
| MIR224 | microRNA 224 | 407009 | hsa-miR-224 | MI0000301 | hsa-miR-224 | |
| MIR181A1 | microRNA 181a-1 | 406995 | hsa-miR-181a1 hsa-miR-181a2 | MI0000289 | hsa-miR-181a | |
| MIR194-1 | microRNA 194-1 | 406969 | hsa-miR-194-1 | MI0000488 | hsa-miR-194 | |
| MIR194-2 | microRNA 194-2 | 406970 | hsa-miR-194-2 | MI0000732 | | |
| MIR584 | microRNA 584 | 693169 | hsa-miR-584 | MI0003591 | hsa-miR-584 | |
| MIR215 | microRNA 215 | 406997 | hsa-miR-215 | MI0000291 | hsa-miR-215 | |
| MIR429 | microRNA 429 | 554210 | hsa-miR-429 | MI0001641 | hsa-miR-429 | |
| MIR200A | microRNA 200a | 406983 | hsa-miR-200a | MI0000737 | hsa-miR-200a | |
| MIR200B | microRNA 200b | 406984 | hsa-miR-200b | MI0000342 | hsa-miR-200b | hsa-miR-200b* |
| MIR886 | microRNA 886 | 100126299 | hsa-miR-886 | MI0005527 | hsa-miR-886-3p | |
| MIR521-1 | microRNA 521-1 | 574494 | hsa-miR-521-1 | MI0003176 | hsa-miR-521 | |
| MIR521-2 | microRNA 521-2 | 574481 | hsa-miR-521-2 | MI0003163 | | |
| MIR432 | microRNA 432 | 574451 | hsa-miR-432 | MI0003133 | hsa-miR-432 | |
| MIR192 | microRNA 192 | 406967 | hsa-miR-192 | MI0000234 | hsa-miR-192 | hsa-miR-192* |

miRNA profiling. miRNA profiling was performed at Dharmacon (Lafayette, Colo.) using their proprietary miRNA probe set and a two color high-density array. The miRNA patterns in OSI906 sensitive (S) and resistant (R) CRC cell lines were confirmed using qRT-PCR. Total RNA was extracted from the following eight colon cancer cell lines: LS513, COLO205, HT29, GEO, HCT-15, RKO, HCT-8, and SW480 using Qiagen's miRNeasy Mini Kit. Next, reverse transcription was performed using Qiagen's miScript Reverse Transcription Kit, followed by Real-time qPCR using miRNA specific primers and the Step One Plus Real-Time PCR Software. The experiment was repeated three times in order to confirm the results. In order to assess the functional significance of miRNA expression with regard to OSI906 sensitivity, transfection was performed on one sensitive cell line with miR-181a and miR-224 antagonists and one resistant cell line with miR-181a and miR-224 mimic. The cells were transfected in 60 mm dishes for 24 hours, after which the samples were plated into 96-well plates, and treated with different doses of OSI906 (5 μM-0.075 μM). The results were analyzed using SRB. The remainder of the samples transfected with miR-224 was plated in 60 mm dishes and qRT-PCR was performed. The miRNAs profiled, and their encoding genes, are described in Table 2b. The sequences and other details of the probed miRNAs can be found at any of a number of online databases, including the Sanger miRNA database "miRBase"; and the NCBI Entrez Gene database (National Center for Biotechnology Information (NCBI), U.S. National Library of Medicine, 8600 Rockville Pike, Building 38A, Bethesda, Md. 20894.

Results and Discussion

Assessment of responsiveness of a panel of CRC cell lines to OSI-906. In order to assess CRC cell lines with differential sensitivity to OSI-906, a panel of 27 CRC cell lines were exposed to increasing concentrations of OSI-906 and proliferation was measured using the SRB assay as described previously (Pitts, T M, et al. Mol Cancer Ther 2009; 8(2):342-9).

Figure 17:
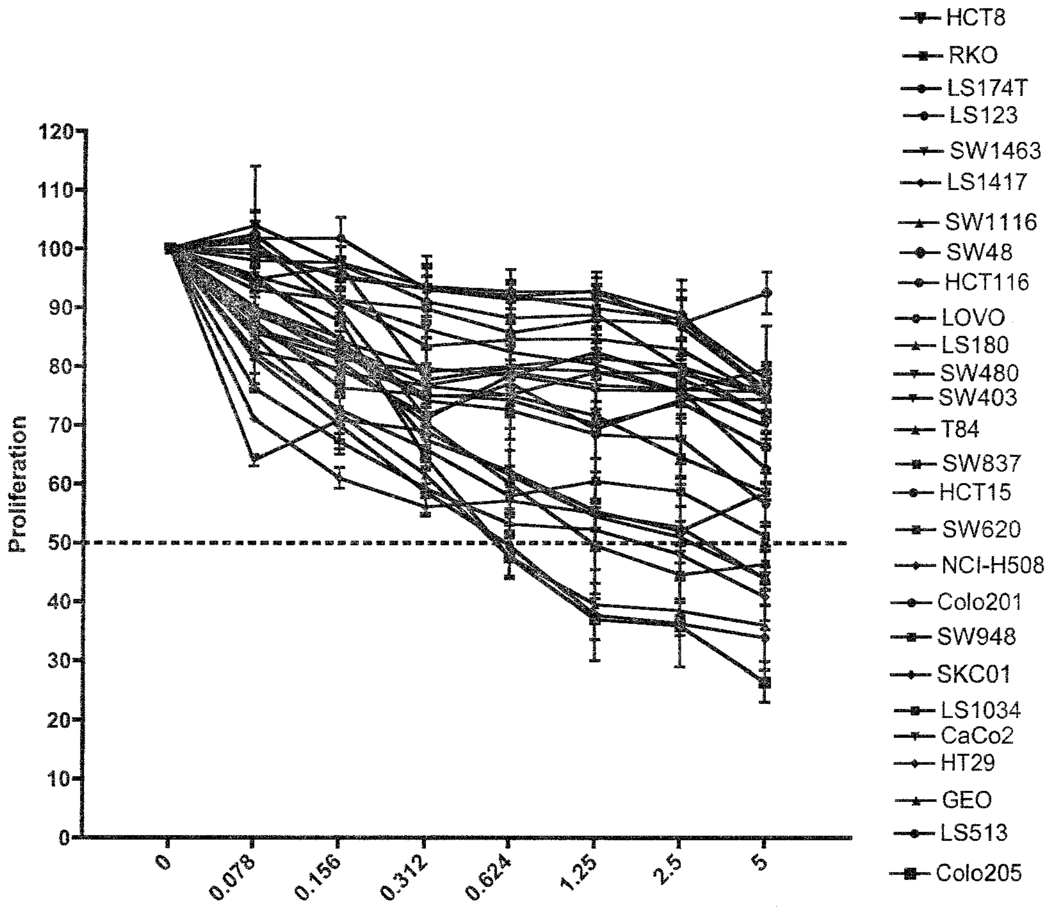
FIG. 17: Results of cell proliferation assay on the panel of 27 CRC cell lines. Cell proliferation was evaluated by SRB following exposure to OSI-906 for 72 hours. Cells were plated at an optimized density in 96-well plates, incubated overnight at 37° C., and then exposed to a serial dilution of OSI-906. After 72 hours incubation, cells were fixed with trichloroacetic acid and an SRB was performed as described in materials and methods.

As depicted in FIG. 17 there was a wide range of sensitivity of the CRC cell lines to OSI-906, the majority of the cell lines failing to reach an IC50 up to 5 μmol/L, but a clear distinction could be made between the cell lines that were sensitive and the cell lines that were resistant. For classification, a sensitive cell line was classified as one with an $IC_{50} \leq 1.5$ μmol/L, whereas resistant cell lines had $IC_{50}$ of >5 μmol/L. Six CRC cell lines from this panel met the criteria as being sensitive (i.e. Colo205, GEO, LS513, HT29, CaCo2 and LS1034), and the remaining 21 were resistant (i.e. Colo201, SK-CO-1, SW948, SW48, NCI-H508, HCT116, HCT15, SW480, RKO, HCT8, LoVo, LS123, T84, LS174T, LS180, SW1417, SW1116, SW837, SW1463, SW620 and SW403).

Figure 18A:
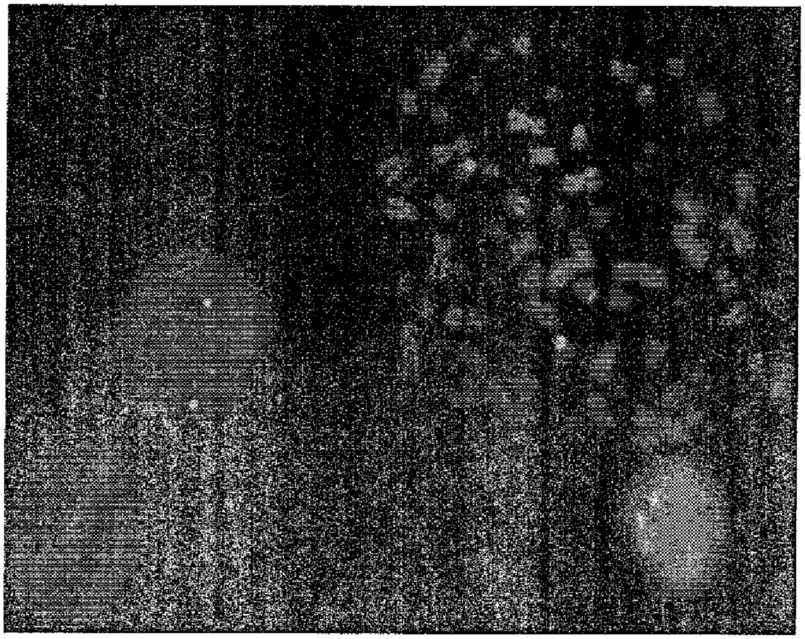
FIG. 18: IGF-IR FISH analysis showing representative images of metaphase spreads and interphase nuclei of a sensitive with unbalanced gain (A) and a resistant with no gain (B).
Figure 18B:
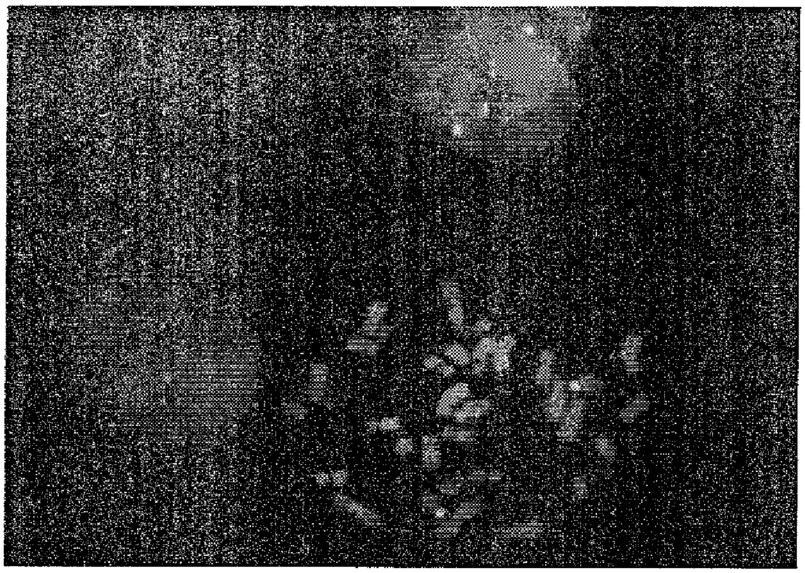

Fluorescent in situ hybridization (FISH) analysis of CRC cell lines for IGF-1R gene copy number. Since previous studies have suggested that increased EGFR copy number may be predictive for EGFR-directed agents, we assessed IGF-1R gene copy number in the panel of cell lines (Hirsch F R, et al. J Clin Oncol 2008; 26(20):3351-7). Using an IGF-1R specific probe, twenty-seven CRC cell lines with differing sensitivities to the IGF-1R inhibitor OSI-906 were subjected to FISH analysis. Although IGF-1R gene amplification was not observed in any of the CRC cell lines, several of them displayed an unbalanced gain (based upon ploidy) of IGF-1R copy number, with a trend (p=0.17) towards a relationship between the presence of unbalanced gain and sensitivity (Table 3). Representative spreads/interphase nuclei are depicted in FIG. 18 for a sensitive (18A) and resistant (18B) cell line.

Assessment of KRAS/BRAF/PI3K gene mutation status by sequencing. Since tumors with mutant KRAS/BRAF or PI3K demonstrate resistance to EGFR-based therapies, we characterized the KRAS/BRAF/PI3K mutational status of the CRC cell lines (Sartore-Bianchi A, et al. Cancer Res 2009; 69(5):1851-7; Di Nicolantonio F, et al. J Clin Oncol 2008; 26(35):5705-12; Perrone F, et al. Ann Oncol 2009; 20(1):84-90; Jimeno A, et al. Cancer J 2009; 15(2):110-3). Although the correlation observed between KRAS status and OSI-906 sensitivity did not reach statistical significance, there was a trend (p=0.3442) towards KRAS wild-type tumors being more sensitive, and KRAS mutants being more resistant. There was no relationship between either BRAF or PI3K mutation status and responsiveness to OSI-906.

TABLE 3

Baseline FISH analysis of OSI-906 sensitive and resistant CRC cell lines demonstrating IGF-IR gain based on ploidy.

| Cell Line | IGF1R/Ploidy | S/I/R to OSI-906 |
|---|---|---|
| CoLo205 | Gain - High | S |
| GEO | Balanced | S |
| HT29 | Gain - High | S |
| LS513 | Gain - Low | S |
| CaCo2 | Gain - Low | S |
| LS1034 | Gain - High | S |
| CoLo201 | Balanced | R |
| SK-CO-1 | Gain - High | R |
| SW948 | Balanced | R |
| SW620 | Balanced | R |
| T-84 | Gain - Low | R |
| HCT116 | Balanced | R |
| HCT15 | Balanced | R |
| HCT8 | Balanced | R |
| LoVo | Gain - High | R |
| LS123 | Gain - Low | R |
| LS174T | Balanced | R |
| LS180 | Balanced | R |
| NCI-H508 | Balanced | R |
| RKO | Balanced | R |
| SW1116 | Gain Low | R |
| SW1417 | Balanced | R |
| SW1463 | Loss | R |
| SW403 | Balanced | R |
| SW48 | Balanced | R |
| SW480 | Balanced | R |
| SW837 | Balanced | R |

Identification of genes that were differentially expressed in OSI-906 sensitive versus OSI-906-resistant CRC cell lines. To initially identify genes that correlated with sensitivity to OSI-906, we analyzed the basal gene expression profiles of the four most sensitive and the four most resistant CRC cell lines. Using the two-sample t-test, 139 genes were identified as differentially expressed in OSI-906 sensitive and OSI-906 resistant CRC cell lines. To characterize these potential biomarkers we decided to focus the top scoring genes (p<0.002) for the initial studies. For example, caldesmon (61-fold up regulated), an actin-binding protein has recently been shown to play a critical role in regulating the formation and dynamics of podosomes and invadopodia, cell adhesion structures that protrude from the plasma membrane and degrade the extracellular matrix (ECM), thus promoting cancer cell invasion (Linder S, et al.: Trends Cell Biol 2003; 13(7):376-85). Interestingly, caldesmon is a negative regulator of the formation podosomes and invadopodia, indicating that CRC cell lines with an invasive/malignant phenotype are more responsive to IGF-1R inhibition. Metallothioneins (MT) as a group were also up-regulated in the resistant CRC cell lines versus the sensitive. MT are a family of ubiquitous, low molecular weight intracellular proteins that bind and detoxify heavy metal ions (Kagi J H. Methods Enzymol 1991; 205:613-26; Bauman J W, et al. Toxicol Appl Pharmacol 1991; 110(2):347-54). This family represented the highest ranked group (9-36-fold increase) of differentially expressed genes. MT can be induced by a variety of stimuli, are involved in other cellular functions such development, differentiation proliferation, and carcinogenesis, and have been associated with a poor prognosis and metastasis in cancer (Bruewer M, et al. World J Surg 2002; 26(6):726-31; Sens M A, et al. Am J Pathol 2001; 159(1):21-6; Cherian M G, et al. Mutat Res 2003; 533(1-2):201-9; Jin R, et al. Br J Cancer 2000; 83(3):319-23). MT may also play a functional role in cancer drug resistance, though the mechanism for this remains poorly understood (Surowiak P, et al. Histol Histopathol 2005; 20(4):1037-44; Saga Y, et al. Int J Urol 2004; 11(6):407-15). Several genes were also up-regulated in the sensitive lines. Of interest was the aldehyde hehydrogenease (ALDH1A1, 83 fold) and the mitogen-activated protein kinase kinase 6 (MAP2K6, 11 fold). ALDH1A1 is an enzyme involved in the metabolism of alcohol and interestingly, the oxidation of all-trans retinal to all-trans retinoic acid (Molotkov A, Duester G. Genetic evidence that J Biol Chem 2003; 278(38):36085-90; Rice K L, et al. Leuk Res 2008; 32(6):873-83). MAP2K6 is a protein that phosphorylates and activates p38 MAP kinase in response to inflammatory cytokines or environmental stress. As an essential component of p38 MAP kinase mediated signal transduction pathway, this gene is involved in many cellular processes such as stress induced cell cycle arrest, transcription activation invasion/migration and apoptosis (Abdollahi T, et al. Apoptosis 2005; 10(6):1383-93; Hsieh Y H, et al. Cancer Res 2007; 67(9):4320-7; Timofeev O, et al. Cell Cycle 2005; 4(1):118-20).

Figure 19:
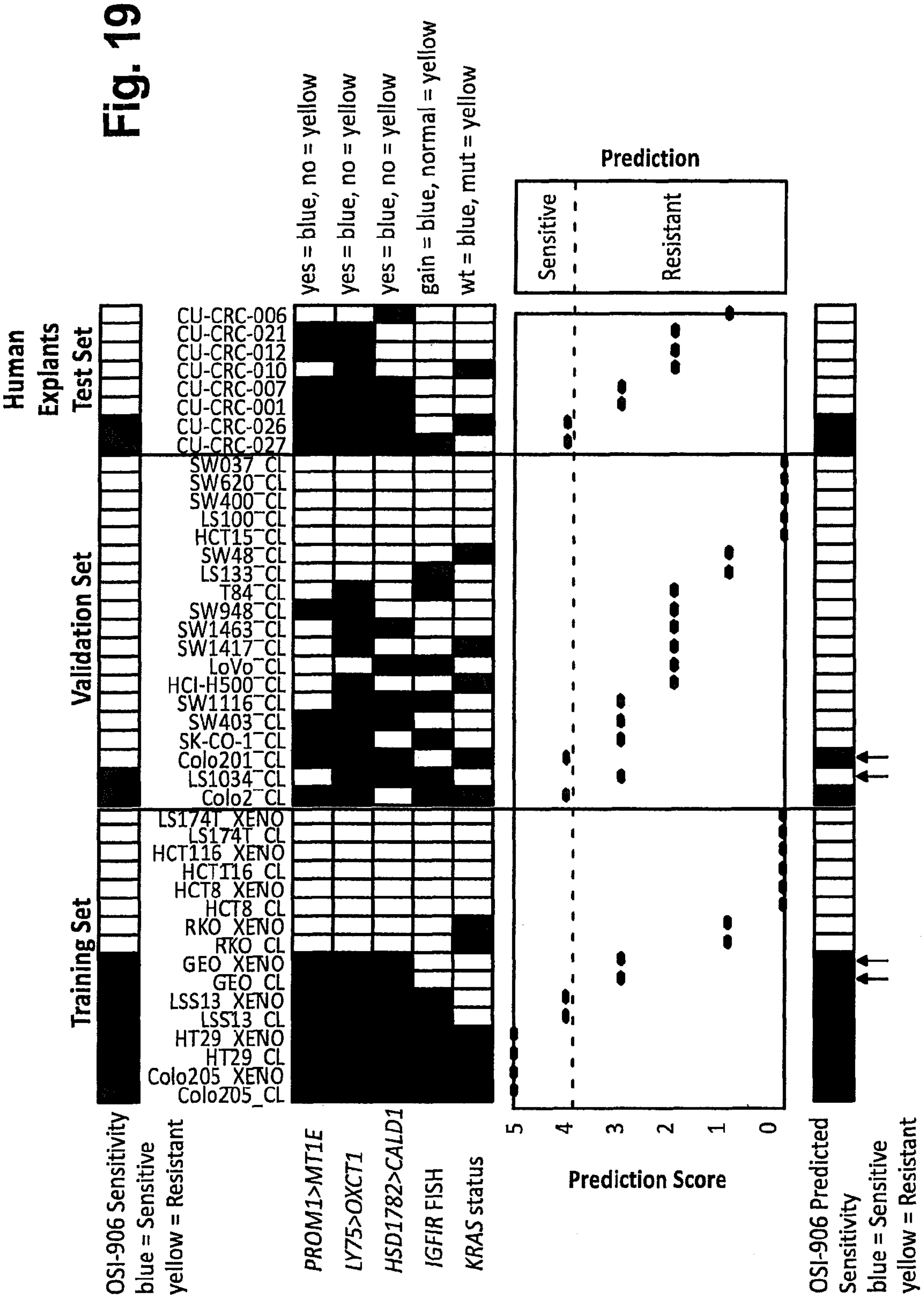
FIG. 19: Diagram demonstrating the predictive classifier to OSI-906.
Figure 20A:
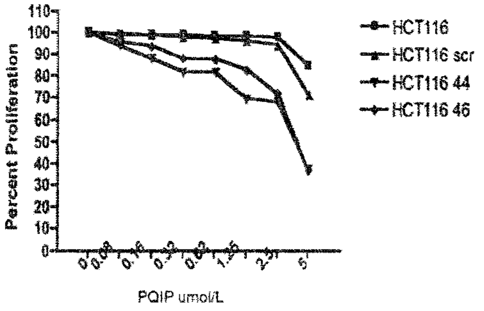
FIG. 20: Proliferation effects of MT2A knockdown on HCT116 and SW480 cells exposed to OSI906. HCT116 (A) and SW480 (B) cells were stably transfected with MT2A shRNA. The cells were then exposed to varying concentrations of OSI-906. Proliferation was assessed by SRB as described in materials and methods. RT-PCR and western blot analysis was performed as described in materials and methods using MT2A as primary antibodies. The blot was stripped and reprobed with anti-actin antibody as a loading control.
Figure 20B:
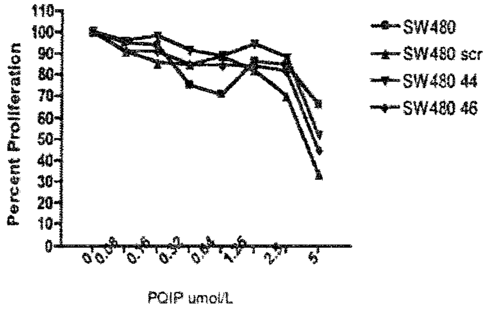
Figure 21A:
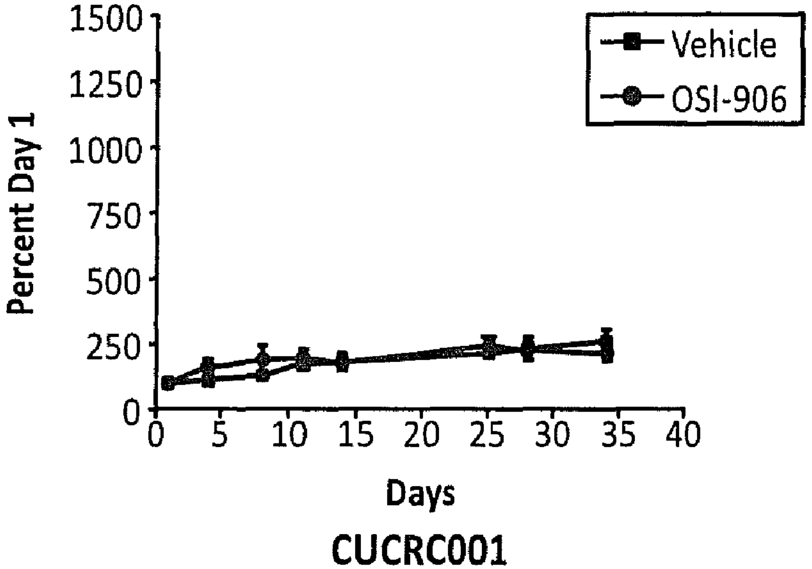
FIG. 21: Antitumor activity of OSI-906 (40 mg/kg) in mouse models with human tumor explants. A and B show representative graphs with resistant tumors. C and D show representative graphs with sensitive tumors.
Figure 21B:
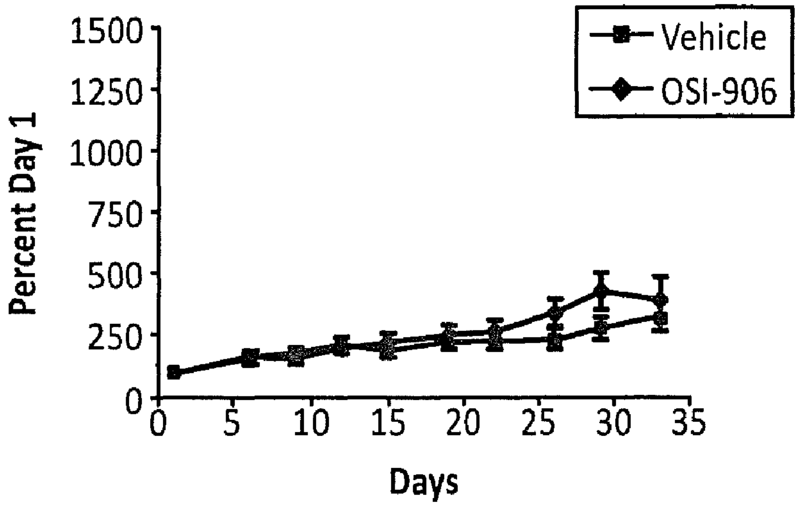
Figure 21C:
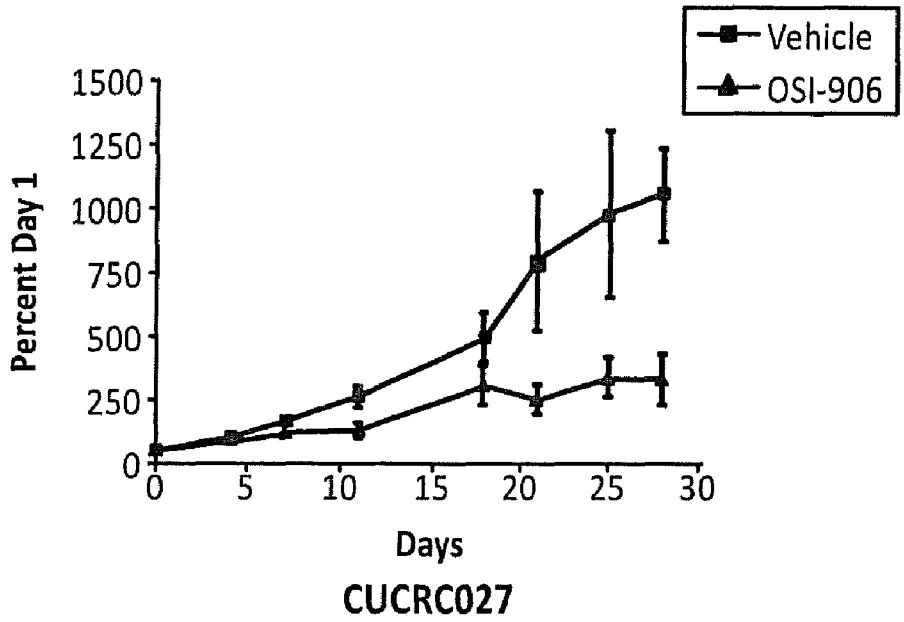
Figure 21D:
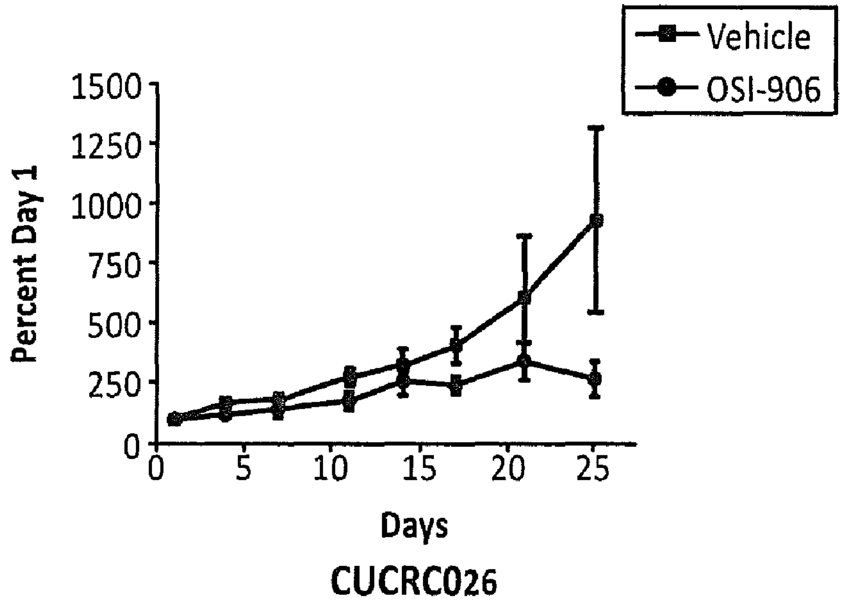

Training and validation of K-TSP classifier for predicting OSI-906 sensitivity. A main goal of this project was to develop a classifier to predict sensitivity to OSI-906. To this end we used both cell lines and xenografts treated with OSI-906 as a training set. We used baseline gene array from the 4 most sensitive and 4 of the most resistant cell lines grown both in vitro and in vivo. In this study we used the K-TSP algorithm as a discriminative classifier (Tan A, et al. Bioinformatics 2005; 2:3896-904), which has been proven in various studies. Using an internal leave-one-out cross-validation, the final k-TSP classifier utilizes the k disjoint pairs of genes, which achieve the k best scores from the training set. In this study, maximum number of pairs (kmax) was fixed as 10. Using four sensitive and resistant cell lines to OSI-906, the k-TSP classifier identified three gene pairs as the final classifier: (PROM1, MT1E), (LY75, OXCT1) and (HSD17B2, CALD1). Interestingly two of these genes, MT1E and CALD1 also appeared in the gene analysis above. In addition to the gene pairs we integrated KRAS mutational (WT) status and IGF-1R FISH (unbalanced gain) analysis to develop a signature of sensitivity to the IGF-1R inhibitor. FIG. 19 shows diagrammatically how this prediction is used. In order for a tumor to predict as sensitive it must meet 4 of the 5 classifiers. From the training data, the integrated genomic classifier achieved an estimated leave-one-out cross-validation of 85.8%. Using this integrated genomic classifier, we validated its prediction in the 18 CRC cell lines not used in the training set. In this validation set, the integrated genomic classifier correctly predicted the OSI-906 sensitivity on 89% (16/18) cell lines.

shRNA knockdown of potential predictive biomarker genes. In order to determine whether any of the highly ranked genes had a functional role in mediating responsiveness to OSI-906 we performed knockdown experiments with shRNA. CRC cell lines were transfected with shRNA for the genes listed above (Caldesmon, Metallothionein 2A (MT2A), MT1E, ALDH1A1, and MAP2K6) and the phenotype was analyzed by exposing the CRC cell lines to increasing concentrations of OSI-906. As depicted in FIG. 20A, shRNA knockdown of MT2A resulted in a robust decrease in MT2A RNA and protein in OSI-906 resistant HCT116 and SW480 cells. These cells, when exposed to increasing concentrations of OSI-906 exhibited a "left-shift" in sensitivity ($IC_{50}$>5 μmol/L to $IC_{50}$=5 μmol/L). In contrast the SW480 cells did not exhibit the same "left shift" FIG. 20B. Similar shRNA knockdown of the other genes noted above, did not demonstrate a functional role in mediating sensitivity (ALDH1A1, MAP2K6) or resistance (CALD1, MT1E) to OSI-906 (data not shown).

K-TSP, FISH, KRAS status can predict sensitivity to OSI-906 in human tumor explants. To further validate the predictive classifier we predicted the sensitivity of 5 human tumor explants prior to treating with OSI-906. The classifier predicted three explants as resistant and two as sensitive. The overall accuracy for the predictor in the human tumor explants was 100%. Following treatment with OSI-906, the two that predicted as sensitive were indeed sensitive (TGI=21-28%) and the three that predicted as resistant were resistant (TGI=130-200%). FIGS. 21A-21D show representative graphs of two resistant explants and two sensitive explants.

Figure 22:
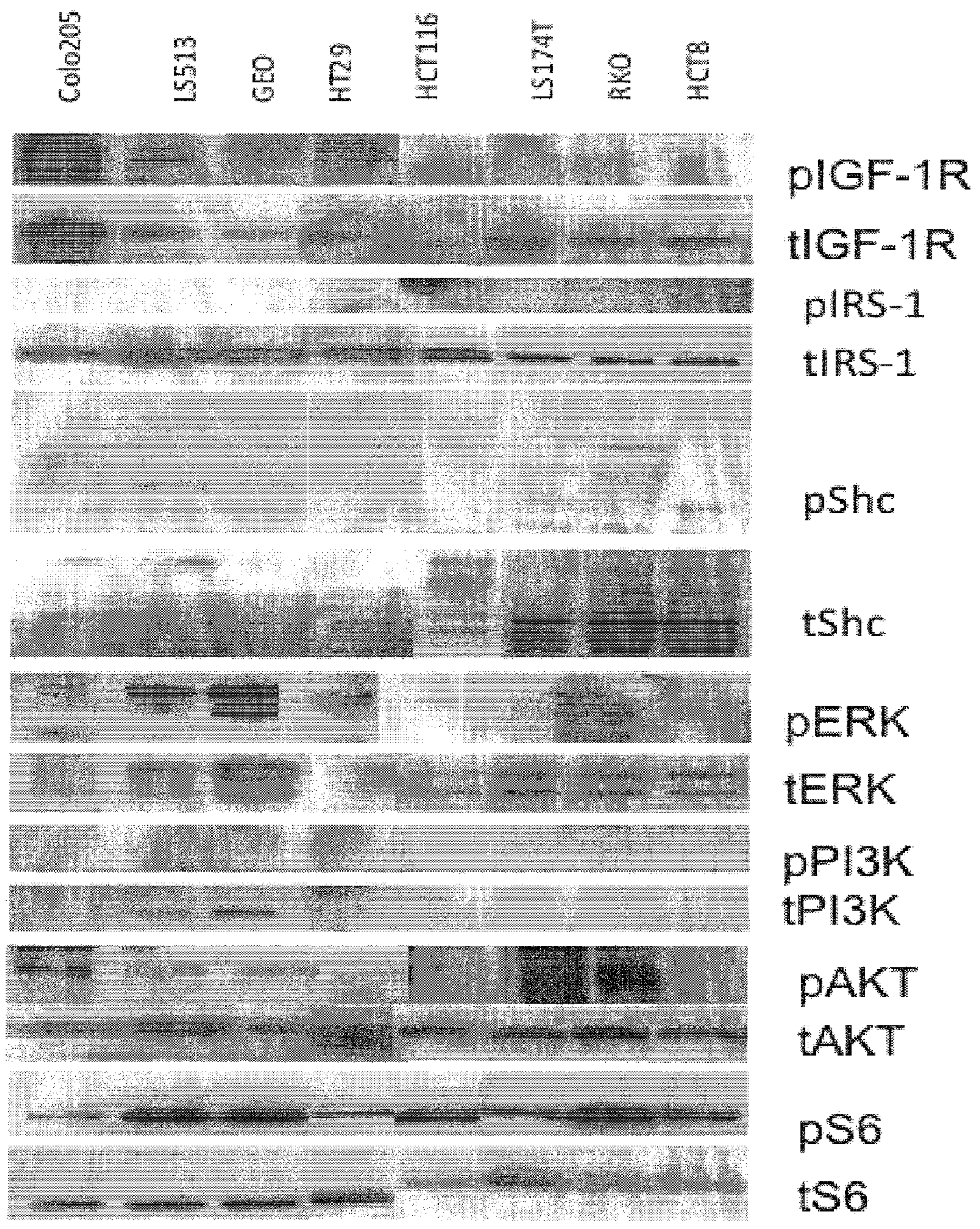
FIG. 22: Baseline expression of IGF-1R cell signaling proteins. 30 μg of total cell proteins were fractionated through SDS-PAGE, transferred to PVDF membranes, and incubated with the appropriate antibodies as described in Materials and Methods. The experiment was done in triplicate.

IGF-1R pathway analysis by immunoblotting and IHC. To determine if, by analyzing downstream effectors of the IGF-1R pathway, a pattern of responsiveness existed, CRC cell lines were subjected to immunoblotting and IHC at baseline. As depicted in FIG. 22, none of the major components of the IGF-1R pathway appeared to predict sensitivity to OSI-906. For example, activated (phosphorylated) IGF-1R, ERK, AKT, IRS-1, mTOR, PI3K, Shc, and S6 kinase were variably present at baseline in both sensitive and resistant cell lines (3A). Similarly, baseline expression of phosphorylated ERK, AKT, IGF-1R, IGF-2R, and total IGF by IHC did not correspond to sensitivity to OSI-906. Table 4 shows IHC scores of the CRC cell lines Pathway analysis of OSI-906-sensitive and -resistant CRC cell lines at baseline and post OSI-906 exposure. To determine whether any particular pathway was associated with responsiveness to OSI-906, pathway enrichment analysis was performed on the CRC cell lines pre-exposure. Sixty-eight KEGG pathways were up regulated in sensitive versus resistant CRC cell lines. Table 5 depicts the top 20 pathways that were overrepresented in the sensitive cell lines, including the Wnt, hedgehog, basal cell carcinoma, and p53 signaling pathways. Within these pathways core genes included several frizzled receptors and their associated wnt ligands. In the p53 pathway, not only was the p53 gene up regulated, but the IGF-1R ligand, IGF-1 was also over expressed. In the OSI-906-resistant cell lines there were also several unique pathways that were up regulated, including ErbB, MAPK, and VEGF signaling as well as those involving cell adhesion, such as cell adhesion molecules (CAM), and focal adhesion kinase. Within these and other pathways several core genes may be involved in conferring resistance to OSI-906.

Figure 23:
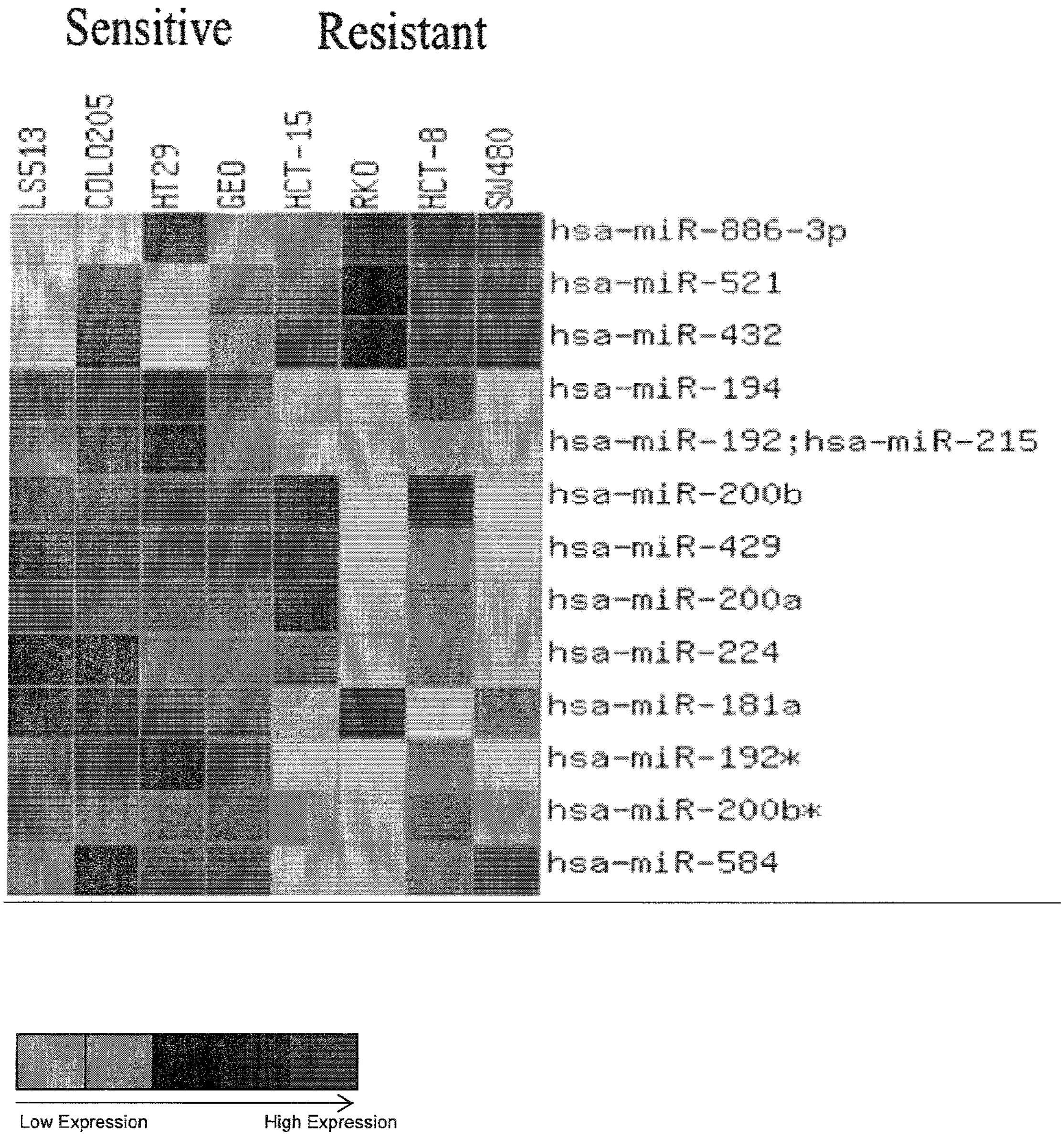
FIG. 23: Heat map of differentially expressed miRNAs in IGF-1R kinase inhibitor sensitive (COLO205, HT29, GEO, LS513) and IGF-1R kinase inhibitor resistant (HCT15, RKO, HCT8, SW480) CRC tumor cell lines. Color key indicates relative expression.
Figure 24:
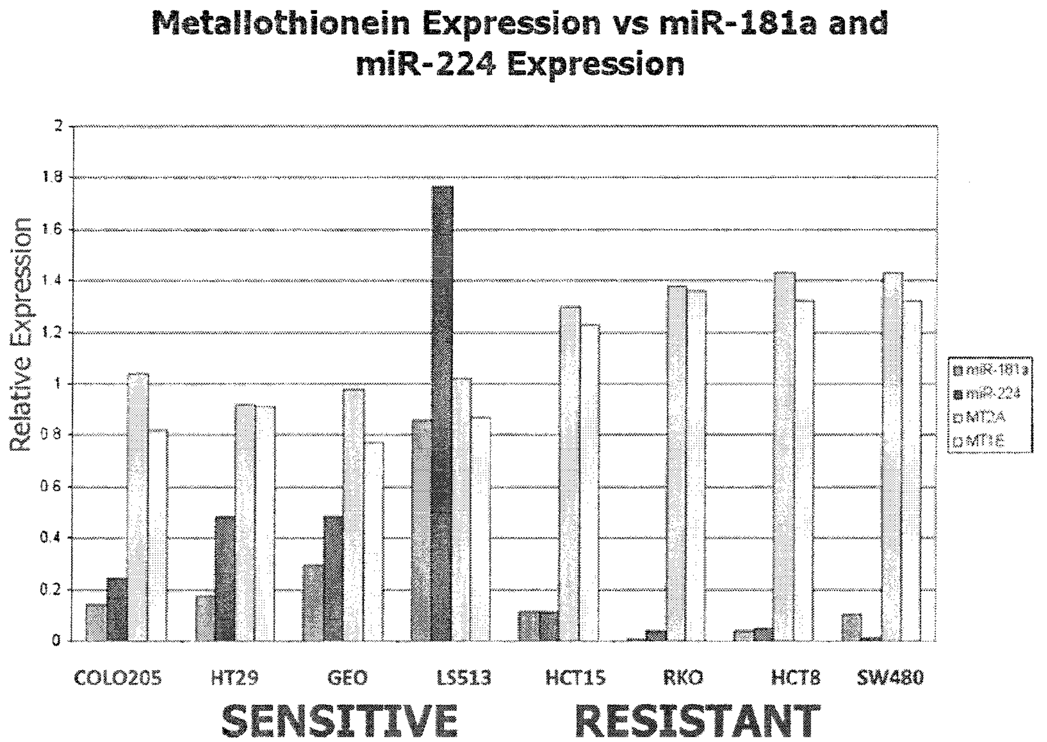
FIG. 24: Relative expression of miRNAs miR-181a and miR-224, and the genes MT2A and MT1E, in IGF-1R kinase inhibitor sensitive (COLO205, HT29, GEO, LS513) and IGF-1R kinase inhibitor resistant (HCT15, RKO, HCT8, SW480) CRC tumor cell lines.

In order to determine which pathways/genes were modulated following exposure to OSI-906, pathway analysis was performed as before on the sensitive and resistant CRC cell lines. In the OSI-906 sensitive cell lines the thyroid cancer, pancreatic cancer and the notch signaling pathways were up regulated. Core genes involved in these pathways include; TP53, ErbB2, STAT3 and CDKN2. Determining pathways and genes that are modulated in resistant cell lines can be extremely beneficial in finding rationale drug combinations that may be able to sensitize tumors to treatments. Pathway analysis of the OSI-906 resistant cell lines demonstrated that several pathways including colorectal cancer, VEGF, and Fc epsilon R1 signaling pathways were all up regulated following exposure. Interestingly genes involved in these pathways include several MAPKs, AKTs and FZD receptors.

miRNA profiling analysis. Following miRNA profiling a heat map was generated showing the differentially expressed miRNAs in OSI-906 sensitive and resistant CRC cell lines (FIG. 23). Two miRNAs, hsa-miR-224 and hsa-miR-181a were shown to be upregulated in the OSI-906 sensitive CRC cell lines. We decided to look at these two miRNAs because they have been shown previously (Prueitt R L, et al. Prostate 2008; 68(10:1152-64) to possibly be associated with metallothionein expression and they show an inverse relationship (FIG. 24).

Figure 25:
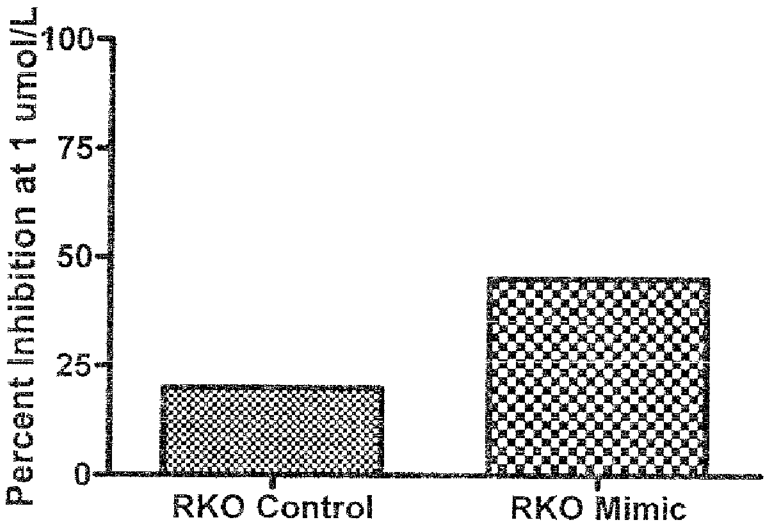
FIG. 25: Proliferation of RKO cell line at 1 μmol/L OSI-906.
Figure 26:
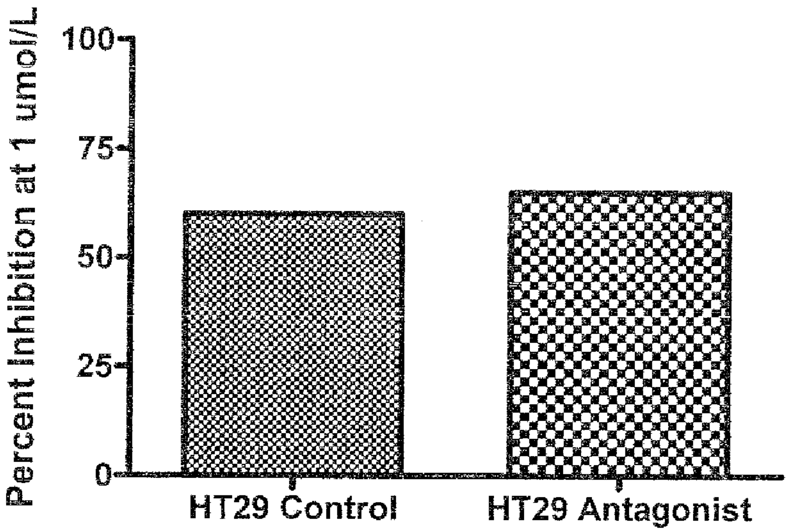
FIG. 26: Proliferation of HT29 cell line at 1 μmol/L OSI-906.

In order to determine if hsa-miR-224 had any effect on proliferation when exposed to OSI-906, a resistant CRC cell line (RKO) was transfected with hsa-miR-224 mimic and proliferation was assessed by SRB assay. As can be seen in FIG. 25 when hsa-miR-224 mimic is transfected into RKO cells an increase in the inhibition of proliferation is seen indicating the hsa-miR-224 may have an effect on the sensitivity to OSI-906. To see if the opposite is true we transfected an OSI-906 sensitive (HT29) cell line with hsa-miR-224 antagonist and proliferation was assessed by the SRB assay. As can be seen in FIG. 26, hsa-miR-224 antagonist does not affect proliferation.

Several other miRNAs were also upregulated, but to a lesser extent, in the OSI-906 sensitive CRC cell lines. These included hsa-miR-194, hsa-miR-192, hsa-miR-215, hsa-miR-200b, hsa-miR-429, hsa-miR-200a, hsa-miR-192*, hsa-miR-200b*, hsa-miR-584. Three miRNAs were upregulated in the OSI-906 resistant CRC cell line, i.e. hsa-miR-886-3p, hsa-miR-521, and hsa-miR-432.

These upregulated miRNAs, in tumor cell lines that are either sensitive or resistant to IGF-1R kinase inhibitors (e.g. OSI-906, anti-IGF-1R antibodies), provide additional biomarkers that may be utilized to predict sensitivity of tumor cell lines to IGF-1R kinase inhibitors. Additionally, the hsa-miR-224 mimic enhancement of the sensitivity of a resistant tumor cell line to inhibition by an IGF-1R kinase inhibitor enables new therapeutic options comprising combinations of an IGF-1R kinase with agents possessing similar hsa-miR-224 mimetic activity.

CONCLUSIONS

A broad range of sensitivity to OSI-906 was observed among the 27 CRC cell lines in vitro that was recapitulated by the 4 sensitive and 4 most resistant cell lines in vivo. To develop the K-TSP classifier, we utilized both in vitro and in vivo baseline gene array for a given cell line in the training set so that differences relating purely to the tumor microenvironment would be minimized. Our integrative genomic classifier differs from other published drug-response gene-expression signatures in two important aspects, first, as opposed to other studies where the gene signatures remain unvalidated, we validated our integrative genomic signature on a set of independent direct-human CRC explants as an intermediate step before moving into the clinic, and second, the classifier is comprised of the relative expression of 3 gene pairs, KRAS mutation status, and IGF-1R FISH analyses, all of which can be readily applied to clinical settings (Zha J, et al. Mol.

Cancer Ther. 2009 August; 8(8):2110-21. Epub 2009 Aug. 11; Watters J W, Roberts C J. Mol Cancer Ther. 2006 October; 5(10):2444-9; Potti A, et al. Nat Med. 2006 November; 12(11): 1294-300. Epub 2006 Oct. 22). In summary, these data demonstrate that an integrated approach to the development of predictive biomarkers in the early clinical development of IGF-1R kinase inhibitors is feasible.

TABLE 4

| IHC baseline patterns | | | | | | | |
|---|---|---|---|---|---|---|---|
| ID | % (+) cells | 0 | 1+ | 2+ | 3+ | 4+ | H Score |
| | | | | | pMAPK | | |
| LS 513 | 5 | 95 | | 2 | 3 | | 13 |
| LS180 | 1 | 99 | | 1 | | | 2 |
| HT29 | 1 | 99 | | | 1 | | 3 |
| Colo201 | 1 | 99 | | | 1 | | 3 |
| SW480 | 90 | 10 | | | 10 | 80 | 350 |
| HCT8 | 20 | 80 | 2 | 2 | 16 | | 54 |
| Colo205 | 1 | 99 | 1 | | | | 1 |
| RKO | 20 | 80 | 5 | 5 | 5 | 5 | 50 |
| HCT116 | 1 | 99 | 1 | | | | 1 |
| SW620 | 90 | 10 | 90 | | | | 90 |
| HCT15 | 1 | 99 | | 1 | | | 2 |
| SW1463 | 10 | 90 | | | 10 | | 30 |
| NCIH508 | 1 | 99 | 1 | | | | 1 |
| SW48 | 90 | 10 | | 10 | 80 | | 260 |
| SW403 | 70 | 30 | | 10 | 60 | | 200 |
| SW1417 | 30 | 70 | | | 30 | | 90 |
| LOVO | 10 | 90 | 2 | 3 | 5 | | 23 |
| CaCo2 | 2 | 98 | | 1 | 1 | | 5 |
| SW837 | 5 | 95 | | 1 | 4 | | 14 |
| LS123 | 30 | 70 | | 5 | 5 | 20 | 105 |
| GEO | 40 | 60 | | | 10 | 30 | 150 |
| LS1034 | 10 | 90 | | | 4 | 6 | 36 |
| SKCO1 | 40 | 60 | | | 20 | 20 | 140 |
| SW1116 | 20 | 80 | | | 18 | 2 | 62 |
| T84 | | | | | | | 0 |
| SW948 | 100 | | 100 | | | | 100 |
| LS174T | 100 | | 60 | 40 | | | 140 |
| | | | | | IGF 2 | | |
| LS 513 | 100 | | | | 95 | 5 | 305 |
| LS180 | 100 | | 80 | | 20 | | 140 |
| HT29 | 100 | | | 90 | 10 | | 210 |
| Colo201 | 100 | | | 99 | 1 | | 201 |
| SW480 | 100 | | 100 | | | | 100 |
| HCT8 | 100 | | | | 100 | | 300 |
| Colo205 | 100 | | | | | 100 | 400 |
| RKO | 100 | | 10 | 30 | 30 | 30 | 280 |
| HCT116 | 100 | | | 80 | | 20 | 240 |
| SW620 | 100 | | | | 100 | | 300 |
| HCT15 | 100 | | | | 10 | 90 | 390 |
| SW1463 | 100 | | | | 90 | 10 | 310 |
| NCIH508 | 100 | | | | 100 | | 300 |
| SW48 | 100 | | | 99 | 1 | | 201 |
| SW403 | 100 | | | | 60 | 40 | 340 |
| SW1417 | 100 | | | | | 100 | 400 |
| LOVO | 100 | | | 99 | 1 | | 201 |
| CaCo2 | 100 | | | | | 100 | 400 |
| SW837 | 100 | | | | 100 | | 300 |
| LS123 | 100 | | | | | 100 | 400 |
| GEO | 100 | | | | 100 | | 300 |
| LS1034 | 100 | | | | | 100 | 400 |
| SKCO1 | 100 | | | 10 | 80 | 10 | 300 |
| SW1116 | 100 | | | 100 | | | 200 |
| T84 | 100 | | | | 100 | | 300 |
| SW948 | 100 | | | | | 100 | 400 |
| LS174T | 100 | | | | 100 | | 300 |
| | | | | | IGF 2r | | |
| LS 513 | 100 | | 98 | | 1 | 1 | 105 |
| LS180 | 100 | | 100 | | | | 100 |
| HT29 | 100 | | 100 | | | | 100 |
| Colo201 | 100 | | | 100 | | | 200 |
| SW480 | 100 | | | 100 | | | 200 |
| HCT8 | 100 | | | 99 | 1 | | 201 |

TABLE 4-continued

| IHC baseline patterns | | | | | | | |
|---|---|---|---|---|---|---|---|
| ID | % (+) cells | 0 | 1+ | 2+ | 3+ | 4+ | H Score |
| Colo205 | 100 | | | 100 | | | 200 |
| RKO | 100 | | | 100 | | | 200 |
| HCT116 | 100 | | 90 | 10 | | | 110 |
| SW620 | 100 | | 80 | 20 | | | 120 |
| HCT15 | 100 | | | 90 | 10 | | 210 |
| SW1463 | 100 | | | | 80 | 20 | 320 |
| NCIH508 | 100 | | | 95 | | 5 | 210 |
| SW48 | 100 | | | 100 | | | 200 |
| SW403 | 100 | | | 95 | 5 | | 205 |
| SW1417 | 100 | | | | 95 | 5 | 305 |
| LOVO | 100 | | | 100 | | | 200 |
| CaCo2 | 100 | | | 95 | 5 | | 205 |
| SW837 | 100 | | | 100 | | | 200 |
| LS123 | 100 | | | 100 | | | 200 |
| GEO | 100 | | | 95 | 5 | | 205 |
| LS1034 | 65 | | | 60 | 5 | | 135 |
| SKCO1 | 100 | | | 90 | 10 | | 210 |
| SW1116 | 100 | | | | 90 | 10 | 310 |
| T84 | 100 | | 80 | 15 | 5 | | 125 |
| SW948 | 100 | | 100 | | | | 100 |
| LS174T | 100 | | | 100 | | | 200 |
| | | | | | IGF 1r | | |
| LS 513 | 100 | | | 100 | | | 200 |
| LS180 | 100 | | 99 | 1 | | | 101 |
| HT29 | 100 | | 99 | 1 | | | 101 |
| Colo201 | 100 | | | | 100 | | 300 |
| SW480 | 100 | | | 50 | 50 | | 250 |
| HCT8 | 100 | | 99 | 1 | | | 101 |
| Colo205 | 100 | | | | 100 | | 300 |
| RKO | 100 | | | 100 | | | 200 |
| HCT116 | 100 | | 100 | | | | 100 |
| SW620 | 100 | | 99 | 1 | | | 101 |
| HCT15 | 100 | | 90 | 10 | | | 110 |
| SW1463 | 100 | | | | 100 | | 300 |
| NCIH508 | 100 | | | | | 100 | 400 |
| SW48 | 100 | | | | | 100 | 400 |
| SW403 | 100 | | | | | | 100 |
| SW1417 | 100 | | | | 90 | 10 | 310 |
| LOVO | 100 | | | | | 100 | 400 |
| CaCo2 | 100 | | | | | 100 | 400 |
| SW837 | 100 | | | | | 100 | 400 |
| LS123 | 100 | | | | 90 | 10 | 310 |
| GEO | 70 | | | 65 | 5 | | 145 |
| LS1034 | 100 | | | 80 | 10 | 10 | 230 |
| SKCO1 | 100 | | | | | 100 | 400 |
| SW1116 | 100 | | | | 10 | 90 | 390 |
| T84 | 100 | | | 10 | 90 | | 290 |
| SW948 | 100 | | | | | 100 | 400 |
| LS174T | 100 | | | | 100 | | 300 |
| | | | | | pIGF1r | | |
| LS 513 | 60 | 40 | 20 | 20 | 10 | 10 | 130 |
| LS180 | 80 | 20 | 5 | 5 | 5 | 5 | 50 |
| HT29 | 40 | 60 | 0 | 10 | 10 | 20 | 130 |
| Colo201 | 90 | 10 | 0 | 10 | 20 | 60 | 320 |
| SW480 | 80 | 20 | 50 | 10 | 15 | 5 | 135 |
| HCT8 | 100 | 0 | 10 | 10 | 70 | 10 | 280 |
| Colo205 | 100 | 0 | 0 | 0 | 10 | 90 | 390 |
| RKO | 90 | 10 | 0 | 0 | 5 | 5 | 35 |
| HCT116 | 100 | 0 | 40 | 40 | 10 | 10 | 190 |
| SW620 | 80 | 20 | 60 | 10 | 10 | 0 | 110 |
| HCT15 | 90 | 10 | 0 | 20 | 0 | 70 | 320 |
| SW1463 | 100 | 0 | 90 | 0 | 10 | 0 | 120 |
| NCIH508 | 60 | 10 | 20 | 0 | 10 | 60 | 290 |
| SW48 | 100 | 0 | 0 | 10 | 10 | 80 | 370 |
| SW403 | 100 | 0 | 90 | 10 | 0 | 0 | 110 |
| SW1417 | 100 | 0 | 0 | 0 | 20 | 80 | 380 |
| LOVO | 100 | 0 | 0 | 10 | 20 | 70 | 360 |
| CaCo2 | 100 | 0 | 0 | 0 | 0 | 100 | 400 |
| SW837 | 100 | 0 | 0 | 50 | 10 | 40 | 290 |
| LS123 | 100 | 0 | 0 | 0 | 80 | 20 | 320 |
| GEO | 100 | 0 | 0 | 0 | 80 | 20 | 320 |
| LS1034 | 100 | 0 | 80 | 0 | 0 | 20 | 160 |
| SKCO1 | 100 | 0 | 0 | 0 | 10 | 90 | 390 |
| SW1116 | 60 | 40 | 10 | 10 | 0 | 40 | 190 |

TABLE 4-continued

| IHC baseline patterns | | | | | | | |
|---|---|---|---|---|---|---|---|
| ID | % (+) cells | 0 | 1+ | 2+ | 3+ | 4+ | H Score |
| T84 | | | | | | | |
| SW948 | | | | | | | |
| LS174T | | | | | | | |

TABLE 5

List of pathways enriched in either OSI-906 sensitive or resistant cell lines pre and post exposure.

| UP IN PRE SEN (UP IN SEN BEFORE EXPOSURE) | UP IN PRE RES (DOWN IN SEN PRE EXPOSURE |
|---|---|
| Aminoacyl-tRNA biosynthesis | Leukocyte transendothelial migration |
| Ribosome | Epithelial cell signaling in *Hellcobacter pylori* infection |
| Glycosphingolipid biosynthesis - ganglioseries | Pathogenic *Escherichia coli* infection - EPEC |
| Basal cell carcinoma | Cell adhesion molecules (CAMs) |
| Methionine metabolism | Pathogenic *Escherichia coli* infection - EHEC |
| Heparan sulfate biosynthesis | Tight junction |
| RNA polymerase | Regulation of actin cytoskeleton |
| Selenoamino acid metabolism | Focal adhesion |
| Cysteine metabolism | MAPK signaling pathway |
| Purine metabolism | Cholera - Infection |
| Hedgehog signaling pathway | Glutathione metabolism |
| Wnt signaling pathway | Sphingolipid metabolism |
| Glycine, serine and threonine metabolism | Type I diabetes mellitus |
| Naphthalene and anthracene degradation | Toll-like receptor signaling pathway |
| Porphyrin and chlorophyll metabolism | Pentose phosphate pathway |
| p53 signaling pathway | Metabolism of xenoblotics by cytochrome P450 |
| Keratan sulfate biosynthesis | ErbB signaling pathway |
| Androgen and estrogen metabolism | Phosphatidylinositol signaling system |
| Glycosylphosphatidylinositol(GPI)-anchor biosynthesis | VEGF signaling pathway |
| Renin-angiotensin system | Glycerophospholipid metabolism |

| UP IN POST SEN | UP IN PRE RES (DOWN IN SEN PRE EXPOSURE |
|---|---|
| gamma-Hexachlorocyclohexane degradation | Leukocyte transendothelial migration |
| Linoleic acid metabolism | Epithelial cell signaling in *Hellcobacter pylori* infection |
| Thyroid cancer | Pathogenic *Escherichia coli* infection - EPEC |
| Glycosphingolipid biosynthesis - neo-lactoseries | Cell adhesion molecules (CAMs) |
| Keratan sulfate biosynthesis | Pathogenic *Escherichia coli* infection - EHEC |
| Glycan structures - biosynthesis 2 | Tight junction |
| Androgen and estrogen metabolism | Regulation of actin cytoskeleton |
| Maturity onset diabetes of the young | Focal adhesion |
| Glycosphingolipid biosynthesis - lactoseries | MAPK signaling pathway |
| Bisphenol A degradation | Cholera - infection |

TABLE 5-continued

List of pathways enriched in either OSI-906 sensitive or resistant cell lines pre and post exposure.

| | |
|---|---|
| Sphingolipid metabolism | Glutathione metabolism |
| Axon guidance | Sphingolipid metabolism |
| O-Glycan biosynthesis | Type I diabetes mellitus |
| Glycan structures - biosynthesis 1 | Toll-like receptor signaling pathway |
| Notch signaling pathway | Pentose phosphate pathway |
| ABC transporters - General | Metabolism of xenoblotics by cytochrome P450 |
| Leukocyte transendothelial migration | ErbB signaling pathway |
| N-Glycan biosynthesis | Phosphatidylinositol signaling system |
| Glycan structures - degradation | VEGF signaling pathway |
| Pancreatic cancer | Glycerophospholipid metabolism |

ABBREVIATIONS

EGF, epidermal growth factor; EMT, epithelial to mesenchymal transition; NSCLC, non-small cell lung carcinoma; HNSCC, head and neck squamous cell carcinoma; CRC, colorectal cancer; MBC, metastatic breast cancer; EGFR, epidermal growth factor receptor; ErbB3, "v-erb-b2 erythroblastic leukemia viral oncogene homolog 3", also known as HER-3; pHER3, phosphorylated HER3; Erk kinase, Extracellular signal-regulated protein kinase, also known as mitogen-activated protein kinase; pErk, phosphorylated Erk; Brk, Breast tumor kinase (also known as protein tyrosine kinase 6 (PTK6)); LC, liquid chromatography; MS, mass spectrometry; IGF-1, insulin-like growth factor-1; IGF-1R or IGFR, insulin-like growth factor-1 receptor; TGFα, transforming growth factor alpha; HB-EGF, heparin-binding epidermal growth factor; LPA, lysophosphatidic acid; TGFα, transforming growth factor alpha; $IC_{50}$, half maximal inhibitory concentration; RT, room temperature; pY, phosphotyrosine; pPROTEIN, phospho-PROTEIN, "PROTEIN" can be any protein that can be phosphorylated, e.g. EGFR, ERK, HER3, S6 etc; wt, wild-type; PI3K, phosphatidyl inositol-3 kinase; GAPDH, Glyceraldehyde 3-phosphate dehydrogenase, PMID, PubMed Unique Identifier; NCBI, National Center for Biotechnology Information.

INCORPORATION BY REFERENCE

All patents, published patent applications and other references disclosed herein are hereby expressly incorporated herein by reference.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of identifying a patient with cancer who is most likely to benefit from treatment with an IGF-1R kinase inhibitor, comprising:

(1) obtaining a sample of the patient's tumor, (2) determining if tumor cells of the sample exhibit the following classifiers of tumor cells that are more likely to be sensitive to growth inhibition by an IGF-1R kinase inhibitor:

(a) higher expression level of the PROM1 gene than the MT1E gene;

(b) higher expression level of the LY75 gene than the OXCT1 gene;

(c) higher expression level of the HSD17B2 gene than the CALD1 gene;

(d) increased levels of IGF-1R gene copy number relative to ploidy;

(e) the absence of a mutant K-RAS gene; and (3) identifying the patient as one most likely to benefit from treatment with an IGF-1R kinase inhibitor if at least four of the five assessed classifiers are present in the tumor cells.

2. The method of claim 1, wherein the IGF-1R kinase inhibitor is a small molecule kinase inhibitor.

3. The method of claim 1, wherein the IGF-1R kinase inhibitor is OSI-906.

4. The method of claim 1, wherein the IGF-1R kinase inhibitor is an anti-IGF-1R antibody.

5. A method of identifying a patient with cancer who is most likely to benefit from treatment with an IGF-1R kinase inhibitor, comprising:

obtaining a sample of the patient's tumor;

assessing the level of the gene MT1E expressed by the tumor cells;

assessing the level of the gene PROM1 expressed by the tumor cells;

determining whether the tumor cells express a higher level of PROM1 than MT1E; and identifying the patient as one most likely to benefit from treatment with an IGF-1R kinase inhibitor if the tumor cells express a higher level of PROM1 than MT1E.

6. A method of identifying a patient with cancer who is most likely to benefit from treatment with an IGF-1R kinase inhibitor, comprising:

obtaining a sample of the patient's tumor;

assessing the level of the gene OXCT1 expressed by the tumor cells;

assessing the level of the gene LY75 expressed by the tumor cells;

determining whether the tumor cells express a higher level of LY75 than OXCT1; and identifying the patient as one most likely to benefit from treatment with an IGF-1R kinase inhibitor if the tumor cells express a higher level of LY75 than OXCT1.

7. A method of identifying a patient with cancer who is most likely to benefit from treatment with an IGF-1R kinase inhibitor, comprising: obtaining a sample of the patient's tumor;

assessing the level of the gene CALD1 expressed by the tumor cells;

assessing the level of the gene HSD17B2 expressed by the tumor cells;

determining whether the tumor cells express a higher level of HSD17B2 than CALD1; and identifying the patient as one most likely to benefit from treatment with an IGF-1R kinase inhibitor if the tumor cells express a higher level of HSD17B2 than CALD1.

8. A method of identifying a patient with cancer who is most likely to benefit from treatment with an IGF-1R kinase inhibitor, comprising:

obtaining a sample of the patient's tumor;

assessing IGF-1R gene copy number in the tumor cells;

determining if there is an increased IGF-1R gene copy number relative to ploidy; and identifying the patient as one most likely to benefit from treatment with an IGF-1R kinase inhibitor if the tumor cells have increased IGF-1R gene copy number.

9. A method of identifying a patient with cancer who is most likely to benefit from treatment with an IGF-1R kinase inhibitor, comprising:

obtaining a sample of the patient's tumor;

determining whether the tumor cells possess a mutant K-RAS gene; and identifying the patient as one most likely to benefit from treatment with an IGF-1R kinase inhibitor if the tumor cells do not possess a mutant K-RAS gene.

10. A method for treating cancer in a patient, comprising the steps of:

(A) diagnosing a patient's likely responsiveness to an IGF-1R kinase inhibitor by determining if the patient has a tumor that is likely to respond to treatment with an IGF-1R kinase inhibitor, by:

obtaining a sample of the patient's tumor, determining if tumor cells of the sample exhibit the following classifiers of tumor cells that are more likely to be sensitive to growth inhibition by an IGF-1R kinase inhibitor:

(a) higher expression level of the PROM1 gene than the MT1E gene;

(b) higher expression level of the LY75 gene than the OXCT1 gene;

(c) higher expression level of the HSD17B2 gene than the CALD1 gene;

(d) increased levels of IGF-1R gene copy number relative to ploidy;

(e) the absence of a mutant K-RAS gene; and identifying the patient as having a tumor that is likely to respond to treatment with an IGF-1R kinase inhibitor if at least four of the five assessed classifiers are present in the tumor cells; and (B) administering to said patient a therapeutically effective amount of an IGF-1R kinase inhibitor if the patient has a tumor identified as likely to respond to treatment with an IGF-1R kinase inhibitor.

11. A method for treating cancer in a patient, comprising the steps of:

(A) diagnosing a patient's likely responsiveness to an IGF-1R kinase inhibitor by determining if the patient has a tumor that is likely to respond to treatment with an IGF-1R kinase inhibitor by:

obtaining a sample of the patient's tumor;

assessing the level of the gene MT1E expressed by the tumor cells;

assessing the level of the gene PROM1 expressed by the tumor cells;

determining whether the tumor cells express a higher level of PROM1 than MT1E; and identifying the patient as likely to benefit from treatment with an IGF-1R kinase inhibitor if the tumor cells express a higher level of PROM1 than MT1E, and (B) administering to said patient a therapeutically effective amount of an IGF-1R kinase inhibitor if the patient is identified as likely to respond to treatment with an IGF-1R kinase inhibitor.

12. A method for treating cancer in a patient, comprising the steps of:

(A) diagnosing a patient's likely responsiveness to an IGF-1R kinase inhibitor by determining if the patient has a tumor that is likely to respond to treatment with an IGF-1R kinase inhibitor by:

obtaining a sample of the patient's tumor;

assessing the level of the gene OXCT1 expressed by the tumor cells;

assessing the level of the gene LY75 expressed by the tumor cells;

determining whether the tumor cells express a higher level of LY75 than OXCT1; and identifying the patient as likely to benefit from treatment with an IGF-1R kinase inhibitor if the tumor cells express a higher level of LY75 than OXCT1, and (B) administering to said patient a therapeutically effective amount of an IGF-1R kinase inhibitor if the patient is identified as likely to respond to treatment with an IGF-1R kinase inhibitor.

13. A method for treating cancer in a patient, comprising the steps of:

(A) diagnosing a patient's likely responsiveness to an IGF-1R kinase inhibitor by determining if the patient has a tumor that is likely to respond to treatment with an IGF-1R kinase inhibitor by:

obtaining a sample of the patient's tumor;

assessing the level of the gene CALD1 expressed by the tumor cells;

assessing the level of the gene HSD17B2 expressed by the tumor cells;

determining whether the tumor cells express a higher level of HSD17B2 than CALD1; and identifying the patient as likely to benefit from treatment with an IGF-1R kinase inhibitor if the tumor cells express a higher level of HSD17B2 than CALD1, and (B) administering to said patient a therapeutically effective amount of an IGF-1R kinase inhibitor if the patient is identified as likely to respond to treatment with an IGF-1R kinase inhibitor.

14. A method for treating cancer in a patient, comprising the steps of:

(A) diagnosing a patient's likely responsiveness to an IGF-1R kinase inhibitor by determining if the patient has a tumor that is likely to respond to treatment with an IGF-1R kinase inhibitor by:

obtaining a sample of the patient's tumor;

assessing IGF-1R gene copy number in the tumor cells;

determining if there is an increased IGF-1R gene copy number relative to ploidy; and identifying the patient as likely to benefit from treatment with an IGF-1R kinase inhibitor if the tumor cells have increased IGF-1R gene copy number, and (B) administering to said patient a therapeutically effective amount of an IGF-1R kinase inhibitor if the patient is identified as likely to respond to treatment with an IGF-1R kinase inhibitor.

15. A method for treating cancer in a patient, comprising the steps of:

(A) diagnosing a patient's likely responsiveness to an IGF-1R kinase inhibitor by determining if the patient has a tumor that is likely to respond to treatment with an IGF-1R kinase inhibitor by:

obtaining a sample of the patient's tumor;

determining whether the tumor cells possess a mutant K-RAS gene; and identifying the patient as likely to benefit from treatment with an IGF-1R kinase inhibitor if the tumor cells do not possess a mutant K-RAS gene, and (B) administering to said patient a therapeutically effective amount of an IGF-1R kinase inhibitor if the patient is identified as likely to respond to treatment with an IGF-1R kinase inhibitor.

16. A method for treating cancer in a patient, comprising:

administering to said patient a therapeutically effective amount of an IGF-1R kinase inhibitor if the patient has been identified as likely to benefit from treatment with an IGF-1R kinase inhibitor using the method of identifying the patient of claim 1.

17. A method for treating cancer in a patient, comprising:

administering to said patient a therapeutically effective amount of an IGF-1R kinase inhibitor if the patient has been identified as likely to benefit from treatment with an IGF-1R kinase inhibitor using the method of identifying the patient of claim 5.

18. A method for treating cancer in a patient, comprising:

administering to said patient a therapeutically effective amount of an IGF-1R kinase inhibitor if the patient has been identified as likely to benefit from treatment with an IGF-1R kinase inhibitor using the method of identifying the patient of claim 6.

19. A method for treating cancer in a patient, comprising:

administering to said patient a therapeutically effective amount of an IGF-1R kinase inhibitor if the patient has been identified as likely to benefit from treatment with an IGF-1R kinase inhibitor using the method of identifying the patient of claim 7.

20. A method for treating cancer in a patient, comprising:

administering to said patient a therapeutically effective amount of an IGF-1R kinase inhibitor if the patient has been identified as likely to benefit from treatment with an IGF-1R kinase inhibitor using the method of identifying the patient of claim 8.

21. A method for treating cancer in a patient, comprising:

administering to said patient a therapeutically effective amount of an IGF-1R kinase inhibitor if the patient has been identified as likely to benefit from treatment with an IGF-1R kinase inhibitor using the method of identifying the patient of claim 9.

* * * * *

SEQUENCE LISTING

<160> NUMBER OF SEQ ID NOS: 123

<210> SEQ ID NO 1
<211> LENGTH: 2116
<212> TYPE: DNA
<213> ORGANISM: Homo sapiens

<400> SEQUENCE: 1

```
atcagaacca aattgctgag ccagtcacct gtgttccagg agccgaatca gaaatgtcat      60

cctcaggcac gccagactta cctgtcctac tcaccgattt gaagattcaa tatactaaga     120

tcttcataaa caatgaatgg catgattcag tgagtggcaa gaaatttcct gtctttaatc     180

ctgcaactga ggaggagctc tgccaggtag aagaaggaga taaggaggat gttgacaagg     240

cagtgaaggc cgcaagacag gcttttcaga ttggatcccc gtggcgtact atggatgctt     300

ccgagagggg gcgactatta tacaagttgg ctgatttaat cgaaagagat cgtctgctgc     360

tggcgacaat ggagtcaatg aatggtggaa aactctattc caatgcatat ctgaatgatt     420

tagcaggctg catcaaaaca ttgcgctact gtgcaggttg ggctgacaag atccagggcc     480

gtacaatacc aattgatgga aatttttta catatacaag acatgaacct attggtgtat      540

gtggccaaat cattccttgg aatttcccgt tggttatgct catttggaag atagggcctg     600

cactgagctg tggaaacaca gtggttgtca aaccagcaga gcaaactcct ctcactgctc     660

tccacgtggc atctttaata aaagaggcag ggtttcctcc tggagtagtg aatattgttc     720

ctggttatgg gcctacagca ggggcagcca tttcttctca catggatata gacaaagtag     780

ccttcacagg atcaacagag gttggcaagt tgatcaaaga agctgccggg aaaagcaatc     840

tgaagagggt gaccctggag cttggaggaa agagcccttg cattgtgtta gctgatgccg     900

acttggacaa tgctgttgaa tttgcacacc atggggtatt ctaccaccag ggccagtgtt     960

gtatagccgc atccaggatt tttgtggaag aatcaattta tgatgagttt gttcgaagga    1020

gtgttgagcg ggctaagaag tatatccttg gaaatcctct gaccccagga gtcactcaag    1080

gccctcagat tgacaaggaa caatatgata aaatacttga cctcattgag agtgggaaga    1140

aagaaggggc caaactggaa tgtggaggag gcccgtgggg gaataaaggc tactttgtcc    1200

agcccacagt gttctctaat gttacagatg agatgcgcat tgccaaagag gagatttttg    1260

gaccagtgca gcaaatcatg aagtttaaat ctttagatga cgtgatcaaa agagcaaaca    1320

atactttcta tggcttatca gcaggagtgt ttaccaaaga cattgataaa gccataacaa    1380

tctcctctgc tctgcaggca ggaacagtgt gggtgaattg ctatggcgtg gtaagtgccc    1440

agtgcccctt tggtggattc aagatgtctg gaaatggaag agaactggga gagtacggtt    1500

tccatgaata tacagaggtc aaaacagtca cagtgaaaat ctctcagaag aactcataaa    1560

gaaaatacaa gagtggagag aagctcttca atagctaagc atctccttac agtcactaat    1620

atagtagatt ttaaagacaa aatttttctt ttcttgattt ttttaaacat aagctaaatc    1680

atattagtat taatactacc catagaaaac ttgacatgta gcttcttctg aaagaattat    1740

ttgccttctg aaatgtgacc cccaagtcct atcctaaata aaaaaagaca aattcggatg    1800

tatgatctct ctagctttgt catagttatg tgattttcct ttgtagctac ttttgcagga    1860

taataatttt atagaaaagg aacagttgca tttagcttct ttcccttagt gactcttgaa    1920

gtacttaaca tacacgttaa ctgcagagta aattgctctg ttcccagtag ttataaagtc    1980

cttggactgt tttgaaaagt ttcctaggat gtcatgtctg cttgtcaaaa gaaataatcc    2040

ctgtaatatt tagctgtaaa ctgaatataa agcttaataa aaacaacctt gcatgaaaaa    2100

aaaaaaaaaa aaaaaa                                                    2116
```

<210> SEQ ID NO 2
<211> LENGTH: 2688
<212> TYPE: DNA
<213> ORGANISM: Homo sapiens

<400> SEQUENCE: 2

-continued

```
atagagctga tgtatccaga ggttatgttg ctagaggtga gatcagttac ctacgtgcaa     60
ctgaaatttc aaacttctgt tcagcaggga cgtgagtgga caatggtgac tgatagttgg    120
aaatatcagc aaacatctta aattttatac tcaaatgaat gagcaatgaa ccaggagaat    180
aggtccagtt ttttttggct ccttgtaatt tttacctttt tacttaaaat tacagcatct    240
ttttcaatga gtgcctatgt gactgtgact tattacaatg aaaccagcaa ctacactgca    300
atagagacat gtgaatgtgg cgtttatgga ttagcttcac cagtggctaa tgctatggga    360
gtggtaggca tccctaagaa caataactac caagcttgtg accacaacac tgagtttagt    420
aatactaaga agccctggat tgcgctgata gaaagaggta attgtacatt ttcagaaaaa    480
attcaaacag cgggcagaag aaatgctgat gctgttgtga tttacaatgc tccagagact    540
ggcaatcaga cgatacagat ggcaaatttt ggtgcagtag acattgttgc aatcatgatc    600
ggcaatctga aaggcacaaa aattctgcaa tctattcaaa gaggcataca agtgacaatg    660
gtcatagaag tagggaaaaa acatggccct tgggtgaatc actattcaat ttttttcgtt    720
tctgtgtcct tttttattat tacggcggca actgtgggct attttatctt ttattctgct    780
cgaaggctac ggaatgcaag agctcaaagc aggaagcaga ggcaattaaa ggcagatgct    840
aaaaaagcta ttggaaggct tcaactacgc acactgaaac aaggagacaa ggaaattggc    900
cctgatggag atagttgtgc tgtgtgcatt gaattgtata aaccaaatga tttggtacgc    960
atcttaacgt gcaaccatat tttccataag acatgtgttg acccatggct gttagaacac   1020
aggacttgcc ccatgtgcaa atgtgacata ctcaaagctt tgggaattga ggtggatgtt   1080
gaagatggat cagtgtcttt acaagtccct gtatccaatg aaatatctaa tagtgcctcc   1140
tcccatgaag aggataatcg cagcgagacc gcatcatctg gatatgcttc agtacaggga   1200
acagatgaac cgcctctgga ggaacacgtg cagtcaacaa atgaaagtct acagctggta   1260
aaccatgaag caaattctgt ggcagtggat gttattcctc atgttgacaa cccaaccttt   1320
gaagaagacg aaactcctaa tcaagagact gctgttcgag aaattaaatc ttaaaatctg   1380
tgtaaataga aaacttgaac cattagtaat aacagaactg ccaatcaggg cctagtttct   1440
attaataaat tggataaatt taataaaata agagtgatac tgaaagtgct cagatgacta   1500
atattatgct atagttaaat ggcttaaaat atttaacctg ttaacttttt tccacaaact   1560
cattataata tttttcatag gcaagtttcc tctcagtagt gataacaaca tttttagaca   1620
ttcaaaactg tcttcaagaa gtcacgtttt tcatttataa caattttctt ataaaaacat   1680
gttgctttta aaatgtggag tagctgtaat cactttattt tatgatagta tcttaatgaa   1740
aaatactact tctttagctt gggctacatg tgtcagggtt tttctccagg tgcttatatt   1800
gatctggaat tgtaatgtaa aaagcaatgc aaacttaggc gagtacttct tgaaatgtct   1860
atttaagctg ctttaagtta atagaaaaga ttaaagcaaa atattcattt ttactttttc   1920
ttatttttaa aattaggctg aatgtacttc atgtgatttg tcaaccatag tttatcagag   1980
attatggact taattgattg gtatattagt gacatcaact tgacacaaga ttagacaaaa   2040
aattccttac aaaaatactg tgtaactatt tctcaaactt gtgggatttt tcaaaagctc   2100
agtatatgaa tcatcatact gtttgaaatt gctaatgaca gagtaagtaa cactaatatt   2160
ggtcattgat cttcgttcat gaattagtct acagaaaaaa aatgttctgt aaaattagtc   2220
tgttgaaaat gttttccaaa caatgttact ttgaaaattg agtttatgtt tgacctaaat   2280
gggctaaaat tacattagat aaactaaaat tctgtccgtg taactataaa ttttgtgaat   2340
gcattttcct ggtgtttgaa aaagaagggg gggagaattc caggtgcctt aatataaagt   2400
```

-continued

```
ttgaagcttc atccaccaaa gttaaataga gctatttaaa aatgcacttt atttgtactc   2460

tgtgtggctt ttgttttaga attttgttca aattatagca gaatttaggc aaaaataaaa   2520

cagacatgta tttttgtttg ctgaatggat gaaaccattg cattcttgta cactgatttg   2580

aaatgctgta aatatgtccc aatttgtatt gattctcttt aaatataaaa tgtaaataaa   2640

atattccaat aaaagtttgt gtctggtgtt agtttaaaaa aaaaaaaa                2688


<210> SEQ ID NO 3
<211> LENGTH: 1879
<212> TYPE: DNA
<213> ORGANISM: Homo sapiens

<400> SEQUENCE: 3

agttccaagt ttggagcttt tagctgccag ccctggccca tcatgtagct gcagcacagc     60

cttccctaac gttgcaactg ggggaaaaat cactttccag tctgttttgc aaggtgtgca    120

tttccatctt gattccctga aagtccatct gctgcatcgg tcaagagaaa ctccacttgc    180

atgaagattg cacgcctgca gcttgcatct ttgttgcaaa actagctaca gaagagaagc    240

aaggcaaagt cttttgtgct cccctccccc atcaaaggaa aggggaaaat gtctcagtcg    300

aaaggcaaga agcgaaaccc tggccttaaa attccaaaag aagcatttga acaacctcag    360

accagttcca caccacctcg agatttagac tccaaggctt gcatttctat tggaaatcag    420

aactttgagg tgaaggcaga tgacctggag cctataatgg aactgggacg aggtgcgtac    480

ggggtggtgg agaagatgcg gcacgtgccc agcgggcaga tcatggcagt gaagcggatc    540

cgagccacag taaatagcca ggaacagaaa cggctactga tggatttgga tatttccatg    600

aggacggtgg actgtccatt cactgtcacc ttttatggcg cactgtttcg ggagggtgat    660

gtgtggatct gcatggagct catggataca tcactagata aattctacaa acaagttatt    720

gataaaggcc agacaattcc agaggacatc ttagggaaaa tagcagtttc tattgtaaaa    780

gcattagaac atttacatag taagctgtct gtcattcaca gagacgtcaa gccttctaat    840

gtactcatca atgctctcgg tcaagtgaag atgtgcgatt ttggaatcag tggctacttg    900

gtggactctg ttgctaaaac aattgatgca ggttgcaaac catacatggc ccctgaaaga    960

ataaacccag agctcaacca gaagggatac agtgtgaagt ctgacatttg gagtctgggc   1020

atcacgatga ttgagttggc catccttcga tttccctatg attcatgggg aactccattt   1080

cagcagctca aacaggtggt agaggagcca tcgccacaac tcccagcaga caagttctct   1140

gcagagtttg ttgactttac ctcacagtgc ttaaagaaga attccaaaga acggcctaca   1200

tacccagagc taatgcaaca tccatttttc accctacatg aatccaaagg aacagatgtg   1260

gcatcttttg taaaactgat tcttggagac taaaaagcag tggacttaat cggttgaccc   1320

tactgtggat tggtgggttt cggggtgaag caagttcact acagcatcaa tagaaagtca   1380

tctttgagat aatttaaccc tgcctctcag agggttttct ctcccaattt tctttttact   1440

ccccctctta agggggcctt ggaatctata gtatagaatg aactgtctag atggatgaat   1500

tatgataaag gcttaggact tcaaaaggtg attaaatatt taatgatgtg tcatatgagt   1560

cctcaagctt ctcagacttc tcttattctt tacaaaatga atgcattggc cctgacaaaa   1620

aggtgctacg gtagtgatga aattataagt agatttgtag tttgtcccat ttattatttt   1680

aatatttatg tttaagtgct tggttgaaaa gattccattt tatacaagaa gggagattca   1740

aaaaaaaaat ataaggttgg gttagcaata tttatagggc ttttattttt taagttcaat   1800

tgtgtctgtg gtccagaaga aattatttaa tatgcatctt tgagaatatt ataaaaatat   1860
```

-continued caaaaaggaa aaaaaaaaa 1879

<210> SEQ ID NO 4
<211> LENGTH: 1575
<212> TYPE: DNA
<213> ORGANISM: Homo sapiens

<400> SEQUENCE: 4
tcccaccccc agcctggggc ctctgggagc cttggtcctg agcagccaac acaccagccc 60
agacagctgc aagtcaccat ggacgctgaa ggcctggcgc tgctgctgcc gcccgtcacc 120
ctggcagccc tggtggacag ctggctccga gaggactgcc cagggctcaa ctacgcagcc 180
ttggtcagcg gggcaggccc ctcgcaggcg gcgctgtggg ccaaatcccc tggggtactg 240
gcagggcagc ctttcttcga tgccatattt acccaactca actgccaagt ctcctggttc 300
ctccccgagg gatcgaagct ggtgccggtg gccagagtgg ccgaggtccg gggccctgcc 360
cactgcctgc tgctggggga acgggtggcc ctcaacacgc tggcccgctg cagtggcatt 420
gccagtgctg ccgccgctgc agtggaggcc gccagggggg ccggctggac tgggcacgtg 480
gcaggcacga ggaagaccac gccaggcttc cggctggtgg agaagtatgg gctcctggtg 540
ggcggggccg cctcgcaccg ctacgacctg ggagggctgg tgatggtgaa ggataaccat 600
gtggtggccg ccggtggcgt ggagaaggcg gtgcgggcgg ccagacaggc ggctgacttc 660
gctctgaagg tggaagtgga atgcagcagc ctgcaggagg ccgtgcaggc agctgaggct 720
ggtgccgacc ttgtcctgct ggacaacttc aagccagagg agctgcaccc cacggccacc 780
gtgctgaagg cccagttccc gagtgtggct gtggaagcca gtgggggcat caccctggac 840
aacctccccc agttctgcgg gccgcacata gacgtcatct ccatggggat gctgacccag 900
gcggccccag cccttgattt ctccctcaag ctgtttgcca aagaggtggc tccagtgccc 960
aaaatccact agtcctaaac cggaagagga tgacaccggc catgggttaa cgtggctcct 1020
caggaccctc tgggtcacac atctttaggg tcagtggcca atggggcaca tttggcacta 1080
gcttgagccc aactctggct ctgccacctg ctgctcctgt gacctgtcag ggctgacttc 1140
acctctgctc atctcagttt cctaatctgt aaaatgggtc taataaagga tcaaccacat 1200
ggggttctgc ggtgataatg agcacatagt gaggggtcag caaatgtcag aagttacctg 1260
ggacagccgg gcacgatggc tcacacctgt aatcccagca ctttgggagg ctgaggcggg 1320
aagatcactt gagttcagga gtttgagacc agcctggcca acatggtgaa accccatctc 1380
taccaaaaat agaagaatta gctgggtgtg gtggcacgcg cctgtaatcc cagctactta 1440
ggaggctgag gcaggagaat cgcttgaacc caggaagtgg aggttgcagt gagctgatgg 1500
tgccactgca ctccagcctg ggtgatagag cgagactctg tctccaaaga agaaaaaaaa 1560
aaaaaaaaaa aaaaa 1575

<210> SEQ ID NO 5
<211> LENGTH: 1486
<212> TYPE: DNA
<213> ORGANISM: Homo sapiens

<400> SEQUENCE: 5
gactccgggt ggcaggcgcc cgggggaatc ccagctgact cgctcactgc cttcgaagtc 60
cggcgccccc cgggagggaa ctgggtggcc gcaccctccc ggctgcggtg gctgtcgccc 120
cccaccctgc agccaggact cgatggagaa tccattccaa tatatggcca tgtggctctt 180
tggagcaatg ttccatcatg ttccatgctg ctgacgtcac atggagcaca gaaatcaatg 240

-continued

```
ttagcagata gccagcccat acaagatcgt attgtattgt aggaggcatt gtggatggat    300

ggctgctgga aacccccttgc catagccagc tcttcttcaa tacttaagga tttaccgtgg    360

ctttgagtaa tgagaatttc gaaaccacat ttgagaagta tttccatcca gtgctacttg    420

tgtttacttc taaacagtca ttttctaact gaagctggca ttcatgtctt cattttgggc    480

tgtttcagtg cagggcttcc taaaacagaa gccaactggg tgaatgtaat aagtgatttg    540

aaaaaaattg aagatcttat tcaatctatg catattgatg ctactttata tacggaaagt    600

gatgttcacc ccagttgcaa agtaacagca atgaagtgct ttctcttgga gttacaagtt    660

atttcacttg agtccggaga tgcaagtatt catgatacag tagaaaatct gatcatccta    720

gcaaacaaca gtttgtcttc taatgggaat gtaacagaat ctggatgcaa agaatgtgag    780

gaactggagg aaaaaaatat taaagaattt ttgcagagtt ttgtacatat tgtccaaatg    840

ttcatcaaca cttcttgatt gcaattgatt ctttttaaag tgtttctgtt attaacaaac    900

atcactctgc tgcttagaca taacaaaaca ctcggcattt caaatgtgct gtcaaaacaa    960

gtttttctgt caagaagatg atcagacctt ggatcagatg aactcttaga aatgaaggca   1020

gaaaaatgtc attgagtaat atagtgacta tgaacttctc tcagacttac tttactcatt   1080

tttttaattt attattgaaa ttgtacatat ttgtggaata atgtaaaatg ttgaataaaa   1140

atatgtacaa gtgttgtttt ttaagttgca ctgatatttt acctcttatt gcaaaatagc   1200

atttgtttaa gggtgatagt caaattatgt attggtgggg ctgggtacca atgctgcagg   1260

tcaacagcta tgctggtagg ctcctgccag tgtggaacca ctgactactg gctctcattg   1320

acttccttac taagcatagc aaacagagga agaatttgtt atcagtaaga aaaagaagaa   1380

ctatatgtga atcctcttct ttatactgta atttagttat tgatgtataa agcaactgtt   1440

atgaaataaa gaaattgcaa taactggcaa aaaaaaaaaa aaaaaa                 1486
```

<210> SEQ ID NO 6
<211> LENGTH: 5607
<212> TYPE: DNA
<213> ORGANISM: Homo sapiens

<400> SEQUENCE: 6

```
gctgagctcc agctgtgcca gaggcacccg agccctgaga gtccgccgcc aacgcgcagg     60

tgctagcggc cccttcgccc tgcagcccct ttgcttttac tctgtccaaa gttaacatgt    120

cactgaaaaa cgagccacgg gtaaatacct ctgcactgca gaaaattgct gctgacatga    180

gtaatatcat agaaaatctg gacacgcggg aactccactt tgagggagag gaggtagact    240

acgacgtgtc tcccagcgat cccaagatac aagaagtgta tatccctttc tctgctattt    300

ataacactca aggatttaag gagcctaata tacagacgta tctctccggc tgtccaataa    360

aagcacaagt tctggaagtg gaacgcttca catctacaac aagggtacca agtattaatc    420

tttacactat tgaattaaca catggggaat ttaaatggca agttaagagg aaattcaagc    480

attttcaaga atttcacaga gagctgctca agtacaaagc ctttatccgc atccccattc    540

ccactagaag acacacgttt aggaggcaaa acgtcagaga ggagcctcga gagatgccca    600

gtttgccccg ttcatctgaa aacatgataa gagaagaaca attccttggt agaagaaaac    660

aactggaaga ttacttgaca aagatactaa aaatgcccat gtatagaaac tatcatgcca    720

caacagagtt tcttgatata agccagctgt ctttcatcca tgatttggga ccaaagggca    780

tagaaggtat gataatgaaa agatctggag gacacagaat accaggcttg aattgctgtg    840

gtcagggaag agcctgctac agatggtcaa aaagatggtt aatagtgaaa gattcctttt    900
```

-continued

```
tattgtatat gaaaccagac agcggtgcca ttgccttcgt cctgctggta gacaaagaat    960
tcaaaattaa ggtggggaag aaggagacag aaacgaaata tggaatccga attgataatc   1020
tttcaaggac acttatttta aaatgcaaca gctatagaca tgctcggtgg tggggagggg   1080
ctatagaaga attcatccag aaacatggca ccaactttct caaagatcat cgatttgggt   1140
catatgctgc tatccaagag aatgctttag ctaaatggta tgttaatgcc aaaggatatt   1200
ttgaagatgt ggcaaatgca atggaagagg caaatgaaga gatttttatc acagactggt   1260
ggctgagtcc agaaatcttc ctgaaacgcc cagtggttga gggaaatcgt tggaggttgg   1320
actgcattct taaacgaaaa gcacaacaag gagtgaggat cttcataatg ctctacaaag   1380
aggtggaact cgctcttggc atcaatagtg aatacaccaa gaggactttg atgcgtctac   1440
atcccaacat aaaggtgatg agacacccgg atcatgtgtc atccaccgtc tatttgtggg   1500
ctcaccatga gaagcttgtc atcattgacc aatcggtggc ctttgtggga gggattgacc   1560
tggcctatgg aaggtgggac gacaatgagc acagactcac agacgtgggc agtgtgaagc   1620
gggtcacttc aggaccgtct ctgggttccc tcccacctgc cgcaatggag tctatggaat   1680
ccttaagact caaagataaa aatgagcctg ttcaaaacct acccatccag aagagtattg   1740
atgatgtgga ttcaaaactg aaaggaatag gaaagccaag aaagttctcc aaatttagtc   1800
tctacaagca gctccacagg caccacctgc acgacgcaga tagcatcagc agcattgaca   1860
gcacctccag ttattttaat cactatagaa gtcatcacaa tttaatccat ggtttaaaac   1920
cccacttcaa actctttcac ccgtccagtg agtctgagca aggactcact agacctcatg   1980
ctgataccgg gtccatccgt agtttacaga caggtgtggg agagctgcat ggggaaacca   2040
gattctggca tggaaaggac tactgcaatt tcgtcttcaa agactgggtt caacttgata   2100
aaccttttgc tgatttcatt gacaggtact ccacgccccg gatgccctgg catgacattg   2160
cctctgcagt ccacgggaag gcggctcgtg atgtggcacg tcacttcatc cagcgctgga   2220
acttcacaaa aattatgaaa tcaaaatatc ggtccctttc ttatcctttt ctgcttccaa   2280
agtctcaaac aacagcccat gagttgagat atcaagtgcc tgggtctgtc catgctaacg   2340
tacagttgct ccgctctgct gctgattggt ctgctggtat aaagtaccat gaagagtcca   2400
tccacgccgc ttacgtccat gtgatagaga acagcaggca ctatatctat atcgaaaacc   2460
agtttttcat aagctgtgct gatgacaaag ttgtgttcaa caagataggc gatgccattg   2520
cccagaggat cctgaaagct cacagggaaa accagaaata ccgggtatat gtcgtgatac   2580
cacttctgcc agggttcgaa ggagacattt caaccggcgg aggaaatgct ctacaggcaa   2640
tcatgcactt caactacaga accatgtgca gaggagaaaa ttccatcctt ggacagttaa   2700
aagcagagct tggtaatcag tggataaatt acatatcatt ctgtggtctt agaacacatg   2760
cagagctcga aggaaaccta gtaactgagc ttatctatgt ccacagcaag ttgttaattg   2820
ctgatgataa cactgttatt attggctctg ccaacataaa tgaccgcagc atgctgggaa   2880
agcgtgacag tgaaatggct gtcattgtgc aagatacaga gactgttcct tcagtaatgg   2940
atggaaaaga gtaccaagct ggccggtttg cccgaggact tcggctacag tgctttaggg   3000
ttgtccttgg ctatcttgat gacccaagtg aggacattca ggatccagtg agtgacaaat   3060
tcttcaagga ggtgtgggtt tcaacagcag ctcgaaatgc tacaatttat gacaaggttt   3120
tccggtgcct tcccaatgat gaagtacaca atttaattca gctgagagac tttataaaca   3180
agcccgtatt agctaaggaa gatcccattc gagctgagga ggaactgaag aagatccgtg   3240
gatttttggt gcaattcccc ttttatttct tgtctgaaga aagcctactg ccttctgttg   3300
```

```
ggaccaaaga ggccatagtg cccatggagg tttggactta agagatattc attggcagct   3360
caaagacttc caccctggag accacactgc acacagtgac ttcctgggga tgtcatagcc   3420
aaagccaggc ctgacgcatt ctcgtatcca acccaaggac cttttggaat gactggggag   3480
ggctgcagtc acattgatgt aaggactgta aacatcagca agactttata attccttctg   3540
cctaacttgt aaaaaggggg ctgcattctt gttggtagca tgtactctgt tgagtaaaac   3600
acatattcaa attccgtata ccaaaatcca tttcctttgt aacaagaatt taccagtaac   3660
tgtgatctag gttgccaaaa gttgtctgaa tctccttatt cttctctgat cttcatttat   3720
gcagccaatg tctagctgga cctgccctca tcttgcagtt catacaggca ctgtttgaga   3780
gattgtttat tattagatgt tgtaatgctg cttcaagatt cttcatggtt acatgggatg   3840
cccctgctca tctggtcctg aagtagtaac attcacccaa atgaggatat agtcattatt   3900
ccttttcagt cactgtacga acacggcaga ctttagccta cacagtagac tgtgttaggc   3960
acttctggta acattgacac tgtatcttga caccactaag caacaggaag gaataaattc   4020
caatattgag acagagattt atttcatttt gctcccaaag gcactgacaa catgagtcct   4080
tgtgattagg cccacctgat caaatgtaaa aacatgcatg ggatatttga ttacgtaaca   4140
accagctaaa actgagagca cacagccttc ggaaaccccc aaggtgtcga ggaggatcag   4200
atccagataa gagaagatga ttccttctag tcctgtaaaa tttcctgtca tccttagctg   4260
ctgggttgat tgaaatttga tctctacatt tcaaaatcaa actagtgaat acagtttgtc   4320
tttcaagaga atcagaggca tcgtaactcc taccaagtta gtaagtatga gtctaacctt   4380
gtttgacatt caggtcttct gctacattat cttctttgag aaaaattaat tgattataaa   4440
atatgtgcta cttcacttac attattaaat atgtattaac gcctctcacc agggcttcca   4500
gtgaagttac aatgccctag tctgtgaatt agtctggaaa cgtgtttttc cttttcggat   4560
gttagagtac cctttgataa actaaatttt actaagctga acaactctga cagtctaaag   4620
agctaatgtg ggttaccaaa aggcctgtac ctgtaaaaca aaatgcaggt gtaatgatta   4680
tacatgtcta tggattacct ggacatactc tcatttgggt tgttcttcaa agaagcaagc   4740
agccgatccc tgttttcata aagctaatac ttcagttgga aaaattaaac aggagcacaa   4800
agtcagggat aggggttagc agaagagaga aatagtgtca catcaagggc aggatctcat   4860
agctagggaa catttcacaa ataaggtgag attttgtaac caataataaa aatgaatgtt   4920
tttataagta aataacttat ttttcatatg gctaaagatg gtaaaatgac ttcattctat   4980
agccattgta aataagaatt tgctattgat gaaagaagtt cagattggca tttgaagtat   5040
tgagtgtatg ggatctctaa ggatttctta gattttatat ttaaatattt tttaaacctt   5100
agaggagtca acaaactggc tcttgatttt cagcacccta ctctcatgaa aaaagcctga   5160
aaggaccctt tcccttataa gtaatttaat ccaatttctc cccattttat agatgaggaa   5220
actgaggctc agatcagatg agaactcact taaatccact caatgtgtag atggtagagc   5280
tgggactagc aacattgctg cagcccattg ttggcctctc tcttcacttt atcattgccc   5340
aagaatgagg atatgcagta aacagaattc aggcaagata cctctaagct gttttgaacc   5400
ctctgatatt ttgtatttat gtgtttgtct gtctccccct actagaatgt aagctccatg   5460
gggcagggac ttcactgtat tttgttcata gtgtatcccc agagcctgga ccagtgcttg   5520
gcacatagga gatggcaata aatgcttgta gaattaataa acaaggtgaa ggagagagct   5580
aatgaaatga aaaaaaaaaa aaaaaaa                                       5607
```

<210> SEQ ID NO 7

-continued

<211> LENGTH: 2383
<212> TYPE: DNA
<213> ORGANISM: Homo sapiens

<400> SEQUENCE: 7

```
cttttctctt gttgagtgca aatggagaac agctgctcac gctcgtcgtc tgacatcagc     60
tatttctcag gatgaccctg cgagacaggc cagggtcatt agacccaatt tggttctcag    120
caaatatgtg tttattcctg catgcgtggg ccacaggctg gtttcttggg tgcaatgaat    180
agctgcaggt ttattagggt gtctttttag atggatgtat gtttcccgat gtctatagaa    240
cactccggac cccggagagt gaagactctg cctgtcggac ttgctttgag aagatccttc    300
tccacctccc catggcagaa gttgcttcac agaggggaac agttttatgg atgtggctga    360
gaccttaaac ttgaggcaac ccatctgagg tggcatccag aggagactgg ctggcccctc    420
cttcaccttg gatgtagtgc tgtttctagg atctcttttc aatcagcaaa acaggggatg    480
ttccaagagg gtgtggattc cctgccatcc cacatggtca agtggagggg acgggaaaaa    540
gctatgaagg gtttgtgacc acacagactc tcctggcccc ctgtcctttt ggaaagaaga    600
cagggatgaa atataatcaa gcaattaacc acccccatca tcaccaagaa caacagtatc    660
aacaagaaga acagggacaa caaaacccac ggatgaaaca ttcctttctc agctcagatc    720
ttatctggtg cgttctctct ctgctctgtc ttggtgtgtg gtttagagaa acatggacaa    780
cgctgtttgg aagaacaggt gagcgagggt ggggaatttc agaggcctgg gcccaccgcc    840
tccacccctt ccccagttta acctttgaca ggatcttcac ctctctctga tcagcattgc    900
ttcttgttca aaggcctcag ccacccagct gtgtcccttt ccccagaaag caagggcaga    960
tggcagtggg tctgttgatg agagaacttt aagggcccaa tcagtccctg ggcacccccct  1020
cctgggctcg ttttctccag gaggctgcat tctgatccat aaaccttctc ctcggggttt   1080
agggtcgagc tgttcctgat gtttatcgga gactgggatc aaagctatcc aggtcataaa   1140
tctctctctg tggctgttgg gccccagggc agctgaagag ggttgacagc cctttggacc   1200
tcaaaggaaa aaatgtgctc tactccaccc actcccagct ctgccaagaa gctgtcctct   1260
gagaagccat ggctgggccg ttccattctg gggagctgct gaaaagagct gggaggccga   1320
gaagaacttg cgtgtgctgg gggagaggaa gcctggcctt gagggagggg tgcaggtgtg   1380
gctcctctgt gtgtgggggc tgggggacct tgtgtgcctt ttccttgtgg ctgtgaaatg   1440
ctttatgagt acttccatag gaggatggac agggagtcgg ggagataaac tcagccacaa   1500
ggccccaggg cctcaggaaa cttgcaccca accctctcat tttacagaag aaaactgtgc   1560
ctggaaggtt gaagggtttg ttcccagtca cacaaccagg gatccttagg acagccagac   1620
caggaaacca tttccaaact gccaagccat ggcagagtat caagacctca ggaaccatcg   1680
agacaccatg gaagcattgg gaaaagcctc cttagctttt gaagctcctc attgttcttg   1740
agtgtgcatg gagcccatga ctgcggggtt ttgtagacac ctcagggatt acatgactgg   1800
taccccctgac aaagtcaagg ctgctggaca aaatgagtcc gaggatttca ggggcagctg  1860
ggcgcaggag ctggtgggct gttgggagtg cccctttact gggcaggctt ccttcctcct   1920
ggtgatgggg ggttcctcag cacaaaagtg aaggggtgga ggggctggag gagcaggaat   1980
ctctcttgtt gataggtatg aggccttgaa gtccttttct ttgtcccagg attcatggac   2040
gcttcggggc tgatctttga gttttcaagc atggggtgca gagacgttta ggtaaactct   2100
taccgtcctc tctcttcgtc agggcttccc aggaatcaac aatgcccaag aaggaaggga   2160
ttgtagaaat agcttaaccc tttcatttac caacgtggaa attgaagccc agggaaggga   2220
```

```
agggaccggt cgtggaaggg agagccatca gcagaaagag accctgagat cttcgcctgg   2280

gattcccagg aagtccagcc cgagctgatt cacagaacaa atgcatgcaa accttgctat   2340

caataaatta cacatgcact tacgtaaaaa aaaaaaaaaa aaa                     2383


<210> SEQ ID NO 8
<211> LENGTH: 4731
<212> TYPE: DNA
<213> ORGANISM: Homo sapiens

<400> SEQUENCE: 8

agcaacagag tttagactgt ctttgcttca tcatctgaag gtaaaatttt ccagatacgg     60

cagacggctt tcagagtaca ataaacaggg aatgagaact atttacatgg aagtttcttt    120

ctcatgatgc ggtggagaag cctcggccac ttggttctgc cagatgttcc tggggttact    180

gtaaatggga aggacaggca gagctaaaca aggtttatca tttaaaagtg cctgtgtgaa    240

gtcacttttg ctggaaaact gcagcttggg agctttcttt gtattcacat cccactcttc    300

tgtcaagtac actttaccct gaccttatga gtggatgaag atacctcagt tgtctgactt    360

tgccaattgc ttaatttcag aatttaaaaa ggggaaagaa aaacatcctg ctaaaatatg    420

aacatctgag tgtcttattt tccaacatcg tcaatagctg tgagcgtcag cattaaatat    480

tctcccaagg agtgccatga tattgaagtc actttattaa taacagctgt atctgcaaaa    540

cagtcaagag actcggacgt tgaaagccag agatgacact gagcatgctt ttattgcggc    600

ctaccatctt taagtgggac atattgattg atgagtgatt gcctgtccat acactctctc    660

atcatcctgt tccttggatt ggacttcact aagcaattta tcactcacct tcagacttac    720

atgtgggagt tttcacaaca gtagttttgg aatcattaga acttggattg atttcatcat    780

ttaacagaaa caaacagccc aaattacttt atcaccatgg ctttgaacgt tgccccagtc    840

agagatacaa aatggctgac attagaagtc tgcagacagt ttcaaagagg aacatgctca    900

cgctctgatg aagaatgcaa atttgctcat ccccccaaaa gttgtcaggt tgaaaatgga    960

agagtaattg cctgctttga ttccctaaag ggccgttgtt cgagagagaa ctgcaagtat   1020

cttcaccctc cgacacactt aaaaactcaa ctagaaatta atggaaggaa caatttgatt   1080

cagcaaaaaa ctgcagcagc aatgcttgcc cagcagatgc aatttatgtt tccaggaaca   1140

ccacttcatc cagtgcccac tttccctgta ggtcccgcga tagggacaaa tacggctatt   1200

agctttgctc cttacctagc acctgtaacc cctggagttg ggttggtccc aacggaaatt   1260

ctgcccacca cgcctgttat tgttcccgga agtccaccgg tcactgtccc gggctcaact   1320

gcaactcaga aacttctcag gactgacaaa ctggaggtat gcagggagtt ccagcgagga   1380

aactgtgccc ggggagagac cgactgccgc tttgcacacc ccgcagacag caccatgatc   1440

gacacaagtg acaacaccgt aaccgtttgt atggattaca taaaggggcg ttgcatgagg   1500

gagaaatgca aatattttca ccctcctgca cacttgcagg ccaaaatcaa agctgcgcag   1560

caccaagcca accaagctgc ggtggccgcc caggcagccg cggccgcggc cacagtcatg   1620

gcctttcccc ctggtgctct tcatccttta ccaaagagac aagcacttga aaaaagcaat   1680

ggtaccagcg cggtctttaa ccccagcgtc ttgcactacc agcaggctct caccagcgca   1740

cagttgcagc aacacgccgc gttcattcca acagggtcag ttttgtgcat gacacccgct   1800

accagtattg tacccatgat gcacagcgct acgtccgcca ctgtctctgc agcaacaact   1860

cctgcaacaa gtgtcccctt cgcagcaaca gccacagcca atcagataat tctgaaataa   1920

tcagcagaaa cggaatggaa tgccaagaat ctgcattgag aataactaaa cattgttact   1980
```

-continued

```
gtacatacta tcctgtttcc tcctcaatag aattgccaca aactgcatgc taaataaaga   2040
tgtagttctt ctggacagac cacaactcta agaagctagt gctgctatct catatatgag   2100
tattaaatat ggtatgctta gtatattcca acctaagata gttaactacc tgagaccagc   2160
tgtgatgttt aaagacataa aggataaagt ttacttttaa agggtttcta aacatagttt   2220
ctgtcctagg aatattgtct tatctccata actatagctg atgcagaaag tccagccagt   2280
ttactcattt cgattcagaa tatttcaaat ttagcaataa acaattagca ttagttaaaa   2340
aagaaacata ttccaagggc aggttcgatt ctagctctaa ttactgtcat gtcatttacc   2400
cactggatca aagggtatgt ttcacttctt gacaatataa atgctgcagc aaagatgaga   2460
ggtgaagtaa aaccgatacc tgtcctgcag gtctaaaatt tgaatggaaa ttcaagcaca   2520
agtactgggg acacatcaaa gtgtggtgtt tggtttgcct ggagatgcca cgttgaatca   2580
tgtgattcta gattaacatt aaatagattg aaaaagaaac tttgcacggt atgagcttca   2640
taccccacca aacaaagtct tgaaggtatt attttacaag tatattttta aagttgtttt   2700
ataagagaga ctttgtagaa gtgcctagat tttgccagac ttcatccagc ttgacaagat   2760
tgagaggccc atgccaacag tctaatctaa gagattagtc tttcaaactc accatccagt   2820
tgcctgttac agaataactc ttcttaacta aaaacctagt caaacaagga agctgtaggt   2880
gaggagatct gtataatatt ctaatttaag taagtttgag tttagtcact gcaaatttga   2940
ctgtgacttt aatctaaatt actatgtaaa caaaaagtag atagtttcac tttttaaaaa   3000
atccattact gttttgcatt tcaaaagttg gattaaaggg ttgtaactga ctacagcatg   3060
gaaaaaaata gttcttttaa ttctttcacc ttaaagcata ttttatgtct caaaagtata   3120
aaaaacttta atacaagtac atacatatta tatatacaca tacatatata tactatatat   3180
ggatgaaaca tattttaatg ttgtttactt ttttaaatac ttggttgatc ttcaaggtaa   3240
tagcgataca attaaatttt gttcagaaag tttgttttaa agtttatttt aagcactatc   3300
gtaccaaata tttcatattt cacattttat atgttgcaca tagcctatac agtacctaca   3360
tagtttttaa attattgttt aaaaaacaaa acagctgtta taaatgaata ttatgtgtaa   3420
ttgtttcaaa catccatttt ctttgtgaac atattagtga ttgaagtatt ttgacttttg   3480
agattgaatg taaaatattt taaatttggg atcatcgcct gttctgaaaa ctagatgcac   3540
caaccgtatc attatttgtt tgaggaaaaa aagaaatctg cattttaatt catgttggtc   3600
aaagtcgaat tactatctat ttatcttata tcgtagatct gataacccta tctaaaagaa   3660
agtcacacgc taaatgtatt cttacatagt gcttgtatcg ttgcatttgt tttaatttgt   3720
ggaaaagtat tgtatctaac ttgtattact ttggtagttt catctttatg tattattgat   3780
atttgtaatt ttctcaacta taacaatgta gttacgctac aacttgccta aaacattcaa   3840
acttgttttc ttttttctgt ttttttcttt gttaattcat ttaaactcat tgaaaacata   3900
gtatacatta ctaaaaggta aattatggga atcactgaaa tatttttgta gattaattgt   3960
tgtaacattg tctttctttt ttttcttttg tttcatgatt ttgattttta aaattattag   4020
cacacaacta ttttcagccc tttaataatg gagcatcaaa aacatcacct gtaaccccaa   4080
gcaaatatag aagactgtat tttttactat gatatccatt ttccagaatt gtgattacaa   4140
tatgcaaaga gtcataaata tgccatttac aataaggagg aggcaaggca aatgcataga   4200
tgtacaaata tatgtacaac agattttgct ttttatttat ttataatgta attttataga   4260
ataattctgg gatttgagag gatctaaaac tatttttctg tataaatatt atttgccaaa   4320
agtttgttta tattcagaag tctgactatg atgaataaat cttaaatgct ttgtttaatt   4380
```

-continued

```
aaaaaacaaa aatcaccaat atccaagaca tgaagatatc agttcaacaa atactgtagt   4440

taagagacta actctccact tgtatgggaa ctacatttca ctcttggttt tcaggatata   4500

acagcacttc accgaaatat tctttcagcc ataccactgg taacatttct actaaatctt   4560

tctgtaacac ttaaagaatt ccctcattca ttaccttaca gtgtaaacag gagtctaatt   4620

tgtatcaata ctatgttttg gttgtaatat tcagttcact cacccaatgt acaaccaatg   4680

aaataaaaga agcatttaaa aggaaaaaaa aaaaaaaaaa aaaaaaaaaa a            4731


<210> SEQ ID NO 9
<211> LENGTH: 5726
<212> TYPE: DNA
<213> ORGANISM: Homo sapiens

<400> SEQUENCE: 9

acgtgggaga gaagggaggg ttgggggaag tgtggaaaac ctgaacctga gctgctgtcg     60

cctgaggaag atttggtggg aggagaagca gaggggaaga gacgggttga gagtgaggtg    120

aggagggcat ctaggtcact gctcccgggg ggcacaaagt tcgcgatgtg gctgaagcct    180

gaggaagtgc ttctgaaaaa tgcgctgaag ctgtggctga tggaaaggtc caacgactac    240

ttcgtgctgc agcggcgtcg gggctacggg gaggaaggcg gagggggggct cacagggctt    300

ctggttggga ctcttgattc agtcttggac tctactgcta aagtagctcc atttcgcatc    360

ctacaccaga caccagattc tcaagtttac ttgtcaattg catgtggagc caacagagaa    420

gaaataacca agcattggga ttggttggaa caaaatatta tgaagacctt atctgtattt    480

gattcaaatg aagatattac taattttgta caaggaaaaa taagaggatt aattgctgaa    540

gagggaaaac attgttttgc aaaagaagat gatcctgaga aatttcgaga agcccttttg    600

aaatttgaaa aatgttttgg tttaccagag aaggagaagt tagtgaccta ttattcatgc    660

agttattgga aaggacgggt tccttgtcag ggttggcttt atcttagcac caactttctg    720

agcttctatt ctttttgtt gggatcagaa ataaaactca ttatctcctg ggatgaagtc    780

tcaaaacttg aaaagacttc aaatgtcata ctgacagaga gtattcacgt gtgttcccaa    840

ggagagaatc actacttttc aatgtttttg cacattaacc aaacatacct tcttatggaa    900

cagctggcaa actatgccat tagaagactt tttgataagg aaacatttga taatgaccca    960

gtcctttata atcctctaca gatcaccaaa agaggtctgg aaaatagagc ccacagtgag   1020

caatttaatg cctttttttag gctgcccaaa ggagagagtt tgaaagaagt acatgaatgt   1080

ttcttatggg taccattcag ccacttcaat actcatggga aaatgtgcat ctcagaaaat   1140

tatatctgct ttgctagcca agatggcaat cagtgtagtg taatcattcc actacgagag   1200

gtcttagcta tagataagac aaatgattcc agcaaatctg tcatcattag catcaaagga   1260

aaaacagctt ttcgcttcca tgaagttaaa gactttgaac aactggtagc aaaactcagg   1320

ctcagatgcg gagcagcttc aactcaatat catgatatta gcacagagct tgctattagt   1380

tctgagtcta cagagccatc tgataatttt gaggtgcaat ctttgacaag tcagagggaa   1440

tgcagtaaaa ctgtgaacac tgaagcctta atgacagtat ttcaccctca gaatttggag   1500

actcttaatt ctaaaatgtt gaaagaaaaa atgaaggaac agtcatggaa aatactgttt   1560

gcagaatgtg gacgtggtgt tagtatgttt cgaaccaaaa agactcgaga tcttgttgta   1620

agagggattc cagaaacatt aagaggagaa ctctggatgc tttttttcagg tgctgttaat   1680

gacatggcta ctaatcctga ctattatact gaagtggttg agcagtcctt agggacctgc   1740

aacttggcta ctgaagaaat tgaacgtgat ttacgtcgct ctctgcctga gcacccagcc   1800
```

-continued

```
tttcagagtg atactggcat atctgctctg agaagggtac tcacagctta tgcatacagg   1860
aatcccaaaa ttggatactg ccaggcaatg aatattttga cttcagtgct gcttctatat   1920
gcaaaagagg aagaagcttt ttggcttctg gttgctgtat gtgaacgaat gttgcctgat   1980
tattttaatc gtcgaattat tggtgccttg gtggatcagg cagtctttga agaacttatc   2040
agggatcacc ttcctcagct gacagaacac atgactgata tgacattctt ttcctcagtt   2100
tctctctctt ggtttctcac actttttatt agtgtgctac ctattgaaag tgcagtgaat   2160
gtggtggact gtttcttcta tgatggaata aaggccattt tgcaactggg attggcaata   2220
cttgactata atttagacaa actgctgact tgtaaagatg atgctgaagc tgtgacagcc   2280
ttaaacaggt tctttgacaa tgtcactaat aaggatagtc cattgccttc aaatgttcag   2340
caaggttcaa atgtgagtga tgaaaaaacc agtcatacta gagtggatat tacagatttg   2400
attagagaat caaatgagaa atatggtaat attcgctatg aagatataca tagtatgcgc   2460
tgtcgaaata ggttgtatgt gatacagacc ctagaggaaa caacaaaaca gaatgtgttg   2520
cgtgttgtat cacaagatgt gaaattgagc cttcaagaat tggatgaact ttatgtcatc   2580
tttaagaaag agctgttttt atcttgttat tggtgtttgg gttgcccagt attgaagcat   2640
catgacccca gtctgccata tttggaacag tatcagattg actgccagca gttcagagcg   2700
ttgtatcact tgttgagtcc ctgggctcat tctgcaaata aagactcact agctttatgg   2760
acattcagat tgttagatga aaactctgat tgccttataa acttcaaaga attctcctct   2820
gcaattgaca taatgtacaa tggaagtttt actgagaagc ttaagctgct ttttaagcta   2880
catattcctc cagcttacac tgaagtgaaa tctaaggatg cttcaaaagg agatgaactt   2940
tccaaggaag aattacttta tttcagtcag ctgcatgttt ccaagcctgc aaatgagaag   3000
gaagcagaat cagcaaaaca cagccctgaa aaaggcaaag ggaaaattga tattcaagca   3060
tatctaagtc aatggcaaga tgagcttttc aaaaaaagaag aaaacattaa ggatttacca   3120
agaatgaatc agtctcagtt tattcagttt tcaaagaccc tctataactt atttcatgag   3180
gaccctgaag aagaatcatt atatcaagcc attgctgttg taaccagcct tttactcagg   3240
atggaagaag ttggaaggaa actacatagc cctacatcat cagccaaagg attctctggt   3300
actgtctgtg gttctggagg acccagtgag gaaaaaacag ggagccactt ggagaaagat   3360
ccttgttcct ttagggagga acctcagtgg tcatttgcat ttgaacagat tcttgcatcg   3420
ctgttgaatg aaccagcatt ggtgaggttt tttgagaaac ccatagatgt aaaagccaag   3480
ctggaaaatg caagaatttc tcagttaagg tctagaacca agatgtaaat ccctaggaat   3540
tgcctatcat agacaagttt actaacattc ctgtagctgt cagtttgatt cctgtgagta   3600
gggctcaggg atttatcttg ttaccaatgt gtctgaaggc caaaatatat atccagaagc   3660
acaatgcatc attcctttgt tgttgataat gggctttgtt agcacttttt aaaacaaaca   3720
aacaaacaaa acaaaaaagc aaaccacatt tgttatctca aattttgatg atattctcaa   3780
atacaaatat actttttat atttcacaat atatgcaata tcaggggaat atgctaaatg   3840
ttaccaccag agggcacaag catatcactt ttagtaagga aattactagc ttgtgttgct   3900
atttacatat gaattactga ttattttgaa aagacggtgt tatgcttggg tgttagtgag   3960
gctgatatgt catgtcaatc gataaaccct actttccaaa ttatctaaaa gattaccatt   4020
tggggccctt gttttcaagt tatctaactg aaatattatt aatttttta agttaatctc   4080
attcagtctt ctagtaataa atgctttttt aagtaccttc tacagtcttc ctacctgagg   4140
ggttcagagg ctgctgactc acactgctaa ctctgttact gacaaaagca aatcaataac   4200
```

-continued

```
tctaaattct gggctgatat aaagaaaaaa acaatattgg atttggattt aatctgggta   4260
aaatcagcct tctgagaagg gctaagaaac agttcaatta actgtatagg tctttcatta   4320
gaccgagaca tcactagaaa ttctgggcac tgctgtttgt ggtatttgtc tcagagtagc   4380
ttatgactgt tttggttcta gctttagatt ttggattttc accagtcatg tgttaattta   4440
cattagatag taaagaatgg ctacactaag actgaattat cttattagtc tggcaagcat   4500
ataaagtata cttgtatgta atgattgcca aggtaacaga attgctgaca tctgtctaaa   4560
aagttttgac tatccaattt agatgtgtaa tttctatata ctttatgctg tttatatttc   4620
agtcattaca ccaagtccat ttagagataa tgggctttgt tagcactttc aaaaaaaaaa   4680
aaagcaaacc atacttgtcc actgtcctgt gctattccta ccaaggacaa tttattaatc   4740
aattgactta gaaaataggg ggagaaatca ttcattggag cttctttctt tagaaaagac   4800
tttggttata agccttttga cttttctaga tgtgaaacca tgaaagggca gacctccttc   4860
agagtgactc aagaggtctc cctttcttgg agggagttgg tacagtcagc ctttgggaag   4920
aatccactgt gaacaaagct taacacatgg ggcttcatcg ctcatagaat atgttatttt   4980
caaagaagtt caagaatttt caagttgagc ctttgaaaat cccataaatt ggttttagct   5040
aaacacttac tagtagtgtc tttaaattat ttaatcaacc ttgtcttttc aaggaaatta   5100
ccacttaaag agatagttgg taaataaaca tctatgcctt ttctcagaaa tgatttgctg   5160
aactatgtcc atattttaca gcttagataa tagtttatat ggaaactatt atacatctgc   5220
tattgtgcaa tgattgttaa attatactga agtagctcta gaaagacaca tgtatacaag   5280
gcactattgt acacactttg ctgaatattt tgtcagttgt atttacaaag aaaggtactt   5340
tcttaagagc atatatgtta ttaatatttg atatgatttt aaagtcagaa tagtacagat   5400
tgctgagtat tatactttag gctagattaa ttaaaattga atactgaaag agattttttg   5460
agttgcaaaa agtttataaa tgcaaagcaa aaagaaaaca tttattttct gagtctgcag   5520
gagaaacaaa ctaaacatta tagttttata gctgctatct tgttaaccaa acaggttgtt   5580
cataatatta aaaatcttac gtagttgtgt taaactgaac cagttcatta taccttatgc   5640
attaaattaa atatgttata aggtggcttt acttgtcttt ataaaaataa atatatctac   5700
taaacatgaa aaaaaaaaaa aaaaaa                                         5726
```

```
<210> SEQ ID NO 10
<211> LENGTH: 3121
<212> TYPE: DNA
<213> ORGANISM: Homo sapiens

<400> SEQUENCE: 10

ccggaagaaa acggctcctg tcacagaagt ctcgtgattg ctctgggagc tttgcttaga     60
cacttgaaac tacaggagaa agaaggatct agcgaaatat ggctacagag agccctgcta    120
cgcgtcgggt ccaggtggca gaacatccta ggttactgaa gctaaaggag atgtttaact    180
ccaagtttgg atctattccc aagttttatg ttcgagcacc aggaagagtc aacataatag    240
gagagcatat agattattgt ggatattctg ttcttcctat ggctgtagaa caagatgtgc    300
taatagctgt agaacctgtg aaaacgtacg ctctccaact ggccaataca aatcccttgt    360
atccggactt cagtactagt gctaataaca tccagattga taaaaccaag cctttgtggc    420
acaactattt cttatgtgga cttaaaggaa ttcaggaaca ctttggtctt agtaacctga    480
ctggaatgaa ctgcctggta gatggaaata tcccaccaag ttctggcctc tccagctcca    540
gtgctttggt ctgttgtgct ggcttggtga cgctcacagt gctgggaagg aatctatcca    600
```

-continued

```
aggtggaact tgcagaaatc tgtgccaaga gtgagcgtta cattggcact gaaggaggag    660
gcatggacca gtctatatca tttcttgcag aagaaggaac tgccaagttg atagaattta    720
gtcctctgag ggcaaccgat gtaaaactcc caagtggagc agtgtttgtg attgccaaca    780
gttgtgtgga gatgaataag gcagcaactt cccatttcaa tatcagggtg atggagtgtc    840
ggctggctgc gaagctcctg gctaaataca aaagcttgca atgggacaaa gtactgaggc    900
tggaggaggt gcaggctaaa ctagggatta gtctagaaga aatgctgttg gtcacagaag    960
atgcccttca tcctgaaccc tataaccctg aggagatctg caggtgtctg ggaattagcc   1020
tggaggaact ccgaacccaa atcctgagtc caaacactca agatgtgctc atcttcaaac   1080
tctatcagcg ggcaaagcat gtgtacagcg aggctgcgcg agtgctccag tttaagaaga   1140
tatgtgaaga agcacctgaa aacatggtcc agctgctggg agagttgatg aaccagagcc   1200
acatgagctg ccgggacatg tatgagtgca gctgccccga gctggatcag ctggtggaca   1260
tctgtcggaa gtttggggct caagggtcac gacttactgg agcaggatgg ggaggctgca   1320
cagtatcaat ggtacctgcg gacaagctgc ccagctttct agcaaatgtg cacaaagctt   1380
attaccagag gagtgatgga agcttagcac cggagaagca aagtttgttt gctaccaaac   1440
ctggaggtgg ggctttggtt ttgcttgagg cctgaaaaaa tgtaaaaagt ctgagagaaa   1500
ctacttaggg cacttaggaa ttggcaggac tttctgtgcc acagtaaatt aatcttcctt   1560
ctgttttgta ttatgatgaa cggttgctat tatatcaaga tatattttca aagaaatggt   1620
tgaaagctct ctatgcttca taatgattct ttttccatct taaaatatgg ttttactatt   1680
aagagccaag atcatgcttg gacagatctt ttaagaataa cttactgaga tttattgatt   1740
tgaagatttt aaagatgaat ggtaaaacac actcttaata ctgattacat ggattggact   1800
tgaattaaat atattgttac aattaaactg ataccactga attgtatgca ttattcttga   1860
atagagttca tttctggttt ctcttagtat tcttcttcct caaagttgta gttgtctgtt   1920
gatgatggtg atgatgatga tgatgacgat agtgatgcca cacattctct ctcaatttca   1980
gcttcggaac gctatgaaaa taatacatga ttaaagtttc acagatcttc ttggacattg   2040
tataattgaa tttgaatgtg agatttctcc agttatcaag agactaagga tttttttttt   2100
tttttgacaa aaggaggata caggaagaaa attcagactc atttgaatat ttgtaaacca   2160
tgtaatatat aaataaccac tttcaattct tttggccctg agctatctcc attacttaat   2220
agaaaaactt agataaaaaa cactttaaga ctcttctatt cacattgaaa taaagaatta   2280
tctagatgat aattcagata attcagtttg ttcatagaat tactttctta tcactctttt   2340
tctactactt tttctcaaat acctctctaa tccaagaggc acttccaaga aattccacac   2400
attccttata tccctttttt gcttgtctag caaagcttgt ttgtatatat gcaccccatt   2460
gtaaagcagg tatgcaggta tgtgggtgaa agtgactatg aaaagactta atgaattctg   2520
ggatttgtaa tggtattgat gggtatctct gtatgtatat caagagtggg cagaaatgtt   2580
tggctggtga tggcaaatga ctggctttct cttgtggatg gactatagga agcactttct   2640
gaattatgta atgatttgga ccaaaaagta ttttgctgaa atactcaggt aattgagata   2700
gcaatggttt tatggcatga attatccaaa aaaatatcag aattacttat tattctgtga   2760
tttcattagc tcattaatgt ttaactcaca gattgggcat caccatctag aatttcagtt   2820
taagggaggc ctgcgcaaag ctagttttat ttcttaaagg ataacagtca tacatagaat   2880
actaggaaag ccaatattct atttaaaaat aaacttctga tgcattttca ttcttagcag   2940
aaaggtaaat gcttgagaaa gcttgagtca aatttgttaa aagaatttg agttctataa    3000
```

-continued atccaaaaat ctgaaacctg aatttattta aatttataat cctttatttt ttaataccgt 3060
gccattttcc acaaaggatt tgtggttggt atataattct ttaaagatac ctggatcagt 3120
g 3121

<210> SEQ ID NO 11
<211> LENGTH: 5360
<212> TYPE: DNA
<213> ORGANISM: Homo sapiens

<400> SEQUENCE: 11
gggagagagg agttgggctg tgccggaggc cgaggaccga gagggctcag gtgacccctg 60
gaaagcctgg gtggctggaa aggagcctag cgcctgcatg aaaggaagaa cctgctggga 120
agtacctgag ctcgagctgt gggttccgcc gcccttcccc tgcgtggtgg cttggtggcc 180
gcgtctgcgc ctcagccctg agaatccgga tggcggtgag gtggacttgg gcaggcaaga 240
gctgcctgct gctggcgttt ttaacagtgg cctatatctt cgtggagctc ttggtctcta 300
cttttcatgc ctccgcagga gccggccgtg ccagggagct ggggtcaaga aggctctcag 360
acctccagaa aaatacggag gatttgtctc gaccgcttta taagaagccc cctgcagatt 420
cccgtgcact tggggagtgg gggaaagcca gcaaactcca gctcaacgag gatgaactga 480
agcagcaaga agaactcatt gagagatacg ccatcaatat ttacctcagt gacaggattt 540
ccctgcatcg acacatagag gataaaagaa tgtatgagtg taagtcccag aagttcaact 600
ataggacact tcctaccacc tctgttatca ttgctttcta taacgaagcc tggtcgactt 660
tgctccgtac cattcacagt gttttagaaa cttctcctgc agttcttttg aaagagatca 720
tcttggtgga tgacttgagt gacagagttt atttgaagac acaacttgaa acttacatca 780
gcaatcttga tagagtacgc ttgattagga ccaataagcg agaggggctg gttagggccc 840
gtctgattgg ggccactttc gccactgggg acgtcctcac tttcctggat tgtcactgtg 900
agtgtaattc cggttggctg gaaccgcttt tggaaaggat tgggagagat gaaacagcag 960
ttgtgtgtcc tgttatagac acaattgatt ggaatacttt tgaattctat atgcagatag 1020
gggagcccat gattggtggg tttgactggc gtttaacatt tcagtggcat tctgtcccca 1080
aacaggaaag ggacaggcgg atatcaagaa ttgaccccat cagatcacct accatggctg 1140
gaggactgtt tgctgtcagc aagaaatatt ttcagtacct tggaacgtat gacacaggaa 1200
tggaagtgtg gggaggtgaa aaccttgagc tgtcttttag ggtgtggcag tgtggtggca 1260
aattggagat ccacccgtgt tcccacgtgg gccatgtgtt ccccaagcgg gcaccatatg 1320
ctcgccccaa tttcctacag aatactgctc gggcagcaga agtttggatg gatgaataca 1380
aagagcactt ctacaataga aaccctccag caagaaaaga agcttatggt gatatttctg 1440
aaagaaaatt actacgagag cggttgagat gcaagagctt tgactggtat ttgaaaaacg 1500
tttttcctaa tttacatgtt ccagaggata gaccaggctg gcatggggct attcgcagta 1560
gagggatctc gtctgaatgt ttagattata attctcctga caacaacccc acaggtgcta 1620
acctttcact gtttggatgc catggtcaag gaggcaatca attctttgaa tatacttcaa 1680
acaaagaaat aaggtttaat tctgtgacag agttatgtgc agaggtacct gagcaaaaaa 1740
attatgtggg aatgcaaaat tgtcccaaag atgggttccc tgtaccagca aacattattt 1800
ggcattttaa agaagatgga actatttttc acccacactc aggactgtgt cttagtgctt 1860
atcggacacc ggagggccga cctgatgtac aaatgagaac ttgtgatgct ctagataaaa 1920
atcaaatttg gagttttgag aaatagagca caacagcact ttcgtcatga gctgacagta 1980

-continued

```
gtgtcaagaa agtcaaagag ccttaagagc ctcagtgaag attgtatttt attttatcaa   2040
aagccaccta gcagtcatct gtggagcact ggaaagctgg ggttcatttt ggtatatcac   2100
actgaaactg ggtacccaga gtgctgctgt ttaatatttc acaatgcctt acttattggt   2160
tgttttatat aagagttttg tcaatatggt ctcttcttaa aagaagttga ctatgaattg   2220
aaacacacaa aacatttaag tgccagactt aatattaaag aatgtaaagg tccaagtaaa   2280
atgaggtatg atttatgttg atgtgtaagt tcaccgcaca tcccactttt taacaaaact   2340
catgaatgtg cagtttgagc cattgctatt ttgattacat agaatttgta tttctttttt   2400
agccagcaca ttaaatttta gattttattt tttaatctaa ttttttteta atcaaaaaga   2460
aaattgagct taaggcaaaa ggcctggttt tagagatatg tgtaattgga agagggcatt   2520
tgtttgagtg tgagtttgga ggccttttta acatgcagac atacccatat ttaaatgaaa   2580
tggggagata tttacattcc gtactttgta aacttgagct attggacttc actgatgtat   2640
atattaatac ctcagattcc tctgattttg taagctgtct tctctgtgaa cgtgtttgtg   2700
tgtgtagggc attttctgat tgcacttcct taagttatga atgtactaga aagggactca   2760
tccagaatac tatgcctccc tttgttaatg cttaatcatt taaagtaaac acaattgaag   2820
cctctctgaa gttaaaccca actatgttta ttaaaatgtg tgaaactgaa agtgggctag   2880
gttctaccaa ggctgtggaa ctctcctacg agttctgctg atcaggaaat ttaagaattt   2940
atcttaaaaa tgcaaggaaa aaagactgcc ttggcaattg tgaatggtgc tttcaatctc   3000
ctagcaccga gcctggcact taggcagctt tcagtaagtg ggtgaatgaa tgactgaatg   3060
aatgaatgaa tggctcagct gaggaatgta actttggtca agttattatg atgtgtttgg   3120
gcttagtttt ctcattggta aaatgtgggt gctggattgg atcttaaaga tcccttccag   3180
ctctgaaatg ctgattgtac agtatattct tcccagattg actcactgtg caatctttac   3240
aatacttttt atcttttcac ttttgacata ggtaatgttg ttgagcagtt gagcaatgtt   3300
cagtccagtt gtgaagctgg agaagagaaa tgggttttaa aaattaagtg aggggaggcc   3360
gggtgcggtg gctcacgcat gtaatcccag cactttggga ggccaaggca ggtggatcac   3420
gaggtcagga gatccagacc atcctggcta acatggtgaa acctcgtctc tactaaaaat   3480
acaaaaaatt agccagctgt ggtggcgggc gcctgtagtc ccagctactc aggaggctga   3540
ggcaggagaa tggcgtgaac ctgtgaggca gagcttacag tgagccgaga tcgtgccact   3600
gcactccagc ctgggcgaca gagcaagact ctgtctcaaa aaaaaaaaat aataataaaa   3660
taagtgagct gaactcacct gaagtggttt acttctgtgg gttaagaagt tctagtcagt   3720
gttcatagtc gtttcgtttt gataattgtt gaaccaattt tgtttttaaa acctttagac   3780
tctgaaagta atattttgac taagaatgta aatatttcca aactaaatta ctcgggaagt   3840
aaacgctttt tttaaaagta tttttactgg ttttatacca atattatatg cagaaatcac   3900
aggatgaatt tagaattaaa tctcaattag ttcactttgg cctagattta tgaaaaatgc   3960
atgcctcgta aagagtccac tgtattcacg agtaaagttg cttttagtgt tcacttgatg   4020
acttggagag taggaatttt gcaaaatctg aatttaagga aattctttag gataaccatt   4080
tcaaaaaata aaattgctat gcaatcttga atattttctc ttttgcctcg taaaatgaaa   4140
atgcattcac agtttctgta aattatttag cagccttaaa gtttatcaaa aaattgtcca   4200
gattccacgt gcagcatgct tggccctgca tttaatttaa gaaggattaa taataatgct   4260
ctgaattttt cgaaagggat tctcctaaac ccacccactt ctcttgccca ggctgctttt   4320
taaaaatatt tttttatttt ttacttattt ttaaatttte tctttttatt tatttttggt   4380
```

-continued

```
tttcttgtta gccacctgtt atatgggaga acgaaaattg ttatattttg aaagtactta   4440

ttacattatt tttattttag tatcttgatg ctcctgtcaa aagggaaatg aggcttttaa   4500

aaataaagta ccttaattct ttattgactt tttgccctaa attgctaggt gtgacccagc   4560

aatcttttag gaagagattt tacagtggtg ctttatttat atcaataatc cagtatagtt   4620

aggctgttca ttcctcataa tagagtacat aacagaaaag tgggactttc acattttcat   4680

atttaggcac gttccaattt aattccaaaa atactctgta attctacatc taaaaaaacc   4740

gattccctaa ttcgaattta ttggtaccaa agctctcttt ggctatagac aattaagagt   4800

tgacctttta agttaatgta tatgcttaaa aacagtttta ggaaaatatt tggtagacaa   4860

agagtttcaa ctttaaatgt tcactatgtc atttagtgtc caactttacg gataggttga   4920

ctatctaaat aggcattttt agtcattaaa aaaaatctag tcaccaggag gatccctata   4980

actcaaaata acttgtttgt aaaagaaaat ttgtttactt acccattagt aagttcctgc   5040

atattcatta taagatggca aatcaaactt ttctaggatg aagacagctt atttttaagt   5100

tgtatagtct tagttggttt agggtctcaa ttttaattaa taaaatactt ggtttttatt   5160

tgcttgtcct tttgaattcc tgttttaata attttaaaat gagcacaaag aacgttgaag   5220

ttcagattaa tctcttctga atgatgtttt tttcctctgt gatgagttgt ttctgacttt   5280

tttccttttg tatttgtaat gttgattaag atgtaaaata aaaagtgtgc ctgattattt   5340

ttgcaaaaaa aaaaaaaaaa                                               5360
```

```
<210> SEQ ID NO 12
<211> LENGTH: 4877
<212> TYPE: DNA
<213> ORGANISM: Homo sapiens

<400> SEQUENCE: 12
```

```
atggatggag gtgctttaac tgatacaagt ctcacagatt cctattttag caccagcttt     60

attggagtca atggatttgg aagccctgta gaaacaaaat atcccctgat gcagagaatg    120

actaatagta gcagctcccc aagccttcta aatgacagtg ccaagccata ttcagcccat    180

gatcctctaa catcacctgc ttcatccttg tttaatgact ttggtgccct caacatctct    240

cagagacgaa agacaccaaa tcctactgca agcgagttta ttcctaaagg aggatcaacc    300

tccaggctga gtaacgtgtc ccagtcaaat atgtctgcct tctctcaagt tttctctcac    360

ccatccatgg gaagccctgc tactgctgga ttagcgccag gaatgtcgtt gtctgctggg    420

tcttcccctc ttcattcccc caagattact ccacatactt ctcctgctcc cagaagaaga    480

agtcacactc caaatccagc aagttacatg gtgccttcta gtgcctctac atctgttaat    540

aatcctgttt ctcagactcc gtcttctggt caggtgatcc aaaaggaaac tgttggtggg    600

acgacttact tctatacaga cacaactcca gcacctttga ctggaatggt gtttccaaac    660

tatcatattt atcctccaac tgcacctcac gttgcttata tgcaaccgaa agcaaacgca    720

ccttccttct tcatggctga tgaactccga caggagctga tcaacagaca tttaataaca    780

atggctcaaa ttgatcaagc agatatgcca gcagttccta cagaggttga cagctaccat    840

agcctattcc ctctagaacc actgccacct cccaaccgga tacagaaatc aagtaatttt    900

ggatatatta catcttgcta caaagctgta aacagcaaag atgatctgcc atattgcctt    960

cggaggatac atggttttcg tcttgttaac acaaagtgca tggtgttggt cgacatgtgg   1020

aagaaaattc aacactcaaa tatcgtaact ttgcgtgaag tatttaccac taaagcattt   1080

gctgagccct ctcttgtgtt tgcatatgat ttccatgctg gaggagaaac tatgatgagc   1140
```

-continued

```
agacacttta atgaccctaa tgctgatgcc tacttcacca agagaaagtg gggtcagcac   1200
gagggaccat tgcccaggca gcatgctgga ttattgccag aatctcttat ttgggcatat   1260
attgtccaac taagttctgc attgcgtacc attcatacag caggtttggc atgtcgagtt   1320
atggatccaa caaagattct gataactggc aaaacaaggt tgcgagtaaa ttgtgttgga   1380
gtttttgatg ttttaacatt tgataacagt caaaataata atccattggc attaatggcc   1440
cagtaccagc aagcagatct gatatcatta ggaaaagttg tgttggcttt ggcttgcaac   1500
tctttggcag gaattcagcg agagaattta cagaaagcca tggaactggt gacaatcaac   1560
tattcctctg acctgaagaa tctgattttg tatttgttga ctgaccaaaa caggatgcga   1620
agtgtaaatg acatcatgcc catgattggt gctcgatttt atactcaatt ggatgctgct   1680
caaatgagaa atgatgtcat agaggaagac cttgcaaagg aggttcaaaa tggaagactg   1740
tttaggctcc tagcaaaatt gggaacaatc aatgagaggc cggagtttca gaaggatccc   1800
acttggtcag agactggaga ccgttatctg ttgaaactct ttagggatca tctttttcat   1860
caggtgacag aagcaggtgc tccctggatt gacctcagtc atataatttc ttgtcttaac   1920
aagctagatg ctggtgtgcc agaaaaaata agcctgattt ccagagatga gaagagtgta   1980
cttgtggtga cctacagtga cttaaagcgc tgctttgaaa atacttttca agaactgatt   2040
gcagctgcaa atggtcagtt gtagtatttg ctaaaaaagc acgcaggaca tggctaaaga   2100
ccttaaccaa tagcaaattg cactacagct gaacttttca tcatctcatt cacatttggg   2160
aaacgaacag gagatgagca aagctgcttg cacttcagtc aggtacactg ttacttgaaa   2220
ggaagaatgt ttcacttacc caagagctat ggctgccatt ggaggctgtt atctgtgaag   2280
aatttatttt agatttagga gcaccatcag gtgaatgatg ttcctgcttt tgtttttttcc   2340
acttgtatat gcactaattt taattttta aagacttttt ctgatctttg aacttttgcc   2400
acattgtata cttataatgg gaaactttgc aaggacattt ttgggaagca atgctgggca   2460
gcgtttttgc cattgagggt tgcagaattt gctcttttg ggatgggttg ccctgaataa   2520
cattacggac caggtaaata atttcataga agttcagtat agtacgtaat tcttgtaaga   2580
gtatcgtatg caagctctct gtatgccacc cactgttagt tcaaattgag atttttgttt   2640
tgttttgttc ttaagaacat accaagaaaa taccagtgaa ttgttggata tgaattccct   2700
gttagttgat ttaaatcctt tctgaataaa gatcagataa acagtaactg aaggagcatg   2760
tatagctctt tccttcaaat tcaactagag ccttttttaaa aagacatttg cctgctagtc   2820
agatacattt acatttatgc aaatttttta aataggagaa aattaagaaa ttgtgttaaa   2880
ggcctaaagt tcaggagtgt attactttag gttctttcca gtttgctggt tttttttttt   2940
tttttttttt tttttttgg gcggggggga ggtttatgaa gttttgctct ttgaaccaca   3000
gctttattat ggtcctttac actggagaca gacacagaga cactgttcag aagatgaact   3060
aaactcagca gtggtctggt atcaagagct ttctgatgtt ttacagcctg aatttggagg   3120
gataacgatc tgctgtgcct ttgcagtcac tgcttagccc aaagtaatag tacttttgat   3180
aataactcac tctgtgcgat attcctgaat aagtccatct caaaagtttg ggattttcct   3240
cctcttaact ttcttaatat ttggacatgc agttgtcgcc aaacttgggt attcatggaa   3300
tttctagtaa atgaaatacc tatactttga tactgaagac tgccaaatac ataggaattt   3360
tctttcttaa aaaacagtaa tgaagactat atctcctttc ccagcactga atgttttact   3420
agcactgggt gctcaccatg caactgaaga aaatgtggaa actcaaaagg tcaggacaga   3480
cttccaagca cttgcaactg atgttactgt cttcaatttt aataattaca catatttgta   3540
```

```
tatttcagag aagtttttaa tatttctctg tccacttttt ataagcttta aaatgatttt   3600

ctctgccttg agatttgcat caagaaaaag cacctctctt cacctgaaag ctttgaagac   3660

tagagacacg ctttacacgt tttaacaagt atattgagtc cacgtttggt agcatcagtt   3720

gttgagttaa aaagaaaatt attgcatttg atctggatgg attttaaaag aatataatgt   3780

tcaatattaa aaggataatt cacatttgcc accataatgt tctttttat gtaaaaagaa   3840

gaacttggag acattaacat gaaaaagtct tttatcatta gctcatgtat ttgaggaaga   3900

gcagctgtct ttttatatgt tttttgacaa atcatattgt attcttttgt acaaaaaaga   3960

actacttgta ttctagaaga aatatgaaat gcttaattta taagcgggct ggagattttt   4020

tccaatattg ttttctttga aaatgaaagg ggatcatcta ttttagtttt ggggtctggg   4080

aactttttga aaatttaatt tgtggaccaa tgttttgtga aagctaaaga gggcaggggt   4140

taaaataggg cttgaatttc tcattctgta tagaccagca aacttccctg tgcaaggcaa   4200

gtttacatca caaatccaag aatgtttgca tcctaaatgc tagtttgctt cagcccctag   4260

ttaacctcag gacttggttt gcatataaaa ggtagacagc tgatatgttt tcatgaataa   4320

atattgtcag ccagaaaagg ttggtgtcag gtaatgcata ttttttaag ctttgtttta   4380

tatttatttt tcatttagtt tttattggga atggttttca aagaactctc agttctgcct   4440

aggtgttttt gggggagccc tgttttccat agtgtaattc catttaagag gttgtctaaa   4500

agtcttttta attaatagaa agattttaat atccaagagt agtcaaatta aggatataaa   4560

ctttccacac cttcctgtcg tgacagataa aagcacagaa aggacaaccc ttgaaatcat   4620

gtaacgttgg tcatttcaat attttgtacc tgttttaaat tctgttagtg tatttacttc   4680

attgtaaata tttttgaggg tacctttgta ttttgctttt gaccttggtt ctgtgatttg   4740

gatgtcaaca acttccctaa aaagcaccag tgtgttaggt tctaatgtca tgacccaatt   4800

tgtgttattc atctttaatc ctgttttcag tctctatgtg tacagcagta tttttaataa   4860

agaattacag agataaa                                                  4877
```

<210> SEQ ID NO 13
<211> LENGTH: 6010
<212> TYPE: DNA
<213> ORGANISM: Homo sapiens

<400> SEQUENCE: 13

```
cgcgggggcg cgcgcgcgcg ggcccgggag aggctcccga gccaggcggt cttcggtcct     60

cgcagcgctt ccagctcccc gcgcccctat gtgagggaga cggggaggcc cgcggcgcgc    120

aggggagggc gaggcatgtg cacgggccgg agggtgctgc agccgcccga ggaagaggag    180

gacggcggcg aggaggagag cggggggctc gcggcggcgg gccccggccg aggggatgca    240

gtggactgtg tgtgtctggc tgtagcagac gcgaggcggc gacgaggcgc cggggacccg    300

cgcgaggggc ggccgggagg cggcggcggc ggccgccaga agtagcagca ggaccggcgg    360

cggcgacggc agccctgaaa tgcattttcc tctccagcgg ccatgttaac caggaaacct    420

tcggccgccg ctcccgccgc ctacccgacc gattggcggc agtaagcaca caatgaatga    480

tcacctgcat gtcggcagcc acgctcacgg acagatccag gttcaacagt tgtttgagga    540

taacagtaac aagcggacag tgctcacgac acaaccaaat gggcttacaa cagtgggcaa    600

aacgggcttg ccagtggtgc cagagcggca gctggacagc attcatagac ggcaggggag    660

ctccacctct ctaaagtcca tggaaggcat ggggaaggtg aaagccaccc ccatgacacc    720

tgaacaagca atgaagcaat acatgcaaaa actcacagcc ttcgaacacc atgagatttt    780
```

-continued

```
cagctaccct gaaatatatt tcttgggtct aaatgctaag aagcgccagg gcatgacagg    840
tgggcccaac aatggtggct atgatgatga ccagggatca tatgtgcagg tgccccacga    900
tcacgtggct tacaggtatg aggtcctcaa ggtcattggg aaggggagct ttgggcaggt    960
ggtcaaggcc tacgatcaca aagtccacca gcacgtggcc ctaaagatgg tgcggaatga   1020
gaagcgcttc caccggcaag cagcggagga gatccgaatc ctggaacacc tgcggaagca   1080
ggacaaggat aacacaatga atgtcatcca tatgctggag aatttcacct tccgcaacca   1140
catctgcatg acgtttgagc tgctgagcat gaacctctat gagctcatca agaagaataa   1200
attccagggc ttcagtctgc ctttggttcg caagtttgcc cactcgattc tgcagtgctt   1260
ggatgctttg cacaaaaaca gaataattca ctgtgacctt aagcccgaga acattttgtt   1320
aaagcagcag ggtagaagcg gtattaaagt aattgatttt ggctccagtt gttacgagca   1380
tcagcgtgtc tacacgtaca tccagtcgcg tttttaccgg gctccagaag tgatccttgg   1440
ggccaggtat ggcatgccca ttgatatgtg gagcctgggc tgcattttag cagagctcct   1500
gacgggttac cccctcttgc ctggggaaga tgaaggggac cagctggcct gtatgattga   1560
actgttgggc atgccctcac agaaactgct ggatgcatcc aaacgagcca aaaattttgt   1620
gagctccaag ggttatcccc gttactgcac tgtcacgact ctctcagatg gctctgtggt   1680
cctaaacgga ggccgttccc ggagggggaa actgaggggc ccaccggaga gcagagagtg   1740
ggggaacgcg ctgaaggggt gtgatgatcc ccttttcctt gacttcttaa aacagtgttt   1800
agagtgggat cctgcagtgc gcatgacccc aggccaggct ttgcggcacc cctggctgag   1860
gaggcggttg ccaaagcctc ccaccgggga gaaaacgtca gtgaaaagga taactgagag   1920
caccggtgct atcacatcta tatccaagtt acctccacct tctagctcag cttccaaact   1980
gaggactaat ttggcgcaga tgacagatgc caatgggaat attcagcaga ggacagtgtt   2040
gccaaaactt gttagctgag ctcacgtccc ctgatgctgg taacctgaaa gatacgacat   2100
tgctgagcct tactgggttg aaaaggagta gctcagacct gtttttattt gctcaataac   2160
tctactcatt tgtatctttt cagcacttaa ttttaatgta agaaagttgt tcattttgtt   2220
tttataaaat acatgaggac aatgctttaa gtttttatac tttcagaaac tttttgtgtt   2280
ctaaaagtac aatgagcctt actgtattta gtgtggcaga ataataacat cagtggcagg   2340
ccactgatta cttcatgact gccacgcatt tacagattgg tgtcaaagac attcactatg   2400
tttttatggt tcatgttata tcctccccag ggtgacagcc ccttaaggcc ctccttttcc   2460
ctccatgctc caggtccatg cacaggtgta gcatgtcctg cttccgtttt tcataaatta   2520
atctgggtgt tgggggtagt gggaggagaa cggtcagaat caaagtgaca ttctaagaaa   2580
aactgtacct tagagatttt cctctagtgc tcaaacaaat acaaaataag atccccaagg   2640
tttaaactgc ccagttagca ttctgacatt ctaaaagccg gcaaagcagc ttttagtgga   2700
taaatgggaa tggaaacgtg tgtgttcctc caaatttttct agtatgatcg gtgagctgtt   2760
ttgtaaagaa gcctcatatt acagagttgc ttttgcacct aaatttagaa ttgtattcca   2820
tgaactgttc ctccctttttc tctgcttttc tcctctctgt tcctctttta ataccacacg   2880
tctgttgctt gcatttagtt tgtcttcttc cttcagctgt gtatcccaga ctgttaatac   2940
agaaaagaga catttcagct gtgattatga ccattgtttc atattccaat taaaaaaaga   3000
acagcagcct agctacttaa ggtggggatt tccatagttc caaagaagat ttagcagatt   3060
agagtgagtt cacacttttc aggtgccact gtaaggttct ctcagcctgg gaaactatca   3120
actctttctt taaaaagaaa gagggttgaa aatcctctgg acgaacagaa gtcactttgg   3180
```

-continued

```
ctgttcagta aggccaatgt taacaacacg tttagaggag gaaaagttca acctcaagtt   3240
aaatggtttg acttattctt cgtatcatta gaagaacccc agagatagca ttcctctatt   3300
ttattttact ttcttttgga ttgcactgat tgtttttgtg ggaatgacac tttatctggc   3360
aaagtaactg agagtttggt aaaagaatat tttcttctct gaataataat tattttcaca   3420
gtgaaaattt cagtatttta tcactaatgt atgagcaatg atctatatca atttcaaggc   3480
acgtgaaaaa aatttttag tatgtgcaat ttaatataga aagatttctg cctgtttgga   3540
caataggttt tgggtagtac agattaggat aagtaagctt atatatgcac agagattatt   3600
gtattacctg taaattgatt tacaagtact taaaagcgtg gtccccagtg aggccaagaa   3660
agtttccggt taagttcttt aataataatc ctacagttta tcttaagaaa aaaaaaaagg   3720
tttgaaaaaa acactttaat ttaggcttcg ttggttgatg gtggaaaaaa atgctcagga   3780
aatatttcag atatttgcca aaaaaccagt aataaggtta ccttattaaa atagtgatat   3840
ttgctttact atttaaggtg tcactgataa attaatttgt acttctgtgt ttagaaatta   3900
tagcttcttt tcccttagtc aaatttttta gcatattata cacatttctg tgtaatctgt   3960
ggaagtgcaa taatatgtta gtaagttaca ttttaaataa tgctcatgtg acaatactcc   4020
caatcaatgg cttatagaat ttaaagatct gtatattaga ttttggctta aaggcatgag   4080
aagtataaga cttggtttgg tggctttgta agaccaccag cctcttaatg atggttagct   4140
tctttaggtc attaaatcaa taaaaacata taatgctgtt ttgctcttct aatgctcctc   4200
ttccatttcc agttatcttc acatttacat ttaaatatac aaacctgagc ctgccattat   4260
taatttccct ataaaatgac gatacatgtg aacatttata aatggactaa tactgcttgt   4320
ctttccccca ccgcacaaaa ctggttctta agatgccagc aatgaatttg agactatctt   4380
tatttataaa tggaaaccgg aaacttttat accaaactat aataatgtgc agcactgtag   4440
ggcttttttt tttttccctc caaatacagt gaaatttttt tattcacaag agctgccaca   4500
tctcagcatt tagtaataga gctgctttaa taaaattcta gtttgattgt catgtcaaaa   4560
aaagaaaaat gttgcatctt tgtgatttta aaacataaat taatgaaggc tctgataggc   4620
tattaggagt tggcttggaa acagtttttg gtctcacagg ttaccattgt ttggggatgt   4680
ctgagctgtt ttcagatcta ggaatagcac agtgttgtct tgtctttggc agtctcattt   4740
ggctctgttt cttgcaccac cagcgtgttc attaccactt aaatatattg ctacagcagt   4800
ggaacaacag agtggtgcaa gacactgtag attaacggta gaggagaaat tgtgccctta   4860
gtgttaacaa tgtgcctttt gttctgaatg ccatgttgta gggcatgcat tttttggcct   4920
ctttaactct tcgaattcta gtcagtaaga atggaaccca tctctgcaaa gatacatctg   4980
tcttaaatat ctagttacag gccttaatag aaaccataag gcatgactca tcttcaggca   5040
ctgaaaaaag ataaccatca ggtagtgtta cacaaggact tcctatattt aaggggttaa   5100
agatggtctt tgttgtatct taacatcaga ctgattttta catttttttt ttgttatgct   5160
aacactagac aaaaatcaac tgtatttgta aaaatttacc tcaaaccatt taattttata   5220
gtgtgattaa tcccagggca tttggtatga accaaagtgc attcctttta tatgtgcctg   5280
gctctagtaa ggatggccag ggatttttac aatttgggtg caaggcactt aagccacttt   5340
taaacttaat gggtggtttg gggtcgtgtt aaatgactcc atcagaatgt tagaaaacac   5400
tttaggcatc agtagcattg ggccatattg gaatcctaaa gtgtgaatta ttttaaggag   5460
agcattcatt tttgtaattt ttttcatcaa aaatatttct ggtaagcaga agacttttta   5520
aaaaaactga tctggtctcg gtaaaggttt taatattgcc caacataatg ctgtaatagc   5580
```

-continued

```
attaaaaaaa gtatttgtga actctgtttc ttaggggctt gtacatctct ctgctatgga   5640

catacataaa attaattgta attatactca gctcaactgc tacagttctg tctaggcagt   5700

ggcttgggtt tttatcgagc aacaacttag acacgtgact gtaatatgct gcaactgtgt   5760

gtactgaaaa tatgtgaaaa tggttgaatg tggactgtgt atatatgtat gtaaaaattt   5820

ctgtgagatg ctgctgtcgc cacttaacat taaatatgtt ctagtggatt ttaatcctag   5880

tggccagttc tatgatactg tatgtattat acagctgatg acaggagtaa gactgtttag   5940

tgaatatctg ttaaatttta ttgttgtggc cagagataat ttcagaataa aattttaatg   6000

tcctacctta                                                          6010
```

<210> SEQ ID NO 14
<211> LENGTH: 5755
<212> TYPE: DNA
<213> ORGANISM: Homo sapiens

<400> SEQUENCE: 14

```
ggcgctcagc gcaggcaggt cccccctgctg ccgggtccca tttgttgccg gctctgactc     60

ggggcggccg cggcgcgcgg agctccgggg agtcaggcgg agcagccgcg cagccacgac    120

ggagcagcag cgggactggc cgccccgcgc cccccttcgcc gccgtgccct tccccggcgc    180

gctcaccccg ttctcgggat gggattgtag cggcggcgcg gactcggcgg ggatcgcggc    240

ggaggcggcg gcgtcggcgg cggcgtcggc ggccgagcgg ggctccatgt tttcccctgg    300

ccaggaggaa cactgcgccc ccaataagga gccagtgaaa tacggggagc tggtggtgct    360

cgggtacaat ggtgctttac ccaatggaga tagaggacgg aggaaaagta gatttgccct    420

ctacaagcgg cccaaggcaa atggtgtcaa acccagcacc gtccatgtga tatccacgcc    480

ccaggcatcc aaggctatca gctgcaaagg tcaacacagt atatcctaca ctttgtcaag    540

gaatcagact gtggtggtgg agtacacaca tgataaggat acggatatgt ttcaggtggg    600

cagatcaaca gaaagcccta tcgacttcgt tgtcacagac acgatttctg gcagccagaa    660

cacggacgaa gcccagatca cacagagcac catatccagg ttcgcctgca ggatcgtgtg    720

cgacaggaat gaaccttaca cagcacggat attcgccgcc ggatttgact cttccaaaaa    780

catatttctt ggagaaaagg cagcaaagtg gaaaaacccc gacggccaca tggatgggct    840

cactactaat ggcgtcctgg tgatgcatcc acgagggggc ttcaccgagg agtcccagcc    900

cggggtctgg cgcgagatct ctgtctgtgg agatgtgtac accttgcgag aaaccaggtc    960

ggcccagcaa cgaggaaagc tggtggaaag tgagaccaac gtcctgcagg acggctccct   1020

cattgacctg tgtggggcca ctctcctctg gagaacagca gatgggcttt ttcatactcc   1080

aactcagaag cacatagaag ccctccggca ggagattaac gccgcccggc ctcagtgtcc   1140

tgtggggctc aacaccctgg ccttccccag catcaacagg aaagaggtgg tggaggagaa   1200

gcagccctgg gcatatctca gttgtggcca cgtgcacggg taccacaact ggggccatcg   1260

gagtgacacg gaggccaacg agagggagtg tcccatgtgc aggactgtgg gccccctatgt   1320

gcctctctgg cttggctgtg aggcaggatt ttatgtagac gcaggaccgc caactcatgc   1380

tttcactccc tgtggacacg tgtgctcgga gaagtctgca aaatactggt ctcagatccc   1440

gttgcctcat ggaactcatg catttcacgc tgcttgccct ttctgtgcta cacagctggt   1500

tggggagcaa aactgcatca aattaatttt ccaaggtcca attgactgac gcccttgaca   1560

gccatctacg actttattaa caggttactg tgaagatttt gccactaact ctagatttta   1620

cctttttgta atgctgttta tcagaggagg gtgacagggg ctggaaataa agagagggga   1680
```

-continued

```
catggtgatg aaacatggca ggagtgtaac agataccagt ggtgtgttgc atgctcaaaa   1740
cagcagcgtc gtcattgaag tctgcttgat taaaccataa tatctttgta ataattggat   1800
ttaaaatgct atgcttctat ttttaacctt gggtttttaa ccaagttttt tttttttgt    1860
aatcttggac aagactttaa atcatatttt acagatgtag aagaaattta ttcaaaagtg   1920
tgggctcatg aagttcactt cagtgcagtg tggtgtaggt gttacgcgaa gggcgcacag   1980
tgtctagaaa tacttgatcg tggctcaaac ctgaccagac agcagagggg cggctctgta   2040
cagtgtgact ggtggacaga tggccttagg cacaggtggt tttgaaatct ggggcttttt   2100
ctgatttatt tttctgactt gttgggggag agaatattca taacttgtgg gctttttttt   2160
tttttaactt cagtggaatt tactttagat attcattcat caaatacatg ggacttcaca   2220
aacaatttc cataactttt tagcctgtct tttgttattt ctgcctaata tgatttgccc    2280
cgatactcat cttgcacggc cagaactgtt tggttgatta aaatacatca gctcttaaaa   2340
actcattaac tgagggtaat tacagtagta gacatggtct gggtactata ctaccatgtt   2400
tatttgctga ctgaattaag atttaagaat gattaaaaat aagcttttac tttttaaaac   2460
cacttgaggt ttcataaagc ttggggtttt tttttttcct ttgttaagaa agccaaccaa   2520
tcacaatgat atagtcattg ttgtgcactc ccttttcacc atctgtcacc ttcccttgca   2580
gcttaaggag cccagtaagt tttgaaaatg tttgcgaatc aaactaaatt taagtgggat   2640
gattagatat acacaacacc aagtggtaca tctgcagaga taattcaaaa ttcctgcttt   2700
tgagagagca aatgagtgtt gctgaggaat aattaaatga gaatttcata ggagctccac   2760
cattcctgtt actttcattt cattttgatt aataattctt ggatgcttgg catcgatcgt   2820
atcactgctc ctagaaggta aagatccttt aggacatgag actggtagaa gctggctgag   2880
ataaaataag tatttattta aactaatgtt ctcttaattt gaccattgca gatttgggtg   2940
actttttttt aacctttgta catatacgta atttatatga ttctaatgta ctatatccat   3000
acttgaattg gttttttcgt attttgccta ctggcaaata ttttgcctat tttcagtcgt   3060
tctaacctat ttgaatacgc ttttccttaa agtgatacga taatattact cttgattgct   3120
gctgcttaat ttgatgtaat atgtttaaag ttcagcctct cagttttaat atagctttat   3180
ttttcagtgg agatcattgt ttaggatgag acatttttgg ttttggtttt gtttgggtaa   3240
attttaaatg gtgtgaaaat cgatgacaac agtcctctta cagatagctt gctgtattct   3300
gtatagctta ctctacctgc agacagaaaa tgaaagaaaa aaatggactt gcctagaata   3360
atatattgaa tgccttttga tttagccaga gtctctgatg attagctttc actgatagag   3420
tatgtctttt cagcctgtaa ttctttgggc cccaaagaat gacaaaggag gcactcgttc   3480
tcttttcttg ctgtatgcct agaaagtggt tgaaggattc ttgatgccct aaaaccatct   3540
tgtaagctaa atggtcttgc atccagaaag gccagatttt acctaccaag aaaaaaagat   3600
atttttccag agagttaggt atatcataat tttccatttc aagtcctgtt tataagtcta   3660
gtcattctgc aacgtgacat atcccccaaa atgaagttac cttccaagtt ggacacgtcc   3720
cgtagttggg catatgtcta actaaaagtt tctgactttt agtaaattca gcttaaatat   3780
aagttgaaat ttgggaaata atttccaagc tcttggaagg ggtaacagtg aaccgccctc   3840
catgggctcc acatcttttc ctttggcttc caaagtcagg tcccgcccac cctgcctaag   3900
gaactgcaga gaggtggcaa atcagcaaaa aggacaccag gctcttcttg gccacttgta   3960
ggaagatccc tttacaattt tgactaagga gatttttttt ttcacagttg agttagtttg   4020
tgaaaataaa gaactctgta gctcaccaag gtggagaaac gcaattcaga aaagtaattt   4080
```

ctccaaggtc acttcttttt ttatgtcttg ccatcacttt aaaggactag ccccactccc 4140
ccatgtgtat acacaaggaa attgcagacc aattagttgt cttggcctga ctctaatgcc 4200
ttttgcaagt agctttccag aagtaaaagt cccagtgatg tattcccata gaaatatttt 4260
tcagttgttt atgtcgttta ctacaaaaaa aaagattcag agtggatgga gtacaactct 4320
gagtattttt ctagtccgga attttttatt aataatcggt gctgccgggt catgcatgct 4380
gcaactctca acatttccct tatttggttc agcttttagc aaaaagggct acagttcacc 4440
ctgcagagta ttaaggtttc tggatttttt tctcccaact gtggcccaaa agaattaaaa 4500
tctgttaata taaatagaga acatatttat cattcctcga tagttaatta tagactttgg 4560
tacctttgtg cctcagggaa gccacgtgat ataactggtt atagaatttc agggttaggg 4620
tttaaagaaa ggagaaagcc attggaaaaa tgatgggctc cattaaggag actaatgaat 4680
ctggatgcag aaatatgtca gaaactggca taaacatgat tgtagtagaa tttattttcc 4740
agtaccaata gggaaattat tttaagttat tacatttact gtattgggaa acttgaggag 4800
aactctttag ttcataaagc ttcaatgtct tttttttttt tttcatggaa aaactcaaac 4860
ctctgttatt tgggagctca gtattgtgtg gacacttacg agagttttct gcttaattga 4920
agtgtaatat aggttgtaga attgttacct gcagttctat ggttttgttt cacttctttt 4980 ctttttttaaa gccattctgt tctttggatg tgcttgaaag ggtgtgtgat tacaccattg 5040
ttaatgctgg gtaaaaacta tcttcttgca gccttgcctc ataacagtgg aatttctgat 5100
agacaaacca caggactttg attttaagcc aaatccatct ccatcccttt actgtcaatc 5160
ttctgtccca gtagtttagc ctttgtggct taggttatga tgcgcctcct tctgtgcgac 5220
caatgagacg acttcagcat ctttttaaaa taatctaagc atcattgaag cagtaacaca 5280
aaaaaaaggt tcagtatttt ctttttagta taacttacat cctttcaaat aagtctttgc 5340
cctcatgaag aatccctaga ggaagataag gaaaataagt attttccagt tttgcttgac 5400
agtttctaaa caaacaaaaa taaactcaat gaaaggaaag atgtttcttt ttagctgaga 5460
tgacagattg cttctctgta ttaaatagtc tagaagttaa ggggatggtc acatttacca 5520
tgtattgtgt tattagcagt taaattttat gaatatgttt gtaaaattgt tgttttatat 5580
ttcatgtcaa attgaaaagt ttatttcttc actattgtac ctgtggaaat acaagccatt 5640
ttacaggaaa aaatcttcaa aaactattaa atggatatca gcctgtttgt gagccaaaaa 5700
aaaaaaaaaa aaaaaaaaaa aaaaaaaaaa aaaaaaaaaa aaaaaaaaaa aaaaa 5755

<210> SEQ ID NO 15
<211> LENGTH: 6453
<212> TYPE: DNA
<213> ORGANISM: Homo sapiens

<400> SEQUENCE: 15
tacaaccagg ctcaactgtt gcatggtagc agatttgcaa acatgagtgc tgaggggtac 60
cagtacagag cgctgtatga ttataaaaag gaaagagaag aagatattga cttgcacttg 120
ggtgacatat tgactgtgaa taaagggtcc ttagtagctc ttggattcag tgatggacag 180
gaagccaggc ctgaagaaat tggctggtta aatggctata atgaaaccac aggggaaagg 240
ggggactttc cgggaactta cgtagaatat attggaagga aaaaaatctc gcctcccaca 300
ccaaagcccc ggccacctcg gcctcttcct gttgcaccag gttcttcgaa aactgaagca 360
gatgttgaac aacaagcttt gactctcccg gatcttgcag agcagtttgc ccctcctgac 420
attgccccgc ctcttcttat caagctcgtg gaagccattg aaaagaaagg tctggaatgt 480

-continued

```
tcaactctat acagaacaca gagctccagc aacctggcag aattacgaca gcttcttgat    540
tgtgatacac cctccgtgga cttggaaatg atcgatgtgc acgttttggc tgacgctttc    600
aaacgctatc tcctggactt accaaatcct gtcattccag cagccgttta cagtgaaatg    660
atttctttag ctccagaagt acaaagctcc gaagaatata ttcagctatt gaagaagctt    720
attaggtcgc ctagcatacc tcatcagtat tggcttacgc ttcagtattt gttaaaacat    780
ttcttcaagc tctctcaaac ctccagcaaa aatctgttga atgcaagagt actctctgaa    840
attttcagcc ctatgctttt cagattctca gcagccagct ctgataatac tgaaaacctc    900
ataaaagtta tagaaatttt aatctcaact gaatggaatg aacgacagcc tgcaccagca    960
ctgcctccta aaccaccaaa acctactact gtagccaaca acggtatgaa taacaatatg   1020
tccttacaag atgctgaatg gtactgggga gatatctcga gggaagaagt gaatgaaaaa   1080
cttcgagata cagcagacgg gacctttttg gtacgagatg cgtctactaa aatgcatggt   1140
gattatactc ttacactaag gaaaggggga aataacaaat taatcaaaat atttcatcga   1200
gatgggaaat atggcttctc tgacccatta accttcagtt ctgtggttga attaataaac   1260
cactaccgga atgaatctct agctcagtat aatcccaaat tggatgtgaa attactttat   1320
ccagtatcca aataccaaca ggatcaagtt gtcaaagaag ataatattga agctgtaggg   1380
aaaaaattac atgaatataa cactcagttt caagaaaaaa gtcgagaata tgatagatta   1440
tatgaagaat atacccgcac atcccaggaa atccaaatga aaaggacagc tattgaagca   1500
tttaatgaaa ccataaaaat atttgaagaa cagtgccaga cccaagagcg gtacagcaaa   1560
gaatacatag aaaagtttaa acgtgaaggc aatgagaaag aaatacaaag gattatgcat   1620
aattatgata agttgaagtc tcgaatcagt gaaattattg acagtagaag aagattggaa   1680
gaagacttga agaagcaggc agctgagtat cgagaaattg acaaacgtat gaacagcatt   1740
aaaccagacc ttatccagct gagaaagacg agagaccaat acttgatgtg gttgactcaa   1800
aaaggtgttc ggcaaaagaa gttgaacgag tggttgggca atgaaaacac tgaagaccaa   1860
tattcactgg tggaagatga tgaagatttg ccccatcatg atgagaagac atggaatgtt   1920
ggaagcagca accgaaacaa agctgaaaac ctgttgcgag ggaagcgaga tggcactttt   1980
cttgtccggg agagcagtaa acagggctgc tatgcctgct ctgtagtggt ggacggcgaa   2040
gtaaagcatt gtgtcataaa caaaacagca actggctatg gctttgccga gccctataac   2100
ttgtacagct ctctgaaaga actggtgcta cattaccaac acacctccct tgtgcagcac   2160
aacgactccc tcaatgtcac actagcctac ccagtatatg cacagcagag gcgatgaagc   2220
gcttactctt tgatccttct cctgaagttc agccaccctg aggcctctgg aaagcaaagg   2280
gctcctctcc agtctgatct gtgaattgag ctgcagaaac gaagccatct ttctttggat   2340
gggactagag ctttctttca caaaaaagaa gtaggggaag acatgcagcc taaggctgta   2400
tgatgaccac acgttcctaa gctggagtgc ttatcccttc tttttctttt tttctttggt   2460
ttaatttaaa gccacaacca catacaacac aaagagaaaa agaaatgcaa aaatctctgc   2520
gtgcagggac aaagaggcct ttaaccatgg tgcttgttaa tgctttctga agctttacca   2580
gctgaaagtt gggactctgg agagcggagg agagagaggc agaagaaccc tggcctgaga   2640
aggtttggtc cagcctggtt tagcctggat gttgctgtgc acggtggacc cagacacatc   2700
gcactgtgga ttatttcatt ttgtaacaaa tgaacgatat gtagcagaaa ggcacgtcca   2760
ctcacaaggg acgctttggg agaatgtcag ttcatgtatg ttcagaagaa attctgtcat   2820
agaaagtgcc agaaagtgtt taacttgtca aaaaacaaaa acccagcaac agaaaaatgg   2880
```

-continued

```
agtttggaaa acaggactta aaatgacatt cagtatataa aatatgtaca taatattgga   2940
tgactaacta tcaaatagat ggatttgtat caataccaaa tagcttctgt tttgttttgc   3000
tgaaggctaa attcacagcg ctatgcaatt cttaattttc attaagttgt tatttcagtt   3060
ttaaatgtac cttcagaata agcttcccca ccccagtttt tgttgcttga aaatattgtt   3120
gtcccggatt tttgttaata ttcatttttg ttatcctttt ttaaaagtaa atgtacagga   3180
tgccagtaaa aaaaaaaaat ggcttcagaa ttaaaactat gaaatatttt acagtttttc   3240
ttgtacagag tacttggctg ttagcccaag gttaaaaagt tcataacaga tttttttttgg   3300
actgttttgt tgggcagtgc ctgataagct tcaaagctgc tttattcaat aaaaaaaaga   3360
aatgaaaaag atatatgaat atgacaaagt attgctgagt ccaacaatgt tgttttaaga   3420
ctcttaaaat acggtacctg gcaatgttta tttcataaag aattgtgaac ttcttgaatc   3480
tagggagggg gaatgtagtg aagggatgta tcaagtgggg tggtgggagg gggaggcaag   3540
gttatatgca ctttctcatg atttacagag aagtgaataa ctgcaaagtg aagttgcttc   3600
ttctacttca gtcttctctc actttgattt gctagttgtt atcaattaat gacaattaca   3660
aacctactgt atctctaata cagtgtgact ggtcaggtat ttcagttctt aggaaggaag   3720
tgccaagttt gtttttgggt tcctggaaca gcgctcacct ttgtttagaa cactggttta   3780
aagggataat catctctgtc acattagact atccatcatg accagcaaat actcatttta   3840
ggaaaaaaaa aagcatgatc tgaaaaatac ttttggtggt atgttggtta ccctcctagc   3900
tttccatttg gtttagaaca taaagcaaat agacacagtc atactgtcac tgctctggac   3960
tgtgtggagc tcgctaaagt catggtcatt gcaggaatcc aagtggcagt ccttctcatt   4020
cattctaatc attgtatgtg cttcactacg ggggggagaa ggaaacgtta gcatcatgtt   4080
tcccatttag ggcaggagtg agaggtctct cttcctgatt tagatatgca aaagctggta   4140
tgttcagtag gaactgtaca tgtgttggga ggcataaaga ctaattagca accataaatat   4200
ggtcactacc ctaatagact aaatgaaatc ttgcaatttc aaattactct ttctccatat   4260
tagatttacc cacagctata tttctgttta agtactaggg tgagggtttt ctgttacttt   4320
gtttttttaat gttgttcctt ttgaaagaat cagtcttgca gctgagtgaa aaatctgtgg   4380
aatgtattat ttgtcctctt tacatgaaac tactcatact taagcaaaag tcagtcttat   4440
agcaagactg ttagccctca aacttgactc tactgatctg accatttccc tctcatcgcc   4500
agacaactga cgatttccct ggttttagtc tgcgtctctg ctttaaagtt attgtgatat   4560
ccttctagat catacacaag tctaacagtt aattagttaa cagtttttaa actaggtttg   4620
tgggtatttt tttggtagca catgtatgct attacataca aatttttatt tctaaaatat   4680
aagatctgag attgaatatt ttcattaaaa gctacagttt tgtgaatctt tgtgcttcaa   4740
cattctttgc aagatgatac ggtatttagg catttgcctt atttttgcat ctcacaaaca   4800
taagtgcaat agatcttttc attgaacagc aaagtaggat tcatcattcc atatgacttg   4860
agttacacca gacctgttct gcccaatgcc tttttgatta cagtgtagct tgcccaccgc   4920
atttgtcgtt ttagatactt tgctagccgg ccactttgga tttcatcaga cagtcctaac   4980
aatattgtct gaacggctga atatgaatag atacagcaga ggcactcctg atatatgatt   5040
tttatccatg cgtcagtttt tcccacccag tgtagcatcc taaagataaa gccagaagct   5100
aagctgcagt gaggctgtga ttgggcgtag aagtgggagc attgggacct cacattacac   5160
acacgagaga tcataaccat gtgaaaaggc aaaaagcatg tgtttgcaac atctgataac   5220
ttcatggcct ttgataaatg tatatatgta tatgtgcatg gactgtgttt ccagtacacc   5280
```

-continued tttcagccaa aacagatcca cagtagttgt tgagttcaag tacataaagt acataacaag 5340
cgaacgtcta gtacaattct tacttatgtg tatgggattt ttccctttga ggttgctttg 5400
ttttgtctta caaaggtgaa aattgtttgt aagtgaagtg agaagttcat atttctttgg 5460 ctttttgtg tttttaaaag ttactccttt tagggagctg gtctgatgac ttgcttagct 5520
tggaaatcct tgttttcagt gtgtcgagtc aaaatgtgtt tatgtgagct gtcactgtgg 5580
ggaaccaatt gctttgtcat atagctggtt atgaactagt aacatgtttg ggaagtccta 5640
ctgatgttcc tttggaagaa aaaatctgct ggttttaaca actgtgcttt tgctatgtat 5700
ggtatccaag ttagttgaaa cgcagacact gagatctgtt tgagtttagg gtcattttta 5760
gaaaggggca gtttaaagca caatgtctca catgggacaa agttccaaaa tgccaaattc 5820 ttattttta aaaagctagt tctataaaat actggtatta tgggtgggga ggaaatagaa 5880
ttgagtcaat tggaaagact atccaactta acatgaaact tgtcaccatg agatagcatt 5940
agctgcccag gatgctgcta tatatatata tatatatata tatgtgtgtg tgtgtgtgtg 6000
tgtgtgtgta tatatatata tatatatata tatatatata tatatatatg tgtgtgtata 6060
tatatatata tgtgtatata tatatgtata tacatatatg tatatatatg cacatatata 6120
tatgtattta aaaaaatcaa aacaaaaaaa aactcattta tacctgtgta ttttttaaag 6180
ctacaatctg ttcaatgttt ttaaaaatct gtttatatga cattgttaaa ataaagttgg 6240
tcttttgacg agagggagga tgtcacggtc agttgtaact ttgccttcac aaggcaactg 6300
gggtgggggg tgggggtagt gtgcctcctt gacatttcgt tcaagttata gattcaatgg 6360
agctatgtct tgttttaagt tgctttaatg cattgtatta gatcttcaaa cagaataaag 6420
gttgttttga aactgaaaaa aaaaaaaaaa aaa 6453

<210> SEQ ID NO 16
<211> LENGTH: 8519
<212> TYPE: DNA
<213> ORGANISM: Homo sapiens

<400> SEQUENCE: 16
cggcggcgga gccaggaccc agacatctgg gactgttgtt ctctcgcggc gcgaccgcct 60
cagtcacttc gcccagagac ccggacctgg tccgctgggg agcaggcggc cataaacccc 120
ctctctcccg gttccctgac gccgcggcag gagctgttac aaacaccctg cggttggtct 180
ccgatgccct tcagtgaggt ggggacgcct ggaccctggt gagcgaaccc caagccaccc 240
cccaccccaa ctcagtgtct tcgccggccc ccggcccgta cgcctgtctg gtcgccatgg 300
ctgaaaacac agagggggat ctgaactcca acctgctcca cgccccctac cacaccgggg 360
accctcagct ggacacggcc atcgggcagt ggctccgctg ggataagaat cccaaaacaa 420
aagagcagat tgaaaacctg ttacggaatg ggatgaacaa ggagctgcga gatcgtcttt 480
gttgccgaat gacttttggg actgcaggac ttcgttctgc catgggggca gggttttgct 540
atattaatga ccttacagta atacagtcaa cacaggggat gtacaaatac cttgagagat 600
gtttctcaga cttcaagcag agaggctttg tggttgggta tgacactcgg ggtcaagtaa 660
ctagcagctg cagcagccag aggcttgcta aactcactgc tgcagtcttg ctggccaaag 720
atgttcctgt gtaccttttt tcaagatatg ttcctacacc ttttgtacca tatgcagttc 780
agaagctcaa agcagttgca ggtgtgatga ttactgcctc tcacaaccgc aaggaagaca 840
atggatacaa ggtttactgg gaaactggtg ctcagatcac atctcctcat gataaagaaa 900
ttctaaaatg tatagaagaa tgtgtggaac cctggaatgg ttcctggaat gataatttag 960

-continued

```
tggataccag cccgctgaag agagaccctc tgcaggacat ttgcaggaga tacatggaag   1020
atctgaaaaa gatctgtttt tacagggagt taaactcgaa gaccaccttg aaatttgtgc   1080
acacatcttt tcatggggtc ggacatgact atgtgcagtt ggcttttaaa gtgtttggtt   1140
ttaagcctcc aattccagta ccagaacaaa aagatcctga tccagacttt tctaccgtta   1200
aatgtccaaa tcctgaagaa ggagaatctg tgctggaact ttccttgaga ctggcagaga   1260
aagaaaatgc ccgggtagtg ctagccacag atcctgatgc agacagactg gcagcagcag   1320
aacttcagga gaatggttgt tggaaagttt tcacagggaa tgagttggca gctttgtttg   1380
gatggtggat gtttgattgc tggaagaaaa ataaatcaag aaatgctgat gtgaagaacg   1440
tttatatgtt agccaccaca gtctcttcta aaattctgaa ggcaattgca cttaaagaag   1500
gatttcattt tgaagaaaca ttaccaggtt ttaaatggat tggaagtagg ataatagacc   1560
tcctggaaaa tgggaaagaa gtcctttttg catttgaaga gtctattggt tttctctgtg   1620
gaacttcagt tttggataaa gatggggtga gtgcagctgt tgtggttgct gagatggcat   1680
cttacctgga aaccatgaat ataacattga aacagcaact ggttaaggtt tatgaaaaat   1740
atggttatca tatttcaaaa acttcctatt tcttgtgtta tgaaccacct accatcaaaa   1800
gtatatttga aaggcttcgt aattttgatt ctccaaaaga atatccaaaa ttttgtggaa   1860
catttgctat attgcatgta cgggacgtta ccactggata tgacagtagc cagcctaata   1920
agaaatcagt gctgcctgtg agtaaaaaca gccaaatgat tacatttact tttcaaaatg   1980
gctgtgttgc taccccttcgg acaagtggaa cagaaccaaa gataaagtat tatgcagaga   2040
tgtgtgcgtc acctgaccag agtgacactg ctttactgga ggaagaactg aagaaactca   2100
ttgatgctct gatagagaat ttcttcagc ctagtaagaa tggactgatc tggcgttctg   2160
tttaggggta caccaatatg tcatgacact gtgtgggcat atggaacaga gcaaccgaga   2220
actgcataca ttgaaccttg tgttagcatt ctctctctat ctcatctggc cgagtatctt   2280
tttcctttta ttttctttct ttttggtcaa ctggctagac taaacaaagt ataagtttga   2340
aatgaaatgg tctagaggga aatgattcaa attttttcat aattcaaaca aaagttatta   2400
cactaaaagt attatagtaa cgtattgtcc ttccgttaac agaaacatca caattcaaaa   2460
gtgagttttc ttattatagt gtgattaagc ctagttctgt atctcgtaat tgtgtatagc   2520
atggtaaaag aaaaaaaaaa agacaggtaa atgttatata attgtagggt tagttaagga   2580
aattagtcca taaaattggc aagaaaatgg tactttcctt gattgttatg aaaaagtgtc   2640
attgtgacat cacaggtatt aatttacaaa ttagagtatt tgaaatagga tatttagcat   2700
ttctgtagtt tagaacagat gttacagtgt gtggttttgg catgtctgtt tcaggtgccc   2760
ttggtgcagt ataaatttac tgtatgtatt taaaattctg atgtttactg aacataaaac   2820
aatagtggca acactcctat tggctttgtt cttatcaaat ttctcagtgc cttctcaggg   2880
tctggtatga acagaaaaaa cagtgttcct gcatttacca taatttaatc agtcaatttg   2940
cagatagcta aggaaaatct tccaaaatct gtaggtgctt cctctatatc aagtgagttt   3000
gctgatttta aaatcttagg aatataaata aagatcttaa taaaagcaag cttaatgtag   3060
ttaaggatct tcatattaga attgtgtcat ttatcaaacc ttttattaca gaaaaaaatc   3120
tgaactgaga aaggagctct gaatttattt gacagtctaa cttttgaatt acatttttgt   3180
aagtagattt attcttttat tttatgaagt aatgttaatt ttactaagaa taaaacatcc   3240
aaattttaag tattatgaaa tactaaaact acatgtttta aaacagaggt ccagtttatt   3300
ctaacatctt gctgacttct gtagaatttc tgattgcatg actattattt atcttctttt   3360
```

-continued agtgtagaaa ataatttttt acaaaaagtc acttttgggc tgggcgcagt ggctcacgcc 3420
tgtaatccca gcactttggg aggctgaggc aggtggatca caatgtcagg agtttgagac 3480
tagcctggcc aatatggtga aaccctgtct ctactaaaaa tacaaaaatt agccgggtgt 3540
ggtggtgggc acctgtagtc ccagctactc gggaggctga ggcaggagaa ttgcttgaac 3600
ctaggaggct gagattgcag tgagccgaaa tcacgccact acactccagc ctgggcaaca 3660
gagggagact ccatctcaaa aaaaaaaaaa gtcacttttg gctaatcatg cagtcttctg 3720
aaaaggttta atagagaaat gctgtttagg ctgggcttgg tggctcacat ctgtaatacc 3780
agcgctttgg gaggctgagg caggaggatt gcttgaggcc aggagtttaa gttacagaac 3840
tatgatcaca ctgccgcact gaagcctgga tgacagagtg agaccttatc tcaaaaaaaa 3900
aaaaaaaaag agagagagag agaaaaagaa atgctgtgtt taatcttctt aaaatgtatc 3960
ttgtcctaca tagttctcag aatacatatg gggtatagtt aggagataac aataacaaga 4020
cctaaacaaa ttgcttatgg gagatagcac tgtaattaga gaatttattt catataaaat 4080
aataatataa agtttgaact gattagaatg ttccttaaat catggtttcg tttgttgcag 4140
ctgtcagcta acatttggtt gagctcatat aatccaaacc taattgtcca actattgtat 4200
tgccactatt gttaatttgt tccttcctta ctttcttatt gttggatctt atatgactgt 4260
atgactgtag ataatagaca gctagctaaa tgtagagcac cattttctc aatgagtttg 4320
ttttcaaagg ctttgcactg gagaagatat gtgtagaatt tttgttttat ttttaaaatg 4380
tgtaaaacat cttttgtttt atatgctttt aagaatgtag attgtaattt aggaaatggc 4440
atatattctg caaagtggta taatgttgta tatatgaaaa acaggtatat ttggtttagt 4500
tctgtgtttc agtgactgat aaacaaaaat gaagctaaaa tgaatcaacg gctcattcat 4560
agttactaaa gccatgtcat gactgtcatt ctattatgaa gaaaacagtt ttatttgagt 4620
gctttaatat aatgcaacat ttaagtcatc ttaaggtgaa aagttattga agtgttcttc 4680
tctcaagtta acaaaatttt acaaatgttc ctgaagtgta tcgattgagg gaattatttt 4740
attctagcct gtcatgagtc tgtctgagca tgatacttaa catgaacttg atgtagtagg 4800
tgcacatttg cctaacagga taaattcagt gatagcccaa gctggtcagg agagacagaa 4860
gtgctggcta ggaggtctca gcctcgggca ctacaatgtt tatctttttc tttttgaaca 4920
atattgtgaa aatgattgca ttctcattga gcatgaaagt caaaactgga attttctaaa 4980
gctttggaga aaaggagaga attagtaggg caagatcaaa gcatacattg gaaataaaca 5040
gtagaaataa gcaaacaata taaagagaca cgggaaatgc ttctcgtgaa gggcaaatgt 5100
aacaccataa cagtagggaa taaactgtgt cccacctgtt tacttgtgtt tatttgttgt 5160
tatgatgagt atgcacctac cattttcctt tattgtgatc actaaaatga ggccaaggtt 5220
taggaggtga gaaaaagtat ccctttttacg gattcagttc ctgctaggat gttgtatcag 5280
aatcatgtga gaactcagga agaggtagag cagaaataaa aaggaagaaa atgtagatta 5340
gaaaataaga cttctgagaa aaagttcaag gaataaagat tgtttgactc tggagaggag 5400
aaagctgttg agatagtttg ctaagtttgc taataaagct ttattgagtc ttttattgaa 5460
gggttcaaag taagaaatac tatgccatag tgttctccat ctctagtgaa gacagaacca 5520
gagggaataa ggatcttttt tttaaagaca gcatggaaag tttaagattt aggaacttct 5580
tgagaaatct tcataatatc ttctattcaa aatctttttt ttatttttaa gggaataaaa 5640
attttaaaaa ttaagagata tacagatgac tttttaaggg tccttctttc cagcacattt 5700
tttttaaaaa ctcaggttag aataaaaatg tcataaaggg cactaaaagt aacatttggg 5760

-continued

```
tttcactcca tatctagaag aatttagctc acaaaacaat ttttgtgtgt tttgagtaac   5820
tgatgcataa gtgcaatgaa taattttcct gcttcactgt tatttttaat ttaacctggc   5880
aaattaagtg agacttgaac aaaattttgt tcatcttgaa gaatgtatag tggcttaggt   5940
tatttgaggt tttcgttttg aatatatatg ttgttatttt gatgtagata cgttagcaga   6000
tggagaggtt ctaagagatt ggatactttg gaatgtcttt atataggaaa tagacctccc   6060
atttcttaag caagttgctt ctggaattga tgcaacaggg atattagctg tagtttaatg   6120
gataagttgt tctatgagct gctgctatca gtactttttt ccacattttc cattgatatt   6180
tgtgatgctt gaaaaatcca aacttcactt ggatacattt aattttatgc ctttttctct   6240
ctacctccca cttttcctag gcacccttgc acattttgtt actgtgaagg actattgccc   6300
tgttacctca ctgataagaa atctcaactg tattcattca gaatgcttta agcttagtca   6360
taaactacat ttgcctatgg acctttggtt attttgttaa tgttgtcatt atatttaaga   6420
cttattgtag gaagtaattt taaatctatt tcataacctg ttttgatctg tctgcatact   6480
gctatatgtt aatttattac ggccttttac aattcacttg tcatctgaga ttgttctaga   6540
aactgatgag gaaagagtcg tactaaccaa aatgaatggg caattgacat aacattctat   6600
ttcaggtttc cttgtacttg gggagccaaa gcacaagatc taaggaaatc ttattcacat   6660
ttgtccctca gagcatctta ccctaagcca tagaggtata aatagtaaga tgagaattgc   6720
tcattgtctg actccttgca cagcatgaat ttaattctag ttggaaacaa agttagtgtt   6780
gactactggt taccttaaag tattcaccat actatatatt tattagacca tctttcctct   6840
ttgtttattc aagactatgt acttataaaa gagaacctat aagaatgtgt agagtgacca   6900
aatagggaca aagtgacata cctagagttt gctgctcaaa tttttccact agcgtaaccc   6960
taaagcagag gggcatgatg aagggggaag gggttctgag agcaaaatca gaatcagcct   7020
accactgaca tgaagtgtgt tctgtcttta aaatgtaagt gaattttgca ttctttataa   7080
taaaactttt aatataaaaa tgatatgttt aatctttact gaaacttatg ccaccacaaa   7140
ggagcaccat gttcatcacg tggctgctca gttttctccc ccagtgccct cacccccagt   7200
ggaggcaagt ccttgagcta cacacactgg ctgtagtgca agatatataa acataggccg   7260
ggctcggtgg ctcatgcctg taatcctagc actttgggag gccgaagcag gtggatcatc   7320
tgaggtcggg agattgagac tagcctgacc gacatggaga aaccctgtgt ccactaaaaa   7380
tacaaaatta gccgggtgtg gtggcacatg cctgtaatcc cagctactcg ggaggctgag   7440
gcaggagaat cacttgaacc caggaggtgg aggttgtggt gagccaagat cgcgccgttg   7500
cactccagcc tgggcaacaa gagtgaaact ccatctcaaa aaaaaaaaaa aaagatatat   7560
aaacatagaa catatccaga ctatttcctg cccttggaat ctgaccttca gaaggattaa   7620
tgccaaacta aactgacctg aaacagtttt gttactattg gcattccttg actaaaaagg   7680
accacctgat gctcagtccc gagagtagga atcgtggttt attatttttc atatccatac   7740
cacctagttc agtacctgtt atagagtgtt taattgctga tactaggaat taagggattt   7800
tttaaaagta gcaaatagtt taaggaacaa tcaaaaaatg aattttctaa ttcagttttt   7860
tcaatgaagt cccatcactg aactttataa tgtaatgttt attaagcaga catcccctta   7920
aatactcagt ttctttggag agagcaaagc atatctctct gtggaaatta tatataatgc   7980
ctggtatttt acactcaaag caaggtgttg gccaggaagg taaagaaatg gtgtctatgt   8040
agacttaata tcactagtct aagtgtcatt ttgagcctag tagcactacc ttccaagtga   8100
gtcacaacaa atttgatcct atttggtatg tttttgtcca ctgttatgat tcatcatgta   8160
```

-continued tcttacaaga gccactcaag caagactctg cttctatgta tggtgaggcc ttgttgttct 8220
aggctagaat aaactctttg tatgcctcat tgaatatgcc aggtaaaata tatgcagtca 8280
agaatgaatt atttttctga ctaaagtgtg tagcagtagt tcaaaattgt gcccttgttt 8340
taacagtttc tgtcaacatc ttctcatttt tccctacaaa aacaccaggg tgtattataa 8400
gtactgcctg tgagaatttg cactttatgt atttgtgtgt ggatttcttg tggttttagc 8460
caaatgaagt gttatcagta ataaacaggt ctcttcatag gaaaaaaaaa aaaaaaaaa 8519

<210> SEQ ID NO 17
<211> LENGTH: 5491
<212> TYPE: DNA
<213> ORGANISM: Homo sapiens

<400> SEQUENCE: 17
attgctgaca ggcggccccg ggggcggtgg ccaaggcggc gaccggagcg cgatggcggg 60
ggcggcggga ctcacggcag aagtgagctg gaaggtcttg gagcgaagag ctcggaccaa 120
gcgctcaggc tcagtttatg aacctcttaa aagcattaat cttccaagac ctgataatga 180
aactctctgg gataagttgg accattatta cagaattgtc aagtcaacat tgctgctgta 240
tcaaagtcca actaccggtc tctttcccac taaaacatgc ggtggtgacc agaaggccaa 300
gatccaggac agcctatact gcgctgctgg ggcctgggct ttggctcttg catacaggcg 360
aattgatgat gacaagggaa ggacccatga gctggagcac tcagctataa aatgcatgag 420
aggaattctc tactgctata tgcgtcaggc cgataaggtc cagcagttta agcaggatcc 480
acgcccaaca acatgtcttc actctgtttt caatgtgcat acaggagatg agttgctttc 540
ctatgaggaa tatggtcatc ttcagataaa tgcagtgtca ctttatctcc tttaccttgt 600
ggaaatgatt tcctcaggac tccagattat ctacaacact gatgaggtct cttttattca 660
aaaccttgta ttttgtgtgg aaagagttta ccgtgtgcct gactttggtg tctgggaaag 720
aggaagcaaa tataataatg gcagcacaga gctacattcg agctcggttg gtttagcaaa 780
agcagctcta gaagcaatta atggattcaa cctttttggc aaccagggct gttcgtggtc 840
agttatattt gtggatctcg atgctcacaa tcgcaacagg caaactttgt gctcgctgtt 900
acccagagaa tcaagatcac ataatacaga tgctgccctg ctcccctgca tcagttatcc 960
tgcatttgcc ctggatgatg aagttctttt tagccagaca cttgataaag tggttagaaa 1020
attaaaagga aaatatggat ttaaacgttt cttgagagat gggtatagaa catcattgga 1080
agatcccaac agatgctact acaagccagc tgaaattaag ctatttgatg gcattgaatg 1140
tgaatttccc atatttttcc tttatatgat gattgatgga gtttttagag gcaatcctaa 1200
gcaagtacag gaatatcagg atcttttgac tccagtactt catcatacca cagaaggata 1260
tcctgttgta ccaaagtact attatgtgcc agctgacttt gtagaatatg aaaaaaaataa 1320 ccctggtagt caaaaaacgat ttcctagcaa ctgtggccgt gatggaaaac tgtttctttg 1380
gggacaagca ctttatatca tcgcaaaact cctggctgat gaacttatta gtcctaaaga 1440
cattgatcct gtccagcgct atgtcccact aaaggatcaa cgtaacgtga gcatgaggtt 1500
ttccaatcag ggcccactgg aaaatgactt ggtagttcat gtggcactta tagcagaaag 1560
ccaaagactt caagtttttc tgaacacata tggtattcaa actcaaactc ctcaacaagt 1620
agaacccatt cagatatggc ctcagcagga gcttgtgaaa gcttatttgc agctgggtat 1680
caatgaaaag ttaggactct ctggaaggcc agacaggccc attggctgcc tcgggacatc 1740
aaagatttat cgcattctag gaaagactgt ggtttgttac ccgattattt tcgacctaag 1800

-continued

```
tgatttctac atgtctcagg atgttttcct gctgatagat gacataaaga atgcgctgca   1860
gttcattaaa caatattgga aaatgcatgg acgtccactt ttccttgttc tcatccggga   1920
agacaatata agaggtagcc ggttcaaccc catattagat atgctggcag cccttaaaaa   1980
aggaataatt ggaggagtca aagttcatgt ggatcgtcta cagacactaa tatctggagc   2040
tgtggtagaa caacttgatt tcctacgaat cagtgacaca gaagagcttc cagaatttaa   2100
gagttttgag gaactagaac ctcccaaaca ttcaaaagtc aaacggcaaa gcagcacccc   2160
tagtgctcct gaactgggac agcagccgga tgtcaacatt agtgaatgga aggacaaacc   2220
cacccacgaa attcttcaaa aactgaatga ttgcagttgt ctggctagcc aagccatcct   2280
gctgggtata ctgctcaaaa gagaaggccc caacttcatc acaaaggaag gtaccgtttc   2340
tgatcacatt gagagagtct atagaagagc tggcagccaa aaactttggt tggcggtgcg   2400
ctacggggct gcatttaccc agaaattttc ttcctctata gccccacaca ttactacttt   2460
tctggtacat gggaaacagg taactctggg tgcctttggg catgaagaag aagttatctc   2520
taatcctttg tctccaagag tgattcaaaa catcatctat tataagtgta acacccatga   2580
tgagagggaa gcggtcattc agcaagaact ggtcatccat attggctgga tcatctccaa   2640
taaccctgag ttattcagtg gcatgctgaa aatacgaatc gggtggatca tccatgccat   2700
ggagtatgaa cttcagatcc gtggcggaga caagccagcc ttggacttgt atcagctgtc   2760
acctagtgaa gttaaacagc ttctgctgga tattctgcag cctcaacaga atggaagatg   2820
ttggctgaac aggcgtcaga tcgatgggtc tttgaataga actcccaccg ggttctatga   2880
ccgagtgtgg cagattctgg agcgcacgcc caatgggatc attgttgctg ggaagcattt   2940
gcctcagcaa ccaaccctgt cagatatgac catgtatgag atgaatttct ctctccttgt   3000
tgaagacacg ttgggaaata ttgaccagcc acagtacaga cagatcgttg tagagttact   3060
tatggttgta tccattgtac tggaaagaaa ccccgagcta gaatttcaag acaaagtaga   3120
tctagacaga ctggtcaaag aagcatttaa tgaatttcaa aaagatcaga gtcggctaaa   3180
ggaaattgaa aaacaagatg acatgacttc cttttacaac actcctcccc tgggaaaaag   3240
aggaacatgc agctatttga caaaggcggt gatgaatctg ctgctggaag gagaagtcaa   3300
gccaaacaat gatgacccgt gtctgattag ctagtgggga aggtgtagga agctctgttg   3360
agacacatgt tctgaagtgt gttgtgtttc atgttcaagc ttaatcaagg cagccattaa   3420
tatacgaact gagcatgctg gggaggtgaa tgccacatcc ttggcggggt tatggacctc   3480
ttgcatgtca tagccaatct aacggtaatg gtaaatgctt ttaatcaagc aggaaaaagt   3540
tctcatgatt atgccaacta taatagtaat cctcactgag tgataaaaat agtttatgaa   3600
ttgaaaattt gccgctgcat gttgtatgat caaatagttc atcaaaatga atctttgctc   3660
tttggactga attcttacca tactgccatt aaaataaatt tgccaactag taatgcatac   3720
tggaaatcaa aagatactga aagaatggtg aacttctctt agtggtattg tcatgctaaa   3780
agatgttaat atacatcata aaagcaaagt cagccagctg atattttggt tctcaaaaac   3840
tgcattatta ataatatttt agtatacaga gctattctac agtttttaca ttgtaaacat   3900
gactgtggtt ttgtatttgc taaatatagg ggttggacta aaatataata aatctgtacc   3960
ttatcaaaca ttttctttga gctcctgcta aaaataggac atgtctatga ttgttcaaaa   4020
atatgttaaa tttaggctca gcacagtagc tcacacctga aatcttagca cttcgggagg   4080
ctgaggcagg tggatcactt gaggttagga gttcaagacc agcccagcca acatggtgaa   4140
aaccctgtct ctactaaaaa tacaaaaatt agccaggcat gatggtgcat gcctttaaac   4200
```

-continued

```
ccagctactg aggaggctga ggcatgagaa ttgcttgaac caggagacgg aggttgcagt   4260
gagctgaaat cctgccactg cacaccagcc tgggtgacag agcgagactc catctcaaaa   4320
aaaaaaaaaa aaaagaaaaa gaaaaaaata tgttaaattt aaggactgtt aacctacgtt   4380
ctactagtaa aaacaacatt aagggtcatt aaattttatt tctgaattaa tgaacatatc   4440
tggacatttt ttgttcctag gttcacaaga ttgagcttca aactcccgag tgttttcatt   4500
taattgattt agaggtagaa tggaagagaa tctgtggtac ctaccattat acacatttag   4560
ttgcccagtt tacttaaact ttaatgaaag tagaaagtag attaaacatt taaattttat   4620
ttctttccta aatagaaaaa aaaaaggccc atgagtttga gcccttgccc caaagagagt   4680
tgtttttctg atcaatctta ctggagtttc acctgagaag atagatttgt cacataaaaa   4740
atgcagctta tttgtagtgt tttgaaagga tgtaagaaag gatgagtggc ttcagtattg   4800
agtcaatcga tatcaaatga atggatgtgt gagcacatgg aaaaatctgc tgtcagtcac   4860
atttctcata acattgaggt acagtgccga gatcttgcat aagaaattgt atggatatta   4920
gttggcaaaa ttgaaatgaa tgagacacag ttgggcccta aagaactaag gagggggatt   4980
gacaaagaat agaattaaac tacttgactc aatatgttaa gagagtttat gaaaagatag   5040
tcgtgaaggg tgaagctaat ttgtaaaact aatgcctgaa aaaaacgtaa gcatgaagtc   5100
catggagagg gaattgagag ctgacacttc ataactggag aaactggaaa ttaaagaaag   5160
ggaaacaaaa gacttaaaat ttttgtttgc cgaaattttt acgaaagtaa actgtgttgt   5220
agttttaaga attttttaa aaaatctgat tagctgagca aagttaccag aaaactgcta   5280
tcctagttga aatcaaacat tacttgcaaa tgtgttttct gagtgttagc ttcctgctta   5340
aatgttacat atgcaaaatt ctgaagtttt cctgtgctac tcctgaaagc attcagaatc   5400
tgtgacacgt attgacttca tgctttgaga ttcaaaattt attgttctga aagttatatt   5460
tagaatcagt aaatcttgat attcaccttt a                                  5491
```

<210> SEQ ID NO 18
<211> LENGTH: 3939
<212> TYPE: DNA
<213> ORGANISM: Homo sapiens

<400> SEQUENCE: 18

```
aactagctcg ccttcagtgc tcacgggaga aggcaagtta gaaagaacct gagacgtgac     60
actgaaaatc agtagaagaa atacgccaca tttattctac cggggaagac agtgggtaag    120
aaaaaaatac cgtaacattt aaattaaaaa ataattaaaa atttaaaagc aaatagaaat    180
taaaacaaaa tacactgata acctcgctgc cagaacaaga tacaccaaaa aaaaattttt    240
tttttgagta tacaaaacat acaaagcatc ctacaaacag aaagaaattg caaacagggt    300
cgaatggtga gatcctacca ttatatttgt cagcactaaa cccgtgcctc ttgcgcctat    360
ccgaagtttc ctcggattaa gaagaaacag ccatggttaa accggtattt gcgacaccaa    420
caattatctg tagccgacgt accccaactt ctacatgagt gaaaaatcgc cagcatagcc    480
agggcgagac tattgcgaat tctaacttgg tatgatttaa aaattccaga cactgctaaa    540
ttttttaaa ttgcattctt cagtacctag attaatacag gagttataaa ccgcacgcat    600
ggctataatg gggctcctta ttacggaaca ggaatttgct actactaaaa ttatgtaggc    660
atggttaaag ccagaattgt tacaaccaga aatcgcaaac tggaataact ctcaacttgc    720
tacggtaaga aataactaaa ctctgacttg gtcagactaa gaaatcagga gtttgagacc    780
agcccaggca acatggcgaa atcctgtctc taggaaggat acaaaaaatt acccgggcgt    840
```

-continued

```
ggtggcgcgt gcctgtggtc ccagctaccc cggaggctgg ggtgggagga tcgcttcagc    900
ccgggaggcg gaggttgcag tgagccgaga tcgcggcact gcactccagc ctgggcgaca    960
gagccggacc ccgtatcaag aaagaaagag aaaagaaaaa gaaccaaaga aaaagaaaag   1020
tcaccatcgc acggttaagt ctgccttgct acagctaaac agtgacttcc taggaccaag   1080
aaatcgcagc cagggctaga ccgatgccct aaatcgggac ttgcttaggc tgagaaatca   1140
cattttggct agttatttgg acaagaggta gaaatagcgg gcaccgcgaa atcgaaactt   1200
gctaggacca agaagccaac gacgggcgaa accgcagggg cctgcgatag agacgccagc   1260
ggcgccgccg gggactgggg ttcaggaggc cgagcaggaa cccgtgcgtc ggcgctcgcg   1320
gcgctgtgaa gagacggcgt ccgcgcagct cctctgcctc tggctcggag gagcggcggg   1380
ctcccccgcc cagcgccggc gtcgcccggg aaccccagac tctgcgcaac tggctgcgat   1440
tccaaatccc tcagatcggc taccagagcg ctgccgccac cgagaaaatg gaggcaccga   1500
ggaacaagat gtgccgcgac caagagaact cggcttggcg aaatggcggt gccgggaccc   1560
taagagtgac gccagccgga ggagttccca aggacaacat ccattttggc ggaaccaacg   1620
gtgttgtcac gcagaaaatg tcgaccctcg gaaaagagag gttctgcgac cgagaaattc   1680
ggtgcaacaa gtgctgtgac agaaaacccc ccgctcggcg ctgctggcga aagagccaac   1740
aaaacgctgg gtgctgccac cgtgacaccg actttaggac cccggcctcg gatggagaaa   1800
ggagggtacg gagccaccac ataacttcct aatgtcttca aatagcgaaa gtgctagccg   1860
gaaactgccg gctgggttta cctattggtg ctcgtgtggg actagcagat tcgagaaacc   1920
agcgggactg gaacctagta cacttcggca gttgagaaat gacttaccag gacaaatact   1980
gcttctggct cgatggtgct gcccatgaac atccgccggc tctgagaaac gagctgcact   2040
gtcagtgaga aaccgtgggc actgagaaac gagcggactg caactgataa ctgcccaccc   2100
agtgccacta cgacaaagtg ctgctggcac tactcccacc ctccgtcctc aaatcagtcc   2160
cctcccgcct aagaagacct ttatttttcc tagcgaagtc atactgaggg ccccatcaac   2220
cgatcccttg cgatgcgcat gggaaaagga ggcagtatag ggaccgagaa tcgggcggat   2280
tgggctggcc ctggtaacaa aagccatccg ggtcgccaac cgtcttccac tgcaagaaac   2340
aaaccttcca gtggctgggc tccgcccttc tccttggtca gagccctcca ggctcctaag   2400
ggcgaagccg acacctcatc cctttggaac ttgaagttct cagtccaaga cctccgtgga   2460
gagtgaaaga ctcaatgcct cctgaccgag gcttcaggcc tgccccggca gctaggtacc   2520
tctccagggg atggaactct gtgggaactg ctatttaatt ctgatggtta actctgtcag   2580
atggccttga tatatgggaa taatcgttgc aggagggtag gggaaataag aatcgcaaga   2640
ctctagcaca ggacgtgtgg attgatggtg aggcctttgc tccctctccc cttgaaatcc   2700
tcaaagggca gttcccgatt tctatcacct ttgaaattca tccctgatgt cttctccatc   2760
tttgggaagt gcaatgcaat ttcaagctct tgaatcttcc ctctcccaca tttgtcaaat   2820
atactgacgc tacaaactcc tttcttacag gaaacctgaa actgccattg agcagaagga   2880
aaacatccct ttccagaacc tttctcgttt ttctaaaaat ctgcactttt ggaagtgatc   2940
ccccaaagag acctccagac tctaccatga gtgtctccag ctgaactcat cgtgtctaat   3000
cctcacccta gcttatcctg ttcaaatcat ttccatcttt ttctggatga acctgggcgg   3060
atgtcagacc agagaagagc acagaatgta ccagagaggt aagaagaccc attttgggct   3120
ctcacttctc acccactccc aagatggtca cctccagtct tccccccctat accttaccct   3180
ttcttcagct agccaaaacc tgccctggta cttgaggctt cttcagttgc cttcttttgc   3240
```

aggcagtaga ataaaggaaa gagggcagtg tcaatagaag aaaagttaca gccactttat 3300
ctaattgaag atactgtgca gagcctttga aaaaacaaaa tatctcaccc accattcctc 3360
tctccgtttc caccctagct tcctatttta gcaaaaatgg tgggatcagc acctctggag 3420
ggaaggggtc actcttccag gttaggaatg tggacaggag ttatggagct tacttcccta 3480
aaggaggagg cattctagtt ccggcattca gattctgtct gattccaata tggtgtttgt 3540
gtggggtggt cagagaaagg gcaagtcggc aactgtatat tcctcagcaa gagactataa 3600
gacatttgca tttggaaaat caggagagat gctgatatgg tttggctccg tgtccccacc 3660
caaatctcac cttgaattgt aataatcccc atgtgtcaag ggtgagacca ggtggagata 3720
attgaatcat ggggttggtt ttccccatgc tgttctcgtg ttagtgagtg ggtctcacga 3780
gatctgatag ttttataatt gcctggcatt ttcccctgct ggcacacatt ctcctgcggc 3840
cctctgaaga ggtgccttcc atcacgattg taagtttcct gaggcctccc cagccatgca 3900
gagctttgag tcaattaaaa cttctttctt tataaatta 3939

<210> SEQ ID NO 19
<211> LENGTH: 5131
<212> TYPE: DNA
<213> ORGANISM: Homo sapiens

<400> SEQUENCE: 19
cctttaaact ttgtttttta aacttcgggg gtgtggtcgc ggcgcctccc ctctcggcgg 60
ctggcagtcc ttgcctctgc cccgccttcc agatgctttg gagtcatgag ccgggagggc 120
gcgggggcag ctttggtagc cgaggtgatc aaagatcgcc tttgttttgc cattctctac 180
agcagaccaa agagtgcatc aaatgtacat tatttcagca tagataatga acttgaatat 240
gagaacttct acgcagattt tggaccactc aatctggcaa tggtttacag atattgttgc 300
aagatcaata agaaattaaa gtccattaca atgttaagga agaaaattgt tcattttact 360
ggctctgatc agagaaaaca agcaaatgct gccttccttg ttggatgcta catggttata 420
tatttgggga gaaccccaga agaagcatat agaatattaa tctttggaga gacatcctat 480
attcctttca gagatgctgc ctatggaagt tgcaatttct acattacact tcttgactgt 540
tttcatgcag taaagaaggc aatgcagtat ggcttcctta atttcaactc atttaacctt 600
gatgaatatg aacactatga aaaagcagaa aatggagatt taaattggat aataccagac 660
cgatttattg ccttctgtgg acctcattca agagccagac ttgaaagtgg ttaccaccaa 720
cattctcctg agacttatat tcaatatttt aagaatcaca atgttactac cattattcgt 780
ctgaataaaa ggatgtatga tgccaaacgc tttacggatg ctggcttcga tcaccatgat 840
cttttctttg cggatggcag caccccctact gatgccattg tcaaagaatt cctagatatc 900
tgtgaaaatg ctgagggtgc cattgcagta cattgcaaag ctggccttgg tcgcacgggc 960
actctgatag cctgctacat catgaagcat tacaggatga cagcagccga gaccattgcg 1020
tgggtcagga tctgcagacc tggctcggtg attgggcctc agcagcagtt tttggtgatg 1080
aagcaaacca acctctggct ggaaggggac tattttcgtc agaagttaaa ggggcaggag 1140
aatggacaac acagagcagc cttctccaaa cttctctctg gcgttgatga catttccata 1200
aatggggtcg agaatcaaga tcagcaagaa cccgaaccgt acagtgatga tgacgaaatc 1260
aatggagtga cacaaggtga tagacttcgg gccttgaaaa gcagaagaca atccaaaaca 1320
aacgctattc ctctcacagt aattcttcaa tccagtgttc agagctgtaa aacatctgaa 1380
cctaacattt ctggcagtgc aggcattact aaaagaacca ccagatctgc ttcaaggaaa 1440

-continued

```
agcagtgtta aaagtctctc catttcaagg actaaaacag tcttgcgtta agtaaaaacc   1500
tgtgaccaga gctgaaggaa gactctagga ctgaaaactg caacagaaat tagcacaatt   1560
tgaaaacaaa acaaaattgc aaaagcctta gttgcttttt ccacctaaga agttgatcaa   1620
tggagaaaat gtccactgga gtttgaataa tgaactttga gtttgggtgc aagcaaatga   1680
ctcagagaag ggtccagctc tcaagctgaa tgacaaacat gctgttgtaa atttagtctc   1740
aggtgtaaat acccaagccc tctggtaccc agggagctgg ctggtctgtg gtgcatgtgt   1800
gtccctgtga tggcaatcat tgtagttgct ggccttcaga agaattgagg atctgatgga   1860
ggtttttat gtatttattt tctgttcacc ttgtgaccct gtgtcaaaat ttataaagat   1920
acaaaaggca ttactgaaat ggtactttct gtaatttgat actatttggc ttaatcatct   1980
tcacttgact atttgtaata ctgttgtaat gttaactctg ttaagtaccc aagctgcttg   2040
tcttccacca aagagtgctt tattaacaag aatctgtgaa aatcacattt aaacactgtt   2100
gcatgttgta agaccaggtg gtaccttagt aacctaaaac ttgcaagaga atattaatgg   2160
tagctttaga agactcagga ggagaaactg acttcagagt tggaagatgt tgcaagtcgt   2220
tcctttttct gtccttcagg gactgaagaa ctgggaggct gcccattgtt tggttgccag   2280
tcatacaaat taaaatcata tttccttcca tgaatggaag aaacacacta ttggtttttc   2340
cccttggaaa cagcaatccc aaataatgtc ggcttacaaa aaaaaaaagt taccactttt   2400
ttagagtcct tccctgtaac attggatttt ttttttccct tatgagatcc acctaaggcc   2460
attgacgtgg cctgcgatct cagtgacaat gatctgcttc tggatctcac tgttgccttt   2520
ggttagggaa cacaactagt aactctgcag agtgccttct cccgcagccc tactggaaca   2580
cagcagagtc tgtgccatga agcagttaca gaaacagaat tgatgtgctg ctaaaaaaaa   2640
aaaaaaaaat ggggcccgaa ataaaagaat atatagtact cacctcagtt ccttccataa   2700
gaagtgggtg gtttaatgat tgttaagcca tttttgcctg tgccgggagc atggagggct   2760
gagatgtcga caggcagtgg gaaacaaatg ccctcctaag ccacaaggcg tgcgccagat   2820
tagtaggcaa ctccatttta agaagctgcc tttttcacaa aactggaaga aataaaagcg   2880
gttggaataa acaagttaaa agtctttaat gcaaaaagta attgaaaggc agtgcctcca   2940
ttttggtgta ctttcttgga agaaagtata aaattgaccg gcatcatgag agacggaaga   3000
tgccgtgttc tcagccaaac aagcaactct ttccccgcca ggcactgtcg ggtggggtca   3060
ggccagcttt taaacactgg ggactggatc acagaaaaac agtggttttc tgtccctgga   3120
aatgaatagg cacaaagacc cacttggctg tgggcagact actcttcaat aagatttggg   3180
tgggaggagg aacattcctt ttgctatttt gagctgagac aatataaata ttcaaactgt   3240
gccatgcata aagcattgaa ttctcagggc acctcttctt ccccttaccc cttttaaggc   3300
catcccctcc attaataata atccaggtag ttgtgaaaat cgtgcttcta tctgatccct   3360
tcttagtttg gcttttcatc ccatcagaac aagtaaacgt aggcgccaca gctcttgtga   3420
gtactgtctc cctcacggtg aatgagcctc ctggtgtttc gtccaagaaa agaaagggtg   3480
tcactggaac cacagccctt tttcatttta taaactgcct cttcatgttg cctgctcaag   3540
tttccaccta gaattgctat cactgtggct ctttctaaaa atctttctat ttaactggtt   3600
cactgaaatt agtcatagaa aacttgtgat ttggtgaaga ggcattcctt gtaataacca   3660
aatgacttgg gatggtgtgc atagcaaggg cagtgttaca cttatgagga ctgtctctag   3720
catccaggaa gtctctgggt ctgagggatg gaaagttctt cctgctatga atgagagtgg   3780
actcttcccc tcacccccaa ctgaaaccac aaacaaccag aatcttctgg aattctgact   3840
```

tagagtcgtt gttatagaag accttgttgc tatggaacat gaaactgtgt gtcagatgga 3900
gagatcccct taacctaaga gccttaaata gccctgaaag tacactggga cggtttgcga 3960
tggaattaaa attggaagtg aatattttta ggtgctcttg aagctttctg ggactcaaa 4020 attatcaaaa gtcagggaca gtccggagga agagcgtctg caaaactggg ttcctagaag 4080
tatagacgga cttagctttt tgtagaattt ggtgaggagc agcgcctcgt gagagcagaa 4140
tggcctggcg tggccagtgc ttcccggcag cacgcagctc tgcggcctcc agaattcccc 4200
tgttctgagc ttgatgcccc tagcctgtcc cctacctact tcctcccctc ctctctagcc 4260
ctctcacagg ggtgattgct acctctctgt tttcttgggc ctaggcaagt tttagaggag 4320
ttcccaagca ttgttatgag gccagtgtgc tcgctgggct gggcgggatg gcctgggctt 4380
gtgtgtggcc tgagggctct cctggggcct tctcttttcc cagtcacctt tggagccaca 4440
gaagcagtgc actcattgga tgtctgttct taacacagct tctctttcta cattaaaaaa 4500
aatcattatt gcattttgga aagcagtgct catcaaaagc aacttttaaa acctatttta 4560
ttgttccttt aaatgttctc tcccgctgaa actgccctgg agaggctatc tgctgctctt 4620
ccatttaccc acatcaggtt attctccatg tcactcagtg gagatgactc cagatgtgtt 4680
taaagactgg acaattcacc tatactgtgt aggaaattac ctccttaatt acctggtaga 4740
attgtcagca gacatgttca tccgatgata gtactgcagt tttctattaa taatttgcag 4800
acttttatct aacctgcact catgtacaga ttattaaaag ttttaaaatg taactgatca 4860
gtattgatca atcattgtct tgattttttt ttacagcgta tatttctaat catatttttt 4920
aaagccaaga gaactggttg aatgaatgtt tattttcctg aaggtatttt taagataaag 4980
cttcctaatg gcgtgtaaac tttgcatatg tatgtagttt gatacatatt gtcacatttg 5040
aaaatcttgt gggttgtaac tggttttata caaaatatcg aatagtggaa attgtataat 5100
tacaatcatg taattaaaag tattaaccca a 5131

<210> SEQ ID NO 20
<211> LENGTH: 1290
<212> TYPE: DNA
<213> ORGANISM: Homo sapiens

<400> SEQUENCE: 20
cgcccagaca tggcggacgg cagcggctgg cagccgccgc gcccctgcga ggcctaccgc 60
gccgagtgga agctctgccg cagcgccagg cacttcctac accactacta cgtccacggc 120
gagcggccgg cctgcgaaca gtggcagcgc gacctggcca gctgccgcga ctgggaggag 180
cgccggaacg ccgaggccca gcaatccctc tgtgagagcg agcgggcacg agtccgggct 240
gcacggaagc acatcctggt gtgggccccg aggcagagcc cccctccaga ctggcatctc 300
cctctgccac aggagaagga cgagtgacaa gcatccctgc cattggcctg tgcagcttcc 360
tcagtctgtt tcaagttgct gttgcacagc cctggggact gtgaccagcc tacacagtct 420
ggtgggtccc tgtgagctct tgctcacagg aacatggagc aggacattgc tagccctact 480
tgcccacccc tcacctgcat gcaggatacc ctgacactgc gatgttctgc aggacaattg 540
caccgcttta gagcttccag gaggccaagc attatggcag gtacttgtga gcagccaggt 600
caggctgggc atggtagcat aggagatggt ggtcctgagg tctaggcttc tcaggtaaac 660
tgaagggtag ccctgacctg tgtggacaca caggtgggtc ataatgaggt agctaaacgg 720
ttgtgccact gtgaatgtct ttcctagtcc ttgggaaact gcctgccacg tcccaggttt 780
ggtgagcatt gtgagtgctc acactctgct ccactcgctc agttccactg cacatgcagg 840

-continued

```
caggtgtgcc gagcaggtag ggcttgctgg cccctctgca ccagcaggct tcacttctta    900

ggctcccagg tcggcccctg gagactctgg tttttaagaa atgcacacag ctacagaaca    960

cacaaccttg cataaagagg gtttgtggac tcagctgaag aaatccaagt ccaagacata   1020

tggaattaag cactccttcc ctcaaaattt cccctggtgg ttaatgtatc aaaagccatt   1080

tcatctgatt tcaaatagaa gctgaaaatt aagttcacac ttgttagatt ttgtgtgtaa   1140

cagtgttgta cctggacagt attagaaatt tgtatgctta ttctcttgtt aagtgtttta   1200

aaatgtatga accaccaaaa aaaaaaaaaa aaaaaaaaaa aaaaaaaaaa aaaaaaaaaa   1260

aaaaaaaaaa aaaaaaaaaa aaaaaaaaaa                                    1290


<210> SEQ ID NO 21
<211> LENGTH: 4540
<212> TYPE: DNA
<213> ORGANISM: Homo sapiens

<400> SEQUENCE: 21

aggagacgcg tagccgccgt cgccgccgcc gggggatgtg gccggcgcct gcctctagcc     60

gcgccgcctc ttgagtacca gccgccgctg cagccgccgc cgccgcctag ccgtgcggtg    120

ccaggccgcg ccctccccgg gcgcccgccg gctcgcatgc cgaggggctc cggggcgtag    180

ctgcgcgccc ggcgccgcct ccgggctcct tcggccccgc catgggctgc tgcagctccg    240

cctcctccgc cgcgcagagc tccaaacgag aatggaagcc gctggaggac cgtagctgca    300

cagacatacc atggctgctg ctcttcatcc tcttctgcat tgggatggga tttatttgtg    360

gcttttcaat agcaacaggt gcagcagcaa gactagtgtc aggatacgac agctatggaa    420

atatctgtgg gcagaaaaat acaaagttgg aagcaatacc aaacagtggc atggaccaca    480

cccagcggaa gtatgtattc tttttggatc catgcaacct ggacttgata aaccggaaga    540

ttaagtctgt agcactgtgt gtagcagcgt gtccaaggca agaactgaaa actctgagtg    600

atgttcagaa gtttgcagag ataaatggtt cagccctatg tagctacaac ctaaagcctt    660

ctgaatacac tacatctcca aaatcttctg ttctctgccc caaactacca gttccagcga    720

gtgcacctat tccattcttc catcgctgtg ctcctgtgaa catttcctgc tatgccaagt    780

ttgcagaggc cctgatcacc tttgtcagtg acaatagtgt cttacacagg ctgattagtg    840

gagtaatgac cagcaaagaa attatattgg gactttgctt gttatcacta gttctatcca    900

tgattttgat ggtgataatc aggtatatat caagagtact tgtgtggatc ttaacgattc    960

tggtcatact cggttcactt ggaggcacag gtgtactatg gtggctgtat gcaaagcaaa   1020

gaaggtctcc caaagaaact gttactcctg agcagcttca gatagctgaa gacaatcttc   1080

gggccctcct catttatgcc atttcagcta cagtgttcac agtgatctta ttcctgataa   1140

tgttggttat gcgcaaacgt gttgctctta ccatcgcctt gttccacgta gctggcaagg   1200

tcttcattca cttgccactg ctagtcttcc aacccttctg gactttcttt gctcttgtct   1260

tgttttgggt gtactggatc atgacacttc tttttcttgg cactaccggc agtcctgttc   1320

agaatgagca aggctttgtg gagttcaaaa tttctgggcc tctgcagtac atgtggtggt   1380

accatgtggt gggcctgatt tggatcagtg aatttattct agcatgtcag cagatgacag   1440

tggcaggagc tgtggtaaca tactatttta ctagggataa aaggaatttg ccatttacac   1500

ctattttggc atcagtaaat cgccttattc gttaccacct aggtacggtg gcaaaaggat   1560

ctttcattat cacattagtc aaaattccgc gaatgatcct tatgtatatt cacagtcagc   1620

tcaaaggaaa ggaaaatgct tgtgcacgat gtgtgctgaa atcttgcatt tgttgccttt   1680
```

-continued

```
ggtgtcttga aaagtgccta aattatttaa atcagaatgc atacacagcc acagctatca   1740
acagcaccaa cttctgcacc tcagcaaagg atgcctttgt cattctggtg gagaatgctt   1800
tgcgagtggc taccatcaac acagtaggag attttatgtt attccttggc aaggtgctga   1860
tagtctgcag cacaggttta gctgggatta tgctgctcaa ctaccagcag gactacacag   1920
tatgggtgct gcctctgatc atcgtctgcc tctttgcttt cctagtcgct cattgcttcc   1980
tgtctattta tgaaatggta gtggatgtat tattcttgtg ttttgccatt gatacaaaat   2040
acaatgatgg gagccctggc agagaattct atatggataa agtgctgatg gagtttgtgg   2100
aaaacagtag gaaagcaatg aaagaagctg gtaagggagg cgtcgctgat tccagagagc   2160
taaagccgat ggcttcggga gcaagttctg cttgaaccta gccgacggtt atggaaaccc   2220
attgacattc caaaacaata tatacacata actatgtatt tgtgtgtgtg ggtgtgtgta   2280
tatatgtata tgtatgtgtg tatatatgta tatgtatata cacacacaca cataaatcag   2340
ccaaaatcag agaaaaggaa cagggattta ataccttttt tatgcttatt tttgtcaaac   2400
atgtactcct ttcatacggg tggcttttac aaggcaactt ccgtcattta atgttttcaa   2460
ctgtaattgt cttaatggaa atgttaaaat tcatatctga ttaacatttt taataactta   2520
gaggagattt taactttatt taaaaatagg taaaattatt gtacctaatt atgtctaaag   2580
tttattcagg ggtaatttcc ctgatgtctg tataaaatca agatcttatt ttactgatgc   2640
ataagtccta gtgggtcaag actaggcata tgctttcaga taaataagga attactccaa   2700
tcagttttcc ccaatcaaag aagccatgtc attttacttt tagaaacata caattgggcc   2760
caatatggga attttcataa tagttcatac atttgtcagc caacattaaa aggtaaccaa   2820
ctcctcaggt atttgtagtt taccctaacg cttctttaaa agaaagtagg taaaaaaaga   2880
aaagggtaga taatctttcg tatgcaaact tttcccttat attttgtctt tctttccttt   2940
ttgactttag tagcatcctc cacacatttg tgtgcctgat ttgaaaggaa gctggggcac   3000
ccagcgagtt tagcctttaa gtttctgtgt attgatttgc agattaagta atgctgggag   3060
gaataaagaa gggacagaaa catggaacat aaagcattga aaattccggt gcttgggctt   3120
cggcttcaga gtaacgtcag tggcttaggg ttaaacggcc attttattca aatgcttgct   3180
atacaatctg aaaacacact ggcaggtgct cctctccttg gcaattcatt gagtatccag   3240
agttctacga tgtttaactg aagaattggc taatgttttg atcctccagt gtgactgttg   3300
tttttgtttg ggggtgggtt tggggttttt tgctttttta ttcctgaagc ttaccagata   3360
tgaatggcta atactccatt gttctgcttg ttgtaatggt gaatgcttta agaaaaaaaa   3420
gtgtaatttg ctaagaataa ttcatgatct gtttatgcga taactccttt ttgttacaat   3480
ttttttaaaa aaagctattt ttgttaatgt aaagtaaata tttcagagca aatttttttaa   3540
acttattgca ctaaatacag gctctgtaca aaaaaaaaaa aaaaaaaaaa gcctcagcat   3600
tttatcattc catggaagga gaatcttttg aaagaaagca ttgcctccta ccagaactag   3660
acagtgaatt agatcggtat tatggaaatg catacaagta atgtcactag ggcttaataa   3720
gcagccgttt gctaatgtgc ttcctttcaa agggttggac ctttaaattg ctgcaaaagg   3780
taaattgtat tttttttaa gtattggtgt tctttactct agctaggcta aaatttgcta   3840
aatgccttgg tttcttttaa aagttcatgt aatatttctg atttttcaga atatttgcaa   3900
taagagtctg gattttaaaa aacacatgca tacacacaat taagagctca tgtcttagca   3960
agatctggga aaccaacatt gcgagagtag ctattttgaa agaataattc tccagaagtt   4020
aacatctaat atctagtatc accaaacagt atcgctgttc tcttttattc atttgaaatg   4080
```

-continued aatataatta tataactaac aattgtccaa atagatgaga gagcaaatca tgtgagaaaa 4140
ttcagaatac catctgtttc atagccgcac agattttgga ctttcacaaa cattgggaac 4200
taaatttaga attggcaaaa gtctagaaga tgggtatcaa aacagaagac attccaggag 4260
ctagcaattt taagaggtgt ccctccaaag tgacctgatg gaagtcctga acttggaaat 4320
taggttctac tcacttggac atccctgcat catggactgt tgctgctccc tgttccatat 4380
gctcgcaatc tcagctattt ggaagctacc aggaatgctt tctaattatc atttgcaact 4440
agaactgtaa tcagaaagaa attttgtatt tttgtataac ttgattgtgt gccattttat 4500
ataacaggtc ctgttttaca aataaatttt gttttactaa 4540

<210> SEQ ID NO 22
<211> LENGTH: 502
<212> TYPE: DNA
<213> ORGANISM: Homo sapiens

<400> SEQUENCE: 22
atgaagacct ttgatagtaa tagcaagagg ttacaaatag cagggaggag gcgagtagtg 60
aatgtcactc caacagtgcc tctttacttg cttctctggg aaatacatgg tactaaatta 120
gtagcacaaa gtttgggaat atgcaaaata atggataacc atttttcaaa atgtacattc 180
tctgaagagg aagcagctgg ttggacagga tttcttgaag agccaggtgc taagggcatc 240
aggtcgacat ccatagtaac catgtgccat aacatctaca catttccact tgttttacag 300
acaaggtaac aggcagaagg aaaatccaga gtcttgcagt aagcagatga caaaacttca 360
atatgcttgg gcaccactta ggtgacccca gggagattta gtgtggcctt aggaaagcaa 420
aagagcactt tttattggaa atatgagctt gtcactggga aagatttgta aaattgatca 480
agaacttgat ttataattat gc 502

<210> SEQ ID NO 23
<211> LENGTH: 1339
<212> TYPE: DNA
<213> ORGANISM: Homo sapiens

<400> SEQUENCE: 23
gagacggcca cgcggttgca ggagtaagag atccctctgt ggcgaattgg ccaacggctc 60
ctttcaaccc tgcctcgttg gtggccactg gagaagcgcg gggggctccc ccagacagcc 120
gtggggacaa gttagagcca gcactttacc ccgggccttg cgtgtagctt cccctcccct 180
actctcggtg ccctggtgtc tggagggggg ttgtgggggt gtgcccgcct tacatggtcc 240
accacccggg caaccctctg ggcttgtgtt ccatctcact cttgcttcct gtactgtggt 300
caaggggaac cactgcatca tgtcccggta tagctaccag agtctcctgg actggctcta 360
tgggggcgtg gaccccagtt ttgcaggcaa tgggggcccc gactgtgctg ccttcctctc 420
ttggcagcag cggctgctgg aaagtgtggt ggtcctgacc ctggctctgt tggagatcct 480
ggtggccctg cggcacatcc tgaggcagac gaaggaggac ggtaggggta gccctggcag 540
ccagccagag caggtgaccc agcggccaga ggaaggcaag gagagcctga gcaagaatct 600
gctcttagta gccctgtgcc tgaccttcgg ggtggaggtg ggctttaagt tcgccaccaa 660
gaccgtcatc tacctgctca accctgtca cctggtcacc atgatgcata tctttctcct 720
ggcctgccct ccatgtcggg gagctatcgt cgtcttcaag ctacagatgc acatgttgaa 780
tggagctctt ctggcattgc tgtttcctgt ggtaaacact cggctgctcc cctttgaatt 840
ggagatttac tacattcagc atgttatgct ctacgtggta cccatctacc tgctttggaa 900

-continued

```
aggaggtgct tacactccag agcccctcag cagtttccgg tgggctcttc tctcaactgg    960

cctcatgttc ttttatcact tcagcgtctt gcagatcctc ggcctggtca ccgaagtgaa   1020

tttgaacaac atgctgtgtc cggccatctc agacccattc tacggcccct ggtatcgcat   1080

ctgggcctcg ggacaccaga ctctcatgac catgacccac gggaagctgg tcatcctgtt   1140

ctcatacatg gctgggccct tgtgtaaata tctgctggat ttgctccggc ttccagccaa   1200

gaaaatagac tgaaggtgct tatttttttt ttttttcctc cctgaggaag caagtcgtga   1260

cttgacttgg agaacaccca gttcttgata aaatcatggg agagggcaaa aaaaaaaaaa   1320

aaaaaaaaaa aaaaaaaaa                                                1339
```

<210> SEQ ID NO 24
<211> LENGTH: 1025
<212> TYPE: DNA
<213> ORGANISM: Homo sapiens

<400> SEQUENCE: 24

```
gtttgttcct aaatctaatc gagctcccaa ggaactagta tcttatagaa cacacataga     60

aaatagtgct ctacagtagt cactttcaca ttttttttctt ggatccaact tcatgataag    120

aaatacattt taactcataa tctattcaca tgtatatgaa taactgaaac agaagtttca    180

caaaattatg attatgtttg ccacaaatgg tgtgctctaa tattttcctt ctgtttcatc    240

agaagaaaaa tactggttac tatccagcta agctgatttt gtgacccatt aatgagtttc    300

agttctcact ttgaaaacac tgttctagaa ttacagaaag gtctagggat gagaactaac    360

accactgtgc atcacagtgt gtcagtctgt gccaggcagc ttataaatat tttttgcctc    420

taatttttat acatttatga ggtaagtatc attttctagg taaggatgct aatctgtctc    480

caagccaaat aacacacagt aaatcatggc accaggattt gaatctgggt ctttatacat    540

catagcccat gctgttctca ctgtattttg ctttttccaa gtataacccc gttttcacac    600

gaatggcccc ttcacatatt tgaagactac cgtcgtgtcc gtgctgaccc tttctccctg    660

ccacacatgg ctggagtgca atggcgcgat ctcggctcac tgcaacctct gtctcccagg    720

ttcaggaaaa tggctttgta aagaagcttg agcctaaatc tggctggatg acttttctag    780

aagttacagg aaagatctgt gaaatgctct tctgtcctga agcaatactg ttgaccagaa    840

aggacactcc atattgtgaa accggcctaa tttttctgac tcttacgaaa acgattgcca    900

acacatactt ctacttttaa ataaacaact ttgatgatgt aacttgacct tccagagtta    960

cagaaatttt gtccctattt aatgaataaa ttgtatgtat ttttctctat aaaaaaaaaa   1020

aaaaa                                                               1025
```

<210> SEQ ID NO 25
<211> LENGTH: 3898
<212> TYPE: DNA
<213> ORGANISM: Homo sapiens

<400> SEQUENCE: 25

```
atgacttgct accgaggctt cttgctgggc agctgttgtc gcgtggcggg cggccgggcg     60

gcggcgctgc ggggaccggg tgcgggaggc cccgccgcgc ggccccggct gggcggtgac    120

ggtggcggcc ggcggcacct ggggcagggg cagccgcgcg agctggcggg ctgtggcagc    180

cgcgcggacg gcggcttccg cccctcccgg gtggtggtgg tggccaaaac cacccggtac    240

gagttcgagc agcagcggta ccgttacgcg gagctctcgg aggaggacct gaagcagctg    300

cttgcattga aaggctctag ttacagtgga cttcttgaac gacatcatat tcacaccaaa    360
```

-continued

```
aatgtagaac atattataga tagtttacgg aatgagggaa ttgaggttcg tctagtaaag    420
aggagagaat atgatgaaga gactgttcga tgggcagatg ctgtcatagc tgcaggaggt    480
gatggcacaa tgctgctggc agcgagtaaa gtcttggaca gacttaaacc agttataggg    540
gtaaacactg atccagaacg gtctgagggt catttatgcc tgcccgttcg atatacacat    600
tcctttccag aagccttaca gaagttctat cgtggtgagt tcaggtggtt gtggaggcag    660
agaatcaggt tataccttga agggactggc ataaaccctg tacctgtgga ccttcacgag    720
cagcagctaa gcttgaatca gcacaataga gcccttaaca ttgaaagagc tcatgatgaa    780
aggtctgagg cttcaggacc ccaacttctg ccagtgagag cactaaatga agtcttcatt    840
ggggagagtc tgtcatccag ggcttcctac tatgagattt cagttgatga tggtccatgg    900
gaaaaacaga agagttcagg gctcaatttg tgtactggaa caggatcaaa ggcctggtca    960
ttcaatatta acagggttgc aactcaggct gtagaagatg ttttaaatat tgcaaaacga   1020
caaggaaatt tgagtcttcc attgaacaga gaattggtag agaaagtaac aaatgaatat   1080
aatgaatcac tgctctacag tccggaagaa ccaaaaatac ttttcagtat tcgagaacca   1140
atagcaaata gagttttctc aagcagtcgt cagcgttgtt tctcctcaaa ggtttgtgtt   1200
cgttctcgtt gttgggatgc ctgtatggtt gtggatggag gaacttcttt tgagtttaat   1260
gatggtgcaa ttgcttcgat gatgatcaat aaagaagatg agcttcgaac tgtgcttctt   1320
gaacagtgaa ggatttcctc atgacaaatt ttgattactg gcgagaatat ttttacttca   1380
gaaacagact accagtcgta aagtgacatt ttttggttat tgttgagact gcttgcccgt   1440
gggctcagaa gtgagatttg cattattctt ctgttggatt ctgatagaaa aaaagacatt   1500
cactgtataa gaaaatggat ggactgaacc aattagaatt gataccagtg aaatttttat   1560
attgcttaca attggtaacc aagagtgctg ataccttttt aaatttagag gggcaggctt   1620
aaataaagga ctaaatattt aggatttgaa acttaactgt ataagtgtgt tttccttccc   1680
tttcctccta attgtgggat tgtcagaact gaacacatat catttgatta gtgcatattt   1740
tttatagtac ctgaaaacca agattttgaa aaaattttca agacagagaa ttttgataaa   1800
tcctgacatt gacctaattg acataggtaa atatgtttgt atatgtgcta ataattttct   1860
aatttcggaa cacgatgatg ttatgactat tgatttaaaa atttcaaata ataatttttg   1920
aaattataga tgaatgcttt catttgagtt tcattctgta attcagcagt tctgggtgaa   1980
atacagatag caaaacaaat catgatgctg ttacaaatgt attagttatc caataagtgt   2040
tttaagtcaa ttttttaaa atgatatgag tcttacaggt ttcttccatc tttaaaatgc   2100
tcaaacatgg attcagggac taaaaggatg aactgattag acattttcta ttaggagttt   2160
ggtaaaatat tgtaaaaata tcttcacctg tgttaggagt attatcagaa agaatggatt   2220
ctttaataaa tatgtaaaac acagtagttt tggaattgcc ttccttagta ttgtggtttt   2280
cacctagctt atattccaag atttacagaa tagcttttag gataagatgt taggactttt   2340
tttttttccc catgagaatt cctttatttt tggaggaaat tattatctaa ttattgatct   2400
acttataagt aatcctagaa tttttgccaa aagatcctgt cgttgcataa tcaaacagtt   2460
ggtattctcg tgccgttgtt caaagtcatg tgtttctttc atttggtgct gaaaatttct   2520
gttcaatcat tgacaaatat ttattgaaca cccactctgt gccatgtaaa actatgtcag   2580
gtgctggata tgttgatgaa tgaaacagac tctatcctta tacaatttga gtcttgtggg   2640
ctcagaagta aattctgtga aagctggacg gatagtcgaa ttgagtgctc ttagttttgc   2700
caatatttaa catgttgttc ttatcaattt tttaaaataa atgttaatgt acaaagttaa   2760
```

```
tctaggtttt gatgtatatc cagagaatca atttttctta aagtatctgc gtagacattc   2820

atagcaaaga atttatgaca tatcagatag aaatacatta aaatgtagtg ttttcccaga   2880

gattgatctg gctttttttt tttgatatac ataagatacc actttataaa gaagctccat   2940

actatagaac ctcccctaac aggcttaaaa taccttcttt tttttttttt tttttttgga   3000

gaacggagtc ttgctttgtc acccaggctg gactgcagtg gcatgatctc ggctctgcaa   3060

cctccatctc ccaggttcaa gcgattctcc tgcctcagcc tcccaagtag ctgggattac   3120

aggcaggcac cactatgcct ggctaatttt ttgtattttt agtagatatg ggattcacc    3180

atgttggtca ggctggtctc gaactcctga ccttgtgatc tgcctgcctc ggcctcccag   3240

tattgggatt acaggcatga gccaccatgc ccggccttaa aatgccttct taaaggaaaa   3300

atgccaactc catccttaat ctcaaggaaa tctgattgtc caaatagatc tgttaatatg   3360

taacatatta ataggtaact tgctgtgtaa aattataagc catattttaa aaggttttaa   3420

aaatacttat tgtgctccat ttgtgatata atttctaaca tttctgctct gtgatggggg   3480

tttatttgta agaataagag gcaaaggaat gttagcatag caaaaatgtg tttgaatgag   3540

ttaacctttt aatcgcaacc ctatgtgaat aaaattactc cactgttacc tcttcttttt   3600

aacatttctt atttccctct caaggggtca ttatttgaaa actagttttc acaaaatgtt   3660

atgtttcaga agtgtttccc cactgctgtg tattattatt ctgtgccctg ttgacttcat   3720

tcactgttaa catttgacat agaatgatta gttattaaat cagggtgaag tgcttacctg   3780

gtcagtgtag gctcttcaga taattttgac ttaatatttt tgatactcct tgtgcattta   3840

cattcatggc ccctgtacat taaatcatat tacatgtttt aaaaaaaaaa aaaaaaaa     3898
```

<210> SEQ ID NO 26
<211> LENGTH: 6603
<212> TYPE: DNA
<213> ORGANISM: Homo sapiens

<400> SEQUENCE: 26

```
aagaaagagc cccgccccta gtcttatgac tcgcactgaa gcgccgattc ctggcttttg     60

caaggctgtg gtcggtggtc atcagtgctc ttgacccagg tccagcgagc cttttccctg    120

gtgttgcagc tgttgttgta ccgccgccgt cgccgccgtc gccgcctgct ctgcggggtc    180

atggtgtgct tccgcctctt cccggttccg ggctcagggc tcgttctggt ctgcctagtc    240

ctgggagctg tgcggtctta tgcattggaa cttaatttga cagattcaga aaatgccact    300

tgcctttatg caaaatggca gatgaatttc acagtacgct atgaaactac aaataaaact    360

tataaaactg taaccatttc agaccatggc actgtgacat ataatggaag catttgtggg    420

gatgatcaga atggtcccaa aatagcagtg cagttcggac ctggcttttc ctggattgcg    480

aattttacca aggcagcatc tacttattca attgacagcg tctcattttc ctacaacact    540

ggtgataaca caacatttcc tgatgctgaa gataaaggaa ttcttactgt tgatgaactt    600

ttggccatca gaattccatt gaatgacctt tttagatgca atagtttatc aactttggaa    660

aagaatgatg ttgtccaaca ctactgggat gttcttgtac aagcttttgt ccaaaatggc    720

acagtgagca caaatgagtt cctgtgtgat aaagacaaaa cttcaacagt ggcacccacc    780

atacacacca ctgtgccatc tcctactaca acacctactc caaaggaaaa accagaagct    840

ggaacctatt cagttaataa tggcaatgat acttgtctgc tggctaccat ggggctgcag    900

ctgaacatca ctcaggataa ggttgcttca gttattaaca tcaaccccaa tacaactcac    960

tccacaggca gctgccgttc tcacactgct ctacttagac tcaatagcag caccattaag   1020
```

-continued tatctagact ttgtctttgc tgtgaaaaat gaaaaccgat tttatctgaa ggaagtgaac 1080
atcagcatgt atttggttaa tggctccgtt ttcagcattg caaataacaa tctcagctac 1140
tgggatgccc ccctgggaag ttcttatatg tgcaacaaag agcagactgt ttcagtgtct 1200
ggagcatttc agataaatac ctttgatcta agggttcagc ctttcaatgt gacacaagga 1260
aagtattcta cagctcaaga ctgcagtgca gatgacgaca acttccttgt gcccatagcg 1320
gtgggagctg ccttggcagg agtacttatt ctagtgttgc tggcttattt tattggtctc 1380
aagcaccatc atgctggata tgagcaattt tagaatctgc aacctgattg attatataaa 1440
aatacatgca aataacaaga ttttcttacc tctcagttgt tgaaacactt tgcttcttaa 1500
aattgatatg ttgaaacttt aattctttta tcaatcccag cattttgaga tcagtcttta 1560
ttaataaaac ctgttctctt taatcagctt aaaatccaaa gtgtcatatt tactggtcct 1620
ggagacaaac ttgttcaaaa gaacatcaac gtgcaatgtt ttaaggtcta tcttaagaag 1680
ccctggccaa attttgatcc taaccttgaa gtatgccttg aacttattaa catggccatt 1740
ataagaataa aatatgtagt tgtgtcttaa tggaattaat aaatgtcatt tcactactgg 1800
tgttctgttt caatgtataa ggactatagt gatttaaact catcaatgtg cctttgcata 1860
aagttcatta aataaatatt gatgtggtat aaatgcccat cagatatgct taaacttggt 1920
tttcagttga atgaagtaga gaatgtcctc aggaccatca gcattttaaa ggttatgtga 1980
cttttgctga tttctctgag ttcaagttaa gcatgaagtt agtacctcaa gcctgtgatt 2040
tttccctagg gatgatacag acccaagagg ctacaacaga acttaaactg gcttcgtaat 2100
tagagttttt aagataattg tttgtttttc agcaatatag actgaaaaga tccaagcata 2160
tttagccact tgcttttttg tttcttgttt tgttcttctt tggatgcctg attagtattg 2220
aaagatagaa atattctatg aactaattag gacagattgt gttgtgtttc tctacctcat 2280
cttgttgatc tctggagcat taaaatctat ttagtgttgt catcagtgtg gtacttatga 2340
aatgtaagct aacagcaatc tcagaaggga ggcagtgaag catagcaact aggctcttgt 2400
ttcttcaaga tggcccctgt ggggcagtgc atagatgggg gtgtaaagag aagctgttgg 2460
cattaaaatg agctagataa tcagcccttg ttgaagcata ttccatggta taagagtagc 2520
acagacatga aacatagata aagaaggaag gcttaataga ctagaagact tccacattga 2580
agtattatta acccattgta tgtatatagg ggcatgatca gagtctctat aacttcctga 2640
ttaacaatac agtgtatctt gttacccagc tgtcagtctt tgagagcttt cagtaaaata 2700
tagtaaattc tttcagcata ggctaatgtg tggttactga gatgagtgtt gtgtactcag 2760
aaccgtagca acatttttat gaatggtaaa agtacaagag gaggaaaagt taaaattaga 2820
agaaaagtac aagttattgc ttaatcataa atcacaccag ataacacatt ttgttaattt 2880
cattagctat tactggaaag gaccttaacg attatttaca gaaaggggag tgaaattcat 2940
tgaggttcca tatcaagtgg gcaacaaaac tattactagc attttgataa aaattgcccc 3000
taatgaaatc tagtcactca acagtaaaac aacagctggt ttacacttga aattatgaga 3060
tcagaattgg gcactttggg cttccgtact atgttttgct taagtttttt ttttaatact 3120
aatatgggct ttttcagtag taatatacca aaacacttct attttaatct ctgtttgcta 3180
cttcaaaacc taatcctcct cagatgggat catgagcata agaggaaaag agaagagaat 3240
gaatacttgt tgacctcttg atgtgtatca gatgctttag aaatgtaatt gtatttaatc 3300
ctcaaatacc ttataggtat tattatcccc ttcttacaga tgaggaaagt gaggcccagt 3360
ttaaataact tgcccaaggt cctttggcta gtactggaag gagtcaagat ttaaacacag 3420

-continued

```
ttctgtctga atccagaact caaaatctac attgcacatg ttgctttcct ggtggttcgg   3480

tggaatggac tgcaacgcat tagatactgc tgttattctt ccaggccacc gctcagctaa   3540

aaataattgt gtgtgtgtgt atatatatat atatgtacac acacacacat atatatacac   3600

acacacatat atatacacat atacatatat atacacatat atatacacac acatatatat   3660

gtatatatat actacattct tgatcctaag tctttttaa cttaaatttt attacttata   3720

cagaattctt atttatactt taattatagg tgtgacgaag agaaagagag tagggaaata   3780

cacaggcagt ggttttaagt gtagatgatg gctccttaac ccagtgtcat tagataatca   3840

aacctaaagt cttcccatat taggcaagcg caattctcta ttttggaccc ttcccattct   3900

tcccttacct tctgcttttc gtactgagga atttcgtgtg attttagata aagtgataat   3960

gagatattga gcaaataaga aaatagaggt aatgctataa aaaactaagc tatgtacact   4020

ttcaaaatgc atgtttcttg catgcttttt actacttaat tgcattcttt gctaatttcc   4080

tttccttgct gtctgttctt ttctaacagc tgaagaatgt tctgctgact ctgacctcaa   4140

ctttcttatt cctgttgcag tgggtgtggc cttgggcttc cttataattg ttgtctttat   4200

ctcttatatg attggaagaa ggaaaagtcg tactggttat cagtctgtgt aatcagttaa   4260

atctagtgtt tgtttgtttt tttcaattag aagttacgtt tccattggct aaaagccagg   4320

acatgctgtg caatagattg tttaagatat gcagactaac ttcagtgagt tcctagctaa   4380

cttgggcatg agtacactta tttaagacaa aatatattag gaccaatttt tttctgtttt   4440

ttttcttcct ttgttaaagt ataattaaaa gaaaaattgt ggcttagaat tttttaagta   4500

aataatgatt ttaagcccct ggatccaatt atgaaagcat ttttgctgat gtgtaatttt   4560

atatgttaca gttacttata ttttactact ttgatgttat ttgcaaaatc aaaggtgtta   4620

aagaatttaa cttgcttcag gaaataaatt caagaacata gtggattcat tttcattggt   4680

ggcagacacg aaatttggtt catgataaga cttcctttcc ccacctcctg atcagcatta   4740

tttaaatctg tatttttctg ttagttaaga aagaaatggc ttcatgatat tgtatttaat   4800

agcaaaagtt tggctgtctt cttcattact gttaatagct actatatttt aacaaggaga   4860

tttctttttt tgttgttgtt gttctagagt ttggaatata ctgattatct cagacttgac   4920

atttatactg aaggatgaag taagacctcc agcttttttt aaaaaaggtg ttgatttgga   4980

acacctgtat gggttatggt ttattaaggt tatggtttag aaagtttttt tccctcagag   5040

ccttaacttg ttaagaaggt tcatttatcc tgcactgaaa acaaaaactc tatatacttt   5100

gtttgtgtgc ctcctgcact ctcccattcc ctatgtgaat atgctctagt tgatattttt   5160

aatatattga tttctttttt ctcacagcaa caagtgctta ctctagaggt tagtgggccc   5220

tgatatgtca tcagtcagat gcctgcctag ccaaagctgg actaagatta ttctgtacat   5280

ttgttgatct tgatatagac ttatatccct gtagggactg ctaatggctc cggcttctgg   5340

agtaaggtac tggagaccac tcatccctgt gtctgcttga ttggttcagc tgttgaattg   5400

cccttttatt tggaagcagt gttgaagttg tctagggttc aaatggctgc tttgtacacc   5460

tgtcattagt ataaggcaga tgtttatttt atcaagctat tttatctcta catttaacta   5520

aaaacaaaag ttcccaaaga tctgccttca cttcagaaat ttttttgga ttaaaaaaat   5580

taagcctgaa ccttaaataa agtgagttgg ttattcattc caaggattaa gtcccaatct   5640

acctctcagc acaatgcaga agctcaccac tgtattgctg ccattaactc atgccagaac   5700

cctttgccaa taactggaat tacaaatttt tgttaaagaa aatttatcaa gatctttctt   5760

tactgccttc tctatatgta catctcaaaa acatgtacat ctcaaaaact ggagtagaaa   5820
```

-continued

```
gttagattgc tcaactacaa ctcctctaga actctatagc tctgacatac agattcacac   5880

tctcctctat ttgctaagta tgtaaagaat gttttctttt aaaatgttct cttttgagaa   5940

caactgctta tttgttataa aagcatttgg ttaaaatgat gtcatcataa aaaacagtgg   6000

ctttgtttca atacatattt ttgagatgat tatctagaag ccagattaat aaaatcagct   6060

tgtgaccttg ctaagcatat aaactggaaa ttcagataca ttcaaaatta tgggttcatt   6120

taaaagtgtt ctaccttttg ggtatgagac taatatcact aattcctcaa tagttatcat   6180

ggctctatct taattaatta gaaaatatgt gtgtttaatt ctttgagaat taaaatagag   6240

aatattaaca gagggttaaa aactgcttca actccaataa gataaaggaa gctcaaaatc   6300

tatgagctga gtgttcaatt agctttgcct actgagttca attttatgtc aatacaacag   6360

tggatcagac agtacgactt tgaactggtg aatgtaaaca attgtttttc acctaagctg   6420

ctttggaaga actgatgctt gctgctaact aaagttttgg atgtatcgat ttagagaacc   6480

aattaatacc tgcaaaataa agcatactgt ggtacttctg tttgatctag tatgtgtgat   6540

tttagattga tggattaaaa attaataaag atcatacatt ccataccaaa aaaaaaaaaa   6600

aaa                                                                 6603
```

<210> SEQ ID NO 27
<211> LENGTH: 2636
<212> TYPE: DNA
<213> ORGANISM: Homo sapiens

<400> SEQUENCE: 27

```
gcggggaggg ggttgcaaaa ggagccgagc ggcttctgct caatggcgga aaagccgccg     60

gtgctctgac ggcctcgttc ccctagcagt tgcgggggag tttcctgccg gcgcggctgg    120

agtctctgat tctcagggtt cggtggttgg aagatgctcc agagagacga ggctgcggcg    180

gaggaggtgg cggcggccga atcggcaacg gcgctagggt ggagagaagg cggcatcggc    240

ggcggcggcg gcgtgagggg ccgggcggtg taaacagccc cggaggcggc ggtcgagacc    300

ccgaggggga agcggcggct gagtcagggt cgcgcctccg ttggaaactt gggctgagta    360

ccgcggcggg cgcgagcgag gcgccctaga catcttctcc ctcccttgcc tcagatttat    420

tgctaaacat gggtgcattt ttggataaac ccaaaactga aaaacataat gctcatggtg    480

ctgggaatgg tttacgttat ggcctgagca gcatgcaagg atggagagtg gaaatggaag    540

atgcacacac agctgttgta ggtattcctc acggcttgga agactggtca ttttttgcag    600

tttatgatgg tcatgctgga tcccgagtgg caaattactg ctcaacacat ttattagaac    660

acatcactac taacgaagac tttagggcag ctggaaaatc aggatctgct cttgagcttt    720

cagtggaaaa tgttaagaat ggtatcagaa ctggattttt gaaaattgat gaatacatgc    780

gtaacttttc agacctcaga aacgggatgg acaggagtgg ttcaactgca gtgggagtta    840

tgatttcacc taagcatatc tactttatca actgtggtga ttcacgtgct gttctgtata    900

ggaatggaca agtctgcttt tctacccagg atcacaaacc ttgcaatcca agggaaaagg    960

agcgaatcca aaatgcagga ggcagcgtga tgatacaacg tgttaatggt tcattagcag   1020

tatctcgtgc tctgggggac tatgattaca agtgtgttga tggcaagggc ccaacagaac   1080

aacttgtttc tccagagcct gaggtttatg aaattttaag agcagaagag gatgaattta   1140

tcatcttggc ttgtgatggg atctgggatg ttatgagtaa tgaggagctc tgtgaatatg   1200

ttaaatctag gcttgaggta tctgatgacc tggaaaatgt gtgcaattgg gtagtggaca   1260

cttgtttaca caagggaagt cgagataaca tgagtattgt actagtttgc ttttcaaatg   1320
```

-continued

```
ctcccaaggt ctcagatgaa gcggtgaaaa aagattcaga gttggataag cacttggaat   1380

cacgggttga agagattatg gagaagtctg gcgaggaagg aatgcctgat cttgcccatg   1440

tcatgcgcat cttgtctgca gaaaatatcc caaatttgcc tcctgggga ggtcttgctg    1500

gcaagcgtaa tgttattgaa gctgtttata gtagactgaa tccacataga gaaagtgatg   1560

gggcctccga tgaagcagag gaaagtggat cacagggaaa attggtggaa gctctcaggc   1620

aaatgagaat taatcatagg ggaaactacc gacaacttct ggaggagatg ctgactagtt   1680

acaggctagc taaagtagag ggagaagaaa gccctgctga accagctgcc acagctactt   1740

cttcgaacag tgatgctgga aacccagtga caatgcagga aagccatact gaatcagaaa   1800

gtggtcttgc tgaattagac agctctaatg aagatgcagg gacaaagatg agtggtgaaa   1860

aaatatgact ttcctttttg gtaatatttt tgtgatcttt gatggttttt aacctaggaa   1920

gtgtaatgta tgcatttata taactgtttt gttatttgaa tcttggaaaa ctagttttat   1980

tatattcaga tagccttgtt ttttaaaaag gcctttgcat acacctttat gagatagtgt   2040

aaaattgact atttatagta ctatggattt aatgaaatta tatgtcattt cacattgtat   2100

gccagaaatt aggctaccaa ttatgaatta aagtcagtag ttaaattaat actagataga   2160

attagaaatt ttgattagag agattatgct atattatgga aaaacttgtt aatgtagaat   2220

tatactgctt catattattt tacctattag tacactcata gttagctttg taataaattt   2280

atgttttctt taataatttt agttcttcaa agaatggctg atgctggcct gtaatttttc   2340

tttcaaggat gataatttgt gtgttgtttg atttgtttat attttacatc tctgtagttt   2400

tatttttaga agttgtgaga tattggatgt gtggctattt ttcctttctc tgtattcttt   2460

atgaaacata acttttgaaa aacctatgta ttattcatac agctttggtt tgtatattct   2520

gtatagccta actacacaca tcaaaatgta tgtcaaccaa gtgtttagaa tgaaattata   2580

agtgtttaag tccaaataaa gcatgtgatg tggaataatc taaaaaaaaa aaaaaa       2636
```

```
<210> SEQ ID NO 28
<211> LENGTH: 1825
<212> TYPE: DNA
<213> ORGANISM: Homo sapiens

<400> SEQUENCE: 28

ttttttttt ttttttttt ttttttaatc ttgcactttg aaaccgcggg accgaggcag       60

ggtgcgcgcg tgtggttggt gcctttttttt tttttcttc ccctccctaa actcctctgt   120

cagtctgtaa acattacctg agaattcccc agccgaaacg gctgctgggg caagaaactt   180

cttgttagaa ctttccacct ccggcttccc cctccacctc ttttaccgtc ccaaccttag   240

gagacgcttt ttctccccca gaggagaatt tatctttttt tttttttttt tttttctttt   300

tctcacccgg tgctttgcat ttgggaagag gtgatttcaa gagtggccag gtgggacgcc   360

tctctcctcc ttattcggtt tactatttat tgttcggggt gtttttttaat tcctgtattg   420

ctcggcccgg ggagtttcgc cccctgcccg gctccgcggc gcggaggatg gtgtggaaac   480

ggctgggcgc gctggtgatg ttccctctac agatgatcta tctggtggtg aaagcagccg   540

tcggactggt gctgcccgcc aagctgcggg acctgtcgcg ggagaacgtc ctcatcaccg   600

gcggcgggag aggcatcggg cgtcagctcg cccgcgagtt cgcggagcgc ggcgccagaa   660

agattgttct ctggggccgg actgagaaat gcctgaagga gacgacggag gagatccggc   720

agatgggcac tgagtgccat tacttcatct gtgatgtggg caaccgggag gaggtgtacc   780

agacggccaa ggccgtccgg gagaaggtgg gtgacatcac catcctggtg aacaatgccg   840
```

-continued

```
ccgtggtcca tgggaagagc ctaatggaca gtgatgatga tgccctcctc aagtcccaac    900

acatcaacac cctgggccag ttctggacca ccaaggcctt cctgccacgt atgctggagc    960

tgcagaatgg ccacatcgtg tgcctcaact ccgtgctggc actgtctgcc atccccggtg   1020

ccatcgacta ctgcacatcc aaagcgtcag ccttcgcctt catggagagc ctgaccctgg   1080

ggctgctgga ctgtccggga gtcagcgcca ccacagtgct gcccttccac accagcaccg   1140

agatgttcca gggcatgaga gtcaggtttc ccaacctctt tcccccactg aagccggaga   1200

cggtggcccg gaggacagtg gaagctgtgc agctcaacca ggccctcctc ctcctcccat   1260

ggacaatgca tgccctcgtt atcttgaaaa gcatacttcc acaggctgca ctcgaggaga   1320

tccacaaatt ctcaggaacc tacacctgca tgaacacttt caaagggcgg acatagagac   1380

aggatgaaga catgcttgag gagccacgga gtttgggggc cacagcacct gggcacacac   1440

ccgagcacct gtccattggc atgcttctgc tgggtgagca ggacagctcc tgtccccagc   1500

gaagaatccg gctgcccctg ggccagtccc aggacctttg cacaggactg atgggtataa   1560

ctgaccccca cagggaggca ggaaaacagc cagaagccac cttgacactt ttgaacattt   1620

ccagttctgt agagtttatt gtcaattgct tctcaagtct aaccagcctc agcagtgtgc   1680

atagaccatt tccaggaggg tctgtcccca gatgctctgc ctcccgttcc aaaacccact   1740

catcctcagc ttgcacaaac tggttgaacg gcaggaatga aaaataaaga gagatggctt   1800

ttgtgaaaaa aaaaaaaaaa aaaaa                                         1825
```

<210> SEQ ID NO 29
<211> LENGTH: 1484
<212> TYPE: DNA
<213> ORGANISM: Homo sapiens

<400> SEQUENCE: 29

```
ggtggtttga actttgagcc ttttgtagtc ctgatgaata atttcatttt cctcaagttt     60

atgacactcg gaacgtcaag aactggaggt ttgtgcaatt tgagaccggt cggcactgtg    120

cagagatcag agtactaaga gacagagatt aaaatggctt ccagaggaaa gacagagaca    180

agcaaattaa agcagaattt agaagaacag ttggatagac tcatgcaaca attacaagat    240

ctggaggaat gcagagagga acttgataca gatgaatatg aagaaaccaa aaaggaaact    300

ctggagcaac taagtgaatt taatgattca ctaaagaaaa ttatgtctgg aaatatgact    360

ttggtagatg aactaagtgg aatgcagctg gctattcagg cagctatcag ccaggccttt    420

aaaaccccag aggtcatcag attgtttgca aagaaacaac caggtcagct tcggacaagg    480

ttagcagaga tggatagaga tctgatggta ggaaagctgg aaagagacct gtacactcaa    540

cagaaagtgg agatactaac agctcttagg aaacttggag agaagctgac tgcagatgat    600

gaggccttct tgtcagcaaa tgcaggtgct atactcagcc agtttgagaa agtctctaca    660

gaccttggct ctggagacaa aattcttgct ctggcaagtt ttgaggttga aaaaacaaaa    720

aaatgacatg gtgcagaagc ttgtaacatt gatcacattc ttaatgtaaa tggtgtcttt    780

cttctggggt tttcagttat tgcaaagaaa tgaagagatt ctggaaatgc atcaataacc    840

taagaaaaag cgacataaaa atatacttat ggcttgtgtt tatgctcttc atcattgtgc    900

gttgtgtgcg gttacctgct tgagtgatcc tgaacttgtt gcgacagagg gactcactgg    960

actctgttcg ttatgatttg tctgtttaag agagaaaaca aagtggactt gatttttatt   1020

aaggctgttt gtttttaagt gttgatagtg aacgaaaaga tgtgaagtaa tgatattttt   1080

ctgcttacaa cttatcccca ctcattggag tgaacagtga cgcaagctca atagacttca   1140
```

-continued

```
taagtgttca tagaatttta caattctgag tgatcttaga aatcatttct gtttttacaa   1200

acaaggaaac tgaggtccag aaagagcaag cgactttgct taaagtcgca tcagagagct   1260

gagggtaaga ctcaggtgtc ctgactccca gtttagtatc ttttgaattt tatttctgta   1320

ccatttaaaa aaaataatta acactatttg tgcaagtcag tgtttttgaa aattcagtgt   1380

cccaataaaa agtggactgc acactaaaaa aaaaaaaaaa aaaaaaaaaa aaaaaaaaaa   1440

aaaaaaaaaa aaaaaaaaaa aaaaaaaaaa aaaaaaaaaa aaaa                    1484


<210> SEQ ID NO 30
<211> LENGTH: 3905
<212> TYPE: DNA
<213> ORGANISM: Homo sapiens

<400> SEQUENCE: 30

cccaaaccca gccactcaca catggcgggc tcagcagcca ccggccccgc ccctcctcgt     60

cgccgcagtc gcaactgcgt ctgcggccac agggcggaca gccacgcctc tgcggagggc    120

gaccggaagt gctcacgtct tcaccttccc cgccacgcca ccgtcctttc aggcccagcg    180

tgcagcagga aggaggactc ttttgccgcg gactcaagcc ggaagccgcc ttcctagtgg    240

agacgcgagt gggggaggag cagtccgagg ggaacgtggg ttgaacgttg caactagggt    300

ggagatcaag ctggaacagg agttccgatc gacccggtac caagaagggg agtgcccgcg    360

gcagggttca ttgaaaaaat ccttagtgat attgacatgt ctcaagtgac ataaattagc    420

caatgactcg gaatgatgga ttctccgaag attggaaatg gtttgccagt gattggacca    480

gggactgata tagggatatc ttcactccac atggtggggt atttgggaaa aaattttgat    540

tcagctaaag ttccatcaga tgagtattgc cctgcttgta gagagaaggg aaagttaaaa    600

gccttaaaga cttaccgaat tagttttcaa gaatctatct tttgtgtgga ggatctgcag    660

tgcatctatc ctttgggctc taaatcactt aataacctaa tttctcctga tttggaagaa    720

tgtcacactc cacataagcc tcagaaaagg aagagcttag aaagcagcta taaggattca    780

cttcttttag caaattccaa aaagactaga aattatattg ctattgacgg tggaaaagtt    840

ttgaacagca aacataatgg agaagtatat gacgaaacct cgtcaaactt acctgatagt    900

agtggtcaac agaatccaat taggacagct gattccttgg agcggaatga gattttggaa    960

gctgatactg ttgacatggc tactacaaaa gatcctgcta cagttgatgt ctctggaact   1020

ggcagacctt cccctcaaaa tgaaggatgt acatctaaac tggaaatgcc actggagagc   1080

aaatgtacat catttcccca ggctttatgt gtccagtgga aaaatgctta tgctctctgt   1140

tggttagact gtatcctgtc agctttggtg cactcggaag agttaaagaa caccgtgact   1200

ggactgtgct cgaaggagga atctatattc tggcggttgc ttacaaaata taatcaagca   1260

aatacacttc tatataccag tcaattgagt ggtgttaaag atggagattg taaaaaactt   1320

acctcagaaa tatttgcaga gatagagacc tgtctgaatg aagttagaga tgaaattttt   1380

attagccttc agccccagct tagatgcaca ttaggtgata tggaaagccc tgtgtttgca   1440

tttcccctgc tcttaaaact agaaacccac attgaaaagc tcttcctata ttctttttct   1500

tgggactttg aatgttcgca gtgtggacac caatatcaaa acaggcatat gaagagtctg   1560

gtcaccttta caaatgtcat ccctgagtgg cacccactta atgctgccca ttttggtcca   1620

tgtaacaatt gcaacagtaa atcacaaata agaaaaatgg tattagaaaa agtatctccc   1680

atattcatgt tgcactttgt agaaggctta ccacagaatg acttgcagca ctatgcattt   1740

cattttgaag gctgtcttta tcagataact tctgtaattc agtatcgagc aaataatcat   1800
```

```
tttataacat ggattttaga tgctgatgga agttggctgg aatgtgatga cttaaaaggc   1860
ccatgttctg aaaggcacaa gaaatttgaa gttcctgctt cagagataca tattgttatt   1920
tgggaaagaa aaatatccca agtgacagat aaagaagctg cctgccttcc acttaaaaag   1980
actaatgacc aacacgctct cagtaatgag aaaccagtat ctttaacatc gtgttctgtg   2040
ggtgatgctg cctcagctga aacagcctca gtaactcacc ctaaagatat atcagttgcc   2100
cctcgtactc tttcacagga cacagctgta actcatggag atcatttact ttcaggtcca   2160
aaaggtttgg ttgacaatat tttacctctg acacttgaag aaactatcca gaaaacagcc   2220
tcagtttcac agttaaattc tgaagctttc ctgttagaaa ataaacctgt agcagaaaat   2280
acaggaattc tcaaaaccaa tactttgcta tcacaagaat cactaatggc ttcttcagta   2340
tcagctccat gtaatgaaaa gcttattcaa gaccaatttg tggacataag ttttccatcc   2400
caagttgtaa atacaaacat gcagtcagta cagctgaata cagaagatac tgtaaatact   2460
aaatctgtga ataatactga tgctactggt cttatacagg gagtgaagtc agtagaaatt   2520
gagaaggacg ctcagttaaa acaattcctt acaccaaaaa ctgaacaatt aaaaccagaa   2580
cgtgtcacat ctcaggtatc taatttgaag aaaaaagaaa ctacagcaga ttctcaaacc   2640
acaacatcta agtcattaca gaatcagtct ctgaaagaaa atcagaagaa gccatttgtg   2700
ggaagttggg ttaaaggctt aataagcagg ggtgcttctt ttatgccact ctgtgtttca   2760
gctcataata gaaacactat aactgattta caaccttcag ttaaaggggt aaataatttt   2820
ggtggcttta aaactaaagg tataaaccag aaggccagcc acgtatccaa gaaagctcgt   2880
aagagtgcaa gtaagcctcc tcccatcagt aagccaccag caggccctcc atcgtctaat   2940
ggcacagctg cccacccaca tgctcatgct gcttcagaag ttttggaaaa gtctggaagc   3000
acctcatgtg gagctcaact caaccacagt tcttatggga atggtatttc ttcagcaaac   3060
catgaagact tggtggaagg tcagattcat aaacttcgtc taaaacttcg taaaaagcta   3120
aaggcagaaa agaagaaatt agctgctctt atgtcttccc cgcaaagcag aacagttcga   3180
agtgaaaatc tagaacaggt gccccaggat gggtctccaa atgattgtga atcaatagag   3240
gacttgttaa atgagctacc atatccaatt gatattgcca gtgagtctgc atgcaccact   3300
gttcctggtg tttccctgta cagtagtcaa actcatgaag aaattttagc ggaattattg   3360
tctcctacac ctgtttcaac agagctgtca gaaaatgggg aaggtgactt taggtatttg   3420
ggaatgggag atagtcatat cccaccacca gtaccaagtg aattcaatga tgtttcccag   3480
aacacacatc tgagacagga ccataattat tgtagcccca ccaagaaaaa tccatgtgaa   3540
gttcagccag actctctgac aaataatgcc tgcgttagaa cattaaactt ggagagtccg   3600
atgaagactg atattttcga tgagtttttt tcctcctcag cattaaatgc tttagcaaat   3660
gacacattag acctacctca tttcgatgaa tatctgtttg agaattattg aattaatgct   3720
tgttaacttt tttcatataa tatttattat tattagaaga acttacaatg tgttcaggta   3780
gtgtttatac actggacttg tgtaattact tgtgtaataa ccatgaacaa aatgcaaggt   3840
ttaacctttg gttctgccca tgaagcatgt aatctttctt acacattaaa atcactgaat   3900
gtgta                                                               3905
```

<210> SEQ ID NO 31
<211> LENGTH: 11185
<212> TYPE: DNA
<213> ORGANISM: Homo sapiens

<400> SEQUENCE: 31

-continued

```
aactgctagt ggctgagtcc ctggcggggc gcggcggtgg aaggtgtcgc gtacgggctt     60
cccgagctga cgtggcttga attgggaggg gggcagctgg agcctcaggc ggcagcgctt    120
ctagaaatgc tgagccgatt atcaggatta gcaaatgttg ttttgcatga attatcagga    180
gatgatgaca ctgatcagaa tatgagggct cccctagacc ctgaattaca ccaagaatct    240
gacatggaat ttaataatac tacacaagaa gatgttcagg agcgcctggc ttatgcagag    300
caattggtgg tggagctaaa agatattatt agacagaagg atgttcaact gcagcagaaa    360
gatgaagctc tacaggaaga gagaaaagct gctgataaca aaattaaaaa actaaaactt    420
catgcgaagg ccaaattaac ttctttgaat aaatacatag aagaaatgaa agcacaagga    480
gggactgttc tgcctacaga acctcagtca gaggagcaac tttccaagca tgacaagagt    540
tctacagagg aagagatgga aatagaaaag ataaaacata agctccagga gaaggaggaa    600
ctaatcagca ctttgcaagc ccagcttact caggcacagg cagaacaacc tgcacagagt    660
tctacagaga tggaagaatt tgtaatgatg aagcaacagc tccaggagaa ggaagaattc    720
attagcactt tacaagccca gctcagccag acacaggcag agcaagctgc acagcaggtg    780
gtccgagaga aagatgcccg ctttgaaaca caagttcgtc ttcatgaaga tgagcttctt    840
cagttagtaa cccaggcaga tgtggaaaca gagatgcaac agaaattgag ggtgctgcaa    900
aggaagcttg aggaacacga agaatccttg gtgggccgtg ctcaggtcgt tgacttgctg    960
caacaggagc tgactgctgc tgagcagaga aaccagattc tctctcagca gttacagcag   1020
atggaagctg agcataatac tttgaggaac actgtggaaa cagaaagaga ggagtccaag   1080
attctactgg aaaagatgga acttgaagtg gcagagagaa aattatcctt ccataatctg   1140
caggaagaaa tgcatcatct tttagaacag tttgagcaag caggccaagc ccaggctgaa   1200
ctagagtctc ggtatagtgc tttggagcag aagcacaaag cagaaatgga agagaagacc   1260
tctcatattt tgagtcttca aaagactgga caagagctgc agtctgcctg tgatgctcta   1320
aaggatcaaa attcaaagct tctccaagat aagaatgagc aagcagttca gtcagcccag   1380
accattcagc aactggaaga tcagctccag caaaaaatcca aagaaattag ccaatttcta   1440
aatagactgc ccttgcaaca acatgaaaca gcatctcaga cttctttccc agatgtttat   1500
aatgagggca cacaggcagt cactgaggag aatattgctt ctttgcagaa gagagtggta   1560
gaactagaga atgaaaaggg agccttgctc cttagttcta tagagctgga ggagctgaaa   1620
gctgagaatg aaaaactgtc ttctcagatt actctcctag aggctcagaa tagaactggg   1680
gaggcagaca gagaagtcag tgagatcagc attgttgata ttgccaacaa gaggagctct   1740
tctgctgagg aaagtggaca agatgttcta gaaaacacat tttctcagaa acataaagaa   1800
ttatcagttt tattgttgga aatgaaagaa gctcaagagg aaattgcatt tcttaaatta   1860
cagctccagg gaaaaagggc tgaggaagca gatcatgagg tccttgacca gaaagaaatg   1920
aaacagatgg agggtgaggg aatagctcca attaaaatga aagtatttct tgaagataca   1980
gggcaagatt ttcccttaat gccaaatgaa gagagcagtc ttccagcagt tgaaaaagaa   2040
caggcgagca ctgaacatca aagtagaaca tctgaggaaa tatctttaaa tgatgctgga   2100
gtagaattga aatcaacaaa gcaggatggt gataaatccc tttctgctgt accagatatt   2160
ggtcagtgtc atcaggatga gttggaaagg ttaaaaagtc aaattttgga gctcgagcta   2220
aactttcata aagcacaaga aatctatgag aaaaatttag atgagaaagc taaggaaatt   2280
agcaacctaa accagttgat tgaggagttt aagaaaaatg ctgacaacaa cagcagtgca   2340
ttcactgctt tgtctgaaga aagagaccag cttctctctc aggtgaagga acttagcatg   2400
```

-continued

```
gtaacagaat tgagggctca ggtaaagcaa ctggaaatga accttgcaga agcagaaagg   2460
caaagaagac ttgattatga aagccaaact gcccatgaca acctgctcac tgaacagatc   2520
catagtctca gcatagaagc caaatctaaa gatgtgaaaa ttgaagtttt acagaatgaa   2580
ctggatgatg tgcagcttca gttttctgag cagagtaccc tgataagaag cctgcaaagc   2640
cagctgcaaa ataaggaaag tgaagtgctt gagggggcag aacgtgtaag gcatatctca   2700
agtaaagtgg aagaactgtc ccaggctctt tcacagaagg aacttgaaat aacaaaaatg   2760
gatcagctct tactagagaa aaagagagat gtggaaaccc tccaacaaac catcgaggag   2820
aaggatcaac aagtgacaga aatcagcttt agtatgactg agaaaatggt tcagcttaat   2880
gaagagaagt tttctcttgg ggttgaaatt aagactctta aagaacagct aaatttatta   2940
tccagagctg aggaagcaaa aaaagagcag gtggaagaag ataatgaagt ttcttctggc   3000
cttaaacaaa attatgatga gatgagccca gcaggacaaa taagtaagga agaacttcag   3060
catgaatttg accttctgaa gaaagaaaat gagcagagaa agagaaagct ccaggcagct   3120
cttattaaca gaaaggagct tctgcaaaga gtcagtagat tggaagaaga attagccaac   3180
ttgaaagatg aatctaagaa agaaatccca ctcagtgaga ctgagagggg agaagtggaa   3240
gaagataaag aaaacaaaga atactcagaa aaatgtgtga cttctaagtg ccaagaaata   3300
gaaatttatt taaaacagac aatatctgag aaagaagtgg aactacagca tataaggaag   3360
gatttggaag aaaagctggc agctgaagag caattccagg ctctggtcaa acagatgaat   3420
cagaccttgc aagataaaac aaaccaaata gatttgctcc aagcagaaat cagtgaaaac   3480
caagcaatta tccagaagtt aatcacaagt aacacggatg caagtgatgg ggactccgta   3540
gcacttgtaa aggaaacagt ggtgataagt ccaccttgta caggtagtag tgaacactgg   3600
aaaccagaac tagaagaaaa gatactggcc cttgaaaaag aaaaggagca acttcaaaag   3660
aagctacagg aagccttaac ctcccgcaag gcaattctta aaaaggcaca ggagaaagaa   3720
agacatctca gggaggagct aaagcaacag aaagatgact ataatcgctt gcaagaacag   3780
tttgatgagc aaagcaagga aaatgagaat attggagacc agctaaggca actccagatt   3840
caagtaaggg aatccataga cggaaaactc ccaagcacag accagcagga atcgtgttct   3900
tccactccag gtttagaaga acctttattc aaagccacag aacagcatca cactcaacct   3960
gttttagagt ccaacttgtg cccagactgg ccttctcatt ctgaagatgc gagtgctctg   4020
cagggcggaa cttctgttgc ccagattaag gcccagctga aggaaataga ggctgagaaa   4080
gtagagttag aattgaaagt tagttctaca acaagtgagc ttactaaaaa atcagaagag   4140
gtatttcagt tacaagagca gataaataaa cagggtttag aaatcgagag tctaaagaca   4200
gtatcccatg aagctgaagt ccatgccgaa agcctgcagc agaaattgga aagcagccaa   4260
ctacaaattg ctggcctaga acatctaaga gaattgcaac ctaaactgga tgaactgcaa   4320
aaactcataa gcaaaaagga agaagacgtt agctaccttt ctggacaact tagtgagaaa   4380
gaagcagctc tcactaaaat acagacagag ataatagaac aagaagattt aattaaggct   4440
ctgcatacac agctagaaat gcaagccaaa gagcatgatg agaggataaa gcagctacag   4500
gtggaacttt gtgaaatgaa gcaaaaacca gaagagattg gagaagaaag tagagcaaag   4560
caacaaatac aaaggaaact gcaagctgcc cttatttccc gaaaagaagc actaaaagaa   4620
aacaaaagtc tccaagagga attgtctttg gccagaggta ccattgaacg tctcaccaag   4680
tctctggcag atgtggaaag ccaagtttct gctcaaaata aagaaaaaga tacggtctta   4740
ggaaggttag ctcttcttca agaagaaaga gacaaactca ttacagaaat ggacaggtct   4800
```

-continued

```
ttattggaaa atcagagtct cagcagctcc tgtgaaagtc taaaactagc tctagagggt   4860
cttactgaag acaaggaaaa gttagtgaag gaaattgaat ctttgaaatc ttctaagatt   4920
gcagaaagta ctgagtggca agagaaacac aaggagctac aaaaagagta tgaaattctt   4980
ctgcagtcct atgagaatgt tagtaatgaa gcagaaagga ttcagcatgt ggtggaagct   5040
gtgaggcaag agaaacaaga actgtatggc aagttaagaa gcacagaggc aaacaagaag   5100
gagacagaaa agcagttgca ggaagctgag caagaaatgg aggaaatgaa agaaaagatg   5160
agaaagtttg ctaaatctaa acagcagaaa atcctagagc tggaagaaga gaatgaccgg   5220
cttagggcag aggtgcaccc tgcaggagat acagctaaag agtgtatgga aacacttctt   5280
tcttccaatg ccagcatgaa ggaagaactt gaaagggtca aaatggagta tgaaaccctt   5340
tctaagaagt ttcagtcttt aatgtctgag aaagactctc taagtgaaga ggttcaagat   5400
ttaaagcatc agatagaagg taatgtatct aaacaagcta acctagaggc caccgagaaa   5460
catgataacc aaacgaatgt cactgaagag ggaacacagt ctataccagg tgagactgaa   5520
gagcaagact ctctgagtat gagcacaaga cctacatgtt cagaatcggt tccatcagcg   5580
aagagtgcca accctgctgt aagtaaggat ttcagctcac atgatgaaat taataactac   5640
ctacagcaga ttgatcagct caaagaaaga attgctggat tagaggagga gaagcagaaa   5700
aacaaggaat ttagccagac tttagaaaat gagaaaaata ccttactgag tcagatatca   5760
acaaaggatg gtgaactaaa aatgcttcag gaggaagtaa ccaaaatgaa cctgttaaat   5820
cagcaaatcc aagaagaact ctccagagtt accaaactaa aggagacagc agaagaagag   5880
aaagatgatt tggaagagag gcttatgaat caattagcag aacttaatgg aagcattggg   5940
aattactgtc aggatgttac agatgcccaa ataaaaaatg agctattgga atctgaaatg   6000
aagaacctta aaaagtgtgt gagtgaattg gaagaagaaa agcagcagtt agtcaaggaa   6060
aaaactaagg tggaatcaga aatacgaaag gaatatttgg agaaaataca aggtgctcag   6120
aaagaacccg gaaataaaag ccatgcaaag gaacttcagg aactgttaaa agaaaaacaa   6180
caagaagtaa agcagctaca gaaggactgc atcaggtatc aagagaaaat tagtgctctg   6240
gagagaactg ttaaagctct agaatttgtt caaactgaat ctcaaaaaga tttggaaata   6300
accaaagaaa atctggctca agcagttgaa caccgcaaaa aggcacaagc agaattagct   6360
agcttcaaag tcctgctaga tgacactcaa agtgaagcag caagggtcct agcagacaat   6420
ctcaagttga aaaaggaact tcagtcaaat aaagaatcag ttaaaagcca gatgaaacaa   6480
aaggatgaag atcttgagcg aagactggaa caggcagaag agaagcacct gaaagagaag   6540
aagaatatgc aagagaaact ggatgctttg cgcagagaaa aagtccactt ggaagagaca   6600
attggagaga ttcaggttac tttgaacaag aaagacaagg aagttcagca acttcaggaa   6660
aacttggaca gtactgtgac ccagcttgca gcctttacta agagcatgtc ttccctccag   6720
gatgatcgtg acagggtgat agatgaagct aagaaatggg agaggaagtt tagtgatgcg   6780
attcaaagca aagaagaaga aattagactc aaagaagata attgcagtgt tctaaaggat   6840
caacttagac agatgtccat ccatatggaa gaattaaaga ttaacatttc caggcttgaa   6900
catgacaagc agatttggga gtccaaggcc cagacagagg tccagcttca gcagaaggtc   6960
tgtgatactc tacaggggga aaacaaagaa cttttgtccc agctagaaga gacacgccac   7020
ctataccaca gttctcagaa tgaattagct aagttggaat cagaacttaa gagtctcaaa   7080
gaccagttga ctgatttaag taactcttta gaaaaatgta aggaacaaaa aggaaacttg   7140
gaagggatca taaggcagca agaggctgat attcaaaatt ctaagttcag ttatgaacaa   7200
```

-continued

```
ctggagactg atcttcaggc ctccagagaa ctgaccagta ggctgcatga agaaataaat   7260
atgaaagagc aaaagattat aagcctgctt tctggcaagg aagaggcaat ccaagtagct   7320
attgctgaac tgcgtcagca acatgataaa gaaattaaag agctggaaaa cctgctgtcc   7380
caggaggaag aggagaatat tgttttagaa gaggagaaca aaaaggctgt tgataaaacc   7440
aatcagctta tggaaacact gaaaaccatc aaaaaggaaa acattcagca aaaggcacag   7500
ttggattcct ttgttaaatc catgtcttct ctccaaaatg atcgagaccg catagtgggt   7560
gactatcaac agctggaaga gcgacatctc tctataatct tggaaaaaga ccaactcatc   7620
caagaggctg ctgcagagaa taataagctt aaagaagaaa tacgaggctt gagaagtcat   7680
atggatgatc tcaattctga gaatgccaag ctagatgcag aactgatcca atatagagaa   7740
gacctgaacc aagtgataac aataaaggac agccaacaaa agcagcttct tgaagttcaa   7800
cttcagcaaa ataaggagct ggaaaataaa tatgctaaat tagaagaaaa gctgaaggaa   7860
tctgaggaag caaatgagga tctgcggagg tcctttaatg ccctacaaga agagaaacaa   7920
gatttatcta aagagattga gagtttgaaa gtatctatat cccagctaac aagacaagta   7980
acagccttgc aagaagaagg tactttagga ctctatcatg cccagttaaa agtaaaagaa   8040
gaagaggtac acaggttaag tgctttgttt tcctcctctc aaaagagaat tgcagaactg   8100
gaagaagaat tggtttgtgt tcaaaaggaa gctgccaaga aggtaggtga aattgaagat   8160
aaactgaaga aagaattaaa gcatcttcat catgatgcag ggataatgag aaatgaaact   8220
gaaacagcag aagagagagt ggcagagcta gcaagagatt tggtggagat ggaacagaaa   8280
ttactcatgg tcaccaaaga aaataaaggt ctcacagcac aaattcagtc ttttggaagg   8340
tctatgagtt ccttgcaaaa tagtagagat catgccaatg aggaacttga tgaactgaaa   8400
aggaaatatg atgccagtct gaaggaattg gcacagttga aagaacaggg actcttaaac   8460
agagagagag atgctcttct ttctgaaacc gccttttcaa tgaactccac tgaggagaat   8520
agcttgtctc accttgagaa acttaaccaa cagctcctat ccaaagatga gcaattgctt   8580
cacttgtcct cacaactaga agattcttat aaccaagtgc agtccttttc caaggctatg   8640
gccagtctgc agaatgagag agatcacctg tggaatgagc tggagaaatt tcgaaagtca   8700
gaggaaggga agcagaggtc tgcagctcag ccttccacca gcccagctga agtacagagt   8760
ttaaaaaaag ctatgtcttc actccaaaat gacagagaca gactactgaa ggaattgaag   8820
aatctgcagc agcaatactt acagattaat caagagatca ctgagttaca tccactgaag   8880
gctcaacttc aggagtatca agataagaca aaagcatttc agattatgca agaagagctc   8940
aggcaggaaa acctctcctg gcagcatgag ctgcatcagc tcaggatgga gaagagttcc   9000
tgggaaatac atgagaggag aatgaaggaa cagtacctta tggctatctc agataaagat   9060
cagcagctca gtcatctgca gaatcttata agggaattga ggtcttcttc ctcccagact   9120
cagcctctca aagtgcaata ccaaagacag gcatccccag agacatcagc ttccccagat   9180
gggtcacaaa atctggttta tgagacagaa cttctcagga cccagctcaa tgacagctta   9240
aaggaaattc accaaaagga gttaagaatt cagcaactga acagcaactt ctctcagcta   9300
ctggaagaga aaaacaccct ttccattcag ctctgcgata ccagtcagag tcttcgtgag   9360
aaccagcagc actatggtga ccttttaaat cactgtgcag tcttggagaa gcaggttcaa   9420
gagctgcagg cggggccact aaatatagat gttgctccag gagctcccca ggaaaagaat   9480
ggagttcaca gaaagagtga ccctgaggaa ctaagggaac cgcagcaaag cttttctgaa   9540
gctcagcagc agctatgcaa caccagacag gaagtgaatg aattaaggaa gctgctggaa   9600
```

```
gaagaacgag accaaagagt ggctgctgag aatgctctct ctgtggccga ggagcagatc   9660

agacggttag agcacagtga atgggactct tcccggactc ctatcattgg ctcctgtggc   9720

actcaggagc aggcactgtt aatagatctt acaagcaaca gttgtcgaag gacccggagt   9780

ggcgttggat ggaagcgagt cctgcgttca ctctgtcatt cacggacccg agtgccactt   9840

ctagcagcca tctactttct aatgattcat gtcctgctca ttctgtgttt tacgggccat   9900

ctatagactt agttgttact ctttggacca ctcccctcaa aacttggaat tctctcacct   9960

ctaacatcag aacatcaatt ccagtggaac agtcttccca tttacaggtc ttctctccaa  10020

ctcttcacgg aaagtgcctg caaaaacaga ggtggatacg aggacaggtt ggagctgcag  10080

ggactggcga gtctgctttc ttctactgcc ctgagcctga acgcttctgc ttaatctgag  10140

aatcacattt ggtttgttga gcctaatatt tgttgagatt ttgcaggacc ctgatctttt  10200

gtggtcctgt aaaagatact gaggaatgtc tttcagccaa gccaagagga tggtttcaat  10260

aaacctaata atctgaagtt cagtatcatt ttgattgata actttctttg ccttgtttgc  10320

ctgtattttc tcctgtttca gggggaaggt ggctctgcca taaacagagt tcagggaaat  10380

gaacatgtca cctcatagga catctgattt aggtctcttg cagaataggg tggtgaaagc  10440

tgaaggaact ccctaggggt tttagctgtt agatcacatg ggaggacagc atcttcttcc  10500

ctgccaattt cagatataat tggagggaga atttcaggtc ttagactata aggatagaat  10560

ccctttgctt ttgcccttga tcacatgtat actaaggtat taagtggccc aagtctttcc  10620

tttcaccaaa gggcagggag aagtgtctat ggacagcagg gttccaattc ttgtcattcc  10680

aggaatatct gaatattcct ggaatgtgga ccctgagaca gtgctcaggg gccactggga  10740

gccaatatta ggcattgact ctcagccagg agtctgactg gtctaacacc acactgcaac  10800

tcctgacctc ttgaagtact aagctacttt gctgttagtg acagttatta cagtttctca  10860

gccccattgt ctctgccctc tgtggcaatg gaaggagaat atagagaaga caaaattaaa  10920

tatagataga cctgagaagg acagccagga tagaattcca tttgtgccta ttccctgcct  10980

cccctcccct cccccatcct accagttggt tattttctca ttgcatacgt gatgtgttca  11040

ctgcctagcc tctccctaaa gaagagagaa gacaagtggg ctgactgatc tgctctaaat  11100

ctactgtggt gattaaatct tggttacaac atcctgggaa gtttcctgaa caactgtaaa  11160

ataataaaat tattttcaga atgaa                                        11185
```

<210> SEQ ID NO 32
<211> LENGTH: 6287
<212> TYPE: DNA
<213> ORGANISM: Homo sapiens

<400> SEQUENCE: 32

```
gcggcggcgg cggcggcggc agcagcgggg ctgggggcgg cgagtggccc gcgcgacacg     60

cgccggcctc gaccctatgc tttgattcgc gtggcgcagg cgcctactgc cccgccggcg    120

gggcccgggc ttcctgccgc gggatgttct cccgaaggag ccacggggat gtgaagaagt    180

ccacccagaa ggtgctggac ccgaagaagg acgtgctgac ccgcctgaag cacctgcggg    240

cgctgctgga taatgtggat gcaaatgatc ttaagcagtt ttttgagacc aactattctc    300

agatatattt catcttctat gaaaatttta tagcactgga aaatagtttg aaattaaaag    360

ggaataataa gtcacaaagg gaggagctgg actccatcct cttccttttt gaaaaaatac    420

tgcagtttct acctgaacga attttctttc gatggcatta ccagagtata ggctcaactt    480

taaagaagct tctacacact ggaaattcta ttaagataag atgtgaagga atcaggctgt    540
```

-continued

```
ttcttctgtg gcttcaagca cttcagacaa actgtgcaga agagcaggtt ctgatttttg    600
cttgcctggt gcctggtttc ccagcagtca tgtcatccag gggcccttgc acactggaga    660
cactcatcaa tcccagccct agtgtagctg atgtaaagat atatccagaa gaaatcactc    720
cactcctacc agccatatca ggggagaaga ttgctgagga ccaaacctgc tttttcttc     780
aaatactgtt gaagtatatg gttattcagg ctgcgagctt ggagtggaag aataaggaga    840
atcaagatac tggttttaaa tttcttttta cattgtttcg aaagtattat cttcctcatt    900
tatttccatc atttactaag ttaacaaaca tctacaaacc tgtacttgac atcccccatt    960
tgagaccaaa gcctgtgtac attactacca ctcgagacaa tgagaacatt tacagtacaa   1020
agattccata tatggcagct cgtgttgttt ttattaagtg gattgtaacc ttctttttgg   1080
aaaaaaagta tctaactgca acacaaaaca ctaaaaatgg agttgatgta ttgcctaaaa   1140
tcatccagac tgttggtggt ggtgctgtgc aggagagagc gcctgagctg gatggtggtg   1200
ggcccacgga gcaggacaaa agccattcta acagcagcac cttgtcggac cgaagactca   1260
gcaactccag cctctgtagc attgaagaag agcaccgaat ggtgtatgaa atggtacagc   1320
ggattctctt gtcaacacga ggttatgtca acttcgtgaa tgaagtattt caccaggcat   1380
ttttgttgcc ttcctgtgag atagctgtaa caagaaaagt agttcaagtg tacagaaagt   1440
ggattctcca ggacaaacct gtgttcatgg aggagccaga tagaaaagat gttgcccaag   1500
aagatgctga aaaattagga ttttccgaga ctgatagcaa ggaggcctca tctgaaagtt   1560
ctggtcataa acgatcttcc agttggggac gcacatactc cttcacaagt gcaatgagca   1620
gagggtgtgt gacagaggag gaaaatacaa atgtgaaagc cggcgtccag gctttgttgc   1680
aggtattttt gacgaactct gcaaacatct tttgttgga accatgtgct gaagttcctg    1740
tgctcttgaa agaacaagtt gatgcttgta aagctgtttt gattattttt aggcgcatga   1800
taatggagct tacaatgaat aaaaagacat gggaacagat gttgcaaata ctactcagga   1860
taacagaagc tgtcatgcag aagccaaagg ataaacaaat aaaggacttg tttgcccaga   1920
gcttggcagg gttactattt aggacgctca tggtagcttg gatccgagca aacctctgtg   1980
tgtacatttc tcgagagctc tgggatgact ttcttggtgt gctgtcctcc ctcacggaat   2040
gggaggaact tataaacgag tggccaaca ttatggactc cttgacagca gtgcttgcaa    2100
gaaccgttta tggagttgag atgacaaacc tacctctgga taaattaagt gaacaaaagg   2160
aaaagaagca acgaggcaaa ggctgtgttc tagatcctca gaaaggaacc accgtgggga   2220
ggtccttttc tctcagctgg cggagccacc cagatgtgac cgaaccgatg cgatttagga   2280
gtgccaccac gtctggagca ccgggagtgg aaaaggcaag aaatattgtt cgccaaaaag   2340
caactgaagt ggaggagtgt caacagtcag aaaatgcacc tgcagccgga tctggccatc   2400
tcacagtggg acagcagcag caggtccttc ggagcagcag cacctccgac atccccgagc   2460
cgctgtgctc agattcttct cagggtcaaa aggcagaaaa cacacagaat tcgagttctt   2520
cagagcctca gcctattcaa gagaataaag gacatgtgaa gagagaacat gaaggaataa   2580
caatcttagt tcgaagaagc agcagccctg ctgaattgga tttgaaagat gatttgcagc   2640
agacacaagg aaaatgtagg gaaagacaga agagtgaaag taccaacagt gacacaactc   2700
tgggctgtac caatgaggca gagctgtcca tgggcccatg gcagacctgt gaggaagacc   2760
cagaactgaa tactcccaca gatgttgtgg ctgatgctga tgcccgtcat tggttacaac   2820
tgagtcccac cgatgcttca aatttaacag atagcagcga gtgcctcaca gatgactgta   2880
gtataatcgc cggggggagc ctcactggtt ggcacccaga ctctgctgct gtgttatggc   2940
```

-continued

```
gaagggtctt ggggatcctc ggagatgtga ataacatcca gtcacccaag atccatgcca   3000

gagttttctg ctatctctat gaactctggt acaaactagc aaagatacgg gataatctag   3060

caataagcct ggataaccag tcttctccat ctcctccagt tttgatccca ccactcagaa   3120

tgtttgcatc atggctgttt aaggcggcga cactgccaaa tgaatataag gaaggcaaac   3180

tacaagccta caggctgatc tgtgccatga tgaccagacg ccaggacgtt ctgccaaact   3240

cagatttcct ggtgcatttt taccttgtga tgcacctggg attaaccagc gaggatcagg   3300

atatcttaaa tacgatcata aggcactgtc caccccgctt tttctccctg ggttttcctg   3360

gcttctcaat gctggtgggg gacttcatca cggccgctgc cagggtcctt agcacagaca   3420

ttttgacggc gcctcgttca gaggctgtca ctgtcctcgg ctctctggtc tgctttccaa   3480

atacctacca ggagattcct ttactgcagt cagtgccaga agtaaatgag gccattacag   3540

gaactgaaga tgtcaagcat tacctcataa atattttact gaagaatgcc acagaagaac   3600

caaatgaata tgcaagatgc attgctgttt gctcccttgg ggtctggata tgtgaagagc   3660

ttgcacagtg tacaagccac cctcaggtga aagaggccat caatgtgata ggagtaactc   3720

tgaagtttcc caacaaaatc gtggcccagg tagcttgcga tgtccttcag ttgctggttt   3780

cctactggga gaagcttcag atgtttgaaa cctctctgcc tcggaaaatg gcagaaatcc   3840

tcgtggccac agttgctttt cttttaccaa gtgcagagta ctcctcagtg gaaacagaca   3900

agaagtttat tgtgtccttg ctactctgcc tcttggactg gtgcatggca ttgcccgtga   3960

gtgtccttct ccaccccgtg tccacagcag tcctagagga gcagcattcg gccagagccc   4020

ccttgctgga ttatatctac agggttttgc actgctgtgt gtgtggctca agcacgtaca   4080

cccaacagag tcactacata ctgaccctgg ctgacttgtc atccacggat tatgacccct   4140

tcctgccact ggcaaatgtg aagagctctg agccagtcca gtatcattca tcagcagaat   4200

tgggtaacct gctgactgtt gaagaggaga agaagagaag aagtttggag ttgatccctt   4260

tgactgctcg aatggtgatg gcccacctgg tgaaccacct ggggcactac cccctcagtg   4320

ggggccctgc catactgcac agccttgtca gcgagaacca tgacaatgcc catgtggaag   4380

gctccgagct gtcctttgag gtgttcagaa gtccaaacct gcagctgttt gtatttaatg   4440

atagcaccct catctcctac cttcagacac ccacagaagg accggtaggg ggatcaccag   4500

tgggctctct ctctgatgtg agagtaattg tgagggatat ctcagggaag tactcttggg   4560

atggtaaggt tttatatgga cctttggaag gctgcttagc acccaatgga agaaatcctt   4620

catttctgat ttcgagctgg catcgtgaca catttggacc tcagaaagac tcttctcaag   4680

ttgaggaggg ggatgatgtt cttgacaaat tacttgaaaa cattggccat acaagtcctg   4740

aatgcctttt accgtcacag ctaaatctaa atgaaccttc cctaacccca tgtggcatga   4800

actatgacca agagaaggaa atcattgagg tcattttgcg ccaaaatgct caagaggatg   4860

agtatatcca gagtcataac ttcgattctg caatgaaagt caccagccaa gggcagccct   4920

ccccagtgga gccccgagga cccttttatt tctgcaggtt attgcttgat gacttgggaa   4980

tgaattcttg ggacagaagg aagaattttc atctattgaa gaaaaattca aaattattga   5040

gagagctgaa aaatttggac tcccgccagt gccgtgagac acacaaaatc gcagtgtttt   5100

acattgctga aggtcaagaa gacaagtgtt caatcctctc taatgaaaga ggaagccaag   5160

catatgaaga ctttgttgct ggacttggat gggaggtgga tctctccacc cactgtgggt   5220

tcatgggtgg ccttcagcgc aatggcagca ccgggcagac ggccccttac tatgctacct   5280

caactgtgga agtgattttc catgtttcca ctcgaatgcc gtcagactca gatgattccc   5340
```

-continued

```
tcaccaaaaa gcttcgtcac ttggggaatg acgaggtcca tatcgtctgg tctgaacact   5400

ccagagacta ccgcaggggt attatcccaa ctgcctttgg agatgtttca atcattattt   5460

acccaatgaa gaatcacatg ttcttcatcg cgataacgaa gaaacctgag gttccatttt   5520

ttgggcctct gtttgatgga gccatagtga gtgggaagct gctgccaagc cttgtatgtg   5580

ccacgtgcat caacgccagc agggctgtga agtgcctcat cccactctac cagagcttct   5640

atgaagagcg agctctgtat ctcgaagcaa taattcagaa ccaccgcgaa gtaatgacat   5700

tcgaggattt cgcagcccaa gtcttttctc cctctcccag ctactccctc agcggaacgg   5760

attaaaacac gtaaaggtct catttcaata tttgagcaag ggccctggc ctccagtctg   5820

agtgctgacc tcgaagagcc cctgagtgag gaggagacag aacaccctct cctgcctctg   5880

ccccgagcca ctaaacccag aatctccagg aaatttcgtt gctgtactag tgccctcagc   5940

aggtcttccc attagtggac ttctgaagcc catggtgaat cccactaccg tgtctcagat   6000

gggactcaaa ctaggctgta tcatcttgtc ctgaaacctc acaaaccttg gacttccaaa   6060

gaagaaaaga aaaagtcacc aaaaaccaga gatgaaccca ctgacacgtg ggcactggtg   6120

tggctgctct gggcagatga cagcaggaaa agattctgcg ctttcaggga gggggcagag   6180

ggcagcttgc ttctgcaccc caagttgttt cttctcattt atgaacccaa gcatgattca   6240

caaaggggct ggcaaaacaa ttgtctaatt gaggaatctg atctgca                6287
```

```
<210> SEQ ID NO 33
<211> LENGTH: 5464
<212> TYPE: DNA
<213> ORGANISM: Homo sapiens

<400> SEQUENCE: 33

aggcaacagc ccggaagccg ctggctgggt taacctgtgg cgcgctccgc ggttccggcg     60

cctgaagttt tagctgcggt ggcggcggca gtcgggaccg actgcaaggc aggttgagat    120

gatggatctg aggcttgcag ctcgcagtcc caacgagcct tagggaccag ggctaccaaa    180

agggtgggga gaacggtggt ggcatctgtc tgttgcctgg gatccaggcg cccggttggg    240

gaatccttac ttcaggaagc gcagccgcgg ctctgtgttt tgagagtgca aatgtcattt    300

gtcagagtga accgctgtgg tccccgagtt ggtgtaagaa agacaccgaa agtaaagaag    360

aagaaaactt cagtgaaaca agaatgggat aataccgtga ctgatctaac cgttcatcgg    420

gcaactcccg aagatctggt acgccgtcat gaaatacaca aatcgaagaa tagagcatta    480

gtacactggg aactccaaga aaaagctttg aagagaaaat ggaggaagca gaaaccagaa    540

actttaaatc ttgagaaaag aagattgtct atcatgaagg agattctttc tgatcaatac    600

cagatgcaag atgtgttgga gaaatctgat catctaatag ctgcagcaaa agagctgttt    660

cctcgtaggc gcacagggtt tccaaatgta acagtggctc ctgattcctc tcagggtccc    720

attgtggtaa atcaagaccc tatcacccaa tctatcttta atgagtctgt catagaacct    780

caggctctta atgatgtaga tggtgaagaa gaaggaactg ttaatagcca gtcaggagaa    840

agtgagaatg agaatgagtt ggataactct ctaaactctc agtctaacac gaatacagac    900

aggtttctcc aacaactaac agaagagaat tttgagttaa ttagtaagtt gtggactgac    960

attcagcaga aaatagcaac ccagtcacaa ataactcctc caggaacgcc atcatctgct   1020

ctttcatcag gggagcaaag agctgctctg aatgctacca atgctgtcaa gagactccaa   1080

accaggcttc agcctgaaga atctactgag actctagact caagctacgt tgtgggacac   1140

gtgctgaact caaggaagca aaaacagctg ttaaataaag tgaaaaggaa accgaatttg   1200
```

-continued

```
catgctcttt ccaagccgaa gaaaaacata tcatcaggta gcacaacctc tgcagactta   1260
ccaaatagga ctaattccaa cctggatgtc ctcaaacaca tgatacatga agtggaacat   1320
gaaatggaag aatatgagcg gtggacaggt cgcgaggtca agggtctgca gagcagtcag   1380
ggtcttacag gcttcacttt gtcgctggtg agctccctct gtcgcctggt tcggtacctt   1440
aaagagagtg agatccagct acgtaaagaa gtagagacaa ggcaacaact ggaacaagta   1500
ttaggtgatc atcgagagct cattgatgct ctgacagctg aaattcttcg tcttagagaa   1560
gaaaacgctg ctacacaggc aagacttcag cagtacatgg tcacaacaga tgagcaactg   1620
atatcactca cacatgctat taagaactgt cctgtgataa ataacagaca agaaattcag   1680
gcatcagaaa gcggagccac aggtagaaga gttatggaca gtccagagcg tccagttgta   1740
aatgccaatg tctcagtgcc attgatgttc agagaggaag tggctgaatt cccacaggaa   1800
gagttgcccg ttaaactgtc tcaggtgcca gaccctccag ataacatgaa tctggccaag   1860
aattttccag cacatatttt tgagccagct gtgttgttaa caccacccag gcagaagagc   1920
aacttaaaat tctctcctct tcaggacgta ttgagaagga ctgttcaaac tcgtcctgct   1980
ccacgacttc ctccaactgt ggaaataatt gagaaggaac aaaattggga agagaagacc   2040
ttacctattg atacagacat tcagaattca agtgaagaga atcgtctctt cactcagaga   2100
tggagagtct ctcacatggg agaagatttg gagaacaaaa ctcaggctcc ttttgttaac   2160
ctctcacagc ccctctgcaa ttcccattcc aacactcaac agtcaagaag ccccacattc   2220
tcagaagagc tcccagtact gggagatggg cagcagctga gaacaaatga gtcattaata   2280
caaagaaagg acataatgac acgaattgct gatttgacat tgcagaattc agctatcaag   2340
gcacatatga ataatattat tgagcccaga ggagagcaag gggatggact ccgggagttg   2400
aacaaacaag aaagtgcaag tgacatgact tctacttttc cagtagcaca gtctctaaca   2460
ccaggtagta tggaggaacg gattgcagaa ttgaatcgac aaagtatgga ggctcgtgga   2520
aaactactgc agttgataga gcagcagaaa cttgttggtt tgaatctttc tccaccaatg   2580
tcacctgttc agttacctct cagagcatgg actgaaggag caaagaggac aattgaggta   2640
tctattccag gagcagaagc cccagaaagc tcaaaatgta gtactgtctc tcccgtcagc   2700
gggataaata caagaagatc ttccggggct actggtaatt cttgttctcc actaaatgcc   2760
acctcaggaa gtgggagatt cacacctctt aatccaagag caaagattga gaaacagaat   2820
gaagaaggct ggtttgctct ttctacccat gtatcataag tgaagtcaag tctcactgag   2880
tttgttctta ataatttatt acttcccttt ccctgctctg acttttaagt ttttatatcc   2940
ttctttcaga taaaacctac aaagatcctg tgaattagta ctaatgaaac agagaaataa   3000
agcaattatt ttttgacttt ctcaaataag ttttcaacaa ccaactgacc tacagctccc   3060
tgtgaatgaa actttgactg tagagaagtt aaagttttgt attttaatac tttcttaagt   3120
attttaaggg tttttttat taatacattt ttacctttat ctttattcag ggttttttga   3180
ggtttagtat atcttagttg atccatttat ttatttattt tcctgaagaa ctaatttgct   3240
ttgcatgtaa cttacaataa aattcctctg tgtgattaga gtctggcttt caggaatatg   3300
taacacccac ttttctttct tttttcttgg gaagtcattg ctgttcatca ctttttccat   3360
caagtgaaat atacagcctt aaaaacaata ggcctgggag tgtttgttta tatttgctta   3420
agcaggtaag agtggttgca tttattataa aatcttatgt agtttttaaa tgtgaaaatg   3480
tcatcaataa tggtaatgca aatcaaataa atatgattct agagctcaaa tgcctaaatg   3540
tggtaacatt gatttaatgg tatatttaat gcttcaaaca attaaataga aaaagttgct   3600
```

-continued attaattttc ccagccctga atttaagcag atctttcagg gtagatttct cttttttttt 3660
tttttttgag acagagtctt gctttattgc ccaggctgga gtgcagttgt ataatctggt 3720
tcactgccac ctcagtctcc tgggttcaag caatcctctt acctcagcct cctgagtagc 3780
taggattata ggttcatgcc accacgccca gctaatttgt gtattttcag tagagacggg 3840
gtttcaccat gttggccagg ctgatctcga actcctgacc tcaaatgatc cacctgcctt 3900
ggtttcccaa agtgccggga ttacaggtgt gagccactgc acccggctca ggatagattt 3960
ttcagggtac ccttttggtt ctgagatgtt tatttctatt ttaaacttgt tttttgaatg 4020
atctctgctc cctggctcta tgataggaat tctcaacctg agtgaacaat tcaaactgag 4080
attacttgtg tttagactca tatattttga taacatatga cttctccagt atgccccaga 4140
aagctgctaa taacttgctc aacctgaaat ttacagtttt ccaaattaca ggttggcaga 4200
gatactggat tgataacaac atccacagtt atcatataat cattcttatg ctgtaaacaa 4260
aattattttg gttagcagaa tttaataatt aactgttaac tacatactag gcaatattgt 4320
agccacttta tgtgcttcat gacaccttat gggataggta ctattatcct cattttgcag 4380
atgaggaaac tgaggtacaa ggaggtattt tctcaaggtc acacaactag ggagtggtgg 4440
cattagaatg ggaacatagg cagtctttct ccaaagccta tgctgtgctg cctcttgttg 4500
gagagtaaac ctgttttaca gtgtgtgtag tatggaagca gcataataat aagaatagct 4560
gttccttatt gagccattac tgtggcagac accgtactat aagctgtggt atcaccatta 4620
tctcatttga atctcatagt agacctatca gttagaggta tgtaaatgct tcctcctctc 4680
ccagcacctt tacagatgag gatgctgagc cctagaggtg aagaaagttg tctaatgaca 4740
gagtgcttgt aagaggtaaa gccaagactt gaagctcttt cttgcagtta ctggatttct 4800
cctaatttac gggaactaat acagtacagt agctaaggat gcaagtactg aaaccagaaa 4860
tcttgcctca aatgccattt ctgccacttg agctgtgtac tttggacaaa ttaatctaat 4920
ctttcccatt tgaaagtcag acataatgtc ttccctagag gcttgtgagg attaagtgag 4980
gcaagtgtat gtaaatgggc tgagatcaga gcttggctca caacactcag taatgatcac 5040
tgccaatttt ttttggtata taaataaata aatacactat ttcccccatg tttccaattt 5100
ttaagacatt gtatagtgaa tttattgtat ctttctcaga ttaacaattg cacacagtgc 5160
ttgaaattta gaggtatttc acctgaaaag atgtctagag attgaaagaa aacatgctgg 5220
gcatatgatt tgaaaatata aataacatgc tatttaaaaa taagtttacc ctatgttttc 5280
tatcttttct ggcacctaga tataccattt aataagtaat agcaaggata atcatttttt 5340
taagccctgg aaaatcttga ttaaagagga catttcagta ttgcaaataa atgcatggta 5400
tttgtgtaac attgtggaaa ctaataaaca caaattgtat tatagcaaaa aaaaaaaaaa 5460
aaaa 5464

<210> SEQ ID NO 34
<211> LENGTH: 1673
<212> TYPE: DNA
<213> ORGANISM: Homo sapiens

<400> SEQUENCE: 34
attcccccgc aggccgggca tgggtggggg cgccgggccg tcacgatgag cgccctgggc 60
agcccggtcc gggcctacga ctttctgctc aagttcctgc tggtgggcga cagcgacgtg 120
ggcaagggcg agatcctggc gagcctgcag gatggcgcgg ccgagtcccc gtacggccac 180
ccggcgggca tcgactacaa gacgaccacc atcctgctgg acgggcggcg ggtgaagctg 240

-continued

```
cagctctggg atacttcagg ccagggaaga ttttgtacca tattccgctc ctactcccgg    300
ggcgcacagg gtgtgatcct ggtctatgac attgcgaacc gctggtcttt tgacggcatt    360
gatcgatgga ttaaggagat cgatgagcat gcccccggag tccccaagat cctggtgggg    420
aaccgcctgc acctggcgtt caagcggcag gtgcccacgg agcaggccca ggcctacgcc    480
gagcgcctgg gcgtgacctt ctttgaggtc agccctctgt gcaatttcaa catcacagag    540
tcgttcacgg agctggccag gatcgtgctg ctgcggcatg ggatggaccg gctctggcgg    600
ccgagcaagg tgctgagctt gcaagacctc tgctgccggg cggtcgtgtc ctgcacgccg    660
gtgcacctgg tggacaagct cccgctcccc attgccttaa gaagccacct caagtccttc    720
tcgatggcca acggcctgaa tgccaggatg atgcacggcg gttcctactc cctcaccacc    780
agctccaccc acaaaaggag cagcctccgc aaagtgaagc tcgtccgccc cccccagagc    840
ccccccaaaa actgcaccag aaacagctgc aaaatttctt aaggaaggca ctgaaagaaa    900
cacggcggaa tctctccagg agaagctcgg cgttaccccc ggcagctggt ggatgcatct    960
cagatcccgg ttcctctcgg cgaatgctgc ttgcgaatgt gtgcgacgcc ttccgtgtga   1020
tggaaacaca ctaccccgtc ggacttcgaa tttctacgtg gatgtgcatg aagctcttgt   1080
tttcgatgtg tgtttgtaaa gggaaaatta gtactctgct cgactcttgg taacatgaaa   1140
ttctgaatgt tactttatca tgattgcact gcaacttttt tccttaaaat aactgctttt   1200
gtaagaacgg tgatattgga gtgattagta taaattcaat ggaatttgag aagcaatggc   1260
agcgggataa tttagagtca ctgatattac gagaggggtc tttttgtaaa cctccttttc   1320
aatgtcaaag caccaattta taaaacgctg cagatgtaga ggttatgtgc aactgatctg   1380
tccagtttgt gtatgaaatg gatttgataa agtttttgct agttatttac tacattttgg   1440
gattaataag tgatttatat gcatattttt ctgtaaatct acagtttttt gtacaagata   1500
ttctacaagt tatgaagcta agggaagaaa atgccaaaga tacctctagt tatgttgaac   1560
acagccagca cagtttcgac aggtcaagga agagctgttt cagtaaagaa tgaagtgaaa   1620
acacttattt aggaaaatgt ttctcaacaa taaaatgtat agttgtttct ctc          1673
```

```
<210> SEQ ID NO 35
<211> LENGTH: 2222
<212> TYPE: DNA
<213> ORGANISM: Homo sapiens

<400> SEQUENCE: 35

ggctcgagtg cctggcgggc tccggcttcc gcgtccgccc ctgctccggc ttcgcccgca     60
gctccgcgcc cgcgggcaac caagccccca gcgaagcccg cacagctccg ggtgccagga    120
cggggggcca tgccgtgccg gagggaggag gaagaggaag ccggcgagga ggcggagggg    180
gaggaagagg aggacgacag cttcctcctg ctgcagcagt cggtgacgct gggcagctcg    240
ggcgaggtgg accggctggt ggcccagatc ggcgagacgc tgcagctgga cgcggcgcag    300
gacagcccgg cctcgccgtg cgcgcccccg ggggtgccgc tgcgggcccc ggggcccctg    360
gctgcggcgg tgccggcgga caaggcccgg cccccggcgg tgccgctgct gctgccgccc    420
gcttcggctg agacggtggg cccggcgccc tctggggccc tgcgctgcgc cctaggggac    480
cgcggccgcg tgcgcggacg cgctgcgccc tactgcgtgg cggaggtcgc cgcaggcccc    540
agcgcgctgc cggggccgtg ccggcgagga tggctcaggg acgcggtcac ctcccgccgc    600
ttgcagcagc gccgatggac ccaagccggg gcacgcgccg gcgacgacga cccgcatcgg    660
ctcctccagc agctcgtgct ctcgggaaac ctcatcaagg aagccgtgcg gagactccaa    720
```

-continued

```
cgagccgtcg ccgcggttgc agccacgggc cccgcaagcg cccctgggcc cgggggaggc    780
cgcagcggac ctgaccgcat tgccctgcag ccctcaggct ccttgctctg acgcaggcct    840
cctggaggag gaagtggagg ccgctgcgta gacccaacag cgtccagttc ctactaactc    900
tgagctgaag ccgacgtcgc cagcctggga gcgaccactt tggctgcggg gaggcgcgtg    960
gggagagatc tcaaccagag aagttaccag ccgcggcgag gccgtcggag aaaacttaag   1020
cgtggagaaa tgtatgcgcc agggtgcttc cgtggggcat gagaatttcc cgggccatcc   1080
aagcccaagg acctgggata aactgggaga actatggcag ctacttgcat cgacttgtac   1140
ctcacttagc ccttgggggc gtcgtgagct tggattgttt aaggagggct caggggtagg   1200
aatcgcgatg gctttataac aatacttgaa aactaacgac acgcatacat tttcttattt   1260
tctggtggag gagcttagta agtggtgcta caattgctgt gcaaagaaat tccagagggg   1320
agaagaatgt aaaagtttgg tggtgggtgg cttggcattg ccccttttc ccaccgattc   1380
ggtggctggt gaaggtggga gatgtgaact ccaattaagg gactggagag aggtgaagaa   1440
ttttgcaggt gggagatttg gatttgaatg tggacttgta aatgacttga ccttgccatc   1500
tgtgttcaag gtcacggttt gctgtggggt tcctgggaga gcttactcac cccggagtct   1560
tttctttctc ttgctccaag aagagccctg ttggtgcttt accaccgctt ggagtctccc   1620
gaggacacaa acaggcagag agggacgtgt agggagagtt ctttcctgtt ttctgtgctt   1680
tcctttttac aggactcccg gaaggccact catggccatg ccaggagctt tctcagaaac   1740
agtcataaac gatctcttga gtctctttct tgtcctccca gctgagcttt cttattccac   1800
cctttctggt gtctatagga atgcatgaga gaccctggac gtttttctgc tctcttctgg   1860
ccctccatgg agtcatgggc ctcggcctcg gcggctcctc accctcacaa tttatttcct   1920
cctcccgtgc cagcccttct tttgtgtctg aaaccggttt taaaatgtga ctctcccaga   1980
gaagaagccg ctggctgtat gaaacttgac ggcgcttttg taaggtgcca cccccaaact   2040
ttaaggtagc taaaccaatt tttaaaagat tcaatggctt gttcatcctc cagatgtagc   2100
tattgatgta cacttcgcaa cggagtgtct gaaattgtgg tggtcctgat ttataggatt   2160
tcataattaa aatgtctgct gaataaattt ggcttttgtt ttggaaaaaa aaaaaaaaaa   2220
aa                                                                  2222
```

<210> SEQ ID NO 36
<211> LENGTH: 4468
<212> TYPE: DNA
<213> ORGANISM: Homo sapiens

<400> SEQUENCE: 36

```
gatttcctga gcatgcctag ggaatgacag gcatctccac aggcaggctg catccacctt     60
ggctggggtg tcgtcattgg ctgcctatta gaaaaacgac aggacaatgc ataccaccgc    120
ctcccgactg taaacatagg ggatatgtgt tcacttagca tggacttctg ggaggggcca    180
aggaagggcg gtctggagtt ttattgaata gagcagtgtg tattcggctg cctgcctgcc    240
cgcctgcttg ctctctggct gtgctcctgc ttaaagaaat cagtccttcc tttccgactt    300
agtcctcggg aagaagtttc agactacaag gtatcattgg aacatttcaa gatcatcaaa    360
tcaaattcca cagggattgg tgaccaacca gaaggctcag acatctgatt gctgacctgt    420
ccagacatca tctggtctcc ctgaacctga aatcacacca tggatgattt tgagcgtcgc    480
agagaactta gaaggcaaaa gagggaggag atgcgactcg aagcagaaag aatcgcctac    540
cagaggaatg acgatgatga agaggaggca gcccgggaac ggcgccgccg agcccgacag    600
```

-continued gaacggctgc ggcagaagca ggaggaagaa tccttgggac aggtgaccga ccaggtggag 660
gtgaatgccc agaacagtgt gcctgacgag gaggccaaga caaccaccac aaacactcaa 720
gtggaagggg atgatgaggc cgcattcctg gagcgcctgg ctcggcgtga ggaaagacgc 780
caaaaacgcc ttcaggaggc tctggagcgg cagaaggagt tcgacccaac aataacagat 840
gcaagtctgt cgctcccaag cagaagaatg caaaatgaca cagcagaaaa tgaaactacc 900
gagaaggaag aaaaaagtga aagtcgccaa gaaagatacg agatagagga aacagaaaca 960
gtcaccaagt cctaccagaa gaatgattgg agggatgctg aagaaaacaa gaaagaagac 1020
aaggaaaagg aggaggagga agaggagaag ccaaagcgag ggagcattgg agaaaatcag 1080
atcaaagatg aaaagattaa aaaggacaaa gaacccaaag aagaagttaa gagcttcatg 1140
gatcgaaaga agggatttac agaagttaag tcgcagaatg gagaattcat gacccacaaa 1200
cttaaacata ctgagaatac tttcagccgc cctggaggga gggccagcgt ggacaccaag 1260
gaggctgagg gcgcccccca ggtggaagcc ggcaaaaggc tggaggagct tcgtcgtcgt 1320
cgcggggaga ccgagagcga agagttcgag aagctcaaac agaagcagca ggaggcggct 1380
ttggagctgg aggaactcaa gaaaaagagg gaggagagaa ggaaggtcct ggaggaggaa 1440
gagcagagga ggaagcagga ggaagccgat cgaaaactca gagaggagga agagaagagg 1500
aggctaaagg aagagattga aaggcgaaga gcagaagctg ctgagaaacg ccagaagatg 1560
ccagaagatg gcttgtcaga tgacaagaaa ccattcaagt gtttcactcc taaaggttca 1620
tctctcaaga tagaagagcg agcagaattt ttgaataagt ctgtgcagaa aagcagtggt 1680
gtcaaatcga cccatcaagc agcaatagtc tccaagattg acagcagact ggagcagtat 1740
accagtgcaa ttgagggaac aaaaagcgca aaacctacaa agccggcagc ctcggatctt 1800
cctgttcctg ctgaaggtgt acgcaacatc aagagtatgt gggagaaagg gaatgtgttt 1860
tcatccccca ctgcagcagg cacaccaaat aaggaaactg ctggcttgaa ggtaggggtt 1920
tctagccgca tcaatgaatg gctaactaaa accccagatg gaaacaagtc acctgctccc 1980
aaaccttctg acttgagacc aggagacgta tccagcaagc ggaacctctg ggaaaagcaa 2040
tctgtggata aggtcacttc cccactaag gtttgagaca gttccagaaa gaacccaagc 2100
tcaagacgca ggacgagctc agttgtagag ggctaattcg ctctgttttg tatttatgtt 2160
gatttactaa attgggttca ttatctttta tttttcaata tcccagtaaa cccatgtata 2220
ttatcactat atttaataat cacagtctag agatgttcat ggtaaaagta ctgcctttgc 2280
acaggagcct gtttctaaag aaacccatgc tgtgaaatag agacttttct actgatcatc 2340
ataactctgt atctgagcag tgataccaac cacatctgaa gtcaacagaa gatccaagtt 2400
taaaattgcc tgcggaatgt gtgcagtatc tagaaaaatg aaccgtagtt tttgtttttt 2460
taaatacaga agtcatgttg tttctgcact ttataataaa gcatggaaga aattatctta 2520
gtaggcaatt gtaacacttt ttgaaagtaa cccatttcag atttgaaata ctgcaataat 2580
ggttgtcttt aaaaaaaaaa aagaaatgta ctgttaaggt attacttttt ttcatgctga 2640
tgattcatat ctaaattaca ttattatgtt agctgacagt ggtactgatt ttttaggttg 2700
gttgttttgt ggatttcttt agtagtgata gtagcctgaa ccacatttta gataactcaa 2760
ttatgtatgt atgtgcatac acatatacaa acacactaat ggtagaatgc ttttttatgt 2820
gctagactat tatatttagt agtatgtcat tgtaactagc caatatcaca gcttttgaaa 2880
aattaaaaaa tcacactata ttaatatttc atatttgcca acagaaacat ggcagatagg 2940
tatcaatatg ttttcaatgc ctgatgacct ataagaagaa agtattgaaa agaagagaga 3000

```
ttagaactgt tagaaggagt tgaaattttc taaaagacat agtatttagt ttataattaa   3060
atgcattctt gaagtccagt gtgaatttta ttaatgctat catctcgacc aagctcaaag   3120
cctacttatt agaaacaatg aagttcacaa taggtcataa ggtctcttcc ttttctaaaa   3180
ttgaaagaca agaaatttag tgccaatatt gtacagacag aaattccatg tatgagtctc   3240
aacaaagact acctttggct aaatgtctag aagcagagaa gtaaagtgag caaaatccag   3300
tgttgaggag tcatgacagt actttgatct ttatatactc tgaagcattt cttcaaactt   3360
ttctactttt atttgtcatt gatacctgta gtaagttgac aatgtggtga aatttcaaaa   3420
ttatatgtaa cttctactag ttttactttc tcccccaagt cttttttaac tcatgatttt   3480
tacacacaca atccagaact tattatatag cctctaagtc tttattcttc acagtagata   3540
atgaaagagt cctccagtgt cttggcaaaa tgttctagta tagctggata catacagtgg   3600
agttctataa actcatacct cagtggactt aaccaaaatt gtgttagtct caattcctac   3660
cacactgagg gagcctccca aataactatt ttcttatctg cagtattcct ccagaagagc   3720
taaccagggc agggctggca tgagaagtga catctgcgtt acaaagtcta tcttcctcat   3780
aagtctgtaa agagcaattg aatcttctag ctttagcaaa cctaagccaa aggaaggaaa   3840
gccacgaaga atgcagaagt caaaccctca tgacaaagta ggcacaagtc tacaataagc   3900
taaatcagaa tttacaaata caagtgtccc aggtagcatt gactcccgtc attggagtga   3960
aatggatcaa agtttgaatt aaggcctatg gtaaggtaac attgctttgt tgtacttttg   4020
aacaagagct cctcctgatc actattacat atttttctag aaaatctaaa gttcagaaga   4080
gaatgtatca ctgctgactt ttattccaat atttggatgg agtaagtttt agggtagaat   4140
tttgttcagt ttggatttaa tcttttgaaa agtaaattcc ttgtttactg gtttgactat   4200
aattctctgt tatctttacg aggtaaaact gcaagctgac tagcatgttc tgtgaatctg   4260
ccattcctaa aaattttata aacacttgat actttcact gataatggat cgctccaata   4320
aacatatatt gtgaaaatgc atccacaata aatggaattc cttcctgcaa aatgtctttt   4380
tctcacttat ttttatgtac aatattgata gtgagaggta tgtctattat aataaagatt   4440
atggcacagt aaaaaaaaaa aaaaaaaa                                     4468
```

<210> SEQ ID NO 37
<211> LENGTH: 3486
<212> TYPE: DNA
<213> ORGANISM: Homo sapiens

<400> SEQUENCE: 37

```
tgtttcatct ttattcatta tcctttgttc tttaaaatct gatatattgg cataaaagta     60
attgtagata tatatatgaa tgtgatttat tttcctttac atatttttgt tgtgtacagc    120
agggcatata cttctcttgt cttggttgga tgcacaaatc tgtgtgcagt gctttttgcc    180
cgttgcctag acgatcactt ggtttctctg aggatgtctg gttctcgtaa agagtttgat    240
gtgaaacaga ttttgaaaat cagatggagg tggtttggtc atcaagcatc atctcctaat    300
tctacagttg acagccagca gggagaattt tggaaccgag gacagactgg agcaaacggt    360
gggagaaagt ttttagatcc atgtagccta caattgcctt tggcttcaat tggttaccga    420
aggtccagcc aactggattt tcagaattca ccttcttggc caatggcatc cacctctgaa    480
gtccctgcat ttgagtttac agcagaagat tgtggcggtg cacattggct ggatagacca    540
gaagtggatg atggcactag tgaagaagaa aatgaatctg attccagttc atgcaggact    600
tccaatagta gtcagacatt atcatcctgt catactatgg agccatgtac atcagatgaa    660
```

-continued

```
tttttccaag cccttaatca tgccgagcaa acatttaaaa aaatggaaaa ctatttgaga    720
cataaacagt tgtgtgatgt aattttagtc gctggtgatc gcagaattcc agctcacaga    780
ttggtgctct cctctgtctc agactatttt gctgccatgt ttactaatga tgtcagagag    840
gcaagacaag aagaaataaa aatggaaggt gtagaaccaa attcgttgtg gtccttgatc    900
cagtatgctt atacaggccg ccttgaatta aaagaagata atattgagtg cctgttatct    960
acagcttgcc ttcttcagct ttcacaggtt gtagaagcat gctgtaagtt tttaatgaaa   1020
cagcttcatc catccaactg tcttggaatt cgttcttttg ctgatgccca aggttgtaca   1080
gatttgcata aagtggctca caattatact atggagcatt tcatggaagt aatcagaaac   1140
caggaatttg tattattacc agccagcgaa attgcaaagc tcttggctag tgatgacatg   1200
aacattccta atgaggagac aatattgaat gcacttctta cttgggtccg tcatgatttg   1260
gaacagagac ggaaagatct aagtaaactt ttggcttata ttaggctacc tcttcttgca   1320
ccacagttcc tggcagacat ggaaaataat gtactttttc gggatgatat agaatgtcag   1380
aaactcatta tggaagcaat gaagtaccat ttattaccag agagacgacc catgttacaa   1440
agtcctcgga caaaacctag gaagtcaact gttggtacat tatttgcagt tgggggaatg   1500
gattcaacaa aaggagcaac aagcattgaa aagtatgatc tccgtacaaa tatgtggact   1560
ccagtagcaa atatgaatgg gaggaggcta cagttcggtg ttgcagtgct agatgacaaa   1620
ctgtatgtgg ttggaggaag agatggactg aagactttga atactgtaga gtgctacaac   1680
cccaaaacaa aaacttggag tgtgatgcca cctatgtcca cacatagaca tggccttggt   1740
gtggctgtac tggaaggtcc catgtatgcc gtaggaggac atgatggctg gagctatctg   1800
aacacagtgg aaagatggga ccctcaggct cgccagtgga attttgttgc cactatgtct   1860
acccctagga gtacagtagg tgtggcagta ctaagtggaa aactttatgc agttggtggt   1920
cgtgatggaa gttcttgtct caaatcagta gaatgttttg atcctcatac taataagtgg   1980
acactgtgtg cacagatgtc aaaaaggaga ggtggcgtag gagtgacgac ctggaatgga   2040
ctgctgtatg ctatagggggg gcacgatgct cccgcatcca acttgacttc cagactctca   2100
gactgtgtgg aaagatatga tcccaaaaca gacatgtgga ctgcagtagc atccatgagc   2160
atcagcagag atgcagtggg ggtctgttta cttggtgata agttatatgc tgttgggggg   2220
tatgatggac aggcatacct taatactgtg gaggcttatg atccccagac aaatgagtgg   2280
acccaggttg ctccactgtg cctaggaaga gctggagctt gtgttgtgac tgtaaaatta   2340
taatttagtg ccccgttttc tacatgaaga caccgtcttc ctttattaat ttagtataat   2400
tattctatca atggatacat ttttagtaaa tgtgcattgt cacaatcctg ggcacaaagt   2460
gcctgatgtc aaaatgaaga tagtaaaaca agggaggaag cagtggatgg accaggatta   2520
attcctttca tttcttagta aattaaaacc tgcagctggt ggattgtgat cacacattcc   2580
cgaagtaata agtgaggacg aatgcactgc tctggaacat aacccagtgc taactggggg   2640
tttcatttat tcagtcaagc acatcttact cacatccaga tttattttcc tacagtgcaa   2700
acacaccaga tgaaacttta aaatgttact ttttgtaagc ttatcataaa tgagttgcag   2760
taatttgttt gcttgtttgt ttaaccacaa ccactatttt aatgatatac taaagataac   2820
actatttagt tttttcagaa acatctgcat tatatgtgtg ttggttgtgg attttgtttc   2880
taaaattggc ttagtccaat aaataaagaa aagcattaag gacttaaagc aacaataacc   2940
aaataaaaac ttgataggat ctttgaagtc tatttaaata ttcattccat tacatctaga   3000
ctcaccaaga actacatgtt atgatgttaa gttgaagttg aaacatgatg ttttgcatta   3060
```

-continued aatttaagat atgcaaattt atgtagagaa aataaatgtt atataccta taatctttca 3120 cctaattagt atttaattat atggatttgt tttatattat aaaagatgtt ttgattttgt 3180
cttttgatat tgacaaaatt gtttggatat ccttatgttc tcaagtctgt atctgcctcc 3240
cctgccttat ttcttatgtt ttgccacagt taacccattg tgcttctttg taatcaaaca 3300
gtttgtggga gaatgggctt attgaatgtc taaaaaataa gtttaaagtg tttgttaccc 3360
taagtttttt acatttttaa actctaatta catatgtgaa tgttattact ctcagtgaat 3420
tgttattgtt tgcaaaaatg cactgggcag taacattttg tgataaatcc tataagatat 3480
aagtca 3486

<210> SEQ ID NO 38
<211> LENGTH: 519
<212> TYPE: DNA
<213> ORGANISM: Homo sapiens

<400> SEQUENCE: 38
aggaacgcgg gcggtgcgga ctcagcgggc cgggtgcagg cgcggagctg ggcctctgcg 60
cccggcccga cctccgtcta taaatagagc agccagttgc agggctccat tctgctttcc 120
aactgcctga ctgcttgttc gtctcactgg tgtgagctcc agcatcccct ttgctcgaaa 180
tggaccccaa ctgctcttgc gccactggtg gctcctgcac gtgcgccggc tcctgcaagt 240
gcaaagagtg caaatgcacc tcctgcaaga agagctgctg ttcctgctgc cccgtgggct 300
gtgccaagtg tgcccagggc tgcgtctgca aaggggcatc ggagaagtgc agctgctgtg 360
cctgatgtgg gaacagctct tctcccagat gtaaatagaa caacctgcac aacctggatt 420
tttttaaaaa tacaacactg agccatttgc tgcatttctt tttatactaa atatgtgact 480
gacaataaaa acaattttga ctttaaaaaa aaaaaaaaa 519

<210> SEQ ID NO 39
<211> LENGTH: 3319
<212> TYPE: DNA
<213> ORGANISM: Homo sapiens

<400> SEQUENCE: 39
gcttccggcc gcggccctgg cgcgtggtct gcgcgcgccc ggccgtgcgt gcggatgcgg 60
ggaggctgcg tgtgtgcgca gggagagaac gccggccacc ttcccgcttc cgagctgggt 120
gcgcgccgag cacaggagat tgcctgcgtt taggaggtgg ctgcgttgtg ggaaaagcta 180
tcaaggaaga aattgccaaa ccatgtcttt ttttctgttt tcagagtagt tcacaacaga 240
tctgagtgtt ttaattaagc atggaataca gaaaacaaca aaaaacttaa gctttaattt 300
catctggaat tccacagttt tcttagctcc ctggacccgg ttgacctgtt ggctcttccc 360
gctggctgct ctatcacgtg gtgctctccg actactcacc ccgagtgtaa agaaccttcg 420
gctcgcgtgc ttctgagctg ctgtggatgg cctcggctct ctggactgtc cttccgagta 480
ggatgtcact gagatccctc aaatggagcc tcctgctgct gtcactcctg agtttctttg 540
tgatgtggta cctcagcctt ccccactaca atgtgataga acgcgtgaac tggatgtact 600
tctatgagta tgagccgatt tacagacaag actttcactt cacacttcga gagcattcaa 660
actgctctca tcaaaatcca tttctggtca ttctggtgac ctcccaccct tcagatgtga 720
aagccaggca ggccattaga gttacttggg gtgaaaaaaa gtcttggtgg ggatatgagg 780
ttcttacatt tttcttatta ggccaagagg ctgaaaagga agacaaaatg ttggcattgt 840
ccttagagga tgaacacctt ctttatggtg acataatccg acaagatttt ttagacacat 900

-continued

```
ataataacct gaccttgaaa accattatgg cattcaggtg ggtaactgag ttttgcccca    960
atgccaagta cgtaatgaag acagacactg atgttttcat caatactggc aatttagtga   1020
agtatctttt aaacctaaac cactcagaga agtttttcac aggttatcct ctaattgata   1080
attattccta tagaggattt taccaaaaaa cccatatttc ttaccaggag tatcctttca   1140
aggtgttccc tccatactgc agtgggttgg gttatataat gtccagagat ttggtgccaa   1200
ggatctatga aatgatgggt cacgtaaaac ccatcaagtt tgaagatgtt tatgtcggga   1260
tctgtttgaa tttattaaaa gtgaacattc atattccaga agacacaaat cttttctttc   1320
tatatagaat ccatttggat gtctgtcaac tgagacgtgt gattgcagcc catggctttt   1380
cttccaagga gatcatcact tttggcaggt catgctaag gaacaccaca tgccattatt   1440
aacttcacat tctacaaaaa gcctagaagg acaggatact ttgtggaaag tgttaaataa   1500
agtaggtact gtggaaaatt catggggagg tcagtgtgct ggcttacact gaactgaaac   1560
tcatgaaaaa cccagactgg agactggagg gttacacttg tgatttatta gtcaggccct   1620
tcaaagatga tatgtggagg aattaaatat aaaggaattg gaggtttttg ctaaagaaat   1680
taataggacc aaacaatttg gacatgtcat tctgtagact agaatttctt aaaagggtgt   1740
tactgagtta taagctcact aggctgtaaa aacaaaacaa tgtagagttt tatttattga   1800
acaatgtagt cacttgaagg ttttgtgtat atcttatgtg gattaccaat ttaaaaatat   1860
atgtagttct gtgtcaaaaa acttcttcac tgaagttata ctgaacaaaa ttttacctgt   1920
ttttggtcat ttataaagta cttcaagatg ttgcagtatt tcacagttat tattatttaa   1980
aattacttca actttgtgtt tttaaatgtt ttgacgattt caatacaaga taaaaaggat   2040
agtgaatcat tctttacatg caaacatttt ccagttactt aactgatcag tttattattg   2100
atacatcact ccattaatgt aaagtcatag gtcattattg catatcagta atctcttgga   2160
ctttgttaaa tattttactg tggtaatata gagaagaatt aaagcaagaa aatctgaagt   2220
attgtcttgt ttttaaaaaa tacagttcct agtgttttta gaagtcactt aatttgtctc   2280
atttttccac ctggaaatta ggaataatgt agaatgcaag gcagtaattt ccttttggaa   2340
aggactctga aggcagaaaa gaagggagag aacctcatgg gcagaatatt ataaaaagag   2400
tgtcatattc cagcatttga attggaaaga gaagagtgaa gatccaagtt gcattattaa   2460
tctgccctgt gtttttttcct tttaacaatc agtttgagct gctgctgtta tgagtttctc   2520
atcaagatga aagccctaat atgtaaagtc aaatccgatt taaattttgt gcttttatag   2580
aaagaaattt cttcatagac gtggtgatat atcatttgtt ggacctgcta atagtaggtc   2640
aaaggggagc actccttgcc ccctgttcct gggtttatgc agttttcttt ttagagttta   2700
tatagggcaa gtggttcttt ttctctgaat tacaggatgg aaaaaggtca tatcctttgt   2760
caggaaatat aaacttgaaa gtatgtagtc agctcttgta atactcatat ttatgattgt   2820
cctatatgaa aaacaacttc agttaaaact ataatgtgtg attctgtata acaaggtgat   2880
gtctgtttcc cagggctcag acctaatcca gttataataa aatcaattaa atgaaatatt   2940
ctatagaatc gatctatgcc cttgttaatc tccatccata taggagtcac gttctttaag   3000
acagatggtg gtagttattt ttgtggcatg gttagatttg actggttttg cagaagatta   3060
cagttatgta ctgcataatg acatatacaa tagtggtccc ataaaattat aatggagcag   3120
aaaatctatt gcctcatgat gttttagccg ttttaatgtc atagcctagt gcattactca   3180
cgtgtctgtg gagatgctgg tgtaaacaaa cctactacac tgccagttgt ataaaagtac   3240
agcacattca gttatgtaca gtatgtaata ctgataatga caataaatga caccggtttg   3300
```

tgtatttact ttttataaa 3319

<210> SEQ ID NO 40
<211> LENGTH: 2295
<212> TYPE: DNA
<213> ORGANISM: Homo sapiens

<400> SEQUENCE: 40
agaccgcgag cgagagcgcc cccgagcagc gcccgcgccc tccgcgcctt ctccgccggg 60
acctcgagcg aaagacgccc gcccgccgcc cagccctcgc ctccctgccc accgggccca 120
ccgcgccgcc accccgaccc cgctgcgcac ggcctgtccg ctgcacacca gcttgttggc 180
gtcttcgtcg ccgcgctcgc cccgggctac tcctgcgcgc cacaatgagc tcccgcatcg 240
ccagggcgct cgccttagtc gtcacccttc tccacttgac caggctggcg ctctccacct 300
gccccgctgc ctgccactgc cccctggagg cgcccaagtg cgcgccggga gtcgggctgg 360
tccgggacgg ctgcggctgc tgtaaggtct gcgccaagca gctcaacgag gactgcagca 420
aaacgcagcc ctgcgaccac accaaggggc tggaatgcaa cttcggcgcc agctccaccg 480
ctctgaaggg gatctgcaga gctcagtcag agggcagacc ctgtgaatat aactccagaa 540
tctaccaaaa cggggaaagt ttccagccca actgtaaaca tcagtgcaca tgtattgatg 600
gcgccgtggg ctgcattcct ctgtgtcccc aagaactatc tctccccaac ttgggctgtc 660
ccaaccctcg gctggtcaaa gttaccgggc agtgctgcga ggagtgggtc tgtgacgagg 720
atagtatcaa ggaccccatg gaggaccagg acggcctcct tggcaaggag ctgggattcg 780
atgcctccga ggtggagttg acgagaaaca atgaattgat tgcagttgga aaaggcagct 840
cactgaagcg gctccctgtt tttggaatgg agcctcgcat cctatacaac cctttacaag 900
gccagaaatg tattgttcaa acaacttcat ggtcccagtg ctcaaagacc tgtggaactg 960
gtatctccac acgagttacc aatgacaacc ctgagtgccg ccttgtgaaa gaaacccgga 1020
tttgtgaggt gcggccttgt ggacagccag tgtacagcag cctgaaaaag ggcaagaaat 1080
gcagcaagac caagaaatcc cccgaaccag tcaggtttac ttacgctgga tgtttgagtg 1140
tgaagaaata ccggcccaag tactgcggtt cctgcgtgga cggccgatgc tgcacgcccc 1200
agctgaccag gactgtgaag atgcggttcc gctgcgaaga tggggagaca ttttccaaga 1260
acgtcatgat gatccagtcc tgcaaatgca actacaactg cccgcatgcc aatgaagcag 1320
cgtttccctt ctacaggctg ttcaatgaca ttcacaaatt tagggactaa atgctacctg 1380
ggtttccagg gcacacctag acaaacaagg gagaagagtg tcagaatcag aatcatggag 1440
aaaatgggcg gggtggtgt gggtgatggg actcattgta gaaaggaagc cttgctcatt 1500
cttgaggagc attaaggtat ttcgaaactg ccaagggtgc tggtgcggat ggacactaat 1560
gcagccacga ttggagaata ctttgcttca tagtattgga gcacatgtta ctgcttcatt 1620
ttggagcttg tggagttgat gactttctgt tttctgtttg taaattattt gctaagcata 1680
ttttctctag gctttttttcc ttttggggtt ctacagtcgt aaaagagata ataagattag 1740
ttggacagtt taaagctttt attcgtcctt tgacaaaagt aaatgggagg gcattccatc 1800
ccttcctgaa gggggacact ccatgagtgt ctgtgagagg cagctatctg cactctaaac 1860
tgcaaacaga aatcaggtgt tttaagactg aatgttttat ttatcaaaat gtagcttttg 1920
gggagggagg ggaaatgtaa tactggaata atttgtaaat gattttaatt ttatattcag 1980
tgaaaagatt ttatttatgg aattaaccat ttaataaaga aatatttacc taatatctga 2040
gtgtatgcca ttcggtattt ttagaggtgc tccaaagtca ttaggaacaa cctagctcac 2100

-continued gtactcaatt attcaaacag gacttattgg gatacagcag tgaattaagc tattaaaata 2160
agataatgat tgcttttata ccttcagtag agaaaagtct ttgcatataa agtaatgttt 2220
aaaaaacatg tattgaacac gacattgtat gaagcacaat aaagattctg aagctaaatt 2280
tgtgatttaa gaaaa 2295

<210> SEQ ID NO 41
<211> LENGTH: 468
<212> TYPE: DNA
<213> ORGANISM: Homo sapiens

<400> SEQUENCE: 41
accacgcttt tcatctgtcc cgctgcgtgt tttcctcttg atcgggaact cctgcttctc 60
cttgcctcga aatggacccc aactgctcct gctcgcctgt tggctcctgt gcctgtgccg 120
gctcctgcaa atgcaaagag tgcaaatgca cctcctgcaa gaagagctgc tgctcctgct 180
gccctgtggg ctgtgccaag tgtgcccagg gctgcatctg caaagggacg tcagacaagt 240
gcagctgctg tgcctgatgc caggacagct gtgctctcag atgtaaatag agcaacctat 300
ataaacctgg attttttttt tttttttttt tgtacaaccc tgacccgttt gctacatctt 360
tttttctatg aaatatgtga atggcaataa attcatctag actaaaaaaa aaaaaaaaaa 420
aaaaaaaaaa aaaaaaaaaa aaaaaaaaaa aaaaaaaaaa aaaaaaaa 468

<210> SEQ ID NO 42
<211> LENGTH: 1059
<212> TYPE: DNA
<213> ORGANISM: Homo sapiens

<400> SEQUENCE: 42
agctataaac tccccggagc ttcagtgccc tcagcaaggc tcagcctcaa gattcacagc 60
atctcagaca cagcctaggc cgcaccagga tgtcggacac cgaggagcag gaatatgagg 120
aggagcagcc ggaagaggag gctgcggagg aggaggagga agccccccgaa gagccggagc 180 cggtggcaga gccagaagag gaacgcccca aaccaagccg ccccgtggtg cctcctttga 240
tcccgccaaa gatcccagaa ggggagcgcg ttgacttcga tgacatccac cgcaagcgca 300
tggagaaaga cctgctggag ctgcagacac tcatcgatgt acatttcgag cagcggaaga 360
aggaggaaga ggagctggtt gccttgaagg agcgcattga gcggcgccgg tcagagagag 420
ccgagcaaca gcgcttcaga actgagaagg aacgcgaacg tcaggctaag ctggcggagg 480
agaagatgag gaaggaagag gaagaggcca agaagcgggc agaggatgat gccaagaaaa 540
agaaggtgct gtccaacatg gggcccatt ttggcggcta cctggtcaag gcagaacaga 600
agcgtggtaa gcggcagacg gggcgggaga tgaaggtgcg catcctctcc gagcgtaaga 660
agcctctgga cattgactac atgggggagg aacagctccg ggcccggtct gcctggctgc 720
ctccatcaca gccctcctgc cctgccaggg agaaagccca ggagctgtcg gactggatcc 780
accagctgga gtctgagaag ttcgacctga tggcgaagct gaaacagcag aaatatgaga 840
tcaacgtgct gtacaaccgc atcagccacg cccagaagtt ccggaagggg gcagggaagg 900
gccgcgttgg aggccgctgg aagtgaggat gccgccccgg acagtggcac ctgggaagcc 960
tgggagtgtt tgtcccatcg gtagcttgaa ataaacgctc ccctcagaca cccgctgggt 1020
tctctgatgt tattatggtt gagatgcaaa aaaaaaaaa 1059

<210> SEQ ID NO 43
<211> LENGTH: 316
<212> TYPE: DNA

<213> ORGANISM: Homo sapiens

<400> SEQUENCE: 43
cctcttctct tctcgcttgg gaacgccggt ctcacctcgg cttgcaatgg accccaactg 60
ctcctgcgcc gctggaggct cctacgcctg cgccggctcc tgcaagtgca aaaagtgcaa 120
atgcacctcc tgcaagaaga gctgctgctc ctgttgcccc ctgggctgtg ccaagtgtgc 180
ccagggctgc atccgcaaag gggcttcgga aaagtgcagc tgctgtgcct gatgtcggga 240
ctgccctgct ctcggatgaa aacagaatga cacgtaaagt ccgggatttt tttttctaca 300
actccgactc atttgc 316

<210> SEQ ID NO 44
<211> LENGTH: 397
<212> TYPE: DNA
<213> ORGANISM: Homo sapiens

<400> SEQUENCE: 44
accacgccct ccacgtgttc cactgcctct tctcttctcg cttgggaact ccagtctcac 60
ctcggcttgc aatggacccc aactgctcct gcgaggctgg tggctcctgc gcctgcgccg 120
gctcctgcaa gtgcaaaaag tgcaaatgca cctcctgcaa gaagagctgc tgctcctgtt 180
gccccctggg ctgtgccaag tgtgcccagg gctgcatctg caaaggggcg tcagagaagt 240
gcagctgctg tgcctgatgt cgggacagcc ctgctgtcag atgaaaacag aatgacacgt 300
aaaatccagg attttttttt tctacaactc cgactcattt gctacattcc tttttttctg 360
tgaaatatgt gaataataat taaacactta gacttga 397

<210> SEQ ID NO 45
<211> LENGTH: 456
<212> TYPE: DNA
<213> ORGANISM: Homo sapiens

<400> SEQUENCE: 45
gccccctccc ctgactatca aagcagcggc cggctgttgg ggtccaccac gccttccacc 60
tgccccactg cttcttcgct tctctcttgg aaagtccagt ctctcctcgg cttgcaatgg 120
accccaactg ctcctgcgcc gctggtgtct cctgcacctg cgctggttcc tgcaagtgca 180
aagagtgcaa atgcacctcc tgcaagaaga gctgctgctc ctgctgcccc gtgggctgta 240
gcaagtgtgc ccagggctgt gtttgcaaag gggcgtcaga gaagtgcagc tgctgcgact 300
gatgccagga caacctttct cccagatgta aacagagaga catgtacaaa cctggatttt 360 tttttatac caccttgacc catttgctac attccttttc ctgtgaaata tgtgagtgat 420
aattaaacac tttagacctg aaaaaaaaaa aaaaaa 456

<210> SEQ ID NO 46
<211> LENGTH: 466
<212> TYPE: DNA
<213> ORGANISM: Homo sapiens

<400> SEQUENCE: 46
cttgccgcgc tgcactccac cacgcctcct ccaagtccca gcgaacccgc gtgcaacctg 60
tcccgactct agccgcctct tcagctcgcc atggatccca actgctcctg cgccgccggt 120
gactcctgca cctgcgccgg ctcctgcaaa tgcaaagagt gcaaatgcac ctcctgcaag 180
aaaagctgct gctcctgctg ccctgtgggc tgtgccaagt gtgcccaggg ctgcatctgc 240
aaaggggcgt cggacaagtg cagctgctgc gcctgatgct gggacagccc cgctcccaga 300

```
tgtaaagaac gcgacttcca caaacctgga ttttttatgt acaaccctga ccgtgaccgt    360

ttgctatatt cctttttcta tgaaataatg tgaatgataa taaaacagct ttgacttgaa    420

aaaaaaaaaa aaaaaaaaaa aaaaaaaaaa aaaaaaaaaa aaaaaa                   466


<210> SEQ ID NO 47
<211> LENGTH: 464
<212> TYPE: DNA
<213> ORGANISM: Homo sapiens

<400> SEQUENCE: 47

ccctgagtag aaaagcagcc gcaggctgtg gcgctccacc acgccgtccg ggtgggccta     60

gcagtcgctc catttatcgc ttgagatctc cagccttacc gcggctcgaa atggacccca    120

actgctcctg caccactggt gtctcctgcg cctgcaccgg ctcctgcaag tgcaaagagt    180

gcaaatgcac ctcctgcaag aagagctgct gctcctgctg ccccgtgggc tgtgccaagt    240

gtgcccacgg ctgtgtctgc aaagggacgt tggagaactg cagctgctgt gcctgatgtg    300

ggaacagctc ttctcccaga tgttaataga acaagctgca caacctggat tttttttcaa    360

tacgatactg agccatttgc tgcatttctt tttatattaa atatgtgagt gacaataaaa    420

caattttgac ttgaatctta aaaaaaaaaa aaaaaaaaaa aaaa                     464


<210> SEQ ID NO 48
<211> LENGTH: 2497
<212> TYPE: DNA
<213> ORGANISM: Homo sapiens

<400> SEQUENCE: 48

actggataag cggtcgctga gcggggcgca ggtgactaaa tttcgacggg gtcttctcac     60

gggtttcatt cagttggcca ctgctgagca gctgagaagg tggcgacgta ggggccatgg    120

ggctgggccg ggtcctgctg tttctggccg tcgccttccc ttttgcaccc ccggcagccg    180

ccgctgagcc ccacagtctt cgttacaacc tcatggtgct gtcccaggat ggatctgtgc    240

agtcagggtt tctcgctgag ggacatctgg atggtcagcc cttcctgcgc tatgacaggc    300

agaaacgcag ggcaaagccc cagggacagt gggcagaaaa tgtcctggga gctaagacct    360

gggacacaga gaccgaggac ttgacagaga atgggcaaga cctcaggagg accctgactc    420

atatcaagga ccagaaagga ggcttgcatt ccctccagga gattagggtc tgtgagatcc    480

atgaagacag cagcaccagg ggctcccggc atttctacta cgatggggag ctcttcctct    540

cccaaaacct ggagactcaa gaatcgacag tgccccagtc ctccagagct cagaccttgg    600

ctatgaacgt cacaaatttc tggaaggaag atgccatgaa gaccaagaca cactatcgcg    660

ctatgcaggc agactgcctg cagaaactac agcgatatct gaaatccggg gtggccatca    720

ggagaacagt gccccccatg gtgaatgtca cctgcagcga ggtctcagag ggcaacatca    780

ccgtgacatg cagggcttcc agcttctatc cccggaatat cacactgacc tggcgtcagg    840

atggggtatc tttgagccac aacacccagc agtgggggga tgtcctgcct gatgggaatg    900

gaacctacca gacctgggtg gccaccagga ttcgccaagg agaggagcag aggttcacct    960

gctacatgga acacagcggg aatcacggca ctcaccctgt gccctctggg aaggcgctgg   1020

tgcttcagag tcaacggaca gactttccat atgtttctgc tgctatgcca tgttttgtta   1080

ttattattat tctctgtgtc ccttgttgca agaagaaaac atcagcggca gagggtccag   1140

agcttgtgag cctgcaggtc ctggatcaac acccagttgg gacaggagac cacagggatg   1200

cagcacagct gggatttcag cctctgatgt cagctactgg gtccactggt tccactgagg   1260
```

gcacctagac tctacagcca ggcggccagg attcaactcc ctgcctggat ctcaccagca 1320
ctttccctct gtttcctgac ctatgaaaca gagaaaataa catcacttat ttattgttgt 1380
tggatgctgc aaagtgttag taggtatgag gtgtttgctg ctctgccacg tagagagcca 1440
gcaaagggat catgaccaac tcaacattcc attggaggct atatgatcaa acagcaaatt 1500
gtttatcatg aatgcaggat gtgggcaaac tcacgactgc tcctgccaac agaaggtttg 1560
ctgagggcat tcactccatg gtgctcattg gagttatcta ctgggtcatc tagagcctat 1620
tgtttgagga atgcagtctt acaagcctac tctggaccca gcagctgact ccttcttcca 1680
cccctcttct tgctatctcc tataccaata aatacgaagg gctgtggaag atcagagccc 1740
ttgttcacga gaagcaagaa gccccctgac cccttgttcc aaatatactc ttttgtcttt 1800
ctctttattc ccacgttcgc cctttgttca gtccaataca gggttgtggg gcccttaaca 1860
gtgccatatt aattggtatc attatttctg ttgtttttgt ttttgttttt gtttttgttt 1920
ttgagacaga gtctcactct gtcacccagg ctgcagttca ctggtgtgat ctcagctcac 1980
tgcaacctct gcctcccagg ttcaagcact tctcgtacct cagactcccg aatagctggg 2040
attacagaca ggcaccacca cacccagcta atttttgtat tttttgtaga gacggggttt 2100
cgccaagttg accagcccag tttcaaactc ctgacctcag gtgatctgcc tgccttggca 2160
tcccaaagtg ctgggattac aagaatgagc caccgtgcct ggcctatttt attatattgt 2220
aatatatttt attatattag ccaccatgcc tgtcctattt tcttatgttt taatatattt 2280
taatatatta catgtgcagt aattagatta tcatgggtga actttatgag tgagtatctt 2340
ggtgatgact cctcctgacc agcccaggac cagctttctt gtcaccttga ggtcccctcg 2400
ccccgtcaca ccgttatgca ttactctgtg tctactatta tgtgtgcata atttataccg 2460
taaatgttta ctctttaaat agaaaaaaaa aaaaaaa 2497

<210> SEQ ID NO 49
<211> LENGTH: 4246
<212> TYPE: DNA
<213> ORGANISM: Homo sapiens

<400> SEQUENCE: 49
gctctcactc tggctgggag cagaaggcag cctcggtctc tgggcggcgg cggcggccca 60
ctctgccctg gccgcgctgt gtggtgaccg caggccccag acatgagggc ggcccgtgct 120
ctgctgcccc tgctgctgca ggcctgctgg acagccgcgc aggatgagcc ggagaccccg 180
agggccgtgg ccttccagga ctgccccgtg gacctgttct ttgtgctgga cacctctgag 240
agcgtggccc tgaggctgaa gccctacggg gccctcgtgg acaaagtcaa gtccttcacc 300
aagcgcttca tcgacaacct gagggacagg tactaccgct gtgaccgaaa cctggtgtgg 360
aacgcaggcg cgctgcacta cagtgacgag gtggagatca tccaaggcct cacgcgcatg 420
cctggcggcc gcgacgcact caaaagcagc gtggacgcgg tcaagtactt tgggaagggc 480
acctacaccg actgcgctat caagaagggg ctggagcagc tcctcgtggg gggctcccac 540
ctgaaggaga ataagtacct gattgtggtg accgacgggc acccccctgga gggctacaag 600 gaaccctgtg gggggctgga ggatgctgtg aacgaggcca agcacctggg cgtcaaagtc 660
ttctcggtgg ccatcacacc cgaccacctg gagccgcgtc tgagcatcat cgccacggac 720
cacacgtacc ggcgcaactt cacggcggct gactggggcc agagccgcga cgcagaggag 780
gccatcagcc agaccatcga caccatcgtg gacatgatca aaaataacgt ggagcaagtg 840
tgctgctcct tcgaatgcca gcctgcaaga ggacctccgg ggctccgggg cgaccccggc 900

-continued

```
tttgagggag aacgaggcaa gccggggctc ccaggagaga agggagaagc cggagatcct    960
ggaagacccg gggacctcgg acctgttggg taccagggaa tgaagggaga aaaagggagc   1020
cgtggggaga agggctccag gggacccaag ggctacaagg gagagaaggg caagcgtggc   1080
atcgacgggg tggacggcgt gaagggggag atggggtacc caggcctgcc aggctgcaag   1140
ggctcgcccg ggtttgacgg cattcaagga ccccctggcc ccaagggaga ccccggtgcc   1200
tttggactga aaggagaaaa gggcgagcct ggagctgacg gggaggcggg gagaccaggg   1260
agctcgggac catctggaga cgagggccag ccgggagagc ctgggccccc cggagagaaa   1320
ggagaggcgg gcgacgaggg gaacccagga cctgacggtg cccccgggga gcggggtggc   1380
cctggagaga gaggaccacg gggacccca ggcacgcggg gaccaagagg agaccctggt   1440
gaagctggcc cgcagggtga tcagggaaga gaaggccccg ttggtgtccc tggagacccg   1500
ggcgaggctg gccctatcgg acctaaaggc taccgaggcg atgagggtcc cccagggtcc   1560
gagggtgcca gaggagcccc aggacctgcc ggaccccctg gagacccggg gctgatgggt   1620
gaaaggggag aagacggccc cgctggaaat ggcaccgagg gcttccccgg cttccccggg   1680
tatccgggca acaggggcgc tcccgggata aacggcacga agggctaccc cggcctcaag   1740
ggggacgagg gagaagccgg ggaccccgga gacgataaca acgacattgc accccgagga   1800
gtcaaaggag caaaggggta ccggggtccc gagggccccc agggaccccc aggacaccaa   1860
ggaccgcctg ggccggacga atgcgagatt ttggacatca tcatgaaaat gtgctcttgc   1920
tgtgaatgca agtgcggccc catcgacctc ctgttcgtgc tggacagctc agagagcatt   1980
ggcctgcaga acttcgagat tgccaaggac ttcgtcgtca aggtcatcga ccggctgagc   2040
cgggacgagc tggtcaagtt cgagccaggg cagtcgtacg cgggtgtggt gcagtacagc   2100
cacagccaga tgcaggagca cgtgagcctg cgcagcccca gcatccggaa cgtgcaggag   2160
ctcaaggaag ccatcaagag cctgcagtgg atggcgggcg gcaccttcac gggggaggcc   2220
ctgcagtaca cgcgggacca gctgctgccg cccagcccga acaaccgcat cgccctggtc   2280
atcactgacg ggcgctcaga cactcagagg gacaccacac cgctcaacgt gctctgcagc   2340
cccggcatcc aggtggtctc cgtgggcatc aaagacgtgt ttgacttcat cccaggctca   2400
gaccagctca atgtcatttc ttgccaaggc ctggcaccat cccagggccg gcccggcctc   2460
tcgctggtca aggagaacta tgcagagctg ctggaggatg ccttcctgaa gaatgtcacc   2520
gcccagatct gcatagacaa gaagtgtcca gattacacct gccccatcac gttctcctcc   2580
ccggctgaca tcaccatcct gctggacggc tccgccagcg tgggcagcca caactttgac   2640
accaccaagc gcttcgccaa gcgcctggcc gagcgcttcc tcacagcggg caggacggac   2700
cccgcccacg acgtgcgggt ggcggtggtg cagtacagcg gcacgggcca gcagcgccca   2760
gagcgggcgt cgctgcagtt cctgcagaac tacacggccc tggccagtgc cgtcgatgcc   2820
atggacttta tcaacgacgc caccgacgtc aacgatgccc tgggctatgt gacccgcttc   2880
taccgcgagg cctcgtccgg cgctgccaag aagaggctgc tgctcttctc agatggcaac   2940
tcgcagggcg ccacgcccgc tgccatcgag aaggccgtgc aggaagccca gcgggcaggc   3000
atcgagatct tcgtggtggt cgtgggccgc caggtgaatg agccccacat ccgcgtcctg   3060
gtcaccggca agacggccga gtacgacgtg gcctacggcg agagccacct gttccgtgtc   3120
cccagctacc aggccctgct ccgcggtgtc ttccaccaga cagtctccag gaaggtggcg   3180
ctgggctagc ccaccctgca cgccggcacc aaaccctgtc ctcccacccc tccccactca   3240
tcactaaaca gagtaaaatg tgatgcgaat ttcccgacc aacctgattc gctagatttt    3300
```

-continued

```
ttttaaggaa aagcttggaa agccaggaca caacgctgct gcctgctttg tgcagggtcc   3360

tccggggctc agccctgagt tggcatcacc tgcgcagggc cctctggggc tcagccctga   3420

gctagtgtca cctgcacagg gccctctgag gctcagccct gagctggcgt cacctgtgca   3480

gggccctctg gggctcagcc ctgagctggc ctcacctggg ttccccaccc cgggctctcc   3540

tgccctgccc tcctgcccgc cctccctcct gcctgcgcag ctccttccct aggcacctct   3600

gtgctgcatc ccaccagcct gagcaagacg ccctctcggg gcctgtgccg cactagcctc   3660

cctctcctct gtccccatag ctggtttttc ccaccaatcc tcacctaaca gttactttac   3720

aattaaactc aaagcaagct cttctcctca gcttggggca gccattggcc tctgtctcgt   3780

tttgggaaac caaggtcagg aggccgttgc agacataaat ctcggcgact cggccccgtc   3840

tcctgagggt cctgctggtg accggcctgg accttggccc tacagccctg gaggccgctg   3900

ctgaccagca ctgaccccga cctcagagag tactcgcagg ggcgctggct gcactcaaga   3960

ccctcgagat taacggtgct aaccccgtct gctcctccct cccgcagaga ctggggcctg   4020

gactggacat gagagcccct tggtgccaca gagggctgtg tcttactaga aacaacgcaa   4080

acctctcctt cctcagaata gtgatgtgtt cgacgtttta tcaaaggccc cctttctatg   4140

ttcatgttag ttttgctcct tctgtgtttt tttctgaacc atatccatgt tgctgacttt   4200

tccaaataaa ggttttcact cctctaaaaa aaaaaaaaaa aaaaaa                 4246
```

<210> SEQ ID NO 50
<211> LENGTH: 1212
<212> TYPE: DNA
<213> ORGANISM: Homo sapiens

<400> SEQUENCE: 50

```
ggagtccaga cccgacggcc ggcccagttc cacgcaccca gcgagcccaa gcgccttctc     60

cgcaccaggg aagccccacc caccagaagc caagatgtcc agcaagcggg ccaaagccaa    120

gaccaccaag aagcggccac agcgggccac atccaatgtc ttcgcaatgt ttgaccagtc    180

ccagatccag gagtttaagg aggctttcaa catgattgac cagaaccgtg atggcttcat    240

tgacaaggag gacctgcacg acatgctggc ctcgctgggg aagaacccca cagacgaata    300

cctggagggc atgatgagcg aggccccggg gcccatcaac ttcaccatgt tcctcaccat    360

gtttggggag aagctgaacg gcacggaccc cgaggatgtg attcgcaacg cctttgcctg    420

cttcgacgag gaagcctcag gtttcatcca tgaggaccac ctccgggagc tgctcaccac    480

catgggtgac cgcttcacag atgaggaagt ggacgagatg taccgggagg cacccattga    540

taagaaaggc aacttcaact acgtggagtt cacccgcatc ctcaaacatg gcgccaagga    600

taaagacgac taggccaccc cagccccctg acaccccagc ccccgccagt cacccctccc    660

cgcacacacc cgtccatacc agctccctgc ccatgaccct cgctcaggga tccccctttg    720

aggggttagg gtcccagttc ccagtggaag aaacaggcca ggagaagtgc gtgccgagct    780

gaggcagatg ttcccacagt gaccccagag ccctgggcta tagtctctga cccctccaag    840

gaaagaccac cttctgggga catgggctgg agggcaggac ctagaggcac caagggaagg    900

ccccattccg gggctgttcc ccgaggagga agggaagggg ctctgtgtgc cccccaggag    960

gaagaggccc tgagtcctgg gatcagacac cccttcacgt gtatccccac acaaatgcaa   1020

gctcaccaag gtcccctctc agtccccttc cctacaccct gaccggccac tgccgcacac   1080

ccacccagag cacgccaccc gccatgggag tgtgctcagg agtcgcgggc agcgtggaca   1140

tctgtcccag agggggcaga atctccaata gaggactgag cactgctaaa aaaaaaaaaa   1200
```

aaaaaaaaaa aa 1212

<210> SEQ ID NO 51
<211> LENGTH: 396
<212> TYPE: DNA
<213> ORGANISM: Homo sapiens

<400> SEQUENCE: 51
actccgcctt ccacgtgcac ccactgcctc ttcccttctc gcttgggaac tctagtctcg 60
cctcgggttg caatggaccc caactgctcc tgtgccgctg gtgtctcctg cacctgcgcc 120
agctcctgca agtgcaaaga gtgcaaatgc acctcctgca agaagagctg ctgctcctgc 180
tgccctgtgg gctgtgccaa gtgtgcccaa ggctgcatct gcaaaggggc atcggagaag 240
tgcagctgct gcgcctgatg tcgggacagc cctgctccca agtacaaata gagtgacccg 300
taaaatctag gattttttgt tttttgctac aatcttgacc cctttgctac attccctttt 360
ttctgtgaaa tatgtgaata ataattaaac acttag 396

<210> SEQ ID NO 52
<211> LENGTH: 1828
<212> TYPE: DNA
<213> ORGANISM: Homo sapiens

<400> SEQUENCE: 52
cagttacagg gagcaccacc agggaacatc tcggggagcc tggttggaag ctgcaggctt 60
agtctgtcgg ctgcgggtct ctgactgccc tgtggggagg gtcttgcctt aacatccctt 120
gcatttggct gcaaagaaat ctgcttggaa gaaggggtta cgctgtttgg ccgggcagaa 180
actccgctga gcagaacttg ccgccagaat gctcctcctg ttgctgagta tcatcgtcct 240
ccacgtcgcg gtgctggtgc tgctgttcgt ctccacgatc gtcagccaat ggatcgtggg 300
caatggacac gcaactgatc tctggcagaa ctgtagcacc tcttcctcag gaaatgtcca 360
ccactgtttc tcatcatcac caaacgaatg gctgcagtct gtccaggcca ccatgatcct 420
gtcgatcatc ttcagcattc tgtctctgtt cctgttcttc tgccaactct tcaccctcac 480 caagggggc aggttttaca tcactggaat cttccaaatt cttgctggtc tgtgcgtgat 540
gagtgctgcg gccatctaca cggtgaggca cccggagtgg catctcaact cggattactc 600
ctacggtttc gcctacatcc tggcctgggt ggccttcccc ctggcccttc tcagcggtgt 660
catctatgtg atcttgcgga aacgcgaatg aggcgcccag acggtctgtc tgaggctctg 720
agcgtacata gggaagggag gaagggaaaa cagaaagcag acaaagaaaa aagagctagc 780
ccaaaatccc aaactcaaac caaaccaaac agaaagcagt ggaggtgggg gttgctgttg 840
attgaagatg tatataatat ctccggttta taaaacctat ttataacact ttttacatat 900
atgtacatag tattgtttgc tttttatgtt gaccatcagc ctcgtgttga gccttaaaga 960
agtagctaag gaactttaca tcctaacagt ataatccagc tcagtatttt tgttttgttt 1020
tttgtttgtt tgttttgttt tacccagaaa taagataact ccatctcgcc ccttcccttt 1080
catctgaaag aagatacctc cctcccagtc cacctcattt agaaaaccaa agtgtgggta 1140
gaaaccccaa atgtccaaaa gcccttttct ggtgggtgac ccagtgcatc caacagaaac 1200
agccgctgcc cgaacctctg tgtgaagctt tacgcgcaca cggacaaaat gcccaaactg 1260
gagcccttgc aaaaacacgg cttgtggcat tggcatactt gcccttacag gtggagtatc 1320
ttcgtcacac atctaaatga gaaatcagtg acaacaagtc tttgaaatgg tgctatggat 1380
ttaccattcc ttattatcac taatcatcta aacaactcac tggaaatcca attaacaatt 1440

-continued

```
ttacaacata agatagaatg gagacctgaa taattctgtg taatataaat ggtttataac   1500

tgcttttgta cctagctagg ctgctattat tactataatg agtaaatcat aaagccttca   1560

tcactcccac atttttctta cggtcggagc atcagaacaa gcgtctagac tccttgggac   1620

cgtgagttcc tagagcttgg ctgggtctag gctgttctgt gcctccaagg actgtctggc   1680

aatgacttgt attggccacc aactgtagat gtatatatgg tgcccttctg atgctaagac   1740

tccagacctt ttgtttttgc tttgcatttt ctgattttat accaactgtg tggactaaga   1800

tgcattaaaa taaacatcag agtaactc                                      1828
```

<210> SEQ ID NO 53
<211> LENGTH: 2990
<212> TYPE: DNA
<213> ORGANISM: Homo sapiens

<400> SEQUENCE: 53

```
agggggcgct gcggcccccc caatccccg ccccgtccgg gctggggcgg aggagcgggc     60

ggggaccaaa ggttggtgtc tttgcgctcg gaccttcgcc agaggggccg ggacatcatg    120

acggtgggag ccaggctccg aagcaaggcg gagagcagcc tcctgcgccg cgggccccga    180

gggcgagggc gaaccgaggg ggacgaggag gcggccgcca tcctggagca cctggagtac    240

gcggacgagg cggaggcggc ggccgagagc gggacgagcg cggcggacga gcggggcccg    300

gggacccggg gcgcgcggag ggtgcacttc gccctcctgc ccgagcgcta cgagccactg    360

gaggagccgg cgccgagcga gcagcccagg aagaggtacc ggaggaagct gaagaagtac    420

ggcaagaatg tcgggaaggt catcatcaaa ggatgccgct acgtggtcat cggcctgcaa    480

ggcttcgctg cagcctactc cgccccgttt gcggtagcca ccagcgtggt atccttcgtg    540

cgctaatggg agctgctgtg gcaggtgccc ccagagtgaa cgggagcccc tgctgtggga    600

actttgtgaa tcctggagca tctcagactt gaacacacag catatttgga agagaaaaca    660

tgcctttctt tgttgaatca cattagtatg atgagtgagt catccctgcc catctgctga    720

gcttctcaca tctctcagtc acacgtggac ccagtggtca atcctgcaga gaattcggcg    780

gaggttaggt ttgggagtgg agctagcgtg ctaaagccag agccttcacg tgaaggtggc    840

aggcactggg gcggaagcca acactcaaca gatgcaagca gtgtgggtgt gcagcagaac    900

agtgatcttg gggaggaag aggatgttac tagagtcaga tgatttgctg tattctcctg    960

aaaggtcgta ggctgacagg cgctcacatt ccttggctgc ctcggttctg agggcagcta   1020

aggagctgtt tattcctcaa gtcatgctcc ccgatctcct tcctctacca ctctgtcacc   1080

aggagtttaa ttacaggctt gaggagaaga aaggaagaaa agatatcttg atgctttgaa   1140

aactgtgttg gcagtgtggc atgactgttt aaagtagata aaaccttgtc attttacccc   1200

atccctgcat gactgtgaag ctggcgagga aggaggaaga agggcaagtt cagatgcagg   1260

ctgggtggct gggacaggtt ggctaaggga ctactctgga gggctcttct gcctggcatt   1320

gcccacttcg gcccagccac gtgtttgcag cgaccagagt ccctgcaaag gtgtggctgg   1380

ctgtggtcag ggtgctacta gcaccatcag cgcactcccg ccattggctc agctcctctc   1440

tgccagtcca actaagagtg ctttgtcctg ggtgggacat aggggctgag agagatgggg   1500

ggagacataa cacccaggaa tgaaaataca gatttagaga aggaaccagt aagtaggaga   1560

cagatgtgaa ggaaatggaa atgaggcaag aggacattgg aagagagaag tttgctgtcc   1620

aggagccagg tctggagcat cagtgtgagg gagttcaggt aggctgggcc tgtgcctcta   1680

ggtagggaca agggaggctg ggtagccagg gctggtgctt aaaacccctg aggccatgag   1740
```

ctcattggct gcctttgtag catcctgtct tcttctgtgc tgcctggttt gatctcatct 1800
cacctggatt caaagggtaa ggtgggcatg ggtcttgggc ctgacaccca ccaaggatga 1860
cctgtggact gccatcggat gctgaacagg gagatgaaag gaggtcctct taccataccc 1920
ctctgccaac cccccagtag gccactgttc tgactttgtt tccagaatat ccagaaatcc 1980
aaaggggctg ttgctgaaca gtctgcagga ccagtgacag cacctacctg ttgtcccaag 2040
gcatacaaag gaggcctcaa cgctcatgct tctctaatca agccctacca agacagacag 2100
aaagacagac agaaaaaagg aaggggtaga ggagaaggtt gaagctgtgg agctagactc 2160
tgcttcactt cctgaagctt caacttcatg tcgaagattc actgggaccc aattcctgca 2220
ttgttaatat ttgtgaggaa aagtgaaaca agtgatctgg ttttagccca gatgatgaaa 2280
gtggatatgg cacattttca cacacgtgag ataattacag cttgccccac aacactgggt 2340
gttggagaaa gggagagata gtcataagtg gaagaaaaag ccaagcatag tgagtgggaa 2400
agagagtgag agcctgtgca ggctgctgac gagccccagg cagcccacaa gtttctcgtg 2460
gggagatgga ggcagagccc agggtagggg acagagctgc tggggccttt ccttgcctgg 2520
gaatctgtcc caggaagagc ttccccactc ccatccccca aattggaaaa accgtacatt 2580
caagcctgtt tggccctgaa attcttaaga atctggttaa gaattaactc actaatgtca 2640
aaagtcaaaa cctcctaggg gttgtcctgg gagtcaggtt cacgggtaca gaagatgaat 2700
ctcagatgtc actcaacctg agccgtcatt ctctgtggca gggctgccct gggtttctct 2760
tactcaatcc ctggagtgta agcatttgga ttgtgtcaca gattaccttt ttaccttttc 2820
tttctttttt tttctttttt tcaatatcag tgcccacacc ttactgagta ttgagtttta 2880
gagctttcgc ttgatgtgct tgaccaagag acttcttttg tatccttttc ttgtcctatg 2940
atgtaaataa aagcctcgat ttatgtaatg ttaaaaaaaa aaaaaaaaaa 2990

<210> SEQ ID NO 54
<211> LENGTH: 1700
<212> TYPE: DNA
<213> ORGANISM: Homo sapiens

<400> SEQUENCE: 54
agcaggactc agaggggaga gttggaggaa aaaaaaaggc agaaaaggga aagaaagagg 60
aagagagaga gagagtgaga ggagccgctg agcccacccc gatggccgcg gacgaagttg 120
ccggaggggc gcgcaaagcc acgaaaagca aactttttga gtttctggtc catggggtgc 180
gccccgggat gccgtctgga gcccggatgc cccaccaggg ggcgcccatg ggcccccccgg 240 gctccccgta catgggcagc cccgccgtgc gacccggcct ggcccccgcg ggcatggagc 300
ccgcccgcaa gcgagcagcg cccccgcccg ggcagagcca ggcacagagc cagggccagc 360
cggtgcccac cgcccccgcg cggagccgca gtgccaagag gaggaagatg gctgacaaaa 420
tcctccctca aaggattcgg gagctggtcc ccgagtccca ggcttacatg gacctcttgg 480
catttgagag gaaactggat caaaccatca tgcggaagcg ggtggacatc caggaggctc 540
tgaagaggcc catgaagcaa aagcggaagc tgcgactcta tatctccaac acttttaacc 600
ctgcgaagcc tgatgctgag gattccgacg gcagcattgc ctcctgggag ctacgggtgg 660
aggggaagct cctggatgat cccagcaaac agaagcggaa gttctcttct ttcttcaaga 720
gtttggtcat cgagctggac aaagatcttt atggccctga caaccacctc gttgagtggc 780
atcggacacc cacgacccag gagacggacg gcttccaggt gaaacggcct ggggacctga 840
gtgtgcgctg cacgctgctc ctcatgctgg actaccagcc tccccagttc aaactggatc 900

-continued

```
cccgcctagc ccggctgctg gggctgcaca cacagagccg ctcagccatt gtccaggccc     960

tgtggcagta tgtgaagacc aacaggctgc aggactccca tgacaaggaa tacatcaatg    1020

gggacaagta tttccagcag atttttgatt gtccccggct gaagttttct gagattcccc    1080

agcgcctcac agccctgcta ttgccccctg acccaattgt catcaaccat gtcatcagcg    1140

tggacccttc agaccagaag aagacggcgt gctatgacat tgacgtggag gtggaggagc    1200

cattaaaggg gcagatgagc agcttcctcc tatccacggc caaccagcag gagatcagtg    1260

ctctggacag taagatccat gagacgattg agtccataaa ccagctcaag atccagaggg    1320

acttcatgct aagcttctcc agagacccca aaggctatgt ccaagacctg ctccgctccc    1380

agagccggga cctcaaggtg atgacagatg tagccggcaa ccctgaagag gagcgccggg    1440

ctgagttcta ccaccagccc tggtcccagg aggccgtcag tcgctacttc tactgcaaga    1500

tccagcagcg caggcaggag ctggagcagt cgctggttgt gcgcaacacc taggagccca    1560

aaaataagca gcacgacgga actttcagcc gtgtcccggg ccccagcatt ttgccccggg    1620

ctccagcatc actcctctgc caccttgggg tgtggggctg gattaaaagt cattcatctg    1680

acaaaaaaaa aaaaaaaaaa                                                1700


<210> SEQ ID NO 55
<211> LENGTH: 2859
<212> TYPE: DNA
<213> ORGANISM: Homo sapiens

<400> SEQUENCE: 55

ctttccgcgg cattctttgg gcgtgagtca tgcaggtttg cagccagccc caaagggggt      60

gtgtgcgcga gcagagcgct ataaatacgg cgcctcccag tgcccacaac gcggcgtcgc     120

caggaggagc gcgcgggcac agggtgccgc tgaccgaggc gtgcaaagac tccagaattg     180

gaggcatgat gaagactctg ctgctgtttg tggggctgct gctgacctgg gagagtgggc     240

aggtcctggg ggaccagacg gtctcagaca atgagctcca ggaaatgtcc aatcagggaa     300

gtaagtacgt caataaggaa attcaaaatg ctgtcaacgg ggtgaaacag ataaagactc     360

tcatagaaaa aacaaacgaa gagcgcaaga cactgctcag caacctagaa gaagccaaga     420

agaagaaaga ggatgcccta aatgagacca gggaatcaga gacaaagctg aaggagctcc     480

caggagtgtg caatgagacc atgatggccc tctgggaaga gtgtaagccc tgcctgaaac     540

agacctgcat gaagttctac gcacgcgtct gcagaagtgg ctcaggcctg gttggccgcc     600

agcttgagga gttcctgaac cagagctcgc ccttctactt ctggatgaat ggtgaccgca     660

tcgactccct gctggagaac gaccggcagc agacgcacat gctggatgtc atgcaggacc     720

acttcagccg cgcgtccagc atcatagacg agctcttcca ggacaggttc ttcacccggg     780

agccccagga tacctaccac tacctgccct tcagcctgcc ccaccggagg cctcacttct     840

tctttcccaa gtcccgcatc gtccgcagct tgatgccctt ctctccgtac gagcccctga     900

acttccacgc catgttccag cccttccttg agatgataca cgaggctcag caggccatgg     960

acatccactt ccatagcccg gccttccagc acccgccaac agaattcata cgagaaggcg    1020

acgatgaccg gactgtgtgc cgggagatcc gccacaactc cacgggctgc ctgcggatga    1080

aggaccagtg tgacaagtgc cgggagatct tgtctgtgga ctgttccacc aacaacccct    1140

cccaggctaa gctgcggcgg gagctcgacg aatccctcca ggtcgctgag aggttgacca    1200

ggaaatacaa cgagctgcta aagtcctacc agtggaagat gctcaacacc tcctccttgc    1260

tggagcagct gaacgagcag tttaactggg tgtcccggct ggcaaacctc acgcaaggcg    1320
```

-continued

```
aagaccagta ctatctgcgg gtcaccacgg tggcttccca cacttctgac tcggacgttc   1380
cttccggtgt cactgaggtg gtcgtgaagc tctttgactc tgatcccatc actgtgacgg   1440
tccctgtaga agtctccagg aagaacccta aatttatgga gaccgtggcg gagaaagcgc   1500
tgcaggaata ccgcaaaaag caccgggagg agtgagatgt ggatgttgct tttgcaccta   1560
cgggggcatc tgagtccagc tccccccaag atgagctgca gccccccaga gagagctctg   1620
cacgtcacca agtaaccagg ccccagcctc caggccccca actccgccca gcctctcccc   1680
gctctggatc ctgcactcta acactcgact ctgctgctca tgggaagaac agaattgctc   1740
ctgcatgcaa ctaattcaat aaaactgtct tgtgagctga tcgcttggag ggtcctcttt   1800
ttatgttgag ttgctgcttc ccggcatgcc ttcattttgc tatgggggc aggcaggggg    1860
gatggaaaat aagtagaaac aaaaaagcag tggctaagat ggtataggga ctgtcatacc   1920
agtgaagaat aaaagggtga agaataaaag ggatatgatg acaaggttga tccacttcaa   1980
gaattgcttg ctttcaggaa gagagatgtg tttcaacaag ccaactaaaa tatattgctg   2040
caaatggaag cttttctgtt ctattataaa actgtcgatg tattctgacc aaggtgcgac   2100
aatctcctaa aggaatacac tgaaagttaa ggagaagaat cagtaagtgt aaggtgtact   2160
tggtattata atgcataatt gatgttttcg ttatgaaaac atttggtgcc cagaagtcca   2220
aattatcagt tttatttgta agagctattg cttttgcagc ggttttattt gtaaaagctg   2280
ttgatttcga gttgtaagag ctcagcatcc caggggcatc ttcttgactg tggcatttcc   2340
tgtccaccgc cggtttatat gatcttcata cctttccctg gaccacaggc gtttctcggc   2400
ttttagtctg aaccatagct gggctgcagt accctacgct gccagcaggt ggccatgact   2460
acccgtggta ccaatctcag tcttaaagct caggcttttc gttcattaac attctctgat   2520
agaattctgg tcatcagatg tactgcaatg gaacaaaact catctggctg catcccaggt   2580
gtgtagcaaa gtccacatgt aaatttatag cttagaatat tcttaagtca ctgtcccttg   2640
tctctctttg aagttataaa caacaaactt aaagcttagc ttatgtccaa ggtaagtatt   2700
ttagcatggc tgtcaaggaa attcagagta aagtcagtgt gattcactta atgatataca   2760
ttaattagaa ttatggggtc agaggtattt gcttaagtga tcataattgt aaagtatatg   2820
tcacattgtc acattaatgt caaaaaaaaa aaaaaaaaa                          2859
```

<210> SEQ ID NO 56
<211> LENGTH: 7445
<212> TYPE: DNA
<213> ORGANISM: Homo sapiens

<400> SEQUENCE: 56

```
tctgcggcgc tcggagcctc ccttgcgatc ccacggccgg gactgcccgg agtgcatggg     60
cgcgggccag ggacgctgag cggtcgcgcc atggagggcg ccgagccccg cgcgcggccc    120
gagcgcctgg ccgaggccga gacgcgggcg gcggacggcg ggcgcctggt ggaggtgcag    180
ctgagcggcg gcgccccgtg gggcttcacc ctgaagggcg gccgcgagca cggcgagccg    240
ctggtcatca ccaagattga agagggcagt aaagccgcgg cggtcgacaa gttactggct    300
ggagatgaga tcgtcggcat caatgacatt ggtctctcag ggtttagaca ggaagcgatt    360
tgcctggtga aggggtccca taagaccctg aagctggtcg tcaaaaggag gagcgagctg    420
ggctggaggc ctcactcctg gcatgccacc aagttctctg acagccaccc cgagctagcg    480
gcctccccat tcacctccac cagcggctgt ccttcctggt ccggccgaca ccacgcgagt    540
tcttcctccc acgacctgtc cagttcctgg gagcagacga acctacagcg caccttagat    600
```

-continued cacttcagct ccttggggag cgttgacagc ctggaccacc cctccagtcg cctctcggtg 660
gccaagtcca acagcagcat cgaccacctg ggcagccaca gcaagcgcga ctcggcctac 720
ggctccttct ccaccagctc tagcactcct gaccacacct tgtccaaagc cgacacgtcc 780
tccgcagaga acatcctcta cactgtgggc ctctgggagg ctcccaggca gggtggccgg 840
caggcccagg ccgcaggcga ccctcagggc tcggaggaga agctcagttg tttcccgccc 900
agggtccccg gtgacagcgg caaaggcccc aggccagagt acaatgccga gcccaagctg 960
gctgcccctg ggaggtccaa ttttggccca gtctggtatg ttcccgataa gaagaaagca 1020
ccatcatccc cacctcctcc ccctccccct ctccgcagtg acagctttgc tgccaccaag 1080
agccacgaga aggcccaggg ccctgtgttc tcagaggcgg ctgcggcaca gcactttacg 1140
gccctggccc aggctcagcc tcgtggtgac cggagaccag agctcaccga tcggccttgg 1200
aggtcagcac acccggggag cctcgggaag ggatcgggag gcccgggctg cccacaggag 1260
gcccacgcag acggcagctg gccgccctcc aaggatggag cttccagtag gctgcaggcc 1320
tctctgtcca gctcagatgt gcgcttccct cagtctcctc atagcggccg acaccctccc 1380
ctatacagcg accacagccc cctctgtgct gacagccttg ggcaggagcc aggggctgcc 1440
agcttccaga acgacagccc tcctcaggtg agggggctca gcagctgtga ccagaagctg 1500
gggagcggct ggcagggtcc ccggccctgt gtgcagggag acctgcaagc agcacagctc 1560
tgggcgggat gctggccttc tgacacagcc cttggagccc tcgagagtct tcccccaccc 1620
acggtgggcc agagcccacg ccatcaccta cctcagcctg agggtcctcc ggatgcccgc 1680
gagacaggac ggtgttaccc gctggacaaa ggggccgagg gctgctccgc gggagcccag 1740
gagcctccca gggccagccg tgcagaaaaa gccagccaga ggctggcagc cagcatcacg 1800
tgggcagatg gggagagcag caggatctgc ccgcaggaga cgcccctgtt gcactccctg 1860
acccaggagg ggaagcgccg gcctgagagc agtccagagg acagcgccac cagaccgcca 1920
ccgttcgacg cccacgtggg caagcccacc cgaagaagcg accgctttgc caccaccctg 1980
cggaatgaga tccagatgca tagagccaag ctgcagaaga gccggagcac agtggctctg 2040
actgcagcag gggaggcgga ggatggcacc ggccgctgga gggccgggtt gggaggtggc 2100
acccaggaag gacccctcgc tggcacctat aaagaccacc tgaaagaggc ccaagcccgg 2160
gtcctgaggg ccacgtcctt caagcgccgc gacttggacc ccaacccagg agacctatac 2220
ccggagtcac tggaacaccg gatgggggat ccagacactg tcccccactt ctgggaggca 2280
ggcctggccc agccaccctc atctacaagt ggcgggcccc acccgccccg catcggaggc 2340
cggagacggt tcacagctga gcagaaattg aagtcctact cggaacctga gaagatgaac 2400
gaggtgggcc tcacgagggg ctacagtcct caccagcacc ccaggacatc tgaggatact 2460
gtgggcacgt ttgctgacag gtggaagttt tttgaggaaa cgagcaaacc tgttccccag 2520
aggcctgccc agaagcaagc tcttcacgga atcccgagag acaagccaga gaggccgcgg 2580
acagcgggcc gcacatgtga gggcacggag ccctggtcgc gcaccacctc ccttggggac 2640
agcctcaacg ctcacagcgc agcggagaag gcagggactt cagacctgcc gcggaggctc 2700
ggcacctttg cagagtatca ggcctcttgg aaggaacaga ggaaacctct ggaggccagg 2760
agctctgggc gctgccactc agcggatgac atcctggatg tgagcctgga cccacaggag 2820
aggccgcagc acgttcatgg gaggtcccgg tcttcaccgt ccacagacca ctacaagcag 2880
gaagcttctg tcgaactgcg aaggcaggca ggggaccccg gcgagcccag agaagagctt 2940
ccctccgcag tccgggccga ggagggacag tccacgccga gacaagcaga tgcccagtgt 3000

-continued

```
cgggaaggca gcccaggatc acagcagcac ccaccgagtc agaaggcacc gaacccaccc   3060
acattctctg aactatctca ctgccgggga gccccagagc tgccccggga gggccggggc   3120
cgagcgggaa ccctacctcg agattataga tactcggagg agagcacccc agcagacttg   3180
ggaccccgag cccagagccc tggctcaccc ctgcatgctc gaggacaaga ctcgtggcca   3240
gtgagctcag ccctgctctc caagaggcca gccccacaga ggccaccgcc acccaagcgc   3300
gagcccagga gatacagggc cacagacggc gcacctgctg acgcccccgt gggcgtcctc   3360
ggcaggccct tcccaacgcc atcccctgcg tccctggatg tgtatgtggc ccgcctgtcc   3420
ctctcccaca gcccctctgt gttcagcagt gcccagcccc aggacacccc gaaggccact   3480
gtctgtgagc gtggaagcca gcatgtgagc ggggacgcat cacgtcctct gccagaagca   3540
ctgctccctc ccaagcagca gcacctgcgc ctgcagacgg ccaccatgga gacctcgcgc   3600
tccccctcgc cccagttcgc cccccagaaa ctgacggaca aacctcccct gctcatccag   3660
gatgaggatt caaccagaat tgagcgggtg atggacaaca acaccacggt gaagatggtg   3720
cccatcaaga tcgtgcactc ggagagccag ccagagaagg agagccgcca gagcctggca   3780
tgccccgccg agccacctgc cctgccccac gggctggaga aagaccagat caagacgctg   3840
agcacatctg agcagttcta ctcgcgcttc tgtctgtaca cgcggcaggg tgctgagccc   3900
gaggccccac atagggccca gccggctgag ccccagcccc tgggcaccca ggtgcccccc   3960
gagaaagacc gctgcacctc ccctccaggg ctcagctaca tgaaggccaa agagaagact   4020
gtggaagacc tgaagtcgga ggagctggcc agggagatcg tggggaagga taagtccctg   4080
gccgacatcc tggatcccag tgtgaagatc aaaaccacta tggacttgat ggaaggcatc   4140
ttccccaaag acgagcacct cctggaagaa gcccagcaac ggaggaagct gctccccaaa   4200
atcccctctc ctagaagcac agaggagagg aaagaggagc ccagcgtgcc tgcggccgtg   4260
tccctggcca ccaattctac ctactacagc acgtcggccc ccaaggcgga gctgctgatc   4320
aagatgaagg acctgcagga gcagcaggag cacgaagagg attcgggaag cgacttggac   4380
cacgacctgt cggtgaagaa gcaggagctc atcgagagca tcagccgcaa gctgcaggtg   4440
ctccgggagg cccgcgagag cctgctggag gacgtgcagg ccaacaccgt gctgggggcc   4500
gaggtggagg ccatcgtgaa aggcgtctgc aagcccagcg agtttgacaa gttccggatg   4560
ttcattggag acctggacaa agtggtgaac ctcctgctgt cgctgtcagg ccgcctggcc   4620
cgggtggaga atgccctcaa taatttggac gacggcgctt ctcccggtga tcggcaatca   4680
ctgcttgaga agcagagagt cctgatccag cagcacgagg acgccaagga gctcaaggag   4740
aacctggacc gccgcgagcg catcgtcttt gacattttgg ccaactatct gagcgaggag   4800
agcctcgcgg actatgagca cttcgtgaag atgaagtcgg ccctcatcat cgagcagcgg   4860
gagctggaag ataaaatcca ccttggtgaa gagcagctga agtgcttatt ggacagcctt   4920
cagcccgaaa ggggcaaata agagaccagt ccccggtgga ggaggggcac ggggcctccg   4980
agctccagct ccgttcccaa ggatactcgt gaagacccca tctgtgttca tggcctggaa   5040
agagacttct cccatagcaa agaggctgtt ataaaagcaa taacttttgt gtttgtgtgg   5100
gatgatttat ttaatttttt agtttcccct ttgattgctg agagccattt tcctttacac   5160
ataactacac ctgacaccag gctctgctgg atgtgagttt ccactgcatg ggctgtgggc   5220
tgggcctgtg gtgcctgccg agtggtcact gtcagtggga aacccgttgt tcctcccgtc   5280
ttcagatgct gagccaactg cttggacagc agccagcgcg tcatgacgtg catgagaggg   5340
ggaccctggt gctcatcttc tcttgtcatt catccaggca tgggctgcca ggttttgtcc   5400
```

ctgctcgttc aacagtgtga gcatttgtct ctgttatcta atgatgttct ctgacccagc 5460
agaaatcatc atcatgatga tgataattta ttaacttttt ggaagggtga atagtttcct 5520
aatggttaaa aaccaactgt gaaaggaacc acctgtgtgg ttgggttcac tcattctcag 5580
attaaattgc cacttaaaga aataacgtgc atgctttaaa aaacacagtc acgcaccaag 5640
caggcaaata gctttagtcc ttctcacctc acatcacagt tgttctgcaa agtaaaattt 5700
tttggttaag agcgtgtcca gtagtaatgt gcttgttagc tgtttctcaa gaccaacaga 5760 agatttttc agttactttc cccccatgta ttttgtatgc atatgattgt ccgtgataat 5820
tggctacttt tccattgttt cctccttaaa tcgtttagca tggcatgagg gccacattcc 5880
atggacggga agaccccttc ctcttcagag gtcccgtgga ctacacagct cctgagcttg 5940
atctttttct gccatgaagt ttaaagattc tatgcccatt tccttgattg aaatggcagg 6000
attctaaaga gagcctggtt tgttaaaaga aaacactgtc atgctgtcag ttcccaattg 6060
acaagtcaca gactgggaga aaatatttgc aaatcgtgta tctgacaaaa ggtttgtgtc 6120
caggatgtac aaagaactct caaaccggat agtaagaaaa caaacagccc aagtgaaaag 6180
caggcaaaag acttgaatag acacttcacc aaagagcata cacgcgtggc aaacaagcac 6240
acgaaaagac gttcagccgc cgatggcttg gttataattt ataacttact tatttttatc 6300
taataattgt agattcagtg tatttcttca aaaaatgttt aattaaatgc atgttaatgg 6360
tgagtgaatc ccttgggtga cttcgtgttt aggtcgtatt agggcatttg ttggatcaac 6420
ggatcatttt aaccctgact tccccttatt cccataaaag aagttttcca gtggaatgga 6480
gatttcattt tgtcagcagc agtgaccaca gccttaccaa agcagacgcg tgcgcgtgca 6540
cagatgcaca cacacagatg tcttaaaaga ctagaatcca cacttcctga gccagagggg 6600
ccgtgttgac ggtaatgcat tctctataga gccaagtcca aactggcaag ctcaatgatg 6660
caggcaataa accgcctttt tggcagccta ccaatgccaa aaggataaat gtctttccaa 6720
aagtgtgtat tcctgttaaa ttaagctctt gctaacttga aaaatccctg ttctgccagc 6780
gaagcttcct cctcctctcc agctggtagt cacttgcgtg aatgctggtc agtctgaaaa 6840
ggtgaagctg gctgtgcact tacccccatc tttctccctc ggggagacga cccaaggaat 6900
ttcagagtat tttgtttggc agagctttta cctgttattc tttgccctca aatacagtat 6960
tgtggtcatt ttgatgatat gtgtgtaaaa tgtgaataat ccaattggtg tctgtactca 7020
gccttttgat gtctttttag gactttctct tctacacagc aatacgtcgt gctcgagtat 7080
ccttgtagca aagcacatag agccagctgt cctgtcagtt cccctgtttg cctctgaaac 7140
gtctggttag tggggaccca aagattctag tgagtcaaca tccataactc tgtatctagt 7200
tgtattattc atagaaaatc aatctggtgc taatggttgg ccctggtgtt gttgggtggc 7260
agctgctcct tcgccctctt gtagtgtggc tgtggagggc tctgcctatg gggggtggcc 7320
tgtggcttgt atccttcagt ccaccacagc aaatgtgtgt agatttcatg ctcgacactt 7380
accactcacc tatcaacaga tcatcctgct tgactgtaac aaaataaata gtgtctcttc 7440
aagtg 7445

<210> SEQ ID NO 57
<211> LENGTH: 2206
<212> TYPE: DNA
<213> ORGANISM: Homo sapiens

<400> SEQUENCE: 57
ggaggaggag gaggaggagg aagaagaggt agcggcaagg tcgcggtctg aggttccggt 60

-continued

```
gctcgccgcc gcccagctcc cagccgaggc tttctcaacc gcgtcaataa aaggccgccc    120

cgacccgccc ccgcgccccg cagccctgcc ggacaccccg ggctgcagct gagcgggcgc    180

agacgggccg aggcgggcgc cgggcgcgca gggaccgagg gaccgagtgc tccccatgag    240

cgcacgtggg ccgggcggtc cgcaagcccg gctgagagcg cgccatgggg caggcgggct    300

gcaaggggct ctgcctgtcg ctgttcgact acaagaccga gaagtatgtc atcgccaaga    360

acaagaaggt gggcctgctg taccggctgc tgcaggcctc catcctggcg tacctggtcg    420

tatgggtgtt cctgataaag aagggttacc aagacgtcga cacctccctg cagagtgctg    480

tcatcaccaa agtcaagggc gtggccttca ccaacacctc ggatcttggg cagcggatct    540

gggatgtcgc cgactacgtc attccagccc agggagagaa cgtctttttt gtggtcacca    600

acctgattgt gacccccaac cagcggcaga acgtctgtgc tgagaatgaa ggcattcctg    660

atggcgcgtg ctccaaggac agcgactgcc acgctgggga agcggttaca gctggaaacg    720

gagtgaagac cggccgctgc ctgcggagag agaacttggc caggggcacc tgtgagatct    780

ttgcctggtg cccgttggag acaagctcca ggccggagga gccattcctg aaggaggccg    840

aagacttcac cattttcata aagaaccaca tccgtttccc caaattcaac ttctccaaaa    900

gcaatgtgat ggacgtcaag gacagatctt tcctgaaatc atgccacttt ggccccaaga    960

accactactg ccccatcttc cgactgggct ccgtgatccg ctgggccggg agcgacttcc   1020

aggatatagc cctggagggt ggcgtgatag gaattaatat tgaatggaac tgtgatcttg   1080

ataaagctgc ctctgagtgc caccctcact attcttttag ccgtctggac aataaacttt   1140

caaagtctgt ctcctccggg tacaacttca gatttgccag atattaccga gacgcagccg   1200

gggtggagtt ccgcaccctg atgaaagcct acgggatccg ctttgacgtg atggtgaacg   1260

gcaagggtgc tttcttctgc gacctggtac tcatctacct catcaaaaag agagagtttt   1320

accgtgacaa gaagtacgag gaagtgaggg gcctagaaga cagttcccag gaggccgagg   1380

acgaggcatc ggggctgggg ctatctgagc agctcacatc tgggccaggg ctgctgggga   1440

tgccggagca gcaggagctg caggagccac ccgaggcgaa gcgtggaagc agcagtcaga   1500

aggggaacgg atctgtgtgc ccacagctcc tggagcccca caggagcacg tgaattgcct   1560

ctgcttacgt tcaggccctg tcctaaaccc agccgtctag cacccagtga tcccatgcct   1620

ttgggaatcc caggatgctg cccaacggga aatttgtaca ttgggtgcta tcaatgccac   1680

atcacaggga ccagccatca cagagcaaag tgacctccac gtctgatgct ggggtcatca   1740

ggacggaccc atcatggctg tctttttgcc ccaccccctg ccgtcagttc ttcctttctc   1800

cgtggctggc ttcccgcact agggaacggg ttgtaaatgg ggaacatgac ttccttccgg   1860

agtccttgag cacctcagct aaggaccgca gtgccctgta gagttcctag attacctcac   1920

tgggaatagc attgtgcgtg tccggaaaag ggctccattt ggttccagcc cactcccctc   1980

tgcaagtgcc gcagcttccc tcagagcata ctctccagtg gatccaagta ctctctctcc   2040

taaagacacc accttcctgc cagctgtttg cccttaggcc agtacacaga attaaagtgg   2100

gggagatggc agacgctttc tgggacctgc ccaagatatg tattctctga cactcttatt   2160

tggtcataaa acaataaatg gtgtcaattt caaaaaaaaa aaaaaa                  2206
```

<210> SEQ ID NO 58
<211> LENGTH: 1298
<212> TYPE: DNA
<213> ORGANISM: Homo sapiens

<400> SEQUENCE: 58

```
agctggagcc gcggcgcgct gagcgagcag gcggggcggg agcgcccaca gctcggagcc     60

accaggcgct gacgaggagc ccggctgagg gaggatgcgc cgctgacgcc tgcgggagcc    120

gcgcgcctgg ggcgggagga tgctccagag gggcctctgg ccgtggcgca cgcggctgct    180

gccgacccct ggcacctggc gcccagcgcg cccgtggccg ctgccgcctc cgccccaggt    240

tttgcgtgtg aagctgtgtg gaaatgtgaa atactaccag tcacaccatt atagtaccgt    300

ggtgccacct gatgaaataa cagttattta tagacatggc cttcccttgg taacacttac    360

cttgccatct agaaaagaac gttgtcaatt cgtagtcaaa ccaatgttgt caacagttgg    420

ttcattcctt caggacctac aaaatgaaga taagggtatc aaaactgcag ccatcttcac    480

agcagatggc aacatgattt cagcttctac cttgatggat attttgctaa tgaatgattt    540

taaacttgtc attaataaaa tagcatatga tgtgcagtgt ccaaagagag aaaaaccaag    600

taatgagcac actgctgaga tggaacacat gaaatctttg gttcacagac tatttacaat    660

cttgcattta gaagagtctc agaaaaagag agagcaccat ttactggaga aaattgacca    720

cctgaaggaa cagctgcagc cccttgaaca ggtgaaagct ggaatagaag ctcattcgga    780

agccaaaacc agtggactcc tgtgggctgg attggcactg ctgtccattc agggtggggc    840

actggcctgg ctcacgtggt gggtgtactc ctgggatatc atggagccag ttacatactt    900

catcacattt gcaaattcta tggtcttttt tgcatacttt atagtcactc gacaggatta    960

tacttactca gctgttaaga gtaggcaatt tcttcagttc ttccacaaga aatcaaagca   1020

acagcacttt gatgtgcagc aatacaacaa gttaaaagaa gaccttgcta aggctaaaga   1080

atccctgaaa caggcgcgtc attctctctg tttgcaaatg caagtagaag aactcaatga   1140

aaagaattaa tcttacagtt ttaaatgtcg tcagattttc cattatgtat tgattttgca   1200

acttaggatg tttttgagtc ccatggttca ttttgattgt ttaatctttg ttattaaatt   1260

cttgtaaaac agaaaaaaaa aaaaaaaaaa aaaaaaaa                            1298
```

<210> SEQ ID NO 59
<211> LENGTH: 971
<212> TYPE: DNA
<213> ORGANISM: Homo sapiens

<400> SEQUENCE: 59

```
gcttgaattc ggcgcgccag atatcacacg tgccaagggc tggctcaagc atggcccggg     60

ggccgctggc cgcccgcgga ctgcggctgc tgctgccgct cctgccgctc ctgccgctcc    120

tgccgctgcc gcaggtggcg ctgggcttcg cggacggcag ctgcgacccc tcggaccagt    180

gcccgcccca ggcccgctgg agcagcctgt ggcacgtggg gctcatcctg ctggcggtcc    240

tcctgcttct gctgtgtggt gtcacagctg gttgtgtccg gttctgctgc ctccggaagc    300

aggcacaggc ccagccacat ctgccaccag cacggcagcc ctgcgacgtg gcagtcatcc    360

ctatggacag tgacagccct gtacacagca ctgtgacctc ctacagctcc gtgcagtacc    420

cactgggcat gcggttgccc ctgccctttg gggagctgga cctggactcc atggctcctc    480

ctgcctacag cctgtacacc ccggagcctc caccctccta cgatgaagct gtcaagatgg    540

ccaagcccag agaggaagga ccagcactct cccagaaacc cagccctctc cttggggcct    600

cgggcctaga gaccactcca gtgccccagg agtcgggccc caatactcaa ctaccacctt    660

gtagccctgg tgccccttga aggaggtagg agaacggacc agagcttgga gaactaatgc    720

ttggagccaa gggccccagc ccaccccacc gtcccacaca ttgctgtggc cccaacctcg    780

gtgccatgtt acaccggccc ctggcgtcac ccactaggca ggctgctgct ttcagcctca    840
```

-continued

```
gcccctggcc cagccccagc aggccctcag cctggaagag gccccttggg cctaagcctc    900

gggtgggagc tcagggccac ctgtgacgtc tgcatcttct tggagagaga ataaagtttg    960

tatttaagtg g                                                         971
```

<210> SEQ ID NO 60
<211> LENGTH: 2748
<212> TYPE: DNA
<213> ORGANISM: Homo sapiens

<400> SEQUENCE: 60

```
agcgggtgcg gggcgggacc ggcccggcct atatattggg ttggcgccgg cgccagctga     60

gccgagcggt agctggtctg gcgaggtttt atacacctga aagaagagaa tgtcaagacg    120

aagtagccgt ttacaagcta agcagcagcc ccagcccagc cagacggaat ccccccaaga    180

agcccagata atccaggcca agaagaggaa aactacccag gatgtcaaaa aaagaagaga    240

ggaggtcacc aagaaacatc agtatgaaat taggaattgt tggccacctg tattatctgg    300

ggggatcagt ccttgcatta tcattgaaac acctcacaaa gaaataggaa caagtgattt    360

ctccagattt acaaattaca gatttaaaaa tctttttatt aatccttcac ctttgcctga    420

tttaagctgg ggatgttcaa aagaagtctg gctaaacatg ttaaaaaagg agagcagata    480

tgttcatgac aaacattttg aagttctgca ttctgacttg gaaccacaga tgaggtccat    540

acttctagac tggcttttag aggtatgtga agtatacaca cttcataggg aaacatttta    600

tcttgcacaa gactttttttg atagatttat gttgacacaa aaggatataa ataaaaatat    660

gcttcaactc attggaatta cctcattatt cattgcttcc aaacttgagg aaatctatgc    720

tcctaaactc caagagtttg cttacgtcac tgatggtgct tgcagtgaag aggatatctt    780

aaggatggaa ctcattatat taaaggcttt aaaatgggaa ctttgtcctg taacaatcat    840

ctcctggcta aatctctttc tccaagttga tgctcttaaa gatgctccta aagttcttct    900

acctcagtat tctcaggaaa cattcattca aatagctcag cttttagatc tgtgtattct    960

agccattgat tcattagagt tccagtacag aatactgact gctgctgcct tgtgccattt   1020

tacctccatt gaagtggtta agaaagcctc aggtttggag tgggacagta tttcagaatg   1080

tgtagattgg atggtacctt ttgtcaatgt agtaaaaagt actagtccag tgaagctgaa   1140

gacttttaag aagattccta tggaagacag acataatatc cagacacata caaactattt   1200

ggctatgctg gaggaagtaa attacataaa caccttcaga aaagggggac agttgtcacc   1260

agtgtgcaat ggaggcatta tgacaccacc gaagagcact gaaaaaccac caggaaaaca   1320

ctaaagaaga taactaagca aacaagttgg aattcaccaa gattgggtag aactggtatc   1380

actgaactac taaagtttta cagaaagtag tgctgtgatt gattgcccta gccaattcac   1440

aagttacact gccattctga ttttaaaact tacaattggc actaaagaat acatttaatt   1500

atttcctatg ttagctgtta aagaaacagc aggacttgtt tacaaagatg tcttcattcc   1560

caaggttact ggatagaagc caaccacagt ctataccata gcaatgtttt tcctttaatc   1620

cagtgttact gtgtttatct tgataaacta ggaattttgt cactggagtt ttggactgga   1680

taagtgctac cttaaagggt atactaagtg atacagtact ttgaatctag ttgttagatt   1740

ctcaaaattc ctacactctt gactagtgca atttggttct tgaaaattaa atttaaactt   1800

gtttacaaag gtttagtttt gtaataaggt gactaattta tctatagctg ctatagcaag   1860

ctattataaa acttgaattt ctacaaatgg tgaaatttaa tgttttttaa actagtttat   1920

ttgccttgcc ataacacatt ttttaactaa taaggcttag atgaacatgg tgttcaacct   1980
```

```
gtgctctaaa cagtgggagt accaaagaaa ttataaacaa gataaatgct gtggctcctt   2040

cctaactggg gctttcttga catgtaggtt gcttggtaat aacctttttg tatatcacaa   2100

tttgggtgaa aaacttaagt accctttcaa actatttata tgaggaagtc actttactac   2160

tctaagatat ccctaaggaa ttttttttt taatttagtg tgactaaggc tttatttatg   2220

tttgtgaaac tgttaaggtc ctttctaaat tcctccattg tgagataagg acagtgtcaa   2280

agtgataaag cttaacactt gacctaaact tctattttct taaggaagaa gagtattaaa   2340

tatatactga ctcctagaaa tctatttatt aaaaaaagac atgaaaactt gctgtacata   2400

ggctagctat ttctaaatat tttaaattag cttttctaaa aaaaaaatcc agcctcataa   2460

agtagattag aaaactagat tgctagttta ttttgttatc agatatgtga atctcttctc   2520

cctttgaaga aactatacat ttattgttac ggtatgaagt cttctgtata gtttgttttt   2580

aaactaatat ttgtttcagt attttgtctg aaaagaaaac accactaatt gtgtacatat   2640

gtattatata aacttaacct tttaatactg tttattttta gcccattgtt taaaaaataa   2700

aagttaaaaa aatttaactg cttaaaagta aaaaaaaaaa aaaaaaaa                2748
```

<210> SEQ ID NO 61
<211> LENGTH: 2346
<212> TYPE: DNA
<213> ORGANISM: Homo sapiens

<400> SEQUENCE: 61

```
ccttcgcgcc ctgggccatc tccctcccac ctccctccgc ggagcagcca gacagcgagg     60

gccccggccg ggggcagggg ggacgccccg tccggggcac ccccccggct ctgagccgcc    120

cgcggggccg gcctcggccc ggagcggagg aaggagtcgc cgaggagcag cctgaggccc    180

cagagtctga gacgagccgc cgccgccccc gccactgcgg ggaggagggg gaggaggagc    240

gggaggaggg acgagctggt cgggagaaga ggaaaaaaac ttttgagact tttccgttgc    300

cgctgggagc cggaggcgcg gggacctctt ggcgcgacgc tgccccgcga ggaggcagga    360

cttggggacc ccagaccgcc tccctttgcc gccggggacg cttgctccct ccctgccccc    420

tacacggcgt ccctcaggcg cccccattcc ggaccagccc tcgggagtcg ccgacccggc    480

ctcccgcaaa gacttttccc cagacctcgg gcgcaccccc tgcacgccgc cttcatcccc    540

ggcctgtctc ctgagccccc gcgcatccta gaccctttct cctccaggag acggatctct    600

ctccgacctg ccacagatcc cctattcaag accacccacc ttctggtacc agatcgcgcc    660

catctaggtt atttccgtgg gatactgaga cacccccggt ccaagcctcc cctccaccac    720

tgcgcccttc tccctgagga cctcagcttt ccctcgaggc cctcctacct tttgccggga    780

gacccccagc ccctgcaggg gcggggcctc cccaccacac cagccctgtt cgcgctctcg    840

gcagtgccgg ggggcgccgc ctccccccatg ccgccctccg ggctgcggct gctgccgctg    900

ctgctaccgc tgctgtggct actggtgctg acgcctggcc ggccggccgc gggactatcc    960

acctgcaaga ctatcgacat ggagctggtg aagcggaagc gcatcgaggc catccgcggc   1020

cagatcctgt ccaagctgcg gctcgccagc cccccgagcc agggggaggt gccgcccggc   1080

ccgctgcccg aggccgtgct cgccctgtac aacagcaccc gcgaccgggt ggccggggag   1140

agtgcagaac cggagcccga gcctgaggcc gactactacg ccaaggaggt cacccgcgtg   1200

ctaatggtgg aaacccacaa cgaaatctat gacaagttca agcagagtac acacagcata   1260

tatatgttct tcaacacatc agagctccga gaagcggtac ctgaacccgt gttgctctcc   1320

cgggcagagc tgcgtctgct gaggctcaag ttaaaagtgg agcagcacgt ggagctgtac   1380
```

cagaaataca gcaacaattc ctggcgatac ctcagcaacc ggctgctggc acccagcgac 1440
tcgccagagt ggttatcttt tgatgtcacc ggagttgtgc ggcagtggtt gagccgtgga 1500
ggggaaattg agggctttcg ccttagcgcc cactgctcct gtgacagcag ggataacaca 1560
ctgcaagtgg acatcaacgg gttcactacc ggccgccgag gtgacctggc caccattcat 1620
ggcatgaacc ggcctttcct gcttctcatg gccaccccgc tggagagggc ccagcatctg 1680
caaagctccc ggcaccgccg agccctggac accaactatt gcttcagctc cacggagaag 1740
aactgctgcg tgcggcagct gtacattgac ttccgcaagg acctcggctg gaagtggatc 1800
cacgagccca agggctacca tgccaacttc tgcctcgggc cctgccccta catttggagc 1860
ctggacacgc agtacagcaa ggtcctggcc ctgtacaacc agcataaccc gggcgcctcg 1920
gcggcgccgt gctgcgtgcc gcaggcgctg gagccgctgc ccatcgtgta ctacgtgggc 1980
cgcaagccca aggtggagca gctgtccaac atgatcgtgc gctcctgcaa gtgcagctga 2040
ggtcccgccc cgccccgccc cgccccggca ggcccggccc caccccgccc cgccccccgct 2100 gccttgccca tgggggctgt atttaaggac acccgtgccc caagcccacc tggggcccca 2160
ttaaagatgg agagaggact gcggatctct gtgtcattgg gcgcctgcct ggggtctcca 2220
tccctgacgt tcccccactc ccactccctc tctctccctc tctgcctcct cctgcctgtc 2280
tgcactattc ctttgcccgg catcaaggca caggggacca gtggggaaca ctactgtagt 2340
tagatc 2346

<210> SEQ ID NO 62
<211> LENGTH: 2746
<212> TYPE: DNA
<213> ORGANISM: Homo sapiens

<400> SEQUENCE: 62
ggctccgact tggactccct gctccgctgc tgccgcttcg gccccgcacg cagccagccg 60
ccagccgccc gcccggccca gctcccgccg cggccccttg ccgcggtccc tctcctggtc 120
ccctcccggt tggtccgggg gtgcgcaggg ggcagggcgg gcgcccaggg gaagctcgag 180
ggacgcgcgc gcgaaggctc ctttgtggac ttcacggccg ccaacatctg ggcgcagcgc 240
gggccaccgc tggccgtctc gccgccgcgt cgccttgggg acccgagggg gctcagcccc 300
aaggacggag acttcgattc gggaccagcc ccccgggatg cggtagcggc cgctgtgcgg 360
aggccgcgaa gcagctgcag ccgccgccgc gcagatccac gctggctccg tgcgccatgg 420
tcacccacag caagtttccc gccgccggga tgagccgccc cctggacacc agcctgcgcc 480
tcaagacctt cagctccaag agcgagtacc agctggtggt gaacgcagtg cgcaagctgc 540
aggagagcgg cttctactgg agcgcagtga ccggcggcga ggcgaacctg ctgctcagtg 600
ccgagcccgc cggcaccttt ctgatccgcg acagctcgga ccagcgccac ttcttcacgc 660
tcagcgtcaa gacccagtct gggaccaaga acctgcgcat ccagtgtgag gggggcagct 720
tctctctgca gagcgatccc cggagcacgc agcccgtgcc ccgcttcgac tgcgtgctca 780
agctggtgca ccactacatg ccgccccctg gagccccctc cttcccctcg ccacctactg 840
aaccctcctc cgaggtgccc gagcagccgt ctgcccagcc actccctggg agtcccccca 900
gaagagccta ttacatctac tccgggggcg agaagatccc cctggtgttg agccggcccc 960
tctcctccaa cgtggccact cttcagcatc tctgtcggaa gaccgtcaac ggccacctgg 1020
actcctatga gaaagtcacc cagctgccgg ggcccattcg ggagttcctg gaccagtacg 1080
atgccccgct ttaaggggta aagggcgcaa agggcatggg tcgggagagg ggacgcaggc 1140

-continued ccctctcctc cgtggcacat ggcacaagca caagaagcca accaggagag agtcctgtag 1200
ctctgggggg aaagagggcg gacaggcccc tccctctgcc ctctccctgc agaatgtggc 1260
aggcggacct ggaatgtgtt ggagggaagg gggagtacca cctgagtctc cagcttctcc 1320
ggaggagcca gctgtcctgg tgggacgata gcaaccacaa gtggattctc cttcaattcc 1380
tcagcttccc ctctgcctcc aaacagggga cacttcggga atgctgaact aatgagaact 1440
gccagggaat cttcaaactt tccaacggaa cttgtttgct ctttgatttg gtttaaacct 1500
gagctggttg tggagcctgg gaaaggtgga agagagagag gtcctgaggg ccccagggct 1560
gcgggctggc gaaggaaatg gtcacacccc ccgcccaccc caggcgagga tcctggtgac 1620
atgctcctct ccctggctcc ggggagaagg gcttggggtg acctgaaggg aaccatcctg 1680
gtaccccaca tcctctcctc cgggacagtc accgaaaaca caggttccaa agtctacctg 1740
gtgcctgaga gcccagggcc cttcctccgt tttaaggggg aagcaacatt tggaggggat 1800
ggatgggctg gtcagctggt ctccttttcc tactcatact ataccttcct gtacctgggt 1860
ggatggagcg ggaggatgga ggagacggga catctttcac ctcaggctcc tggtagagaa 1920
gacaggggat tctactctgt gcctcctgac tatgtctggc taagagattc gccttaaatg 1980
ctccctgtcc catggagagg gacccagcat aggaaagcca catactcagc ctggatgggt 2040
ggagaggctg agggactcac tggagggcac caagccagcc cacagccagg gaagtgggga 2100
gggggggcgg aaacccatgc ctcccagctg agcactggga atgtcagccc agtaagtatt 2160
ggccagtcag gcgcctcgtg gtcagagcag agccaccagg tcccactgcc ccgagccctg 2220
cacagccctc cctcctgcct gggtggggga ggctggaggt cattggagag gctggactgc 2280
tgccaccccg ggtgctcccg ctctgccata gcactgatca gtgacaattt acaggaatgt 2340
agcagcgatg gaattacctg gaacagtttt ttgtttttgt ttttgttttt gtttttgtgg 2400
gggggggcaa ctaaacaaac acaaagtatt ctgtgtcagg tattgggctg gacagggcag 2460
ttgtgtgttg gggtggtttt tttctctatt tttttgtttg tttcttgttt tttaataatg 2520
tttacaatct gcctcaatca ctctgtcttt tataaagatt ccacctccag tcctctctcc 2580 tccccccctac tcaggccctt gaggctatta ggagatgctt gaagaactca acaaaatccc 2640
aatccaagtc aaactttgca catatttata tttatattca gaaaagaaac atttcagtaa 2700
tttataataa agagcactat tttttaatga aaaaaaaaaa aaaaaa 2746

<210> SEQ ID NO 63
<211> LENGTH: 4059
<212> TYPE: DNA
<213> ORGANISM: Homo sapiens

<400> SEQUENCE: 63
ataaacacag ggcgttcatc taccccacta actggagaga aggaaaacgc tgggtaaata 60
gaatggagag gcctggctgt gatcgatcag cctcaagaaa ggagacaggg taaaagggag 120
aaagaaaagg aagacccaaa gtaacccagg aaatcagcac atagaagaga cgaacagccc 180
agcacgaagc gctgactcac cgctccacgc cttcctggtc cttaatgatt ggcggctgga 240
agcgggaaga aaagatccgt ggtgccattt gattggccaa cgaattgctc ccttgccatt 300
ggctcagagg gcttttgatg aacagatcca gaaaatatgt gaagcgaaac gcccaccgcc 360
ccttgagggg ctgttctaga cctttgctcc tggtgtcgta tagagcgggg gatatttcaa 420
gctggagatc cgttttcttg tcccagtgaa caggtgcact atgttgaaat aagagtggtg 480
acggaggcct tgtttatctt gtatcttatt gtaaaaggtc atcaagaacc caccttggcc 540

-continued

```
aatcaagaga ggagtcagct ggctaatcac cgggcaggca ccgccttttt cttcccgctg    600
cctagcttgt ttgctttcga ccagccaagg agacctggtg gcagggttga tctcatattt    660
cttgtgcctc aaaatccctt ctctgaagtc tgccttccct ggagaagcaa gatggcagaa    720
tcggattcta ctgactttga cctgctgtgg tatctagaga atctcagtga caaggaattt    780
cagagtttta agaagtatct ggcacgcaag attcttgatt tcaaactgcc acagtttcca    840
ctgatacaga tgacaaaaga agaactggct aacgtgttgc caatctctta tgagggacag    900
tatatatgga atatgctctt cagcatattt tcaatgatgc gtaaggaaga tctttgtagg    960
aagatcattg gcagacgaaa ccgcaatcag gaggcatgca aagctgtcat gaggagaaaa   1020
ttcatgctgc aatgggaaag tcacactttt ggaaaatttc attataaatt ttttcgtgac   1080
gtttcgtcag atgtgttcta catacttcaa ttagcctatg attctaccag ctattattca   1140
gcaaacaatc tcaatgtgtt cctgatggga gagagagcat ctggaaaaac tattgttata   1200
aatctggctg tgttgaggtg gatcaagggt gagatgtggc agaacatgat ctcgtacgtc   1260
gttcacctca ctgctcacga aataaaccag atgaccaaca gcagcttggc tgagctaatc   1320
gccaaggact ggcctgacgg ccaggctccc attgcagaca tcctgtctga tcccaagaaa   1380
ctccttttca tcctcgagga cttggacaac ataagattcg agttaaatgt caatgaaagt   1440
gctttgtgta gtaacagcac ccagaaagtt cccattccag ttctcctggt cagtttgctg   1500
aagagaaaaa tggctccagg ctgctggttc ctcatctcct caaggcccac acgtgggaat   1560
aatgtaaaaa cgttcttgaa agaggtagat tgctgcacga ccttgcagct gtcgaatggg   1620
aagagggaga tatattttaa ctctttcttt aaagaccgcc agagggcgtc ggcagccctc   1680
cagcttgtac atgaggatga aatactcgtg ggtctgtgcc gagtcgccat cttatgctgg   1740
atcacgtgta ctgtcctgaa gcggcagatg gacaaggggc gtgacttcca gctctgctgc   1800
caaacaccca ctgatctaca tgcccacttt cttgctgatg cgttgacatc agaggctgga   1860
cttactgcca atcagtatca cctaggtctc ctaaaacgtc tgtgtttgct ggctgcagga   1920
ggactgtttc tgagcaccct gaatttcagt ggtgaagacc tcagatgtgt tgggtttact   1980
gaggctgatg tctctgtgtt gcaggccgcg aatattcttt tgccgagcaa cactcataaa   2040
gaccgttaca agttcataca cttgaacgtc caggagtttt gtacagccat tgcatttctg   2100
atggcagtac ccaactatct gatcccctca ggcagcagag agtataaaga gaagagagaa   2160
caatactctg actttaatca agtgtttact ttcatttttg gtcttctaaa tgcaaacagg   2220
agaaagattc ttgagacatc ctttggatac cagctaccga tggtagacag cttcaagtgg   2280
tactcggtgg gatacatgaa acatttggac cgtgacccgg aaaagttgac gcaccatatg   2340
cctttgtttt actgtctcta tgagaatcgg gaagaagaat ttgtgaagac gattgtggat   2400
gctctcatgg aggttacagt ttaccttcaa tcagacaagg atatgatggt ctcattatac   2460
tgtctggatt actgctgtca cctgaggaca cttaagttga gtgttcagcg catctttcaa   2520
aacaaagagc cacttataag gccaactgct agtcaaatga agagccttgt ctactggaga   2580
gagatctgct ctctttttta tacaatggag agcctccggg agctgcatat ctttgacaat   2640
gaccttaatg gtatttcaga aaggattctg tctaaagccc tggagcattc tagctgtaaa   2700
cttcgcacac tcaagttgtc ctatgtctcg actgcttctg gttttgaaga cttactcaag   2760
gctttggctc gtaatcggag cctgacatac ctgagtatca actgtacgtc catttcccta   2820
aatatgtttt cacttctgca tgacatcctg cacgagccca catgccaaat aagtcatctg   2880
agcttgatga aatgtgattt gcgagccagc gaatgtgaag aaatcgcctc tctcctcatc   2940
```

agtggcggga gtctgagaaa actgacctta tccagcaatc cgctgaggag cgacgggatg 3000
aacatactgt gtgatgcctt gcttcatccc aactgcactc ttatatcact ggtgttagtc 3060
ttctgctgtc tcactgaaaa ttgctgcagc gcccttggaa gagtgcttct gttcagccca 3120
actctaagac aactagacct gtgtgtgaat cgcttaaaaa attacggagt gttgcatgtg 3180
acgtttccct tgctgtttcc aacctgtcag ttagaggagc ttcatctgtc tggctgtttc 3240
tttagcagcg atatctgtca atatattgcc atagttattg ctactaatga aaaactgagg 3300
agcctggaga ttgggagcaa caaaatagaa gatgcaggaa tgcagctgct atgtggtggt 3360
ttgagacatc ccaactgcat gttggtgaat attgggctag aagagtgcat gttaaccagt 3420
gcctgctgtc gatctcttgc ctctgttctt accaccaaca aaacactaga aagactcaac 3480
ttgcttcaaa atcacttggg caatgatgga gttgcaaaac ttcttgagag cttgatcagc 3540
ccagattgtg tacttaaggt agttgggctt ccattaactg gcctgaacac acaaacccag 3600
cagttgctga tgactgtaaa ggaaagaaaa cccagtttga tctttctgtc tgaaacttgg 3660
tctttaaagg aaggcagaga aattggtgtg acacctgctt ctcagccagg ttcaataata 3720
cctaattcta atttggatta catgtttttc aaatttccca gaatgtctgc agccatgaga 3780
acgtcaaata cagcatctag gcaacccctt tgatcatgtt gtacgtaaac agtatttatt 3840
ataaattact accgtgactg ggatgcaaga gaattaggac tataattttc ctatttgatg 3900
tgtgtgtgtg tgtgtgtgtg tgtgtgtgtg tgtgtgtgtg tgtgaccttg atccagtcaa 3960
ccacttcaaa ttcctacact gtctcaagag tattaaaagg attatatgaa gtaataaagg 4020
ataaaatgca ttggaaaaag caaaaaaaaa aaaaaaaaa 4059

<210> SEQ ID NO 64
<211> LENGTH: 3686
<212> TYPE: DNA
<213> ORGANISM: Homo sapiens

<400> SEQUENCE: 64
ggctgcccga gcgagcgttc ggacctcgca ccccgcgcgc cccgcgccgc cgccgccgcc 60
ggcttttgtt gtctccgcct cctcggccgc cgccgcctct ggaccgcgag ccgcgcgcgc 120
cgggaccttg gctctgccct tcgcgggcgg gaactgcgca ggacccggcc aggatccgag 180
agaggcgcgg gcgggtggcc gggggcgccg ccggccccgc catggagctc cgggcccgag 240
gctggtggct gctatgtgcg gccgcagcgc tggtcgcctg cgcccgcggg gacccggcca 300
gcaagagccg gagctgcggc gaggtccgcc agatctacgg agccaagggc ttcagcctga 360
gcgacgtgcc ccaggcggag atctcgggtg agcacctgcg gatctgtccc cagggctaca 420
cctgctgcac cagcgagatg gaggagaacc tggccaaccg cagccatgcc gagctggaga 480
ccgcgctccg ggacagcagc cgcgtcctgc aggccatgct tgccacccag ctgcgcagct 540
tcgatgacca cttccagcac ctgctgaacg actcggagcg gacgctgcag gccaccttcc 600
ccggcgcctt cggagagctg tacacgcaga acgcgagggc cttccgggac ctgtactcag 660
agctgcgcct gtactaccgc ggtgccaacc tgcacctgga ggagacgctg gccgagttct 720
gggcccgcct gctcgagcgc ctcttcaagc agctgcaccc ccagctgctg ctgcctgatg 780
actacctgga ctgcctgggc aagcaggccg aggcgctgcg gcccttcggg gaggccccga 840
gagagctgcg cctgcgggcc acccgtgcct tcgtggctgc tcgctccttt gtgcagggcc 900
tgggcgtggc cagcgacgtg gtccggaaag tggctcaggt cccccctgggc ccggagtgct 960 cgagagctgt catgaagctg gtctactgtg ctcactgcct gggagtcccc ggcgccaggc 1020

-continued

```
cctgccctga ctattgccga aatgtgctca agggctgcct tgccaaccag gccgacctgg   1080

acgccgagtg gaggaacctc ctggactcca tggtgctcat caccgacaag ttctggggta   1140

catcgggtgt ggagagtgtc atcggcagcg tgcacacgtg gctggcggag gccatcaacg   1200

ccctccagga caacagggac acgctcacgg ccaaggtcat ccagggctgc gggaacccca   1260

aggtcaaccc ccagggcccc gggcctgagg agaagcggcg ccggggcaag ctggccccgc   1320

gggagaggcc accttcaggc acgctggaga agctggtctc cgaagccaag gcccagctcc   1380

gcgacgtcca ggacttctgg atcagcctcc cagggacact gtgcagtgag aagatggccc   1440

tgagcactgc cagtgatgac cgctgctgga acgggatggc cagaggccgg tacctccccg   1500

aggtcatggg tgacggcctg gccaaccaga tcaacaaccc cgaggtggag gtggacatca   1560

ccaagccgga catgaccatc cggcagcaga tcatgcagct gaagatcatg accaaccggc   1620

tgcgcagcgc ctacaacggc aacgacgtgg acttccagga cgccagtgac gacggcagcg   1680

gctcgggcag cggtgatggc tgtctggatg acctctgcag ccggaaggtc agcaggaaga   1740

gctccagctc ccggacgccc ttgacccatg ccctcccagg cctgtcagag caggaaggac   1800

agaagacctc ggctgccagc tgcccccagc ccccgacctt cctcctgccc ctcctcctct   1860

tcctggccct tacagtagcc aggccccggt ggcggtaact gccccaaggc cccagggaca   1920

gaggccaagg actgactttg ccaaaaatac aacacagacg atatttaatt cacctcagcc   1980

tggagaggcc tggggtggga cagggagggc cggcggctct gagcaggggc aggcgcagag   2040

gtcccagccc caggcctggc ctcgcctgcc tttctgcctt ttaattttgt atgaggtcct   2100

caggtcagct gggagccagt gtgcccaaaa gccatgtatt tcagggacct caggggcacc   2160

tccggctgcc tagccctccc cccagctccc tgcaccgccg cagaagcagc ccctcgaggc   2220

ctacagagga ggcctcaaag caacccgctg gagcccacag cgagcctgtg ccttcctccc   2280

cgcctcctcc cactgggact cccagcagag cccaccagcc agccctggcc cacccccag   2340

cctccagaga agccccgcac gggctgtctg ggtgtccgcc atccagggtc tggcagagcc   2400

tctgagatga tgcatgatgc cctcccctca gcgcaggctg cagagcccgg ccccacctcc   2460

ctgcgccctt gaggggcccc agcgtctgca gggtgacgcc tgagacagca ccactgctga   2520

ggagtctgag gactgtcctc ccacagacct gcagtgaggg gccctccatg cgcagatgag   2580

gggccactga cccacctgcg cttctgctgg aggaggggaa gctgggccca aaggcccagg   2640

gaggcagcgt gggctctgcc aatgtgggct gcccctcgca cacagggctc acagggcagg   2700

ccttgctggg gtccagggct gttggaggac cccgagggct gaggagcagc caggacccgc   2760

ctgctcccat cctcacccag atcaggaacc agggcctccc tgttcacggt gacacaggtc   2820

agggctcaga gtgaccctca gctgtcacct gctcacaggg atgctggtgg ctggtgagac   2880

cccgcactgc agacgggaat gcctaggtcc cttcccgacc cagccagctg cagggcacgg   2940

ggacctggat agttaagggc ttttccaaac atgcatccat ttactgacac ttcctgtcct   3000

tgttcatgga gagctgttcg ctcctcccag atggcttcgg agggccgcag ggcccacctt   3060

ggaccctggt gacctcctgt cactcactga ggccatcagg gccctgcccc aggcctggac   3120

gggccctcct tccctcctgt gccccagctg ccaggcggcc ctggggaggg gtggtgtggt   3180

gttgggaagg ggtcctgcag ggggaggagg acttggaggg tctgggggca gctgtcctga   3240

accgactgac cctgaggagg ccgcttagtg ctgctttgct tttcatcacc gtcccgcaca   3300

gtggacggag gtccccggtt gctggtcagg tccccatggc ttgttctctg gaacctgact   3360

ttagatgttt tgggatcagg agcccccaac acaggcaagt ccaccccata ataaccctgc   3420
```

```
cagtgccagg gtgggctggg gactctggca cagtgatgcc gggcgccagg acagcagcac   3480

tcccgctgca cacagacggc ctaggggtgg cgctcagacc ccaccctacg ctcatctctg   3540

gaaggggcag ccctgagtgg tcactggtca gggcagtggc caagcctgct gtgtccttcc   3600

tccacaaggt ccccccaccg ctcagtgtca gcgggtgacg tgtgttcttt tgagtccttg   3660

tatgaataaa aggctggaaa cctaca                                        3686
```

<210> SEQ ID NO 65
<211> LENGTH: 1793
<212> TYPE: DNA
<213> ORGANISM: Homo sapiens

<400> SEQUENCE: 65

```
ccgaggtccc agacgcccgg cgcagcggga gcggcggggc gtgcctggcc tgcgggacgc     60

gactgatcgc agtggggcga agcggggccg gagccgcccg cggtcaggag cagcaatgtc    120

tgtgcaggta gcggctcctg gaagtgcagg gctgggccca gagcgcctga gccctgagga    180

gctggtgcgg cagacgcggc aagtggtcca ggggctggag gcgctgcggg cagagcacca    240

tggcctggct gggcacctgg cggaggccct ggcgggacag ggcccggcag ccggcttgga    300

gatgctggag gaaaagcagc aggtggtgag ccactcgctg gaggccatcg agctggggct    360

gggcgaggcc caggtgctgc tggccctgtc ggcacatgtg ggtgcactgg aggcagagaa    420

gcagcggctg cgctcgcagg cccggcggct ggcccaggag aacgtgtggc tgcgggagga    480

actggaggag acgcagcggc ggcttcgggc cagcgaggag tccgtggccc agctggagga    540

ggagaagcgc cacctggagt tcctggggca gctgcgacag tacgacccac cggcggagag    600

ccagcagtct gagtccccgc ctcgccgaga cagcctggcc tccctgttcc ccagcgagga    660

ggaggagagg aaaggtcctg aggccgcagg agcagcagct gctcagcagg gtggctatga    720

gatccctgcc cgccttcgga ccctgcataa cctcgtgatc cagtacgcgg ggcagggccg    780

ctatgaggtg gcggtgcctc tgtgccgcca ggccttggag gacctggagc gcagctcggg    840

ccactgccac cctgacgtgg ccaccatgct caacatcctg gcgctggtgt accgggacca    900

gaacaagtac aaagaagcca cagaccttct ccatgatgcc ctgcagatcc gggagcagac    960

gctgggccct gagcaccccg cggtggccgc cacgctcaac aacttggctg tcctctatgg   1020

gaagcgtggg cgttaccggg aggcagagcc cctgtgccag cgcgctttgg agatccgaga   1080

gaaggtcctg ggtgctgacc acccagatgt ggccaagcag ctcaacaacc tggccctgct   1140

gtgccagaac cagggcaagt ttgaggacgt ggagcggcac tatgcccggg ccctgagcat   1200

ctatgaggca ctgggcgggc cccatgaccc caacgtggcc aagaccaaga acaacctggc   1260

ctcagcctac ctgaaacaga acaagtatca acaagcggaa gagctgtaca aagaaatcct   1320

ccacaaggag gacctacccg cccctctcgg tgcccccaac acaggcacag ctggtgacgc   1380

agaacaggcc cttcgccgca gcagctcact ctccaagatc cgtgagtcta tcaggcgagg   1440

aagtgagaag ctggtctccc ggctccgagg cgaggcggcg gcaggagcag ccggaatgaa   1500

gagagccatg tcactcaaca cactgaacgt ggatgctcca agggctcctg ggactcagtt   1560

tcccagctgg cacctggaca aggcccctcg gaccctcagc gccagcaccc aggacctgag   1620

cccccactaa cgtccagtga actgcgctgg ccgcagcttc ttgggaacag tgcaggaggg   1680

atgggctggt ggggtgagag ggggtctatc atctcctggc ccccccttgc ctctgggtac   1740

ctggtggata gctgccttct cctgcgatta aaggctgtgg acgtgacagt gag          1793
```

<210> SEQ ID NO 66

<211> LENGTH: 1368
<212> TYPE: DNA
<213> ORGANISM: Homo sapiens

<400> SEQUENCE: 66

```
ggagctgcga gccgcgaccg ccgggagcgc acctgccccg cctccgccag gcggtccgcg      60
gggcatgcag cggaccgggg gcggggctcc gaggcccggg cgcaaccacg ggctcccagg     120
cagcctccgc cagccggacc ccgtcgccct cctgatgctg ctcgtggacg ctgatcagcc     180
ggagcccatg cgcagcgggg cgcgcgagct cgcgctcttc ctgacccccg agcctggggc     240
cgaggcgaag gaggtggagg agaccatcga gggcatgctc ctcaggctgg aagagttttg     300
cagcctggct gacctgatca ggagtgatac ttcacagatc ctggaggaaa acatcccagt     360
ccttaaggcc aaactgacag aaatgcgtgg catctatgcc aaagtggacc ggctagaggc     420
cttcgtcaag atggttggac accacgtcgc cttcctggaa gcagacgtgc ttcaggctga     480
gcgggaccat ggggccttcc ctcaggccct gcggaggtgg ctgggatccg cagggctccc     540
ctccttcagg aacgtggagt gcagtggcac aatcccagct cgctgcaacc tccgcctccc     600
gggttcaagt gattctcctg cctccgcctc ccaagtagct gggattacag aagtcacctg     660
caccggtgcc cgtgacgtac gagctgccca cactgtatag gacggaggac tattttcctg     720
tggacgccgg ggaagcacag caccaccccc gcacctgccc tcggcctttg tgagctttgt     780
ggtcttccca tcaggaacgc tggaaagtga cattgtgtac acactgcagc ttgggggttt     840
tttctttgta ttgctgttta ttttatattt taaaaatatt taaaaaaatg tcgagatggg     900
gtctcactat gttgtccaga ctgatctcaa actcctgggc tcaagtgatc cacccacctt     960
ggccttccaa agtggtggga ttatgggcag gagcctccgt gcccaggctg ctgccatttt    1020
caaatttcct ccctgcctca tgtgagacca cagggtttgg agaagcagtt ggaacccacg    1080
tgtggtgatg cctcccacat cggcctgctt ggggttctac aggggttgag ggaccaggcc    1140
tggccggggc tgatggacag tggggacttt ccttctctcc atgatggctt tgcaggggct    1200
ccatggtcct tctctctgtg atgggttttt gcacggggtg tgctctgcca ctgtggtggg    1260
tgggtggatg ctgcttctgt tgcctccaga cctcggtgcc cacagccttg aggatccttc    1320
caataaaggt gtcaagagct caaaaaaaaa aaaaaaaaaa aaaaaaaa                 1368
```

<210> SEQ ID NO 67
<211> LENGTH: 3376
<212> TYPE: DNA
<213> ORGANISM: Homo sapiens

<400> SEQUENCE: 67

```
attatttgaa gacgctcacg gagcggctgg ctaggctgag gagagctcgc cgggctctga      60
ggcgcaggaa ttcaataaag aaaatggcag ctcttactcc aaggaagagg aagcaggatt     120
ctttgaagtg tgacagcctt ttacacttca ctgaaaatct gtttccatca cctaataaaa     180
agcactgttt ttatcaaaac agtgataaaa atgaagaaaa cctgcattgc tctcaacaag     240
agcattttgt tttaagtgcg ctcaaaacaa ctgaaataaa tagactgcca tcagcaaatc     300
aaggctcacc atttaaatct gcgctctcca ctgtatcttt ttacaaccaa aataagtggt     360
acctcaatcc actggagaga aagctgataa aagagagtag atctacttgt ctaaaaacta     420
atgatgaaga taaatctttt cccattgtga cagaaaaaat gcaaggaaaa ccagtctgct     480
ccaagaagaa caacaaaaaa ccacagaaga gtttaactgc taagtatcaa ccaaagtata     540
gacacatcaa gcctgtatca aggaattcta gaaattccaa gcaaaatcga gtgatctata     600
```

-continued

```
agccaattgt ggagaaggaa aataattgtc attcagctga aaataattcc aatgctcctc    660
gggttctgag ccaaaaaata aaaccacaag ttacactcca gggtggagca gcattttttg    720
ttagaaaaaa atcttctctt agaaaatcgt ccctggaaaa tgagccgtca ctgggacgca    780
cccaaaagag taaatcagaa gtcattgaag attctgatgt agagactgtc agtgaaaaaa    840
aaacttttgc gacaaggcaa gtgccaaagt gcttggtcct agaagagaaa ttgaaaattg    900
gactactgag tgcaagcagt aaaaataaag agaaattaat aaaggattca tcagatgaca    960
gagtttcttc aaaggaacat aaagttgata aaaatgaggc tttttcttca gaggattctc   1020
ttggtgagaa taagacaatt tctcctaagt ccactgtcta tccaatcttc agtgcatctt   1080
cagtcaattc aaaaagatct ttaggtgaag aacagttttc tgtgggatct gtcaacttca   1140
tgaaacagac caatatccag aaaaatacta ataccagaga tacaagtaaa aaaacaaaag   1200
accagctcat catcgacgct ggtcagaaac attttggggc tactgtgtgc aagtcttgtg   1260
gtatgatata tactgcttcc aaccctgaag atgaaatgca gcatgtacag catcaccaca   1320
ggtttctgga aggaatcaaa tatgtgggtt ggaagaaaga acgtgtagta gcagagtttt   1380
gggatgggaa aatcgtgttg gttctgccac atgatccaag ctttgctatc aaaaaggtag   1440
aagatgtcca agaacttgtt gataatgaat tgggcttcca gcaagttgtt cctaaatgtc   1500
caaacaaaat aaaaactttt ctttttatat ctgatgaaaa gagagtagtt gggtgtttaa   1560
ttgcagaacc catcaaacag gcatttcgtg tcctgtctga accaattggt ccagaatccc   1620
caagctctac ggaatgtcct agggcttggc aatgttcaga tgtaccagaa cctgcagtct   1680
gtgggataag tagaatctgg gttttcagac tgaagagaag aaagcgcatt gcaagacgac   1740
tggttgatac cctcaggaat tgcttcatgt ttggctgttt tctcagcact gatgaaatag   1800
cattttctga cccaacacca gatggcaagt tatttgcaac caagtactgc aacaccccta   1860
atttcctcgt atataatttt aatagttaaa gctgatttca gttataaagg agttactatc   1920
tggataagtt caaagagctc cttattataa aatacaaact atttaatatc aaaataaaaa   1980
ataccgagac tcacactcat acacacacac acacacacgc acacacacat atcacagttt   2040
tgttccttat gagttgaaaa gtcaggaata aatttgttga aaattatctg gggattcaaa   2100
ggaaaaatct ttgggtgatt ccctgattag cactctgaat gtttaattat gaaactttgt   2160
agctataact ggaaaattac ctgactcttt gtaagagtat taaatacaaa gtgatttttc   2220
tctagaaatg tgacctggtc ttttataaag cccactctta gaccaggatt atctaatgcc   2280
acatcagaag caaacaggca aatttaaact tgggcaagta atttctgtgc ccaatttgta   2340
aagggaattc ctgaattttt tttttttttt aatagaggca tgggtctcac tgtgttgccc   2400
aggctggtct gaaactttg ggctcaagcg atcctcccaa aacgctggga ttacagtcat   2460
gagccaccgt gcccagccta attcctgact tctctataca gagtcttcac ttgataggca   2520
ctcgtctgta gtaactcagt ttgaatatct ttagaaaatg tttagaattt atttgtaaca   2580
agatggtaag gaataagatt atcccatatg catttctgta gagcagaatt tgatagctta   2640
gtgttcaatc tttttgaaaa taaatgttta cctgtcatca gatttaatta aaattatact   2700
tagtaattgc actattactt agttaatttt tgttgtatgg aaatattggt agtactactt   2760
tgggaacctg ttactgacaa ttgatgtcat taacaaaatg cctagttgga ttagatgttt   2820
tcatttteta atttttgct tgtttaaaat gcaccttact tgttctgaga tacctggcaa   2880
aagtctttac aaaatgtatg gtaatagaac caaggttagt aaatatacat aggctggtgg   2940
atgagagacc atggaactgt gtaaatacac ttaaatgttc acacattttt ctagtgtaat   3000
```

-continued tcttggatac tttaaaaagc aaaacattgt tcaaattgtt ttgattctga aaaatcattc 3060
aactgctaac tggcaataag actctaggca agtcgttttc cagattgtaa ttatatgtag 3120
aaactattca tctgcattca ttttatttgc ctgtaagtta acatgtttcc aaaatttaaa 3180
agcctgggtc cccaaaagaa tgtggaagta ttaaaatgta tgtaattatg caaacatttt 3240
aatgctattt tctgcactta tttcttttaa atattttatt taaaattttt aattaacatt 3300
ttgtttgctt aatgcttttg ttatgaatca attaaaattc tttattttat acaactaaaa 3360
aaaaaaaaaa aaaaaa 3376

<210> SEQ ID NO 68
<211> LENGTH: 5954
<212> TYPE: DNA
<213> ORGANISM: Homo sapiens

<400> SEQUENCE: 68
cttcgggggc gagcgcgcgt gtgtgtgagt gcgcgccggc cagcgcgcct tctgcggcag 60
gcggacagat cctcggcgcg gcagggccgg ggcaagctgg acgcagcatg atgcgcgcag 120
tgtgggaggc gctggcggcg ctggcggcgg tggcgtgcct ggtgggcgcg gtgcgcggcg 180
ggcccgggct cagcatgttc gcgggccagg cggcgcagcc cgatccctgc tcggacgaga 240
acggccaccc gcgccgctgc atcccggact ttgtcaatgc ggccttcggc aaggacgtgc 300
gcgtgtccag cacctgcggc cggcccccgg cgcgctactg cgtggtgagc gagcgcggcg 360
aggagcggct gcgctcgtgc cacctctgca acgcgtccga ccccaagaag gcgcacccgc 420
ccgccttcct caccgacctc aacaacccgc acaacctgac gtgctggcag tccgagaact 480
acctgcagtt cccgcacaac gtcacgctca cactgtccct cggcaagaag ttcgaagtga 540
cctacgtgag cctgcagttc tgctcgccgc ggcccgagtc catggccatc tacaagtcca 600
tggactacgg gcgcacgtgg gtgcccttcc agttctactc cacgcagtgc cgcaagatgt 660
acaaccggcc gcaccgcgcg cccatcacca agcagaacga gcaggaggcc gtgtgcaccg 720
actcgcacac cgacatgcgc ccgctctcgg gcggcctcat cgccttcagc acgctggacg 780
ggcggccctc ggcgcacgac ttcgacaact cgcccgtgct gcaggactgg gtcacggcca 840
cagacatccg cgtggccttc agccgcctgc acacgttcgg cgacgagaac gaggacgact 900
cggagctggc gcgcgactcg tacttctacg cggtgtccga cctgcaggtg ggcggccggt 960
gcaagtgcaa cggccacgcg gcccgctgcg tgcgcgaccg cgacgacagc ctggtgtgcg 1020
actgcaggca caacacggcc ggcccggagt gcgaccgctg caagcccttc cactacgacc 1080
ggccctggca gcgcgccaca gcccgcgaag ccaacgagtg cgtggcctgt aactgcaacc 1140
tgcatgcccg gcgctgccgc ttcaacatgg agctctacaa gctttcgggg cgcaagagcg 1200
gaggtgtctg cctcaactgt cgccacaaca ccgccggccg ccactgccat tactgcaagg 1260
agggctacta ccgcgacatg ggcaagccca tcacccaccg gaaggcctgc aaagcctgtg 1320
attgccaccc tgtgggtgct gctggcaaaa cctgcaacca aaccaccggc cagtgtccct 1380
gcaaggacgg cgtgacgggt atcacctgca accgctgcgc caaaggctac cagcagagcc 1440
gctctcccat cgccccctgc ataaagatcc ctgtagcgcc gccgacgact gcagccagca 1500
gcgtggagga gcctgaagac tgcgattcct actgcaaggc ctccaagggg aagctgaaga 1560
ttaacatgaa aaagtactgc aagaaggact atgccgtcca gatccacatc ctgaaggcgg 1620
acaaggcggg ggactggtgg aagttcacgg tgaacatcat ctccgtgtat aagcagggca 1680
cgagccgcat ccgccgcggt gaccagagcc tgtggatccg ctcgcgggac atcgcctgca 1740

-continued

```
agtgtcccaa aatcaagccc ctcaagaagt acctgctgct gggcaacgcg gaggactctc   1800
cggaccagag cggcatcgtg gccgataaaa gcagcctggt gatccagtgg cgggacacgt   1860
gggcgcggcg gctgcgcaag ttccagcagc gtgagaagaa gggcaagtgc aagaaggcct   1920
agcgccgagg cagcgggcgg gcgggcgggc gggcgccagg gcggggccga gcgagagcgg   1980
gcgccttggc ccggccgccg cggacttggc ccgcgagggc tttcccaggt ggggggaggg   2040
agggggcggg gccgcacggc gcggggggcg ggaccctcgg cggcccctcc ccctaccccc   2100
accctgcgcg ctctgggcgg gagccgcgtg cacgcggggc ggggtgcgcc gccggccggg   2160
ccctggagaa atgacgagac gtagctacct cacggggctc cttccagagc agagacgcgc   2220
ttccctgggc ctgggcgcgg ccgccgtgga ggggctgggg gcagcctgcc ctggggcccg   2280
ggggcgggcg cagaatcgca caactggggc cccaggcgcg gggcgtggat ggcgcggaga   2340
cgtggacggg aggagaactg tgaattctca agcccgtagt gtgggcgggg cgcggagcac   2400
ccaccaaacc accacccgac acgcagccga cgggatcccc ccctttctcc ccggcccctt   2460
ctagcagttc cccgcgggcc acctggctgt cacagcctgg actcctccat ctgaaggggc   2520
ctggcagcat ttggggagtg gacagctcct gtccagccag catgccccag gcggcctctg   2580
tctccactgc tacctgctga gtgggtccta ctgggtgggg gcttggggtc ggtgagtggt   2640
tcacctgtgg agagaggaga ggaagcccct gctgctgcct gtctctgccc ctgcccctgc   2700
ccctgcccag cgtggggctg gcccatccgg aaggcagtgg gcccagggac acccctgaga   2760
agcccaagcc gggtggtcac cgcctcatgc tggagctgcc tgttggagga ggcatcgcaa   2820
acgcaaaacc tcccagagag tttccttttg gaaacttgga accagccctt tttatgacgt   2880
tttccagggg gagggggagg ggcactggct gggtttacgg cagtgacact atttatgtaa   2940
atgacatcag ctcccgcaag gcccctcagc aatgtcaaca gctggaaagg gcctgaacgg   3000
gcttggagtc tgcaggctgc gaaggcactt gggcctggct tggggccggg ggcttgtttg   3060
agctgggatg gggtttgctg gctcagtgaa gtaccagagt gcctgagcca tgggtgggca   3120
ggggcacagg aatgaccagg ttcctggggg ccaaggaggc catgctggct tctccaaggg   3180
aaggcacaga ggctgccggc ctgcccccta cagctgtctt gggtctggcc tgggccacac   3240
cttgaccgtg cctttccaga cggtctttgt ggagtctgcc cgtgccctcc actgtgcccc   3300
agccctcctt ccaaaatctc ctagagacac ggtcctcaag caggcagccc cttttgttct   3360
gacctcctca cacagggtcc attcctgtgc cctggggcct cctggctccc tgccttcctg   3420
ggctctctgc actgcccggg cctctggccc acatcctcac acccggcgca ctgaattaag   3480
aggcctggct cccctcacag tcaggaaatt ggtttcactt tcccggccag agtttggctg   3540
ctcaaaaggg tcataccaag tatgaagctc ggcccccggt ggtctggctt ccctccgcct   3600
tccccacatt tacccgcatc acggctgcca tttattgagc acctgctgtg tgccaggcac   3660
tttacccaca tgctcccagt gtgtactcat gacaaccctg tgggacaggg actcattatc   3720
accagcaagg agactggagt acacgtgccc aaggtcatgc tgcaaattgg tggcaggact   3780
ggggctcaaa ctccagagcc cgactttctg accaggggcc acgctggccc tcactgcact   3840
ccagctctgc agcctacccg cccaatccct gtgcaggctg ggagggtgct cttgggggag   3900
tggccaccga gcccctggcc ctggttactg cctcttgagg acactggcat ctgggctgga   3960
gaacaggagc ccggggtggg gtagggcatg gggacaatca catcttcaga ggaggcagca   4020
aagtggtgcg ggatgcaggg acggacttgc cagatggcag ctccaggttc caggaaggca   4080
ggccttggat gctccgaaga ggtggtagaa aggtgttttt agaaaggtgt tttggctgcc   4140
```

-continued

```
tcagggtggt tggagagact ccaggagaga ctggcagagg tgcctcaggg gcagggagca   4200

gacagacctg ccctgggaag gggcatttgg cttccctgaa tccagcccaa ggctagaaga   4260

cagggcccct ctccaagctg tcagcgcccc tcggatgccc agtgtggtgt gctgggcgcc   4320

atcagcatca caaggcacta cgctgctggg gcggttgtcc tatttctgtc tatgccagtg   4380

tggtttcttc accctgccca gaagggctgt ggcagcccca cgatatccca ccctgggtct   4440

gggtctcacg ggtgtcctgt gaggggcttg catttgtggt ggtctctgag gccacctcag   4500

caacggagct ggcgacacgc caagcaacaa ggcatcttgc ggaaaattca gccagtgtcc   4560

tgcccctccc ttcggctcag caccccgcag ggcacaggct gtccgcccgg tggtctggcc   4620

cttggggaat gcgtcagggt gaccagatcc accatgctag cagccaggtc actgttggga   4680

ttgcacggtc gtcacgagct gcctttccta tccacacacc cagccaggac ccagcccacc   4740

actcccgact gcagccccgg cctctgcggt gagcaccatc cttgggaaag cacccctcct   4800

ccactccggt gccccactcc aaggagcaga gggaaatggg aattgaggtg tcccggtttg   4860

tacagttagg aagggatgta aaacggaact agattttgat tttgaagagt gtattaacca   4920

gaattgtgct atgtaggtgt ttgtttgaag aaaaacatac cagattagtc tttgtttttg   4980

aaacagcttc cccagttgtc ctttttctta ccagctgggt ggtctggtgc ccctgacagc   5040

tgagtgcctg ctttacggac acgcagtaat gccgaagatt tgcgggggag gacatagggc   5100

tgtccccggg attcacctgc tggctgtggt ctctgcccac tgcttctgtc cttggaaagc   5160

agggcaggag gcagcatccc caggggcctc tatgtgggag ggagggacac ctggggtcac   5220

aacccaggga gggagggtca cagcccaggg aggctgggag ctgctccaag gccctggaac   5280

tctgcctcag tcgcggcatg ctggagaggg gtacggactt actttcttgg agttgtccca   5340

ggttggaatg agactgaact caagaagaga ccctaaggga ctggggaatg gttcctgcct   5400

tcaggaaagt gaaagacgct taggctgtca acacttaaag gaagtcccct tgaagcccag   5460

agtggacaga ctagacccat tgatggggcc actggccatg gtccgtggac aagacattcc   5520

tgtgggccat ggcacaccgg gggggatcaa aatgtgtact tgtggggtct cgccccttgc   5580

caaaagccaa accagtccca ctcctgtcat tggacgtttc ttcccattcc ctcctcccaa   5640

atgcacttcc cctcctccct ctgccccctc ctgtgttttg gatttctgtt cactcagaat   5700

tgtaaatgtt tagttgtgac catgacgtat tgtttgggtc aatgtccctt tccaatgcat   5760

actaatatat tatggttatt atatatgaat atatttaatg acatggaaaa agttgtggat   5820

tttctttctt tcctttttt tgggggggg tgggggggttg gttagagttg taatggaccc   5880

agatggaact tgtaatgtgg gccccacatg atagaactaa attcagatat cattaaataa   5940

actcttgtac acta                                                     5954
```

<210> SEQ ID NO 69
<211> LENGTH: 1196
<212> TYPE: DNA
<213> ORGANISM: Homo sapiens

<400> SEQUENCE: 69

```
tgcccccagc cgaggggcag ccccggggcc gggcccggcg cgcacccggc cagcgcgccc     60

tcgccagctg cgctctgagt tctgggccag ctccccagag gcctaggcgc cgccgccgcg    120

agggcgcggg gcagacaaag gaggcagaca aaggcgggcg cagcccagca gccgtgcggg    180

caccgggcga ggcaggccca ctcctcccgg tagcgggaag gatgaccacg ctcacacgac    240

aagacctcaa ctttggccaa gtggtggccg atgtgctctg cgagttcctg gaggtggctg    300
```

-continued

```
tgcatctcat cctctacgtg cgcgaggtct accccgtggg catcttccag aaacgcaaga    360
agtacaacgt gccggtccag atgtcctgcc acccggagct gaatcagtat atccaggaca    420
cgctgcactg cgtcaagcca ctcctggaga agaatgatgt ggagaaagtg gtggtggtga    480
ttttggataa agagcaccgc ccagtggaga aattcgtctt tgagatcacc cagcctccac    540
tgctgtccat cagctcagac tcgctgttgt ctcatgtgga gcagctgctc cgggccttca    600
tcctgaagat cagcgtgtgc gatgccgtcc tggaccacaa ccccccaggc tgtaccttca    660
cagtcctggt gcacacgaga gaagccgcca ctcgcaacat ggagaagatc caggtcatca    720
aggatttccc ctggatcctg gcggatgagc aggatgtcca catgcatgac cccggctga     780
taccactaaa aaccatgacg tcggacattt taaagatgca gctttacgtg gaagagcgcg    840
ctcataaagg cagctgaggg ggcacctgcc accccactga tgcccaaact gtcagacttt    900
gggggatccc cgcctagggc agtgctgcat ggctgccctg attccaagtg ctcttatcgc    960
ctctgtgtgt ggatcgcccg ccccagcccg gggccgctca ggtctgcttg gaggatgcct   1020
cccccaggag ggcagtgagg gatgccgcaa cctcgacttc tcagcctcct ggggttccgc   1080
cggccaacac tgtctgtctc aaatactgtg ctgtgagttg tttcaataaa ggggccccaa   1140
gggctgggct gaaaaaaaaa aaaaaaaaaa aaaaaaaaaa aaaaaaaaaa aaaaaa       1196
```

<210> SEQ ID NO 70
<211> LENGTH: 3648
<212> TYPE: DNA
<213> ORGANISM: Homo sapiens

<400> SEQUENCE: 70

```
gcttgggcag cgacagctgt tccaggcact ccgcgtcgag caccggagtc ccgagccgtg     60
gctgccacgg gcggtgggcg ggcggaggag agcaccggac caccagtgca ggctgccgag    120
tcggggcggc cgcccacggg gaagctgcga ggcgcgggag cacctggggg accgcttgca    180
gcggggacgc gaggacccgg gctgggcttt cctcacccgg gtaccttgtt atcccataac    240
tttggtatcc tgaaatctga ggattccacc aagataatat gataagaact ttcagtgatt    300
tggggccata tcctacttag actaatgtgg aatttccaga tttcctgaga gcttggtaca    360
gcagcacaca ctgcttgcta atcagcacag gcaataatgc catctctgcc tcaagaagga    420
gttattcagg gaccctctcc cctggatttg aatacagaat taccttatca aagcacaatg    480
aaaaggaaag tcagaaagaa gaaaaagaag ggaaccatta cagcaaatgt tgccgggaca    540
aagtttgaaa ttgttcgttt agtaatagat gaaatgggat ttatgaaaac tccagatgag    600
gatgaaacaa gtaatcttat atggtgtgat tctgctgttc agcaggagaa aatttcagag    660
ctgcaaaatt atcagaggat caaccatttt ccaggaatgg gggagatctg taggaaggat    720
ttcttagcaa gaaatatgac caaaatgatc aagtctcggc ctctggatta tacctttgtt    780
cctcgaactt ggatctttcc tgctgaatat actcaattcc aaaattatgt gaaagaattg    840
aagaaaaaac ggaagcagaa aacttttata gtgaaaccag ctaatggtgc aatgggtcat    900
gggatttctt tgataagaaa tggtgacaaa cttccatctc aggatcattt gattgttcaa    960
gaatacattg aaaagccttt cctaatggaa ggttacaagt ttgacttacg aatttatatt   1020
ctggttacat cgtgtgatcc actaaaaata tttctctacc atgatgggct tgtgcgaatg   1080
ggtacagaga agtacattcc acctaatgag tccaatttga cccagttata catgcatctg   1140
acaaactact ccgtgaacaa gcataatgag cattttgaac gggatgaaac tgagaacaaa   1200
ggcagcaaac gttccatcaa atggtttaca gaattccttc aagcaaatca acatgatgtt   1260
```

-continued

```
gctaagtttt ggagtgatat ttcagaattg gtggtaaaga ccctgattgt agcagaacct   1320
catgtcctgc atgcctatcg aatgtgtaga cctggtcaac ctccaggaag cgaaagtgtc   1380
tgctttgaag tcctgggatt tgatattttg ttggatagaa aactaaagcc atggcttctg   1440
gagattaacc gagccccaag ctttggaact gatcagaaaa tagactatga tgtaaaaagg   1500
ggagtgctgc taaatgcgtt gaagctacta aacataagga ccagtgacaa aagaagaaac   1560
ttggccaaac aaaaagctga ggctcaaagg aggctctatg gtcaaaattc aattaaaagg   1620
ctcttaccag gctcctcaga ctgggaacag cagagacacc agttggagag gcggaaagaa   1680
gagttgaaag agagactcgc tcaagtacga aagcagatct cacgagaaga acatgaaaat   1740
cgacatatgg ggaattatag acgaatttat cctcctgaag ataaagcatt acttgaaaag   1800
tatgaaaatt tgttagctgt tgcctttcag accttccttt caggaagagc agcttcattc   1860
cagcgagagt tgaataatcc tttgaaaagg atgaaggaag aagatatttt ggatcttctg   1920
gagcaatgtg aaattgatga tgaaaagttg atgggaaaaa ctaccaagac tcgaggacca   1980
aagcctctgt gttctatgcc tgagagtact gagataatga aaagaccaaa gtactgcagc   2040
agtgacagca gttatgatag tagcagcagc tcttcagaat ctgacgaaaa tgaaaaagaa   2100
gagtaccaaa ataagaaaag agaaaagcaa gttacatata atcttaaacc ctccaaccac   2160
tacaaattaa ttcaacaacc cagctccata agacgttcag tcagctgccc tcggtccatc   2220
tctgctcaat caccttccag tggggacacc cgcccatttt ctgctcaaca aatgatatct   2280
gtgtcacggc caacttctgc atctcggtca cattccttaa accgtgcttc ctcctacatg   2340
aggcatctgc ctcacagtaa tgatgcctgc tctaccaact ctcaagtgag tgagtctttg   2400
cggcaactga aaacaaaaga acaagaagat gatctaacaa gtcagacctt atttgttctc   2460
aaagacatga agatccggtt tccaggaaag tcagatgcag aatcagaact tctgatagaa   2520
gatatcattg ataactggaa gtatcataaa accaaagtgg cttcatattg gctcataaaa   2580
ttggactctg taaaacaacg aaaagttttg gacatagtga aaacaagtat tcgtacagtt   2640
cttccacgca tctggaaggt gcctgatgtt gaagaagtaa atttatatcg gattttcaac   2700
cgggttttta atcgcttact ctggagtcgt ggccaagggc tgtggaactg tttctgtgat   2760
tcaggatcct cttgggagag tatattcaat aaaagcccgg aggtggtgac tcctttgcag   2820
ctccagtgtt gccagcgcct agtggagctt tgtaaacagt gcctgctagt ggtttacaaa   2880
tatgcaactg acaaaagagg atcactttca ggcattggtc ctgactgggg taattccagg   2940
tatttactac cagggagcac ccaattcttc ttgagaacac caacctacaa cttgaagtac   3000
aattcacctg gaatgactcg ctccaatgtt ttgtttacat ccagatatgg ccatctgtga   3060
aacagaaggg aagatcgcca ttggttatac ataacagcaa ttcatttttt tcctctgaag   3120
ttgaacatgc aaagaacatg accattaagt gctgttttat gtatataaga catatatatg   3180
tgtgaaaata tatgcacata tgcaccctaa taacatatat ttattatatt aaatgatata   3240
tgaaagaaga attagcagaa aatggaatat aagacttaac ctttctggaa acgtaataaa   3300
ccatgttaaa attgtttaca caaatatgtg aatgtctaga atctgctagg tttataatta   3360
attccttcct actagaaatg ttatttttgc tgcagagtat ataaaacaaa ttgatcttga   3420
agatccaatt acagtgttaa attattttct agataacatg ccttttgacc tgaaaaaggg   3480
tttagtataa taccttaaaa attctcatat atagtagcca ttttaaatga aacaaaaaga   3540
tttagaagcc tggtgttgct tgatgataag attaagaagt ttaaaacggg tttatcatta   3600
ctatagcaca ctgtaaagtg ctagaaaagt cataacctga ttctccaa                3648
```

<210> SEQ ID NO 71
<211> LENGTH: 3631
<212> TYPE: DNA
<213> ORGANISM: Homo sapiens

<400> SEQUENCE: 71
tgagtcccgg ccggagcccc acggccgcgg gcggcgccta ggacggcgat ccgcgccctg 60
gaggatccgc cggccgcccg gctccactac agctccagcc gcctgcagcg gggccctcct 120
gaggccccag aggaagagac catgaaagtg aggtcggccg gcggcgatgg agatgccttg 180
tgcgttacag aagaggacct ggcgggtgac gacgaggaca tgccgacctt cccatgcacc 240
cagaagggcc ggccagggcc ccgctgcagc cgctgccaga agaacctatc tttgcacaca 300
tcggtgcgga ttctttacct cttcctggcc ctgctcctgg tggccgtggc tgtgttggcc 360
tctctggttt tcagaaaagt ggactctctc tccgaagaca tctccttgac ccagtctatt 420
tatgacaaga agcttgtgtt aatgcagaaa aatctccagg gcctggatcc gaaagccctg 480
aacaactgct ctttctgcca tgaagctggg cagctggggc cagagatccg aaaactgcag 540
gaggagctgg agggaattca gaagctgctt ctggcccagg aggtgcagct ggaccagacc 600
ttacaggccc aggaggtgct ctccaccacc agcagacaaa tctcccagga gatgggcagt 660
tgctccttct ccatccacca ggttaaccag tctctggggc tcttcctggc ccaggtgaga 720
ggctggcagg ccaccacagc tggcctggac ctctctctga aggacctcac ccaggagtgc 780
tacgatgtca aggctgcagt gcaccagatc aacttcaccg tggggcagac ttccgagtgg 840
atccacggga tccagcggaa gacagacgag gagaccctga ccctccagaa gattgtcacc 900
gactggcaga actacacacg gctcttcagc ggcctgcgca ccacctccac caagactgga 960
gaggcggtca agaacatcca ggccaccctg gggggcctcct cacagcgcat cagccagaac 1020
tcagagagca tgcacgacct ggtactccag gtcatgggct tgcagctgca gctggataac 1080
atctcgtcct tcctggatga ccacgaagag aacatgcatg atcttcagta ccatacccac 1140
tacgcccaga accgcactgt ggagaggttt gagtctctgg aaggacgcat ggcttctcac 1200
gagattgaaa ttggcaccat cttcaccaac atcaatgcca ccgacaacca cgtgcacagc 1260
atgctcaagt acctggatga cgtgcggctc tcctgcacgc tgggcttcca cacccatgcc 1320
gaggagctct actacctgaa caagtctgtc tccatcatgc tgggcaccac agacctgctc 1380
cgggagcgct tcagcctgct cagtgcccgg ctggacctca acgtccggaa cctctccatg 1440
atcgtggagg agatgaaggc agtggacaca cagcatggag aaatccttcg caatgtcacc 1500
atcctacgag gtgcccccgg ccctccagga ccaagaggat tcaaaggaga tatgggcgtg 1560
aaagggcctg ttggcggcag aggcccgaaa ggagaccccg gcagcttggg ccccctggga 1620
ccccagggtc ctcaggggca acctggagag gccgggcctg tgggagaaag gggccctgtt 1680
ggccctcgag ggttcccagg cctcaaaggc tcaaagggca gctttggaac tggagggccg 1740
agaggacagc caggcccaaa aggggacata gggcccccag ggccagaagg gcccccgggg 1800
tctccagggc cctcagggcc tcagggaaaa ccgggaattg cagggaagac agggtcacca 1860
ggccagcggg gggccatggg gcctaagggt gaaccaggga tccagggtcc ccctggtctc 1920
ccggggcctc caggtccacc aggaagccag agcttctact gaggagggct gtggcagagc 1980
cactgtcaca cagaatgccg gaggggcgca gagcagatcc aggccccaga aagcctcacc 2040
tacagacagc tgtggtcctc tgattccaat gagggggctc cccagggctg accctgcagc 2100
tttgggctcc cccatagtga ctgtgccata ggaaagcagc ccctcctcac acatacatgt 2160

```
gcacatgcac acacatgcat gcacacacat gcacacatac acgcacatgc acacatacac   2220

atgcatgcac acatacacag gcatacatgc atgcacacac acatgcacgc acacacacat   2280

gcacacatac acgtgcacac atacacaggc acacatgcat gcacacatac acatgcacac   2340

acacatgcac acatatatgc acaggcacac acatgtacgc acacacacat gcactgcaca   2400

catatccatg cacacaaaca catatataca catgcacata cacagatttt tctgctggcc   2460

aggtgggcca actgggtttc cctggctggg caggaggaga gggcagagga agaccccctc   2520

tcctgtgact gagcctgcca gggaggcagc tacctcggga ggaaggtctc acatctgtct   2580

ctgggcaccc atgctggcca gcagtttccc agggctccct ggggttgaaa agccccaagg   2640

aaacctttgc gggtggggcg ttactgccaa aactccagag gcaaagtgga cctggcaacc   2700

acaagaccct ccccataagc aggggaccag catacccggg agctgtccct gtctgtcaca   2760

gcacagtggg gccacgaggc tgacattctc tggccttgca cacagtgccc cctgagaagt   2820

tcaacattta tttcttcacg tgtccagaaa attcctcaat tcatccttgc ctctgccctt   2880

caggagcagc ctggaaggaa tccaagcagg agtttcatct gcatgggggc actctgcagg   2940

ccctggaaca ttgggcctga gtggagatgg gagacagagg caggccagaa ggttctctct   3000

gcacagctgc ctcccttgct ctccctgagg ctggcctgcc ccattcccca agggggctcc   3060

tctggagtgg tggggaggat taggctgcag aagggccaac cccttgcaac agggcagctc   3120

tcgcctcccg cacacggctc tcctgatcac agctgcatgc cgaccttgtc ccaccgggac   3180

ccacaatggc ccgagccctc tttgcatggg cagccagctg gactaggagt gggaagggcc   3240

tggacactca cagaggcccc ctctgtcatc actccttggc acccaccaac ttcctgcaca   3300

cactggcaga gaggggcgct gggaaatcac cccacagggt ggaggtctcc tgttggctac   3360

actctaaagc tgctttgcct tcatgttcaa acagattcag gcaccacccc ctccaccgcc   3420

cgcaaggtta gggcatagag ttgtctcctt cccaacacgg acccagagag cagcccttcc   3480

ctgctcaaag cctttccgca ccctcctgac tgtcctggat gtgcaactgg tttgcactgc   3540

acaccccacg gccatgtaac tctcctgtcc acatatgata ataccattct gcatagtatt   3600

actgactcag taaagagcta tttccaggag t                                  3631
```

<210> SEQ ID NO 72
<211> LENGTH: 1363
<212> TYPE: DNA
<213> ORGANISM: Homo sapiens

<400> SEQUENCE: 72

```
agcgtcggac taccgttggt ttccgcaact tcctggatta tcctcgccaa ggactttgca     60

atatattttt ccgccttttc tggaaggatt tcgctgcttc ccgaaggtct tggacgagcg    120

ctctagctct gtgggaaggt tttgggctct ctggctcgga ttttgcaatt tctccctggg    180

gactgccgtg gagccgcatc cactgtggat tataattgca acatgacgct ggaagagctc    240

gtggcgtgcg acaacgcggc gcagaagatg cagacggtga ccgccgcggt ggaggagctt    300

ttggtggccg ctcagcgcca ggatcgcctc acagtggggg tgtacgagtc ggccaagttg    360

atgaatgtgg acccagacag cgtggtcctc tgcctcttgg ccattgacga ggaggaggag    420

gatgacatcg ccctgcaaat ccacttcacg ctcatccagt ccttctgctg tgacaacgac    480

atcaacatcg tgcgggtgtc gggcatgcag cgcctggcgc agctcctggg agagccggcc    540

gagacccagg gcaccaccga ggcccgagac ctgcattgtc tcctggtcac gaaccctcac    600

acggacgcct ggaagagcca cggcttggtg gaggtggcca gctactgcga agaaagccgg    660
```

```
ggcaacaacc agtgggtccc ctacatctct cttcaggaac gctgaggccc ttcccagcag    720
cagaatctgt tgagttgctg ccacaaacaa aaaatacaat aaatatttga accccctccc    780
ccccagcaca acccccccaa aacaacccaa cccacgagga ccatcggggg cagagtcgtt    840
ggagactgaa gaggaagagg aggaggagaa ggggagtgag cggccgcccc cagggcggag    900
atccaggagc tggcggccgc cgatccgatg gagaaggggg gacccaggcc agcaggagac    960
aggacccccg aagctgaggc cttgggatgg agcagaagcc ggagtggcgg ggcacgctgc   1020
cgccttcccc atcacggagg gtccagactg tccactcggg ggtggagtga gactgactgc   1080
aagccccacc ctccttgaga ctggagctgg cgtctgcata cgagagactt ggttgaactt   1140
ggttggtcct tgtctgcacc ctcgacaaga ccacactttg ggacttggga gctggggctg   1200
aagttgctct gtacccatga actcccagtt tgcgaattat agagacaatc tattttgtta   1260
cttgcacttg ttattcgaac cactgagagc gagatgggaa gcatagatat ctatattttt   1320
atttctacta tgagggcctt gtaataaatt tctaaagcct ctg                     1363
```

<210> SEQ ID NO 73
<211> LENGTH: 2176
<212> TYPE: DNA
<213> ORGANISM: Homo sapiens

<400> SEQUENCE: 73

```
tgcaggtgcc gggccgggag cgagcggcgg cggcggcggc ggcggcacca tgggccgggc     60
ccggcgcttc cagtggccgc tgctgctgct gtgggcggcc gcggcggggc caggggcagg    120
acaggaagta cagacagaga acgtgacagt ggctgagggt ggggtggctg agatcacctg    180
ccgtctgcac cagtatgatg ggtccatagt tgtcatccag aacccagccc ggcagaccct    240
cttcttcaat ggcacccgtg ccttgaagga tgagcgtttc cagcttgagg agttctcccc    300
acgccgggtg cggatccggc tctcagatgc ccgcctggag gacgaggggg gctatttctg    360
ccagctctac acagaagaca cccaccacca gattgccacg ctcacggtac tagtggcccc    420
agagaatcct gtggtggagg tccgggagca ggcggtagag ggcggcgagg tggagctcag    480
ctgcctcgtt ccgcggtccc gtccggctgc caccctgcgc tggtaccggg accgcaagga    540
gctgaaagga gtgagcagca gccaggaaaa tggcaaggtc tggagcgtgg caagcacagt    600
acggtttcgt gtggaccgta aggacgacgg tggtatcatc atctgtgagg cgcagaacca    660
ggcgctgccc tccggacaca gcaagcagac gcagtacgtg ctggatgtgc agtactcccc    720
cacggcccgg attcatgcct cccaagctgt ggtgagggag ggagacacgc tggtgttgac    780
gtgtgctgtc acggggaacc ccaggccaaa ccagatccgc tggaaccgcg ggaatgagtc    840
tttgccggag agggcggagg ccgtgggaga gacgctcacg ctgccgggtc tggtatccgc    900
ggataacggc acctacactt gcgaggcgtc caataagcac ggccatgcga gggcgctcta    960
cgtacttgtg gtctacgacc ctggtgcggt ggtagaggct cagacgtcgg ttccctatgc   1020
cattgtgggc ggcatcctgg cgctgctggt gtttctgatc atatgtgtgc tagtgggcat   1080
ggtctggtgc tcggtacggc agaagggttc ctatctgacc cacgaagcca gtggcttgga   1140
tgaacaggga gaagcaagag aagccttcct caatggcagc gacggacaca agaggaaaga   1200
ggaattcttc atctgaccct atccccaccc caggcctagg cctgggcctg ggctggggtc   1260
ccccccactg ccagctgcaa ggaaccagca aagacattta ccagagtctg ggatggtggg   1320
cttctccccc caccactaac acctcagacg cttgggcagg gatgggggtg ttggatgcct   1380
ggatctctgt aagggccaga agtgagggcc cagaggtctg ggtcccccag ggggcagggg   1440
```

-continued

```
ccaaaggtcc agacccccca agtccagtga gggcagtagg gattgggttg ggggaagata   1500

actgggggaa ggccagggcc cctaggctac aaaaccaggt cttgtgggga gggggtcagt   1560

ttctgggaag ggtggggggg gcagggaagg ggaacacaga tttctttggg ggtcctagac   1620

cccatgccag ccattgtaag agttccacag agctctgggc acttctttgc aaagccatgt   1680

ttgcacggtg gggggatggg tggggggagg gcgtggaaat agggattctg tgtctttgtg   1740

tcataacttt gatgggggca gtgagggaga cagccccaac ccttttctcc aatcccccctt   1800

ccccaggttc ctgggctccc cttctctcta ccttctcccc caacgtctgt cccatccata   1860

tttgtctctc tgtccaccca ctcctggggg ggccttcccc atctctcctc caggcccccc   1920

ggggaggggg aaaggagttt ggggaggatt cgtggtcttc atggttttat atataatata   1980

ttaaaaaatc aaaagtctgt atgaaaatat cagattgcac ccccctctcc ccattcctgg   2040

cttttgcccc ctttttcttg ttaaaaaaca aaaaacaaaa aacaaaaaac cacacacaca   2100

ttttgtacgg ggtggggagg ggaatgggga gggggtttgg caatctcact aaccaccatt   2160

aaactgagga gagaac                                                   2176
```

<210> SEQ ID NO 74
<211> LENGTH: 3563
<212> TYPE: DNA
<213> ORGANISM: Homo sapiens

<400> SEQUENCE: 74

```
aacgcagctg cggcggctgc gggtctcgtg ggggcggagc ggtcgccgct gccgccgcag     60

ctcgggtcgg gatttgaaag attagaaact tcgggtggag agggcggcgg cgttgaatgt    120

gtggcggaag cgctgggggt cacggctccg cgcgccgccg gacagccggc ggcgtctcca    180

cagcatgaat tacccgggcc gcgggtcccc acggagcccc gagcataacg gccgaggcgg    240

cggcggcggc gcctgggagc tgggctcaga cgcgaggcca gcgttcggcg gcggcgtctg    300

ctgcttcgag cacctgcccg gcggggaccc ggacgacggc gacgtgcccc tggccctgct    360

gcgcggggaa cccgggctgc atttggcgcc gggcaccgac gaccacaacc accacctcgc    420

gctggacccc tgcctcagtg acgagaacta tgacttcagc tccgccgagt cgggctcctc    480

gctgcgctac tacagcgagg gtgagagcgg cggcggcggc agctccttgt cgctgcaccc    540

gccgcagcag cctccgctgg tcccgacgaa ctcgggggggc ggcggcgcga caggagggtc    600

cccgggggaa aggaaacgta cccggcttgg cggcccggcg gcccggcacc gctatgaggt    660

agtgacggag ctgggcccgg aggaggtacg ctggttctac aaggaggaca agaagacctg    720

gaagcccttc atcggctacg actcgctccg catcgagctc gccttccgga ccctgctgca    780

gaccacgggt gcccggcccc agggcgggga ccgggacggc gaccatgtgt gctcccccac    840

gggcccagcc tccagttccg gagaagatga cgatgaggac cgcgcctgcg gcttctgcca    900

gagtacgacg gggcacgagc cggagatggt ggagcttgtg aacatcgagc ctgtgtgcgt    960

gcggggcggc ctctacgagg tggatgtgac ccaaggagag tgctacccgg tgtactggaa   1020

ccaggctgat aaaataccag taatgcgtgg acagtggttt attgacggca cttggcagcc   1080

tctagaagag gaagaaagta atttaattga gcaagaacat ctcaattgtt ttaggggcca   1140

gcagatgcag gaaaatttcg atattgaagt gtcaaaatcc atagatggaa aagatgctgt   1200

tcatagtttc aagttgagtc gaaaccatgt ggactggcac agtgtggatg aagtatatct   1260

ttatagtgat gcaacaacat ctaaaattgc aagaacagtt acccaaaaac tgggattttc   1320

taaagcatca agtagtggta ccagacttca tagaggttat gtagaagaag ccacattaga   1380
```

```
agacaagcca tcacagacta cccatattgt atttgttgtg catggcattg ggcagaaaat   1440

ggaccaagga agaattatca aaaatacagc tatgatgaga gaagctgcaa gaaaaataga   1500

agaaaggcat ttttccaacc atgcaacaca tgttgaattt ctgcctgttg agtggcggtc   1560

aaaacttact cttgatggag acactgttga ttccattact cctgacaaag tacgaggttt   1620

aagggatatg ctgaacagca gtgcaatgga cataatgtat tatactagtc cactttatag   1680

agatgaacta gttaaaggcc ttcagcaaga gctgaatcga ttgtattccc ttttctgttc   1740

tcggaatcca gactttgaag aaaaaggggg taaagtctca atagtatcac attccttggg   1800

atgtgtaatt acttatgaca taatgactgg ctggaatcca gttcggctgt atgaacagtt   1860

gctgcaaaag gaagaagagt tgcctgatga acgatggatg agctatgaag aacgacatct   1920

tcttgatgaa ctctatataa ctaaacgacg gctgaaggaa atagaagaac ggcttcacgg   1980

attgaaagca tcatctatga cacaaacacc tgccttaaaa tttaaggttg agaatttctt   2040

ctgtatggga tccccattag cagttttctt ggcgttgcgt ggcatccgcc caggaaatac   2100

tggaagtcaa gaccatattt tgcctagaga gatttgtaac cggttactaa atatttttca   2160

tcctacagat ccagtggctt atagattaga accattaata ctgaaacgct acagcaacat   2220

ttcacctgtc cagatccact ggtacaatac ttcaaatcct ttaccttatg aacatatgaa   2280

gccaagcttt ctcaacccag ctaaagaacc tacctcagtt tcagagaatg aaggcatttc   2340

aaccatacca agccctgtga cctcaccagt tttgtcccgc cgacactatg gagaatctat   2400

aacaaatata ggcaaagcaa gcatattagg ggctgctagc attggaaagg gacttggagg   2460

aatgttgttc tcaagatttg gacgttcatc tacaacacag tcatctgaaa catcaaaaga   2520

ctcaatggaa gatgagaaga agccagttgc ctcaccttct gctaccaccg tagggacaca   2580

gacccttcca catagcagtt ctggcttcct cgattctgca ttggagttgg atcacaggat   2640

tgattttgaa ctcagagaag gccttgtgga gagccgctat tggtcagctg tcacgtcgca   2700

tactgcctat tggtcatcct tggatgttgc cctttttctt ttaaccttca tgtataaaca   2760

tgagcacgat gatgatgcaa aacccaattt agatccaatc tgaactctct tgaaggacat   2820

gaatggccta aaactgattt tttttttttc cgttaaaatg tgtgtgtcaa gatacggaga   2880

tttcagggtt aaagtatatt tcagttttct ttagggcaac atatatttga atttaaaagc   2940

actttattta aaaaaaaaag aagttttcag ttctgaagaa gtcatttaca gtttgcatca   3000

ttttaattat gagtctgaca aaaccttctc cagagaatca agcaagacct ggatgtgaag   3060

aaggtttggg taaactgcat gtaaaggcta caaatcacaa tctgattcct cccaaatata   3120

aaggcatatg gaacataatg tattaaccaa agtatgttat aaatcaaaaa tggtcaaggt   3180

tcagcatatt ctatatgaag atcacaaggt ggtatcgttt tagatttcta tgaaggcttt   3240

catttgtaca tccctttgaa aaaatataac agatttaaaa tgttttgaat ttaacttgtt   3300

tagaaaaact aatgcttaaa acaatatttg aactactgta tttataattt attacctcta   3360

attgctttat ttcagtgtat gagacattac tgttttaatg tttgctttga acataattta   3420

agaaccagat ttattttcta tagtgataaa cccttttttc tcagaactcc atctttgtac   3480

tcttcagatg aatatataga cactgtggca tacatttttt ttcattaaaa acttatggct   3540

tcatacaaaa aaaaaaaaaa aaa                                            3563
```

<210> SEQ ID NO 75
<211> LENGTH: 1596
<212> TYPE: DNA
<213> ORGANISM: Homo sapiens

<400> SEQUENCE: 75

```
ccctcttccg ggccgcgagc cccctgcgcg ccgctttggg gctgcgctca ctcgtgtgcg     60
cgctcgtccg cccgccagtc ctctcaacgc gcgcttggcc gcccgacgac gcgggagccg    120
cacgcgccgg acgaggctcg ctgcgctccc tgttgcccag cgcgggcccg ttgaggcgga    180
gccctcagtt cccggccagg acacggtctg ggccgccgaa tctccggccg aagagcggcg    240
gcggcagcgg cgggaaaaaa atgaagaatg aaattgctgc cgttgtcttc tttttcacaa    300
ggctagttcg aaaacatgat aagttgaaaa aagaggcagt tgagaggttt gctgagaaat    360
tgaccctaat acttcaagaa aaatataaaa atcactggta tccagaaaaa ccatcgaaag    420
gacaggccta cagatgtatt cgtgtcaata aatttcagag agttgatcct gatgtcctga    480
aagcctgtga aaacagctgc atcttgtata gtgacctggg cttgccaaag gagctcactc    540
tctgggtgga cccatgtgag gtgtgctgtc gtagagatgg ggtttcacca tgttggccag    600
actgctctca aactcctgac ctcgtgatcc gcccgccttg gcctcccaaa gcgctggatt    660
acaggcgtga gccactgcgc ccggcctcct cctttttgat tatgtatgga gagaaaaaca    720
atgcattcat tgttgccagc tttgaaaata aagatgagaa caaggatgag atctccagga    780
aagttaccag ggcccttgat aaggttacct ctgattatca ttcaggatcc tcttcttcag    840
atgaagaaac aagtaaggaa atggaagtga aacccagttc ggtgactgca gccgcaagtc    900
ctgtgtacca gatttcagaa cttatatttc cacctcttcc aatgtggcac cctttgccca    960
gaaaaaagcc aggaatgtat cgagggaatg gccatcagaa tcactatcct cctcctgttc   1020
catttggtta tccaaatcag ggaagaaaaa ataaaccata tcgcccaatt ccagtgacat   1080
gggtacctcc tcctggaatg cattgtgacc ggaatcactg gattaatcct cacatgttag   1140
cacctcacta acttcgtttt tgattgtgtt ggtgtcatgt tgagaaaaag gtagaataaa   1200
ccttactaca cattaaaagt taaaagttct tactaatagt agtgaagtta gatgggccaa   1260
accatcaaac ttatttttat agaagttatt gagaataatc tttcttaaaa aatatatgca   1320
ctttagatat tgatatagtt tgagaaattt tattaaagtt agtcaagtgc ctaagttttt   1380
aatattggac ttgagtattt atatattgtg catcaactct gttggatacg agaacactgt   1440
agaagtggac gatttgttct agcacctttg agaatttact ttatggagcg tatgtaagtt   1500
atttatatac aaggaaatct attttatgtc gttgtttaag agaattgtgt gaaatcatgt   1560
agttgcaaat aaaaaatagt ttgaggcatg acaaaa                             1596
```

<210> SEQ ID NO 76
<211> LENGTH: 6757
<212> TYPE: DNA
<213> ORGANISM: Homo sapiens

<400> SEQUENCE: 76

```
atggtcggcc gcggcgtccc tctgtgcgct gcgcagcccg cggtggccga gggcggcccg     60
gcccgcgagc cgccgccgct gctggaggtg tccccccgaa agaggctacc cgccgggccc    120
gaccaggacc catgcggcag ccgccctgct cccgaaggcg ccggggccgg cccagagcag    180
ggccactcgg ccggcggagg cggctggtgc cgccactgcc acacgaagct ggtggagctc    240
aagcgacagg cgtggaagct ggtcagcggg cccgggacca ccctccggga tccttgcctc    300
tctgccctgc ttctcgacaa gctaccagca cctggggccc tgccagcctg tcgcccagag    360
gccgagcgcc gctgtgacgt ctgcgccaca cacctgcagc agctcacacg ggaggccatg    420
cacctgctgc aggcccctgc cagccatgag gaccttgacg ccccccatgg aggccccagc    480
```

-continued

```
ctcgcacccc ccagcaccac gaccagctcg agggacacgc caggaccagc gggtcctgca    540
gggaggcagc caggacgagc tgggccagac aggaccaagg ggctggcctg gtcccccggg    600
cccagtgtcc aggtgtctgt agcacctgcg ggtcttggag gggcgctgag cacggtcacc    660
atccaggccc agcagtgcct ggagggcatg tggagtgtct cgcgggtcaa cagcttcctc    720
ccgccggcgt gcctggccga ggcagcggtg gcggccgtgg cggtggcaga cacggtccga    780
gaatgccccc ccgtggccgg ccctgatggc ttgtcgaagg cctggggccg tggtggagtc    840
tgcacgtcag ccctggtcac ccccaccccg ggctcggtgg ggggctccac aggcccctca    900
gctgcagcct ccttcttcat aagggctatg cagaagctca gcctggcctc caagaggaag    960
aagccccacc cgccaccgcc tccagccacc cgcggcacct ccacctaccc caccgacttc   1020
agcggggtcc tgcagctgtg gccgccccccg gcgcccccct gcctgctcag ggccgcctcc   1080
aagaccaagg acaaccctgg cagcatcggg aaggtgaagg ttatgctgcg gatctggccc   1140
gcacaggggg cccagcgctc ggccgaggcc atgtccttcc tgaaggtgga ccctcggaag   1200
aagcaggtga tcctctacga tcccgccgcc ggtcccccag gcagcgcagg cccccggcga   1260
gccgccactg ctgcagttcc caagatgttt gccttcgatg ccgtcttccc ccaggactcc   1320
gagcaggccg aagtctgctc ggggaccgtg gccgacgtgc tccagtcggt ggtcagtggg   1380
gctgatggct gcattttttc ctttggccac atgagcctgg gcaagtcgta caccatgatc   1440
gggaaggaca gctcacccca gagcctgggc atcgtgccct gcgccatctc ctggctcttc   1500
aggctcatcg aggagcgcag ggagaggacg ggcacccgct tctccgtccg ggtctcagcc   1560
gtggaggtgt gcgggcgcga ccagagcctg cgggacctgc tggccgaggt ggcccctggc   1620
agcctccagg acacccagtc tccgggagtg tacctgcggg aggaccccgt gtgtggggcg   1680
cagctccaga accaaagcga gctgcgggca cccacggccg agaaggcggc tttctacctg   1740
gatgcggccc tggcggcccg cagcaccagc cgagcgggct gtggcgagga cgcccgacgc   1800
agctcccaca tgttgttcac gctgcacgtc taccagtacc gcatggagaa gtgcggccgg   1860
ggaggaatgt ccggaggccg cagccgcctg cacctcatcg acctgggcag ctgtgaggcg   1920
gcggctggca gggccgggga ggctgctggg ggtcccctgt gtctgtccct gtcggccctg   1980
ggcagcgtca tcttggccct ggtcaacgga gccaagcatg tgccgtatcg ggaccacagg   2040
ctcaccatgc tgctgcgtga atccctggcc accgctggct gccgcaccac catgatcgcc   2100
cacgtgtcgg atgcgccagc ccagcacgca gagacactca gcaccgtgca gctcgccgcc   2160
cgcatccacc gcctgcgcag gaagaaggcc aagtacgcct ccagctcctc tggcggggag   2220
agctcctgtg aggaaggccg ggcccgtcgg cccccgcacc tgcggccctt ccacccacgc   2280
actgtggccc tggaccccga ccgcacgcct ccctgcctgc ccggtgaccc cgattactcc   2340
tccagcagcg agcagtcctg tgacacggtc atctacgtgg ggcccggtgg ggcggcgctg   2400
tcagaccggg agctcaccga caacgaaggt ccgcctgact tcgtgcccat catccctgcc   2460
ctgagccgcc accggccctc caagggtccc cgagacgcag accacttccg ctgcagcacc   2520
ttcgcggagc tgcaggagcg gctggaatgc atggacggca acgagggtcc ctcaggaggt   2580
ccaggtggca ccgacggagc tcaggccagc cccgcccgag gggccggaa gccctcgcca    2640
ccagaggctg catcccccag gaaggccgtg ggcaccccga tggctgccag cacccctcga   2700
ggcagttctg gtccagacac ccaccagggt acccctgagc cctgcaaggc cattgtctgg   2760
ggtgaccaga gagaggacag cagcgcttgg cctgagctgc tggtcccgga aaaggctgca   2820
gtgagtggag gcaggaggcc actgcccagc ccggctcccc cacctcctca gttgctggaa   2880
```

-continued gcctgcagag ccccagaaga gcctggggga gggggcactg atggagtggc acggacccct 2940
cccgtgggca tgagtgggca ggtggctggg tccccgatgc ttcctggggc cacctgcccc 3000
cgcctggctg ctggcagtcg ctgtccggag cggggcctgc tcaccaccac agtgaccctg 3060
cagcggccag tggagctcaa cggcgaggac gagctggtgt tcacggtggt ggaggagctg 3120
tccctggggg cgcttgccgg agctgggcgg cccaccagcc tggctagctt cgacagtgac 3180
tgctccctgc gggccctggc ctcggggtcc cggccagtca gcatcatcag cagcatcaat 3240
gatgagtttg acgcctacac ctctcaggcc cctgaggggg ggcccctgga gggggcagcc 3300
tgggccggca gcagtcacgg ctcctccatc agctcctggc tcagcgaggt cagcgtctgc 3360
actgccgaca gccgtgaccc cacgccgcag ccccgcttca gccccgactc gctggcaggg 3420
cttgaccctg gggccccccc tgccctggat ggttccctgg gggatggaag ctctgggttc 3480
ctggggccag acagacctga cagtcctggg ccaacctggg gtccgtgccc tggggaagtg 3540
gctgcagtgg ccccatcccg acccggcagg gagccccagg ccgggccctc gcggtgggca 3600
tccgcagccc agaccatcca ctccagcctc ccccggaaac cgaggactgc ctctgccacc 3660
acccgtgtgg gctgtgctcg cctgggccag agcccacctg gccgtggagg cctgtttgag 3720
gacccatggc tgctccgggt aggggagtgt gatacccagg cagcttctgc tggcagggcc 3780
cccagcccca cacttggctc cccccggctg cctgaggccc aggtgatgct agcctgtgcc 3840
cagagagtgg tggacgggtg tgaggtggca gccagggcgg cccgcaggcc agaggctgtg 3900
gctcggatcc caccgctgcg gaggggtgcc accacgctgg gtgtgacaac gccagctgtg 3960
tcctggggag atgctcccac ggaggtggtg gcctgctcgg ggagcctgaa ggcctccccc 4020
accagcaaga agggtctggc tcccaaggcg ggcttcctcc cgaggcccag tggggcggcc 4080
cccccggccc cacccacgcg gaagtccagc ctggagcaga ggagcagccc ggcctcggcc 4140
cctccgcatg ctgtgaaccc ggcgcgggtc ggggctgctg ctgtccttcg aggggaggag 4200
gagcccagac ccagcagccg ggctgaccac tctgtcccca gggccacgtc cagcctgaag 4260
gcccgggcca gcaaggtaga agcagcacac cgtcttgccg gacacgcgtc tctggagcgg 4320
tacgaaggcc tggcgcacag cagcagcaag ggccgggaag cccctgggcg gcctccccgg 4380
gctgtaccca agctgggtgt gccaccctcc agccccacac acggtccagc tcccgcctgt 4440
aggagcggcg cagccaaggc tgtgggggcc cccaagcccc ctgttggtgg aggcaagggc 4500
cgtggcctag tggctggtgg gtcgcgggct ctggggcctt cggtgaagct gtctacggcc 4560
tctgtgacgg gcaggagccc tggcggccct gtggccggtc ccagagcagc cccacgggcc 4620
gggcccagtg tcggggcgaa ggctggccgg ggtaccgtca tgggcacaaa gcaggcgctc 4680
cgggctgctc acagccgcgt ccatgagctg tcagccagtg gagccccggg ccgaggtggc 4740
tcctcgtggg gctcggcgga ctcagacagc ggccatgaca gcggcgtgaa cgtgggggag 4800
gagcggccac ccacgggccc ggccctgccc tccccctaca gcaaggtgac cgccccacgg 4860
cggccccagc gctacagcag cggccatggc agcgacaaca gcagcgtgct gagtggagag 4920
ctgccgcccg ccatgggccg caccgccctt ttccaccaca gcggtggcag cagtggctat 4980
gagagcctgc ggcgcgacag cgaggccacc ggcagcgcct cctccgcccc tgactccatg 5040
agcgagagtg gggctgcctc cccaggcgcc cgcacccgca gcctcaagtc ccccaagaag 5100
agggccacag gtctgcagcg gcggcgcctg attcccgccc cactgcccga caccactgcc 5160
ctgggccgta agcccagcct ccccgggcag tgggtggacc tgcccccgcc cctggctggc 5220
tccctgaagg agccgttcga gatcaaggtg tacgagatcg atgacgtgga gcgccttcag 5280

-continued cggccccgcc ccaccccgag ggaggccccc acccagggtc tggcgtgcgt cagtacaagg 5340
ctgcggctgg cggagcgcag gcagcagcgg ctgcgggagg tgcaggccaa gcacaagcac 5400
ctgtgtgagg agctggccga gacccagggc cggctgatgc tggagcctgg ccgctggctg 5460
gagcagtttg aggtggaccc ggagctggag cccgagtcgg ccgagtacct ggcggccctg 5520
gagcgagcca cggcggccct ggagcagtgc gtgaacctgt gcaaggcgca cgtcatgatg 5580
gtcacctgct tcgacatcag cgttgcagcc agtgctgcca tcccggggcc gcaggaggtg 5640
gacgtctgag gctgggcgcc ggacaagagg agggggcgtg cagcgggctg gaggacggga 5700
cgtgggacgg agcgaggatg tggtgggggc tgcgggggga ggatgcggag gggtttctgt 5760
gcaggacggg agtctcagag aggagacgga gtgtggggga gggagggccg gccacgcggt 5820
ggacagagcg agggtgccag ggtgaccaga agaccgtcac cacccgacag caacgcaagt 5880
gcctttgacc ttgatttgga cttttctccc ttttgcattt ggtgctacag acttgagaca 5940
ccagcagaag ttgtgttcag cccggccccg ctgcgcctgt ccgggccggg gctggcgccg 6000
gttgtgtttg tgtccacctt gccttctttg cagccaagca gtttttgtgg agtggagtgg 6060
gacttacctg cacgccccag gggtctttca ggattcagga tgacttttct tttacaatgg 6120
tttcctctcg gcagagcccg ggttgtgggg gatctgtgtg gggttctcaa cgcagatcca 6180
tcctggggtc tcccgggcag ggatggctga cctcgagtcc cctcccttcc cgagaacccg 6240
ctctgtcccg agggcagcta acaagggctg agccccaggt acaggttgcc tcttccacgg 6300
caggaatttt taccaaaacc acaagcaaaa aacaaaacag accaccacga ccaacaacaa 6360
agatgggggg tagggtttg taaaggttct gttaggttca tatttttata tcattttgcc 6420
cataaatgcg gaatttgccg tgggaatttg aagacaaatg atctatgttt ttatggtttt 6480
ctagggaagg tgttctgggg gccgggctct ctccagctgt gggaggcctg ctccctctgg 6540
ggggcaccct gggcagggtg ggggggcctt gggaggcgct tcttgccaaa tgcagacgag 6600
gggtgagcct gccagcgttt gcgacgtccc cgcacgacag gctcatactt tctgaggatc 6660
gtgcatagca taggacgtct gaacctttgt acaaatgtgt agatgacatc ttgctacagc 6720
ttttatttgt gaattaaaga tgcatcgatg gttccca 6757

<210> SEQ ID NO 77
<211> LENGTH: 3868
<212> TYPE: DNA
<213> ORGANISM: Homo sapiens

<400> SEQUENCE: 77
gggccgtgct cttgctcccg ccgcctggca gcctcacgct cggctccagc ggccaagagc 60
cggagaaagt cctgctggtg ggcggccgcg gggctgaggg cgtccggcat cccggggccg 120
ctccggcccg ggcggcgaga gtgcccggcg gtccatgcat ccgccgccgc ccgccgccgc 180
gatggatttc agtcagaaca gcctgttcgg ttacatggag gacctgcagg agctcaccat 240
catcgagagg ccggtccgcc ggagcctcaa gacaccggaa gaaatagaaa gattgacagt 300
cgatgaagac ctcagtgata ttgaaagggc tgtttatctg ctcagtgctg gtcaagatgt 360
ccaaggaaca agtgtgattg caaatctccc atttttgatg cgacagaatc ccactgagac 420
gcttcggaga gtgttgccaa aagtcagaga agccctgcat gttgcaggag tggaaatgca 480
gttaacggct gcgatgtcat ttctgaccat tctgcaggac gaatcagtgt caattcatgc 540
atatacccac tcattcctcc aagtcattct cctgcatctg gagcacaggg acacaggtgt 600
cagcaatgca tggctggaaa ctcttctgtc tgttatagaa gtattgccaa aagaaaccct 660

-continued

```
acggcatgag attttgaatc cacttgtttc caaggcacaa ctttcccaaa cagtccagtc    720
tcgtttagtt agttgtaaaa ttttaggaaa attgaccaac aaatttgatg cccacaccat    780
taagcgagaa atacttcctc tggtaaaatc actctgtcaa gatgtagaat atgaagttcg    840
atcttgtatg tgtcggcaat tagaaaatat agcccagggc attgggacag aacttacaaa    900
aagtgtggtg ctccctgaat taatagaact ttctagggat gaaggcagca gtgtacgact    960
tgcagctttt gaaactttgg ttaatctgct tgatatattt gatacagatg acagaagtca   1020
aactatactt cccttagtga aatcattttg tgaaaaatct ttcaaagcag atgaatcaat   1080
tcttatttct ttatctttcc atttaggaaa actatgtcat ggactatatg gaattttcac   1140
tccagatcag cacttgagat ttttggaatt ttataagaaa ctttgtacat tgggtttgca   1200
acaagaaaat ggacacaatg aaaaccagat tccaccccaa atcctagagc aggagaagaa   1260
atatatttca gtacggaaga actgtgctta taactttccg gccatgattg tttttgttga   1320
tcctaaaaac ttccacatgg aactctattc tacattcttc tgcctttgcc atgaccctga   1380
agtaccagtc agatacacta ttgctatttg cttttatgaa gtatctaagc ttctgaattc   1440
tggagtatat ttaatacata aagaactaat aacattatta caagatgaat cactggaggt   1500
actagatgct cttatagatc atcttccaga aatcttggaa cttatgtcta ctggtggaga   1560
aagcagtgtt caagaaaata agttatcttc tctgcctgac ttgattccag cactcacagc   1620
tgctgaacag cgagctgcag cctctttaaa atggagaact catgagaagc tacttcagaa   1680
atatgcctgc ctgccacatg tcatatcaag cgatcagatt tattaccgtt tcttacaaag   1740
aatgttcaca atcatgatga caaataatgt tttacctgtc caaaaggcgg cttcacgaac   1800
tctatgcatt tttctgcgtt ataatcgtaa acaagaacag agacatgagg tcattcaaaa   1860
attaattgaa caattgggcc aaggaaaaag ttactggaat agacttcgat tttggatac    1920
ctgtgaattt attatagaga tattttcaaa atcatttttc tgtaaatatt tctttctacc   1980
tgctattgaa ctgacacatg atccagtagc aaatgtgaga atgaaacttt gctacctgtt   2040
gcccaaagtg aaatctactc tgaagattcc tgctgataag catctacttc agcagttaga   2100
aatgtgtgtg aggaaactcc tgtgtcaaga aaaagataaa gatgttctgg ctattgtaaa   2160
aagaactgta ttagagttgg acagaatgga aatgtctatg gatgcttttc agaaaaagtt   2220
ttatgagaaa gatttgttgg atcaagagaa agaaagagaa gaactacttc ttttggaaat   2280
ggaacaatta gagaaagaaa agcaacagaa tgatggaagg cccatgagtg ataaaatgtt   2340
tgaaaagaaa cgtagagaca ctaagacacc aacgcaaagt ctgcccaaga acatccccat   2400
ttctgttcct ggaccctctt ctgtcacccc atcgacaagt aaagaaatca agaaatccaa   2460
actgattcga agccagtctt ttaataatca agcttttcat gcaaaatatg gcaacttaga   2520
gaaatgtgct agtaaaagtt ctacaacagg atatacaact tctgtctcag ggttaggaaa   2580
gacttctgtg ctttcactag ctgatgattc attccggact cgtaatgcca gtagcgttcc   2640
atcttccttt tctcctaata ctcccttacc gagtacttcc cgtgggacag gtaactcagt   2700
tgaccccaag agcagtggaa gtaaagatac acaaccacgg aaggctacct taaaatccag   2760
aaaatccaat ccttaaatca actgcttgat gaaggaggca aaacaaaggc agcaggagat   2820
aatgtgattg gtacacaaaa gctaaagcag tggctggggc tttgttttta aattttgggt   2880
ttttttttt gttgttgtta atgagcagaa agagagacat aatgacagct gatgttaaac    2940
ttttcatatt tcaaattaga ttccctagga ggtataaatat atatttcttg agtaataatg   3000
tggttacgga attccaatgt tatagtgaag tgtaatgaaa aacatctcta ggaatgtgct   3060
```

-continued

```
ttaaccactg ctgcaaaaga gacaagtctg catttatttg tgcaggaaac cagccattta   3120

attgttctag agttttagca tttaaaaatc gtatgaaagt ctacatcagc tgaattgtcc   3180

tagcttgata agcacttgga gggggacttg gaaggtgaga aagatactgc attttctcat   3240

gagtctccaa gcccacttga aaagtcacac tgaaaggatg caaatagccg tctgcgattt   3300

tggcggccct ccggattgtg gtgacaatat gttgtacccg gacattccca aatttaaatt   3360

tggcagtgaa aattccacaa agatttctgg taactttgag ctataaatac cttaaaaata   3420

atagattgat gattttcttt atttcctaga gaatttattt tataaatact ttgtttacat   3480

tttagattgt acttgtcttt atttaaaatg atgaatctag tctgaatcag ctgttattcc   3540

aagctatcat gcttaagcta tgtcaacagc atttatttgt actaatgcta atatttccat   3600

caaaatttgc ctgtggaata tatacagttc ttaattttaa actgtcagtt cttgagatat   3660

accgtgtgaa gctattgtca gcttctctat ttcaaaatgc aatcagcata taactatatt   3720

gatattagaa gatatttgtt ttttaaaata tattgatgta tgataaagat gatctaattt   3780

gtgaatgcat atgtatgtgt ggttactttt tataatgtga aataatgaat aatgaattta   3840

ctcaaaataa aacataggtt aatgagat                                      3868
```

<210> SEQ ID NO 78
<211> LENGTH: 1515
<212> TYPE: DNA
<213> ORGANISM: Homo sapiens

<400> SEQUENCE: 78

```
ccggcccacg ccagctcccg gccgcggcac agcagccccg gcgctccccg cgccgccccg     60

cgcaggcgcc cccgccccgc cgtcgccgcc gccgcagcca ggagccgctg caccatgccc    120

cgcatagatg cggacctcaa gctcgacttc aaggatgtcc tgctccgacc taagcggagc    180

agcctcaaga gccgagccga ggtggatctt gaacgcacct tcacgtttcg aaattcaaag    240

cagacctact cagggattcc catcatcgtg gccaacatgg acactgtggg cacgtttgag    300

atggcagccg tgatgtcaca gcactccatg tttacagcaa ttcataagca ttactccctg    360

gatgactgga agctctttgc cacaaatcac ccagaatgcc tgcagaatgt agccgtgagt    420

tcaggcagtg ggcagaatga tctggaaaag atgaccagca tcctggaagc tgtgccacag    480

gttaagttta tttgcctgga tgtggccaat gggtattcag aacattttgt ggaattcgtg    540

aaacttgtcc gtgccaaatt tcctgaacac accattatgg cagggaacgt ggtgacagga    600

gaaatggtag aagagcttat tctttccgga gcagatatca tcaaagtggg agttggacca    660

ggttctgtgt gcaccacccg caccaagacg ggagtggggt acccccagct gagtgccgtc    720

attgagtgtg ccgactctgc ccatggcctg aagggccaca tcatctctga tggaggctgt    780

acgtgtccag ggatgtcgcc caaagccttt ggagctggag cagattttgt catgctggga    840

ggaatgtttt cgggtcatac ggagtgtgct ggagaagtgt ttgagaggaa cggacggaag    900

ctcaagctct tctacgggat gagctctgac accgccatga acaagcacgc aggaggagtt    960

gctgagtaca gagcctctga gggtaagact gtggaagttc cttacaaagg agatgtggaa   1020

aacactatcc tggatattct cgggggactg aggtccacgt gcacctacgt gggggccgcc   1080

aaactcaagg agctcagcag gagggcaaca ttcatccggg tgacccagca gcacaacacc   1140

gtgttcagct aaccctgggg acaaagcagc gtctggctcg agtggaagcg tccaaacctg   1200

cttttcccat ctcccccaa gtctgttccg tcagagcttc tggctgctcc tgaatggtgg   1260

aatgctgtgt cctctcttct gtctcctgct gcctggaggc ttcggggctc tcccgcctgc   1320
```

cttctcgggg cccagacgca aggcaccgat tgggccaaca tcagagccct gctgcccaga 1380
actcataacc tcattgttca aaccaacact tgcacctttc tctttttctc tttctctctc 1440
cctttctttg tttttctttc ttttttaaaa gaagatggtt tcactttaat ataatgctat 1500
tatcttaaga cttaa 1515

<210> SEQ ID NO 79
<211> LENGTH: 3293
<212> TYPE: DNA
<213> ORGANISM: Homo sapiens

<400> SEQUENCE: 79
atggcccggc ccgtgcagct ggcgccgggc tcgctggcgc tagtgctgtg ccggctggag 60
gcgcagaagg cggcgggggc cgcggaggag cctggtgggc gcgcggtgtt ccgcgctttc 120
cgtcgcgcca acgcgcgctg cttctggaac gcgcggctgg cgcgcgccgc ctcgcggctg 180
gccttccagg gctggctgcg gcggggggtg ctgctggtgc gcgcgccccc cgcctgcctg 240
caggtgctgc gcgatgcctg gcggcgccgg gccctgcggc cgccgcgcgg cttccgcatc 300
agggcggtgg gtgatgtctt tccagtgcaa atgaatccaa taactcaatc tcagttcgta 360
cctttgggtg aagttctttg ctgtgctata tctgatatga atacagctca gattgtagta 420
acgcaggaat cacttttgga gcgtttgatg aaacattacc caggcattgc aattccatcg 480
gaagatattc tttataccac tctgggaacg ctgattaaag aaaggaagat ttatcacact 540
ggagaaggat acttcatagt tactcctcag acttacttca ttacaaatac aaccacccag 600
gaaaataaga gaatgctgcc atcagatgaa agtcgcctga tgccagcttc catgacatat 660
ctggtgagca tggagagctg tgcagagtca gcccaagaga atgctgcccc catatcccac 720
tgtcagtctt gccagtgttt ccgggacatg cacactcagg atgttcagga agcaccagtt 780
gctgcagaag tgactaggaa gagtcacaga ggtcttgggg aatccgtatc ttgggtacag 840
aatggggcag tttcagtgtc tgcggagcac cacatttgtg agagcaccaa acctttacca 900
tacacaagag ataaagaaaa aggcaagaag tttggtttta gtctcttatg gcgcagctta 960
tctagaaagg agaagcccaa aacagaacac agcagtttct ctgctcagtt cccacctgaa 1020
gaatggcccg tccgagatga agatgacttg gacaatatcc ctcgagatgt tgaacatgag 1080
ataatcaaac gaattaaccc cattttgact gttgacaatt taatcaaaca cactgtccta 1140
atgcaaaaat acgaagaaca gaaaaaatat aatagccagg gcacttccac tgacatgctg 1200
acaatcgggc ataagtatcc ttcaaaagag ggggttaaga aaaggcaggg tctgtctgca 1260
aaacctcaag ggcagggcca ttctcgaagg gatagacaca aagccaggaa tcagggaagt 1320
gagtttcagc caggaagcat tagactggag aaacacccca agctccctgc tacacagccc 1380
atccccagaa ttaaaagccc aaatgaaatg gtaggtcaga aaccacttgg tgagattaca 1440
acagtgctag gttcccattt gatttacaaa aagcgaatca gtaatccttt ccagggtttg 1500
tctcaccgag gaagcacaat atccaaaggg cacaaaattc agaagacgag tgatctgaaa 1560
cccagccaga ctggaccaaa ggaaaagcct ttccaaaagc ctaggtcctt ggattcctca 1620
agaatctttg atggtaaagc caaagagcca tatgctgaac aacctaatga taaaatggaa 1680
gcagaatcca tttacataaa tgaccctact gtcaaaccca tcaatgatga cttcagaggt 1740
cacctcttca gtcaccctca acagagcatg ttgcaaaatg atggtaaatg ctgtcccttt 1800
atggaaagca tgttgagata tgaagtgtat ggtggagaaa atgaggtaat tcctgaagtc 1860
ttgaggaaaa gtcattccca ctttgacaaa ttaggggaga ccaaacagac tccgcatagt 1920

```
ctgccatcac gaggtgcctc cttttcagac cgaacaccct ctgcttgtag attagtggat   1980

aacacaatac accagtttca aaatcttggc cttttggatt acccagttgg cgtgaaccct   2040

ttaagacaag ctgcaagaca agacaaagac tcagaagaat tattgagaaa aggatttgtc   2100

caggatgcag agactacaag cctagaaaat gaacagcttt ctaacgatga ccaggccttg   2160

tatcagaatg aagtggaaga tgatgatggt gcctgtagtt cattatatct agaggaggat   2220

gacatttctg agaatgacga cttacgtcaa atgctgcctg gccacagtca gtattccttc   2280

acaggtggaa gccagggaaa tcatttagga aaacaaaaag tgattgagag atctctgacc   2340

gagtacaaca gcacaatgga gagggttgag tctcaggtgc ttaaaagaaa tgaatgctac   2400

aaacccactg ggctgcatgc taccccaggt gaaagccaag aacctaacct ctctgctgaa   2460

agttgtggcc taaattcagg ggcccagttt ggttttaact acgaagaaga acccagtgtt   2520

gctaaatgtg tacaggcctc agcacctgct gatgaaagaa tctttgatta ctatagcgca   2580

agaaaagcca gttttgaagc tgaagtcata caagacacta ttggtgacac aggaaagaag   2640

ccagctagct ggagtcagag tcctcagaat caggaaatga gaaaacattt cccacaaaag   2700

ttccaacttt tcaacacttc acatatgcca gtgttggctc aggatgtcca atatgaacac   2760

agtcacttgg aagggacaga aaatcacagc atggcaggag atagtggaat agattctcca   2820

cggacacaga gtctgggatc taataattca gtcattttgg atggactaaa aagaagacag   2880

aattttctgc aaaatgtcga aggcacaaag agcagtcaac cactcacatc taattcctta   2940

ctaccgctaa ctccagtcat aaacgtttaa ttttcttttg gaaacctact tttttcttta   3000

taaaaaggta gagcattatt acagaatctt tcaatcatgt aagaattgag tatataagaa   3060

ttgtctaaag gcaagcatat ctatactatt aaccacatta cacattttgt tctaattact   3120

ggcttttttt cctcttttgg tgtcttaagg ctttttgaag cttattttac tgtgagttta   3180

ttgggagtat atagattatt ttcgattaaa aagtggaatt attggtcccc ttccaattgt   3240

aattatcttg aatttttata cattagtttc tcaaatatat agaatgccaa ttt          3293
```

<210> SEQ ID NO 80
<211> LENGTH: 4273
<212> TYPE: DNA
<213> ORGANISM: Homo sapiens

<400> SEQUENCE: 80

```
gactcccggg tccccgcgcc ggactgggac tgggagcagg cagcccgggc ggagcgggcc     60

ggtgccgagg acggccccag gcattgctct gccccgggca ttgcgcggcg cgcgtgaggg    120

ggatgcggca ggaggcggcg cggcgggagg agtaggcggc ggcgccctcg ggagggagct    180

gcgcgcgggc cagacggcgc ccggaggctc cgcagtgccg ccgccgtcgc ccgggaggct    240

ccgcgcggga gccatgtaac cctgcggcgg gctccgggct gctccgtcct tccccagctc    300

ccgggctagc gcggcagcgg ggccacgatg aagaagcagt tcaatcgcat gcgccagctg    360

gccaaccaga cggtgggcag ggctgaaaag acagaagttt tgagtgaaga ccttcttcag    420

gtggagaagc gtctggagct ggtgaaacag gtgtcccaca gcacgcacaa gaagctcacc    480

gcatgtctgc agggccagca aggggcagag gctgacaagc gctccaaaaa gttgcctttg    540

acaacactgg ctcagtgtct gatggagggg tcagctatcc tgggagatga cacacttctt    600

gggaagatgc tgaaactctg tggagagacg gaggacaagc tggctcagga gctgatacat    660

tttgagttgc aagtagagag agacgtgatt gagcccctgt tttgctggc ggaggtggaa     720

atcccaaata ttcaaaagca gaggaaacac ttagccaagt tggtgctgga catggattcc    780
```

-continued

```
tcacgaacca ggtggcagca gacttccaag tcttcaggtt tgtccagcag cttacagcct    840
gcgggtgcca aggctgatgc cctcagggaa gaaatggaag aggctgccaa cagagtggag    900
atttgcaggg accagctctc agctgatatg tacagttttg tggccaaaga aattgactat    960
gcaaactact ttcaaacgct aatagaagtg caagctgaat accacaggaa gtccctgaca   1020
ctattgcagg ctgtattgcc tcagatcaaa gcacaacagg aggcctgggt agagaagcct   1080
tccttcggga agccgctgga ggagcacctc accatcagcg gccgggagat cgccttcccc   1140
atcgaggcgt gtgtgaccat gctgcttgag tgtgggatgc aggaggaggg actcttccga   1200
gtagcccccct ctgcctccaa actgaagaag ctgaaagcgg ccctggactg ctgcgtggtg   1260
gatgtgcagg agtactcggc agacccccac gcaattgcag gagctttgaa atcttacctc   1320
cgagagttgc cagaacctct tatgaccttt gaactctatg atgagtggat ccaggcttcc   1380
aatgtccagg agcaagacaa gaagcttcag gctctatgga atgcttgtga aaagttgccc   1440
aaggccaatc acaacaacat ccgatacttg ataaaatttt tatccaagct gtcagaatat   1500
caagatgtaa acaagatgac tcccagtaat atggcaattg ttttaggacc caacctccta   1560
tggccacaag cagaagggaa cattacagag atgatgacca cagtgtcgct gcaaattgtt   1620
gggatcattg aacctatcat ccagcatgca gactggttct tccctgggga gatagagttc   1680
aacattactg gcaattatgg gagtccagta cacgtgaacc ataatgccaa ctacagctca   1740
atgccctccc cagacatgga ccctgctgac cggcgccagc ccgagcaggc ccgccggccc   1800
ctcagcgtcg ccacggataa tatgatgctg gagttttaca aaaaggatgg ccttaggaaa   1860
atccaaagca tgggtgtgag ggtcatggac acaaactggg tggctcgaag aggctcctcg   1920
gccggtcgga aagtgtcctg cgccccgccc tccatgcagc ctcccgcccc gcccgccgag   1980
ctggctgcgc ccctgccttc gccgctgccg gagcagcccc tggacagccc cgcggccccc   2040
gcgctctctc catccggcct gggcctccag cctgggcccg agcgcaccag cacaacaaaa   2100
agcaaggaac tttctccagg ctctgcacag aaaggaagtc caggctccag ccagggcaca   2160
gcctgtgcag ggactcaacc aggggctcaa cctggagctc agccgggcgc cagccccagc   2220
cccagccagc cgcctgcaga ccagagtcct cacaccctcc ggaaagtttc aaagaagctg   2280
gcaccgattc cacccaaggt cccctttggc cagccggggg ctatggcaga ccagtccgct   2340
ggccagccgt ccccagtcag cctgtccccc accccgccca gcaccccgtc accctatgga   2400
ctgagctacc ctcaggggta ctccttggcc tcgggccagc tctccccagc tgcagctcct   2460
cccctggcct ctccttctgt ctttacaagc actttgagca aatcgcggcc cactcctaag   2520
ccgcgacaga gacctactct gccgcctcct cagcctccca cagtaaacct ctcggcctct   2580
agtccacagt ccacggaggc cccccatgcta gatggcatgt cccctgggga aagcatgtct   2640
acagatcttg tccactttga tattccctcg atccacatag agctcgggtc gacgctccgc   2700
ctgagtcccc tggagcacat gcggcgacac tcagtaactg acaagaggga ctcggaggag   2760
gagtctgaga gcaccgccct ctgacatgac accgcccatc ctgcctcgcg tgtacataca   2820
tcacgggccc taggaacgcc gccaggagca gcgtccatga gcttgccaag tgttctctgc   2880
tggctctttc ctgccactgc caacacgagg ttggaatttg gcagaaaatt gtgatctcca   2940
gtccgtgtgg tgatgctggt ggtgcaggtt ttgtttgttc ctttcgggtg gtgacttcgg   3000
ccttttgttt gacctttgcc ttttgacttt gtgcctcttt tgatccactt tcagcctcca   3060
tgccagaaaa cacccacctc tccatccaag gctggtcagg aacgtccttt gcagggtcgg   3120
ggtggtgcgg gagaggctca ctttgcctgg ttagacccaa gggctgctac cttttccttg   3180
```

```
gacggctcat gtcaggtctt gcaggatcag tttaatggcc acagaaagga agcaggacag   3240
cagggcccct ctcacccaca actggaccag gtccaggatt ctagcagtcc tggggcactg   3300
acctttgcca gctacctggg ggagggcttg ccactggaaa acctttcagg ccgcccccat   3360
cagtgggctc caaagtaaat ggctgaaaac aaaaatgttt cacttcctaa cagttttcct   3420
ttttccactg tgtgactgaa agctcctata tcattttata tttctgaatc tataaaacaa   3480
aacaaacaag cctgacagtg tctggaggag ccaaaggtgg cctccctgtc cccaaatata   3540
ttggctatat gagagtaatt ttacccctct acgtacctaa aggcacccag ttcactagtc   3600
tgtggggtcc tggagcctgt ctcttctttc tggaggttca aactgaatag caataattac   3660
gttacccaaa gcatgtggag gaaaagtgaa accagccacg gagacgctgg cccacgggct   3720
cggcctgcgg tgtggcctgc tttgctcacc agcgtcagcc gctcatttcc ttctcatgaa   3780
gtcccatctg gtcatgggga cgagggccgg gagggcaccg ggtagccttt tcacacttgg   3840
ggattagggg agtgagaaaa gatttgggcc atgcatgcaa agtcaaagtt taaaatttta   3900
tccttttcaa atagatgata taatatacct atacatgata taatatttgt atatatgaaa   3960
tctctctata tttgtttaat ttgagccatt caatctaaac caatgtacag gtgtacaatg   4020
aaaaatttaa atgcttagtt atttttccca acacagtgta aagtcaccct cctctgagag   4080
tgggatgtgc agagttttga tgttgcagct ttgctcactt cctggcaagg gcaggtcatg   4140
cctcaatttg taatgggagt ctggggtaag ggtgggggtt gaaagttgtt atctttaaat   4200
acatgtacaa atcgttgtca aaagtaacgt tattaaaata gatttattat ccctgaaaaa   4260
aaaaaaaaaa aaa                                                      4273
```

<210> SEQ ID NO 81
<211> LENGTH: 4532
<212> TYPE: DNA
<213> ORGANISM: Homo sapiens

<400> SEQUENCE: 81

```
gaacgaagaa ggcgtcccgg catcggccaa gattctacat tgctcatctg ggcatctgag     60
cctccttcga agtttcctgt cacaactgtc ctcttgacag catggatgag gaggaagaca    120
atctgtctct gctgaccgca ctgctggaag aaaatgagtc agccttggat tgtaattcag    180
aagaaaataa cttcttgacg cgggaaaatg gcgagcccga cgcatttgat gagctctttg    240
atgccgacgg cgacggtgaa tcttatacag aagaggctga tgatggagaa acaggagaga    300
caagagacga aaaggaaaat ctggccactc tctttggaga tatggaggac ttaacagatg    360
aagaagaagt tcccgcatca cagtcaactg aaaatagggt cctccctgct cctgcccccca    420
ggcgagagaa aacgaatgaa gagttgcaag aggaattaag gaatttgcaa gagcaaatga    480
aggccttaca agagcagcta aaagtaacaa caattaaaca gacagcaagc ccagcccgtc    540
tgcaaaaatc ccctgagaag tctccccggc cacctcttaa ggagaggaga gttcagagaa    600
ttcaggagtc aacatgcttt tctgcggagc ttgatgtccc tgcgctacca agaaccaaga    660
gggtggctcg aacaccaaag gcttcacctc cagatcccaa aagctcatct tcaaggatga    720
caagtgcacc ctcccaaccc ctacagacga tttctcggaa caaacctagt gggataacta    780
gaggtcaaat tgtggggacc ccaggaagtt ctggggaaac gactcaaccc atctgtgtgg    840
aagccttctc tggtctgcgg ctcaggcggc ctcgagtatc ctccacagaa atgaacaaga    900
aaatgaccgg ccgaaaactg atcagactgt ctcagatcaa ggaaaagatg gccagagaga    960
agctggaaga aatagattgg gtgacatttg ggttatatt gaagaaggtt acgccacaga   1020
```

-continued

```
gtgtgaatag tggaaaaacc ttcagcatat ggaaactgaa tgatcttcgt gacctgacac   1080
aatgtgtgtc cttgttctta tttggagaag ttcacaaagc gctctggaag acggagcagg   1140
ggactgtcgt agggatcctc aatgccaacc ccatgaagcc caaggatggt tcagaggagg   1200
tgtgtttatc tatcgatcat cctcagaagg tcttaattat gggtgaagct cttgacctgg   1260
gaacctgtaa agccaagaag aagaatggag agccgtgcac gcagactgtg aatttgcgtg   1320
actgtgagta ctgtcagtac catgtccagg ctcagtacaa gaagctcagc gcaaagcgtg   1380
cggatctgca gtccaccttc tctggaggac gaattccaaa gaagtttgcc cgcagaggca   1440
ccagcctcaa agaacggctg tgccaagatg gcttttacta cggaggggtt tcttctgcct   1500
cgtatgcagc ttcaattgca gcagctgtgg ctcctaagaa gaagattcaa accactctga   1560
gtaatctggt tgttaagggc acaaacttga tcatccagga aacacggcaa aaactcggaa   1620
taccccagaa gagcctgtct tgctctgagg agttcaagga actgatggac ctgccgacgt   1680
gtggagccag gaacttaaaa caacatttag ccaaagccac agcttcaggg attatgggga   1740
gcccaaaacc agccatcaag tccatctcgg cctcagcact cttgaagcaa cagaagcagc   1800
ggatgttgga gatgaggaga aggaaatcag aagaaataca gaagcgattt ctgcagagct   1860
caagtgaagt tgagagccca gctgtgccat cttcatcaag acagcccct gctcagcctc   1920
cacggacagg atccgagttc cccaggctgg agggagcccc ggccacaatg acgcccaagc   1980
tggggcgagg tgtcttggaa ggagatgatg ttctctttta tgatgagtca ccaccaccaa   2040
gaccaaaact gagtgcttta gcagaagcca aaaagttagc tgctatcacc aaattaaggg   2100
caaaaggcca ggttcttaca aaaacaaacc caaacagcat taagaagaaa caaaaggacc   2160
ctcaggacat cctggaggtg aaggaacgtg tagaaaaaaa caccatgttt tcttctcaag   2220
ctgaggatga attggagcct gccaggaaaa aaaggagaga acaacttgcc tatctggaat   2280
ctgaggaatt tcagaaaatc ctaaaagcaa aatcaaaaca cacaggcatc ctgaaagagg   2340
ccgaggctga gatgcaggag cgctactttg agccactggt gaaaaaagaa caaatggaag   2400
aaaagatgag aaacatcaga gaagtgaagt gccgtgtcgt gacatgcaag acgtgcgcct   2460
atacccactt caagctgctg gagacctgcg tcagtgagca gcatgaatac cactggcatg   2520
atggtgtgaa gaggtttttc aaatgtccct gtggaaacag aagcatctcc ttggacagac   2580
tcccgaacaa gcactgcagt aactgtggcc tctacaaatg ggaacgggac ggaatgctaa   2640
aggaaaagac tggtccaaag ataggaggag aaactctgtt accaagagga gaagaacatg   2700
ctaaatttct gaacagcctt aaataacccg aacttcagac attttcccac agacttcctg   2760
gcctcctgtg actctggaaa gcaaaggatt ggctgtgtat tgtccattga ttcctgattg   2820
acgccgtcaa aaacaaatgc ttgttaagcc cataagcttt gcctgcttac tttctgccat   2880
tgggttggtt tgataccaca tttaacattg acatttaagt ggaaaaccaa gttatcattg   2940
tcttttctaa gctcagtgtg gatgattgca ttacttcatt cactgaagtt tttgcccaaa   3000
aattggaagg taaacagaga gctatgtttc tgtatctttt ggttatagag tgttcacttc   3060
tttatcataa caaaattcta gtgtttatac gaacacccag aggcaaaaga atttggctta   3120
attctcactc caggtaagta gcttaacttc tgggcttcag ttttctcatc tgtaaaatca   3180
ggaagattgg actaagtgat cctgaaatgt attttttagc actggatttc tacaaataat   3240
aaaactttcc catctagata atgatgatca catagtcttg atgtacggac attaaaagcc   3300
agatttcttc attcaattct gttatctctg ttttactctt tgaaattgat caagccactg   3360
aatcactttg catttcagtt tatatatata gagagaaaga aggtgtctgc tcttacatta   3420
```

-continued ttgtggagcc ctgtgataga aatatgtaaa atctcatatt attttttttt taattttttt 3480 atttttatg acagggtctc actatgtcac cctggctgga gtgcagtagt gcgatcgcgg 3540
cacactgcag ccttggcttc cctgggctca agcagtcctc ccacctcagt ctcccaaata 3600
gctaggacta caggcgtgcg tgaccaagcc cagctaattt ttgcattttt tgtagagatg 3660
gggttttgcc atgttgctca ggctggtctc aaactcctga gcactagcaa tccacccacc 3720
tctgtttcca aaaaaaaaaa aaaaatgaaa ggtcaacccc tatgcaaatt accacagcaa 3780
aggtttcatt caggagattc ttccatctgg gcaacctggt tttccaaata tcatttgacc 3840
taagtgaatg ttgatactag ctaaagattg ggtaaattgg ttgaattatt gtattgaagc 3900
ttgagctgta gctaaaagta atttaggttt cccctaagat gttattatgt tagggacata 3960
acacttttgg gaggttgttg tgggagatgg ttgatttagg ttttcaaaag ctagaaataa 4020
aatttacatg ccttagattt cataaaattc tgctctaatt gggtggaagg tgctgtatct 4080
aacttgtgtt cctcctaagg ttatgtccta ataactattc ttttaggagt atacttctac 4140
tttatagaag gttgcttttc tttttaattt tttctaacaa agaaaagaat aaagtattta 4200
ttaataagaa ccagaaagca cttgaaactg atgtttttaa tggctcattt agggtagatt 4260
tatttatctc attaacttaa aacagctatg tgtatgaaat aggtcacaac agaacttgaa 4320
caccaggttg gtgtctgagc aatccctttc ttatgggaaa aacaatgttc ttgtttgaac 4380
agagggtatc attgcagtca gtattcacgt gtatattgtt atataagttg tataatatgc 4440
ttgtaaaggc tgagggtgag ctgtatctgg atgccttttt acaatttgat tttaactttt 4500
aaaataaatt taaaacataa aaaaaaaaaa aa 4532

<210> SEQ ID NO 82
<211> LENGTH: 3563
<212> TYPE: DNA
<213> ORGANISM: Homo sapiens

<400> SEQUENCE: 82
aacgcagctg cggcggctgc gggtctcgtg ggggcggagc ggtcgccgct gccgccgcag 60
ctcgggtcgg gatttgaaag attagaaact tcgggtggag agggcggcgg cgttgaatgt 120
gtggcggaag cgctgggggt cacggctccg cgcgccgccg gacagccggc ggcgtctcca 180
cagcatgaat tacccgggcc gcgggtcccc acggagcccc gagcataacg gccgaggcgg 240
cggcggcggc gcctgggagc tgggctcaga cgcgaggcca gcgttcggcg gcggcgtctg 300
ctgcttcgag cacctgcccg gcggggaccc ggacgacggc gacgtgcccc tggccctgct 360
gcgcggggaa cccgggctgc atttggcgcc gggcaccgac gaccacaacc accacctcgc 420
gctggacccc tgcctcagtg acgagaacta tgacttcagc tccgccgagt cgggctcctc 480
gctgcgctac tacagcgagg gtgagagcgg cggcggcggc agctccttgt cgctgcaccc 540
gccgcagcag cctccgctgg tcccgacgaa ctcgggggggc ggcggcgcga caggagggtc 600
ccccggggaa aggaaacgta cccggcttgg cggcccggcg gcccggcacc gctatgaggt 660
agtgacggag ctgggcccgg aggaggtacg ctggttctac aaggaggaca agaagacctg 720
gaagcccttc atcggctacg actcgctccg catcgagctc gccttccgga ccctgctgca 780
gaccacgggt gcccggcccc agggcgggga ccgggacggc gaccatgtgt gctcccccac 840
gggcccagcc tccagttccg gagaagatga cgatgaggac cgcgcctgcg gcttctgcca 900
gagtacgacg gggcacgagc cggagatggt ggagcttgtg aacatcgagc ctgtgtgcgt 960
gcggggcggc ctctacgagg tggatgtgac ccaaggagag tgctacccgg tgtactggaa 1020

-continued

```
ccaggctgat aaaataccag taatgcgtgg acagtggttt attgacggca cttggcagcc   1080
tctagaagag gaagaaagta atttaattga gcaagaacat ctcaattgtt ttaggggcca   1140
gcagatgcag gaaaatttcg atattgaagt gtcaaaatcc atagatggaa aagatgctgt   1200
tcatagtttc aagttgagtc gaaaccatgt ggactggcac agtgtggatg aagtatatct   1260
ttatagtgat gcaacaacat ctaaaattgc aagaacagtt acccaaaaac tgggattttc   1320
taaagcatca agtagtggta ccagacttca tagaggttat gtagaagaag ccacattaga   1380
agacaagcca tcacagacta cccatattgt atttgttgtg catggcattg ggcagaaaat   1440
ggaccaagga agaattatca aaaatacagc tatgatgaga gaagctgcaa gaaaaataga   1500
agaaaggcat ttttccaacc atgcaacaca tgttgaattt ctgcctgttg agtggcggtc   1560
aaaacttact cttgatggag acactgttga ttccattact cctgacaaag tacgaggttt   1620
aagggatatg ctgaacagca gtgcaatgga cataatgtat tatactagtc cactttatag   1680
agatgaacta gttaaaggcc ttcagcaaga gctgaatcga ttgtattccc ttttctgttc   1740
tcggaatcca gactttgaag aaaaaggggg taaagtctca atagtatcac attccttggg   1800
atgtgtaatt acttatgaca taatgactgg ctggaatcca gttcggctgt atgaacagtt   1860
gctgcaaaag gaagaagagt tgcctgatga acgatggatg agctatgaag aacgacatct   1920
tcttgatgaa ctctatataa ctaaacgacg gctgaaggaa atagaagaac ggcttcacgg   1980
attgaaagca tcatctatga cacaaacacc tgccttaaaa tttaaggttg agaatttctt   2040
ctgtatggga tccccattag cagttttctt ggcgttgcgt ggcatccgcc caggaaatac   2100
tggaagtcaa gaccatattt tgcctagaga gatttgtaac cggttactaa atatttttca   2160
tcctacagat ccagtggctt atagattaga accattaata ctgaaacgct acagcaacat   2220
ttcacctgtc cagatccact ggtacaatac ttcaaatcct ttaccttatg aacatatgaa   2280
gccaagcttt ctcaacccag ctaaagaacc tacctcagtt tcagagaatg aaggcatttc   2340
aaccatacca agccctgtga cctcaccagt tttgtcccgc cgacactatg gagaatctat   2400
aacaaatata ggcaaagcaa gcatattagg ggctgctagc attggaaagg gacttggagg   2460
aatgttgttc tcaagatttg gacgttcatc tacaacacag tcatctgaaa catcaaaaga   2520
ctcaatggaa gatgagaaga agccagttgc ctcaccttct gctaccaccg tagggacaca   2580
gacccttcca catagcagtt ctggcttcct cgattctgca ttggagttgg atcacaggat   2640
tgattttgaa ctcagagaag gccttgtgga gagccgctat tggtcagctg tcacgtcgca   2700
tactgcctat tggtcatcct tggatgttgc ccttttttctt ttaaccttca tgtataaaca   2760
tgagcacgat gatgatgcaa aacccaattt agatccaatc tgaactctct tgaaggacat   2820
gaatggccta aaactgattt tttttttttc cgttaaaatg tgtgtgtcaa gatacggaga   2880
tttcagggtt aaagtatatt tcagttttct ttagggcaac atatatttga atttaaaagc   2940
actttattta aaaaaaaaag aagttttcag ttctgaagaa gtcatttaca gtttgcatca   3000
ttttaattat gagtctgaca aaaccttctc cagagaatca agcaagacct ggatgtgaag   3060
aaggtttggg taaactgcat gtaaaggcta caaatcacaa tctgattcct cccaaatata   3120
aaggcatatg gaacataatg tattaaccaa agtatgttat aaatcaaaaa tggtcaaggt   3180
tcagcatatt ctatatgaag atcacaaggt ggtatcgttt tagatttcta tgaaggcttt   3240
catttgtaca tccctttgaa aaaatataac agatttaaaa tgttttgaat ttaacttgtt   3300
tagaaaaact aatgcttaaa acaatatttg aactactgta tttataattt attacctcta   3360
attgctttat ttcagtgtat gagacattac tgttttaatg tttgctttga acataattta   3420
```

agaaccagat ttattttcta tagtgataaa cccttttttc tcagaactcc atctttgtac 3480
tcttcagatg aatatataga cactgtggca tacatttttt ttcattaaaa acttatggct 3540
tcatacaaaa aaaaaaaaaa aaa 3563

<210> SEQ ID NO 83
<211> LENGTH: 5032
<212> TYPE: DNA
<213> ORGANISM: Homo sapiens

<400> SEQUENCE: 83
gcggcggcgg cggcggcggc ggcagcggcg gccaagcggc caggttggcg gccggggctc 60
cgggccgcgc gaggccacgg ccacgccgcg ccgctgcgca caaccaacga ggcagagcgc 120
cgcccggcgc gagactgcgg ccgaagcgtg gggcgcgcgt gcggaggacc aggcgcggcg 180
cggctgcggc tgagagtgga gcctttcagg ctggcatgga gagcttaagg ggcaactgaa 240
ggagacacac tggccaagcg cggagttctg cttacttcag tcctgctgag atactctctc 300
agtccgctcg caccgaagga agctgccttg ggatcagagc agacataaag ctagaaaaat 360
ttcaagacag aaacagtctc cgccagtcaa gaaaccctca aaagtatttt gccatggata 420
tagaagatga agaaaacatg agttccagca gcactgatgt gaaggaaaac cgcaatctgg 480
acaacgtgtc ccccaaggat ggcagcacac ctgggcctgg cgagggctct cagctctcca 540
atgggggtgg tggtggcccc ggcagaaagc ggcccctgga ggagggcagc aatggccact 600
ccaagtaccg cctgaagaaa aggaggaaaa caccagggcc cgtcctcccc aagaacgccc 660
tgatgcagct gaatgagatc aagcctggtt tgcagtacac actcctgtcc cagactgggc 720
ccgtgcacgc gcctttgttt gtcatgtctg tggaggtgaa tggccaggtt tttgagggct 780
ctggtcccac aaagaaaaag gcaaaactcc atgctgctga gaaggccttg aggtctttcg 840
ttcagtttcc taatgcctct gaggcccacc tggccatggg gaggaccctg tctgtcaaca 900
cggacttcac atctgaccag gccgacttcc ctgacacgct cttcaatggt tttgaaactc 960
ctgacaaggc ggagcctccc ttttacgtgg gctccaatgg ggatgactcc ttcagttcca 1020
gcggggacct cagcttgtct gcttccccgg tgcctgccag cctagcccag cctcctctcc 1080
ctgtcttacc accattccca cccccgagtg ggaagaatcc cgtgatgatc ttgaacgaac 1140
tgcgcccagg actcaagtat gacttcctct ccgagagcgg ggagagccat gccaagagct 1200
tcgtcatgtc tgtggtcgtg gatggtcagt tctttgaagg ctcggggaga aacaagaagc 1260
ttgccaaggc ccgggctgcg cagtctgccc tggccgccat ttttaacttg cacttggatc 1320
agacgccatc tcgccagcct attcccagtg agggtcttca gctgcattta ccgcaggttt 1380
tagctgacgc tgtctcacgc ctggtcctgg gtaagtttgg tgacctgacc gacaacttct 1440
cctcccctca cgctcgcaga aaagtgctgg ctggagtcgt catgacaaca ggcacagatg 1500
ttaaagatgc caaggtgata agtgtttcta caggaacaaa atgtattaat ggtgaataca 1560
tgagtgatcg tggccttgca ttaaatgact gccatgcaga aataatatct cggagatcct 1620
tgctcagatt tctttataca caacttgagc tttacttaaa taacaaagat gatcaaaaaa 1680
gatccatctt tcagaaatca gagcgagggg ggtttaggct gaaggagaat gtccagtttc 1740
atctgtacat cagcacctct ccctgtggag atgccagaat cttctcacca catgagccaa 1800
tcctggaagg gtctcgctct tacacccagg ctggagtgca gtggtgcaat catggctcac 1860
tgcagcctcg acctcctggg ctcttaagcg atccttccac ctcaaccttc caaggagctg 1920
ggactacaga accagcagat agacacccaa atcgtaaagc aagaggacag ctacggacca 1980

```
aaatagagtc tggtgagggg acgattccag tgcgctccaa tgcgagcatc caaacgtggg   2040
acggggtgct gcaaggggag cggctgctca ccatgtcctg cagtgacaag attgcacgct   2100
ggaacgtggt gggcatccag ggatccctgc tcagcatttt cgtggagccc atttacttct   2160
cgagcatcat cctgggcagc ctttaccacg gggaccacct ttccagggcc atgtaccagc   2220
ggatctccaa catagaggac ctgccacctc tctacaccct caacaagcct ttgctcagtg   2280
gcatcagcaa tgcagaagca cggcagccag ggaaggcccc caacttcagt gtcaactgga   2340
cggtaggcga ctccgctatt gaggtcatca acgccacgac tgggaaggat gagctgggcc   2400
gcgcgtcccg cctgtgtaag cacgcgttgt actgtcgctg gatgcgtgtg cacggcaagg   2460
ttccctccca cttactacgc tccaagatta ccaagcccaa cgtgtaccat gagtccaagc   2520
tggcggcaaa ggagtaccag gccgccaagg cgcgtctgtt cacagccttc atcaaggcgg   2580
ggctgggggc ctgggtggag aagcccaccg agcaggacca gttctcactc acgccctgac   2640
ccgggcagac atgatggggg gtgcaggggg ctgtgggcat ccagcgtcat cctccagaac   2700
ctcacatctg aactgggggc aggtgcatac cttggggagg gagtaggggg acacgggga    2760
ccaccaggtg tccacggttg tccccagcat ctcacatcag acctggggca ggtgcgcagt   2820
gtggggaggg gatggggtgc gtcagggccc agcatcgccg cctggcatct ctctgccgca   2880
gcatttcccc ttctgaaccg tccagtgact gctttcaatc tcggtttacg tttagaaatt   2940
gagttctact gagtagggct tccttaagtt taggaaaata gaaattactt tgtgtgaaat   3000
tcttgaataa ataatttatt cagagctagg aatgtggttt ataaaatagg aagtaattgt   3060
gtcaggtcac ttttatgcca cattatttta attgcaaaaa agcatctata tatggaggag   3120
ggtgggaaaa tagaggtagg aaatagtagc ctaaaggaaa tcgccacacg tctgtctaaa   3180
cttaggtctc ttttctccgt aggtacctcc ctgggtagtt ccacacacta ggttgtaaca   3240
gtctctccct gaggagcaga ctcccagcat ggtgtagcgt ggccctgtca tgcacatggg   3300
gtcccgcagc agtgactgtg tgtcctgcag aggcgtgacc caggcccctg tagccctcag   3360
cctcctctag aagcttctgt actccttgta ggatcagatc atggaaaact tttctcagtt   3420
tacttctaag taatcacaga taatacatgg ccagtaatcc caggctggcc attcattcag   3480
gtttttaaa ggatatttaa cttttatgga ctagaaggaa tcacgagggc tactgcacaa   3540
tacatggcct aagttccctc tgttccttcc tctgaatcga atggatgtgg gtgaccgccc   3600
gaaggccttc acaggatgga agtagaatga tttcagtaga tactcattct tggaaaatgc   3660
catagtttta aattattgtt tccagcttta tcaaagacat gtttgaaaaa taaaaagcat   3720
ccaagtgaga gctggtgaga ccacgtgctg ctggcgtagt gtaggccaga cattgacagt   3780
cctgacggga gctcagggct gcccagcgcc cagcgtgcac gggacggccc cacgacagag   3840
ggagtcagcc cgggaggtca ggagcgcggc gggcgagggc cctgtgtgga ccacctccac   3900
caagctcaga gatttgcacc aggtgccttg ttgcctccgc tcaggatgaa agaggagctg   3960
agagaagtgc tctgcctgcc agtgcagtgc ccagctccaa ggctctagag ggtgttcagg   4020
tacactgagg aggggacggc tccgtcttca cattgtgcac agatctgagg atgggattag   4080
cgaagctgtg gagactgcac atccggacct gcccatgtct caaaacaaac acatgtacag   4140
tggctctttt tccttctcaa acactttacc ccagaagcag gtggtctgcc ccaggcataa   4200
agaaggaaaa ttggccatct ttcccacctc taaattctgt aaaattatag acttgctcaa   4260
aagattcctt tttatcatcc ccacgctgtg taagtggaaa gggcattgtg ttccgtgtgt   4320
gtccagttta cagcgtctct gccccctagc gtgttttgtg acaatctccc tgggtgagga   4380
```

-continued gtgggtgcac ccagccccga ggccagtggt tgctcggggc cttccgtgtg agttctagtg 4440
ttcacttgat gccggggaat agaattagag aaaactctga cctgccgggt tccagggact 4500
ggtggaggtg gatggcaggt ccgactcgac catgacttag ttgtaagggt gtgtcggctt 4560
tttcagtctc atgtgaaaat cctcctgtct ctggcagcac tgtctgcact ttcttgttta 4620
ctgtttgaag ggacgagtac caagccacaa gaacacttct tttggccaca gcataagctg 4680
atggtatgta aggaaccgat gggccattaa acatgaactg aacggttaaa agcacagtct 4740
atggaacgct aatggagtca gcccctaaag ctgtttgctt tttcaggctt tggattacat 4800
gcttttaatt tgattttaga atctggacac tttctatgaa tgtaattcgg ctgagaaaca 4860
tgttgctgag atgcaatcct cagtgttctc tgtatgtaaa tctgtgtata caccacacgt 4920
tacaactgca tgagcttcct ctcgcacaag accagctgga actgagcatg agacgctgtc 4980
aaatacagac aaaggatttg agatgttctc aataaaaaga aaatgtttca ct 5032

<210> SEQ ID NO 84
<211> LENGTH: 1369
<212> TYPE: DNA
<213> ORGANISM: Homo sapiens

<400> SEQUENCE: 84
agtctaactt ccgcgcatct acgagggccg ggactgccgc tacctttctg gaaggcgccg 60
gccggccagt caccggaggg atcccgccag aggcggctcc gcgtctccag cagcggggca 120
gggacccggg cgccccgccc tcgccagcgc ccgcccccgc ccgcccccgg cccgccctct 180
gtatctggcc cctgggcagc tgcccgggga ggcggccagc gagctggggc cgcgcaatgt 240
cgcacggagc cgggctcgtc cgcaccacgt gcagcagcgg cagcgcgctc ggacccgggg 300
ccggcgcggc ccagcccagc gcgagcccct tggaggggct gctggacctc agctaccccc 360
gcacccacgc ggccctgctg aaagtggcgc aaatggtcac cctgctgatt gccttcatct 420
gtgtgcggag ctccctgtgg accaactaca gcgcctacag ctactttgaa gtggtcacca 480
tttgcgactt gataatgatc ctcgcctttt acctggtcca cctcttccgc ttctaccgcg 540
tgctcacctg tatcagctgg cccctgtcgg aacttctgca ctatttaatc ggtaccctgc 600
tcctcctcat cgcctccatt gtggcagctt ccaagagtta caaccagagc ggactggtag 660
ccggagcgat ctttggtttc atggccacct tcctctgcat ggcaagcata tggctgtcct 720
ataagatctc gtgtgtaacc cagtccacag atgcagccgt ctgatgaggc cacaacccct 780
aggcccctca ggagctttgc agagaggagg acgtgtactc caggcgaggc ctctggacct 840
gtgttcctgt gccaaagtcc tgtcaggctg gtgggcacca ggaaaggcct gcaccctctt 900
cctgctctcc caggaagcca gctccctgag ctcctgagcc agccggaaac tcttcctcca 960
gccttccggg gagaacatcc ctcccattct gggaaaggaa agcagcctcc agggaaatgt 1020
tttctgcctt cctgcttcta gaaccacctc aggtactgat gaaccccact tagcacagct 1080
gaaggggttt gtgaatactc ccgcctaaat cccttctact tcactcctca ggggagtgaa 1140
gtgccttaag aaacaaagcc ctgtcctaat ttatctagct tgtcagtccg gtcttagaga 1200
taccctcttt cctgaagtga ggcgtgcctg tagaaacact atgtggtcag cctgtcccca 1260
aggagatctt gtgtctcctc tccatctctg cctttgttac cagtgtgcat gtgtttgtgt 1320 gtttttttaat aaaatattga ctcggccagt taaaaaaaaa aaaaaaaaa 1369

<210> SEQ ID NO 85
<211> LENGTH: 2579
<212> TYPE: DNA

<213> ORGANISM: Homo sapiens

<400> SEQUENCE: 85
gcagagcagc ggcggcagcg gcggcggcgg cagcagccac ccgatgtctt cggcgcccga 60
gaagcagcag ccaccgcacg gcggcggcgg cggcggcggc gggggaggcg gcgcggccat 120
ggaccccgcg tcgtccggcc cgtccaaggc caagaagacc aacgccggca tccggcgccc 180
ggagaagccg ccctattcct acatcgcgct catcgtcatg gccatccaga gttcacccac 240
caagcgcctg acgctgagcg agatctacca gttcctgcag agccgcttcc ccttcttccg 300
gggctcctac cagggctgga agaactccgt gcgccacaac ctctcgctca acgagtgctt 360
catcaagcta cccaagggcc ttgggcggcc cggcaagggc cactactgga ccatcgaccc 420
ggccagcgag ttcatgttcg aggagggctc ctttcggcgg cggccgcgcg gcttccgaag 480
gaaatgccag gcgctcaagc ccatgtacag catgatgaac gggctcggct tcaaccacct 540
cccggacacc tacggcttcc agggctcggc cggcggcctc tcgtgcccgc ccaacagcct 600
ggcgctggag ggcggcctgg gcatgatgaa cggccacttg ccgggcaacg tggacggcat 660
ggccctgccc agccactcgg tgccccacct gccttccaac ggcggccact cgtacatggg 720
cggctgcggc ggcgcggcgg ccggcgagta cccgcaccac gacagctcgg tgcccgcctc 780
cccgctgctg cccaccggcg ccggtggggt catggagccg cacgccgtct actcgggctc 840
ggcggcggcc tggccgccct cggcgtccgc ggcgctcaac agcggcgcct cttatatcaa 900
gcagcagccc ctgtcccccct gtaaccccgc ggccaacccc ctgtccggca gcctctccac 960
gcactccctg gagcagccgt atctgcacca gaacagccac aacgccccag ccgagctgca 1020
aggcatcccg cggtatcact cgcagtcgcc cagcatgtgt gaccgaaagg agtttgtctt 1080
ctctttcaac gccatggcgt cctcttccat gcactcggcc ggcgggggct cctactacca 1140
ccagcaggtc acctaccaag acatcaagcc ttgcgtgatg tgaggctgcc gccgcaggcc 1200
ctcctggtgc aggcaggcgg gtcacaggga ccctggaccg gcacaagaaa ctgctttctt 1260
ctcgaggtat aaccgtcggc agaagaaaag ggttccacct ctccccaacc ggagtttttg 1320
gcaaggagtc cccaatgcaa agacacagcg ctgcggttgg cacctccttc ctcactcctt 1380
caaaattgtt aagaaatgtt agtggtgggt ctgatctgac tgcagccatc ggtaaataaa 1440
agtttttgat cctgttgaac ccgcctgaga cggtgctgtg caggggaaag cccccgcacc 1500
cacacaggaa ttctgctgag gtccccccctc cttccggcca atggcagaag tgggggaaaa 1560
tttttagaag aaaagcaaac atgtgagacc aatcattatc aaatactttt attttttggt 1620
tgagtattta tctttttatt ttttattttt tttttgaaag aatgtcttgg aatgcgcaag 1680
tctcccttta gagccgtctt ttgcagggag cgggaagtga caagagctca gatctccctc 1740
ccgatctccc tccccacctc cgaagtctcc tccgtggacc acaggtggat ctttgtgcga 1800
acaacttgca tttcggaagc cactgtccgt ctttaaacag aaagtcaaag gagccacgaa 1860
gcaagcggcc gtccgggcgt ccgcctccgt cccccttccat gttcctcctc ttccttcgct 1920
tcagcctctt ctgttatgtt ttgtcttgaa ttttatttag actttttcag tgggtatttt 1980
tctgtctccc aacctctact gtaaactttc tggtccgaga acgagccgaa cacagcgcga 2040
cgcagggact aggacggccc ggtgaccgcg cggattcagg attgcgggga cgcagaaagg 2100
ttaaggcact tttaaaaact atagcaaggc tcctgtttat ttattctact ttctttccct 2160
aataatcaaa acaccgcgta ggctcctccg tttatcagta ttaatggtgt aactttgttg 2220
gcaatatttg ccgtgtagaa ttttttttag atatccattg taaatttgaa acaaagaccg 2280
atctgtgtaa aaacaaattt ccatatgttt tatataaata tatatataat atgaaggact 2340
accctccttt tttttttttg tattttggct gctagagtgc agcatttgtg acacgtattt 2400
gaaatttgaa atttccttct gcactgtata aaaggaccat ttgaggatgt tttgcctttt 2460
gtgtattttt tcctaaaaaa agaacaaaaa taaaaatgta taacatttgt acatggcctt 2520
taaaattgta tcaactagaa ataaaattgc atgagtattt taaaaaaaaa aaaaaaaaa 2579

<210> SEQ ID NO 86
<211> LENGTH: 6453
<212> TYPE: DNA
<213> ORGANISM: Homo sapiens

<400> SEQUENCE: 86
agtgggtttg gttgcacggc ggctttggcg cattttcggc tggtttgatt catccatttt 60
gaagagacgg gggagcgggg ggctcgtctg ttccaggagc cctgaaccaa agagcagcgg 120
agtttgagaa gccagcagct cggggttcgg cagcagcggt cccatcggct gaagttcggg 180
gggggtgggg cgccgagcgc gcggggtggg gggggtcctg gtctttggct tctcgactcg 240
gtcctgtttc gacagcgaac atgtcgcggc ctgtcagaaa taggaaggtt gttgattact 300
cacagtttca ggaatctgat gatgcagatg aagattatgg aagagattcg ggccctccca 360
ctaagaaaat tcgatcatct ccccgagaag ctaaaaataa gaggcgatct ggaaagaatt 420
cacaggaaga tagtgaggac tcagaagaca aagatgtgaa gaccaagaag gatgattctc 480
actcagcaga ggatagtgaa gatgaaaaag aagatcataa aaatgtgcgc caacaacggc 540
aggcggcatc taaagcagct tctaaacaga gagagatgct catggaagat gtgggcagtg 600
aggaagaaca agaagaggag gatgaggcac cattccagga gaaagattcc ggcagcgatg 660
aagatttcct aatggaagat gatgacgata gtgactatgg cagttcgaaa aagaaaaaca 720
aaaagatggt taagaagtcc aaacctgaaa gaaaagaaaa gaaaatgccc aaacccagac 780
taaaggctac agtgacgcca agtccagtga aaggcaaagg gaaagtgggt cgccccacag 840
cttcaaaggc atcaaaggaa aagactcctt ctcccaaaga agaagatgag gaaccggaaa 900
gcccgccaga aaagaaaaca tctacaagcc ccccacccga gaaatctggg gatgaagggt 960
ctgaagatga agccccttct ggggaggatt aaaagtgatg atggtctggg gagagatttt 1020
attaaaaaaa aaaagaaaaa aaaagaaaaa agagggagga aaaaaaagaa cctacttaag 1080
atagaacatg gttttggcta tggcttgact catgggcttt cagtgctttt ttccatttgt 1140
tgaaagtaac atttctctct ctctctcttt tttttttttt tttttaaag caaaccattg 1200 tatgtgtaag tgtttaagtt acctttttgt ctattggtct ctttgccagc cctccccttt 1260
cccaatgaaa gccatgtcaa attaatcact ggattgactg cttcatcttt ttattttttaa 1320 tgaaaggtgt accacggttg taaagcaata agatttgaga tgaacactat tgaaacttcg 1380
ctttttgcta aaaaatagca agttgaatag taatcaaaaa acatagaaag attttagttc 1440
aaaatgattg ctcctttctc tacctggact tttaaaaaat caattgtcat ctaatatgag 1500
tttatttgtc tatagacaca agtatcaatg tctaaaaaaa atcatgactt taaacttcca 1560
ccgatgaggc aggtaggaga taaagatgaa ttctgaactg ttactaaaag tactcatttt 1620
ttaccttgta gggagggtgg gcaatggggt tacctgacct tatttgaggg tatgggcttt 1680 ctttttttatt tcatcacttg ttatctcaaa gagactcgga gccagtgatc cttttatcct 1740
gctacagtct ttagggagct aaaaaaaaaa aaaaagcagg ggctgccaaa actcttgatt 1800
tcatatttcc ttctctaaat atatatgtat cctgtttttt ggataaaatt ttaccaagaa 1860

-continued

```
tccaaaaaaa aaaaaaccct agaatttaat caacaagatc agtctacagg tcacagtgga   1920
tttcttttca aactgacaat gtttaggttt taagcaaata aagttccagt taatgtgaaa   1980
ctcagtcaca aagagttgag atttttcctt tatgaaatag aattgacatt cttttatgct   2040
ataaatgtgc attcaggtcc cattaaccat gctctgcttt tatttgggga tagaacattt   2100
tctttttcat atcccgatct tcccatttct tcatagaaat gtgataagaa gtacatccct   2160
gtgatcctgc tgcttcgtag agcaccactg cacaccctac cccgagtgcc aaccacctct   2220
gctataggac actattttcc tggccctatt cttcacttac ttcccatcct gtccttgact   2280
aggaatatgt taaatgctgc tcccatacaa ttcagttagc tcttgtcttt ttatttggtc   2340
caacccctgc tttactgctc atgctgctta aagcaggagg gactagagaa acaaggcatt   2400
ttaggaggcc tgtgtgcagt tgaaaaccga cttttacacg ccttataaaa gcagtcagga   2460
gatagatccg taggtttgat ccttcacatc taataccagg cgctaatggg aacaaggttt   2520
aaagggtcct ggtatgctaa taaattgaaa aattagtgaa atttaaactt ctgccttttt   2580
ttcctgcctt ttaatctaga tttgcttcct caatatccta ctttgtggtt tactaggaac   2640
atgcttactc tgatcttttt ttaaaaaaca cacagtggca gagtcatttc actattgcac   2700
tgtgtgttaa agaatgaata aggagttttc agttacatgg ccaaaaatac aggacttgaa   2760
cataaatagc agttggatca ttctctttca tgacggttaa attcagaggt gtgaactttg   2820
taatgagggt gttaaagatt aatctatttg cctaaatggg tttgttcagg tatccatttt   2880
taacaaagaa gtttgtgttc atatagtaaa agacctatca gtgtttccac catgcacttc   2940
tatttttag gagtttataa ttttaagtct tacattccta gtaacatttg ggcttttctt   3000
aggttatgtt tcgtgaagat ttggggggag ggctctttta aaacttcagc ctcagttgtt   3060
taacagtctc tttaatatat taatctgcac taacatctct gtgatatatg cacatatttt   3120
agaggtaatc atgtcttcta gattacttgt gtgcatttga ttgggcttct tgtttagggt   3180
ccctttttaaa attaattcat tagattgaaa aatgtattct atatttctga tagactggac   3240
agaaggatct gtgtccccaa gtgagacagg ctctgaataa cctttgtttt ctccactttt   3300
tattgatgat ttaaaacact ctagtcttcc cctcaaatca tgcatgcaaa taggaggaca   3360
gtggtggtga ctcaactgga tacaggtgct caatagtcag gcttgatagt gatgtcagga   3420
cgcattacaa gctgtaagcc gatactgact ggccattggc accatccttg actaaccttc   3480
ctctttttct ctagtgtgcc tatggtgaaa tggcaatagc attcactgtc gtattttgca   3540
gtgctcagga agtgggacgt taactttgaa ggtgcttgtt tgtattagct ctgctaggtt   3600
tacctctaca acgtagattt cagcagctat gctgactgac actacattct agttcttaag   3660
atttttttc cagatccccc cttccccagc tagacatacg tagcatactt tcatcttatt   3720
cagtctttct gtaacctgct gctgctttta gtcctcctca cctcagatcg gaatcaatgg   3780
agtgggccca gaggatacat tttaattcca gtaatggtag gtagatttgt cctgctttct   3840
aaaacatctc ctcatttcat atttccactc catattgatt ccataaggga aaattaatgg   3900
gtgtttcctc ctttagggag gtaatgcaaa gagtgtggac atcttctaat cttgaggaac   3960
agtagttgat ttcccttgaa ggagcttaca tattgactgt tttcacaata acctgtttgc   4020
cccagttcaa tcctcatttt aatacttaat ttggtactgg ctcaaatagc attttcttac   4080
agataacaaa tcaagagtga aatttgaggt tatactccag taaagttttt aacacttgtg   4140
aatatggtca gctagactaa acttgactct tttttttaat ggctttttta tctgtgaaca   4200
ttcagataag tggattttca agtactggtt ggggatggga atcgtgcttt tctttaaact   4260
```

```
tcagtttacg agatgctttg agagcgttag gcaaaagcag aaataaatat caggagcaac   4320
ggggaaagct ttataaaaga tcatggtggc cactgttgca gctttgaaga atgagtgctg   4380
gcttgaacag ttctttgcct gcatcattgg tagctgcact gaaaggaaaa aactttcacc   4440
ttaagaattt gaaaaggaag aaacctgggc tctggtcttc atggcattta gactgagatg   4500
cttaaacaga acagaagtaa tacgcatttc ctgccatagg atagggaaaa tgtaacaagc   4560
tggttgctct tgaggttaga aaattgtctg tttctctgtg gatgaagctg gatttacttg   4620
aaaatggaga gttggcttat tgtttgaata ttgggacatc aagctatcta tagccaagtt   4680
tcagtcgcaa ccagttttcc ctttgtctgg ggtaaattcg atacaaaatg attctttttg   4740
aatcctgaat ccataaatta cacttttttt tttcaaattc acaaaattca cagtggtgct   4800
gactgtgtaa taaccactat tgggaaacat cccgtaaacc tgcctgttgc catgccaatg   4860
gagtgactga actggtgaca tctgtttgag catgctttgt gtggctggta gaatgccacc   4920
gttgtgcata cactttgtac atcaggggtg aagggagggt tttctagatt attgggggag   4980
ggtaaaattg ggattttttt gttgttcctt ttttgatggg gtgtgggggt atagtactca   5040
gcttatgccc taaaataaca tgtataaaaa cccctgaagt attgtgtggg tgtgtacgtg   5100
tgagtgtgtg tttgtataca tctggcaatt aaagctttgt cttctggaac ttagtgaatt   5160
cttttctctt tttcctccag aagtatttgt tacaagattt gtaaataaga gctctactta   5220
gtttgtttac catgaacatg ttgcagcaaa ccttatgcat ctaattccta caaggttaaa   5280
gaaaggcttt tagacttgcc aggttaagca acagccaagt tctcagtaat tgtttgcctt   5340
gatttatctt ttagacttca ttttgccagc tctaaaactc ccagtcttcc ttgattttag   5400
tccttaatct tttatgttct gagcaggaag ggtaaaagac aggaacctgc ttcactgtat   5460
taactagtcc atgggctgag accggggcat ctcttttctt catactgcaa tgttgctaga   5520
tacatgatca gacaccagag ggttgggcat tcttgcaata ccttaacagt gctgaaatct   5580
gcagcatggt actaaggaag ttaaagtttg aatgtaacca ctttatttaa aaggtttttt   5640
tctttaattt aaatgaaatg gggttgaagt gaacatgatt ttgttgacca tgttcgtgaa   5700
ttacagatgc aacatgcatt ggtagaatcg tgtgatggtc ttttgtgata cttaattttt   5760
acatatccca gtctctgtat gtatctgcat agacaaagaa aaaacaaact cctgctttgc   5820
ttttattgaa gggtttccag gactgcgtgt ctgctcctga gctctgtttt aagtatgtgt   5880
atcctttgct tgtattttgt attaaaaaaa taagaaaaag aagcctttat tgttgagcat   5940
gttggcattg tccccttat ttttttctct ttttgggaca tatgaagcaa gttattcttt   6000
ttctgtatct ttttttcttt tgtaaacttt ttttttgttt tgtttaaaaa tggctttata   6060
aaagggcttt tataacccag atgtgtgctc tgtgtacttc ttgtaatacc ttaaagcaaa   6120
cacactaact tacacagctt tgttaatcag ctcccagttc agcctgactt tgtgggaact   6180
tatttcccta ataaattatt tagaaacttt aacagtgacc atccctgttg ttggtaaaag   6240
ataaacatgt cttggttcaa aagttaatac ctcaggatgg aatcaagaag cagtagactt   6300
accagtttga ttaattaagg gagcactgga ctgggtgcgt aaggattctt aattagcatt   6360
ttttctcatg tttacatcca aggttatgaa gtgttgtgga aagcaaagtt taacaatcat   6420
atataataaa agataatgtt tatactcaca gaa                                6453
```

<210> SEQ ID NO 87
<211> LENGTH: 2929
<212> TYPE: DNA
<213> ORGANISM: Homo sapiens

<400> SEQUENCE: 87

```
gtttgcagcc tccgtgccag ggccgggggt gcggttcggg acgcgggatc ctaggtcggg     60
tcctgccccg cccatgtggc gccggcgtct gtgttgtctg cggtctccag ggcagcgccg    120
gggcgggcgg gggcccgggc ggcggcggcg gcggcgcggg aggatgcggg gcccgtccgg    180
gtcgcggccg cggaggagcg ccgggcaggt aacgcttttg tgaaccacaa ctttaaatat    240
cagccagctg ctcctatcaa cacgagtatc ccctgttaat tttttgcatt tttcaagatg    300
agtaaacgta aactaattcc caagctctct attcaatctc ctgtccttca taccaactta    360
aatgtccagt ccacacaccc acctttgaag aaagaagact tacatcggat ttcaaaagac    420
tccttggaat ctgattcaga aagcctcacg caagagatta tgtgccattc tgagtttgat    480
gatcgaatcc ggggcaacgg tatggagccc gacagcttag acgaggagga aagccctcga    540
tggggaagcc tgcacgagat ggaagaggaa gcaagtggaa aagcagctca gatggctcgc    600
gagcaaaacc accatacctg ggaccagggc gccaataaca ggcaacaacc aatagaagac    660
aaatattcag acctccgcta tgacccgaac tggaagagta agaaggagga agggcagctg    720
ctgtctgtgg aagcgttgcc ggagtccacg gacagctctt tagaaaatct gcctttggct    780
cccctctacc cttcccagga gacgtcaatg gaactctccg gggaaaaagg cgagcagaaa    840
gagagtccac agagtgcagc ttctttactt ggtagtgaat tttaagccc aaactatgag    900
catggtgccc gtcgcagcaa gccgttttca gagctgagcg acagtgacct ggaggagaag    960
tcgagcagcc tttctccgta cgtgaagagc tcaagttcac ataacgaggt tttcctgccg   1020
ggatcacgtg gccctcggcg aaggaaatcc aaacaacatt ttgtggaaaa aaacaagctc   1080
actttgggat tacccacccc gaaaacggac tcttatcttc aacttcacaa taaaaaaaga   1140
ggggaatctc atccagaaca gatctcctac cccgtcagag taacagacaa gacgtctatt   1200
cagaatgcca aggaaatgga aaatgctgcc atcgatcctg aagataaatg gcatcaaaga   1260
gcacaacagc taaagaatta ccaggaacac tggtctcaat atgaaagtac aaaatcaagc   1320
aatgtaccaa gagggcaacc ttctgacatg gtgaatgacc atcaaccttc cagaagacca   1380
gccaagctca agattcgaaa gcagtgtaaa caccagaatg gcctgaagtc ttccacaacg   1440
gaagaggtga ctgccagtca ggggaaccag aataaccctc ccaggcagca acaaaaccaa   1500
aataagcctc ttgatacttc aacaaagcct gaatcgattg tgattatgca tgcctctaac   1560
aatgatgtac aagcctcaag ggcacttaga agccacaatc tcaaagaaac ctccaataca   1620
tttgctccac caaaacaggc ttttgacaag gtcttatcta aaaactctac tggatgtgac   1680
tctgggctga atgttaataa agaaagagga cacaaagacc aagaagagaa aagattttca   1740
tatcagcagc tacacaccct ttctgacatg gatttgaaca accttaatga actttctaag   1800
agacacgtgc tcctgagcca gaaaggctct cagtttgttt atcacataaa tactcatgga   1860
tcaaccaaaa ataagaaaca actcaaacag ccttatacag agacaaaata caggaactta   1920
gaaatgttat ggaaattcca ttcttcttct gacagccaga cggttagagc ttctccagat   1980
tcatggctca cccagataat ggagcagcat cagcaagcct tggtgcagct gaccgacgtg   2040
cagcccagtg aaggggcctt atccagcgtc acgcttccac ctatactgtc aagggtagaa   2100
agtgaatccc aactcagttc agagagaagc caaagaaacc aagtgaaaat tagccgtagc   2160
aattctgaag gctatctgtt tcaactggaa aagggaaaaa agcataagaa aagaagcagc   2220
agtaagaaca ccaagctgaa aggttatcag aaaagagacg tgaagcttgg aggcctcgga   2280
cctgactttg agtccatcag agacaaaacg caaaaattaa tacagcaaaa ggaatatgca   2340
```

-continued aaacaagtca aggagtacaa catgaagaca ctatccattc tatcaaaacc acaaacagaa 2400
aaaactcaaa agaaatctgc tatccctcgg cagaaggctt tggaatacgc taagaccatc 2460
cccaaaccca aaccatcaaa tctgactcat caagcatcaa aggaacaaaa aaatccaacc 2520
tatgctggga aagaagaaag tttacctgaa atctcactgc tggaaatact gcagaacaga 2580
cacgaaaggg aaaaacaggc tgtggctgct ttcaaagtcc ttcacatcgt atagacaaca 2640
tttgatagga aggagaccaa aaatggtcca ggaatgaacg tggagaaaag aaacgccaac 2700
caccttctct gcgttgagag taatggccta ttattatcat ctatctgccg tccatgtttg 2760
ctttctgcag gatttaaaat atgaggccca attggattat ggtgccatat tttactttct 2820
aggaagaaaa ttttttaaat tatttatttt caaatcagtt agaattggag ctgaataata 2880
actagagaat aaagcttttg ttttatattg aaaaaaaaaa aaaaaaaaa 2929

<210> SEQ ID NO 88
<211> LENGTH: 1634
<212> TYPE: DNA
<213> ORGANISM: Homo sapiens

<400> SEQUENCE: 88
gggggagggg cggtcctagg aggagcagga gcctggtgct ttctatcagg gagggatcac 60
accggctcac tgctgagccg gccaggcaga cacaggcttg ggctctgctg ggcatcatac 120
ttgtcactgg gtaaacagtt tgcccactta ccgcaggatg aagctgcttg ccagggctct 180
ccggctctgt gagtttggga ggcaggcatc ttccaggagg ctggtggctg gccagggatg 240
tgtggggccc cggcgagggt gctgcgctcc cgtccaggtg gttgggccca gggctgatct 300
cccaccctgt ggagcctgca ttactggaag gatcatgcgg ccagatgatg ccaacgtggc 360
cggcaatgtc cacgggggga ccatcctgaa gatgatcgag gaggcaggcg ccatcatcag 420
cacccggcat tgcaacagcc agaacgggga gcgctgtgtg gccgccctgg ctcgtgtcga 480
gcgcaccgac ttcctgtctc ccatgtgcat cggtgaggtg gcgcatgtca gcgcggagat 540
cacctacacc tccaagcact ctgtggaggt gcaggtcaac gtgatgtccg aaaacatcct 600
cacaggtgcc aaaaagctga ccaataaggc caccctgtgg tatgtgcccc tgtcgctgaa 660
gaatgtggac aaggtcctcg aggtgcctcc tgttgtgtat tcccggcagg agcaggagga 720
ggagggccgg aagcggtatg aagcccagaa gctggagcgc atggagacca agtggaggaa 780
cggggacatc gtccagccag tcctcaaccc agagccgaac actgtcagct acagccagtc 840
cagcttgatc cacctggtgg ggccttcaga ctgcaccctg cacggctttg tgcacggagg 900
tgtgaccatg aagctcatgg atgaggtcgc cgggatcgtg gctgcacgcc actgcaagac 960
caacatcgtc acagcttccg tggacgccat taattttcat gacaagatca gaaaaggctg 1020
cgtcatcacc atctcgggac gcatgacctt cacgagcaat aagtccatgg agatcgaggt 1080
gttggtggac gccgaccctg ttgtggacag ctctcagaag cgctaccggg ccgccagtgc 1140
cttcttcacc tacgtgtcgc tgagccagga aggcaggtcg ctgcctgtgc cccagctggt 1200
gcccgagacc gaggacgaga agaagcgctt tgaggaaggc aaagggcggt acctgcagat 1260
gaaggcgaag cgacagggcc acgcggagcc tcagccctag actccctcct cctgccactg 1320
gtgcctcgag tagccatggc aacgggccca gtgtccagtc acttagaagt tccccccttg 1380
gccaaaaacc caattcacat tgagagctgg tgttgtctga agttttcgta tcacagtgtt 1440
aacctgtact ctctcctgca aacctacaca ccaaagcttt atttatatca ttccagtatc 1500
aatgctacac agtgttgtcc cgagcgccgg gaggcgttgg gcagaaaccc tcgggaatgc 1560

-continued

```
ttccgagcac gctgtagggt atgggaagaa cccagcacca ctaataaagc tgctgcttgg   1620

ctggaaaaaa aaaa                                                      1634


<210> SEQ ID NO 89
<211> LENGTH: 5472
<212> TYPE: DNA
<213> ORGANISM: Homo sapiens

<400> SEQUENCE: 89

cttcgatcgt ccgattctcc cagccgcacc acgggtgctc ccacctgcgg agaaccggag     60

tctggcgatg ccaaggcgct tctgggaatt gtagttccgg gcgggatgag ggcagcacgc    120

ctggctccgc tccttcttac gcatgcgcga ctccgagctg gccaaagaag ttcgtcccct    180

ttgtgaggcc cgggatggga ggctccagcg ccgtaggact gaggcagact ccacggtgag    240

aaagagaccc gatctaaccc aggcctttca tcagagccca ggagggaagg caggaagtgg    300

gaccacgagg cccggggggc ttctaactcg tctggccagg gagatctgaa ttggggtgaa    360

gagcagaatc tccagaacaa ggaggaggtg gtgatcatgg agacagattt ggctgaaatg    420

cctgagaaag gagctctgtc ttcccaggat tctccccatt tccaagagaa gagcacagaa    480

gagggagaag tggctgctct gcgcctcacg gccagatccc aggaaacagt gacattcaag    540

gatgtggcca tggactttac accagaggag tgggggaagc tggatcctgc acaaagggat    600

gtgatgctgg agaactatag gaacctagtc tcactttggc ttccagtttc caaacctgag    660

agctacaact tggagaatgg aaaagaacca ttgaagcttg agagaaaagc ccccaaaagc    720

agctattcag acatggagac tagaccacag agcaaggatt caacttcagt gcaagatttt    780

tccaaagcag aatcatgcaa agttgcaata atagacagac tgacacggaa tagtgtctat    840

gactctaact tggaagcagc ccttgaatgt gaaaattggt tagagaatca gcaaggaaat    900

caggagagac atttgagaga aatgttcact cacatgaatt cactctctga ggaaacagac    960

cataagcatg atgtatactg gaaaagcttc aatcagaaat ctgtccttat cactgaagac   1020

agagttccca aaggatctta tgccttccat acacttgaaa aaagcttgaa acaaaaatca   1080

aacttaatga aaaagcagag aacttataaa gagaaaaaac ctcataaatg taatgattgt   1140

ggtgaactct tcacctacca ttcagtgctt attcgacacc agagagtcca tactggagag   1200

aaaccctata cctgcaatga atgtgggaaa tcttttagcc acagagctaa tttaactaaa   1260

caccagagaa ctcatactag aattctcttt gaatgcagtg aatgcaagaa aaccttcaca   1320

gaaagctcat cccttgcaac acatcagaga attcacgttg gagagagacc ttatgaatgc   1380

aatgaatgtg ggaaaggttt taatcgaagt acacatcttg tgcagcatca gttgattcat   1440

actggagtga agccttatga atgtaatgaa tgtgataaag cttttattca ttcatcagca   1500

ctcattaaac atcaaagaac tcatactgga gagaaacctt ataaatgtca agaatgtggg   1560

aaagccttta gccattgctc atccctaact aagcatcaga gagttcatac tggagaaaag   1620

ccatatgaat gcagtgaatg tggaaaaact tttagtcaga gcacacatct tgttcaacat   1680

cagagaattc acactggaga gaaaccctat gagtgtaatg aatgtgggaa aaccttcagc   1740

cggagctcca attttgctaa acatcaaaga attcatattg gaaagaaacc gtacaaatgt   1800

agcgagtgtg gaaaagcctt cattcattca tcagctctca ttcaacatca gagaactcat   1860

accggagaga aaccctttag atgtaatgag tgtgggaaaa gctttaagtg cagttcatct   1920

ctcatcagac atcaaagagt tcacactgaa gagcaaccct gaaaaattac tgaatgtgaa   1980

gaaatgtaag ttggttttat cactgtatta aatacttgag tgtttaggtg gaaggcgcat   2040
```

-continued

```
ccataatatg catgtgagga ccaattctgt atgcatctaa tttcatttgc gtaatacata   2100
gttttgagcc ataagcaggt tctttatgtc cgttaatttg ataattatga aatctagcca   2160
gcgatttcaa aattttaatc tccaacgtcc caaatagcta tctgtggaaa ttcaagaagt   2220
ccctgagagt aggtagcagt acgaacattg tgaaatccag ttttcccctc tcttgtttat   2280
gtcagagctt tgttgtaagc ctctcacttt gtaaggaaat tcttattggg taggttaggc   2340
tgagggctta catccttatc atcaggaaga cacaatgttg ttatttatta ctccttgaga   2400
tctagataca catatggtat aattcatcta gagtgtaatt tcttttatat tagccttaaa   2460
aaccaaaaat gctgggttca aagtccttag aattcccttc ctccctcaac aagctgctgt   2520
ctatgttgat gaccataact gggatgtata atatttacag acaactctaa gttacgttca   2580
catggattat gtacatcatt gatttttttt tttttttttt tttgagacag agtcttgctc   2640
tgttgcccgg gctggagtgc agtggcgcga tctcggctca ctgcaacctc cacctcccag   2700
gttcatgcca ttctcttgtc tcagcctccc aagtagctgg gactacaggc acctgccagt   2760
acgcctggct aatttttttt gtatttttag tagagatggg gtttcaccat gttagccagg   2820
atggtcttga tctcctgacc tcgtgatctg cctgcctcgg cctcccaaag tgctgggatt   2880
acaggcatga gccaccatgc ctggcatcat cattgattta tgtcattgtt atccctctac   2940
cgcggagacc ttctttcatt ttccatttcc ctgggagttc acgtgaagta gtgaatgggt   3000
caaaatctta acagtggttg ttgatcaagt ccttcctttc ttatccttgg cactgaataa   3060
atctttggtt ttccataatc aaagggtgag ggagacttct tttgtctaca ttattcagct   3120
ttctgaaagc tatgctgtgt ccatttgaga aaaagcccca gggatattga aggtctgaga   3180
agttgagtgg ttcagtgtgt tattatattt agggtcccag taaagaagaa ctgaagcaac   3240
tgtgagacac cagggcatac ttccctgtat gagtggaaaa caaggcacgg aaaatagctc   3300
acaggatagt cctcaactga cttgcttgag gataagcagc ttcccttcgt gaagaagttg   3360
ccatttctct ggccttcata tttatctact ttttgttatt gttgtctgta tcggttcaat   3420
ctcacactgc tataaagaaa tgcctgagac tgggtaactt ataaagaaaa aaggtttaat   3480
tggctcatgg ttccatgggc tgtacaggaa gtatgactgg ggaggtctca gggagctttt   3540
actcatggca aaaggcaaag ccagagcagg tatcttcaca gggctagagc aagaggaaaa   3600
gagagagggg aggtgctaca cactttttat gcaaccaaat ctcatgagaa ctctatcacg   3660
agacagcagt agggggacag tgctaaatca ttcatgagaa actacctgcg tggtccagtc   3720
accttgcacc aggccccacc tcccacattg gggattacaa ttaaacatga gatttgggtg   3780
gggatacaga tctaaactgt atcattactc aaaaaaaaaa aaaaaaagaa agaaaagaaa   3840
acacaggaaa aggaactcac ctcttttatc atcttagtat ttagtactaa tggtttagag   3900
caggaattga caaactgtgg cctggactca tggaccaact ctggcccacc acctgtttct   3960
cagaagaaaa ttttattgga actcagccac acttactcat ttacatgttg tccttgactg   4020
cctttgtgtc cagtgtcaga actgagtagc tgcagcggag gttgtgcctc tgggctttaa   4080
tatcacaaac agagcagctt ataagcaaca gaaacttact tctcacagtt ttggaggctg   4140
ggaagtccaa gatcaaggtg tcaacatatt tagggtctag ggaaggtctg cttcttggtt   4200
aatagaaagc acctttcact gtgtcttcac atggtagaag gggagagctc tggtatcttc   4260
agccccttat aagggcacta atcccattca tgagagctcc accctcacga cctaatcacc   4320
tccaaaaggc cccatttcgt aataccgtca gttaagtttc attatatgac tttgatgggg   4380
atatagccca tagtaggttg tatgtccctg aaagcctaaa atatttactg tttggctctt   4440
```

```
tacagaaaat attttcttgg cccctgttcc agagcattca tcaagtcaga taaagggttt   4500

aaaccagtca gagaaactag gtggaatgga aaagtactga gagataattg gggacagaaa   4560

aataaaagag atgggaaatg ctgcatcaaa atactcctac ctctaggatg ttactatata   4620

ttgttaggag aattcaagtt attgaaactt gccaaattct tgagtgaaga ggaattcatt   4680

tgagagccaa aatttgacta aggaaagaag accaacatgg gctttccaaa gttgagtttg   4740

aattctgcca tccccactaa gcagtcatgt gaccttggaa aaactcccta ctctgagtct   4800

cagtttcttt atctgtatta ggtttcaaca aagggaataa atcattggct tctcatgagg   4860

ttgtcataag gattaaataa gacaatgcat ataaaagaac tggcagacaa taaatataga   4920

gtcccccact cctgcttggt gctctctttc tctctccttc tctacataga gaagtgccag   4980

agcatccgtc agtagaagtt acttaaggtt ggctgtgtct tccacatctt ttgtttaccc   5040

atgaagaact gtgaccatct tgttctgtgt cttgtcataa agatgggacg tgacttcttt   5100

ctgctcttgc ttccatctgg tgctgttttc tgcacagcct ccttgagacc ttccagaacc   5160

ttcttttttc ctacttcata tcacttaacc agtagctatc tgggatggtt ccagaggctg   5220

aagtttgcag ttgaataaca ttttaaatag tgttaagcga cttgggatct ctggcccttt   5280

gcgtttcagt atttgtcctt tttatgcctg atgtttaacc tgccacatgt ttgtactgca   5340

acatgaatct tggaaatttt aatgttatgc atttcaaatg tttttggtta tctgtaaact   5400

aaatgtgccc ttattggctc acttgtcaat aaagatgttt gtatatgtat tgtcagaaaa   5460

aaaaaaaaaa aa                                                       5472
```

<210> SEQ ID NO 90
<211> LENGTH: 2450
<212> TYPE: DNA
<213> ORGANISM: Homo sapiens

<400> SEQUENCE: 90

```
ggggcggggc tggcggcgcc ggcgcagccc gggggcggcg ggaggaggag gtggcggcgg     60

tggcgctggg agctcctgtc accgctgggg ccgggccggg cgggagtgca ggggacgtga    120

gggcgcaagg gccgggacat ggggcccgcc agccccgctg ctcgcggtct aagtcgccgc    180

ccgggccagc cgccgctgcc gctgctgctg ccactattgc tgctgcttct gcgcgcgcag    240

cccgccatcg ggagcctggc cggtgggagc ccccggcgcgg ccgaggcccc ggggtcggcc    300

caggtggctg gactatgcgg gcgcctaacc cttcaccggg acctgcgcac cggccgctgg    360

gaaccagacc cacagcgctc tcgacgctgt ctccgggacc cgcagcgcgt gctggagtac    420

tgcagacaga tgtacccgga gctgcagatt gcacgtgtgg agcaggctac gcaggccatc    480

cccatggagc gctggtgcgg gggttcccgg agcggcagct gcgcccaccc ccaccaccag    540

gttgtgccct tccgctgcct gcctggtgaa tttgtgagtg aggccctgct ggtgcctgaa    600

ggctgccggt tcttgcacca ggagcgcatg gaccaatgtg agagttcaac ccggaggcat    660

caggaggcac aggaggcctg cagctcccag ggcctcatcc tgcacggctc gggcatgctc    720

ttaccctgtg gctcggatcg gttccgtggt gtggagtatg tgtgctgtcc ccctccaggg    780

acccccgacc catctgggac agcagttggt gacccctcca cccggtcctg gcccccgggg    840

agcagagtag agggggctga ggacgaggaa gaggaggaat ccttcccaca gccagtagat    900

gattacttcg tggagcctcc gcaggctgaa gaggaagagg aaacggtccc acccccaagc    960

tcccatacac ttgcagtggt cggcaaagtc actcccaccc cgaggcccac agacggtgtg   1020

gatatttact ttggcatgcc tggggaaatc agtgagcacg aggggttcct gagggccaag   1080
```

atggacctgg aggagcgtag gatgcgccag attaatgagg tgatgcgtga atgggccatg 1140
gcagacaacc agtccaagaa cctgcctaaa gccgacagac aggccctgaa tgagcacttc 1200
cagtccattc tgcagactct ggaggagcag gtgtctggtg agcgacagcg cctggtggaa 1260
acccacgcca cccgcgtcat cgcccttatc aacgaccagc gccgggctgc cttggagggc 1320
ttcctggcag ccctgcaggc agatccgcct caggcggagc gtgtcctgtt ggccctgcgg 1380
cgctacctgc gtgcggagca gaaggaacag aggcacacgc tgcgccacta ccagcatgtg 1440
gccgccgtgg atcccgagaa ggcacagcag atgcgcttcc aggtgcatac ccaccttcaa 1500
gtgattgagg agagggtgaa tcagagcctg ggcctgcttg accagaaccc ccacctggct 1560
caggagctgc ggccccaaat ccaggaactc ctccactctg aacacctggg tcccagtgaa 1620
ttggaagccc ctgcccctgg gggcagcagc gaggacaagg gtgggctgca gcctccagat 1680
tccaaggatg cagacacccc catgaccctt ccaaaagggt ccacagaaca agatgctgca 1740
tcccctgaga aagagaagat gaacccgctg gaacagtatg agcgaaaggt gaatgcgtct 1800
gttccaaggg gtttcccttt ccactcatcg gagattcaga gggatgagct ggcaccagct 1860
gggacagggg tgtcccgtga ggctgtgtcg ggtctgctga tcatgggagc gggcggaggc 1920
tccctcatcg tcctctccat gctgctcctg cgcaggaaga agccctacgg ggctatcagc 1980
catggcgtgg tggaggtgga ccccatgctg accctggagg agcagcagct ccgcgaactg 2040
cagcggcacg gctatgagaa ccccacttac cgcttcctgg aggaacgacc ctgacccggc 2100
ccccttcacc ccttcagccg agcccagacc tcccctcttc ctggagcccc agaaccccaa 2160
ctcccagcct agggcagcag ggagtcttga agtgatcatt tcacaccctt ttgtgagacg 2220
gctggaaatt cttatttccc ctttccaatt ccaaaattcc atccctaaga attcccagat 2280
agtcccagca gcctccccac gtggcacctc ctcaccttaa tttatttttt aagtttattt 2340
atggctcttt aaggtgaccg ccaccttggt cctagtgtct attccctgga attcaccctc 2400
tcatgtttcc ctactaacat cccaataaag tcctcttccc taccaggcca 2450

<210> SEQ ID NO 91
<211> LENGTH: 2066
<212> TYPE: DNA
<213> ORGANISM: Homo sapiens

<400> SEQUENCE: 91
aagttgcagt gactctccgg cgtcactgtt gcgcttcata gacgccgcgt gtacccggtt 60
gtcctcaggc gctgtcagat ctgtggtttt tctacttgaa ggacacaatg ttttccaaac 120
tagcacattt gcagaggttt gctgtactta gtcgcggagt tcattcttca gtggcttctg 180
ctacatctgt tgcaactaaa aaaacagtcc aaggccctcc aacctctgat gacatttttg 240
aaagggaata taagtatggt gcacacaact accatccttt acctgtagcc ctggagagag 300
gaaaaggtat ttacttatgg gatgtagaag gcagaaaata ttttgacttc ctgagttctt 360
acagtgctgt caaccaaggg cattgtcacc ccaagattgt gaatgctctg aagagtcaag 420
tggacaaatt gaccttaaca tctagagctt tctataataa cgtacttggt gaatatgagg 480
agtatattac taaacttttc aactaccaca aagttcttcc tatgaataca ggagtggagg 540
ctggagagac tgcctgtaaa ctagctcgta agtggggcta taccgtgaag ggcattcaga 600
aatacaaagc aaagattgtt tttgcagctg ggaacttctg ggtaggacg ttgtctgcta 660 tctccagttc cacagaccca accagttacg atggttttgg accatttatg ccgggattcg 720
acatcattcc ctataatgat ctgcccgcac tggagcgtgc tcttcaggat ccaaatgtgg 780
ctgcgttcat ggtagaacca attcagggtg aagcaggcgt tgttgttccg gatccaggtt 840
acctaatggg agtgcgagag ctctgcacca ggcaccaggt tctctttatt gctgatgaaa 900
tacagacagg attggccaga actggtagat ggctggctgt tgattatgaa aatgtcagac 960
ctgatatagt cctccttgga aaggcccttt ctgggggctt ataccctgtg tctgcagtgc 1020
tgtgtgatga tgacatcatg ctgaccatta agccagggga gcatgggtcc acatacggtg 1080
gcaatccact aggctgccga gtggccatcg cagcccttga ggttttagaa gaagaaaacc 1140
ttgctgaaaa tgcagacaaa ttgggcatta tcttgagaaa tgaactcatg aagctacctt 1200
ctgatgttgt aactgccgta agaggaaaag gattattaaa cgctattgtc attaaagaaa 1260
ccaaagattg ggatgcttgg aaggtgtgtc tacgacttcg agataatgga cttctggcca 1320
agccaaccca tggcgacatt atcaggtttg cgcctccgct ggtgatcaag gaggatgagc 1380
ttcgagagtc cattgaaatt attaacaaga ccatcttgtc tttctgaggg tagccagctg 1440
ttttcagtgg tccctgggag ccagctggag acaggtggtc ctgtaaaagc tttattccta 1500
atgtgggcac attccactcc catgagtctt caaaaacttt ttttttgaat atattttttt 1560
cagttgatac ataatagaac aacgtttatg aacctgccgt ttgctttgta acgtaactaa 1620
ataatgtaat ggcatctata ttcagttgaa gtgttttgat gtgcatgtgt acttcctaag 1680
gtgaaatgca tctatataca gacagcctct aaatcaagtc cttcagtata attgatatat 1740
gtttttataa tttcctcact ggtataagtg tttcatattt gaaaaagtta tctctgggta 1800
ttgcataaaa ggcttcatct tataaagtga aatcattgtt attgaatttt aggaaggatt 1860
aatggttaag tgtatataaa atactaatat taagtaaact tcatattggc caacaccagg 1920
gttgtattct atggatgtca ttattttgaa ttaagaatta gtgtttaaca ttcctaaatt 1980
gttttgagtg cttgattata atttgtaaaa aatgtttatt ttcaatactt ctttaaattt 2040
aaaataaagc ttatatttca aatgtc 2066

<210> SEQ ID NO 92
<211> LENGTH: 3284
<212> TYPE: DNA
<213> ORGANISM: Homo sapiens

<400> SEQUENCE: 92
aaagcgcatg cgccagctag atgggcagcg aggagagccg caactgccag tccctcgaag 60
gggttagctg tcgttgaacg tcagcacgca gatgcaactg gctctcggca ggggggcgcg 120
cgcaccgctg cggagcgccg gcccgtaggc gcgggagcct ccctattaag ggcacgcgac 180
atcgaggcaa tagtgcgcag gtgcttagcc agaggcggag cccgagaggc aggcagcgga 240
cttccggttc cgggagcaac gaacagccgc ggaggcgaca gctaccgctt cagaggaggc 300
ggccgcggag gaggaggaag gggaggaggg cgaggcggga ggtgcaggag ggaccctcgc 360
catgggtcca cgggcctaga gtggcggaag ataccggcct ggtgccaaac tggctactgc 420
tgcttcctgt ggcctccatg gctgaggact ggctggactg cccggccctg ggccctggct 480
ggaagcgccg cgaagtcttt cgcaagtcag gggccacctg tggacgctca gacacctatt 540
accagagccc cacaggagac aggatccgaa gcaaagttga gctgactcga tacctgggcc 600
ctgcgtgtga tctcaccctc ttcgacttca aacaaggcat cttgtgctat ccagccccca 660
aggcccatcc cgtggcggtt gccagcaaga agcgaaagaa gccttcaagg ccagccaaga 720
ctcggaaacg tcaggttgga ccccagagtg gtgaggtcag gaaggaggcc ccgagggatg 780
agaccaaggc tgacactgac acagccccag cttcattccc tgctcctggg tgctgtgaga 840

-continued

```
actgtggaat cagcttctca ggggatggca cccaaaggca gcggctcaaa acgttgtgca    900
aagactgtcg agcacagaga attgccttca accgggaaca gagaatgttt aagcgtgtgg    960
gctgtgggga gtgtgcagcc tgccaggtaa cagaagactg tggggcctgc tccacctgcc   1020
tcctgcagct gccccatgat gtggcatcgg ggctgttctg caagtgtgaa cggagacgct   1080
gcctccggat tgtggaaagg agccgagggt gtggagtatg ccggggctgt cagacccaag   1140
aggattgtgg ccattgcccc atctgccttc gccctccccg ccctggtctc aggcgccagt   1200
ggaaatgtgt ccagcgacgt tgcctacggg gtaaacatgc ccgccgcaag ggaggctgtg   1260
actccaagat ggctgccagg cggcgccccg gagcccagcc actgcctcca ccaccccat    1320
cacagtcccc agagcccaca gagccgcacc ccagagccct ggccccctcg ccacctgccg   1380
agttcatcta ttactgtgta gacgaggacg agctacagcc ctacacgaac cgccggcaga   1440
accgcaagtg cggggcctgt gcagcctgcc tacggcggat ggactgtggc cgctgcgact   1500
tctgctgcga caagcccaaa ttcgggggca gcaaccagaa gcgccagaag tgtcgttggc   1560
gccaatgcct gcagtttgcc atgaagcggc tgctgcccag tgtctggtca gagtctgagg   1620
atggggcagg atcgccccca ccttaccgtc gtcgaaagag gcccagctct gcccgacggc   1680
accatcttgg ccctaccttg aagcccacct tggctacacg cacagcccaa ccagaccata   1740
cccaggctcc aacgaagcag gaagcaggtg gtggctttgt gctgcccccg cctggcactg   1800
accttgtgtt tttacgggaa ggcgcaagca gtcctgtgca ggtgccgggc cctgttgcag   1860
cttccacaga agccctgttg caggaggccc agtgctctgg cctgagttgg gttgtggcct   1920
taccccaggt gaagcaagag aaggcggata cccaggacga gtggacacca ggcacagctg   1980
tcctgacttc tcccgtattg gtgcctggct gccctagcaa ggcagtagac ccaggcctgc   2040
cttctgtgaa gcaagagcca cctgacccag aggaggacaa ggaggagaac aaggatgatt   2100
ctgcctccaa attggcccca gaggaagagg caggaggggc tggcacaccc gtgatcacgg   2160
agattttcag cctgggtgga acccgcttcc gagatacagc agtctggttg ccaaggtcca   2220
aagaccttaa aaaacctgga gctagaaagc agtagactgg aggcttctac agactgtagg   2280
attcaagtct gcagggcagg cactcgggaa gggaagatgg atgtaaagtg tgggagaccg   2340
aggacacagt ggagcccacg agcacgagct ggaacccacg aggatggcct ggaacccatg   2400
tcagtctctc accacctcca gcttcgatga tgtgggtgtc ctgcagaaga agctggtgcc   2460
cttcctcaca gagttaaata tgcatctggc ccaggaatta gagaagctga aaggatgatc   2520
ctggggaagg tggagcagct gcaggcctgg ctgcaggcct gactactgcc cacaccaacg   2580
aggtgatcta gcagatacat ggcaacgtgt gaactgcaac aacgcctggt gccccagcac   2640
caaccttcca agtgtaaaaa caatgtgctg ctgcttcact tccgccctcc ggttatcaag   2700
caaaatgtct cttgtggccc atcttactgg aagagagttc cgggaaacat agcctcacca   2760
aggtgacaca ttacaaagcc accctaccat gaatccgctc ccaagggtct cactgctcac   2820
ctgaggataa ctcaatataa ctatgtggct gaaaatgcaa agctgaagac catggatttc   2880
atggtgattc cagcaagtac agagattcta tgaagcccac ccagaaaaaa cttgctggtc   2940
ctggctattt ttgtgtcatt tattcaagta ttgagaacct ggcctgtggt aggcactgta   3000
cttaatacta ggatacagaa atgcaaaaga tacggcccat gcaattttat taaatgcatc   3060
aatatgtatt acaaatggtg aatggatttc caactttatc atggaattta atgctgaata   3120
tatagaattc agaaaattgt tgggaggaca gcccttttgt gaaccttgtt tggggcacag   3180
taggaattgg aaataattta gtttctatct ctaagctgtt ctattttaaa attattttta   3240
```

-continued aatttttatt gtcccactta aaaaaaaaaa aaaaaaaaaa aaaa 3284

<210> SEQ ID NO 93
<211> LENGTH: 3172
<212> TYPE: DNA
<213> ORGANISM: Homo sapiens

<400> SEQUENCE: 93
gtcggttccc gattctggtc cccggccccc agcagcgcct gccccccttcc caccggggcc 60 ccccatgatg ccaccaccct tcatgccccc tccagggatc cccccaccct ttcctccgat 120
ggggctaccc cccatgagtc agagaccacc agctatcccc cccatgccac ctggcatcct 180
gcccccaatg cttccaccaa tgggggcgcc accaccactc acacagatac caggaatggt 240
acctccgatg atgccaggaa tgctgatgcc agcggtgcct gtcaccgcag cgacggctcc 300
gggtgcggac accgccagct ctgctgtggc tgggacaggc cctccgaggg ccctatggag 360
tgagcatgtg gccccagatg ggcgcatcta ctactacaat gctgacgaca agcagtccgt 420
gtgggagaag cccagcgtgc tcaagtccaa ggcagagctg ctcctgtccc aatgtccctg 480
gaaagagtac aagtcggaca caggcaaacc ttattactat aacaaccaga gtaaagagtc 540
ccgctggacc cggcccaagg atctggatga cctagaggtt ctagtcaaac aagaggctgc 600
agggaaacag cagcagcagc tgccacagac acttcagcca cagccacctc agccacagcc 660
tgacccccca cctgtgcctc ctggccccac cccagtgccc acaggcctcc tggaacctga 720
gccaggtggg agtgaagatt gtgatgtgtt ggaggccacc cagcccctgg aacaggggtt 780
cctgcagcag ctggaggagg gccccagcag ttctggacag catcagccac agcaggagga 840
ggaggaatca aagccagaac cagagaggtc tggcctcagt tggagcaacc gggagaaggc 900
aaagcaggca ttcaaggaac tgctgaggga caaggctgtc ccctccaatg cctcatggga 960
acaggccatg aagatggtgg tcaccgaccc ccgttacagt gccttgccta aactgagtga 1020
gaaaaagcag gcattcaatg cctacaaggc gcagcgggag aaggaggaga aggaggaggc 1080
ccggctaagg gccaaagagg ccaagcagac cctgcagcat ttcctggagc agcatgaacg 1140
catgacctcc accacccgct accggcgggc agaacagacc tttggggagc tggaggtctg 1200
ggctgtggtc cctgagaggg atcgaaaaga ggtttatgat gatgtcctct tcttcctggc 1260
caagaaggag aaggaacagg ccaagcagct ccggcgccgc aatatccagg ccctaaagag 1320
catcctggat gggatgagta gtgtcaactt ccaaaccacg tggtcccagg cccagcagta 1380
cctcatggat aaccccagct ttgctcagga ccatcagctg cagaacatgg acaaggaaga 1440
tgcactgatc tgttttgagg agcacatccg agctttggag agggaagagg aggaggaacg 1500
ggagcgggcc cggcttcggg agcgacgcca acaacgcaag aatcgggagg ccttccagac 1560
cttcctggac gagctgcatg agacagggca gctgcactct atgtccacct ggatggagct 1620
atatccagca gtcagcactg atgtccgctt tgccaacatg ctgggccagc cgggctccac 1680
ccctctggac ttattcaagt tctatgtgga ggagttgaag gcacgattcc atgatgaaaa 1740
gaagatcatt aaggacatcc ttaaggaccg gggcttctgc gtggaggtga acacggcctt 1800
tgaggacttc gcccacgtca taagctttga caagagggct gccgcactgg acgcaggcaa 1860
catcaagctg accttcaata gtctgctgga gaaagcagag gcacgggaga gggagcggga 1920
gaaggaggag gcacgcagga tgcggcgcag ggaagctgcc tttcgaagca tgctgaggca 1980
ggctgtgcct gctctggagc taggcactgc ctgggaagag gtccgtgagc gttttgtgtg 2040
tgactcagcc tttgagcaga tcaccctgga gtcggagcgg atccggctct tccgggagtt 2100

-continued

```
cctacaggtg ctggagcaga ctgaatgcca gcacctccac accaaaggcc gaaagcatgg   2160
caggaaaggc aagaagcacc atcacaagcg ttcccactca ccctcaggct ctgagtcaga   2220
agaagaggag ctgcccccac catctctccg gcccccaag cggaggaggc ggaacccctc   2280
agagtcaggc tctgagccct cttcctcact tgattcagtt gaaagtgggg gtgctgccct   2340
tggaggacgg ggctcccctt cctcccatct tcttggagca gatcatggcc ttcggaaagc   2400
caagaaacca aaaaagaaaa ctaagaagag aagacacaag tcgaatagtc ctgagagtga   2460
gacagaccct gaggagaaag ctggcaagga gagcgatgag aaagaacaag aacaggacaa   2520
ggacagggag ctccaacagg cagagctccc taaccgttcc ccaggctttg gaatcaagaa   2580
ggagaagaca ggctgggaca cgtcagaaag tgagctgagt gagggtgagc tggagaggcg   2640
gcggcggaca ctcctacagc agctggatga tcaccagtga cccaatgagc tgttctctgc   2700
ctcgggtctg tgtgaggcca tggctcctgg gccaccctca ccgtctgcct cagacttctt   2760
ccttagtctg gtctgtgtcc actttttcta aagtaacccc acccccagca caccattgtt   2820
ggcacctctc aaggttgctc ttggtgttca agggtcccct actccctgga ctagtgcagt   2880
ccttgccctc agccccagac cagagatggg tggtatatgc catgtggggt gggtgatgcc   2940
agtagataaa agtgtgagag aaggggtctc cagggaagag tcacaggctg ttggacacag   3000
cctgggtggc agagggcagg gtcatcaccc tctagcatca gtgcctgctc ctgcctgccc   3060
tggccctgag gctccaccac ttcttcctcc acccaggacc taatgtacgt gtgttttgtt   3120
ttttgttttt taaataacaa tatttataac atggaaaaaa aaaaaaaaaa aa           3172
```

<210> SEQ ID NO 94
<211> LENGTH: 3884
<212> TYPE: DNA
<213> ORGANISM: Homo sapiens

<400> SEQUENCE: 94

```
ggcggggaca gcggcgggga cagcggcggg cggctgggac ggcgggtgcg gcggggccga     60
gcccgcacga tgcctcactt caccgtggtg ccagtggacg ggccgaggcg cggcgactat    120
gacaacctcg aggggctcag ttgggtggac tacggggagc gcgccgagct ggatgactcg    180
gacggacatg gcaaccacag agagagcagc ccttttcttt ccccccttgga ggcttccaga    240
ggaattgact actatgacag gaacctggca ctgtttgagg aagagctgga catccgccca    300
aaggtatcgt ctcttctggg aaagctcgtc agctacacca acctcaccca gggcgccaaa    360
gagcatgagg aggccgagag tggggagggc acccgccgga gggcagccga ggcacccagc    420
atgggcaccc tcatgggggt gtacctgccc tgcctgcaga atatctttgg ggttatcctc    480
ttcctgcggc tgacctggat ggtgggcaca gcaggtgtgc tacaggccct cctcatcgtg    540
cttatctgct gctgttgtac cctgctgacg gccatctcca tgagtgccat cgccaccaac    600
ggtgtggttc cagctggggg ctcctatttc atgatctctc gttcactggg gccagaattt    660
ggaggtgctg tgggcctgtg cttctacctg ggaacaacat tcgcagcagc catgtacatc    720
ctgggggcca tcgagatctt gctgacctac attgccccac cagctgccat tttttaccca    780
tcgggtgctc atgacacgtc gaatgccact ttgaacaata tgcgtgtgta tgggaccatt    840
ttcctgacct tcatgaccct ggtggtgttt gtgggggtca agtatgtgaa caaatttgcc    900
tcgctcttcc tggcctgtgt gatcatctcc atcctctcca tctatgctgg gggcataaag    960
tctatatttg accctcccgt gtttccggta tgcatgctgg gcaacaggac cctgtcccgg   1020
gaccagtttg acatctgtgc caagacagct gtagtggaca atgagacagt ggccacccag   1080
```

```
ctatggagtt tcttctgcca cagccccaac cttacgaccg actcctgtga cccctacttc   1140
atgctcaaca atgtgaccga gatccctggc atccccgggg cagctgctgg tgtgctccag   1200
gaaaacctgt ggagcgccta cctggagaag ggtgacatcg tggagaagca tgggctgccc   1260
tccgcagatg ccccgagcct gaaggagagc ctgcctctgt acgtggtcgc tgacatcgcc   1320
acatccttca ccgtgctggt cggcatcttc ttcccttctg taacaggcat catggctggc   1380
tcaaaccgct ctggggacct tcgtgacgcc cagaagtcta tccctgtggg gaccattctg   1440
gccatcatta caacttccct cgtgtacttc agcagtgtgg ttctctttgg tgcctgcatt   1500
gagggtgtgg ttctccggga caagtatggc gatggtgtca gcaggaactt ggtggtgggc   1560
acactggcct ggccttcacc ctgggtcatc gtcatcggct ccttcttttc aacgtgtggc   1620
gctggcctcc agagcctcac aggggcacca cgcctattgc aggccattgc caaggacaac   1680
atcatcccct tcctccgggt gtttggccac gggaaggtga atggtgaacc cacatgggca   1740
ctcctcctga cggcactcat cgccgagctg ggcatcctca tcgcctccct cgacatggtg   1800
gcccccatct tatccatgtt ctttctgatg tgctacctgt tcgtgaacct cgcctgtgcg   1860
gtgcagacac tcctgaggac ccccaactgg cggccccggt tcaagtacta tcactgggcg   1920
ctgtccttcc tgggcatgag tctctgcctg gcccttatgt ttgtctcctc ctggtactat   1980
gccctggtgg ccatgctcat cgccggcatg atctacaaat acatcgagta ccaaggggct   2040
gagaaggagt ggggtgacgg gatccgaggc ctgtccctga gcgctgcccg ctacgcgctg   2100
ttgcggctgg aggaggggcc tcctcacacc aagaactggc ggccgcagct gctggtgctg   2160
ctgaagctgg acgaggacct ccacgtgaag tacccgcggc tcctcacctt cgcctcccag   2220
ctcaaggctg gcaagggcct gaccattgtt ggttctgtca tccaggggag cttcttggag   2280
agctatggcg aggctcaggc cgccgagcag accatcaaga acatgatgga aattgagaag   2340
gtgaagggct tctgccaggt ggtggtggcc agcaaggtgc gggaggggct ggcccacctc   2400
atccagtcct gtggcctggg aggcatgcgg cataactccg tggtgctggg ctggccctac   2460
ggctggcgac agagcgagga cccccgtgcc tggaagacct tcattgacac cgtgcgctgc   2520
actacggctg cccacctggc cctgctcgtg cccaagaaca tcgccttcta ccccagcaac   2580
cacgagcgct acctggaggg ccacatagac gtgtggtgga tcgtgcacga tggtggcatg   2640
ctcatgcttc tgcccttcct gctgcgccag cataaggtct ggaggaagtg ccggatgcgc   2700
atcttcacag tggcccagat ggatgacaac agcatccaga tgaagaagga cctggctgtc   2760
tttctgtacc atctgcgcct tgaggccgag gtggaggtgg tggagatgca taacagtgac   2820
atctctgcat acacctacga gcggacgctg atgatggagc agcggtcgca gatgctgcgg   2880
cagatgagac tgaccaagac tgagcgggag cgagaagccc agctggtcaa ggatcggcac   2940
tcggccctga ggctggagag cctgtactcg gacgaggaag atgagtctgc agtgggggct   3000
gacaagatcc agatgacgtg gaccagggac aagtacatga ctgagacctg ggaccccagc   3060
catgcccctg acaatttccg gggagctggtg cacattaagc cggaccaatc caatgtgcgg   3120
cgcatgcaca ctgctgtgaa gctcaatgaa gtcattgtca cgcgctccca cgacgcccgc   3180
ctggttctcc taaacatgcc tggcccaccc aggaacagtg agggcgacga gaactacatg   3240
gagttcctcg aggtgctgac cgagggcctt gagcgggtgc tgttggtgcg cggtggtggc   3300
cgtgaagtca tcaccatcta ctcctgagcc cagtgtcatc ttgtggcctg gagtcgaggt   3360
cttggccagg acataacaag ctgtggtctg gggtaacagc ctcttcccag cacccacctg   3420
ccagccctgc ttgcctggcc ctgtcctgga cccagctttg ctaggtctcc ttggaaacca   3480
```

ggcctgggcc tcaaaatgga gatggatccc aggtcttgtg ggaccctggg atgtttgggg 3540
actttactat ctagcacccc agtaggcctg tcctggccag agaagactgg taggggccga 3600
gtggggtttg aaggcagccg gcccggccca gcccaggagc gctatttatt gcatatttat 3660
tgtttggatg tcaccatcag agacgaaggg aagggtagcc agggagggag tccagcccag 3720
ctgcctgcag gaagatctgg ctcagtctac tatgggcagg gccccccacc aagctgagcc 3780
gaatggagac agctgagctg aggcctgact ttttcaataa aacattgtgt agttctgggc 3840
aaaaaaaaaa aaaaaaaaaa aaaaaaaaaa aaaaaaaaaa aaaa 3884

<210> SEQ ID NO 95
<211> LENGTH: 3742
<212> TYPE: DNA
<213> ORGANISM: Homo sapiens

<400> SEQUENCE: 95
cttcctttcc ttacgcacgc tgcgcgcgga cgtcggcctc tgacgtcgtc gcctcagcgc 60
cggctcccgg ccgggccgcg gccgccgacc gttgagccgc cggctgagcc gcctgctgaa 120
gtccctccct caggaacccc tccgccaccc tccacctccg aaccgctctc gcggcggcga 180
cccatgtggg ggttcaggct cctgcggtcg ccgccgttgc tgctcctgct gccgcagctc 240
ggaatcggaa acgcctcgtc ctgctctcag gccagaacca tgaacccggg cggcagcggc 300
ggcgcgcgat gctccctctc ggccgaggtg cgccgccgtc agtgcctgca gctttccacc 360
gtgcctggag ccgatccgca gcgcagcaac gaattgctcc tgttggcggc ggccggggag 420
ggactggagc ggcaggacct ccccggggac ccagcgaagg aggagccgca gccgccgccc 480
cagcatcacg tcctctattt ccctggggat gtgcagaatt accatgaaat tatgactcgt 540
catcctgaga attatcaatg ggaaaactgg agtctagaaa atgttgctac cattttagcc 600
caccggttcc ccaatagtta tatttgggtg ataaaatgtt cccgaatgca tttgcacaaa 660
ttcagctgct atgacaattt tgtgaaaagt aacatgtttg gtgccccaga acacaatact 720
gactttggag cttttaagca cctttatatg ttattagtta atgcttttaa tttaagtcag 780
aatagtttat caaagaaaag tttgaatgtt tggaataagg actccatagc atctaactgt 840
agatccagtc cttctcatac tacgaatggt tgccagggag aaaaagtgag gacctgtgaa 900
aaatctgatg agtctgccat gagtttttat ccaccatcac taaatgacgc atcttttact 960
ttgattggat tcagtaaagg ttgtgttgtt ttgaatcagt tgctttttga attgaaagaa 1020
gccaagaaag acaagaacat agatgctttt atcaaaagca taagaacaat gtattggctg 1080
gatggtggtc attctggagg aagcaatact tgggttactt atccagaagt cttgaaagaa 1140
tttgcacaaa caggaattat cgttcacact catgtaacac cttaccaagt acgtgatcca 1200
atgagatctt ggattggaaa ggagcacaag aaatttgttc agatacttgg ggatcttggt 1260
atgcaggtga ctagccaaat tcattttaca aaggaagctc cttccataga gaatcacttc 1320
agggttcatg aagtattttg agattacagg tatattaatg aacttgttca gtggaagaac 1380
ataagcactt ttgagtgtta taaattcaga taatgggatg taattcatag ctgcattgtc 1440
agttttgggg tatgggggga agcacacatt cctaaaatgt gagtgtaatg tgcaatagta 1500
ttttttgctt gtgaatgtga gcagttatta atttggattg agttagaatt agttaatttg 1560
aaatctaaca aggtggtttg taataatgct gaggagatat aagaccctta aaatgaaagt 1620
tacaacattg ttcttataaa aggtaactaa aattgttact gttggaaata actgattttc 1680
tgagtaatgt tttaaactaa tttggtgaca ttttaacagt aattagctat tttgagtgga 1740

-continued aatattttca tttctcttca aacaaaagca aaggtacgat gctgttttct atcattttgg 1800
aataactgca ccctgccttt tgtgtttttg taaactcctt gactcattct ttcatgtgtc 1860
accaagtact tttctcatga gagtcaacat atatttgttt ccaaatgtcc acaagtgtac 1920
aatagtgtaa aggtggtttt taaaaacata gccaggtgtg gtggcacgtg cctttagttc 1980
cagctactca ggaggctaag gcaggaggat tgcttgagcc caggctgtgt ggttcaccat 2040
aattgtgttt gtgactagct actgcactcc aacctgggca acatagtggg acttcatctc 2100
taaaacaaaa caaaacaaaa ttacacttaa gcactattgt ttaattttta attgtcagtt 2160
tatcattatt ttgggtaaga cattctgggg tttcttgaat cttgtccaaa aaccagttgt 2220
tttggaaaat tgctttaaat tgagcatatt tatgtatatt ggataaaaat gtactacaga 2280
gcaaatttca aatttttcat tatatcagtc tttttgaaag gatcaacttg gataaaataa 2340
atatataatg ctctatttgt tagagctcta ttaaaaagga aacagattcc atagatctaa 2400
gtcaatgttt ctccagaagc atgattttgt ctgccaaaag aaaatagctc tctttggcca 2460
aaatgcaaaa ttacattgct ataagaaaag ttacaaggga aagtttgaag acacaaatga 2520
tttaattttg gctcaaaaac tgaatttgct taacactgct acataatttg ggtgaagttt 2580
ccttctgccc gtttttcttg acctagataa atacactttg agaaatccag atctaataaa 2640
tgtcaaccaa cattgacatt gtaattgggt gattacaata aaaggtgagc agtttgttgt 2700
ttattaataa ttagcttttg caggtaatga aatagcaggg aagtaacatg ctgctttagg 2760
actaaaaaaa aaaaaaaaaa aaagacactg aagcttaata ccttaatgac ccagaagacc 2820
tagatttata aagccatata gaataaaaat gttaatttct tggtttcttc ccagaattat 2880
attttaatga ctccataaat acattccaaa tattcagaga ttcatgagaa aggattctta 2940
acaaatgttt aaaaataaca tttctttttg gtgttttaac acttaatttt ataaactgca 3000
gaacagcatc tctaaatggc tttttttttt tttttaaaga caaagtagta ttatgttgct 3060
tcagtttctt taaatacctc gtttcttttg agaccaaaaa ttcccatcaa ggaaataaat 3120
cagcctgatt ttaacatttt acatattaca ttgcctttaa gcactatgat tggatggctt 3180
tttttctatt tgtttaataa tccttggcta aattcacatg tatctaaagt aaaatagctg 3240
agttactgaa ttctataagg ggaagaaaaa gcatttattt tcacatgatt aactgaaatg 3300
gaaaagtaag acatttagca gaataattca tttaaaaata attttaaaaa atcagacata 3360
tttaaaaatc taggttgtct atccagtatg tgaatgctta attataattg ttacatgttg 3420
aatgggtatt aagagtaagt caccaggtac acaaaactgc catcatagca aaatgagaca 3480
gtgttgaaaa gacaaaatat tttctggaat gaaaatatat tcaagttgat ccatattcag 3540
atgttttctg tttaatactt cagattggtc ctttgtccac atttgtttaa aacttattgt 3600
aatgttaatt tatacttttg gattgtgcct ttgtcatgag ttgagaaaag tagtcctaca 3660
aataatgtga aagttgttac caccacagca tgaatgtata attgtattaa aattgatcat 3720
ccacagaaaa aaaaaaaaaa aa 3742

<210> SEQ ID NO 96
<211> LENGTH: 1580
<212> TYPE: DNA
<213> ORGANISM: Homo sapiens

<400> SEQUENCE: 96
caagggttcg tgccgggcag cgtctcccgg ggccaggtcg cctcctgccg ggacccgggc 60
gcgctgcagc cgcggagccg ggtgccccgc cctcttcccg ccggcggcgg agtcgctgcc 120

-continued

```
gctccgggtt cccgtccccg cctccgagac ccccgcgcgc ctcctccagg cgagctgcgg    180

ggcgggaagg gtccggccac cgtgggccgc tgccagccgc ggggctgccg agggccgcgg    240

gcacggggcg ctggctccgg gtctggcggc cgctgatggg agtcggagcc cgggcgggcg    300

agcggcggcg cggcggccac catggggaac aagcagacca tcttcaccga agagcagcta    360

gacaactacc aggactgcac cttcttcaat aagaaggaca tcctcaagct gcattcgcga    420

ttctatgagc tggcccccaa cctcgtccca atggactaca ggaagagccc catcgtccac    480

gtgcccatga gcctcatcat ccagatgcca gagctccggg agaatccctt caaagaaagg    540

atcgtggcgg cgttttccga ggatggtgag gggaacctca ctttcaacga ctttgtggac    600

atgttttccg tgctctgcga gtcggctccc cgagagctca aggcaaacta tgccttcaag    660

atctatgact tcaacactga caacttcatc tgcaaggagg acctggagct gacgctggcc    720

cggctcacta agtcagagct ggatgaggag gaggtggtgc ttgtgtgcga caaggtcatt    780

gaggaggctg acttggacgg tgacggcaag ctgggcttg  ctgacttcga ggacatgatt    840

gccaaggccc ctgacttcct cagcactttc cacatccgga tctgaggaca ctgccgaggc    900

tgtaggggcc tagaagtcca ccatcctgcc ctgcagtcac atgggtgtgg cctccaagct    960

ccccaggaaa gcagtggcag cctctggggt ttacaccaca aatatatcct gtggcccttt   1020

cagcaaaaaa aaaaccttaa ccaggaaggg ggcctgtgaa ggttaggacc cttcccacag   1080

ccccgctgtg gtccagcccc gggacccatg gcctctctcc aggccctccg caccccgccc   1140

catgccccag tcctttccta ctccagaaat gctccccacc cccccaaaga gggaaaagca   1200

gataacccaa caggaggtgg tggggtctga cgtgtccaag tgctggcaga caccctggtc   1260

acccaggaca gagcggaaaa aaaaaaaaga ggtcagggtt ttaacgagct atgcaatctt   1320

tttccaaaac ccaaggttgg gctgcttccc acccctgcct gttccccttc tcccggcctc   1380

cttcacaatg tgaagctgtg ggtgcagtgg gcccaagggc tcttgctcct gtctctgcct   1440

ctgggtcatg agtaccaccc tgcctgcctc cccaacaccg tggaatcctc actggtgtgc   1500

tgtccacaga tttgtgaact cctggtagta aaacactttt gcatcccaaa aaaaaaaaaa   1560

aaaaaaaaaa aaaaaaaaaa                                               1580
```

<210> SEQ ID NO 97
<211> LENGTH: 4079
<212> TYPE: DNA
<213> ORGANISM: Homo sapiens

<400> SEQUENCE: 97

```
ggagcggcgg gcgggcggga gggctggcgg ggcgaacgtc tgggagacgt ctgaaagacc     60

aacgagactt tggagaccag agacgcgcct ggggggacct ggggcttggg gcgtgcgaga    120

tttcccttgc attcgctggg agctcgcgca gggatcgtcc catggccggg gctcggagcc    180

gcgacccttg gggggcctcc gggatttgct accttttttgg ctccctgctc gtcgaactgc    240

tcttctcacg ggctgtcgcc ttcaatctgg acgtgatggg tgccttgcgc aaggagggcg    300

agccaggcag cctcttcggc ttctctgtgg ccctgcaccg gcagttgcag ccccgacccc    360

agagctggct gctggtgggt gctccccagg ccctggctct tcctgggcag caggcgaatc    420

gcactggagg cctcttcgct tgcccgttga gcctggagga gactgactgc tacagagtgg    480

acatcgacca gggagctgat atgcaaaagg aaagcaagga gaaccagtgg ttgggagtca    540

gtgttcggag ccaggggcct gggggcaaga ttgttacctg tgcacaccga tatgaggcaa    600

ggcagcgagt ggaccagatc ctggagacgc gggatatgat tggtcgctgc tttgtgctca    660
```

-continued

```
gccaggacct ggccatccgg gatgagttgg atggtgggga atggaagttc tgtgagggac    720
gcccccaagg ccatgaacaa tttgggttct gccagcaggg cacagctgcc gccttctccc    780
ctgatagcca ctacctcctc tttggggccc caggaaccta taattggaag ggggttgcttt   840
ttgtgaccaa cattgatagc tcagaccccg accagctggt gtataaaact ttggaccctg    900
ctgaccggct cccaggacca gccggagact tggccctcaa tagctactta ggcttctcta    960
ttgactcggg gaaaggtctg gtgcgtgcag aagagctgag ctttgtggct ggagcccccc   1020
gcgccaacca caagggtgct gtggttatcc tgcgcaagga cagcgccagt cgcctggtgc   1080
ccgaggttat gctgtctggg gagcgcctga cctccggctt tggctactca ctggctgtgg   1140
ctgacctcaa cagtgatggc tggccagacc tgatagtggg tgccccctac ttctttgagc   1200
gccaagaaga gctgggggggt gctgtgtatg tgtacttgaa ccaggggggt cactgggctg   1260
ggatctcccc tctccggctc tgcggctccc ctgactccat gttcgggatc agcctggctg   1320
tcctggggga cctcaaccaa gatggctttc cagatattgc agtgggtgcc ccctttgatg   1380
gtgatgggaa agtcttcatc taccatggga gcagcctggg ggttgtcgcc aaaccttcac   1440
aggtgctgga gggcgaggct gtgggcatca agagcttcgg ctactccctg tcaggcagct   1500
tggatatgga tgggaaccaa taccctgacc tgctggtggg ctccctggct gacaccgcag   1560
tgctcttcag ggccagaccc atcctccatg tctcccatga ggtctctatt gctccacgaa   1620
gcatcgacct ggagcagccc aactgtgctg gcggccactc ggtctgtgtg gacctaaggg   1680
tctgtttcag ctacattgca gtccccagca gctatagccc tactgtggcc ctggactatg   1740
tgttagatgc ggacacagac cggaggctcc ggggccaggt tccccgtgtg acgttcctga   1800
gccgtaacct ggaagaaccc aagcaccagg cctcgggcac cgtgtggctg aagcaccagc   1860
atgaccgagt ctgtggagac gccatgttcc agctccagga aaatgtcaaa gacaagcttc   1920
gggccattgt agtgaccttg tcctacagtc tccagacccc tcggctccgg cgacaggctc   1980
ctggccaggg gctgcctcca gtggccccca tcctcaatgc ccaccagccc agcacccagc   2040
gggcagagat ccacttcctg aagcaaggct gtggtgaaga caagatctgc cagagcaatc   2100
tgcagctggt ccacgcccgc ttctgtaccc gggtcagcga cacggaattc caacctctgc   2160
ccatggatgt ggatggaaca acagccctgt ttgcactgag tgggcagcca gtcattggcc   2220
tggagctgat ggtcaccaac ctgccatcgg acccagccca gccccaggct gatggggatg   2280
atgcccatga agcccagctc ctggtcatgc ttcctgactc actgcactac tcaggggtcc   2340
gggccctgga ccctgcggag aagccactct gcctgtccaa tgagaatgcc tcccatgttg   2400
agtgtgagct ggggaacccc atgaagagag gtgcccaggt caccttctac ctcatcctta   2460
gcacctccgg gatcagcatt gagaccacgg aactggaggt agagctgctg ttggccacga   2520
tcagtgagca ggagctgcat ccagtctctg cacgagcccg tgtcttcatt gagctgccac   2580
tgtccattgc aggaatggcc attccccagc aactcttctt ctctggtgtg gtgaggggcg   2640
agagagccat gcagtctgag cgggatgtgg gcagcaaggt caagtatgag gtcacggttt   2700
ccaaccaagg ccagtcgctc agaaccctgg gctctgcctt cctcaacatc atgtggcctc   2760
atgagattgc caatgggaag tggttgctgt acccaatgca ggttgagctg gagggcgggc   2820
aggggcctgg gcagaaaggg ctttgctctc ccaggcccaa catcctccac ctggatgtgg   2880
acagtaggga taggaggcgg cgggagctgg agccacctga gcagcaggag cctggtgagc   2940
ggcaggagcc cagcatgtcc tggtggccag tgtcctctgc tgagaagaag aaaaacatca   3000
ccctggactg cgcccggggc acggccaact gtgtggtgtt cagctgccca ctctacagct   3060
```

ttgaccgcgc ggctgtgctg catgtctggg gccgtctctg gaacagcacc tttctggagg 3120
agtactcagc tgtgaagtcc ctggaagtga ttgtccgggc caacatcaca gtgaagtcct 3180
ccataaagaa cttgatgctc cgagatgcct ccacagtgat cccagtgatg gtatacttgg 3240
accccatggc tgtggtggca gaaggagtgc cctggtgggt catcctcctg gctgtactgg 3300
ctgggctgct ggtgctagca ctgctggtgc tgctcctgtg gaagatggga ttcttcaaac 3360
gggcgaagca ccccgaggcc accgtgcccc agtaccatgc ggtgaagatt cctcgggaag 3420
accgacagca gttcaaggag gagaagacgg gcaccatcct gaggaacaac tggggcagcc 3480
cccggcggga gggcccggat gcacacccca tcctggctgc tgacgggcat cccgagctgg 3540
gccccgatgg gcatccaggg ccaggcaccg cctaggttcc catgtcccag cctggcctgt 3600
ggctgccctc catcccttcc ccagagatgg ctccttggga tgaagagggt agagtgggct 3660
gctggtgtcg catcaagatt tggcaggatc ggcttcctca ggggcacaga cctctcccac 3720
ccacaagaac tcctcccacc caacttcccc ttagagtgct gtgagatgag agtgggtaaa 3780
tcagggacag ggccatgggg tagggtgaga agggcagggg tgtcctgatg caaaggtggg 3840
gagaagggat cctaatccct tcctctccca ttcaccctgt gtaacaggac cccaaggacc 3900
tgcctccccg gaagtgcctt aacctagagg gtcggggagg aggttgtgtc actgactcag 3960
gctgctcctt ctctagtttc ccctctcatc tgaccttagt ttgctgccat cagtctagtg 4020
gtttcgtggt ttcgtctatt tattaaaaaa tatttgagaa caaaaaaaaa aaaaaaaaa 4079

<210> SEQ ID NO 98
<211> LENGTH: 2659
<212> TYPE: DNA
<213> ORGANISM: Homo sapiens

<400> SEQUENCE: 98
ggcaggtcta cactggagct tcctctccgc ctccttcgcc tagcctgcga gtgttctgag 60
ggaagcaagg aggcggcggc ggccgcagcg agtggcgagt agtggaaacg ttgcttctga 120
ggggagccca agatgaccgg ttctaacgag ttcaagctga accagccacc cgaggatggc 180
atctcctccg tgaagttcag ccccaacacc tcccagttcc tgcttgtctc ctcctgggac 240
acgtccgtgc gtctctacga tgtgccggcc aactccatgc ggctcaagta ccagcacacc 300
ggcgccgtcc tggactgcgc cttctacgat ccaacgcatg cctggagtgg aggactagat 360
catcaattga aaatgcatga tttgaacact gatcaagaaa atcttgttgg gacccatgat 420
gcccctatca gatgtgttga atactgtcca gaagtgaatg tgatggtcac tggaagttgg 480
gatcagacag ttaaactgtg ggatcccaga actccttgta atgctgggac cttctctcag 540
cctgaaaagg tatataccct ctcagtgtct ggagaccggc tgattgtggg aacagcaggc 600
cgcagagtgt tggtgtggga cttacggaac atgggttacg tgcagcagcg cagggagtcc 660
agcctgaaat accagactcg ctgcatacga gcgtttccaa acaagcaggg ttatgtatta 720
agctctattg aaggccgagt ggcagttgag tatttggacc caagccctga ggtacagaag 780
aagaagtatg ccttcaaatg tcacagacta aaagaaaata atattgagca gatttaccca 840
gtcaatgcca tttcttttca caatatccac aatacatttg ccacaggtgg ttctgatggc 900
tttgtaaata tttgggatcc atttaacaaa aagcgactgt gccaattcca tcggtacccc 960
acgagcatcg catcacttgc cttcagtaat gatgggacta cgcttgcaat agcgtcatca 1020
tatatgtatg aaatggatga cacagaacat cctgaagatg gtatcttcat tcgccaagtg 1080
acagatgcag aaacaaaacc caagtcacca tgtacttgac aagatttcat ttacttaagt 1140

```
gccatgttga tgataataaa acaattcgta ctccccaatg gtggatttat tactattaaa   1200
gaaaccaggg aaaatattaa ttttaatatt ataacaacct gaaaataatg gaaaagaggt   1260
ttttgaattt ttttttttaa ataaacacct tcttaagtgc atgagatggt ttgatggttt   1320
gctgcattaa aggtatttgg gcaaacaaaa ttggagggca agtgactgca gttttgagaa   1380
tcagttttga ccttgatgat tttttgtttc cactgtggaa ataaatgttt gtaaataagt   1440
gtaataaaaa tccctttgca ttctttctgg accttaaatg gtagaggaaa aggctcgtga   1500
gccatttgtt tcttttgctg gttatagttg ctaattctaa agctgcttca gactgcttca   1560
tgaggaggtt aatctacaat taaacaatat ttcctcttgg ccgtccatta ttttctgaag   1620
cagatggttc atcatttcct gggctgttaa acaaagcgag gttaaggtta gactcttggg   1680
aatcagctag ttttcaatct tattagggtg cagaaggaaa actaataaga aaacctccta   1740
atatcatttt gtgactgtaa acaattattt attagcaaac aattgatccc agaagggcaa   1800
attgtttgag tcagtaatga gctgagaaaa gacagagcat atctgtgtat ttggaaaaat   1860
aattgtaacg taattgcagt gcatttagac aggcatctat ttggacctgt ttctatctct   1920
aaatgaattt ttggaaacat taatgaggtt tacatatttc tctgacattt atatagttct   1980
tatgtccatt tcagttgacc agccgctggt gattaaagtt aaaaagaaaa aaattatagt   2040
gagaatgaga ttcatttcaa tgtaatgcac taaagcagaa cacgaactta gcttggccta   2100
ttctaggtag ttccaaatag tatttttgtt gtcaaacttt aaaatttata ttaatttgca   2160
aatgtatgtc tctgagtagg acttggacct ttcctgagat ttattttatc cgtgatgtat   2220
tttttttaat tcttttgata cagagaaggg tctttttttt tttaagtatt tcagtgaaaa   2280
cttggtgtaa gtctgaaccc atcttttgaa atgtattttc ttcattgcag gtccacctaa   2340
tcatcctgtg aaagtggttt ctctatggaa agctttgttt gcttcctaca aatacatgct   2400
tattccttaa gggatgtgtt agagttactg tggatttctc tgttttctgt cttacaagaa   2460
acttgtctat gtaccttaat actttgttta ggatgaggag tctttgtgtc cctgtacagt   2520
agtctgacgt atttcccctt ctgtccccta gtaagcccag ttgctgtatc tgaacagttt   2580
gagctctttt tgtaatatac tctaaacctg ttatttctgt gctaataaac gagatgcaga   2640
acccttgaaa aaaaaaaaa                                                2659
```

<210> SEQ ID NO 99
<211> LENGTH: 2061
<212> TYPE: DNA
<213> ORGANISM: Homo sapiens

<400> SEQUENCE: 99

```
atgaggcgga caggccccga ggaggaggcc tgcggcgtgt ggctggacgc ggcggcgctg     60
aagaggcgga aagtgcagac acatttaatc aaaccaggca ccaaaatgct aacactcctt    120
cctggagaaa gaaaggctaa tatttatttt actcaaagaa gagctccatc tacaggcatt    180
caccagagaa gcattgcttc cttcttcacc ttgcagccag gaaagacaaa tggcagtgac    240
cagaagagtg tttcatctca tacagaaagt cagatcaaca aagagtccaa gaaaaatgcg    300
acccagctag accatttgat cccaggctta gcacacgatt gcatggcatc ccctttagcc    360
acttcaacca ctgcggacat ccaggaagct ggactctctc ctcagtccct ccagacttct    420
ggccaccaca gaatgaaaac cccattttca actgagctat ctttgctcca gcctgatact    480
ccagactgtg ctggagatag tcataccccca ctggcttttt ccttcaccga ggacttggaa    540
agttcttgtt tgctagaccg aaaggaagaa aaaggggatt ctgccaggaa atgggaatgg    600
```

```
cttcatgagt ctaagaagaa ctatcagagt atggagaaac acaccaaact acctggggac    660
aaatgctgtc agcccttagg caagactaaa ttggaaagaa aggtgtctgc caaagaaaac    720
aggcaggccc ctgtcctcct tcaaacatac agggaatcct ggaatggaga aaacatagaa    780
tcggtgaaac aaagccgtag tccagtttct gtgttttcct gggacaatga aaagaatgac    840
aaggactcct ggagtcaact tttcactgaa gattctcaag gccagcgggt cattgcccac    900
aacactagag ctccttttca agatgtaacc aataactgga attgggactt agggccgttt    960
cctaacagtc cttgggctca gtgccaggag gatgggccaa ctcaaaatct gaagcctgat   1020
ttgctcttta cccaggactc tgaaggtaat caagttatca gacaccaatt ctaaatgttt   1080
gaagctttgt ttctaaaagt accttgaaat gatagagatg taggaaaata tagttgtggg   1140
tggagagagg agtgagtttg tttaggtggg aaggtggcat gggatgaagt tgtcattact   1200
gagcatcttc tctgtgtaaa taaagggcag taccattgtt aagacagtgg gattggcatc   1260
atggctttcc ctcaggaagg tggtggctgg taaattccct gaatgagtct atgatgaaca   1320
ctgaggcagc acagtgggta tttatctcta tgaaagtgcc ttttactcag cctgcacaga   1380
gccatctctt tgcccttcca gatgtctgac tgggaccttg cttatggatg tgtttttttt   1440
tttttttttt tgagatggag tctcgctctg tcgccaggct ggagtgcagt ggtgcgacct   1500
cagctcactg caccctctgt gtcccggatt caagcgattc tcctgcctca gcctcccgaa   1560
tagcagggac tacaggcatg cgccaccacg cccagctaat ttttttgga tttttagtag    1620
agacgaggtt tcaccatatt agccaggatg gtctccatct cctgacctcc tgatccgccc   1680
acctcagcct cccaaagtgc tgagattaca ggcataagcc accgcgccca gccagatgtg   1740
tgagctttta atctctggct gatcttaacc cacatcagcc taagcttggg atgattactc   1800
ttgacccttt tttttcagtg attagcaaat ctccccacaa cccaggtgtg gagagaagag   1860
aggtagaatg gtgctagttt cctattttat ttttgtggta actgtacagc actttaaagt   1920
tatatactct atgtttaaat atctccctta aaaagcctga gctgtacaac aatctggatg   1980
tgactctgtt accctttcc cacaagatag gagggaatcc cctttgtaaa actatgaatc    2040
caaataaatg tttacaaagt g                                              2061
```

<210> SEQ ID NO 100
<211> LENGTH: 5611
<212> TYPE: DNA
<213> ORGANISM: Homo sapiens

<400> SEQUENCE: 100

```
aatcgctcgg cctcccccat cccccggtaa cggtcgctgg tgagtttaaa tgagcagggg     60
ctggccgggc cggagccgct acaggggggg cctgaggcac tgcagaaagt gggcctgagc    120
ctcgaggatg acggtgctgc aggaacccgt ccaggctgct atatggcaag cactaaacca    180
ctatgcttac cgagatgcgg ttttcctcgc agaacgcctt tatgcagaag tacactcaga    240
agaagccttg tttttactgg caacctgtta ttaccgctca ggaaaggcat ataaagcata    300
tagactcttg aaaggacaca gttgtactac accgcaatgc aaatacctgc ttgcaaaatg    360
ttgtgttgat ctcagcaagc ttgcagaagg ggaacaaatc ttatctggtg gagtgtttaa    420
taagcagaaa agccatgatg atattgttac tgagtttggt gattcagctt gctttactct    480
ttcattgttg ggacatgtat attgcaagac agatcggctt gccaaaggat cagaatgtta    540
ccaaaagagc cttagtttaa atcctttcct ctggtctccc tttgaatcat tatgtgaaat    600
aggtgaaaag ccagatcctg accaaacatt taaattcaca tctttacaga actttagcaa    660
```

-continued

```
ctgtctgccc aactcttgca caacacaagt acctaatcat agtttatctc acagacagcc    720
tgagacagtt cttacggaaa caccccagga cacaattgaa ttaaacagat tgaatttaga    780
atcttccaat tcaaagtact ccttgaatac agattcctca gtgtcttata ttgattcagc    840
tgtaatttca cctgatactg tcccactggg aacaggaact tccatattat ctaaacaggt    900
tcaaaataaa ccaaaaactg gtcgaagttt attaggagga ccagcagctc ttagtccatt    960
aaccccaagt tttgggattt tgccattaga aaccccaagt cctggagatg gatcctattt   1020
acaaaactac actaatacac ctcctgtaat tgatgtgcca tccaccggag ccccttcaaa   1080
aaagactttt cgtgttttac agtctgttgc cagaatcggc caaactggaa caaagtctgt   1140
cttctcacag agtggaaata gccgagaggt aactccaatt cttgcacaaa cacaaagttc   1200
tggtccacaa acaagtacaa cacctcaggt attgagcccc actattacat ctcccccaaa   1260
cgcactgcct cgaagaagtt cacgactctt tactagtgac agctccacaa ccaaggagaa   1320
tagcaaaaaa ttaaaaatga agtttccacc taaaatccca aacagaaaaa caaaaagtaa   1380
aactaataaa ggaggaataa ctcaacctaa cataaatgat agcctggaaa ttacaaaatt   1440
ggactcttcc atcatttcag aagggaaaat atccacaatc acacctcaga ttcaggcctt   1500
taatctacaa aaagcagcag cagaaggttt gatgagcctt cttcgtgaaa tggggaaagg   1560
ttatttagct ttgtgttcat acaactgcaa agaagctata aatattttga gccatctacc   1620
ttctcaccac tacaatactg gttgggtact gtgccaaatt ggaagggcct attttgaact   1680
ttcagagtac atgcaagctg aaagaatatt ctcagaggtt agaaggattg agaattatag   1740
agttgaaggc atggagatct actctacaac actttggcat cttcaaaaag atgttgctct   1800
ttcagttctg tcaaaagact taacagacat ggataaaaat tcgccagagg cctggtgtgc   1860
tgcagggaac tgtttcagtc tgcaacggga acatgatatt gcaattaaat tcttccagag   1920
agctatccaa gttgatccaa attacgctta tgcctatact ctattagggc atgagtttgt   1980
cttaactgaa gaattggaca aagcattagc ttgttttcga aatgctatca gagtcaatcc   2040
tagacattat aatgcatggt atggtttagg aatgatttat tacaagcaag aaaaattcag   2100
ccttgcagaa atgcatttcc aaaaagcgct tgatatcaac cctcaaagtt cagttttact   2160
ttgccacatt ggagtagttc aacatgcact gaaaaaatca gagaaggctt tggataccct   2220
aaacaaagcc attgtcattg atcccaagaa ccctctatgc aaatttcaca gagcctcagt   2280
tttatttgca aatgaaaaat ataagtctgc tttacaagaa cttgaagaat tgaaacaaat   2340
tgttcccaaa gaatccctcg tttacttctt aataggaaag gtttacaaga agttaggtca   2400
aacgcacctc gccctgatga atttctcttg ggctatggat ttagatccta aaggagccaa   2460
taaccagatt aaagaggcaa ttgataagcg ttatcttcca gatgatgagg agccaataac   2520
ccaagaagaa cagatcatgg gaacagatga atcccaggag agcagcatga cagatgcgga   2580
tgacacacaa cttcatgcag ctgaaagtga tgaattttaa cttctggaaa tcagactttt   2640
acaactggat gtgtgactag tgctgacgtg tttcttgtcc ctctgtatac tgagtcttta   2700
ctcttgagct ggcggtgtca tcgtccgtca cttataccat gagtgtgcca ctttcattgg   2760
accctgactg tatacagaat gaaaggcagt gcaatattta gctgctaaca agactggctc   2820
ttttaccagt atgaatgaca atttatgggg ggtagggtgg ggaactttct tttctgtttt   2880
tctttaatct ccctttgttg gaaagtatca tgaaaggaag agttatgctt tatcttgaag   2940
gaaccattag atatggaaaa tagtgatgaa ccagagtttc ttggttgctt tttcaaaaat   3000
ttgtttttat ttggttctgt tcctgataaa cagagtaact gaccttcatt tctaggttct   3060
```

-continued

```
tcaagaatgg tgtttgcaag tgccagatgg aacaataaaa gacgttgcct ataacagtga   3120
cttgattgcc aaggaatgta aattacctta aacttgcagt atctcccata aacaaatgta   3180
atgggcatat tgggactcgt atgtaggaat caaatatccc tccatacagt gtactcttat   3240
tcttggcaag aatgctttaa tgtctaacca agaattttaa tttattcatc ttgcttcaaa   3300
gtgttgatca ttgttgtctt ggtattgcaa actttaaaat tgtttcttac catattgcct   3360
cttctctttg agctctgtgg gatcaccttt aacattcaga gatgatagag tggttcccca   3420
ctgagaagcc aaaacaaggc ccttaataac cccttaagtt caccatatga atcagaagga   3480
gaacactaaa gtggagagac ttttaagaga tcatgatagt gaaagcctta atataatcag   3540
aattgtacca taaccttgaa tctatatttg ttcaaaacat ccctttgact tttctaagtg   3600
tttgcttaag cagagtgtaa gaatgtgtgg ttacctttgg ttgagatcct ttccattctt   3660
tttgactctc tgcttcagat tttttcagta gtgtgagtca ccaaaacatt tactaagagt   3720
aattgggttt aggatgttgg aaatttttag cttgggggaa aaaacattct tatgaaggag   3780
ataggttctc ttctgagttt gtcataatat agattggtgt ctttggaaaa tggccacaat   3840
tttaagaatt caattatgca tataaaatga taattattgg aattccacag taacagattt   3900
aaacagtctt aaattgttta tctcctttac tgtaatgtat tgaaattttt agagaaattt   3960
tagttgttaa cattttatta agtgccagtg tcagaatata acaaattata gtttcttatg   4020
aatgacaggc ctacagttat tattctggat tatttgatgg aggacaaact tacctgtatt   4080
tgttagtcaa gctgtgaaaa taaggtggat tacaaaagat gtgaaaaaaa ttttagtctg   4140
tagactcagt aatttctat aatttactgt taatctcatt tgaacatgga ttaggtacaa    4200
tttataaatt aattcaagtc agggtcttta ggtatcaggt gccagagaga tatttaacag   4260
atttccctac ctaaatttat gtatatgtac tgtctaaaac aatacttttt taaaaaaaag   4320
gaacagttgg gagaaaataa atataatgaa aaattcccag aggctagcac ttggattcta   4380
acacgtatgc tattgtatta tccattagtt ctgtaatatt taattttaga ttcttttatt   4440
tttttaattg gcaaagcaca aggtgctgta taacagtgtc atttagagtt ttatagaaag   4500
cttcaacctg agttctgcgt tataaagcct ggagaaagct aagcttagaa cataacttgc   4560
tgaagtataa ttatcttttt gtagcaggaa tttatgtgcc agaggtgaga gtctttctgg   4620
tactgatttt ttgagaccaa ggataaaagg atcgttttgt aagacatgcc atggcaatgg   4680
ctggttgggg gacagtttcc gcccaagctt ggcctatttt atttttcctc atacctactt   4740
tcaaagtcat ttaggtattt gaagccttat ttcccacgta gtaacacttt ctggcttttg   4800
cagtttcttt ttttgtttgg ttttgttttt tgcatggaat ggggatcaaa caacccgaag   4860
aagaacacat tttgatcaag caaaatgttt gcttcaaatt tcagaagttt attttacaga   4920
aattaaatta agtagtttga catccttttc tctgtttcac acatatatta ggttggtgca   4980
taagtaattg tggtttttgc catgactttt atggcaaaac ctgcaattac ttttgcacca   5040
acttaataca tctatataca tatatatata cgcgcacaca cttgttcaga agttatgttg   5100
tggccttgga tttgtttttc cccttggaaa tggttcttaa ctctgggatt ttagaaggtt   5160
agaatatttt ttcaagagaa cagtggtact caaaagaatg aaaggtggtc cctacatttt   5220
ctgtattcat cacttaaaat ttttaatttt tccgagaact acaagtaaca tttgaaccat   5280
gctgctgttg taccttaaac aaaaactcag tgataaccag tatttagtct attaaaaatg   5340
ctctttttga agaaaaaagt ttggaagtct ctgattagcc agagtatagt atgagtcttc   5400
actgagaaat atggtgaccc attttctttg tgaaaacctg ggaaaatgca agtgtgggta   5460
```

-continued tgaagtgtgt gttctgtttg cattgaaaca atgtaatttt gtgtcttctt tttgctttaa 5520
ctgacttatt tcagaaattg tacagtgttg agggggaaag tcttttctgt taatatattt 5580
gcaattcatt aaaggatatg gaaaatccaa a 5611

<210> SEQ ID NO 101
<211> LENGTH: 1908
<212> TYPE: DNA
<213> ORGANISM: Homo sapiens

<400> SEQUENCE: 101
gcggaaggaa ccgccggggg ccatggacgg agcagtgatg gaagggccgc tttttttgca 60
gagtcagcgc tttgggacca agaggtggag gaagacctgg gccgtgctct acccggccag 120
tccccacggc gtagcgcggc tcgagttctt tgaccataag ggtcgagct ctgggggtgg 180 ccgagggagc tcgcgccgcc tggactgcaa agtgatccgt ctggctgagt gtgtgagtgt 240
ggcccccgtc accgtggaga cccccccctga gcccggcgcc actgccttcc gcctggacac 300
tgctcagcgc tcgcacctgc tggcggccga cgcgccgtcc agtgcagcct gggtgcagac 360
gctgtgccga aacgcctttc cgaaaggcag ctggactctg gcgcctaccg ataacccacc 420
taagctttct gccctggaga tgctggagaa ctccttgtac agccctacct gggaaggatc 480
ccaattctgg gtaacggtgc agaggactga ggccgccgag cgctgtggcc tgcatggctc 540
ctacgtgctg agggtggagg ctgaaaggct gactctcctg accgtggggg cccagagtca 600
gatactggag ccactcctgt cctggcccta cactctgttg cgtcgctatg gccgggacaa 660
ggtcatgttc tctttcgagg ccggccgccg ctgccccctca ggccctggaa ccttcacctt 720
ccagacggca cagggaaatg acatcttcca ggcagttgag actgccatcc accggcagaa 780
ggcccaggga aaggccggac aggggcacga tgttctcaga gctgactccc atgaagggga 840
ggtggcagag gggaagttgc cttccccacc tggcccccaa gagctcctcg acagtccccc 900
agccctgtat gctgagccct tagactccct gcgcattgct ccatgccctt cccaggactc 960
cctatactca gacccccttgg acagcacgtc tgctcaggca ggagagggag tacaacggaa 1020
gaaacctctc tattgggact tgtatgagca tgcgcagcag cagttgctga aggccaagct 1080
gacagacccc aaagaggatc ccatctatga tgaacctgag ggcctggccc cagtccctcc 1140
ccagggcctt tatgatctgc ctcgggagcc caaggatgca tggtggtgcc aagctcgggt 1200
gaaggaggag ggctatgagc tcccctacaa ccctgccact gatgactacg ctgtgccacc 1260
ccctcggagc acaaagcccc tccttgctcc caagccccag ggcccagcct tccctgaacc 1320
tggtactgca actggcagtg gcatcaaaag ccacaactca gccctgtaca gccaggtcca 1380
gaagagcggg gcctcaggga gctgggactg tgggctctct agagtaggga ctgacaagac 1440
tggggtcaag tcagagggct ctacctgaga aggacggcaa ggctgaggtg gctaaggggg 1500
accatgggga ggtggcacta gggatcaaag aagatggtta gaaccagcag aagccagagg 1560
gtgggagggg ccatgctgtg tgagaccagg ggaccagagg gatgggagag tcaagggaag 1620
gacaatccca ggaagtccta agaagtgggg cagatggcag ggctgaggat gggctctgca 1680
tcccccaaag ccatcccttc cctacttccc caaatgaagg gacggctgtg ggaccaggtc 1740
tgtggaaagt ggtgcatggt cagaatgggt gcagtttgag gggcctgtgt ggaggcctca 1800
gggagatgtt ggactgtgcc tggatcctta ctcctgcatt gttctttgcc agagacctat 1860
ttaaaaattt taaaattctc attaaagtca aaaaaaaaaa aaaaaaaa 1908

<210> SEQ ID NO 102

<211> LENGTH: 2018
<212> TYPE: DNA
<213> ORGANISM: Homo sapiens

<400> SEQUENCE: 102

```
gaagaggggg cgggaccaga gagtggatgg cagaggtggg ctgtagagcc aaagtggggt     60
gggagcgcga agatggcagc tgctgaggag gagccgaagc ccaaaaagct gaaggtggag    120
gcgccgcaag cgctgagaga aaatattctc tttggaatgg gaaatcctct gcttgacatc    180
tctgctgtag tggacaaaga tttccttgat aagtattctc tgaaaccaaa tgaccaaatc    240
ttggctgaag acaaacacaa ggaactgttt gatgaacttg tgaaaaaatt caaagtcgaa    300
tatcatgctg gtggctctac ccagaattca attaaagtgg ctcagtggat gattcaacag    360
ccacacaaag cagcaacatt ttttggatgc attgggatag ataaatttgg ggagatcctg    420
aagagaaaag ctgctgaagc ccatgtggat gctcattact acgagcagaa tgagcagcca    480
acaggaactt gtgctgcatg catcactggt gacaacaggt ccctcatagc taatcttgct    540
gctgccaatt gttataaaaa ggaaaaacat cttgatctgg agaaaaactg gatgttggta    600
gaaaaagcaa gagtttgtta tatagcaggc ttttttctta cagtttcccc agagtcagta    660
ttaaaggtgg ctcaccatgc ttctgaaaac aacaggattt tcactttgaa tctatctgca    720
ccgtttatta gccagttcta caaggaatca ttgatgaaag ttatgcctta tgttgatata    780
ctttttggaa atgagacaga agctgccact tttgctagag agcaaggctt tgagactaaa    840
gacattaaag agatagccaa aaagacacaa gccctgccaa agatgaactc aaagaggcag    900
cgaatcgtga tcttcaccca agggagagat gacactataa tggctacaga aagtgaagtc    960
actgcttttg ctgtcttgga tcaagaccag aaagaaatta ttgataccaa tggagctgga   1020
gatgcatttg ttggaggttt tctgtctcaa ctggtctctg acaagcctct gactgaatgt   1080
atccgtgctg gccactatgc agcaagcatc ataattagac ggactggctg cacctttcct   1140
gagaagccag acttccactg atggaagagc tgaaaacaca agcccaggag tgcagacact   1200
gccctaattg cttcctgaga attcccatat taataaagaa gaaaattatc tgccattttt   1260
tcctactata ataatgctga atcttaattt agagggtaca agggtatggt aatgcttgta   1320
gaatctttat tatctcaaca atctaaaaaa tgatgtttat ttccatagtt tgatagtgcc   1380
acttaaatgc caattaaaca agaatataac atttcaatag aaatttttat ttcattttca   1440
attactttgt aaattcgtgt gtatttagta cactgatttg tttttttaca tttctgcttt   1500
gaatgcagat gcaatttaat ataatagatt ttttaatgaa ttaatcttaa catagtaatc   1560
tttagctttt tatacaaata tatttaattt aggagtatat gtgtgtctat acacacacat   1620
acataaatat accacatata cacctgatag tcaaataagg tacagaaatt ttatcttgtc   1680
aattatgcca aataatctct ttaatgtgca ctcaaacatg taataaactt tggataatta   1740
aataatgtgc caaatttaag ttgtaccaca atattcaaat catagtctta tggaactctg   1800
taattggaca caaacaaaaa cttgtcatat aggaattttt ttctgtcttt tccctgtgta   1860
cagcaaactg aggaagaaag atcattattt aatactgggc cctgaaatga cacccaattt   1920
gttaatggaa ttatgaagaa cagcaatata atacactgaa gaataactta gtatcagaga   1980
ccaataaatc actttttaa ggatgacaaa atggtata                            2018
```

<210> SEQ ID NO 103
<211> LENGTH: 2174
<212> TYPE: DNA
<213> ORGANISM: Homo sapiens

<400> SEQUENCE: 103

```
ggagagaccg ggaacgggga gcgcggctgc cagcacccct gagccgccgc cggaccctcc     60
gtcgccccgg gccgcccccc gcccccctgcg gtccccggtg tgtccgtctc gggacggttc    120
gattccctcc agagccgggg aagggacggg gggggcccag aggaggggc ctcgggcgcc      180
ccgcctgcgc ctgctgcccc cgccccggcg gcgatgcgct cctggccgtg acccccgctg    240
ggggcggggg ccggggtcca tgcgcggagt ccccacccgg cccggcgcct gccgctgacg    300
gcggcggggg tggggggcg cgcgcctggc ctcctgccca cccctggcg tcaacaccgc      360
gggccgtcag gggctgcggc cccgggctgc gccctccccc gcggccaggc tctggaggga    420
cccaggagct gccgccggcc tcagcccatg gcccggaggt atgatgagct gccgcactac    480
ccaggcatcg tggatggccc cgcagccctg gctagcttcc cagagacagt gcccgcagta    540
ccagggccct atggcccgca ccggcctccc cagcccctgc ccccaggctt ggacagcgac    600
ggcctgaaga gggagaagga tgagatctat ggacacccgc tcttcccccct cttggccctg   660
gtctttgaga aatgtgaact ggctacatgc tctccccgtg acggggccgg agctgggctg    720
gggacacccc ctggaggtga cgtctgctcc tctgattcct tcaacgagga catcgctgcc    780
tttgccaagc aggttcgctc tgagaggccc ctcttctcct ccaacccaga actggacaat    840
ctgatgatcc aggccatcca ggtgctgcgg ttccacctgc tggagctgga gaaggtccac    900
gacctgtgcg acaacttctg tcaccgctac atcacctgcc tcaagggaaa gatgcccatc    960
gacctggtca tcgaggatcg ggacggcggc tgcagggagg acttcgagga ctacccagcc   1020
tcctgcccca gcctcccaga ccagaataat atgtggattc gagaccatga ggatagtggg   1080
tctgtacatt tggggacccc aggtccatcc agtgggggcc tggcctccca gagtggggac   1140
aactccagtg accaaggaga cgggctggac accagcgtgg cctctcccag ttctggtgga   1200
gaagatgagg acttggacca ggagcgacgg cgaaacaaga agaggggggat cttccccaag  1260
gtggccacca acatcatgcg agcctggttg ttccagcacc tctcgagacg ctcagaagcg   1320
ccggttctcc cagacgtctg cctgggcctg ggctccccat cccccggacc ccggtgggcc   1380
agaccttggg gttcagactg cggccggcca ggcaggcaga gtgactcttg ctggtggctg   1440
cagcacccgt accccctcgga ggagcagaag aaacagctgg cgcaggacac ggggctcacc  1500
atcctgcaag tcaacaactg gttcattaac gcccggagac gcatcgtgca acctatgatc   1560
gatcaatcca accgcacagg gcagggtgca gccttcagcc cagagggcca gcccatcggg   1620
ggctataccg agacgcagcc acacgtggcc gtccggcctc cgggatcagt ggggatgagt   1680
ttgaacttgg aaggagaatg gcattatcta tagaggctga tgcaggagag acccagcctc   1740
cggctgtgac cccccagcctc acacctgcct ctggttcccg cctggtcctc cagcttcagg  1800
accccacctc caaaggcccc tctgctcaat gcctacctcc ctagggccct gctgggacat   1860
gggggcctga gtgcccatcc aagggctctc aaggacaccg gcaaggcctc caggccctga   1920
gccccacttc tgccttcacc tctgcctggg acccgagctg ggctcctggg ccttggtccc   1980
cagaagatgg cggctagggc ctcgccgcca ggacagagaa gggacggggt ggctgggcag   2040
tcagggaagg agggtcgccc ggatccgaca ttttggagag attccttcac tctcctgtcc   2100
cccctacctc ccttctctaa tttcttcttt tttttaatga taaagtctta aaaacacgaa   2160
aaaaaaaaaa aaaa                                                      2174
```

<210> SEQ ID NO 104
<211> LENGTH: 2071
<212> TYPE: DNA

<213> ORGANISM: Homo sapiens

<400> SEQUENCE: 104
gtagaggctg aggcaccgcc cagagctcgc tgagacagag actgagaacg cccccggcca 60
gattcccccc ggagagaccc gggtagggac agggacagag agacgcctct aggggcagag 120
gccctgggag gcaaagaccc ccaggagaga tttacccacc ccagacggaa agcgcggctc 180
agagtcggac gaggggagac tgtcagagga caacgccccc taggtctcct gggagacccc 240
gaagcgaccc cgggggcagc ccgggccgtg tccgggcgag ggtgacctat ccttggttga 300
gagcgatggg gacacaagcc ctgcagggct tcctctttct cctcttcctc ccgctgctgc 360
agccgcgtgg ggcctcggct gggagcctgc acagtccagg cctgtccgaa tgcttccagg 420
tgaatggggc tgactaccgc ggccaccaga accgcactgg cccgcgcggg gcgggccgcc 480
cgtgcctctt ctgggaccag acgcagcaac acagctacag cagcgccagc gacccccacg 540
gccgctgggg gctgggcgcg cacaacttct gccgtaaccc agacggtgac gtgcagccgt 600
ggtgctacgt ggctgagaca gaggagggca tctactggcg ctactgcgac atcccctcct 660
gtcacatgcc aggctacctg ggatgctttg tggactcagg ggcaccccca gccctcagcg 720
gccccagcgg cacctccacg aagctcacgg tccaggtgtg cctacgcttc tgccgcatga 780
aggggtacca gctggcgggc gtggaggccg gttacgcctg cttctgtggc tctgaaagcg 840
acctggcccg gggacgcctg gcccccgcca ccgactgtga ccagatctgt ttcggccacc 900
ctggacagct gtgtggcggc gatgggcggc tgggcgtcta tgaagtgtcg gtgggctcct 960
gccaggggaa ctggacagcg cctcagggcg tcatctactc cccggacttc ccggacgagt 1020
acgggccgga ccggaactgc agctgggccc tgggcccgcc aggcgccgcg ctggagctca 1080
ccttccgcct cttcgagctg gccgacccgc gcgaccggct ggagctgcgc gacgcggctt 1140
cgggcagcct gctccgcgcc ttcgatggcg cccgcccacc gccgtccggg ccgctgcgcc 1200
tgggcactgc cgcgctgctg ctcaccttcc gaagcgacgc gcgcggccac gcgcaaggct 1260
tcgcgctcac ctaccgcggg ctgcaggacg ccgctgagga cccagaggcc cccgagggct 1320
cggcccagac cccgcggcg ccccctcgacg gggccaacgt gagctgcagc cccaggcctg 1380
gggctccgcc ggccgcgatt ggggcccggg tcttctcgac ggtgacggct gtctcggtgc 1440
tgctgctgct gctcctgggg ctgctgcgtc cgctgcgccg acggagctgt ctgctggctc 1500
cgggaaaagg gcccccggcg ctgggggctt ccaggggccc caggagaagc tgggctgtgt 1560
ggtaccaaca gccccgaggg gtggccttgc cctgctcccc cggggacccc caggctgagg 1620
gttctgccgc gggctaccgg cctctgagtg cctccagcca gagctccctg cgctcgctca 1680
tctccgctct ctgactctgg gccccgaggg tccgctgggc ccgccgccgg cgagatggac 1740
acctgagatg ctgtgctgcg ccctgcctcg gccttgcgcc tgtgtagggg cagctcggcc 1800
tctggtcgcc ttggggagac caaaagtcgg acaggaaaca tctggtgcta ttatctggga 1860
cttggcctga ccgtgggggt ccagatggtc caggccctct ccatggacct gtatgtgggg 1920
gtggtctctg gtttcggagg tctttgaacc cctctggggg tggtcctgga ctgccgtcct 1980
cagtgagagg tcacaggtca gcaaaaacag tcaaaaaacc cccacagatt ttgaataaag 2040
gatctacttt ggtaaaaaaa aaaaaaaaaa a 2071

<210> SEQ ID NO 105
<211> LENGTH: 5451
<212> TYPE: DNA
<213> ORGANISM: Homo sapiens

<400> SEQUENCE: 105
gcggccgcct ctgctgcggc cggaaacaat agtggaggaa cccgagccgc acggaacggc 60
ggtggtggcc cgcggagccg gacggggcac tatgaacgaa gaggagcagt ttgtaaacat 120
tgatttgaat gatgacaaca tttgcagtgt ttgtaaactg ggaacagaca aagaaacact 180
ctccttctgc cacatttgtt ttgagctaaa tattgagggg gtaccaaagt ctgatctctt 240
gcacaccaaa tcattaaggg gccataaaga ctgctttgaa aaataccatt taattgcaaa 300
ccagggttgt cctcgatcta agctttcaaa aagtacttat gaagaagtta aaaccatttt 360
gagtaagaag ataaactgga ttgtgcagta tgcacaaaat aaggatctgg attcagattc 420
tgaatgttct aaaaaccccc agcatcatct gtttaatttc aggcataagc cagaagaaaa 480
attactccca cagtttgact cccaagtacc aaaatattct gcaaaatgga tagatggaag 540
tgcaggtggc atctctaact gtacacaaag aattttggag cagagggaaa atacagactt 600
tggactttct atgttacaag attcaggtgc cactttatgt cgtaacagtg tattgtggcc 660
tcatagtcac aaccaggcac agaaaaaaga agagacaatc tctagtccag aggctaatgt 720
ccagacccag catccacatt acagcagaga ggaattgaat tcgatgactc ttggtgaggt 780
agagcaactg aatgcaaagc tcctacagca aatccaggaa gtttttgaag agttaactca 840
ccaagtgcaa gaaaaagatt ctttggcctc acagctccat gtccgccacg ttgccatcga 900
acagcttctg aagaactgtt ctaagttacc atgtctgcaa gtagggcgaa caggaatgaa 960
gtcgcaccta cccataaaca actgacctaa acagacttac ttcgtatgcc ctgcccttta 1020
ttggtctccc agacatgcaa actttgaaga agtttgaaga aagttgtggt ccgttttttt 1080
atggtcatta aatttgccaa acataaggca gtatttaaca tctttgtcaa ataaagcaga 1140
tcattatact ctagtcttct agggctaatc attttggctc atttggggac tctttttcc 1200
cagaattact aaacaaattt tatcacatgt gactacttaa atatactgtt acagtgtcat 1260
tttattaaac attttaattc acctgtcaaa acaacagatt aactccttag tgtaaactac 1320
tagagataat ttttaagagg gaaatggaat tcatatcacc tcttatttat tatgagcaat 1380
attttaatat aaaaatttta tatgtgaaaa tgctatttta ggtactttgc cattctcttt 1440
ataaatgtgt atttgagtgg ttctgtatat ttatttacat tatcatgtgt gaatatgttc 1500
acccatattt caggtcactg cattttattc tcttaataca atgttttcac aacggttacc 1560
ttgctttcca aagataaata tattttggat tagaaatctg agttgtttta atttctaata 1620
cctcttgtaa aagaagaatt aataactttt taaagcagta ttcaggtaaa tacaatacat 1680
tattttgttt tctaacaaaa gcagttctta gttcaggaag aaaagactaa tctggcttct 1740
atgtcaattt gtctccatag aaatgaaagc ctcctcttgc ttctttcatt attagcttca 1800
caccagtgac tgtgatgcat tagaatttgg acagagtaag tcaagcctca cttccaattc 1860
aaatataatg tctatcttca aattgagtgt gctgtgaaat tgttctgtct ttgaaaaaaa 1920
aaagtaagat tattttgtgt gccactttgg gtaaagtttc aagaatactt aaactgtcca 1980
aattgtatta tcaccatcat tgaacttagt gctcaaagaa agcattgtga ggtatttttc 2040
taaactttag actctataga gaaatatagg attgttctac agaagaaaag caaaactcct 2100
aattaaaaaa aaataaacct atgtattaag agaatgttct cgtaagttgc ctatgatgct 2160
tccaaagagt ttttatctaa cagattgtgc caaacagcta gataaatttt aataatgtat 2220
tacagtaaag gctataacca atgcagaatt aaaatgggct ctaaattctg tttttaactc 2280
atgtttagaa tgtacttatg aggtagatcc ttgcttgaaa gtatctgctg aaaagcccag 2340

-continued

```
taacgtggca gcttcatgca taaagatata aatgacattt gccttaaatt tggcagccta   2400
ccctggcttg ggtcagattt tgttgttgaa cacaagaaag tatttaagca aagaaacact   2460
tcagtttaat tgaaaacaac tttttgtaat gctgacgtgt taaattggcc tgagggtatt   2520
aattgatatc tgttgatttt gtttttcttt gaagtataac attacttttt ggagggaatt   2580
tttgaaagat gctttcgatt tctctcaatt ctttaagtca tgcaaaatga atttaaaatc   2640
cagggagtat ggatgcattg ccttagtttt gatgagcttt aaattaaatg tgtgcaatat   2700
caaaatattc aaacttacaa gctgggtaaa tacatttcct gattaatatc ttagtgctta   2760
attgttccca cattttcaaa tttgacttta ctctttttg gcgtaattca gtaagattgt    2820
taccagccag tgtgtttgca cacatttggg tttgtgttta gatgagttag ggacagtcat   2880
aaaagttggg gatatgttgc atttgatatc aatagtagca tatttccaga atatgagcca   2940
taagttgcag tcctgaatac aacagtgtta tccaaagaaa ggagttttct gacaaatata   3000
catagctttg ctaatgagta cggaacaagt ggatgaacgt gtgcatgtgc taaggtctta   3060
agtgggactc tgatttattc catttagata tttctactta agctctaaaa aggagaggtg   3120
ctcttaaaaa aaactttgtg gtgctggtac tcacactact ttatttggat gagttcctag   3180
taaaaaaaac tttttgttga agtattttgc acagcagttt atccaaatgt ttggtaaact   3240
tataatttag tcctatgtta gttttcttaa tcaaatatgc aattactgtg tatgcaaata   3300
taagtatcag gtacagagtt gagttctaac aagagaacat gaaatatcac aaatattgtt   3360
ttccacactt ggctattctc tacagttgtt agtaattttt gagaatgttt tgaagcatat   3420
ctcatgtact actgtttaaa aagtggcaaa acagactgcc agtcatccat tactaaattt   3480
tcagagctta tatgattaag gggagtgaga taagacaaat ctttttcacg ttcagtttta   3540
taatttgaca cgttaaattg agttttaaaa attagaaaag tgtttttgac cacacaggtt   3600
gttctcttta aagttcagcc ttataatgaa gctaaaaatc aattatgttt tactttgaga   3660
ttatcatctt atcctttgat cctcatatta atatctaaat tagtcttttt taaaaggcat   3720
gcacttgaga ctccagtaat agatgattca ggcagcagaa tagtgttttg ttgtgtcgtt   3780
gactatgcac aatggtggag caaagacaca ttcttagttt ttcaaaacac atgttcattt   3840
taccacaaag tgcccatttt tatatacatt taaggattat tttttcaatg tcaagttcat   3900
gttagtgatt tcagaaatat agtcaaaata tatagtcaaa tatatcttga caggcatctt   3960
gagatttggt ttttcatttt actatattta tgactgaaaa tggttttgtg ttttctttat   4020
gttgtttata tattttttac cttagtgttt acactggtaa ggcttgttag tccatttttg   4080
tagttttttt aaagtaagct tttagatcta tttgtgtttt aatgtttccc agtttgggtt   4140
ttgttttgtt ttggaagaat ctgctttcat tattaaatta taaaatgtaa atgctctaaa   4200
gtaggaattt ttaaagagta aattatttgt gtagcttatt aggaggttca ggttagtgac   4260
cataaagtgg gttacttgta catgaaaatt tgaaatggta ccatgtaaaa ttcttctatt   4320
gtcaactttt tctgatgtat gccagttcat ttactgacaa atgttgttac taagtgctta   4380
ttaagaagtg taatacgcta taaaaaagtt aatacttttt gttcagatgt aaggcaaaga   4440
taattgatgc cgtttcagtg tatgattgta tttttaactt ttacgttggt gggagtaact   4500
atttgaggaa atttgtggtg agaattagta agagataaaa cccccaacag tttattctta   4560
ccaagtaaag ttttgtggtc atggggcagg gaagagttta tttaccagaa tactagagcc   4620
ctcacacaaa ataaaggtaa cttggaggag ggctataatg cttgcatctc agtattttca   4680
tttcacttca tcctttcata attgccttga ttatggtgca gtctaaccta ttaagcaact   4740
```

-continued tctggctatg gtaacattga tatgaaccat attatatcaa gtctccaaaa catctagttt 4800
gttaacatac actttccctg ttctttttag tttgagtcca cattactaat acattttaat 4860
aatatttaat tatttcacaa ttttaagttt accaaagtaa acaaaaattc atgaagatga 4920
gtattgccct ctcccaaaaa aggtttaaag attagttgaa cttccctcaa ctacacctaa 4980
agcaaagggg aattttagta agtgtgtgta ccttgtttct ttcagacgca tctagaatgt 5040
ttttctttca ccgtacctcc aaaagaggca atttagaaag tattaagtag tgacttttgt 5100
tcagttccat tttgtgtgtg tgtgtgtgtg tgtgtgtgtg tgtgtgaacc ttgctttaaa 5160
acagtagcgt atactatggt cattgaactt aatctctctg gtgttagaaa tttactttac 5220
aaaattgtgt taagactttt ggaaaaagaa aatgaaactg ctgtggtaaa aaccaagttt 5280
gtttcaaaaa agtaggcaat tatttggctg ttatattttc tttgaaaact gcaataattt 5340
atatatttgt attgctctgc ttgggaactg tatatatgct tgtctactat ttttaatttt 5400
acaacaataa aataagtatt ttgttatctg ctaaaaaaaa aaaaaaaaaa a 5451

<210> SEQ ID NO 106
<211> LENGTH: 4234
<212> TYPE: DNA
<213> ORGANISM: Homo sapiens

<400> SEQUENCE: 106
gcggagcgcg aggaggtgga gccgcgggct gcgggctccg gcgcctgcgt ccgcccggcc 60
agcccggctc tgcgctgcga gaggccggac ggcagtcgcg gctgcgctcg ggagagagcg 120
cgggggacat ggggcgcggc ggcccgcctg ggcctcgcag gctccggagc cccgagggct 180
ccccgctagg ccccctcagt ggcccctcct tctcacctgg gtctcgggtc ccctagtgag 240
cgagagcgtc cccagccgcc tacctggcca tggccaacgg agtgatcccg ccgcccgggg 300
gcgcctcccc cctaccccag gtccgggtgc ccttggagga gccccctcta agtccagacg 360
tggaggagga ggacgatgac ttgggcaaga ccttggctgt gagcaggttt ggggacctca 420
tcagcaagcc cccggcctgg gaccccgaga agcccagccg cagctacagc gagcgggact 480
ttgagtttca ccggcacaca tcccaccaca cccaccaccc gctctcagcg cgcctgcctc 540
caccccacaa gctgcggcgg ctgccccccca cctctgcccg gcacaccagg agaaagagga 600
agaaggagaa aacctctgct cctccctccg aggggacccc tcccatccag gaggaggggg 660
gagctggagt ggatgaggaa gaggaggaag aggaggaaga ggaaggagaa tctgaggcag 720
aacctgtgga gccccccccc tcagggaccc cacagaaggc aaagttctcc attggaagtg 780
acgaggatga cagtccaggc ctccctggga gggctgctgt caccaagccc ctgccctcgg 840
tgggcccaca cactgacaag agcccccagc actccagcag ctcccccagc cccccgggccc 900 gggcctcccg actcgctggg gagaaaagcc ggccctggag cccatcggcc agttatgacc 960
tgcgggagcg actgtgccca ggcagtgccc tgggcaaccc aggtggtcca gagcagcagg 1020
tgcccacaga tgaggcggag gcccagatgc tgggttctgc agacctggac gacatgaaga 1080
gtcaccgact ggaggacaac cctggtgtgc ggcgacactt agtgaaaaag ccctcccgga 1140
cgcagggcgg gaggggcagt cccagcggcc tggcccccat ccttcgcagg aagaagaaga 1200
agaaaaagct ggaccggagg cctcatgagg tgttcgtgga gctgaacgag ctgatgctgg 1260
accgcagcca ggagccccac tggcgggaga cggcccgctg gatcaagttt gaggaggacg 1320
tggaggagga gacggagcgc tgggggaagc cccatgttgc ctcgctctcc ttccgtagcc 1380
ttctggagct caggaggacc atcgcccatg gagctgccct cctggacctg gagcaaacca 1440

-continued

```
ccctgccagg cattgcacac ctcgtggtgg agaccatgat tgtgtctgac cagatccggc   1500
cggaggacag ggccagcgtc ctacgtaccc tgctactgaa gcacagccat cccaacgatg   1560
acaaggacag tggcttcttt ccccgaaacc catcgagctc cagcatgaac tcggttctgg   1620
ggaatcatca cccaactccc agccatggcc ctgatggggc ggtgcctacc atggctgatg   1680
acctggggga gccagcccca ctctggccac atgaccctga cgccaaggag aagcccctcc   1740
acatgcctgg gggagatggt caccggggga aaagcctgaa gctgctggag aagatccctg   1800
aagatgctga ggccacggtt gtgcttgtgg gttgtgtgcc tttcttggag cagcctgcag   1860
cagccttcgt gcgtctgaat gaggctgtac tcctggagtc tgtgcttgag gtccctgtcc   1920
cggtccgctt cctcttcgtg atgctggggc ccagccacac cagcactgac tatcacgagc   1980
ttgggcgctc cattgccacc cttatgtctg acaagctgtt tcatgaggct gcctaccagg   2040
cagatgaccg gcaagacctc ctaagtgcca tcagcgagtt cctggatggc agcattgtga   2100
tccccccgtc cgaggtggag ggccgtgacc tgctgcgctc cgtggctgct ttccagcgag   2160
agctgcttag gaagcggcga gagcgtgaac agaccaaagt cgagatgacc acacggggtg   2220
gctacacggc cccctgggaaa gaactgtctt tggagttggg gggctctgag gcgacccctg   2280
aagatgaccc cttgctgcgg acgggctcgg tatttggggg gcttgtgcgg gatgtgaggc   2340
gccggtaccc gcactacccc agtgacctgc gagatgcgct gcactcccag tgtgtggccg   2400
ctgtgctctt catctacttc gcagccctca gccctgccat caccttcggg gggctgctgg   2460
gagagaagac cgaggggctg atgggcgtgt ccgagctgat cgtgtccacc gctgtgctcg   2520
gcgtcctctt ctctctgctg ggagctcagc cgctgcttgt ggttggcttc tctgggccgc   2580
tgcttgtgtt tgaggaagcc ttcttcaagt tctgccgagc ccaggacctg gagtacctca   2640
ctggccgggt gtgggttggt ctctggctgg tggtcttcgt ccttgccctg gtggccgccg   2700
aaggcagctt cctggtccgc tacatctcgc ctttcaccca ggagatcttt gcctttctca   2760
tctcactcat tttcatctac gagaccttct acaagctcta caaggtgttc acagagcacc   2820
cactgctgcc gttctacccc cctgaggggg ccctggaggg gtccctggat gctggtctgg   2880
agccaaatgg cagtgccctg ccccccaccg agggcccccc cagcccgagg aaccagccca   2940
atacggcact gctctcactc atcctcatgc tcgggacctt cttcatagcc ttcttcctgc   3000
gcaagttcag gaacagccgc ttcctggggg gcaaggctcg tcgcatcatc ggggactttg   3060
gcatccccat ctccatcctg gtgatggtcc tggtggatta ctccatcaca gacacctaca   3120
cgcagaagct gacagtgcct acagggctct cagtgacctc tcccgataag cgctcgtggt   3180
tcatcccacc cctgggcagt gcccgtcctt tcccgccgtg gatgatggtg gcagccgctg   3240
ttcccgccct cctcgtcctc atcctgatct tcatggagac acagatcacg gcgcttatcg   3300
tcagccagaa ggcgcggagg ctgctcaagg gctccggttt ccacctggac ctgctcctca   3360
ttggctccct gggggggctc tgtgggctgt ttgggttgcc ctggctcacg gctgccacgg   3420
tccgctccgt cacccatgtc aatgcgttga cagtgatgcg tactgccatc gcgcctggtg   3480
acaagcccca gatccaggag gtgcgggagc agcgggtcac tggtgtgctc atcgccagcc   3540
tcgtgggcct gtccatcgtc atgggggctg tgctgcgtcg gatcccattg gctgtgctct   3600
ttgggatctt cctgtacatg gggtcacgt ccctgtctgg tatccagctg tcccagcgtt   3660
tgttgctcat cctcatgccg gcaaaacacc atcctgagca gccctatgtg accaaggtga   3720
agacgtggcg gatgcatctg ttcacctgca tccagctggg ctgcatcgca ctgctctggg   3780
tggtcaagtc cacggcggcc tcactcgcct ttcccttcct gctgctgctc acggtgcctc   3840
```

-continued

```
tgaggcattg ccttctgccc cggctcttcc aggacaggga gctgcaggcg ctggactcgg   3900

aagatgctga accaaacttc gatgaggatg gccaggatga gtacaatgag ctgcacatgc   3960

cagtgtgacc cttgaagaca gtgcccctca gagaccccaa gaccttaggg attgacacct   4020

gggcctcagg cagagcccag ccctgggctg gggggctcct caggacccag agatgtgcct   4080

ggaaccactc ctgatgccat ggctagagtg gcccccctga cttctgcccg gggtgttgac   4140

ctcgcctcac ctttcacaga ccagaccggc acaggctttg agctcattat aaccacactc   4200

cttgtctcgt gtctgcctca aaaaaaaaaa aaaa                               4234
```

<210> SEQ ID NO 107
<211> LENGTH: 3014
<212> TYPE: DNA
<213> ORGANISM: Homo sapiens

<400> SEQUENCE: 107

```
caggtggccc tgaattcatt gcctgctcag caaaataaag gcccagtgtg gaagccggaa     60

cttgcatttg aagaaggatg ggaaggatgg gttgaggagg gcccatcccc agcagcccga    120

gagggaggag gccacggaga cttggagcat tcccgtttct tccagagcgc tgcgggataa    180

aggaggagcg tcctgcttcc cggctgccct gttgctgtcg gagtcacagg atggcggctg    240

tcatcctgcc ctcgactgct gctccgtctt ccctgttccc agcctctcag caaaaaggac    300

acacacaggg cggagagctg gttaatgagc tcctgacaag ctggctacgg ggcttggtaa    360

ccttcgagga tgtggccgtg gagttcaccc aggaggagtg ggcgttgctg gaccctgccc    420

aaaggacact gtacagggat gtgatgctgg agaactgcag gaacctggcc tcactagggt    480

gtcgtgttaa taaacccagt ctgatatccc agttggaaca agacaagaag gtggtgacag    540

aggaaagagg aattctacca agcacctgtc cagatttgga gactctactt aaagccaaat    600

ggttaactcc taagaagaat gttttcagaa aagaacagtc taaaggtgta aaaacggaaa    660

gaagtcatcg tggagtgaaa ctcaatgaat gtaatcagtg ttttaaagtc ttcagcacga    720

aatctaacct aactcagcac aagagaattc atactggaga aaaaccctat gactgtagtc    780

aatgtgggaa gtccttcagt agcagatctt accttactat tcataagaga atccataatg    840

gggagaaacc ctatgaatgc aatcactgtg ggaaagcatt tagtgatccc tcatccctta    900

gactgcattt gagaattcac actggagaaa aaccctatga atgtaaccag tgttttcacg    960

ttttccgcac cagttgtaac ctcaaaagcc acaagaggat tcacacgggg gagaatcacc   1020

atgaatgtaa tcagtgtgga aaagctttca gcacaaggtc ctctctcact gggcacaata   1080

gcattcatac aggggagaaa ccttatgaat gtcacgattg tgggaaaacc ttcaggaaga   1140

gctcctatct gacacagcac gtaagaactc atactggaga aaaaccctat gaatgtaacg   1200

agtgtgggaa atccttcagc agtagctttt ctcttactgt gcacaagaga atacataccg   1260

gagagaaacc ctacgagtgc agtgactgtg gaaaagcctt taataatctc tcagctgtga   1320

agaaacactt aagaactcac actggagaaa aaccctatga atgtaatcat tgtgggaaat   1380

ccttcacaag taactcctat ctttctgtgc acaagagaat acataataga tggatatgaa   1440

ttactgcagg aacttctgga ggaaagcact cattgatctt tcatccctaa gatagtttga   1500

gagagctcac actggatata taagttattt gttgcagcat aacaaatgat ccccgcaaat   1560

tttgtggctt caaacacgaa atgtttattc tctaacaatt tctacagatc aggaattcaa   1620

gaacagctta tctctgtagt tacactgcag gatctctcat gcctttactt acaatcaaga   1680

tgtcagccaa agctatagtc atctaacatc tttactgatg aacagtccac ttccaagatg   1740
```

```
acttattcac atgcctggaa agttgatgtt ggttgttgtc aggggacctt cagtcattac   1800
catgtaggcc tctttacaag gcccagctcc ttgacaattt ggcaataagt tctcgccaag   1860
gttagtgatc caagagagga ccaatacaga ggccaaaatg gcttttatgg cctatcctca   1920
ggaggactgc taagctttca cttatttcct attgtgttgg tctcacaaca caccaatcct   1980
gatacaatgt gagagactgc agaaggtatg aataccagga aacagataac tcagaagcat   2040
ctgggaaatt tgccatggaa ttaatgaaga aaagccctca gcacatcatc cttctactct   2100
aatcaatatg aaatagcatt cagtaactcc tattaattca ctctgaagag aaaccttttg   2160
aggacaatct gtatggtaaa gctctcagct cgaattctca ccttcatggg cccagaagat   2220
tatgtactga gagaatcctg aagaatggaa cagctgtaga aagccttcag tgctatcagc   2280
agggattcat gtgacagctc acactaaggg agaaaacctg tgaaggtctc agaaggcttc   2340
agtgacagtc atcccttaag acacactgga aatcacacaa tggaacaaca ctcagaaatg   2400
cggaataccc tgcagcaaaa gtgttcacat tactgagcaa actatagtgt ggtattctgc   2460
agtgactatg ggaaagcctt gaatgttcta tcggttttta agggacttga gaattaattc   2520
tggagagaat gccccattga acatcatcaa tattggagag ctttctgttt ttctacattt   2580
gttaggaaac ttgtgagcat tcacactaca gagaaacttg aaatataaag aagaagagaa   2640
agccttcagt gatgcctctg tgttagggaa aatatggaac ttctccctgg atgcaaaacc   2700
tatgagtata ttaatattgg aaaatttttc agtgattctt ctctttcttg tatatgagag   2760
aacttacatg gagaaacccc taggaatgta atcagtgtta ggatgcctca gcctgaactc   2820
ttcactgagt ggccacaatt ttcactggga acaaaaagta taatcactgt tttgagtgtg   2880
ggatatcctt tatcagtgtc tcatctgtag attggactgc tggctcatta atttttttag   2940
tcttttttc ttttaatata aacatttgtg tatagctgtt ccctaaaata aacattaaca   3000
tatttcataa tttt                                                     3014
```

<210> SEQ ID NO 108
<211> LENGTH: 2931
<212> TYPE: DNA
<213> ORGANISM: Homo sapiens

<400> SEQUENCE: 108

```
gcggccgcgg cggggcggcg cgggaaccgg gccccggggg gagtcggccg ggctgctgct     60
gctgctgctc caggtgctgc cgcccggggc tacggcaggg ccgggacgcc ggggcacgcg    120
gggcgctggc gctggcggcg gcggcgtctg ctggcccggc gcggccccag cctttccccg    180
ggacgcgcgg ctgctgctgc tcctgccgcc gctgccgcca ctgtcgccgc cgccgccgag    240
ctccgcgccc gcagcctccg cctcccggat ggacgctctg ccccgcagcg ggctgaacct    300
gaaggaggag ccgctgctgc ccgccggcct gggctcagtg cgctcctgga tgcagggcgc    360
gggcatcctg gacgccagca ccgcggcgca gagtggcgtg ggtctggcac gagcacattt    420
tgagaagcag cctccctcca acctcaggaa atccaacttc ttccacttcg tgctggccat    480
gtacgaccgg caggggcagc ccgtggaggt ggagcgcaca gccttcatcg acttcgtgga    540
aaaggaccga gagcccgggg cggaaaagac taacaatggg atccattacc gcctccggct    600
ggtgtataac aatggactgc ggacagagca agacctctac gtgcgtctca tcgactccat    660
gtccaaacag gccatcatct atgaggggca ggacaagaac cccgaaatgt gccgagtgct    720
gctcacccat gagatcatgt gcagccggtg ctgtgaccgg aagagctgtg gcaaccggaa    780
tgagacgccc tcagaccccg tcatcattga caggttcttc ctcaagttct tcctcaaatg    840
```

-continued

```
caaccagaac tgcctgaaga atgcggggaa tcccagagac atgcgccgct tccaggtggt    900
ggtgtccacg acggtgagcg tggacggaca cgtgctggcc gtgtccgaca acatgtttgt    960
gcacaacaac tccaagcatg gccgcagggc gcgccgcctg gacccctccg aagctgccac   1020
cccctgcatc aaggccatca gccccgggga gggctggacc acgggcggcg ccaccgtcat   1080
tgtcatcggc gacaacttct tcgacgggtt gcaggtcgtg ttcggaaacg tgctcgtgtg   1140
gagcgagctc atcacgcccc acgccatccg ggtgcagacg cccccgcggc acatccccgg   1200
ggtggtggag gtgaccctct cctacaagtc caagcagttt tgcaagggat gccccggccg   1260
ctttgtctac acagctctga acgagcccac cattgactac ggattccaga ggctacagaa   1320
agtcattccc agacaccccg gagaccccga gaggctgccc aaggaagtgc tgctgaagcg   1380
ggcggccgac ttggcagaag ccctgtacgg agtgcccggc agtaaccagg agctgctcct   1440
gaagcgcgcg gcggacgtgg ccgaggctct gtacagcacc ccccgcgcac ccgggccgct   1500
cgcacccctg gccccgagcc acccacaccc cgccgtcgtg ggcatcaacg ccttcagcag   1560
cccgctggcc atcgccgtcg gggacgccac cccggggccc gagccgggct acgcgcgcag   1620
ctgcagcagc gcgtcccccc gcgggttcgc gcccagcccc ggctcgcagc agagcggcta   1680
cggcggcggc ctcggagctg gcctgggcgg ctacggcgcg ccgggcgtgg ccggcctcgg   1740
cgtgcctggg tcccccagct tcctcaatgg ctccaccgcc acctcgccct tcgccatcat   1800
gccctctagc cccccgctgg cggctgcctc ctccatgtcc ctcccggccg ctgcccccac   1860
caccagcgtg ttctccttct cgcctgtcaa catgatctcc gccgtcaaac agaggagcgc   1920
cttcgccccc gtgctgcgcc ccccaagctc ccccaccccag gcctgcccca gagcccacgg   1980
agaggggctt ccagaccagt cttttgagga ttctgacaag tttcactctc cagcccgggg   2040
gcttcagggc ctggcatact cctaattacg gtctgcagct gttcccatgg agcccggact   2100
ggaggtccct ctgggattca cagccacacc ccggatggtg gcacagacag atgcagggcc   2160
agggccatgg gcggacctca acccgtgagc tgaacgggga gaggccttca ccccatgctc   2220
aagcctcccc gctagcagcc ccacaggctt ctctcgcctc cctgtcttgg ggtagtcaga   2280
agccccagca ctgtgcagat gctcttggca ggacagcatc gcagggaggt gctgggattc   2340
tgggcctcac tgtctgggtc ttggttcctc tgaaagagat ggatcttgtg cagaccaggg   2400
ttgttgagtg aggggagcgt gggatgggga ccgtgggaaa gaggacagct cagggagaag   2460
tgacctggaa aggtcctgtt tgcatctgac ccatctcaac tggcccagca tcccaacttc   2520
tctgcagcga aagggtggcg ccccgcagcc tcgggaggcc tgcccaggct cccgtggagc   2580
ttccaacagc tgcttggccc cgcagctgcc cccacttcct ttgagacctg cactctcatg   2640
cttgccgcat catgcctccc tgtgggggct ttgggcatgg aggaggcaga agaggggggtg   2700
ccaggcctcc tgtatttggg gtcttccccc agtggatgtc tcatggactc tggccccaca   2760
cactcacaat gactctggct ggccccacgc agcgggccca gccgccccccc aggtggcctc   2820
acattctgct ctgctaagtt tggagaaaac agaacaataa accagatgca ggtggtgccc   2880
gcccggcctc tcacctgcct ccttggtgtg aaaaaaaaaa aaaaaaaaaa a            2931
```

<210> SEQ ID NO 109
<211> LENGTH: 3533
<212> TYPE: DNA
<213> ORGANISM: Homo sapiens

<400> SEQUENCE: 109

```
gggtctcgcg gtttgggagc gctactcgcc aggtggactc ggagtccgcg agcgtcgtcg     60
```

-continued

```
gcaagcggcc gcctttccac ggtaaccgcg cgccggcggg gagggcgtgg cgcggagccg    120
acgggaacgt ccgcgctgcg gagcagggca gggaagccgg gaggcgggcc cggcccgagc    180
ttgtccttgt cgcgcaggta ctccgagcac tatgtcgtcc ccggcgtcga ccccgagccg    240
ccgcggcagc cggcgtggaa gggccacccc cgcccagacg cctcggagtg aggatgccag    300
gtcatctccc tctcagagac gtagaggcga ggattccacc tccacggggg agttgcagcc    360
gatgccaacc tcgcctggag tggacctgca gagccctgct gcgcaggacg tgctgttttc    420
cagccctccc caaatgcatt cttcagctat ccctcttgac tttgatgtta gttcaccact    480
gacatacggc actcccagct ctcgggtaga gggaacccca agaagtggtg ttaggggcac    540
acctgtgaga cagaggcctg acctgggctc tgcacagaag ggcctgcaag tggatctgca    600
gtctgacggg gcagcagcag aagatatagt ggcaagtgag cagtctctag gccaaaaact    660
tgtgatctgg ggaacagatg taaatgtggc agcatgcaaa gaaaactttc agagatttct    720
tcagcgtttt attgaccctc tggctaaaga agaagaaaat gttggcatag atattactga    780
acctctatac atgcaacgac ttggggagat taatgttatt ggtgagccat ttttaaatgt    840
gaactgtgaa cacatcaaat catttgacaa aaatttgtac agacaactca tctcttaccc    900
acaggaagtt attccaactt ttgacatggc tgtcaatgaa atcttctttg accgttaccc    960
tgactcaatc ttagaacatc agattcaagt aagaccattc aacgcattga agactaagaa   1020
tatgagaaac ctgaatccag aagacattga ccagctcatc accatcagcg gcatggtgat   1080
caggacatcc cagctgattc ccgagatgca ggaggccttc ttccagtgcc aagtgtgtgc   1140
ccacacgacc cgggtggaga tggaccgcgg ccgcattgca gagcccagtg tgtgcgggcg   1200
ctgccacacc acccacagca tggcactcat ccacaaccgc tccctcttct ctgacaagca   1260
gatgatcaag cttcaggagt ctccggaaga catgcctgca gggcagacac cacacacagt   1320
tatcctgttt gctcacaatg atctcgttga caaggtccag cctggggaca gagtgaatgt   1380
tacaggcatc tatcgagctg tgcctattcg agtcaatcca agagtgagta atgtgaagtc   1440
tgtctacaaa acccacattg atgtcattca ttatcggaaa acggatgcaa aacgtctgca   1500
tggccttgat gaagaagcag aacagaaact tttttcagag aaacgtgtgg aattgcttaa   1560
ggaactttcc aggaaaccag acatttatga gaggcttgct tcagccttgg ctccaagcat   1620
ttatgaacat gaagatataa agaagggaat tttgcttcag ctctttggcg ggacaaggaa   1680
ggattttagt cacactggaa ggggcaaatt tcgggctgag atcaacatct tgctgtgtgg   1740
cgaccctggt accagcaagt cccagctgct gcagtacgtg tacaacctcg tccccagggg   1800
ccagtacacg tctgggaagg gctccagtgc agttggcctc actgcgtacg taatgaaaga   1860
ccctgagaca aggcagctgg tcctgcagac aggtgctctt gtcctgagtg acaacggcat   1920
ctgctgtatc gatgagttcg acaagatgaa tgaaagtaca agatcggtat tgcatgaagt   1980
catggaacag cagactctgt ccattgcaaa ggctgggatc atctgtcagc tcaatgcgcg   2040
cacctctgtc ctggcagcag caaatcccat tgagtctcag tggaatccta aaaaaacaac   2100
cattgaaaac atccagctgc ctcatacttt attatcaagg tttgatttga tcttcctctt   2160
gctggaccct caggacgaag cctatgacag gcgtctggct caccacctgg tcgcactgta   2220
ctaccagagc gaggagcagg cagaggagga gctcctggac atggcggtgc taaaggacta   2280
cattgcctac gcgcacagca ccatcatgcc gcggctaagt gaggaagcca gccaggctct   2340
catcgaggct tatgtagaca tgaggaagat tggcagtagc cggggaatgg tttctgcata   2400
ccctcgacag ctagagtcat taatccgctt agcagaagcc catgctaaag taagattgtc   2460
```

taacaaagtt gaagccattg atgtggaaga ggccaaacgc ctccatcggg aagctctgaa 2520
gcagtctgca actgatcccc ggactggcat cgtggacata tctattctta ctacggggat 2580
gagtgccacc tctcgtaaac ggaaagaaga attagctgaa gcattgaaaa agcttatttt 2640
atctaagggc aaaacaccag ctctaaaata ccagcaactt tttgaagata ttcggggaca 2700
atctgacata gcaattacta aagatatgtt tgaagaagca ctgcgtgccc tggcagatga 2760
tgatttcctg acagtgactg ggaagaccgt gcgcttgctc tgaagccttg tgagcaagga 2820
aggctccctg catgtcctgc ttgctgcacg ccacatgggt gtggtctgca tctcagttgg 2880
ccgccatcag tgtaaataga gcttaaagtc atggtttggc tgcataaaaa ttttctaact 2940
tgggttcaat atttgtagtg aagtatctgt tttcattttt ttcacgttat aaataaaaat 3000
actatgctgg ccgggcgcgg tggctcacac ctgtaatccc agcactttgg gaggccaatg 3060
tgggtggatc atgaggtcag gagttcaaga ccagcctagc caagatggtg aaaccccgtc 3120
tctagtaaag ataacaaaaa attagctggg cttgatggca tgcgcctgta atcccagcta 3180
ctcgggaggt tgaggcagga gaatcgctta aacccaggcg gcagaggttg cagtgagcca 3240
agatcgcgcc actgcactcc agcctcagca atagagtgag actgtctcaa aaaaaaaaaa 3300
aaaaaaaaaa cctgccaatt ttcaaacata ccgtagagat tattttcagg tgccatttta 3360
tagtatagca gcagggcttt tactctgtgt atgcacagat gcagtctggg gcatggtttg 3420
tgtgctggac tttctcatgg ccatcatcag tatgcttatg gatttgatga caggcatagc 3480
ctgggcatat cacctcattg gtaaagggct agagcctttc ttttttatgg cac 3533

<210> SEQ ID NO 110
<211> LENGTH: 5916
<212> TYPE: DNA
<213> ORGANISM: Homo sapiens

<400> SEQUENCE: 110
gcccctccct ccgcccgccc gccggcccgc ccgtcagtct ggcaggcagg caggcaatcg 60
gtccgagtgg ctgtcggctc ttcagctctc ccgctcggcg tcttccttcc tcctcccggt 120
cagcgtcggc ggctgcaccg gcggcggcgc agtccctgcg ggaggggcga caagagctga 180
gcggcggccg ccgagcgtcg agctcagcgc ggcggaggcg gcggcggccc ggcagccaac 240
atggcggcgg cggcggcggc gggcgcgggc ccggagatgg tccgcgggca ggtgttcgac 300
gtggggccgc gctacaccaa cctctcgtac atcggcgagg gcgcctacgg catggtgtgc 360
tctgcttatg ataatgtcaa caaagttcga gtagctatca agaaaatcag cccctttgag 420
caccagacct actgccagag aaccctgagg gagataaaaa tcttactgcg cttcagacat 480
gagaacatca ttggaatcaa tgacattatt cgagcaccaa ccatcgagca aatgaaagat 540
gtatatatag tacaggacct catggaaaca gatctttaca agctcttgaa gacacaacac 600
ctcagcaatg accatatctg ctatttttctc taccagatcc tcagagggtt aaaatatatc 660
cattcagcta acgttctgca ccgtgacctc aagccttcca acctgctgct caacaccacc 720
tgtgatctca agatctgtga ctttggcctg gcccgtgttg cagatccaga ccatgatcac 780
acagggttcc tgacagaata tgtggccaca cgttggtaca gggctccaga aattatgttg 840
aattccaagg gctacaccaa gtccattgat atttggtctg taggctgcat tctggcagaa 900
atgctttcta acaggcccat ctttccaggg aagcattatc ttgaccagct gaaccacatt 960
ttgggtattc ttggatcccc atcacaagaa gacctgaatt gtataataaa tttaaaagct 1020
aggaactatt tgctttctct tccacacaaa aataaggtgc catggaacag gctgttccca 1080

-continued

```
aatgctgact ccaaagctct ggacttattg gacaaaatgt tgacattcaa cccacacaag   1140
aggattgaag tagaacaggc tctggcccac ccatatctgg agcagtatta cgacccgagt   1200
gacgagccca tcgccgaagc accattcaag ttcgacatgg aattggatga cttgcctaag   1260
gaaaagctca aagaactaat tttgaagag actgctagat tccagccagg atacagatct    1320
taaatttgtc aggacaaggg ctcagaggac tggacgtgct cagacatcgg tgttcttctt   1380
cccagttctt gacccctggt cctgtctcca gcccgtcttg gcttatccac tttgactcct   1440
ttgagccgtt tggaggggcg gtttctggta gttgtggctt ttatgctttc aaagaatttc   1500
ttcagtccag agaattcctc ctggcagccc tgtgtgtgtc acccattggt gacctgcggc   1560
agtatgtact tcagtgcacc tactgcttac tgttgcttta gtcactaatt gctttctggt   1620
ttgaaagatg cagtggttcc tccctctcct gaatcctttt ctacatgatg ccctgctgac   1680
catgcagccg caccagagag agattcttcc ccaattggct ctagtcactg gcatctcact   1740
ttatgatagg gaaggctact acctagggca ctttaagtca gtgacagccc cttatttgca   1800
cttcaccttt tgaccataac tgtttcccca gagcaggagc ttgtggaaat accttggctg   1860
atgttgcagc ctgcagcaag tgcttccgtc tccggaatcc ttggggagca cttgtccacg   1920
tcttttctca tatcatggta gtcactaaca tatataaggt atgtgctatt ggcccagctt   1980
ttagaaaatg cagtcatttt tctaaataaa aaggaagtac tgcacccagc agtgtcactc   2040
tgtagttact gtggtcactt gtaccatata gaggtgtaac acttgtcaag aagcgttatg   2100
tgcagtactt aatgtttgta agacttacaa aaaaagattt aaagtggcag cttcactcga   2160
catttggtga gagaagtaca aaggttgcag tgctgagctg tgggcggttt ctggggatgt   2220
cccagggtgg aactccacat gctggtgcat atacgccctt gagctacttc aaatgtgggt   2280
gtttcagtaa ccacgttcca tgcctgagga tttagcagag aggaacactg cgtctttaaa   2340
tgagaaagta tacaattctt tttccttcta cagcatgtca gcatctcaag ttcatttttc   2400
aacctacagt ataacaattt gtaataaagc ctccaggagc tcatgacgtg aagcactgtt   2460
ctgtcctcaa gtactcaaat atttctgata ctgctgagtc agactgtcag aaaaagctag   2520
cactaactcg tgtttggagc tctatccata ttttactgat ctctttaagt atttgttcct   2580
gccactgtgt actgtggagt tgactcggtg ttctgtccca gtgcggtgcc tcctcttgac   2640
ttccccactg ctctctgtgg tgagaaattt gccttgttca ataattactg taccctcgca   2700
tgactgttac agctttctgt gcagagatga ctgtccaagt gccacatgcc tacgattgaa   2760
atgaaaactc tattgttacc tctgagttgt gttccacgga aaatgctatc cagcagatca   2820
tttaggaaaa ataattctat ttttagcttt tcatttctca gctgtccttt tttcttgttt   2880
gatttttgac agcaatggag aatgggttat ataaagactg cctgctaata tgaacagaaa   2940
tgcatttgta attcatgaaa ataaatgtac atcttctatc ttcacattca tgttaagatt   3000
cagtgttgct ttcctctgga tcagcgtgtc tgaatggaca gtcaggttca ggttgtgctg   3060
aacacagaaa tgctcacagg cctcactttg ccgcccaggc actggcccag cacttggatt   3120
tacataagat gagttagaaa ggtacttctg tagggtcctt tttacctctg ctcggcagag   3180
aatcgatgct gtcatgttcc tttattcaca atcttaggtc tcaaatattc tgtcaaaccc   3240
taacaaagaa gccccgacat ctcaggttgg attccctggt tctctctaaa gagggcctgc   3300
ccttgtgccc cagaggtgct gctgggcaca gccaagagtt gggaagggcc gccccacagt   3360
acgcagtcct caccacccag cccagggtgc tcacgctcac cactcctgtg gctgaggaag   3420
gatagctggc tcatcctcgg aaaacagacc cacatctcta ttcttgccct gaaatacgcg   3480
```

-continued

```
cttttcactt gcgtgctcag agctgccgtc tgaaggtcca cacagcattg acgggacaca   3540
gaaatgtgac tgttaccgga taacactgat tagtcagttt tcatttataa aaaagcattg   3600
acagttttat tactcttgtt tctttttaaa tggaaagtta ctattataag gttaatttgg   3660
agtcctcttc taaatagaaa accatatcct tggctactaa catctggaga ctgtgagctc   3720
cttcccattc cccttcctgg tactgtggag tcagattggc atgaaaccac taacttcatt   3780
ctagaatcat tgtagccata agttgtgtgc tttttattaa tcatgccaaa cataatgtaa   3840
ctgggcagag aatggtccta accaaggtac ctatgaaaag cgctagctat catgtgtagt   3900
agatgcatca ttttggctct tcttacattt gtaaaaatgt acagattagg tcatcttaat   3960
tcatattagt gacacggaac agcacctcca ctatttgtat gttcaaataa gctttcagac   4020
taatagcttt tttggtgtct aaaatgtaag caaaaaattc ctgctgaaac attccagtcc   4080
tttcatttag tataaaagaa atactgaaca agccagtggg atggaattga aagaactaat   4140
catgaggact ctgtcctgac acaggtcctc aaagctagca gagatacgca gacattgtgg   4200
catctgggta gaagaatact gtattgtgtg tgcagtgcac agtgtgtggt gtgtgcacac   4260
tcattccttc tgctcttggg cacaggcagt gggtgtagag gtaaccagta gctttgagaa   4320
gctacatgta gctcaccagt ggttttctct aaggaatcac aaaagtaaac tacccaacca   4380
catgccacgt aatatttcag ccattcagag gaaactgttt tctctttatt tgcttatatg   4440
ttaatatggt ttttaaattg gtaactttta tatagtatgg taacagtatg ttaatacaca   4500
catacatacg cacacatgct ttgggtcctt ccataatact tttatatttg taaatcaatg   4560
ttttggagca atcccaagtt taagggaaat atttttgtaa atgtaatggt tttgaaaatc   4620
tgagcaatcc ttttgcttat acatttttaa agcatttgtg ctttaaaatt gttatgctgg   4680
tgtttgaaac atgatactcc tgtggtgcag atgagaagct ataacagtga atatgtggtt   4740
tctcttacgt catccacctt gacatgatgg gtcagaaaca aatggaaatc cagagcaagt   4800
cctccagggt tgcaccaggt ttacctaaag cttgttgcct tttcttgtgc tgtttatgcg   4860
tgtagagcac tcaagaaagt tctgaaactg ctttgtatct gctttgtact gttggtgcct   4920
tcttggtatt gtaccccaaa attctgcata gattatttag tataatggta agttaaaaaa   4980
tgttaaagga agattttatt aagaatctga atgtttattc attatattgt tacaatttaa   5040
cattaacatt tatttgtggt atttgtgatt tggttaatct gtataaaaat tgtaagtaga   5100
aaggtttata tttcatctta attcttttga tgttgtaaac gtacttttta aaagatggat   5160
tatttgaatg tttatggcac ctgacttgta aaaaaaaaaa actacaaaaa aatccttaga   5220
atcattaaat tgtgtccctg tattaccaaa ataacacagc accgtgcatg tatagtttaa   5280
ttgcagtttc atctgtgaaa acgtgaaatt gtctagtcct tcgttatgtt ccccagatgt   5340
cttccagatt tgctctgcat gtggtaactt gtgttagggc tgtgagctgt tcctcgagtt   5400
gaatggggat gtcagtgctc ctagggttct ccaggtggtt cttcagacct tcacctgtgg   5460
gggggggggt aggcggtgcc cacgcccatc tcctcatcct cctgaacttc tgcaacccca   5520
ctgctgggca gacatcctgg gcaacccctt ttttcagagc aagaagtcat aaagatagga   5580
tttcttggac atttggttct tatcaatatt gggcattatg taatgactta tttacaaaac   5640
aaagatactg gaaaatgttt tggatgtggt gttatggaaa gagcacaggc cttggaccca   5700
tccagctggg ttcagaacta ccccctgctt ataactgcgg ctggctgtgg gccagtcatt   5760
ctgcgtctct gctttcttcc tctgcttcag actgtcagct gtaaagtgga agcaatatta   5820
cttgccttgt atatggtaaa gattataaaa atacatttca actgttcagc atagtacttc   5880
```

aaagcaagta ctcagtaaat agcaagtctt tttaaa 5916

<210> SEQ ID NO 111
<211> LENGTH: 6927
<212> TYPE: DNA
<213> ORGANISM: Homo sapiens

<400> SEQUENCE: 111
gcgctcagca ggcggggcgg gagccgcgtg cgcccgagga cccggccgga aggcttgcgc 60
cagctcagga tgaggacagg ctgggcgacc cctcgccgcc cggcggggct cctcatgctg 120
ctcttctggt tcttcgatct cgcggagccc tctggccgcg cagctaatga ccccttcacc 180
atcgtccatg gaaatacggg caagtgcatc aagccagtgt atggctggat agtagcagac 240
gactgtgatg aaactgagga caagttatgg aagtgggtgt cccagcatcg gctctttcat 300
ttgcactccc aaaagtgcct tggcctcgat attaccaaat cggtaaatga gctgagaatg 360
ttcagctgtg actccagtgc catgctgtgg tggaaatgtg agcaccactc tctgtacgga 420
gctgcccggt accggctggc tctgaaggat ggacatggca cagcaatctc aaatgcatct 480
gatgtctgga agaaaggagg ctcagaggaa agcctttgtg accagcctta tcatgagatc 540
tataccagag atgggaactc ttatgggaga ccttgtgaat ttccattctt aattgatggg 600
acctggcatc atgattgcat tcttgatgaa gatcatagtg ggccatggtg tgccaccacc 660
ttaaattatg aatatgaccg aaagtggggc atctgcttaa agcctgaaaa cggttgtgaa 720
gataattggg aaaagaacga gcagtttgga agttgctacc aatttaatac tcagacggct 780
ctttcttgga aagaagctta tgtttcatgt cagaatcaag gagctgattt actgagcatc 840
aacagtgctg ctgaattaac ttaccttaaa gaaaaagaag gcattgctaa gatttctgg 900 attggtttaa atcagctata ctctgctaga ggctgggaat ggtcagacca caaaccatta 960
aactttctca actgggatcc agacaggccc agtgcaccta ctataggtgg ctccagctgt 1020
gcaagaatgg atgctgagtc tggtctgtgg cagagctttt cctgtgaagc tcaactgccc 1080
tatgtctgca ggaaaccatt aaataataca gtggagttaa cagatgtctg gacatactca 1140
gatacccgct gtgatgcagg ctggctgcca aataatggat tttgctatct gctggtaaat 1200
gaaagtaatt cctgggataa ggcacatgcg aaatgcaaag ccttcagtag tgacctaatc 1260
agcattcatt ctctagcaga tgtggaggtg gttgtcacaa aactccataa tgaggatatc 1320
aaagaagaag tgtggatagg ccttaagaac ataaacatac caactttatt tcagtggtca 1380
gatggtactg aagttactct aacatattgg gatgagaatg agccaaatgt tccctacaat 1440
aagacgccca actgtgtttc ctacttagga gagctaggtc agtggaaagt ccaatcatgt 1500
gaggagaaac taaaatatgt atgcaagaga aagggagaaa aactgaatga cgcaagttct 1560
gataagatgt gtcctccaga tgagggctgg aagagacatg gagaaacctg ttacaagatt 1620
tatgaggatg aggtcccttt tggaacaaac tgcaatctga ctatcactag cagatttgag 1680
caagaatacc taaatgattt gatgaaaaag tatgataaat ctctaagaaa atacttctgg 1740
actggcctga gagatgtaga ttcttgtgga gagtataact gggcaactgt tggtggaaga 1800
aggcgggctg taaccttttc caactggaat tttcttgagc cagcttcccc gggcggctgc 1860
gtggctatgt ctactggaaa gtctgttgga aagtgggagg tgaaggactg cagaagcttc 1920
aaagcacttt caatttgcaa gaaaatgagt ggaccccttg ggcctgaaga agcatcccct 1980
aagcctgatg acccctgtcc tgaaggctgg cagagtttcc ccgcaagtct ttcttgttat 2040
aaggtattcc atgcagaaag aattgtaaga aagaggaact gggaagaagc tgaacgattc 2100

-continued

```
tgccaagccc ttggagcaca cctttctagc ttcagccatg tggatgaaat aaaggaattt   2160
cttcactttt taacggacca gttcagtggc cagcattggc tgtggattgg tttgaataaa   2220
aggagcccag atttacaagg atcctggcaa tggagtgatc gtacaccagt gtctactatt   2280
atcatgccaa atgagtttca gcaggattat gacatcagag actgtgctgc tgtcaaggta   2340
tttcataggc catggcgaag aggctggcat ttctatgatg atagagaatt tatttatttg   2400
aggccttttg cttgtgatac aaaacttgaa tgggtgtgcc aaattccaaa aggccgtact   2460
ccaaaaacac cagactggta caatccagac cgtgctggaa ttcatggacc tccacttata   2520
attgaaggaa gtgaatattg gtttgttgct gatcttcacc taaactatga agaagccgtc   2580
ctgtactgtg ccagcaatca cagctttctt gcaactataa catcttttgt gggactaaaa   2640
gccatcaaaa acaaaatagc aaatatatct ggtgatggac agaagtggtg gataagaatt   2700
agcgagtggc caatagatga tcattttaca tactcacgat atccatggca ccgctttcct   2760
gtgacatttg gagaggaatg cttgtacatg tctgccaaga cttggcttat cgacttaggt   2820
aaaccaacag actgtagtac caagttgccc ttcatctgtg aaaaatataa tgtttcttcg   2880
ttagagaaat acagcccaga ttctgcagct aaagtgcaat gttctgagca atggattcct   2940
tttcagaata agtgttttct aaagatcaaa cccgtgtctc tcacattttc tcaagcaagc   3000
gatacctgtc actcctatgg tggcaccctt ccttcagtgt tgagccagat tgaacaagac   3060
tttattacat ccttgcttcc ggatatggaa gctactttat ggattggttt gcgctggact   3120
gcctatgaaa agataaacaa atggacagat aacagagagc tgacgtacag taactttcac   3180
ccattattgg ttagtgggag gctgagaata ccagaaaatt tttttgagga agagtctcgc   3240
taccactgtg ccctaatact caacctccaa aaatcaccgt ttactgggac gtggaatttt   3300
acatcctgca gtgaacgcca ctttgtgtct ctctgtcaga aatattcaga agttaaaagc   3360
agacagacgt tgcagaatgc ttcagaaact gtaaagtatc taaataatct gtacaaaata   3420
atcccaaaga ctctgacttg gcacagtgct aaaagggagt gtctgaaaag taacatgcag   3480
ctggtgagca tcacggaccc ttaccagcag gcattcctca gtgtgcaggc gctccttcac   3540
aactcttcct tatggatcgg actcttcagt caagatgatg aactcaactt tggttggtca   3600
gatgggaaac gtcttcattt tagtcgctgg gctgaaacta atgggcaact cgaagactgt   3660
gtagtattag acactgatgg attctggaaa acagttgatt gcaatgacaa tcaaccaggt   3720
gctatttgct actattcagg aaatgagact gaaaaagagg tcaaaccagt tgacagtgtt   3780
aaatgtccat ctcctgttct aaatactccg tggataccat ttcagaactg ttgctacaat   3840
ttcataataa caaagaatag gcatatggca acaacacagg atgaagttca tactaaatgc   3900
cagaaactga atccaaaatc acatattctg agtattcgag atgaaaagga gaataacttt   3960
gttcttgagc aactgctgta cttcaattat atggcttcat gggtcatgtt aggaataact   4020
tatagaaata agtctcttat gtggtttgat aagaccccac tgtcatatac acattggaga   4080
gcaggaagac caactataaa aaatgagaag tttttggctg gtttaagtac tgacggcttc   4140
tgggatattc aaacctttaa agttattgaa gaagcagttt attttcacca gcacagcatt   4200
cttgcttgta aaattgaaat ggttgactac aaagaagaat ataatactac actgccacag   4260
tttatgccat atgaagatgg tatttacagt gttattcaaa aaaaggtaac atggtatgaa   4320
gcattaaaca tgtgttctca aagtggaggt cacttggcaa gcgttcacaa ccaaaatggc   4380
cagctctttc tggaagatat tgtaaaacgt gatggatttc cactatgggt tgggctctca   4440
agtcatgatg gaagtgaatc aagttttgaa tggtctgatg gtagtacatt tgactatatc   4500
```

-continued

```
ccatggaaag gccaaacatc tcctggaaat tgtgttctct tggatccaaa aggaacttgg   4560
aaacatgaaa aatgcaactc tgttaaggat ggtgctattt gttataaacc tacaaaatct   4620
aaaaagctgt cccgtcttac atattcatca agatgtccag cagcaaaaga gaatgggtca   4680
cggtggatcc agtacaaggg tcactgttac aagtctgatc aggcattgca cagtttttca   4740
gaggccaaaa aattgtgttc aaaacatgat cactctgcaa ctatcgtttc cataaaagat   4800
gaagatgaga ataaatttgt gagcagactg atgagggaaa ataataacat taccatgaga   4860
gtttggcttg gattatctca acattctgtt gaccagtctt ggagttggtt agatggatca   4920
gaagtgacat ttgtcaaatg ggaaaataaa agtaagagtg gtgttggaag atgtagcatg   4980
ttgatagctt caaatgaaac ttggaaaaaa gttgaatgtg aacatggttt tggaagagtt   5040
gtctgcaaag tgcctctggg ccctgattac acagcaatag ctatcatagt tgccacacta   5100
agtatcttag ttctcatggg cggactgatt tggttcctct tccaaaggca ccgtttgcac   5160
ctggcgggtt tctcatcagt tcgatatgca caaggagtga atgaagatga gattatgctt   5220
ccttctttcc atgactaaat tcttctaaaa gttttctaat ttgcactaat gtgttatgag   5280
aaattagtca cttaaaatgt cccagtgtca gtatttactc tgctccaaag tagaactctt   5340
aaatactttt tcagttgttt agatcttagg catgtgctgg tatccacagt taattccctg   5400
ctaaatgcca tgtttatcac cctaattaat agaatggagg ggactccaaa gctggaactg   5460
aagtccaaat tgtttgtaca gtaatatgtt taatgttcat ttctctgta tgaatgtgat   5520
tggtaactag gatatgtata ttttaataga atttttaaca aaacttctta gaaaattaaa   5580
ataggcatat tactaggtga catgtctact ttttaatttt taagagcatc cggccaaatg   5640
caaaattagt acctcaaagt aaaaattgaa ctgtaaactc tatcagcatt gtttcaaaat   5700
agtcattttt agcactgggg aaaaataaac aataagacat gcttactttt taatttttat   5760
tttttgaga ctgagtctct ctctgttgcc caggctggag tacaatggcg tgatctcggc   5820
tcactgcaaa tctccgcctc ccaggttcaa gcgattctcc tgcctcagcc tcctgagtag   5880
ctgggattac aggcaactgc caccatgccc ggctaatttt tgtattttta gtagagatgg   5940
ggtttcacca tgttggccag gctggtctcg aactcgtgac cgcaggtgat cctcccgcct   6000
cggcctccca aagtgctggg attacaggca tgagccaccg cgcctggcct ctgcttactt   6060
tttatatagc aaaatgattc ctcttggcaa gatgtttctt atattattcc aaagttattt   6120
cataccatta ttatgtaaat atgaagagtt tttttctgtt tataattgtt tataaaacaa   6180
tgacttttaa agatttagtg cttaacattt tcccaagtgt gggaacatta tttttagatt   6240
gagtaggtac cttgtagcag tgtgctttgc attttctgat gtattacatg actgtttctt   6300
ttgtaaagag aatcaactag gtatttaaga ctgataattt tacaatttat atgcttcaca   6360
tagcatgtca acttttgact aagaattttg ttttactttt ttaacatgtg ttaaacagag   6420
aaagggtcca tgaaggaaag tgtatgagtt gcatttgtaa aaatgagact ttttcagtgg   6480
aactctaaac cttgtgatga ctactaacaa atgtaaaatt atgagtgatt aagaaaacat   6540
tgctttgtgg ttatcacttt aagttttgac acctagatta tagtcttagt aatagcatcc   6600
actggaaaag gtgaaaatgt tttattcggc atttaactta catttgtact ttatttttgt   6660
ataaaatcca tagatttatt ttacatttag agtatttaca ctatgataaa gttgtaaata   6720
attttctaag acagttttta tatagtctac agttgtcctg atttcttatt gaatttgtta   6780
gactagttct cttgtcctgt gatctgtgta caattttagt cactaagact ttcctccaag   6840
aactaagcca acttgatgtg aaaagcacag ctgtatataa tggtgatgtc ataataaagt   6900
```

tgttttatct tttaagtaaa agtaaaa 6927

<210> SEQ ID NO 112
<211> LENGTH: 3977
<212> TYPE: DNA
<213> ORGANISM: Homo sapiens

<400> SEQUENCE: 112
ggatggtgcc ttgagtgaat gaccccttg gagaacattc ttccgcatcc ctcgcctcaa 60
gccagcctca gacagaaaac tgaagattca gcagatccag tgcttcctgc tcctcttctg 120
cccaggaaca cgcttgcctt ccccaaggct tccagaagct ctgaggcagg aggcaccaag 180
ttctacctca tgtttggagg atcttgctag ctatggccct cgtactcggc tccctgttgc 240
tgctggggct gtgcgggaac tccttttcag gagggcagcc ttcatccaca gatgctccta 300
aggcttggaa ttatgaattg cctgcaacaa attatgagac ccaagactcc cataaagctg 360
gacccattgg cattctcttt gaactagtgc atatctttct ctatgtggta cagccgcgtg 420
atttcccaga agatactttg agaaaattct tacagaaggc atatgaatcc aaaattgatt 480
atgacaagcc agaaactgta atcttaggtc taaagattgt ctactatgaa gcagggatta 540
ttctatgctg tgtcctgggg ctgctgttta ttattctgat gcctctggtg gggtatttct 600
tttgtatgtg tcgttgctgt aacaaatgtg gtggagaaat gcaccagcga cagaaggaaa 660
atgggccctt cctgaggaaa tgctttgcaa tctccctgtt ggtgatttgt ataataataa 720
gcattggcat cttctatggt tttgtggcaa atcaccaggt aagaacccgg atcaaaagga 780
gtcggaaact ggcagatagc aatttcaagg acttgcgaac tctcttgaat gaaactccag 840
agcaaatcaa atatatattg gcccagtaca acactaccaa ggacaaggcg ttcacagatc 900
tgaacagtat caattcagtg ctaggaggcg gaattcttga ccgactgaga cccaacatca 960
tccctgttct tgatgagatt aagtccatgg caacagcgat caaggagacc aaagaggcgt 1020
tggagaacat gaacagcacc ttgaagagct tgcaccaaca aagtacacag cttagcagca 1080
gtctgaccag cgtgaaaact agcctgcggt catctctcaa tgaccctctg tgcttggtgc 1140
atccatcaag tgaaacctgc aacagcatca gattgtctct aagccagctg aatagcaacc 1200
ctgaactgag gcagcttcca cccgtggatg cagaacttga caacgttaat aacgttctta 1260
ggacagattt ggatggcctg gtccaacagg gctatcaatc ccttaatgat atacctgaca 1320
gagtacaacg ccaaaccacg actgtcgtag caggtatcaa aagggtcttg aattccattg 1380
gttcagatat cgacaatgta actcagcgtc ttcctattca ggatatactc tcagcattct 1440
ctgtttatgt taataacact gaaagttaca tccacagaaa tttacctaca ttggaagagt 1500
atgattcata ctggtggctg ggtggcctgg tcatctgctc tctgctgacc ctcatcgtga 1560
ttttttacta cctgggctta ctgtgtggcg tgtgcggcta tgacaggcat gccaccccga 1620
ccacccgagg ctgtgtctcc aacaccggag gcgtcttcct catggttgga gttggattaa 1680
gtttcctctt ttgctggata ttgatgatca ttgtggttct tacctttgtc tttggtgcaa 1740
atgtggaaaa actgatctgt gaaccttaca cgagcaagga attattccgg gttttggata 1800
caccctactt actaaatgaa gactgggaat actatctctc tgggaagcta tttaataaat 1860
caaaaatgaa gctcactttt gaacaagttt acagtgactg caaaaaaaat agaggcactt 1920
acggcactct tcacctgcag aacagcttca atatcagtga acatctcaac attaatgagc 1980
atactggaag cataagcagt gaattggaaa gtctgaaggt aaatcttaat atctttctgt 2040
tgggtgcagc aggaagaaaa aaccttcagg attttgctgc ttgtggaata gacagaatga 2100
attatgacag ctacttggct cagactggta aatcccccgc aggagtgaat cttttatcat 2160
ttgcatatga tctagaagca aaagcaaaca gtttgccccc aggaaatttg aggaactccc 2220
tgaaaagaga tgcacaaact attaaaacaa ttcaccagca acgagtcctt cctatagaac 2280
aatcactgag cactctatac caaagcgtca agatacttca acgcacaggg aatggattgt 2340
tggagagagt aactaggatt ctagcttctc tggattttgc tcagaacttc atcacaaaca 2400
atacttcctc tgttattatt gaggaaacta agaagtatgg gagaacaata ataggatatt 2460
ttgaacatta tctgcagtgg atcgagttct ctatcagtga gaaagtggca tcgtgcaaac 2520
ctgtggccac cgctctagat actgctgttg atgtcttttct gtgtagctac attatcgacc 2580
ccttgaattt gttttggttt ggcataggaa aagctactgt atttttactt ccggctctaa 2640
tttttgcggt aaaactggct aagtactatc gtcgaatgga ttcggaggac gtgtacgatg 2700
atgttgaaac tatacccatg aaaaatatgg aaaatggtaa taatggttat cataaagatc 2760
atgtatatgg tattcacaat cctgttatga caagcccatc acaacattga tagctgatgt 2820
tgaaactgct tgagcatcag gatactcaaa gtggaaagga tcacagattt ttggtagttt 2880
ctgggtctac aaggactttc caaatccagg agcaacgcca gtggcaacgt agtgactcag 2940
gcgggcacca aggcaacggc accattggtc tctgggtagt gctttaagaa tgaacacaat 3000
cacgttatag tccatggtcc atcactattc aaggatgact ccctcccttc ctgtctattt 3060
ttgtttttta ctttttttaca ctgagtttct atttagacac tacaacatat ggggtgtttg 3120
ttcccattgg atgcatttct atcaaaactc tatcaaatgt gatggctaga ttctaacata 3180
ttgccatgtg tggagtgtgc tgaacacaca ccagtttaca ggaaagatgc attttgtgta 3240
cagtaaacgg tgtatatacc ttttgttacc acagagtttt ttaaacaaat gagtattata 3300
ggactttctt ctaaatgagc taaataagtc accattgact tcttggtgct gttgaaaata 3360
atccattttc actaaaagtg tgtgaaacct acagcatatt cttcacgcag agattttcat 3420
ctattatact ttatcaaaga ttggccatgt tccacttgga aatggcatgc aaaagcaatc 3480
atagagaaac ctgcgtaact ccatctgaca aattcaaaag agagagagag atcttgagag 3540
agaaatgctg ttcgttcaaa agtggagttg ttttaacaga tgccaattac ggtgtacagt 3600
ttaacagagt tttctgttgc attaggataa acattaattg gagtgcagct aacatgagta 3660
tcatcagact agtatcaagt gttctaaaat gaaatatgag aagatcctgt cacaattctt 3720
agatctggtg tccagcatgg atgaaacctt tgagtttggt ccctaaattt gcatgaaagc 3780
acaaggtaaa tattcatttg cttcaggagt ttcatgttgg atctgtcatt atcaaaagtg 3840
atcagcaatg aagaactggt cggacaaaat ttaacgttga tgtaatgaaa ttccagatgt 3900
aggcattccc cccaggtctt ttcatgtgca gattgcagtt ctgattcatt tgaataaaaa 3960
ggaacttgga aaacatg 3977

<210> SEQ ID NO 113
<211> LENGTH: 3572
<212> TYPE: DNA
<213> ORGANISM: Homo sapiens

<400> SEQUENCE: 113
atcgaagcta aagggctgac agaagggctg tagcggcaag tgtgcgccaa cacagctgca 60
cacgcccaga cacctgaggc gctgagagga acttccccgc gatccgcccc ggctgcacag 120
agcctcttct ccccgccggg gccccgccca gcctcacttc ttttaaaagc agcagccagc 180
agcgcgccgg tggcgtgcgg ctcgaaaggc cgggaggacg tcatcgacgc gctgtcgagc 240

-continued

```
ctccagcccg cccgggtttc cttcgcagtc gcgcaccgac gctcaaacgc gcgctccaac    300

ccgcagcctc ctcctgcctc accgcccgaa gatggcggct ctcaaactcc tctcctccgg    360

gcttcggctc tgcgcctctg cccgcggatc tggggcaacc tggtacaagg gatgtgtttg    420

ttccttttcc accagtgctc atcgccatac caagttttat acagatccag tagaagctgt    480

aaaagacatc cctgatggtg ccacggtttt ggttggtggt tttgggctat gtggaattcc    540

agagaatctt atagatgctt tactgaaaac tggagtaaaa ggactaactg cagtcagcaa    600

caatgcaggg gttgacaatt ttggtttggg gcttttgctt cggtccaagc agataaaacg    660

catggtctct tcatatgtgg gagaaaatgc agaatttgaa cgacagtact tatctggtga    720

attagaagtg gagctgacac cacagggcac acttgcagag aggatccgtg caggcggggc    780

tggagttcct gcattttaca ccccaacagg gtatgggacc ctggtacaag aaggaggatc    840

gcccatcaaa tacaacaaag atggcagtgt tgccattgcc agtaagccaa gagaggtgag    900

ggagttcaat ggtcagcact ttattttgga ggaagcaatt acaggggatt ttgctttggt    960

gaaagcctgg aaggcggacc gagcaggaaa cgtgattttc aggaaaagtg caaggaattt   1020

caacttgcca atgtgcaaag ctgcagaaac cacagtggta gaggttgaag aaattgtgga   1080

tattggagca tttgctccag aagacatcca tattcctcag atttatgtac atcgccttat   1140

aaagggagaa aaatatgaga aaagaattga gcgtttatca atccggaaag agggagatgg   1200

ggaagccaaa tctgctaaac ctggagatga cgtaagggaa cgaatcatca agagggccgc   1260

tcttgagttt gaggatggca tgtatgctaa tttgggcata ggaatccctc tcctggccag   1320

caattttatc agcccaaata taactgttca tcttcaaagt gaaaatggag ttctgggttt   1380

gggtccatat ccacgacaac atgaagctga tgcagatctc atcaatgcag gcaaggaaac   1440

agttactatt cttccaggag cctctttttt ctccagcgat gaatcatttg caatgattag   1500

aggtggacac gtcgatctga caatgctagg agcgatgcag gtttccaaat atggtgacct   1560

ggctaactgg atgatacctg ggaagatggt gaaaggaatg ggaggtgcta tggatttagt   1620

gtccagtgcg aaaaccaaag tggtggtcac catggagcat tctgcaaagg gaaatgcaca   1680

taaaatcatg gagaaatgta cattaccatt gactggaaag caatgtgtca accgcattat   1740

tactgaaaag gctgtgtttg atgtggacaa gaagaaaggg ttgactctga ttgagctctg   1800

ggaaggcctg acagtggatg acgtacagaa gagtactggg tgtgattttg cagtttcacc   1860

aaaactcatg ccaatgcagc agatcgcaaa ttgaaatatg gatatttgta ccaggctgcg   1920

tgtttttcat tttaaacaca caagatttaa ttgaaaggac atcaataatc ataattgtgt   1980

atttaacagg tggtttttta ttagttttct tgtgtttcag actttatgca gccatataaa   2040

ctgttctcta ggcatgctgt gacattttaa taaaaagcaa aaggagcatt tataattatc   2100

tcatttgtta aggctgagaa ggttgttttt ataataggta attatattga atgcattttc   2160

actgaatatg gtatgtatgc taaattatat gaacctttcc ccaagaaggg ccctagaaat   2220

tgatgtggct ttcctcttaa atattaatta ttagtcctga aagaaagata acatatgtga   2280

tttttgtggt taggagagtt gctgtcatga ttgtttttttc ttcagcctcc tctgactttt   2340

cttttggggc ttcagatttt atgattacat cttgtccccc tagaacatcc cccttcctcc   2400

catactgctt ttaaacagat gcccaagaag gcaagcagga atgcctcttg tgggggaggg   2460

cagggagaaa taactagttc aaaccaacta tctatctatg ctttgcaaag actaaggcgt   2520

attataggaa gagggctaga aacctaactg attcttctca gttttctcat tttaaaacag   2580

cccagtattc ctttgtatcc tcaagggtcc ttgagaatac ttctgttatt gagaccctgt   2640
```

gggctacttg tactgtacct cctctcaagc caagaagggc tgtgggataa tttaccatga 2700
atccttagta gcaatgacag cagagttaaa aaataaaagg tgttttactt tcaggctctt 2760
gttttggttc agaggagatt ttaaatattg aatgacactt ctacagaaca acggtttttc 2820
ttctgccaag gctacttcct ttaacgaagt gcctttaatt cagccttatc caactaggga 2880
aaataatgtt ggacaagtct aggatttgaa gagtcagtga acttttagtg tcagggaata 2940
aacatggtgg gtagattagg tttgaaaaaa acttccttag aggtatttat tctcaatacc 3000
tgacaggggc ccatgggaat gacttcagaa gcatcccgga taatagatgg gtaaaaagtc 3060
taggcaccct gaagaacagg tgagacagct ggcctctgga cagaggtagg catagtacag 3120
tacgatatat cattcctctg gtcctaaata tacaaactta ttcatgtttt taggtgatga 3180
tggtcattga aactcacttc ttttcaggtg tagctacaat tgtgtaatgt acaatattag 3240
agaaaggaca ggctttttat gagtaacaca caccatatat aaaacagcct ttctggctga 3300
ccacatggtt aaatgcatac cttcccagta ctggggggaa aaaatgaccc ttcttagaat 3360
gtgcaagttc catgagagta atatattgat atgattttga aaagaattgt tgatagttac 3420
atcttcaaac ttatcattcc agtatgcatc tttaagataa tgtgattcta agtagatgac 3480
tttatattct tgattaaaga gtgctataca tgttaagaaa tgcattaagg aatacaataa 3540
atattctaaa gtgatgtaaa aaaaaaaaaa aa 3572

<210> SEQ ID NO 114
<211> LENGTH: 29
<212> TYPE: DNA
<213> ORGANISM: Artificial Sequence
<220> FEATURE:
<223> OTHER INFORMATION: Metallothionein 2A-specific 29mer shRNA

<400> SEQUENCE: 114
gtaaagaacg cgacttccac aaacctgga 29

<210> SEQ ID NO 115
<211> LENGTH: 20
<212> TYPE: DNA
<213> ORGANISM: Artificial Sequence
<220> FEATURE:
<223> OTHER INFORMATION: Forward primer

<400> SEQUENCE: 115
aacacatttc aagccccaaa 20

<210> SEQ ID NO 116
<211> LENGTH: 24
<212> TYPE: DNA
<213> ORGANISM: Artificial Sequence
<220> FEATURE:
<223> OTHER INFORMATION: Reverse primer

<400> SEQUENCE: 116
gaaactggtt tcaaaatatt cgtt 24

<210> SEQ ID NO 117
<211> LENGTH: 23
<212> TYPE: DNA
<213> ORGANISM: Artificial Sequence
<220> FEATURE:
<223> OTHER INFORMATION: Forward primer

<400> SEQUENCE: 117
gctttttctg taaatcatct gtg 23

```
<210> SEQ ID NO 118
<211> LENGTH: 21
<212> TYPE: DNA
<213> ORGANISM: Artificial Sequence
<220> FEATURE:
<223> OTHER INFORMATION: Reverse primer

<400> SEQUENCE: 118

ctgagatcag ccaaattcag t                                   21


<210> SEQ ID NO 119
<211> LENGTH: 20
<212> TYPE: DNA
<213> ORGANISM: Artificial Sequence
<220> FEATURE:
<223> OTHER INFORMATION: Forward primer

<400> SEQUENCE: 119

catttgctcc aaactgacca                                     20


<210> SEQ ID NO 120
<211> LENGTH: 20
<212> TYPE: DNA
<213> ORGANISM: Artificial Sequence
<220> FEATURE:
<223> OTHER INFORMATION: Reverse primer

<400> SEQUENCE: 120

tactccaaag cctcttgctc                                     20


<210> SEQ ID NO 121
<211> LENGTH: 20
<212> TYPE: DNA
<213> ORGANISM: Artificial Sequence
<220> FEATURE:
<223> OTHER INFORMATION: Forward primer

<400> SEQUENCE: 121

acattcgaaa gaccctagcc                                     20


<210> SEQ ID NO 122
<211> LENGTH: 21
<212> TYPE: DNA
<213> ORGANISM: Artificial Sequence
<220> FEATURE:
<223> OTHER INFORMATION: Reverse primer

<400> SEQUENCE: 122

caattcctat gcaatcggtc t                                   21


<210> SEQ ID NO 123
<211> LENGTH: 29
<212> TYPE: DNA
<213> ORGANISM: Artificial Sequence
<220> FEATURE:
<223> OTHER INFORMATION: Metallothionein 2A-specific 29mer shRNA

<400> SEQUENCE: 123

gtaaagaacg cgacttccac aaacctgga                           29
```